(12) United States Patent
Habashita et al.

(10) Patent No.: US 7,759,336 B2
(45) Date of Patent: Jul. 20, 2010

(54) NITROGEN-CONTAINING HETEROCYCLIC COMPOUNDS AND MEDICINAL USE THEREOF

(75) Inventors: Hiromu Habashita, Mishima-gun (JP); Masaya Kokubo, Mishima-gun (JP); Shiro Shibayama, Tsukuba (JP); Hideaki Tada, Tsukuba (JP); Tatsuya Tanihiro, Tsukuba (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 679 days.

(21) Appl. No.: 10/538,758

(22) PCT Filed: Dec. 9, 2003

(86) PCT No.: PCT/JP03/15718

§ 371 (c)(1),
(2), (4) Date: Jun. 10, 2005

(87) PCT Pub. No.: WO2004/052862

PCT Pub. Date: Jun. 24, 2004

(65) Prior Publication Data

US 2007/0167459 A1     Jul. 19, 2007

(30) Foreign Application Priority Data

Dec. 10, 2002   (JP)   ............... 2002-357446
Jun. 6, 2003    (JP)   ............... 2003-162706

(51) Int. Cl.
*A01N 43/00*    (2006.01)
*A61K 31/55*    (2006.01)
*C07D 223/00*   (2006.01)

(52) U.S. Cl. .................. 514/212.01; 540/484
(58) Field of Classification Search ........ None
See application file for complete search history.

(56) References Cited

U.S. PATENT DOCUMENTS

2002/0137755 A1* 9/2002 Bilodeau et al. ............ 514/256

FOREIGN PATENT DOCUMENTS

| GB | 1113918 A | | 5/1968 |
|----|-----------|---|--------|
| JP | 2002-348288 A | | 12/2002 |
| WO | WO9837079 | * | 8/1998 |
| WO | 00/56729 A1 | | 9/2000 |
| WO | 01/40227 A1 | | 6/2001 |
| WO | 02/22599 A2 | | 3/2002 |
| WO | 02/45652 A2 | | 6/2002 |
| WO | 03/062236 A1 | | 7/2003 |
| WO | WO2004048365 | * | 6/2004 |
| WO | WO2004080966 | * | 9/2004 |

OTHER PUBLICATIONS

"Inflammation", http://www.nlm.nih.gov/cgi/mesh/2008/MB_cgi, accessed Feb. 20, 2008.*
Hypersensitivity:, http://www.nlm.nih.gov/cgi/mesh/2008/MB_cgi, accessed Feb. 20, 2008.*
"Infection", http://www.nlm.nih.gov/cgi/mesh/2008/MB_cgi, accessed Feb. 20, 2008.*
"Cerebral arterial disease", http://www.nlm.nih.gov/cgi/mesh/2008/MB_cgi?mode=&index=2433&field=all&HM=&II=&PA=&form=&input=, accessed Feb. 20, 2008.*
"Cardiovascular diseases", http://www.nlm.nih.gov/cgi/mesh/2008/MB_cgi, accessed Feb. 20, 2008.*
"Metabolic diseases", http://www.nlm.nih.gov/cgi/mesh/2008/MB_cgi, accessed Feb. 20, 2008.*
"Neoplasms", http://www.nlm.nih.gov/cgi/mesh/2008/MB_cgi, accessed Feb. 20, 2008.*
Vippagunta et al. Advanced Drug Delivery Reviews, 2001, 48, 3-26.*
Jantzen and Robinson. Modern Pharmaceutics, 1996, p. 596.*

(Continued)

Primary Examiner—James O Wilson
Assistant Examiner—Noble Jarrell
(74) Attorney, Agent, or Firm—Sughrue Mion, PLLC

(57) ABSTRACT

The compound represented by formulae (I) and (II), the salt thereof, the N-oxide thereof or the solvate thereof, or the prodrug thereof and the pharmaceutical composition comprising thereof have a CXCR4-regulating effect, and they are effective in treatment and prevention of various inflammatory disease, various allergic disease, acquired immunodeficiency syndrome infection with human immunodeficiency virus, or agents for regeneration therapy.

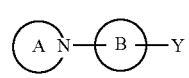

(I)

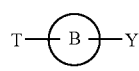

(II)

(wherein ring A represents a nitrogen-containing heterocyclic group which may have a substituent(s); ring B represents a homocyclic group which may have a substituent(s) or a heterocyclic group which may have a substituent(s); and Y represents a hydrocarbon group which may have a substituent(s), a heterocyclic group which may have a substituent(s), an amino group which may be protected, a hydroxyl group which may be protected or a mercapto group which may be protected; T represents ring A or an amino group which may be protected.)

8 Claims, No Drawings

OTHER PUBLICATIONS

Greene et al. Protective Groups in Organic Synthesis, 1999, pp. 17-23, 454-458, 494-503.*

"Definition of cancer", http://www.medterms.com/script/main/art.asp?articlekey=2580, accessed Jan. 27, 2007.*

"There is no cure for cancer", http://www.fwhc.org/health/nocure.htm, accessed Feb. 20, 2008.*

Postovskii et al., Doklady Akademii Nauk SSSR, 1966, 166(5), 1136-9.*

"Overview of HIV prevention", http://www.avert.org/prevent-hiv.htm, accessed Feb. 20, 2008.*

Fuijii et al. Expert Opinion in Investigational Drugs, 2003, 12(2), 185-195.*

Gupta, C.M. et al, "Drugs acting on the central nervous system. Synthesis of substituted quinazolinones and quinazolines and triazepino- and triazocinoquinazolinones", Journal of Medical Chemistry, vol. 11, No. 2, (1968), pp. 392-395.

International Search Report dated Feb. 17, 2004.

* cited by examiner

NITROGEN-CONTAINING HETEROCYCLIC COMPOUNDS AND MEDICINAL USE THEREOF

TECHNICAL FIELD

The present invention relates to CXCR4 regulators that are useful as medicament.

More particularly, it relates to (1) compounds of formula (I)

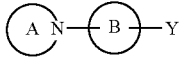

(I)

(wherein all the symbols have the same meanings as defined hereinafter), salts thereof, N-oxides thereof or solvates thereof, or prodrugs of the same, (2) pharmaceutical compositions comprising compounds of formula (I)

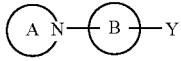

(I)

(wherein all the symbols have the same meanings as defined hereinafter), salts thereof, N-oxides thereof or solvates thereof, or prodrugs of the same, (3) CXCR4 regulator comprising compounds of formula (II)

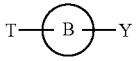

(II)

(wherein all the symbols have the same meanings as defined hereinafter), salts thereof, N-oxides thereof or solvates thereof, or prodrugs of the same, as an active ingredient, and (4) methods for preparation thereof.

Chemokine is known as a basic protein having endogeneous leukocyte chemotactic and activating abilities and strong heparin-binding abilities. At present, it is considered that chemokine is related to not only the control of infiltration of specific leukocyte at the time of inflammations and immune responses but also the development and homing of lymphocyte under physiological conditions and migration of hemocyte precursor cells and somatic cells.

Differentiation, proliferation and cell death of hemocytes are controlled by various types of cytokine. In the living body, inflammations are found topically and differentiation, maturation and the like of lymphocytes are carried out at certain specified sites. That is, various necessary cells migrate into certain specified sites and accumulate therein to cause a series of inflammations and immune responses. Accordingly, migration of cells is also an indispensable phenomenon in addition to differentiation, proliferation and death of cells.

Migration of hemocytes in the living body starts firstly in the development stage by the shift of hematopoiesis started in the AGM region into permanent hematopoiesis in bone marrow via fetal liver. Furthermore, precursor cells of T cells and thymus dendritic cells migrate from the fetal-liver into the bone marrow and then into the thymus gland and cytodifferentiate under thymus environment. The T cell which received clone selection migrates into secondary lymphoid tissues and takes part in an immune response in the periphery. The Langerhans' cell of the skin activated and differentiated by capturing an antigen migrates into the T cell region of a topical lymph node and activates naive T cell therein as a dendritic cell. The memory T cell performs its homing again into the lymph node via lymphatic and blood vessels. Also, B cell, T cell in the intestinal epithelium, γδ T cell, NKT cell and dendritic cell migrate from bone marrow without passing through the thymus gland and differentiate to take part in an immune response.

Chemokines are deeply involved in these various cell migration. For example, an SDF-1 (stromal cell derived factor-1) and its receptor CXCR4 act on various immunological and inflammatory reactions. They are reported to be involved in accumulation and activation of CD4+T cells in a synovial membrane derived from a human patient having a rheumatoid arthritis (*J. Immunol.*, 165, 6590-6598 (2000)). In addition, a CXCR4 inhibitor suppressed recruitment of leukocytes into a joint also in CIA model mice and reduces the arthritis score dramatically (*J. Immunol.*, 167, 4648-4692 (2001)). In a mouse OVA-induced airway hypersensitivity model, an anti-CXCR4 antibody reduced the number of eosinophiles recruited into a pulmonary interstice to suppress the airway hypersensitivity (*J. Immunol.*, 165, 499-508 (2000)).

SDF-1 and its receptor CXCR4 are also reported to play an important role in maintaining hemopoietic stem cells in a bone marrow (*J. Exp. Med.*, 185, 111-120 (1997), *Blood*, 97, 3354-3360 (2001)). Accordingly, the inhibition of SDF-1 and CXCR4 is expected to regulate the recruitment of the hemopoietic stem cells into a peripheral blood and to be useful in a peripheral blood stem cell transplantation and this also in a regeneration transplantation therapy.

SDF-1 and CXCR4 are involved in an infiltration of cells of various cancers such as mammary cancer, prostate cancer and ovarian cancer (*Nature*, 410, 50-56 (2001), *Cancer Res.*, 62, 1832-1837 (2002), *Cancer Res.*, 62, 5930-5938 (2002)), and an anti-CXCR4 antibody inhibited metastasis of a mammary cancer cell into a lung in a human mammary cancer cell line transfusion model in SCID mice. Also, since SDF-1 is highly expressed in a human ovarian epithelial tumor, it promotes accumulation of a plasmocytic dendric cell to inhibit the action of a bone marrow dendric cell involved in a tumor immune, resulting in an inhibition of the tumor immune (*Nat. Med.*, 12, 1339 (2001)). In addition, it is involved also in proliferation and movement of a non-hodgkin lymphoma cell, and an anti-CXCR4 antibody inhibits proliferation of tumor cells in a human non-hodgkin lymphoma cell transfusion model in BID/SCID mice, resulting in an improvement in the mortality in mice (*Cancer Res.*, 62, 3106-3112 (2002)).

SDF-1 and CXCR4 play important roles in formation of a hippocampal dentate gyrus granulocyte essential for memory and learning, and are involved in progression of an adult disease associated with plasticity and hippocampal pathology such as Alzheimer's disease, cerebral stroke, epilepsy and the like (*Development*, 129, 4249-4260 (2002), *Trends Neuroscience*, 25, 548-549 (2002)).

SDF-1 and CXCR4 are essential for a function of an autoreactive B cell involved in progression of a diabetes, and an anti-SDF-1 antibody reduced the blood sugar level in NOD mice and reduced the mature IgM+B cell count in a peripheral tissue (*Immunology*, 107, 222-232 (2002)). SDF-1 was highly expressed in a human arteriosclerotic plaque, resulting in an activation of platelets (*Circ. Res.*, 86, 131-138 (2000)).

Results observed in SDF-1/CXCR4 knockout mice also indicated that SDF-1 is essential for functions of the blood vessels in central nervous tissues, heart and gastrointestinal tracts in addition to lymphocytes (*Nature*, 382, 635-639 (1996), *Nature*, 393, 591-594 (1998), *Nature*, 393, 595-599 (1998)). Accordingly, it is believed to be involved in diseases of such tissues.

Thus, chemokine receptors are greatly related to the control of inflammation and immune responses through a mechanism in which they are expressed at certain specified periods in variously specific cells and the effector cells are accumulated in a region where chemokine is produced.

Acquired immunodeficiency syndrome (called AIDS) which is induced by human immunodeficiency virus (hereinafter referred to as "HIV") is one of the diseases of which their therapeutic methods are most earnestly desired in recent years. Once infection with HIV is completed in a CD4-positive cell which is a principal target cell, HIV repeats its proliferation in the body of the patient and, sooner or later, completely destroys T cell which takes charge of the immunological function. During this process, the immunological function is gradually reduced to cause fever, diarrhea, lymph node enlargement and the like various immunodeficiency conditions which are apt to cause complications with pneumocystis carinii pneumonia and the like various opportunistic infections. Such conditions are the onset of AIDS, and it is well known that they induce and worsen Kaposi sarcoma and the like malignant tumors.

As the recent preventive and therapeutic methods for AIDS, attempts have been made to, e.g., (1) inhibit growth of HIV by the administration of a reverse transcriptase inhibitor or a protease inhibitor and (2) prevent or alleviate opportunistic infections by the administration of a drug having immunopotentiation activity.

Helper T cells which take charge of the central of immune system are mainly infected with HIV. It is known since 1985 that HIV uses the membrane protein CD4 expressing on the membrane of T cells in the infection (*Cell*, 52, 631 (1985)). The CD4 molecule is composed of 433 amino acid residues, and its expression can be found in macrophages, some B cells, vascular endothelial cells, Langerhans' cells in skin tissues, dendritic cells in lymphoid tissues, glia cells of the central nervous system and the like, in addition to the mature helper T cells. However, since it has been revealed that the infection with HIV is not completed by the CD4 molecule alone, a possibility has been suggested on the presence of factors other than the CD4 molecule, which are related to the infection of cells with HIV.

In 1996, a cell membrane protein called Fusin was identified as a factor other than the CD4 molecule, which is related to the HIV infection (*Science*, 272, 872 (1996)). It was confirmed that this Fusin molecule is a receptor (namely, CXCR4) of SDF-1. In addition, it was confirmed also in vitro that the SDF-1 specifically inhibits infection of T cell tropic (X4) HIV (*Nature*, 382, 829 (1996), *Nature*, 382, 833 (1996)). That is, it is considered that the HIV infection was inhibited by the binding of SDF-1 to CXCR4 preceding HIV, thereby depriving HIV of a foothold for infecting cells.

Also at that time, it was discovered that another chemokine receptor CCR5, which is a receptor of RANTES, MIP-1α and MIP-1β, is also used at the time of the infection with a macrophage tropic (R5) EV (*Science*, 272, 1955 (1996)).

Accordingly, substances which can compete with CXCR4 and CCR5 for HIV, or which can bind to HIV virus thus causing the virus unable to bind to CXCR4 and CCR5, could become HIV infection inhibitors. Also, there is a case in which a low molecular compound initially discovered as an HIV infection inhibitor was actually a CXCR4 antagonist (*Nature Medicine*, 4, 72 (1998)).

Based on the above, a chemokine and a chemokine receptor are deeply involved in inflammation, immune disease or HIV infection. A compound having an ability of regulating CXCR4 is effective in treatment and prevention, for example, of an inflammatory/immune disease, allergic disease, infectious disease, especially HIV infection and accompanying diseases, psychoneurotic disease, cerebral disease, cardiovascular disease, metabolic disease and cancerous disease. In addition, it is also useful in cell medicine and regeneration medicine. The cell medicine includes peripheral blood stem cell recruitment and in vitro and in vivo proliferation of a stem cell for the purpose of a gene therapy. The regeneration medicine includes transplantation medicine such as various organ transplantations including bone marrow transplantation, peripheral blood stem cell transplantation and tissue repair. The transplantation medicine agent is an agent used in the bone marrow transplantation, peripheral blood stem cell transplantation or various organ transplantation. The transplantation medicine agent includes, for example, an infection-preventing agent or immunosuppressant. Those included also are agents intended to supplement and/or enhance the therapeutic effect in the regeneration medicine. An transplantation medicine agent has an effect, for example, of migrating a stem cell from a bone marrow into a peripheral blood or to increase leukocyte rapidly to a normal level.

The inflammatory/immune diseases include, for example, rheumatoid arthritis, arthritis, gout, transplanted organ rejection, graft versus host disease (GVHD), nephritis, psoriasis, rhinitis, conjunctivitis, multiple sclerosis, ulcerative colitis, Crohn's disease, shock accompanied with bacterial infection, pulmonary fibrosis, systemic response syndrome (SIRS), acute pulmonary disorder, diabetes and the like.

The allergic diseases include, for example, asthma, atopic dermatitis, rhinitis, conjunctivitis and the like.

The infectious diseases, especially HIV infection and accompanying diseases, include, for example, acquired immunodeficiency syndrome (AIDS), candidosis, carinii pneumonia, cytomegalovirus retinitis, Kaposi's sarcoma, malignant lymphoma, AIDS encephalopathy, bacterial sepsis and the like.

The psychoneurotic diseases and the cerebral diseases include, for example, dementia such as Alzheimer's disease, Parkinson's disease, cerebral stroke, cerebral infarction, cerebral hemorrhage, epilepsy, schizophrenia, peripheral nervous disorder and the like.

The cardiovascular diseases include, for example, arteriosclerosis, ischemic reperfusion injury, hypertension, myocardial infarction, angina pectoris, cardiac insufficiency and the like.

The metabolic diseases include, for example, diabetes, osteoporosis, prostatic hypertrophy, pollakiuia and the like.

The cancerous diseases include, for example, mammary cancer, malignant tumor such as malignant lymphoma, cancer metastasis, post-radiotherapy/chemotherapy bone marrow suppression or thrombocytopenia and the like.

BACKGROUND ART

In specification of WO01/14333, it is described that piperazine or piperidine derivatives of formula (A)

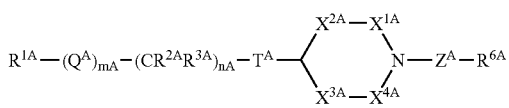

are chemokine receptor (specifically CCR1 or CCR3) regulator, and they are useful as treatment for inflammatory diseases, autoimmune diseases, gastrointestinal discomforts, HIV diseases and systemic diseases etc.

In specification of WO00/58305, it is described that 1,4-piperidine derivatives of formula (B)

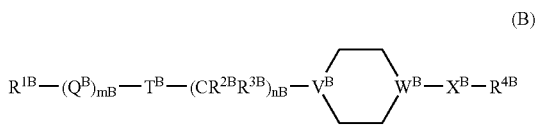

are useful for diseases related to chemokine receptor.

In specification of JP-A-6-192235, it is described that quinazoline derivatives of formula (C)

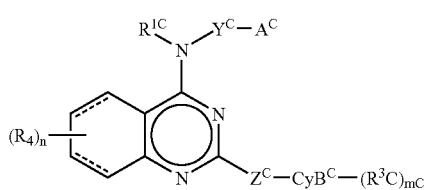

having an effect of inhibiting cGMP phosphodiesterase and TXA2.

In specification of U.S. Pat. No. 3,956,495, it is described that N-[4-(4-morpholinyl)-2-quinazolinyl]-1,2-ethanediamine dihydrochloride (CAS No. 59870-53-0), N,N-diethyl-N'-[2-(1-pyrrolidinyl)-4-quinazolinyl]-1,2-ethanediamine (CAS No. 59870-50-70) and N,N-diethyl-N'-[2-(1-pyrrolidinyl)-4-quinazolinyl]-1,2-ethanediamine dihydrochloride (CAS No. 59870-51-8) are having an effect of inhibiting platelet aggregation.

In specification of JP-A-3-14568, N,N-diethyl-N'-[2-(4-phenyl-1-piperidinyl)-4-pyrimidinyl]-1,2-ethylenediamine (CAS No. 131039-38-8) is described as nervous system drugs.

In specification of WO95/05383, N-[(3,4-dihydro-2H-1-benzopyran-2-yl)methyl]-N'-[2-(1-piperidinyl)-4-pyrimidinyl]-1,3-propanediamine oxalate (CAS No. 169747-23-3) is having an effect of vasoconstriction.

In specification of DE1794396, it is described that 7-[4-[4,6-bis(hexahydro-1H-azepin-1-yl)-1,3,5-triazin-2-yl]amino-2H-1,2,3-triazol-2-yl]-3-phenyl-2H-1-benzopyran-2-one (CAS No. 19695-38-6) is useful as fluorescent brightening agent.

In specification of JP-A-51-9759, N-[4-(hexahydro-1H-azepin-1-yl)thieno[3,2-d]pyrimidin-2-yl-1,4-butanediamine (CAS No.31895-98-4) is described.

Other than those above, N-[(3,4-dihydro-2H-1-benzopyran-2-yl)methyl]-N'-[2-(1-piperidinyl)-4-pyrimidinyl]-1,3-propanediamine (CAS No. 169747-22-2), 4-ethoxy-6-(hexahydro-1H-azepin-1-yl)-N-[3-(4-morpholinyl)propyl]-1,3,5-triazin-2-amine (CAS No. 295344-71-7), 4-(hexahydro-1H-azepin-1-yl)-6-methyl-N-[3-(4-morpholinyl)propyl]-1,3,5-triazin-2-amine (CAS No. 332167-02-9), 4-chloro-6-(hexahydro-1H)-azepin-1-yl)-N-[2-(4-morpholinyl)ethyl]-1,3,5-triazin-2-amine (CAS No. 337484-66-9), 4-(hexahydro-1H-azepin-1-yl)-6-methoxy-N-[3 -(4-morpholinyl)propyl-1,3,5-triazin-2-amine (CAS No. 384845-62-9) are known.

DISCLOSURE OF THE INVENTION

It is desired that safety CXCR4 regulators that are useful as preventives and/or treatments for various inflammatory diseases, various allergic diseases, acquired immunodeficiency syndrome, infection with human immunodeficiency virus, or agents for regeneration therapy are developed.

In order to find a compound binding CXCR4, the present inventors have conducted intensive studies and found that the compounds represented by formulae (I) and (II), salts thereof, N-oxides thereof or solvates thereof, or prodrugs of the same regulate CXCR4 and they are useful as preventing and/or treatment for various diseases, and thus the present invention has been accomplished.

The present invention relates to

[1] a compound represented by formula (I):

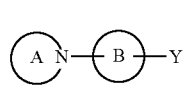

wherein ring A represents a nitrogen-containing heterocyclic group which may have a substituent(s); ring B represents a homocyclic group which may have a substituent(s) or a heterocyclic group which may have a substituent(s); and Y represents a hydrocarbon group which may have a substituent(s), a heterocyclic group which may have a substituent(s), an amino group which may be protected, a hydroxyl group which may be protected or a mercapto group which may be protected, a salt thereof, an N-oxide thereof, a solvate thereof, or a prodrug thereof,

[2] the compound according to the above-described [1], wherein ring A is a 5- to 10-membered nitrogen-containing heterocyclic group which may have a substituent(s),

[3] the compound according to the above-described [1], wherein ring B is a nitrogen-containing heterocyclic group which may have a substituent(s),

[4] the compound according to the above-described [1], wherein Y is

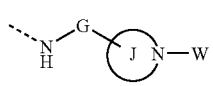

wherein G represents a bond or a spacer containing 1 to 3 atoms as a main chain; ring J represents a 4- to 7-membered nitrogen-containing heterocyclic group; and W represents hydrogen, a hydrocarbon group which may have a substituent(s) or a heterocyclic group which may have a substituent(s),

[5] the compound according to the above-described [1], which is represented by formula (I-1):

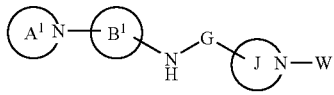 (I-1)

wherein ring $A^1$ represents a 5- to 10-membered nitrogen-containing saturated heterocyclic group which may have a substituent(s), or a 5- to 10-membered nitrogen-containing heterocyclic group which has one double bond and which may have a substituent(s); ring $B^1$ represents a 6- to 11-membered nitrogen-containing monocyclic or bicyclic heterocyclic group which may have a substituent(s); and other symbols have the same meanings as those described in the above-described [4],

[6] the compound according to the above-described [1], which is represented by formula (I-2):

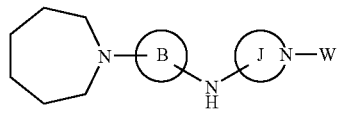 (I-2)

wherein all symbols have the same meanings as those described in the above-described [1] or [4],

[7] a compound represented by formula (I-A):

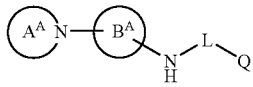 (I-A)

wherein ring $A^A$ represents a 4- to 15-membered monocyclic, bicyclic or tricyclic heterocyclic group which is saturated or has one double bond and which contains at least one nitrogen atom and may further contain 1 to 3 nitrogen atoms, 1 or 2 oxygen atoms and/or one sulfur atom;

ring $B^A$ represents $B^{A1}$ or $B^{A2}$;

$B^{A1}$ represents:

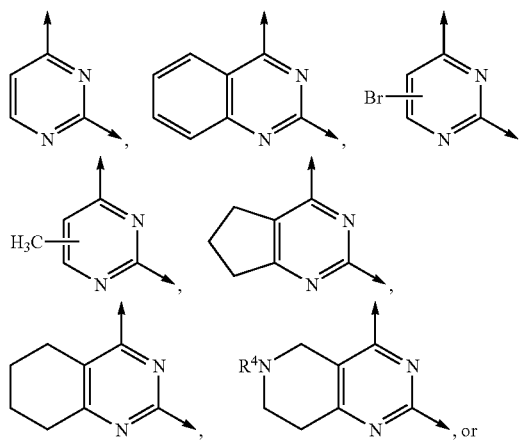

$B^{A2}$ represents:

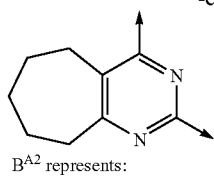

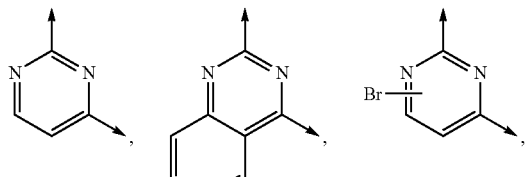

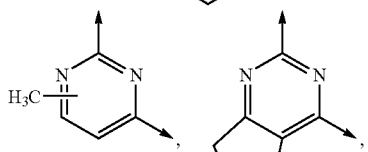

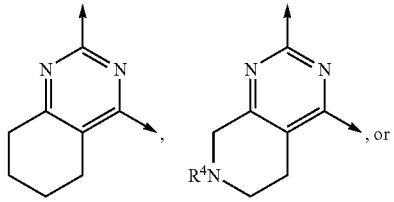

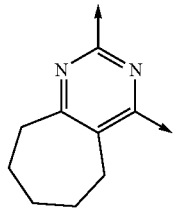

$R^4$ represents (i) hydrogen, (ii) C1-15 alkyl, C2-15 alkenyl or C2-15 alkynyl which may be substituted with 1 to 5 of $R^{10}$, (iii) a C3-8 carbocyclic group which may be substituted with 1 to 5 of $R^3$, (iv) a 5- to 15-membered heterocyclic group which contains 1 or 2 nitrogen atoms, 1 or 2 oxygen atoms and/or one sulfur atom and which may be substituted with 1 to 5 of $R^3$, (v) $COR^5$ wherein $R^5$ represents C1-15 alkyl, C2-15 alkenyl, C2-15 alkynyl or phenyl, or (vi) $COOR^6$ wherein $R^6$ represents C1-15 alkyl, C2-15 alkenyl, C2-15 alkynyl or phenyl; the upward arrow represents a binding position to ring $A^A$; and the right-downward arrow represents a binding position to the nitrogen atom bound to L;

L represents (1) a bond, (2) C1-8 alkylene, C2-8 alkenylene or C2-8 alkynylene, wherein the alkylene, alkenylene and alkynylene each may be substituted with 1 to 5 of $R^{10}$, or (3) a C3-8 carbocyclic group which may be substituted with $R^3$;

Q represents (1) $NR^1R^2$ wherein $R^1$ and $R^2$ each independently represents (i) hydrogen, (ii) C1-15 alkyl, C2-15 alkenyl or C2-15 alkynyl which may be substituted with 1 to 5 of $R^{10}$, (iii) a C3-8 carbocyclic group which may be substituted with 1 to 5 of $R^3$, or (iv) a 5- to 15-membered heterocyclic group which contains 1 or 2 nitrogen atoms, 1 or 2 oxygen atoms and/or one sulfur atom and which may be substituted 1 to 5 of $R^3$, or (2) ring C;

ring C represents a 4- to 15-membered heterocyclic group which contains at least one nitrogen atom and may further contain 1 or 2 nitrogen atoms, 1 or 2 oxygen atoms and/or one sulfur atom and which may be substituted with 1 to 5 of $R^3$;

plural $R^3$'s each independently represents (1) C1-15 alkyl, C2-15 alkenyl or C2-15 alkynyl, wherein the alkyl, alkenyl and alkynyl may be substituted with 1 to 5 of $R^{10}$, (2) oxo, or (3)$R^{10}$;

plural $R^{10}$'s each independently represents (1) $OR^{11}$, (2) $OCOR^{12}$, (3) $OCOOR^{13}$, (4) $NR^{14}R^{15}$, (5) $NR^{16}COR^{12}$, (6) $NR^{16}CONR^{14}R^{15}$, (7) $NR^{16}COOR^{13}$, (8) $COOR^{13}$, (9) $COR^{12}$, (10) $CONR^{14}R^{15}$, (11) $SO_2R^{12}$, (12) $SOR^{22}$, (13) $SO_2NR^{24}R^{25}$, (14) $NR^{16}SO_2R^{12}$, (15) $B(OH)_2$, (16) $SR^{11}$, (17) halogen, (18) nitro, (19) cyano, or (20) ring D;

$R^{11}$ represents (i) hydrogen, (ii) C1-15 alkyl, C2-15 alkenyl or C2-15 alkynyl, wherein the alkyl, alkenyl and alkynyl may be substituted with 1 to 5 of halogen, $NR^{14}R^{15}$, $OR^{21}$, $SR^{21}$, $COOR^{13}$, or ring D, or (iii) ring D;

$R^{12}$, $R^{13}$, $R^{14}$, $R^{15}$ and $R^{16}$ each independently represents (i) hydrogen, (ii) C1-15 alkyl, C2-15 alkenyl or C2-15 alkynyl which may be substituted with ring D, or (iii) ring D;

ring D represents a C3-15 monocyclic, bicyclic or tricyclic carbocyclic group, or a 5- to 15-membered monocyclic, bicyclic or tricyclic heterocyclic group which contains 1 to 4 nitrogen atoms, 1 or 2 oxygen atoms and/or one sulfur atom; and ring D may be substituted with 1 to 5 of the groups selected from the following (1) to (22):

(1) C1-15 alkyl, C2-15 alkenyl or C2-15 alkynyl, wherein the alkyl, alkenyl or alkynyl may be substituted with 1 to 5 of $OR^{21}$, $OCOR^{22}$, $OCOOR^{23}$, $NR^{24}R^{25}$, $NR^{26}COR^{22}$, $NR^{26}CONR^{24}R^{25}$, $NR^{26}COOR^{23}$, $COOR^{23}$, $COR^{22}$, $CONR^{24}R^{25}$, $SO_2R^{22}$, $SOR^{22}$, $SO_2NR^{24}R^{25}$, $NR^{26}SO_2R^{22}$, $B(OH)_2$, $SR^{21}$, halogen, nitro or cyano, (2) oxo, (3) $OR^{21}$, (4) $OCOR^{22}$, (5) $OCOOR^{23}$, (6) $NR^{24}R^{25}$, (7) $NR^{26}COR^{22}$, (8) $NR^{26}CONR^{24}R^{25}$, (9) $NR^{26}COOR^{23}$, (10) $COOR^{23}$, (11) $COR^{22}$, (12) $CONR^{24}R^{25}$, (13) $SO_2R^{22}$, (14) $SOR^{22}$, (15) $SO_2NR^{24}R^{25}$, (16) $NR^{26}SO_2R^{22}$, (17) $B(OH)_2$, (18) $SR^{21}$, (19) halogen, (20) nitro, (21) cyano or (22) ring E;

$R^{21}$ represents (i) hydrogen, (ii) C1-15 alkyl, C2-15 alkenyl or C2-15 alkynyl which may be substituted with $COR^{22}$, $NR^{24}R^{25}$ or ring E, or (iii) ring E;

$R^{22}$, $R^{23}$, $R^{24}$, $R^{25}$ and $R^{26}$ each independently represents (i) hydrogen, (ii) C1-15 alkyl, C2-15 alkenyl or C2-15 alkynyl which may be substituted with ring E, or (iii) ring E;

ring E represents a C3-15 monocyclic, bicyclic or tricyclic carbocyclic group, or a 5- to 15-membered monocyclic, bicyclic or tricyclic heterocyclic group which contains 1 to 4 nitrogen atoms, 1 or 2 oxygen atoms and/or one sulfur atom, and ring E may be substituted with 1 to 5 of (i) C1-15 alkyl which may be substituted with phenyl, (ii) halogen, (iii) phenyl, (iv) C1-15 alkoxy, (v) hydroxyl, (vi) amino, (vii) mono (C1-8 alkyl)amino, or (viii) di(C1-8 alkyl)amino;

ring $A^A$ may be substituted with 1-5 of $R^a$;
ring $B^A$ may be substituted with 1-5 of $R^b$;
$R^a$ and $R^b$ each independently represents a group which has the same meaning as the group represented by $R^3$; and wherein the following compounds (1) to (6) are excluded:
(1) N-[4-(4-morpholinyl)-2-quinazolinyl]-1,2-ethanediamine dihydrochloride,
(2) N,N-dimethyl-N'-[2-(4-phenyl-1-piperidinyl)-4-pyrimidinyl]-1,2-ethylenediamine,
(3) N-[(3,4-dihydro-2H-1-benzopyran-2-yl)methyl]-N'-[2-(1-piperidinyl)-4-pyrimidinyl]-1,3-propanediamine,
(4) N-[(3,4-dihydro-2H-1-benzopyrane-2-yl)methyl]-N'-[2-(1-piperidinyl)-4-pyrimidinyl]-1,3-propanediamine oxalate,
(5) N,N-diethyl-N'-[2-(1-pyrrolidinyl)-4-quinazolinyl-1,2-ethanediamine, and
(6) N,N-diethyl-N'-[2-(1-pyrrolidinyl)-4-quinazolinyl-1,2-ethanediamine dihydrochloride, a salt thereof, an N-oxide thereof, a solvate thereof, or a prodrug thereof,

[8] a compound represented by formula (I-B):

(I-B)

wherein ring $A^B$ represents a 7- to 15-membered monocyclic, bicyclic or tricyclic heterocyclic group which is saturated or contains one double bond and which contains at least one nitrogen atom and may further contain 1 to 3 nitrogen atoms, 1 or 2 oxygen atoms and/or one sulfur atom;

ring $B^B$ represents:

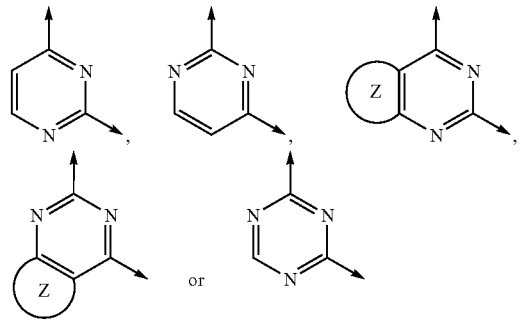

wherein ring Z represents a C5-10 monocyclic or bicyclic carbocyclic group, or a 5- to 10-membered monocyclic or bicyclic heterocyclic group which may contain 1 or 2 nitrogen atoms, one oxygen atom and/or one sulfur atom; the upward arrow represents a binding position to ring $A^B$; and the right-downward arrow represents a binding position to the nitrogen atom bound to L;

ring $A^B$ may be substituted with 1 to 5 of $R^a$; ring $B^B$ may be substituted with 1 to 5 of $R^b$; and $R^a$, $R^b$ and other symbols have the same meanings as those described in the above-described [7], and wherein the following compounds (1) to (7) are excluded:
(1) N-[4-(hexahydro-1H-azepin-1-yl)thieno[3,2-d]pyrimidin-2-yl]-1,4-butandiamine dihydrochloride,
(2) 7-[4-[4,6-bis(hexahydro-1H-azepin-1-yl)-1,3,5-triazin-2-yl]amino-2H-1,2,3-triazol-2-yl]-3-phenyl-2H-1-benzopyran-2-one,
(3) 4-ethoxy-6-(hexahydro-1H-azepin-1-yl)-N-[3-(4-morpholinyl)propyl]-1,3,5-triazin-2-amine,
(4) 4-(hexahydro-1H-azepin-1-yl)-6-methyl-N-[3-(4-morphblinyl)propyl]-1,3,5-triazin-2-amine,
(5) 4-chloro-6-(hexahydro-1H)-azepin-1-yl)-N-[2-(4-morpholinyl)ethyl]-1,3,5-triazin-2-amine,
(6) 4-(hexahydro-1H-azepin-1-yl)-6-methoxy-N-[3-(4-morpholinyl)propyl-1,3,5-triazin-2-amine, and
(7) N-[4-(hexahydro-1H-azepin-1-yl)thieno[3,2-d]pyrimidin-2-yl-1,4-butanediamine, or a salt thereof, an N-oxide thereof, a solvate thereof, or a prodrug thereof,

[9] the compound according to any one of the above-described [1], [7] and [8], which is (1) N-(4-azepan-1-ylpyrimidin-2-yl)ethane-1,2-diamine,
(2) N'-(4-azepan-1-ylpyrimidin-2-yl)-N²,N²-dimethyl-ethane-1,2-diamine,
(3) 4-azepan-1-yl-N-((3S)-1-cyclohexylpyrrolidin-3-yl)pyrimidin-2-amine,
(4) 4-azepan-1-yl-N-((3S)-1-benzylpyrrolidin-3-yl)pyrimidin-2-amine,
(5) 4-azepan-1-yl-N-((3S)-1-(2-ethylbutyl)piperidin-3-yl)pyrimidin-2-amine,
(6) 4-azepan-1-yl-N-[(3S)-1-cyclohexylpiperidin-3-yl]pyrimidin-2-amine,
(7) 4-azepan-1-yl-N-[(3S)-1-tetrahydro-2H-pyran-4-ylpiperidin-3-yl]pyrimidin-2-amine,
(8) 4-(3S)-3-[(4-azepan-1-ylpyrimidin-2-yk)amino]piperidin-1-ylcyclohexanol, or
(9) (3S)-N-(4-azepan-1-ylpyrimidin-2-yl)-1'-(cyclohexylcarbonyl)-1,4'-bipiperidin-3-amine,

[10] a pharmaceutical composition, which comprises a compound represented by formula (I):

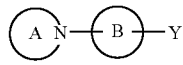

(I)

wherein all symbols have the same meanings as those described in the above-described [1], a salt thereof, an N-oxide thereof, a solvate thereof, or a prodrug thereof,

[11] the pharmaceutical composition according to the above-described [10], which is a CXCR4 regulating agent,

[12] the pharmaceutical composition according to the above-described [11], wherein the CXCR4 regulating agent is a CXCR4 antagonist,

[13] the pharmaceutical composition according to the above-described [12], which is a preventive and/or therapeutic agent for human immunodeficiency virus infection,

[14] the pharmaceutical composition according to the above-described [13], which is a preventive and/or therapeutic agent for acquired immunodeficiency syndrome,

[15] the pharmaceutical composition according to the above-described [10], which is an agent for regeneration medicine,

[16] the pharmaceutical composition according to the above-described [15], wherein the agent for regeneration medicine is an agent for transplantation medicine,

[17] a CXCR4 regulating agent, which comprises a compound represented by formula (II):

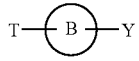

(II)

wherein T represents

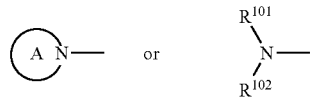

wherein $R^{101}$ and $R^{102}$ each independently represents hydrogen or a hydrocarbon group which may have a substituent(s); ring A has the same meaning as that described in the above-described [1]; and other symbols have the same meanings as those described in the above-described [1], a salt thereof, an N-oxide thereof, a solvate thereof, or a prodrug thereof, as an active ingredient,

[18] the agent according to the above-described [17], wherein the CXCR4 regulating agent is a CXCR4 antagonist,

[19] a CXCR4 regulating agent, which comprises a compound represented by formula (I-3):

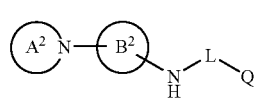

(I-3)

wherein ring $A^2$ represents a 4- to 15-membered monocyclic, bicyclic or tricyclic heterocyclic group which contains at least one nitrogen atom and may further contain 1 to 3 nitrogen atoms, 1 or 2 oxygen atoms and/or one sulfur atom; ring $B^2$ represents a 5- to 15-membered monocyclic, bicyclic or tricyclic heterocyclic group which contains at least one nitrogen atom and may further contain 1 to 3 nitrogen atoms, 1 or 2 oxygen atoms and/or one sulfur atom; ring $A^2$ may be substituted with 1 to 5 of $R^a$; ring $B^2$ may be substituted with 1 to 5 of $R^b$; and $R^a$, $R^b$ and other symbols have the same meanings as those described in the above-described [7], a salt thereof, an N-oxide thereof, a solvate thereof, or a prodrug thereof, as an active ingredient,

[20] the CXCR4 regulating agent according to the above-described [19], which is a CXCR4 antagonist,

[21] a CXCR4 regulating agent, which comprises the compound represented by formula (I-A) according to the above-described [7], a salt thereof, an N-oxide thereof, a solvate thereof, or a prodrug thereof, as an active ingredient,

[22] the CXCR4 regulating agent according to the above-described [21], which is a CXCR4 antagonist,

[23] a CXCR4 regulating agent, which comprises the compound represented by formula (I-B) according to the above-described [8], a salt thereof, an N-oxide thereof, a solvate thereof, or a prodrug thereof, as an active ingredient,

[24] the CXCR4 regulating agent according to the above-described [23], which is a CXCR4 antagonist,

[25] the CXCR4 regulating agent according to the above-described [17] or [19], which is a preventive and/or therapeutic agent for inflammatory/immune diseases, allergic diseases, infectious diseases, HIV infection or diseases accompanied therewith, psychoneurotic diseases, cerebral diseases, cardiovascular diseases, metabolic diseases and cancerous diseases,

[26] the CXCR4 regulating agent according to the above-described [25], which is a preventive and/or therapeutic agent for HIV infection or diseases accompanied therewith,

[27] the CXCR4 regulating agent according to the above-described [17] or [19], which is useful for regeneration medicine,

[28] a medicament which comprises the compound according to any one of the above-described [1], [7], [8] and [17], a salt thereof, an N-oxide thereof, a solvate thereof, or a prodrug thereof, in combination with one or at least two of a reverse transferase inhibitor, a protease inhibitor, a CCR2 antagonist, a CCR3 antagonist, a CCR4 antagonist, a CCR5 antagonist, a fusion inhibitor, an antibody against a surface antigen of HIV-1, and a vaccine of HIV-1,

[29] the medicament according to the above-described [28], wherein the reverse transferase inhibitor is one or at least two selected from zidovudine, didanosine, zalcitabine, stavudine, lamivudine, abacavir, adefovir, dipivoxil, emtricitabine, tenofovir, nevirapine, nevirapine, efavirenz and capravirine,

[30] the medicament according to the above-described [28], wherein the protease inhibitor is one or at least two selected from indinavir, ritonavir, nelfinavir, saquinavir, amprenavir, lopinavir and lopinavir,

[31] a method for antagonizing CXCR4 in a mammal, which comprises administering to a mammal an effective amount of a compound represented by formula (II):

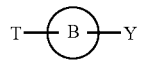

(II)

wherein all symbols have the same meanings as those described in the above-described [1] or [17], a salt thereof, an N-oxide thereof, a solvate thereof, or a prodrug thereof,

[32] use of a compound represented by formula (II):

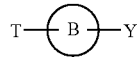

(II)

wherein all symbols have the same meanings as described in the above-described [1] or [17], a salt thereof, an N-oxide thereof, a solvate thereof, or a prodrug thereof for the manufacture of a CXCR4 antagonist.

DETAILED DESCRIPTION

The "nitrogen-containing heterocycle" in the "nitrogen-containing heterocyclic group which may have a substituent(s)" represented by ring A in the compound represented by formula (I) according to the present invention refers to a monocyclic, bicyclic or tricyclic heterocycle which may contain, in addition to the nitrogen atom indicated in ring A in formula (I), 1 to 6 hetero atoms selected from nitrogen, oxygen and sulfur atoms. The "nitrogen-containing heterocycle" includes, for example, a "3- to 15-membered nitrogen-containing unsaturated monocyclic, bicyclic or tricyclic heterocycle", "3- to 15-membered nitrogen-containing saturated monocyclic, bicyclic or tricyclic heterocycle" and the like.

The "3- to 15-membered nitrogen-containing unsaturated monocyclic, bicyclic or tricyclic heterocycle" includes, for example, pyrrole, imidazole, triazole, tetrazole, pyrazole, azepine, diazepine, indole, isoindole, indazole, purine, benzimidazole, benzazepine, benzodiazepine, benzotriazole, carbazole, beta-carboline, phenothiazine, phenoxazine, perimidine, pyrroline, imidazoline, triazoline, tetrazoline, pyrazoline, dihydropyridine, tetrahydropyridine, dihydropyrazine, tetrahydropyrazine, dihydropyrimidine, tetrahydropyrimidine, dihydropyridazine, tetrahydropyridazine, dihydroazepine, tetrahydroazepine, dihydrodiazepine, tetrahydrodiazepine, dihydrooxazole, dihydroisoxazole, dihydrothiazole, dihydroisothiazole, dihydrofurazan, dihydrooxadiazole, dihydrooxazine, dihydrooxadiazine, dihydrooxazepine, tetrahydrooxazepine, dihydrooxadiazepine, tetrahydrooxadiazepine, dihydrothiadiazole, dihydrothiazine, dihydrothiadiazine, dihydrothiazepine, dihydrothiadiazepine, tetrahydrothiadiazepine, indoline, isoindoline, dihydroindazole, dihydroquinoline, tetrahydroquinoline, dihydroisoquinoline, tetrahydroisoquinoline, dihydrophthalazine, tetrahydrophthalazine, dihydronaphthyridine, tetrahydronaphthyridine, dihydroquinoxaline, tetrahydroquinoxaline, dihydroquinazoline, tetrahydroquinazoline, dihydrocinnoline, tetrahydrocinnoline, dihydrobenzoxazine, dihydrobenzothiazine, pyrazinomorpholine, dihydrobenzoxazole, dihydrobenzothiazole, dihydrobenzimidazole, dihydrobenzazepine, tetrahydrobenzazepine, dihydrobenzodiazepine, tetrahydrobenzodiazepine, dihydrobenzoxazepine, tetrahydrobenzoxazepine, dihydrocarbazole, tetrahydrocarbazole, dihydroacridine, tetrahydroacridine, hexahydroazocine, hexahydroazonine, hexahydrodiazocine, hexahydrodiazonine, octahydroazecine, octahydrodiazecine ring etc.

The "3- to 15-membered nitrogen-containing saturated monocyclic, bicyclic or tricyclic heterocycle" includes, for example, aziridine, azetidine, pyrrolidine, imidazolidine, triazolidine, tetrazolidine, pyrazolidine, piperidine, piperazine, perhydropyrimidine, perhydropyridazine, perhydroazepine, perhydrodiazepine, perhydroazocine, tetrahydrooxazole (oxazolidine), tetrahydroisoxazole (isoxazolidine), tetrahydrothiazole (thiazolidine), tetrahydroisothiazole (isothiazolidine), tetrahydrofurazan, tetrahydrooxadiazole (oxadiazolidine), tetrahydrooxazine, tetrahydrooxadiazine, perhydrooxazepine, perhydrooxadiazepine, tetrahydrothiadiazole (thiadiazolidine), tetrahydrothiazine, tetrahydrothiadiazine, tetrahydrothiazepine, perhydrothiazepine, perhydrothiadiazepine, morpholine, thiomorpholine, perhydroindazole, perhydroquinoline, perhydroisoquinoline, perhydrophthalazine, perhydronaphthyridine, perhydroquinoxaline, perhydroquinazoline, perhydrocinnoline, perhydrobenzoxazole, perhydrobenzothiazole, perhydrobenzimidazole, perhydrocarbazole, perhydroacridine, perhydroazonine, perhydroazecine, azaundecane, azadodecane, azatridecane, azatetradecane, azapentadecane, perhydrodiazocine, perhydrodiazonine, perhydrodiazecine, diazaundecane, diazadodecane, diazatridecane, diazatetradecane, diazapentadecane, perhydroindole, perhydroisoindole, perhydro-beta-carboline, perhydrophenazine, perhydrophenothiadine, perhydrophenoxadine, perhydrophenanthridine, perhydrophenanthroline, perhydroperimidine, azabicyclo[3.2.2]nonane, azabicyclo[3.3.2]decane, azabicyclo[2.2.2]octane, azabicyclo[3.3.3]undecane, azabicyclo[4.3.3]dodecane, azabicyclo[4.4.3]tridecane, azabicyclo[4.4.4]tetradecane etc.

The "Nitrogen-containing heterocycle" represented by ring A is preferably "5- to 10-membered nitrogen-containing heterocycle". Concretely, "5- to 10-membered nitrogen-containing unsaturated heterocycle" includes, for example, pyrrole, imidazole, triazole, tetrazole, pyrazole, azepine, diazepine, indole, isoindole, indazole, purine, benzimidazole, benzotriazole, pyrroline, imidazoline, triazoline, tetrazoline, pyrazoline, dihydropyridine, tetrahydropyridine, dihydropyrazine, tetrahydropyrazine, dihydropyrimidine, tetrahydropyrimidine, dihydrbpyridazine, tetrahydropyridazine, dihydroazepine, tetrahydroazepine, dihydrodiazepine, tetrahydrodiazepine, dihydrooxazole, dihydroisoxazole, dihydrothiazole, dihydroisothiazole, dihydrofurazan, dihydrooxadiazole, dihydrooxazine, dihydrooxadiazine, dihydrooxazepine, tetrahydrooxazepine, dihydrooxadiazepine, tetrahydrooxadiazepine, dihydrothiadiazole, dihydrothiazine, dihydrothiadiazine, dihydrothiazepine, tetrahydrothiazepine, dihydrothiadiazepine, tetrahydrothiadiazepine, indoline, isoindoline, dihydroindazole, dihydroquinoline, tetrahydroquinoline, dihydroisoquinoline, tetrahydroisoquinoline, dihydrophthalazine, tetrahydrophthalazine, dihydronaphthyridine, tetrahydronaphthyridine, dihydroquinoxaline, tetrahydroquinoxaline, dihydroquinazoline, tetrahydroquinazoline, dihydrocinnoline, tetrahydrocinnoline, dihydrobenzoxazine, dihydrobenzothiazine, pyrazinomorpholine, dihydrobenzoxazole, dihydrobenzothiazole, dihydrobenzimidazole, hexahydroazocine, hexahydroazonine, hexahydrodiazocine, hexahydrodiazonine, octahydroazecine, octahydrodiazecine ring etc.

The "5- to 10-membered nitrogen-containing saturated heterocycle" includes, for example, pyrrolidine, imidazolidine, triazolidine, tetrazolidine, pyrazolidine, piperidine, piperazine, perhydropyrimidine, perhydropyridazine, perhydroazepine, perhydrodiazepine, perhydroazocine, tetrahydrooxazole (oxazolidine), tetrahydroisoxazole (isoxazolidine), tetrahydrothiazole (thiazolidine), tetrahydroisothiazole (isothiazolidine), tetrahydrofurazan, tetrahydrooxadiazole (oxadiazolidine), tetrahydrooxazine, tetrahydrooxadiazine, perhydrooxazepine, perhydrooxadiazepine, tetrahydrothiadiazole (thiadiazolidine), tetrahydrothiazine, tetrahydrothiadiazine, perhydrothiazepine, perhydrothiadiazepine, morpholine, thiomorpholine, perhydroindazole, perhydroquinoline, perhydroisoquinoline, perhydrophthalazine, perhydronaphthyridine, perhydroquinoxaline, perhydroquinazoline, perhydrocinnoline, perhydrobenzoxazole, perhydrobenzothiazole, perhydrobenzimidazole, perhydroazonine, perhydroazecine, perhydrodiazocine, perhydrodiazonine, perhydrodiazecine, perhydroindole, perhydroisoindole, azabicyclo[3.2.2]nonane, azabicyclo[3.3.2]decane, azabicyclo[2.2.2]octane etc.

More preferably, ring A is perhydroazepine, perhydroazocine, piperidine,

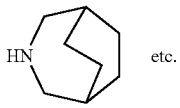 etc.

Ring A may be substituted with 1 to 5 of $R^a$ ($R^a$ has the same meaning as $R^3$ which has the same meanings as described above.).

The "Homocycle" in the "homocyclic group which may have a substituent(s)" represented by ring B includes, for example, a "cyclic hydrocarbon" etc. The "cyclic hydrocarbon" includes, for example, "unsaturated cyclic hydrocarbon" or "saturated cyclic hydrocarbon". The "saturated cyclic hydrocarbon" includes, for example, "3- to 15-membered saturated cyclic hydrocarbon" such as cycloalkane which includes cyclopropane, cyclobutane, cyclopentane, cyclohexane, cycloheptane, cyclooctane, cyclononane, cyclodecane, cycloundecane, cyclododecane, cyclotridecane, cyclotetradecane or cyclopentadecane etc; perhydropentalene; perhydroazulene; perhydroindene; perhydronaphthalene; perhydroheptalene; spiro[4.4]nonane; spiro[4.5]decane; spiro[5.5]undecane; bicyclo[2.2.1]heptane; bicyclo[3.1.1]heptane; bicyclo[2.2.2]octane; adamantane; noradamantane etc. The "unsaturated cyclic hydrocarbon" includes, for example, "3- to 15-membered unsaturated cyclic hydrocarbon" such as cycloalkene which is cyclopentene, cyclohexene, cycloheptene, cyclooctene, cyclopentadiene, cyclohexadiene, cycloheptadiene or cyclooctadiene etc; benzene; pentalene; azulene; indene; indan; naphthalene; dihydronaphthalene; tetrahydronaphthalene; heptalene; biphenylene; as-indacene; s-indacene; acenaphthene; acenaphthylene; fluorene; phenalene; phenanthrene; anthracene; bicyclo[2.2.1]hept-2-ene; bicyclo[3.1.1]hept-2-ene; bicyclo[2.2.2]oct-2-ene etc.

The "heterocycle" in The "heterocyclic group which may have a substituent(s)" represented by ring B refers to a monocyclic, bicyclic or tricyclic heterocycle which may contain 1 to 7 hetero atoms selected from nitrogen, oxygen and sulfur atoms. The "heterocycle" includes, for example, a "3- to 15-membered unsaturated monocyclic, bicyclic or tricyclic heterocycle", a "3- to 15-membered saturated monocyclic, bicyclic or tricyclic heterocycle" and the like.

The "3- to 15-membered unsaturated monocyclic, bicyclic or tricyclic heterocycle" includes, for example, pyrrole, imidazole, triazole, tetrazole, pyrazole, pyridine, pyrazine, pyrimidine, pyridazine, triazine, azepine, diazepine, furan, pyran, oxepine, thiophene, thiopyran, thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, benzoxazole, benzothiazole, benzimidazole, chromene, benzoxepine, benzoxazepine, benzoxadiazepine, benzothiepine, benzothiazepine, benzothiadiazepine, benzazepine, benzodiazepine, benzofurazan, benzothiadiazole, benzotriazole, carbazole, beta-carboline, acridine, phenazine, dibenzofuran, xanthene, dibenzothiophene, phenothiazine, phenoxazine, phenoxathiin, thianthrene, phenanthridine, phenanthroline, perimidine, pyrroline, imidazoline, triazoline, tetrazoline, pyrazoline, dihydropyridine, tetrahydropyridine, dihydropyrazine, tetrahydropyrazine, dihydropyrimidine, tetrahydropyrimidine, dihydropyridazine, tetrahydropyridazine, tetrahydrotriazine, dihydroazepine, tetrahydroazepine, dihydrodiazepine, tetrahydrodiazepine, dihydrofuran, dihydropyran, dihydrooxepine, tetrahydrooxepine, dihydrothiophene, dihydrothiopyran, dihydrothiepine, tetrahydrothiepine, dihydrooxazole, dihydroisoxazole, dihydrothiazole, dihydroisothiazole, dihydrofurazan, dihydrooxadiazole, dihydrooxazine, dihydrooxadiazine, dihydrooxazepine, tetrahydrooxazepine, tetrahydrooxadiazepine, dihydrothiadiazole, dihydrothiazine, dihydrothiadiazine, dihydrothiazepine, tetrahydrothiazepine, dihydrothiadiazepine, tetrahydrothiadiazepine, indoline, isoindoline, dihydrobenzofuran, dihydroisobenzofuran, dihydrobenzothiophene, dihydroisobenzothiophene, dihydroindazole, dihydroquinoline, tetrahydroquinoline, dihydroisoquinoline, tetrahydroisoquinoline, dihydrophthalazine, tetrahydrophthalazine, dihydronaphthyridine, tetrahydronaphthyridine, dihydroquinoxaline, tetrahydroquinoxaline, dihydroquinazoline, tetrahydroquinazoline, dihydrocinnoline, tetrahydrocinnoline, benzoxathiane, dihydrobenzoxazine, dihydrobenzothiazine, pyrazinomorpholine, dihydrobenzoxazole, dihydrobenzothiazole, dihydrobenzimidazole, dihydrobenzazepine, tetrahydrobenzazepine, dihydrobenzodiazepine, tetrahydrobenzodiazepine, benzodioxepane, dihydrobenzoxazepine, tetrahydrobenzoxazepine, dihydrocarbazole, tetrahydrocarbazole, dihydro-beta-carboline, tetrahydro-beta-carboline, dihydroacridine, tetrahydroacridine, dihydrodibenzofuran, dihydrodibenzothiophene, tetrahydrodibenzofuran, tetrahydrodibenzothiophene, dioxaindan, benzodioxane, chroman, benzodithiolane, benzodithiane, 6,7,8,9-tetrahydro-5H-pyrido[4',3':4,5]pyrrolo[2,3-b]pyridine, 2,3,4,5-tetrahydro-1H-pyrido[4,3-b]indole, 6,7,8,9-tetrahydro-5H-pyrido[3',4':4,5]pyrrolo[2,3-b]pyridine,

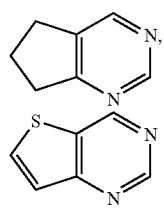 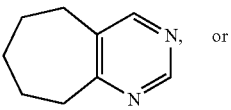 etc.

"3- to 15-membered saturated monocyclic, bicyclic or tricyclic heterocycle" includes, for example, aziridine, azetidine, pyrrolidine, imidazolidine, triazolidine, tetrazolidine, pyrazolidine, piperidine, piperazine, perhydropyrimidine, perhydropyridazine, perhydroazepine, perhydrodiazepine, perhydroazocine, oxirane, oxetane, tetrahydrofuran, tetrahydropyran, perhydrooxepine, thiirane, thietane, tetrahydrothiophene, tetrahydrothiopyran, perhydrothiepine, tetrahydrooxazole (oxazolidine), tetrahydroisoxazole (isoxazolidine), tetrahydrothiazole (thiazolidine), tetrahydroisothiazole (isothiazolidine), tetrahydrofurazan, tetrahydrooxadiazole (oxadiazolidine), tetrahydrooxazine, tetrahydrooxadiazine, perhydrooxazepine, perhydrooxadiazepine, tetrahydrothiadiazole (thiadiazolidine), tetrahydrothiazine, tetrahydrothiadiazine, perhydrothiazepine, perhydrothiadiazepine, morpholine, thiomorpholine, oxathiane, perhydrobenzofuran, perhydroisobenzofuran, perhydrobenzothiophene, perhydroisobenzothiophene, perhydroindazole, perhydroquinoline, perhydroisoquinoline, perhydrophthalazine, perhydronaphthyridine, perhydroquinoxaline, perhydroquinazoline, perhydrocinnoline, perhydrobenzoxazole, perhydrobenzothiazole, perhydrobenzimidazole, perhydrocarbazole, perhydro-beta-carboline, perhydroacridine, perhydrodibenzofuran, perhydrodibenzothiophene, dioxolane, dioxane, dithiolane, dithiane etc.

Ring B is preferably a "nitrogen-containing heterocycle which may have a substituent(s)". The "nitrogen-containing heterocycle" represents a monocyclic, bicyclic or tricyclic heterocycle which contains at least one nitrogen atom and may further contain 1 to 3 hetero atoms selected from nitrogen, oxygen and sulfur atoms. The "nitrogen-containing heterocyclic ring" includes, for example, a "5- to 15-membered nitrogen-containing unsaturated monocyclic, bicyclic or tricyclic heterocycle" or a "5- to 15-membered nitrogen-containing saturated monocyclic, bicyclic or tricyclic heterocycle" etc. The "5- to 15-membered nitrogen-containing unsaturated monocyclic, bicyclic or tricyclic heterocycle" includes, for example, pyrrole, imidazole, triazole, tetrazole, pyrazole, pyridine, pyrazine, pyrimidine, pyridazine, triazine, azepine, diazepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, indolizine, indazole, quinoline, isoquinoline, quinolizine, purine, phthalazine, pteridine, naphthyridine, quinoxaline, quinazoline, cinnoline, benzoxazole, benzothiazole, benzimidazole, benzoxazepine, benzoxadiazepine, benzothiazepine, benzothiadiazepine, benzazepine, benzodiazepine, benzofurazan, benzothiadiazole, benzotriazole, carbazole, beta-carboline, acridine, phenazine, phenothiazine, phenoxazine, phenanthridine, phenanthroline, perimidine, pyrroline, imidazoline, triazoline, tetrazoline, pyrazoline, dihydropyridine, tetrahydropyridine, dihydropyrazine, tetrahydropyrazine, dihydropyrimidine, tetrahydropyrimidine, dihydropyridazine, tetrahydropyridazine, tetrahydrotriazine, dihydroazepine, tetrahydroazepine, dihydrodiazepine, tetrahydrodiazepine, dihydrooxazole, dihydroisoxazole, dihydrothiazole, dihydroisothiazole, dihydrofurazan, dihydrooxadiazole, dihydrooxazine, dihydrooxadiazine, dihydrooxazepine, tetrahydrooxazepine, dihydrooxadiazepine, tetrahydrooxadiazepine, dihydrothiadiazole, dihydrothiazine, dihydrothiadiazine, dihydrothiazepine, tetrahydrothiazepine, dihydrothiadiazepine, tetrahydrothiadiazepine, indoline, isoindoline, dihydroindazole, dihydroquinoline, tetrahydroquinoline, dihydroisoquinoline, tetrahydroisoquinoline, dihydrophthalazine, tetrahydrophthalazine, dihydronaphthyridine, tetrahydronaphthyridine, dihydroquinoxaline, tetrahydroquinoxaline, dihydroquinazoline, tetrahydroquinazoline, dihydrocinnoline, tetrahydrocinnoline, dihydrobenzoxazine, dihydrobenzothiazine, pyrazinomorpholine, dihydrobenzoxazole, dihydrobenzothiazole, dihydrobenzimidazole, dihydrobenzazepine, tetrahydrobenzazepine, dihydrobenzodiazepine, tetrahydrobenzodiazepine; dihydrobenzoxazepine, tetrahydrobenzoxazepine, dihydrocarbazole, tetrahydrocarbazole, dihydro-beta-carboline, tetrahydro-beta-carboline, dihydroacridine, tetrahydroacridine,

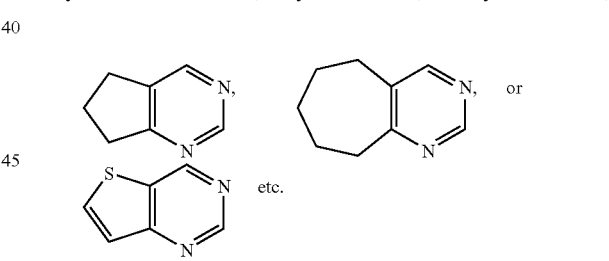 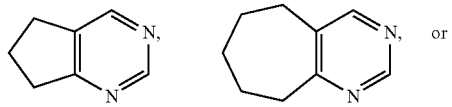 etc.

The "5- to 15-membered nitrogen-containing saturated monocyclic, bicyclic or tricyclic heterocycle" includes, for example, pyrrolidine, imidazolidine, triazolidine, tetrazolidine, pyrazolidine, piperidine, piperazine, perhydropyrimidine, perhydropyridazine, perhydroazepine, perhydrodiazepine, perhydroazocine, tetrahydrooxazole (oxazolidine), tetrahydroisoxazole (isoxazolidine), tetrahydrothiazole (thiazolidine), tetrahydroisothiazole (isothiazolidine), tetrahydrofurazan, tetrahydrooxadiazole (oxadiazolidine), tetrahydrooxazine, tetrahydrooxadiazine, perhydrooxazepine, perhydrooxadiazepine, tetrahydrothiadiazole (thiadiazolidine), tetrahydrothiazine, tetrahydrothiadiazine, perhydrothiazepine, perhydrothiadiazepine, morpholine, thiomorpholine, perhydroindazole, perhydroquinoline, perhydroisoquinoline, perhydrophthalazine, perhydronaphthyridine, perhydroquinoxaline, perhydroquinazoline, perhydrocinnoline, perhydrobenzoxazole, perhydrobenzothiazole, perhydrobenzimidazole, perhydrocarbazole, perhydrobeta-carboline, perhydroacridine etc. The "Nitrogen-containing heterocyclic ring" is preferably a "6- to 11-membered nitrogen-containing monocyclic or bicyclic heterocycle" etc. The ¢6- to 11-membered nitrogen-containing monocyclic or bicyclic heterocycle" includes, for example, a "6- to 11-membered unsaturated monocyclic or bicyclic heterocycle" or a "6- to 11-membered saturated monocyclic or bicyclic heterocycle" etc. The "6- to 11-membered unsaturated monocyclic or bicyclic heterocycle" includes, for example, pyridine, pyrazine, pyrimidine, pyridazine, triazine, azepine, diazepine, oxazine, oxadiazine, oxazepine, oxadiazepine, thiazine, thiadiazine, thiazepine, thiadiazepine, indole, isoindole, indolizine, indazole, quinoline, isoquinoline, quinolizine, purine, phthalazine, pteridine, naphthyridine, quinoxaline, quinazoline, cinnoline, benzoxazole, benzothiazole, benzimidazole, benzoxazepine, benzoxadiazepine, benzothiazepine, benzothiadiazepine, benzazepine, benzodiazepine, benzofurazan, benzothiadiazole, benzotriazole dihydropyridine, tetrahydropyridine, dihydropyrazine, tetrahydropyrazine, dihydropyrimidine, tetrahydropyrimidine, dihydropyridazine, tetrahydropyridazine, tetrahydrotriazine, dihydroazepine, tetrahydroazepine, dihydrodiazepine, tetrahydrodiazepine, dihydrooxazine, dihydrooxadiazine, dihydrooxazepine, tetrahydrooxazepine, dihydrooxadiazepine, tetrahydrooxadiazepine, dihydrothiazine, dihydrothiadiazine, dihydrothiazepine, tetrahydrothiazepine, dihydrothiadiazepine, tetrahydrothiadiazepine, indoline, isoindoline, dihydroindazole, dihydroquinoline, tetrahydroquinoline, dihydroisoquinoline, tetrahydroisoquinoline, dihydrophthalazine, tetrahydrophthalazine, dihydronaphthyridine, tetrahydronaphthyridine, dihydroquinoxaline, tetrahydroquinoxaline, dihydroquinazoline, tetrahydroquinazoline, dihydrocinnoline, tetrahydrocinnoline, dihydrobenzoxazine, dihydrobenzothiazine, pyrazinomorpholine, dihydrobenzoxazole, dihydrobenzothiazole, dihydrobenzimidazole, dihydrobenzazepine, tetrahydrobenzazepine, dihydrobenzodiazepine, tetrahydrobenzodiazepine, dihydrobenzoxazepine, tetrahydrobenzoxazepine,

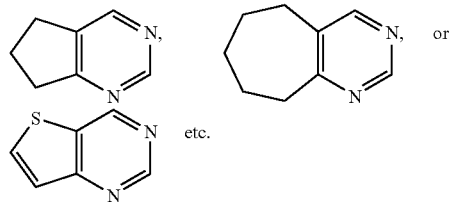

The "6- to 11-membered saturated monocyclic or bicyclic heterocycle" includes, for example, piperidine, piperazine, perhydropyrimidine, perhydropyridazine, perhydroazepine, perhydrodiazepine, perhydroazocine, perhydrooxazepine, perhydrooxadiazepine, tetrahydrothiadiazole (thiadiazolidine), tetrahydrothiazine, tetrahydrothiadiazine, perhydrothiazepine, perhydrothiadiazepine, morpholine, thiomorpholine, perhydroindazole, perhydroquinoline, perhydroisoquinoline, perhydrophthalazine, perhydronaphthyridine, perhydroquinoxaline, perhydroquinazoline, perhydrocinnoline, perhydrobenzoxazole, perhydrobenzothiazole, perhydrobenzimidazole etc. Ring B is more preferably pyridine, quinoline, isoquinoline, pyrimidine, quinazoline, tetrahydroquinazoline,

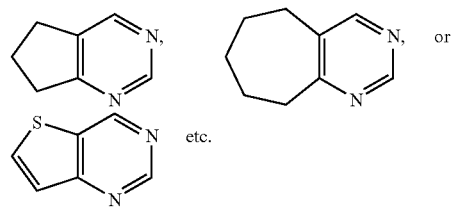

Ring B may be substituted with 1 to 5 of $R^b$ ($R^b$ has the same meaning as $R^3$ which has the same meanings as described above.).

The "hydrocarbon group" in the "hydrocarbon group which may have a substituent(s)" represented by Y includes, for example, C1-15 alkyl such as methyl, ethyl, propyl, isopropyl, butyl, isobutyl, s-butyl, t-butyl, pentyl, hexyl, heptyl, octyl, nonyl, decyl, undecyl, dodecyl, tridecyl, tetradecyl, pentadecyl etc.; C2-10 alkenyl such as vinyl, allyl, 2-methylallyl, 2-butenyl, 3-butenyl, 3-octenyl etc.; C2-10 alkynyl such as ethynyl, 2-propynyl, 3-hexynyl etc.; cyclic hydrocarbon group (the "cyclic hydrocarbon" has the same meaning as "cyclic hydrocarbon" defined with above-mentioned ring B.); C7-16 aralkyl such as benzyl, phenylethyl etc.; (C3-8 cycloalkyl)-(C1-4 alkyl) such as cyclohexylmethyl, cyclohexylethyl, cyclohexylpropyl, 1-methyl-1-cyclohexylmethyl etc.

The "substituent" in the "hydrocarbon group which may have a substituent(s)" include, for example, (1) nitro, (2) hydroxy, (3) oxo, (4) thioxo, (5) cyano, (6) carbamoyl, (7) aminocarbonyl substituted by C1-8 hydrocarbon (e.g. N-butylaminocarbonyl, N-cyclohexylmethylaminocarbonyl, N-butyl-N-cyclohexylmethylaminocarbonyl, N-cyclohexylaminocarbonyl, phenylaminocarbonyl etc.), (8) carboxy, (9) C1-4 alkoxy-carbonyl such as methoxycarbonyl, ethoxycarbonyl etc., (10) sulfo, (11) halogen such as fluorine, chlorine, bromine or iodine, (12) C1-8 alkoxy such as methoxy, ethoxy, propoxy, isopropoxy, butoxy, isobutoxy, s-butoxy, t-butoxy, cyclohexylmethyloxy or benzyloxy etc., (13) C3-8 cycloalkoxy such as cyclohexyloxy etc., (14) phenoxy, (15) halogenophenoxy such as o-, m- or p-chlorophenoxy, or o-, m- or p-bromophenoxy etc., (16) C1-4 lower alkylthio such as methylthio, ethylthio, n-propylthio, isopropylthio, n-butylthio, t-butylthio etc., (17) phenylthio, (18) C1-4 lower alkylsulfinyl such as methylsulfinyl or ethylsulfinyl etc., (19) C1-4 lower alkylsulfonyl such as methylsulfonyl or ethylsulfonyl etc., (20) amino, (21) C1-6 lower acylamino such as acetylamino or propionylamino etc., (22) primary or secondary amine substituted by hydrocarbon group (e.g. methylamino, ethylamino, n-propylamino, isopropylamino, n-butylamino, dimethylamino, diethylamino, cyclohexylamino, 1-carbamoyl-2-cyclohexylethylamino, N-butyl-N-cyclohexylmethylamino or phenylamino etc.), (the "hydrocarbon group" has the same meanings as above "hydrocarbon group" and may be substituted by oxo, amino or carbamoyl etc.), (23) C1-4 lower acyl such as formyl or acetyl etc., (24) benzoyl, (25) 5 or 6 membered hetero cyclic ring group such as 2- or 3-thienyl, 2- or 3-furyl, 3-, 4-or 5-pyrazolyl, 4-tetrahydopyranyl, 2-, 4- or 5-thiazolyl, 3-, 4- or 5-isothiazolyl, 2-, 4- or 5-oxazolyl, 3-, 4- or 5-isoxazolyl, 2-, 4- or 5-imidazolyl, 1,2,3- or 1,2,4-triazolyl, 1H or 2H-tetrazolyl, 2-, 3- or 4-pyridyl, 2-, 4- or 5-pyromidinyl, 3- or 4-pyridazinyl, quinolyl, isoquinolyl or indolyl etc. which includes 1 to 4 hetero atoms selected from oxygen, sulfur and nitrogen besides carbon atom, and optionally has 1 to 4 substituents selected from (a)

e.g. halogen such as fluorine, chlorine, bromine or iodine, (b) hydrocarbon such as methyl, ethyl, propyl, isopropyl, benzyl, cyclohexyl, cyclohexylmethyl or cyclohexylethyl etc. optionally substituted by oxo or hydroxy etc., (the "hydrocarbon group" has the same meanings as above "hydrocarbon group"), (c) halogenophenoxy such as o-, m- or p-chlorophenoxy, or o-, m- or p-bromophenoxy etc., and (d) oxo etc., (26) C1-10 haloalkyl such as difluoromethyl, trifluoromethyl, trifluoroethyl or trichloroethyl etc., (27) hydroxyimino, (28) alkyloxyimino such as methyloxyimino or ethyloxyimino etc., (29) sulfamoyl, (30) aminosulfonyl substituted by hydrocarbon (e.g. methylaminosulfonyl etc.), (31) aminosulfonyl substituted by hydrocarbon substituted by amino (e.g. dimethylaminoethylaminosulfonyl or dimethylaminopropylaminosulfonyl etc.), or (32) sulfonylamino substituted by hydrocarbon (e.g. methylsulfonylamino etc.) etc. The "hydrocarbon group which may have a substituent(s)" can have 1 to 5 of substituents selected from above (1) to (32). If the "hydrocarbon group" is cycloalkyl, cycloalkenyl, aryl or aralkyl, it may be have 1 to 4 of C1-4 lower alkyl such as methyl, ethyl, propyl, isopropyl or butyl etc. as substituent. When the number of substituents is two or more, each substituent may be same or different.

The "heterocycle" in "heterocyclic group which may have a substituent(s)" represented by Y has the same meaning as "heterocycle" defined in above-mentioned ring B. The "heterocycle" represented by Y may be substituted with 1 to 5 of $R^3$ ($R^3$ has the same meaning as described above.).

A protecting group of amino group in the "amino group which may be protected" includes, for example, (1) hydrocarbon group which may have a substituent(s), (2) $NR^1R^2$ ($R^1$ and $R^2$ have the same meanings as described above respectively.), (3) ring C optionally substituted with 1 to 5 of $R^3$ (ring C and $R^3$ have the same meanings as described above respectively), (4)

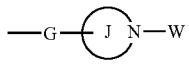

(wherein all symbols have the same meanings as described above.) etc. The "hydrocarbon group which may have a substituent(s)" as the "protecting group" in the "amino group which may be protected" represented by Y has the same meaning as described above.

The "protecting group" in the "hydroxyl group which may be protected" or the "mercapto group which may be protected" represented by Y has the same meaning as the "protecting group" in the "amino group which may be protected".

Preferred as Y is, for example, amino group which may be protected etc. More preferred is

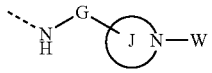

(wherein all symbols have the same meanings as described above.).

The "spacer containing 1 to 3 atoms as a main chain" represented by G means a space formed by 1 to 3 continued atoms. In this case, the "number of atoms as a main chain" should be counted such that atoms as a main chain become minimum. The "spacer having from 1 to 3 atoms as a main chain" include, for example, a bivalent group comprising 1 to 3 selected from methylene (—$CH_2$—) which may have 1 or 2 of substituents, nitrogen atom (—NH—) which may have some substituents, —CO—, —O—, —S—, —SO— and —$SO_2$—. In the case, the substituent of methylene and imino have the same meanings as the "substituent" of above-described the "hydrocarbon group which may have a substituent(s)". Specifically, it is includes, for example, —$CR^{104}R^{105}$—, —$NR^{106}$—, —CO—, —O—, —$NR^{106}CO$—, —$CONR^{106}$—, —$NR^{106}COCR^{104}R^{105}$—, —$CONR^{106}CR^{104}R^{105}$— (wherein $R^{104}$-$R^{106}$ have the same meaning as the "substituent" of above-described the "hydrocarbon group which may have a substituent(s)".) etc.

Preferred as G is, for example, a bond or spacer containing one atom as a main chain etc. More preferred as G is, for example, a bond or methylene.

The "nitrogen-containing heterocycle" in the "4- to 7-membered nitrogen-containing heterocyclic group which may have a substituent(s)" represented by ring J refers to a monocyclic heterocycle which may contain, in addition to the nitrogen atom indicated in ring J in formula (I), 1 to 3 hetero atoms selected from nitrogen, oxygen and sulfur atoms. The "4- to 7-membered nitrogen-containing heterocycle" includes, for example, a "4- to 7-membered nitrogen-containing unsaturated monocyclic heterocycle", a "4- to 7-membered nitrogen-containing saturated monocyclic heterocycle" and the like.

The "4- to 7-membered nitrogen-containing unsaturated monocyclic heterocycle" includes, for example, pyrrole, imidazole, triazole, tetrazole, pyrazole, pyrroline, imidazoline, triazoline, tetrazoline, pyrazoline, dihydropyridine, tetrahydropyridine, dihydropyrazine, tetrahydropyrazine, dihydropyrimidine, tetrahydropyrimidine, dihydropyridazine, tetrahydropyridazine, dihydroazepine, tetrahydroazepine, dihydrodiazepine, tetrahydrodiazepine, dihydrooxazole, dihydroisoxazole, dihydrothiazole, dihydroisothiazole, dihydrofurazan, dihydrooxadiazole, dihydrooxazine, dihydrooxadiazine, dihydrooxazepine, tetrahydrooxazepine, dihydrooxadiazepine, tetrahydrooxadiazepine, dihydrothiadiazole, dihydrothiazine, dihydrothiadiazine, dihydrothiazepine, tetrahydrothiazepine, dihydrothiadiazepine, tetrahydrothiadiazepine ring etc.

"4- to 7-membered nitrogen-containing saturated monocyclic heterocycle" includes, for example, azetidine, pyrrolidine, imidazolidine, triazolidine, tetrazolidine, pyrazolidine, piperidine, piperazine, perhydropyrimidine, perhydropyridazine, perhydroazepine, perhydrodiazepine, tetrahydrooxazole (oxazolidine), tetrahydroisoxazole (isoxazolidine), tetrahydrothiazole (thiazolidine), tetrahydroisothiazole (isothiazolidine), tetrahydrofurazan, tetrahydrooxadiazole (oxadiazolidine), tetrahydrooxazine, tetrahydrooxadiazine, perhydrooxazepine, perhydrooxadiazepine, tetrahydrothiadiazole (thiadiazolidine), tetrahydrothiazine, tetrahydrothiadiazine, perhydrothiazepine, perhydrothiadiazepine, morpholine, thiomorpholine etc.

Preferred as J is, for example, "4- to 7-membered nitrogen-containing saturated monocyclic heterocycle". More preferred as J is, for example, azetidine, pyrrolidine, piperidine or perhydroazepine etc.

Ring J may be substituted with 1 to 5 of $R^3$ ($R^3$ has a same meaning as described above.).

The "hydrocarbon group which may have a substituent(s)" represented by W has the same meaning as the "hydrocarbon group which may have a substituent(s)" defined in abovementioned Y.

The "heterocyclic group which may have a substituent(s)" represented by W has the same meaning as the "heterocyclic group which may have a substituent(s)" defined in above-mentioned ring B.

Preferred as W is, for example, hydrogen atom or C1-8 hydrocarbon group which may have a substituent(s). The "hydrocarbon group" has a same meaning as described above. More preferred as W is, for example, hydrogen atom, methyl, isobutyl, 2-ethylbutyl, cyclohexylmethyl, cyclohexyl, benzyl or tetrahydropyran-4-yl etc.

The "5- to 10-membered nitrogen-containing saturated heterocyclic group which may have a substituent(s), or a 5- to 10-membered nitrogen-containing heterocyclic group which has one double bond and which may have a substituent(s)" represented by ring $A^1$ in formula (I-1) include a monocyclic or bicyclic heterocycle which is fully saturated or comprising one double bond and which may contain, in addition to the nitrogen atom indicated in ring $A^1$ in formula (I), 1 to 3 hetero atoms selected from nitrogen, oxygen and sulfur atoms. The "5- to 10-membered nitrogen-containing saturated heterocycle" includes, for example, pyrrolidine, imidazolidine, triazolidine, tetrazolidine, pyrazolidine, piperidine, piperazine, perhydropyrimidine, perhydropyridazine, perhydroazepine, perhydrodiazepine, perhydroazocine, tetrahydrooxazole (oxazolidine), tetrahydroisoxazole (isoxazolidine), tetrahydrothiazole (thiazolidine), tetrahydroisothiazole (isothiazolidine), tetrahydrofurazan, tetrahydrooxadiazole (oxadiazolidine), tetrahydrooxazine, tetrahydrooxadiazine, perhydrooxazepine, perhydrooxadiazepine, tetrahydrothiadiazole (thiadiazolidine), tetrahydrothiazine, tetrahydrothiadiazine, tetrahydrothiazepine, perhydrothiazepine, perhydrothiadiazepine, morpholine, thiomorpholine, perhydroindazole, perhydroquinoline, perhydroisoquinoline, perhydrophthalazine, perhydronaphthyridine, perhydroquinoxaline, perhydroquinazoline, perhydrocinnoline, perhydrobenzoxazole, perhydrobenzothiazole, perhydrobenzimidazole, perhydroazonine, perhydroazecine, perhydrodiazocine, perhydrodiazonine, perhydrodiazecine, perhydroindole, perhydroisoindole, azabicyclo[3.2.2]nonane, azabicyclo[3.3.2]decane, azabicyclo[2.2.2]octane etc.

"5- to 10-membered nitrogen-containing heterocyclic group which has one double bond" includes, for example, pyrroline, imidazoline, triazoline, tetrazoline, pyrazoline, tetrahydropyridine, tetrahydropyrazine, tetrahydropyrimidine, tetrahydropyridazine, tetrahydroazepine, tetrahydrodiazepine, dihydrooxazole, dihydroisoxazole, dihydrothiazole, dihydroisothiazole, dihydrofurazan, dihydrooxadiazole, dihydrooxazine, dihydrooxadiazine, tetrahydrooxazepine, tetrahydrooxadiazepine, dihydrothiadiazole, dihydrothiazine, dihydrothiadiazine, tetrahydrothiazepine, tetrahydrothiadiazepine, hexahydroazocine, hexahydroazonine, hexahydrodiazocine, hexahydrodiazonine, octahydroazecine, octahydrodiazecine etc.

Preferred as ring $A^1$ is, for example, 5- to 10-membered nitrogen-containing saturated heterocycle etc. More preferred is, for example, perhydroazepine, perhydroazocine, piperidine or

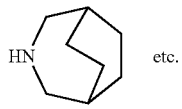 etc.

Ring $A^1$ may be substituted with 1 to 5 of $R^a$ ($R^a$ has a same meaning as $R^3$, which has a same meaning as described above.).

The "6- to 11-membered nitrogen-containing monocyclic or bicyclic heterocycle" has a same meaning as described above. Preferred as ring $B^1$ is, for example, pyridine, quinoline, isoquinoline, pyrimidine, quinazoline, tetrahydroquinazoline,

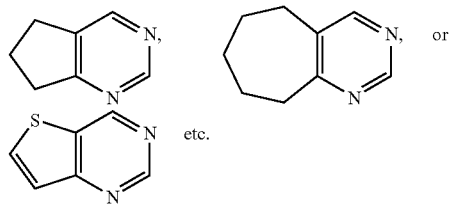

etc.

Ring $B^1$ may be substituted with 1 to 5 of $R^b$ ($R^b$ has a same meaning as $R^3$, which has a same meaning as described above.).

In formula (I-3) of the present invention, the 4- to 15-membered monocyclic, bicyclic or tricyclic heterocyclic group which contains at least one nitrogen atom and may further contain 1 to 3 nitrogen atoms, 1 or 2 oxygen atoms and/or one sulfur atom represented by ring $A^2$ includes 4- to 15-membered monocyclic, bicyclic or tricyclic heterocyclic aryl which may be partially or fully saturated and which contains at least one nitrogen atom and may further contain 1 to 3 nitrogen atoms, 1 or 2 oxygen atoms and/or one sulfur atom.

The 4- to 15-membered monocyclic, bicyclic or tricyclic heterocyclic aryl which contains at least one nitrogen atom and may further contain 1 to 3 nitrogen atoms, 1 or 2 oxygen atoms and/or one sulfur atom. includes, for example, pyrrole, imidazole, triazole, tetrazole, pyrazole, azepine, diazepine, indole, isoindole, indazole, purine, benzimidazole, benzotriazole, carbazole, β-carboline, phenothiazine, phenoxazine, perimidine etc.

The 4- to 15-membered monocyclic, bicyclic or tricyclic heterocyclic aryl which is partially or fully saturated and which contains at least one nitrogen atom and may further contain 1 to 3 nitrogen atoms, 1 or 2 oxygen atoms and/or one sulfur atom includes, for example, aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, perhydroazocine, dihydrodiazepine, tetrahydrodiazepine, perhydrodiazepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, indoline, isoindoline, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dihydrobenzazepine, tetrahydrobenzazepine, dihydrobenzodiazepine, tetrahydrobenzodiazepine, dihydrobenzoxazepine, tetrahydrobenzoxazepine, dihydrocarbazole, tetrahydrocarbazole, perhydrocarbazole, dihydroacridine, tetrahydroacridine, perhydroacridine, hexahydroazocine, hexahydroazonine, hexahydrodiazocine, hexahydodiazonine, octahydroazecine, octahydrodiazecine, perhydroazonine, perhydroazecine, azaundecane, azadodecane, azatridecane, azatetradecane, azapentadecane, perhydrodiazocine, perhydrodiazonine, perhydrodiazecine, diazaundecane, diazadodecane, diazatridecane, diazatetradecane, diazapentadecane, perhydroindole, perhydroisoindole, perhydro-beta-carboline, perhydrophenazine, perhydrophenothiazine, perhydrophenoxazine, perhydrophenanthridine, perhydrophenanthrodine, perhydroperimidine etc.

In formula (I-3) in the present invention, the 5- to 15-membered monocyclic, bicyclic or tricyclic heterocyclic group which contains at least one nitrogen atom and may further contain 1 to 3 nitrogen atoms, 1 or 2 oxygen atoms and/or one sulfur atom represented by ring $B^2$ includes a 5- to 15-membered monocyclic, bicyclic or tricyclic heterocyclic aryl which may be partially or fully saturated and which contains at least one nitrogen atom and may further contain 1 to 3 nitrogen atoms, 1 or 2 oxygen atoms and/or one sulfur atom.

The 5- to 15-membered monocyclic, bicyclic or tricyclic heterocyclic aryl which contains at least one nitrogen atom and may further contain 1 to 3 nitrogen atoms, 1 or 2 oxygen atoms and/or one sulfur atom includes, for example, pyrrole, imidazole, triazole, tetrazole, pyrazole, pyridine, pyrazine, pyrimidine, pyridazine, triazine, azepine, diazepine, oxazine, isoxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, indolizine, indazole, quinoline, isoquinoline, quinolizine, purine, phthalazine, pteridine, naphthyridine, quinoxaline, quinazoline, cinnoline, benzoxazole, benzothiazole, benzimidazole, benzoxazepine, benzoxadiazepine, benzothiazepine, benzothiadiazepine, benzazepine, benzodiazepine, benzofirazan, benzothiadiazole, benzotriazole, carbazole, beta-carboline, acridine, phenazine, phenothiazine, phenoxazine, phenanthridine, phenanthroline, perimidine etc.

The 5- to 15-membered monocyclic, bicyclic or tricyclic heterocyclic aryl which is partially or fully saturated and which contains at least one nitrogen atom and may further contain 1 to 3 nitrogen atoms, 1 or 2 oxygen atoms and/or one sulfur atom includes, for example, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, tetrahydrotriazine, dihydroazepine, tetrahydroazepine, perhydroazepine, dihydrodiazepine, tetrahydrodiazepine, perhydrodiazepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofirazan, dihydrooxadiazole, tetrahydrooxadiazole (oxadiazolidine), dihydrooxazine, tetrahydrooxazine, dihydrooxadiazine, tetrahydrooxadiazine, dihydrooxazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, indoline, isoindoline, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dihydrobenzazepine, tetrahydrobenzazepine, dihydrobenzodiazepine, tetrahydrobenzodiazepine, dihydrobenzoxazepine, tetrahydrobenzoxazepine, dihydrocarbazole, tetrahydrocarbazole, perhydrocarbazole, dihydro-beta-carboline, tetrahydro-beta-carboline, perhydro-beta-carboline, dihydroacridine, tetrahydroacridine, perhydroacridine, 6,7,8,9-tetrahydro-5H-pyrido[4',3':4,5]pyrrolo[2,3-b]pyridine, 2,3,4,5-tetrahydro-1H-pyrido[4,3-b]indole, 6,7,8,9-tetrahydro-5H-pyrido[3',4':4,5]pyrrolo[2,3-b]pyridine,

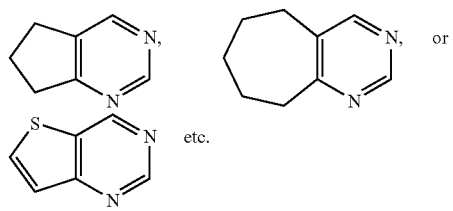

etc.

In formula (I-A) of the present invention, 4- to 15-membered monocyclic, bicyclic or tricyclic heterocycle which is saturated or has one double bond and which contains at least one nitrogen atom and may further contain 1 to 3 nitrogen atoms, 1 or 2 oxygen atoms and/or one sulfur atom by ring $A^A$ includes, for example, azetidine, pyrroline, pyrrolidine, imidazoline, imidazolidine, triazoline, triazolidine, tetrazoline, tetrazolidine, pyrazoline, pyrazolidine, tetrahydropyridine, piperidine, tetrahydropyrazine, piperazine, tetrahydropyrimidine, perhydropyrimidine, tetrahydropyridazine, perhydropyridazine, tetrahydroazepine, perhydroazepine, tetrahydrodiazepine, perhydroazocine, perhydrodiazepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofirazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, tetrahydrooxazepine, perhydrooxazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, tetrahydrothiazepine, perhydrothiazepine, tetrahydrothiadiazepine, perhydrothiadiazepine, morpholine, thiomorpholine, perhydroindazole, perhydroquinoline, perhydroisoquinoline, perhydrophthalazine, perhydronaphthyridine, perhydroquinoxaline, perhydroquinazoline, perhydrocinnoline, perhydrobenzoxazole, perhydrobenzothiazole, perhydrobenzimidazole, perhydrocarbazole, perhydroacridine, hexahydroazocine, hexahydroazonine, hexahydrodiazocine, hexahydrodiazonine, octahydroazecine, octahydrodiazecine, perhydroazonine, perhydroazecine, azaundecane, azadodecane, azatridecane, azatetradecane, azapentadecane, perhydrodiazocine, perhydrodiazonine, perhydrodiazecine, diazaundecane, diazadodecane, diazatridecane, diazatetradecane, diazapentadecane, perhydroindole, perhydroisoindole, perhydro-beta-carboline, perhydrophenazine, perhydrophenothiadine, perhydrophenoxadine, perhydrophenanthridine, perhydrophenanthroline, perhydroperimidine etc.

In formula (I-B) of the present invention, 7- to 15-membered monocyclic, bicyclic or tricyclic heterocycle which is saturated or contains one double bond and which contains at least one nitrogen atom and may further contain 1 to 3 nitrogen atoms, 1 or 2 oxygen atoms and/or one sulfur atom represented by ring $A^B$ includes, for example, tetrahydroazepine, perhydroazepine, tetrahydrodiazepine, perhydrodiazepine, perhydroazocine, tetrahydrooxazepine, perhydrooxazepine, tetrahydrooxadiazepine, perhydrooxadiazepine, tetrahydrothiazepine, perhydrothiazepine, tetrahydrothiadiazepine, perhydrothiadiazepine, perhydroindazole, perhydroquinoline, perhydroisoquinoline, perhydrophthalazine, perhydronaphthyridine, perhydroquinoxaline, perhydroquinazoline, perhydrocinnoline, perhydrobenzoxazole, perhydrobenzothiazole, perhydrobenzimidazole, perhydrocarbazole, perhydroacridine, hexahydroazocine, hexahydroazonine, hexahydrodiazocine, hexahydrodiazonine, octahydroazecine, octahydrodiazecine, perhydroazonine, perhydroazecine, azaundecane, azadodecane, azatridecane, azatetradecane, azapentadecane, perhydrodiazocine, perhydrodiazonine, perhydrodiazecine, diazaundecane, diazadodecane, diazatridecane, diazatetradecane, diazapentadecane, perhydroindole, perhydroisoindole, perhydro-beta-carboline, perhydrophenazine, perhydrophenothiadine, perhydrophenoxadine, perhydrophenanthridine, perhydrophenanthroline, perhydroperimidine etc.

The bicyclic heterocycle represented by above-described $A^2$ in formula (I-3), $A^A$ in formula (I-A) or $A^B$ in formula (I-B) includes a bridged bicyclic heterocycle. The bridged bicyclic heterocycle includes, for example, azabicyclo[3.2.2]nonane, azabicyclo[3.3.2]decane, azabicyclo[2.2.2]octane, azabicyclo[3:3:3]undecane, azabicyclo[4.3.3]dodecane, azabicyclo[4.4.3]tridecane, azabicyclo[4.4.4]tetradecane etc. The bridged bi-heterocyclic ring may have one double bond.

In formula (I-B) of the present invention, ring $B^B$ is pyrimidine or 1,3,5-triazine that may be fused with ring Z.

In the present invention, the C5-10 monocyclic or bicyclic carbocycle represented by ring Z includes, for example, cyclopentene, cyclohexene, cycloheptene, cyclooctene, cyclononene, cyclodecene, cyclopentadiene, cyclohexadiene, cycloheptadiene, cyclooctadiene, benzene, pentalene, azulene, indene, indan, naphthalene, dihydronaphthalene, tetrahydronaphthalene etc.

In the present invention, the 5- to 10-membered monocyclic or bicyclic heterocycle which may contain 1 or 2 nitrogen atoms, one oxygen atom and/or one sulfur atom represented by ring Z includes a 5- to 10-membered mono- or bi-heterocyclic aryl which may be partially saturated and which may contain 1 or 2 nitrogen atoms, one oxygen atom and/or one sulfur atom.

The 5- to 10-membered mono- or bi-heterocyclic aryl which may contain 1 or 2 nitrogen atoms, one oxygen atom and/or one sulfur atom includes, for example, pyrrole, imidazole, triazole, pyrazole, pyridine, pyrazine, pyrimidine, pyridazine, azepine, diazepine, furan, pyran, oxepine, thiophene, thiopyran, thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, benzoxazole, benzothiazole, benzimidazole, chromene, benzofurazan, benzothiadiazole, benzotriazole ring etc.

The 5- to 10-membered mono- or bi-heterocyclic aryl which is partially saturated and which may contain 1 or 2 nitrogen atoms, one oxygen atom and/or one sulfur atom includes, for example, pyrroline, imidazoline, pyrazoline, dihydropyridine, tetrahydropyridine, dihydropyrazine, tetrahydropyrazine, dihydropyrimidine, tetrahydropyrimidine, dihydropyridazine, tetrahydropyridazine, dihydroazepine, tetrahydroazepine, dihydrodiazepine, tetrahydrodiazepine, dihydrofuran, dihydropyran, dihydrooxepine, tetrahydrooxepine, dihydrothiophene, dihydrothiopyran, dihydrothiepine, tetrahydrothiepine, dihydrooxazole, dihydroisoxazole, dihydrothiazole, dihydroisothiazole, dihydrofurazan, dihydrooxadiazole, dihydrooxazine, dihydrooxadiazine, dihydrooxazepine, tetrahydrooxazepine, dihydrooxadiazepine, tetrahydrooxadiazepine, dihydrothiadiazole, dihydrothiazine, dihydrothiadiazine, dihydrothiazepine, tetrahydrothiazepine, dihydrothiadiazepine, tetrahydrothiadiazepine, dihydrooxazine, dihydrothiazine, oxathiane, indoline, isoindoline, dihydrobenzofuran, dihydroisobenzofuran, dihydrobenzothiophene, dihydroisobenzothiophene, dihydroindazole, dihydroquinoline, tetrahydroquinoline, dihydroisoquinoline, tetrahydroisoquinoline, dihydrophthalazine, tetrahydrophthalazine, dihydronaphthyridine, tetrahydronaphthyridine, dihydroquinoxaline, tetrahydroquinoxaline, dihydroquinazoline, tetrahydroquinazoline, dihydrocinnoline, tetrahydrocinnoline, benzoxathiane, dihydrobenzoxazine, dihydrobenzothiazine, pyrazinomorpholine, dihydrobenzoxazole, dihydrobenzothiazole, dihydrobenzimidazole, dioxaindan, benzodioxane, chroman, benzodithiolane, benzodithiane etc.

In the present invention, C1-8 alkylene represented by L means methylene, ethylene, propylene, butylene, pentylene, hexylene, heptylene, octylene or isomeric groups thereof.

In the present invention, C2-8 alkenylene represented by L means ethylene, propylene, butylene, pentylene, hexylene, heptylene, octylene and isomeric groups thereof having one or two double bond(s), concretely, ethenylene, propenylene, butenylene, pentenylene, hexenylene, heptenylene, octenylene, hexadienylene, heptadienylene, octadienylene or isomeric groups thereof.

In the present invention, C2-8 alkynylene represented by L means ethylene, propylene, butylene, pentylene, hexylene, heptylene, octylene and isomeric groups thereof having one triple bond, concretely, ethynylene, propynylene, butynylene, pentynylene, hexynylene, heptynylene, octynylene or isomeric groups thereof.

In the present invention, C3-8 carbocycle represented by L, $R^1$, $R^2$ and $R^4$ means C3-8 monocyclic or bridged bicyclic carbocycle, for example, cyclopropane, cyclobutane, cyclopentane, cyclohexane, cycloheptane, cyclooctane, cyclopentene, cyclohexene, cycloheptene, cyclooctene, cyclopentadiene, cyclohexadiene, cycloheptadiene, cyclooctadiene, benzene, bicyclo[2.2.1]heptane, bicyclo[2.2.2]octane etc.

In the present invention, C1-15 alkyl means methyl, ethyl, propyl, butyl, pentyl, hexyl, heptyl, octyl, nonyl, decyl, undecyl, dodecyl, tridecyl, tetradecyl, pentadecyl or isomeric groups thereof.

In the present invention, C2-15 alkenyl means ethenyl, propenyl, butenyl, pentenyl, hexenyl, heptenyl, octenyl, nonenyl, decenyl, undecenyl, dodecenyl, tridecenyl, tetradecenyl, pentadecenyl or isomeric groups thereof.

In the present invention, C2-15 alkynyl means ethynyl, propynyl, butynyl, pentynyl, hexynyl, heptynyl, octynyl, nonynyl, decynyl, undecynyl, dodecynyl, tridecynyl, tetradecynyl, pentadecynyl or isomeric groups thereof.

In the present invention, the 4- to 15-membered heterocycle which contains at least one nitrogen atom and may further contain 1 or 2 nitrogen atoms, 1 or 2 oxygen atoms and/or one sulfur atom represented by ring C includes a 4- to 15-membered heterocyclic aryl which may be partially or fully saturated and which contains at least one nitrogen atom and may further contain 1 or 2 nitrogen atoms, 1 or 2 oxygen atoms and/or one sulfur atom.

The 4- to 15-membered heterocyclic aryl which contains at least one nitrogen atom and may further contain 1 or 2 nitrogen atoms, 1 or 2 oxygen atoms and/or one sulfur atom includes, for example, pyrrole, imidazole, triazole, pyrazole, pyridine, pyrazine, pyrimidine, pyridazine, azepine, diazepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, indolizine, indazole, quinoline, isoquinoline, quinolizine, phthalazine, naphthyridine, quinoxaline, quinazoline, cinnoline, benzoxazole, benzothiazole, benzimidazole, benzoxazepine, benzoxadiazepine, benzothiazepine, benzothiadiazepine, benzazepine, benzodiazepine, benzofurazan, benzothiadiazole, benzotriazole, carbazole, beta-carboline, acridine, phenazine, xanthene, phenothiazine, phenoxazine, phenoxathiin, phenanthridine, phenanthroline, perimidine etc.

The 4- to 15-membered heterocyclic aryl which is partially or fully saturated and which contains at least one nitrogen atom and may further contain 1 or 2 nitrogen atoms, 1 or 2 oxygen atoms and/or one sulfur atom includes, for example, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, perhydroazocine, dihydrodiazepine, tetrahydrodiazepine, perhydrodiazepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dihydrobenzazepine, tetrahydrobenzazepine, dihydrobenzodiazepine, tetrahydrobenzodiazepine, benzodioxepane, dihydrobenzoxazepine, tetrahydrobenzoxazepine, dihydrocarbazole, tetrahydrocarbazole, perhydrocarbazole, dihydroacridine, tetrahydroacridine, perhydroacridine, hexahydroazocine, hexahydroazonine, hexahydrodiazocine, hexahydodiazonine, octahydroazecine, octahydrodiazecine, perhydroazonine, perhydroazecine, azaundecane, azadodecane, azatridecane, azatetradecane, azapentadecane, perhydrodiazocine, perhydrodiazonine, perhydrodiazecine, diazaundecane, diazadodecane, diazatridecane, diazatetradecane, diazapentadecane, perhydroindole, perhydroisoindole, perhydro-beta-carboline, perhydrophenazine, perhydrophenothiazine, perhydrophenoxazine, perhydrophenanthridine, perhydrophenanthrodine, perhydroperimidine etc.

In the present invention, the 5- to 15-membered monocyclic, bicyclic or tricyclic heterocycle which contains 1 to 4 nitrogen atoms, 1 or 2 oxygen atoms and/or one sulfur atom represented by ring D and E includes a 5- to 15-membered monocyclic, bicyclic or tricyclic heterocyclic aryl which may be partially or fully saturated and which contains 1 to 4 nitrogen atoms, 1 or 2 oxygen atoms and/or one sulfur atom. The 5- to 15-membered monocyclic, bicyclic or tricyclic heterocyclic aryl which contains 1 to 4 nitrogen atoms, 1 or 2 oxygen atoms and/or one sulfur atom includes, for example, pyrrole, imidazole, triazole, tetrazole, pyrazole, pyridine, pyrazine, pyrimidine, pyridazine, azepine, diazepine, furan, pyran, oxepine, thiophene, thiopyran, thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, benzoxazole, benzothiazole, benzimidazole, chromene, benzoxepine, benzoxazepine, benzoxadiazepine, benzothiepine, benzothiazepine, benzothiadiazepine, benzazepine, benzodiazepine, benzofurazan, benzothiadiazole, benzotriazole, carbazole, beta-carboline, acridine, phenazine, dibenzofuran, xanthene, dibenzothiophene, phenothiazine, phenoxazine, phenoxathiin, thianthrene, phenanthridine, phenanthroline, perimidine etc.

The 5- to 15-membered monocyclic, bicyclic or tricyclic heterocyclic aryl which is partially or fully saturated and which contains 1 to 4 nitrogen atoms, 1 or 2 oxygen atoms and/or one sulfur atom includes, for example, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofuirazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dihydrobenzazepine, tetrahydrobenzazepine, dihydrobenzodiazepine, tetrahydrobenzodiazepine, benzodioxepane, dihydrobenzoxazepine, tetrahydrobenzoxazepine, dihydrocarbazole, tetrahydrocarbazole, perhydrocarbazole, dihydroacridine, tetrahydroacridine, perhydroacridine ring etc.

In the present invention, C3-15 monocyclic, bicyclic or tricyclic carbocycle represented by ring D and ring E includes C3-15 monocyclic, bicyclic or tricyclic carbocyclic aryl which may be saturated partially or fully, bicyclic heterocycle having spiro bond and bridged bicyclic heterocycle, for example, cyclopropane, cyclobutane, cyclopentane, cyclohexane, cycloheptane, cyclooctane, cyclononane, cyclodecane, cycloundecane, cyclododecane, cyclotridecane, cyclotetradecane, cyclopentadecane, cyclopentene, cyclohexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indan, naphthalene, dihydronaphthalene, teterahydronaphthalene, perhydronaphthalene, heptalene, perhydroheptalene, biphenylene, as-indacene, s-indacene, acenaphthylene, acenaphthene, fluorene, phenalene, phenanthrene, anthracene, spiro[4.4]nonane, spiro[4.5]decane, spiro[5.5]undecane, bicyclo[2.2.1]heptane, bicyclo[2.2.1]hept-2-ene, bicyclo[3.1.1]heptane, bicyclo[3.1.1]hept-2-ene, bicyclo[2.2.2]octane, bicyclo[2.2.2]oct-2-ene, adamantane, noradamantane ring etc.

In the present invention, C1-15 alkoxy which is the substituent of ring E means methoxy, ethoxy, propoxy, butoxy, pentyloxy, hexyloxy, heptyloxy, octyloxy, nonyloxy, decyloxy, undecyloxy, dodecyloxy, tridecyloxy, tetradecyloxy, pentadecyloxy and isomeric groups thereof.

In the present invention, mono(C1-8 alkyl)amino group which is the substituent of ring E means methylamino, ethylamino, propylamino, butylamino, pentylamino, hexylamino, heptylamino, octylamino and isomeric groups thereof In the present invention, di(C1-8 alkyl)amino group which is the substituent of ring E means amino group substituted by same or different two C1-8 alkyl, for example, dimethylamino, diethylamino, dipropylamino, dibutylamino, dipentylamino, dihexylamino, diheptylamino, dioctylamino, ethylmethylamino, ethylpropylamino, methylpropylamino and isomeric groups thereof.

The "hydrocarbon group which may have substituent(s)" represented by $R^{101}$ and $R^{102}$ has the same meaning as the "hydrocarbon group which may have substituent(s)" defined in Y.

In the present invention, halogen atom is fluorine, chlorine, bromine and iodine.

In the present invention, the CXCR4-regulating agent includes, as a matter of course, an agonist and an antagonist. The agonist includes a full agonist, partial agonist and inverse agonist, while the antagonist includes a full antagonist and partial antagonist.

Also, in the present invention, the CXCR4-regulating agent may be any compound which has an affinity for CXCR4 by itself or in combination with a CXCR4 ligand (for example, SDF-1, gp120 and the like) or with HIV and which may have either an agonistic or antagonistic effect.

Thus, as used herein, the CXCR4-regulating agent may be any compound capable of inhibiting the binding between CXCR4 and an intrinsic ligand (for example, SDF-1)-or HIV. Therefore, it may be an agonist or antagonist, preferably antagonist.

Unless otherwise specifically mentioned, all isomers are included in the present invention. For example, alkyl, alkoxy and alkylene include straight chain and branched ones. Moreover, all of isomers due to double bond, ring and fused ring (E-, Z-, cis- and trans-forms), isomers due to presence of asymmetric carbon(s), etc. (R-, S-, α- and β-configuration, enantiomer and diastereomer), optically active substances having optical rotation (D-, L-, d- and l-forms), polar compound by chromatographic separation (high-polar compound and low-polar compound), equilibrium compounds, rotational isomers, a mixture thereof in any proportion and a racemic mixture are included in the present invention.

According to the present invention, unless otherwise indicated and as is apparent for those skilled in the art, symbol  indicates that it is bound to the opposite side of the sheet (namely α-configuration), symbol  indicates that it is bound to the front side of the sheet (namely β-configuration), symbol  indicates that it is α-configuration, β-configuration or a mixture thereof, and symbol  indicates that it is a mixture of α-configuration and β-configuration.

The compound of the present invention can be converted into a salt by known methods.

The salt is preferably water-soluble.

The salt of the present invention are, for example, salt with alkaline metal (such as potassium, sodium and lithium), salt with alkaline earth metal (such as calcium and magnesium), ammonium salt (such as tetramethylammonium salt and tetrabutylammonium salt), salt with organic amine (such as triethylamine, methylamine, dimethylamine, cyclopentylamine, benzylamine, phenethylamine, piperidine, monoethanolamine, diethanolamine, tris(hydroxymethyl)methylamine, lysine, arginine and N-methyl-D-glucamine) and acid addition salt (such as inorganic acid salt (e.g., hydrochloride, hydrobromide, hydroiodide, sulfate, phosphate and nitrate) and organic acid salt (e.g., acetate, trifluoroacetate, lactate, tartrate, oxalate, fumarate, maleate, benzoate, citrate, methanesulfonate, ethanesulfonate, benzenesulfonate, toluenesulfonate, isothionate, glucuronate and gluconate), etc.).

N-oxide means a compound of formula (I) which nitrogen is oxidized. The compounds of the present invention can be converted to N-oxide by arbitrary methods. Salt and N-oxide of the compound of the present invention include solvate, or solvate of salt with alkaline (earth) metal, of ammonium salt, of salt with organic amine and of acid addition salt, of the compound of the present invention.

The solvate is preferably non toxic and water-soluble. The suitable solvate is, for example, solvate of water or alcohol (e.g. ethanol).

A prodrug of the compound of formula (I) means a compound which is converted to the compound of formula (I) by reaction with an enzyme, gastric acid or the like in the living body. For example, with regard to a prodrug of the compound of formula (I), when the compound of formula (I) has an amino group, compounds in which the amino group is, for example, acylated, alkylated or phosphorylated (e.g., compounds in which the amino group of the compound of formula (I) is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, acetoxymethylated, tert-butylated, etc.); when the compound of formula (I) has a hydroxyl group, compounds where the hydroxyl group is, for example, acylated, alkylated, phosphorylated or borated (e.g., compounds in which the hydroxyl group of the compound of formula (I) is acetylated, palmitoylated, propanoylated, pivaloylated, succinylated, fumarylated, alanylated or dimethylaminomethylcarbonylated); and that the carboxyl group of the compound of formula (I) is, for example, esterified or amidated (e.g., compounds in which the carboxyl group of the compound of formula (I) is made into ethyl ester, phenyl ester, phenylethyl ester, carboxymethyl ester, dimethylaminomethyl ester, pivaloyloxymethyl ester, ethoxycarbonyloxyethyl-ester, phthalidyl ester, (5-methyl-2-oxo-1,3-dioxolen-4-yl)methyl ester, cyclohexyloxycarbonylethyl ester or methylamide). Those compounds may be produced by a known method per se. The prodrug of the compound of formula (I) may be either a hydrate or a non-hydrate.

In the compound of the present invention represented by formula (I-3), preferred ring $A^2$ is any compound which is 4- to 15-membered monocyclic, bicyclic or tricyclic heterocycle which contains at least one nitrogen atom and may further contain 1 to 3 nitrogen atoms, 1 or 2 oxygen atoms and/or one sulfur atom. More preferred is 5- to 10-membered monocyclic or bicyclic heterocycle, concretely, pyrrolidine, piperidine, morpholine, tetrahydropyridine, perhydroquinoline, perhydroisoquinoline, perhydrodiazepine, perhydroazepine, perhydroazocine, perhydroazonine, perhydroazecine, 2-azabicyclo[3.2.2]nonane, 3-azabicyclo[3.2.2]nonane, 1-azabicyclo[2.2.2]octane or 2-azabicyclo[2.2.2]octane etc., and most preferred is piperidine or perhydroazepine etc.

In the present invention, $R^a$ is all preferred and more preferred is C1-4 alkyl which may be substituted with ring D, $OR^{11}$, $OCOR^{12}$, $NR^{14}R^{15}$, $NR^{16}COR^{12}$, $NR^{16}CONR^{14}R^{15}$, $COOR^{13}$, $COR^{12}$, $CONR^{14}R^{15}$ or ring D etc. More preferred is C1-4 alkyl, phenyl, benzyl, acetyl, benzyloxycarbonyl, hydroxy, ethoxycarbonyl, carbamoyl, piperidinyl or cyclohexyl etc.

In the compound of the present invention represented by formula (I-3), preferred ring $B^2$ is any compound which is 5- to 15-membered monocyclic, bicyclic or tricyclic heterocycle which contains at least one nitrogen atom and may further contain 1 to 3 nitrogen atoms, 1 or 2 oxygen atoms and/or one sulfur atom. More preferred is 6 membered heterocyclic ring which may be fused with ring Z and which contains 1 to 3 nitrigen atoms.

Preferred as the above-described 6 membered heterocyclic ring is pyridine, pyrazine, pyrimidine, triazine, piperidine, piperazine, tetrahydropyridine, tetrahydropyrazine, tetrahydropyrimidine, tetrahydrotriazine etc.

In the present invention, preferred ring Z is C5-7 monocyclic carbocycle or 5- to 7-membered monocyclic heterocycle etc.

In the present invention, preferred ring $B^2$ is ring $B^{41}$ or ring $B^{42}$. Moreover,

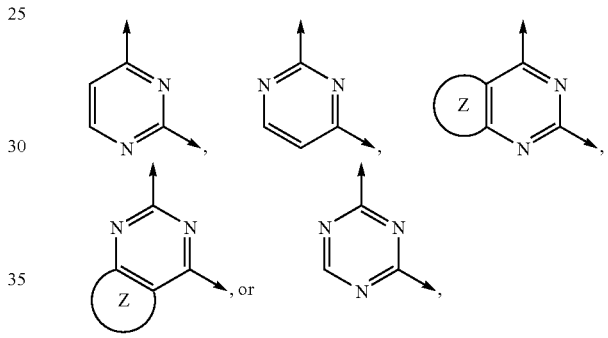

(wherein the upward arrow represents a binding position to ring $A^2$; and the right-downward arrow represents a binding position to the nitrogen atom bound to L.) etc. is also preferred.

In the present invention, $R^b$ is all preferred, and more preferred is C1-4 alkyl which may be substituted with ring D, $OR^{11}$, $OCOR^{12}$, $NR^{14}R^{15}$, $NR^{16}COR^{12}$, $NR^{16}CONR^{14}R^{15}$, $COOR^{13}$, $COR^{12}$, $CONR^{14}R^{15}$ or ring D etc. More preferred is C1-4 alkyl, phenyl, benzyl, acetyl, benzyloxycarbonyl, hydroxy, ethoxycarbonyl, carbamoyl, piperidinyl or cyclohexyl etc.

In the compound represented by formula (I-A) of the present invention, 4- to 15-membered monocyclic, bicyclic or tricyclic heterocycle which is saturated or has one double bond and which contains at least one nitrogen atom and may further contain 1 to 3 nitrogen atoms, 1 or 2 oxygen atoms and/or one sulfur atom is all preferred as ring $A^4$, and particularly preferred is 5- to 10-membered monocyclic or bicyclic heterocycle which is saturated or has one double bond and which contains at least one nitrogen atom and may further contain 1 to 3 nitrogen atoms, 1 or 2 oxygen atoms and/or one sulfur atom.

In the compound represented by formula (I-A) of the present invention, the ring described in ring $B^{41}$ and ring $B^{42}$ is all preferred as ring $B^4$. More preferred is

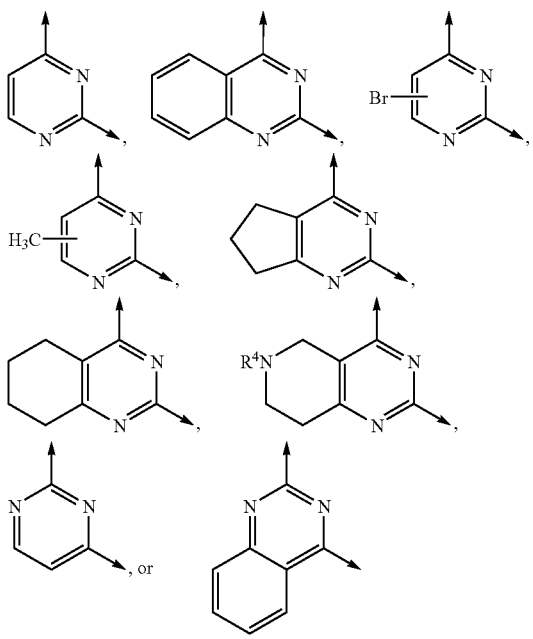

(wherein the upward arrow represents a binding position to ring $A^A$; and the right-downward arrow represents a binding position to the nitrogen atom bound to L.) etc.

In the compound represented by formula (I-B) of the present invention, 7- to 15-membered monocyclic, bicyclic or tricyclic heterocycle which is saturated or contains one double bond and which contains at least one nitrogen atom and may further contain 1 to 3 nitrogen atoms, 1 or 2 oxygen atoms and/or one sulfur atom is all preferred as ring $A^B$, and particularly preferred is 7- to 10-membered monocyclic, bicyclic or tricyclic heterocycle which is saturated or contains one double bond and which contains at least one nitrogen atom and may further contain 1 to 3 nitrogen atoms, 1 or 2 oxygen atoms and/or one sulfur atom.

In the compound represented by formula (I-B) of the present invention, ring $B^B$ is all preferred, and pyrimidine which may be fused with ring Z etc. is more preferred. Preferred ring Z is C5-7 monocyclic carbocycle or 5 to 7 membered monocyclic heterocycle etc.

In the present invention, L is all preferred. Bond, C1-6 alkylene or C3-8 carbocycle etc. is more preferred. Bond, C1-4 alkylene or C3-7 carbocycle etc. is particularly preferred.

In the present invention, both $NR^1R^2$ and ring C are preferable as Q.

In the present invention, preferable as $R^1$ and $R^2$ among $NR^1R^2$ represented by Q is hydrogen atom, C1-12 alkyl substituted with $R^{10}$, C2-12 alkenyl, or C1-12 alkyl or C2-12 alkenyl substituted with ring D. More preferable is hydrogen atom, methyl, ethyl, propyl, isobutyl, butyl or methylthiopropyl etc.

In the present invention, preferable as ring C represented by Q is azetidine, pyrrolidine, morpholine, piperazine, thiomorpholine, perhydroazepine, perhydroazocine, perhydroazonine or perhydroazecine etc.

In the present invention, preferable as ring D is C3-10 carbocycle or 5- to 15-membered heterocycle etc. More preferable is benzene, benzofuran, benzothiophene, pyrazole, benzodioxole, tetrahydrobenzene, furan, thiazole, naphthalene, thiophene, cyclopropane, quinoline, pyridine or cyclohexane etc.

In the present invention, preferable as $R^3$ is C1-10 alkyl, C2-10 alkenyl, C2-10 alkynyl, C1-10 alkyl substituted with $R^{10}$, $COOR^{12}$, $OR^{11}$, $NR^{14}R^{15}$, $COR^{12}$, $CONR^{14}R^{15}$ or ring E.

In the present invention, preferable as $R^{10}$ among $R^3$ is $COOR^{12}$, $OR^{11}$, $NR^{14}R^{15}$, $COR^{12}$, $CONR^{14}R^{15}$ or ring E.

In the present invention, $R^4$ is all preferable. More preferable is hydrogen atom, C1-8 alkyl, phenyl, $COR^5$ or $COOR^6$.

In the compound represented by formula (I), compounds represented by formulae (I-1), (I-2), (I-3), (I-A) and (I-B) etc. are preferable.

Among the compound represented by formula (I-3), preferred compounds are compounds represented by formula (IA-1)

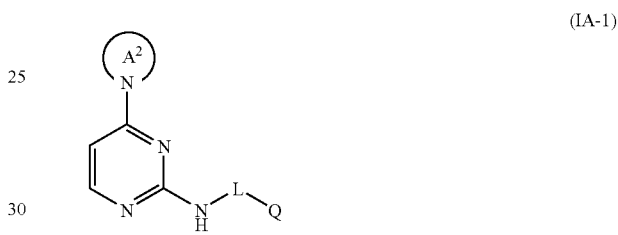

(wherein all symbols have the same meanings as described above.), compounds represented by formula (IA-2)

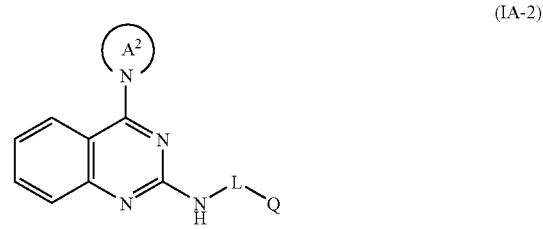

(wherein all symbols have the same meanings as described above.), compounds represented by formula (IA-3)

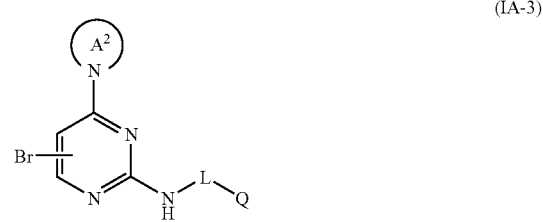

(wherein all symbols have the same meanings as described above.), compounds represented by formula (IA-4)

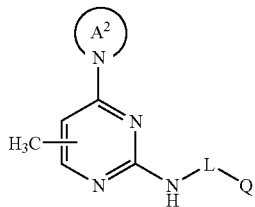

(IA-4)

(wherein all symbols have the same meanings as described above.), compounds represented by formula (IA-5)

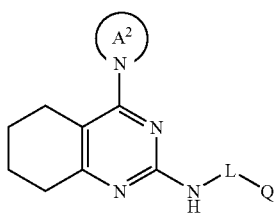

(IA-5)

(wherein all symbols have the same meanings as described above.), compounds represented by formula (IA-6)

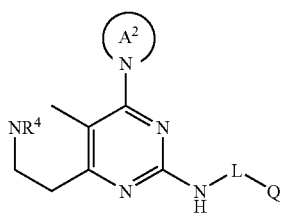

(IA-6)

(wherein all symbols have the same meanings as described above.), compounds represented by formula (IA-7)

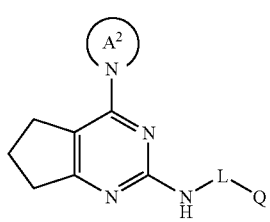

(IA-7)

(wherein all symbols have the same meanings as described above.), compounds represented by formula (IA-8)

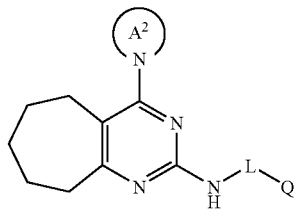

(IA-8)

(wherein all symbols have the same meanings as described above.), compounds represented by formula (IB)

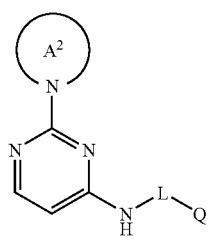

(IB)

(wherein all symbols have the same meanings as described above.), and compounds represented by formula (IC)

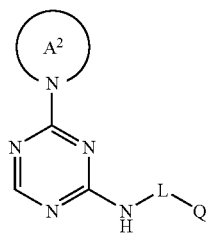

(IC)

(wherein all symbols have the same meanings as described above.).

Compounds represented in example and compounds represented below, salts thereof, N-oxides thereof or solvates thereof, or prodrugs thereof are included as a specific compound of the present invention.

(1) $N^1$-(4-azepan-1-yl-5,6,7,8-tetrahydroquinazolin-2-yl)-$N^2$,$N^2$-dimethylethane-1,2-diamine, (2) $N^1$-(4-azepan-1-yl-5,6,7,8-tetrahydroquinazolin-2-yl)-$N^2$-(2-ethylbutyl)-$N^2$-methylethane-1,2-diamine, (3) $N^1$-(4-azepan-1-yl-5,6,7,8-tetrahydroquinazolin-2-yl)-$N^2$-methyl-$N^2$-nonylethane-1,2-diamine, (4) $N^1$-(4-azepan-1-yl-5,6,7,8-tetrahydroquinazolin-2-yl)-$N^2$-methyl-$N^2$-[2-(methylsulfanyl)ethyl]ethane-1,2-diamine, (5) $N^1$-(4-azepan-1-yl-5,6,7,8-tetrahydroquinazolin-2-yl)-$N^2$-benzyl-$N^2$-methylethane-1,2-diamine, (6) $N^1$-(4-azepan-1-yl-5,6,7,8-tetrahydroquinazolin-2-yl)-$N^2$-{4-[3 -(dimethylamino)propoxy]benzyl}-$N^2$-methylethane-1,2-diamine, (7) $N^1$-(4-azepan-1-yl-5,6,7,8-tetrahydroquinazolin-2-yl)-$N^2$-methyl-$N^2$-[(3-phenyl-1H-pyrazol-4-yl)methyl]ethane-1,2-diamine, (8) $N^1$-(4-azepan-1-yl-5,6,7,8-tetrahydroquinazolin-2-yl)-$N^2$-methylethane-1,2-diamine, (9) 4-azepan-1-yl-N-[(1-methylpyrrolidin-2-yl)methyl]-5,6,7,8-tetrahydroquinazolin-2-amine,

(10) 4-azepan-1-yl-N-{[1-(2-ethylbutyl)pyrrolidin-2-yl]methyl}-5,6,7,8-tetrahydroquinazolin-2-amine,

(11) 4-azepan-1-yl-N-[(1-nonylpyrrolidin-2-yl)methyl]-5,6,7,8-tetrahydroquinazolin-2-amine,

(12) 4-azepan-1-yl-N-({1-[2-(methylsulfanyl)ethyl]pyrrolidin-2-yl}methyl)-5,6,7,8-tetrahydroquinazolin-2-amine,

(13) 4-azepan-1-yl-N-[(1-benzylpyrrolidin-2-yl)methyl]-5,6,7,8-tetrahydroquinazolin-2-amine,

(14) 4-azepan-1-yl-N-[(1-{4-[3-(dimethylamino)propoxy]benzyl}pyrrolidin-2-yl)methyl]-5,6,7,8-tetrahydroquinazolin-2-amine,

(15) 4-azepan-1-yl-N-({1-[(3-phenyl-1H-pyrazol-4-yl)methyl]pyrrolidin-2-yl}methyl)-5,6,7,8-tetrahydroquinazolin-2-amine,

(16) 4-azepan-1-yl-N-(pyrrolidin-2-ylmethyl)-5,6,7,8-tetrahydroquinazolin-2-amine,

(17) 4-azepan-1-yl-N-[(1-methylpiperidin-2-yl)methyl]-5,6,7,8-tetrahydroquinazolin-2-amine,

(18) 4-azepan-1-yl-N-{[1-(2-ethylbutyl)piperidin-2-yl]methyl}-5,6,7,8-tetrahydroquinazolin-2-amine,

(19) 4-azepan-1-yl-N-[(1-nonylpiperidin-2-yl)methyl]-5,6,7,8-tetrahydroquinazolin-2-amine,

(20) 4-azepan-1-yl-N-({1-[2-(methylsulfanyl)ethyl]piperidin-2-yl}methyl)-5,6,7,8-tetrahydroquinazolin-2-amine,

(21) 4-azepan-1-yl-N-[(1-benzylpiperidin-2-yl)methyl]-5,6,7,8-tetrahydroquinazolin-2-amine,

(22) 4-azepan-1-yl-N-[(1-{4-[3-(dimethylamino)prbpoxy]benzyl}piperidin-2-yl)methyl]-5,6,7,8-tetrahydroquinazolin-2-amine,

(23) 4-azepan-1-yl-N-({1-[(3-phenyl-1H-pyrazol-4-yl)methyl]piperidin-2-yl}methyl)-5,6,7,8-tetrahydroquinazolin-2-amine,

(24) 4-azepan-1-yl-N-(piperidin-2-ylmethyl)-5,6,7,8-tetrahydroquinazolin-2-amine,

(25) 4-azepan-1-yl-N-(1-methylpyrrolidin-3-yl)-5,6,7,8-tetrahydroquinazolin-2-amine,

(26) 4-azepan-1-yl-N-[1-(2-ethylbutyl)pyrrolidin-3-yl]-5,6,7,8-tetrahydroquinazolin-2-amine,

(27) 4-azepan-1-yl-N-(1-nonylpyrrolidin-3-yl)-5,6,7,8-tetrahydroquinazolin-2-amine,

(28) 4-azepan-1-yl-N-{1-[2-(methylsulfanyl)ethyl]pyrrolidin-3-yl}-5,6,7,8-tetrahydroquinazolin-2-amine,

(29) 4-azepan-1-yl-N-(1-benzylpyrrolidin-3-yl)-5,6,7,8-tetrahydroquinazolin-2-amine,

(30) 4-azepan-1-yl-N-(1-{$^4$-[3-(dimethylamino)propoxy]benzyl}pyrrolidin-3-yl)-5,6,7,8-tetrahydroquinazolin-2-amine,

(31) 4-azepan-1-yl-N-{1-[(3-phenyl-1H-pyrazol-4-yl)methyl]pyrrolidin-3-yl}-5,6,7,8-tetrahydroquinazolin-2-amine,

(32) 4-azepan-1-yl-N-pyrrolidin-3-yl-5,6,7,8-tetrahydroquinazolin-2-amine,

(33) 4-azepan-1-yl-N-(1-methylpiperidin-3-yl)-5,6,7,8-tetrahydroquinazolin-2-amine,

(34) 4-azepan-1-yl-N-[1-(2-ethylbutyl)piperidin-3-yl]-5,6,7,8-tetrahydroquinazolin-2-amine,

(35) 4-azepan-1-yl-N-(1-nonylpiperidin-3-yl)-5,6,7,8-tetrahydroquinazolin-2-amine,

(36) 4-azepan-1-yl-N-{1-[2-(methylsulfanyl)ethyl]piperidin-3-yl}-5,6,7,8-tetrahydroquinazolin-2-amine,

(37) 4-azepan-1-yl-N-(1-benzylpiperidin-3-yl)-5,6,7,8-tetrahydroquinazolin-2-amine,

(38) 4-azepan-1-yl-N-(1-{4-[3-(dimethylamino)propoxy]benzyl}piperidin-3-yl)-5,6,7,8-tetrahydroquinazolin-2-amine,

(39) 4-azepan-1-yl-N-{1-[(3-phenyl-1H-pyrazol-4-yl)methyl]piperidin-3-yl}-5,6,7,8-tetrahydroquinazolin-2-amine,

(40) 4-azepan-1-yl-N-piperidin-3-yl-5,6,7,8-tetrahydroquinazolin-2-amine,

(41) $N^1$-(4-azepan-1-yl-5,6,7,8-tetrahydroquinazolin-2-yl)-$N^2$-methylcyclohexane-1,2-diamine,

(42) $N^1$-(4-azepan-1-yl-5,6,7,8-tetrahydroquinazolih-2-yl)-$N^2$-(2-ethylbutyl)cyclohexane-1,2-diamine,

(43) $N^3$-(4-azepan-1-yl-5,6,7,8-tetrahydroquinazolin-2-yl)-$N^2$-nonylpiperidine-2,3-diamine,

(44) $N^3$-(4-azepan-1-yl-5,6,7,8-tetrahydroquinazolin-2-yl)-$N^2$-[2-(methylsulfanyl)ethyl]piperidin-2,3-diamine,

(45) $N^3$-(4-azepan-1-yl-5,6,7,8-tetrahydroquinazolin-2-yl)-$N^2$-benzylpiperidine-2,3-diamine,

(46) $N^3$-(4-azepan-1-yl-5,6,7,8-tetrahydroquinazolin-2-yl)-$N^2$-{4-[3-(dimethylamino)propoxy]benzyl}piperidin-2,3-diamine,

(47) $N^3$-(4-azepan-1-yl-5,6,7,8-tetrahydroquinazolin-2-yl)-$N^2$-[(3-phenyl-1H-pyrazol-4-yl)methyl]piperidine-2,3-diamine,

(48) N-(4-azepan-1-yl-5,6,7,8-tetrahydroquinazolin-2-yl)cyclohexane-1,2-diamine,

(49) $N^1$-(4-azepan-1-yl-5,6,7,8-tetrahydroquinazolin-2-yl)-$N^2$-methylcyclopentane-1,2-diamine,

(50) $N^1$-(4-azepan-1-yl-5,6,7,8-tetrahydroquinazolin-2-yl)-$N^2$-(2-ethylbutyl)cyclopentane-1,2-diamine,

(51) $N^1$-(4-azepan-1-yl-5,6,7,8-tetrahydroquinazolin-2-yl)-$N^2$-nonylcyclopentane-1,2-diamine,

(52) $N^1$-(4-azepan-1-yl-5,6,7,8-tetrahydroquinazolin-2-yl)-$N^2$-[2-(methylsulfanyl)ethyl]cyclopentane-1,2-diamine,

(53) $N^1$-(4-azepan-1-yl-5,6,7,8-tetrahydroquinazolin-2-yl)-$N^2$-benzylcyclopentane-1,2-diamine,

(54) $N^1$-(4-azepan-1-yl-5,6,7,8-tetrahydroquinazolih-2-yl)-$N^2$-{4-[3-(dimethylamino)propoxy]benzyl}cyclopentane-1,2-diamine,

(55) $N^1$-(4-azepan-1-yl-5,6,7,8-tetrahydroquinazolin-2-yl)-$N^2$-[(3-phenyl-1H-pyrazol-4-yl)methyl]cyclopentane-1,2-diamine,

(56) N-(4-azepan-1-yl-5,6,7,8-tetrahydroquinazolin-2-yl)cyclopentane-1,2-diamine,

(57) $N^1$-(4-azepan-1-yl-5,6,7,8-tetrahydropyrido[4,3-d]pyrimidin-2-yl)-$N^2$,$N^2$-dimethylethane-1,2-diamine,

(58) $N^1$-(4-azepan-1-yl-5,6,7,8-tetrahydropyrido[4,3-d]pyrimidin-2-yl)-$N^2$-(2-ethylbutyl)-$N^2$-methylethane-1,2-diamine,

(59) $N^1$-(4-azepan-1-yl-5,6,7,8-tetrahydropyrido[4,3-d]pyrimidin-2-yl)-$N^2$-methyl-$N^2$-nonylethane-1,2-diamine,

(60) $N^1$-(4-azepan-1-yl-5,6,7,8-tetrahydropyrido[4,3-d]pyrimidin-2-yl)-$N^2$-methyl-$N^2$-[2-(methylsulfanyl)ethyl]ethane-1,2-diamine,

(61) $N^1$-(4-azepan-1-yl-5,6,7,8-tetrahydropyrido[4,3-d]pyrimidin-2-yl)-$N^2$-benzyl-$N^2$-methylethane-1,2-diamine,

(62) $N^1$-(4-azepan-1-yl-5,6,7,8-tetrahydropyrido[4,3-d]pyrimidin-2-yl)-$N^2$-{4-[3-(dimethylamino)propoxy]benzyl}-$N^2$-methylethane-1,2-diamine,

(63) $N^1$-(4-azepan-1-yl-5,6,7,8-tetrahydropyrido[4,3-d]pyrimidin-2-yl)-$N^2$-methyl-$N^2$-[(3-phenyl-1H-pyrazol-4-yl)methyl]ethane-1,2-diamine,

(64) $N^1$-(4-azepan-1-yl-5,6,7,8-tetrahydropyrido[4,3-d]pyrimidin-2-yl)-$N^2$-methylethane-1,2-diamine,

(65) 4-azepan-1-yl-N-[(1-methylpyrrolidin-2-yl)methyl]-5,6,7,8-tetrahydropyrido[4,3-d]pyrimidin-2-amine,

(66) 4-azepan-1-yl-N-{[1-(2-ethylbutyl)pyrrolidin-2-yl]methyl}-5,6,7,8-tetrahydropyrido[4,3-d]pyrimidin-2-amine,
(67) 4-azepan-1-yl-N-[(1-nonylpyrrolidin-2-yl)methyl]-5,6,7,8-tetrahydropyrido[4,3-d]pyrimidin-2-amine,
(68) 4-azepan-1-yl-N-({1-[2-(methylsulfanyl)ethyl]pyrrolidin-2-yl}methyl)-5,6,7,8-tetrahydropyrido[4,3-d]pyrimidin-2-amine,
(69) 4-azepan-1-yl-N-[(1-benzylpyrrolidin-2-yl)methyl]-5,6,7,8-tetrahydropyrido[4,3-d]pyrimidin-2-amine,
(70) 4-azepan-1-yl-N-[(1-{4-[3-(dimethylamino)propoxy]benzyl}pyrrolidin-2-yl)methyl]-5,6,7,8-tetrahydropyrido[4,3-d]pyrimidin-2-amine,
(71) 4-azepan-1-yl-N-({1-[(3-phenyl-1H-pyrazol-4-yl)methyl]pyrrolidin-2-yl}methyl)-5,6,7,8-tetrahydropyrido[4,3-d]pyrimidin-2-amine,
(72) 4-azepan-1-yl-N-(pyrrolidin-2-ylmethyl)-5,6,7,8-tetrahydropyrido[4,3-d]pyrimidin-2-amine,
(73) 4-azepan-1-yl-N-[(1-methylpiperidin-2-yl)methyl]-5,6,7,8-tetrahydropyrido[4,3-d]pyrimidin-2-amine,
(74) 4-azepan-1-yl-N-{[1-(2-ethylbutyl)piperidin-2-yl]methyl}-5,6,7,8-tetrahydropyrido[4,3-d]pyrimidin-2-amine,
(75) 4-azepan-1-yl-N-[(1-nonylpiperidin-2-yl)methyl]-5,6,7,8-tetrahydropyrido[4,3-d]pyrimidin-2-amine,
(76) 4-azepan-1-yl-N-({1-[2-(methylsulfanyl)ethyl]piperidin-2-yl}methyl)-5,6,7,8-tetrahydropyrido[4,3-d]pyrimidin-2-amine,
(77) 4-azepan-1-yl-N-[(1-benzylpiperidin-2-yl)methyl]-5,6,7,8-tetrahydropyrido[4,3-d]pyrimidin-2-amine,
(78) 4-azepan-1-yl-N-[(1-{4-[3-(dimethylamino)propoxy]benzyl}piperidin-2-yl)methyl]-5,6,7,8-tetrahydropyrido[4,3-d]pyrimidin-2-amine,
(79) 4-azepan-1-yl-N-({1-[(3-phenyl-1H-pyrazol-4-yl)methyl]piperidin-2-yl}methyl)-5,6,7,8-tetrahydropyrido[4,3-d]pyrimidin-2-amine,
(80) 4-azepan-1-yl-N-(piperidin-2-ylmethyl)-5,6,7,8-tetrahydropyrido[4,3-d]pyrimidin-2-amine,
(81) 4-azepan-1-yl-N-(1-methylpyrrolidin-3-yl)-5,6,7,8-tetrahydropyrido[4,3-d]pyrimidin-2-amine,
(82) 4-azepan-1-yl-N-[1-(2-ethylbutyl)pyrrolidin-3-yl]-5,6,7,8-tetrahydropyrido[4,3-d]pyrimidin-2-amine,
(83) 4-azepan-1-yl-N-(1-nonylpyrrolidin-3-yl)-5,6,7,8-tetrahydropyrido[4,3-d]pyrimidin-2-amine,
(84) 4-azepan-1-yl-N-{1-[2-(methylsulfanyl)ethyl]pyrrolidin-3-yl}-5,6,7,8-tetrahydropyrido[4,3-d]pyrimidin-2-amine,
(85) 4-azepan-1-yl-N-(1-benzylpyrrolidin-3-yl)-5,6,7,8-tetrahydropyrido[4,3-d]pyrimidin-2-amine,
(86) 4-azepan-1-yl-N-(1-{4-[3-(dimethylamino)propoxy]benzyl}pyrrolidin-3-yl)-5,6,7,8-tetrahydropyrido[4,3-d]pyrimidin-2-amine,
(87) 4-azepan-1-yl-N-{1-[(3-phenyl-1H-pyrazol-4-yl)methyl]pyrrolidin-3-yl}-5,6,7,8-tetrahydropyrido[4,3-d]pyrimidin-2-amine,
(88) 4-azepan-1-yl-N-pyrrolidin-3-yl-5,6,7,8-tetrahydropyrido[4,3-d]pyrimidin-2-amine,
(89) 4-azepan-1-yl-N-(1-methylpiperidin-3-yl)-5,6,7,8-tetrahydropyrido[4,3-d]pyrimidin-2-amine,
(90) 4-azepan-1-yl-N-[1-(2-ethylbutyl)piperidin-3-yl]-5,6,7,8-tetrahydropyrido[4,3-d]pyrimidin-2-amine,
(91) 4-azepan-1-yl-N-(1-nonylpiperidin-3-yl)-5,6,7,8-tetrahydropyrido[4,3-d]pyrimidin-2-amine,
(92) 4-azepan-1-yl-N-{1-[2-(methylsulfanyl)ethyl]piperidin-3-yl}-5,6,7,8-tetrahydropyrido[4,3-d]pyrimidin-2-amine,
(93) 4-azepan-1-yl-N-(1-benzylpiperidin-3-yl)-5,6,7,8-tetrahydropyrido[4,3-d]pyrimidin-2-amine,
(94) 4-azepan-1-yl-N-(1-{4-[3-(dimethylamino)propoxy]benzyl}piperidin-3-yl)-5,6,7,8-tetrahydropyrido[4,3-d]pyrimidin-2-amine,
(95) 4-azepan-1-yl-N-{1-[(3-phenyl-1H-pyrazol-4-yl)methyl]piperidin-3-yl}-5,6,7,8-tetrahydropyrido[4,3-d]pyrimidin-2-amine,
(96) 4-azepan-1-yl-N-piperidin-3-yl-5,6,7,8-tetrahydropyrido[4,3-d]pyrimidin-2-amine,
(97) $N^1$-(4-azepan-1-yl-5,6,7,8-tetrahydropyrido[4,3-d]pyrimidin-2-yl)-$N^2$-methylcyclohexane-1,2-diamine,
(98) $N^1$-(4-azepan-1-yl-5,6,7,8-tetrahydropyrido[4,3-d]pyrimidin-2-yl)-$N^2$-(2-ethylbutyl)cyclohexane-1,2-diamine,
(99) $N^3$-(4-azepan-1-yl-5,6,7,8-tetrahydropyrido[4,3-d]pyrimidin-2-yl)-$N^2$-nonylpiperidine-2,3-diamine,
(100) $N^3$-(4-azepan-1-yl-5,6,7,8-tetrahydropyrido[4,3-d]pyrimidin-2-yl)-$N^2$-[2-(methylsulfanyl)ethyl]piperidine-2,3-diamine,
(101) $N^3$-(4-azepan-1-yl-5,6,7,8-tetrahydropyrido[4,3-d]pyrimidin-2-yl)-$N^2$-benzylpiperidine-2,3-diamine,
(102) $N^3$-(4-azepan-1-yl-5,6,7,8-tetrahydropyrido[4,3-d]pyrimidin-2-yl)-$N^2$-{4-[3-(dimethylamino)propoxy]benzyl}piperidine-2,3-diamine,
(103) $N^3$-(4-azepan-1-yl-5,6,7,8-tetrahydropyrido[4,3-d]pyrimidin-2-yl)-$N^2$-[(3-phenyl-1H-pyrazol-4-yl)methyl]piperidine-2,3-diamine,
(104) N-(4-azepan-1-yl-5,6,7,8-tetrahydropyrido[4,3-d]pyrimidin-2-yl)cyclohexane-1,2-diamine,
(105) $N^1$-(4-azepan-1-yl-5,6,7,8-tetrahydropyrido[4,3-d]pyrimidin-2-yl)-$N^2$-methylcyclopentane-1,2-diamine,
(106) $N^1$-(4-azepan-1-yl-5,6,7,8-tetrahydropyrido[4,3-d]pyrimidin-2-yl)-$N^2$-(2-ethylbutyl)cyclopentane-1,2-diamine,
(107) $N^1$-(4-azepan-1-yl-5,6,7,8-tetrahydropyrido[4,3-d]pyrimidin-2-yl)-$N^2$-nonylcyclopentane-1,2-diamine,
(108) $N^1$-(4-azepan-1-yl-5,6,7,8-tetrahydropyrido[4,3-d]pyrimidin-2-yl)-$N^2$-[2-(methylsulfanyl)ethyl]cyclopentane-1,2-diamine,
(109) $N^1$-(4-azepan-1-yl-5,6,7,8-tetrahydropyrido[4,3-d]pyrimidin-2-yl)-$N^2$-benzylcyclopentane-1,2-diamine,
(110) $N^1$-(4-azepan-1-yl-5,6,7,8-tetrahydropyrido[4,3-d]pyrimidin-2-yl)-$N^2$-{4-[3-(dimethylamino)propoxy]benzyl}cyclopentane-1,2-diamine,
(111) $N^1$-(4-azepan-1-yl-5,6,7,8-tetrahydropyrido[4,3-d]pyrimidin-2-yl)-$N^2$-[(3-phenyl-1H-pyrazol-4-yl)methyl]cyclopentane-1,2-diamine,
(112) N-(4-azepan-1-yl-5,6,7,8-tetrahydropyrido[4,3-d]pyrimidin-2-yl)cyclopentane-1,2-diamine,
(113) $N^1$-(4-azepan-1-yl-6,7-dihydro-5H-cyclopenta[d]pyrimidin-2-yl)-$N^2$,$N^2$-dimethylethane-1,2-diamine,
(114) $N^1$-(4-azepan-1-yl-6,7-dihydro-5H-cyclopenta[d]pyrimidin-2-yl)-$N^2$-(2-ethylbutyl)-$N^2$-methylethane-1,2-diamine,
(115) $N^1$-(4-azepan-1-yl-6,7-dihydro-5H-cyclopenta[d]pyrimidin-2-yl)-$N^2$-methyl-$N^2$-nonylethane-1,2-diamine,
(116) $N^1$-(4-azepan-1-yl-6,7-dihydro-5H-cyclopenta[d]pyrimidin-2-yl)-$N^2$-methyl-$N^2$-[2-(methylsulfanyl)ethyl]ethane-1,2-diamine,
(117) $N^1$-(4-azepan-1-yl-6,7-dihydro-5H-cyclopenta[d]pyrimidin-2-yl)-$N^2$-benzyl-$N^2$-methylethane-1,2-diamine,
(118) $N^1$-(4-azepan-1-yl-6,7-dihydro-5H-cyclopenta[d]pyrimidin-2-yl)-$N^2$-{4-[3-(dimethylamino)propoxy]benzyl}-$N^2$-methylethane-1,2-diamine,
(119) $N^1$-(4-azepan-1-yl-6,7-dihydro-5H-cyclopenta[d]pyrimidin-2-yl)-$N^2$-methyl-$N^2$-[(3-phenyl-1H-pyrazol-4-yl)methyl]ethane-1,2-diamine,
(120) $N^1$-(4-azepan-1-yl-6,7-dihydro-5H-cyclopenta[d]pyrimidin-2-yl)-$N^2$-methylethane-1,2-diamine, (121) 4-azepan-1-yl-N-[(1-methylpyrrolidin-2-yl)methyl]-6,7-dihydro-5H-cyclopenta[d]pyrimidin-2-amine,
(122) 4-azepan-1-yl-N-{[1-(2-ethylbutyl)pyrrolidin-2-yl]methyl}-6,7-dihydro-5H-cyclopenta[d]pyrimidin-2-amine,
(123) 4-azepan-1-yl-N-[(1-nonylpyrrolidin-2-yl)methyl]-6,7-dihydro-5H-cyclopenta[d]pyrimidin-2-amine,
(124) 4-azepan-1-yl-N-({1-[2-(methylsulfanyl)ethyl]pyrrolidin-2-yl}methyl)-6,7-dihydro-5H-cyclopenta[d]pyrimidin-2-amine,
(125) 4-azepan-1-yl-N-[(1-benzylpyrrolidin-2-yl)methyl]-6,7-dihydro-5H-cyclopenta[d]pyrimidin-2-amine,
(126) 4-azepan-1-yl-N-[(1-{4-[3-(dimethylamino)propoxy]benzyl}pyrrolidin-2-yl)methyl]-6,7-dihydro-5H-cyclopenta[d]pyrimidin-2-amine,
(127) 4-azepan-1-yl-N-({1-[(3-phenyl-1H-pyrazol-4-yl)methyl]pyrrolidin-2-yl}methyl)-6,7-dihydro-5H-cyclopenta[d]pyrimidin-2-amine,
(128) 4-azepan-1-yl-N-(pyrrolidin-2-ylmethyl)-6,7-dihydro-5H-cyclopenta[d]pyrimidin-2-amine,
(129) 4-azepan-1-yl-N-[(1-methylpiperidin-2-yl)methyl]-6,7-dihydro-5H-cyclopenta[d]pyrimidin-2-amine,
(130) 4-azepan-1-yl-N-{[1-(2-ethylbutyl)piperidin-2-yl]methyl}-6,7-dihydro-5H-cyclopenta[d]pyrimidin-2-amine,
(131) 4-azepan-1-yl-N-[(1-nonylpiperidin-2-yl)methyl]-6,7-dihydro-5H-cyclopenta[d]pyrimidin-2-amine,
(132) 4-azepan-1-yl-N-({1-[2-(methylsulfanyl)ethyl]piperidin-2-yl}methyl)-6,7-dihydro-5H-cyclopenta[d]pyrimidin-2-amine,
(133) 4-azepan-1-yl-N-[(1-benzylpiperidin-2-yl)methyl]-6,7-dihydro-5H-cyclopenta[d]pyrimidin-2-amine,
(134) 4-azepan-1-yl-N-[(1-{4-[3-(dimethylamino)propoxy]benzyl}piperidin-2-yl)methyl]-6,7-dihydro-5H-cyclopenta[d]pyrimidin-2-amine,
(135) 4-azepan-1-yl-N-({1-[(3-phenyl-1H-pyrazol-4-yl)methyl]piperidin-2-yl}methyl)-6,7-dihydro-5H-cyclopenta[d]pyrimidin-2-amine,
(136) 4-azepan-1-yl-N-(piperidin-2-ylmethyl)-6,7-dihydro-5H-cyclopenta[d]pyrimidin-2-amine,
(137) 4-azepan-1-yl-N-(1-methylpyrrolidin-3-yl)-6,7-dihydro-5H-cyclopenta[d]pyrimidin-2-amine,
(138) 4-azepan-1-yl-N-[1-(2-ethylbutyl)pyrrolidin-3-yl]-6,7-dihydro-5H-cyclopenta[d]pyrimidin-2-amine,
(139) 4-azepan-1-yl-N-(1-nonylpyrrolidin-3-yl)-6,7-dihydro-5H-cyclopenta[d]pyrimidin-2-amine,
(140) 4-azepan-1-yl-N-{1-[2-(methylsulfanyl)ethyl]pyrrolidin-3-yl}-6,7-dihydro-5H-cyclopenta[d]pyrimidin-2-amine,
(141) 4-azepan-1-yl-N-(1-benzylpyrrolidin-3-yl)-6,7-dihydro-5H-cyclopenta[d]pyrimidin-2-amine,
(142) 4-azepan-1-yl-N-(1-{4-[3-(dimethylamino)propoxy]benzyl}pyrrolidin-3-yl)-6,7-dihydro-5H-cyclopenta[d]pyrimidin-2-amine,
(143) 4-azepan-1-yl-N-{1-[(3-phenyl-1H-pyrazol-4-yl)methyl]pyrrolidin-3-yl}-6,7-dihydro-5H-cyclopenta[d]pyrimidin-2-amine,
(144) 4-azepan-1-yl-N-pyrrolidin-3-yl-6,7-dihydro-5H-cyclopenta[d]pyrimidin-2-amine,
(145) 4-azepan-1-yl-N-(1-methylpiperidin-3-yl)-6,7-dihydro-5H-cyclopenta[d]pyrimidin-2-amine,
(146) 4-azepan-1-yl-N-[1-(2-ethylbutyl)piperidin-3-yl]-6,7-dihydro-5H-cyclopenta[d]pyrimidin-2-amine,
(147) 4-azepan-1-yl-N-(1-nonylpiperidin-3-yl)-6,7-dihydro-5H-cyclopenta[d]pyrimidin-2-amine,
(148) 4-azepan-1-yl-N-{1-[2-(methylsulfanyl)ethyl]piperidin-3-yl}-6,7-dihydro-5H-cyclopenta[d]pyrimidin-2-amine,
(149) 4-azepan-1-yl-N-(1-benzylpiperidin-3-yl)-6,7-dihydro-5H-cyclopenta[d]pyrimidin-2-amine,
(150) 4-azepan-1-yl-N-(1-{4-[3-(dimethylamino)propoxy]benzyl}piperidin-3-yl)-6,7-dihydro-5H-cyclopenta[d]pyrimidin-2-amine,
(151) 4-azepan-1-yl-N-{1-[(3-phenyl-1H-pyrazol-4-yl)methyl]piperidin-3-yl}-6,7-dihydro-5H-cyclopenta[d]pyrimidin-2-amine,
(152) 4-azepan-1-yl-N-piperidin-3-yl-6,7-dihydro-5H-cyclopenta[d]pyrimidin-2-amine,
(153) $N^1$-(4-azepan-1-yl-6,7-dihydro-5H-cyclopenta[d]pyrimidin-2-yl)-$N^2$-methylcyclohexane-1,2-diamine,
(154) $N^1$-(4-azepan-1-yl-6,7-dihydro-5H-cyclopenta[d]pyrimidin-2-yl)-$N^2$-(2-ethylbutyl)cyclohexane-1,2-diamine,
(155) $N^3$-(4-azepan-1-yl-6,7-dihydro-5H-cyclopenta[d]pyrimidin-2-yl)-$N^2$-nonylpiperidine-2,3-diamine,
(156) $N^3$-(4-azepan-1-yl-6,7-dihydro-5H-cyclopenta[d]pyrimidin-2-yl)-$N^2$-[2-(methylsulfanyl)ethyl]piperidine-2,3-diamine,
(157) $N^3$-(4-azepan-1-yl-6,7-dihydro-5H-cyclopenta[d]pyrimidin-2-yl)-$N^2$-benzylpiperidine-2,3-diamine,
(158) $N^3$-(4-azepan-1-yl-6,7-dihydro-5H-cyclopenta[d]pyrimidin-2-yl)-$N^2$-{4-[3-(dimethylamino)propoxy]benzyl}piperidine-2,3-diamine,
(159) $N^3$-(4-azepan-1-yl-6,7-dihydro-5H-cyclopenta[d]pyrimidin-2-yl)-$N^2$-[(3-phenyl-1H-pyrazol-4-yl)methyl]piperidine-2,3-diamine,
(160) N-(4-azepan-1-yl-6,7-dihydro-5H-cyclopenta[d]pyrimidin-2-yl)cyclohexane-1,2-diamine,
(161) $N^1$-(4-azepan-1-yl-6,7-dihydro-5H-cyclopenta[d]pyrimidin-2-yl)-$N^2$-methylcyclopentane-1,2-diamine,
(162) $N^1$-(4-azepan-1-yl-6,7-dihydro-5H-cyclopenta[d]pyrimidin-2-yl)-$N^2$-(2-ethylbutyl)cyclopentane-1,2-diamine,
(163) $N^1$-(4-azepan-1-yl-6,7-dihydro-5H-cyclopenta[d]pyrimidin-2-yl)-$N^2$-nonylcyclopentane-1,2-diamine,
(164) $N^1$-(4-azepan-1-yl-6,7-dihydro-5H-cyclopenta[d]pyrimidin-2-yl)-$N^2$-[2-(methylsulfanyl)ethyl]cyclopentane-1,2-diamine,
(165) $N^1$-(4-azepan-1-yl-6,7-dihydro-5H-cyclopenta[d]pyrimidin-2-yl)-$N^2$-benzylcyclopentane-1,2-diamine,
(166) $N^1$-(4-azepan-1-yl-6,7-dihydro-5H-cyclopenta[d]pyrimidin-2-yl)-$N^2$-{4-[3-(dimethylamino)propoxy]benzyl}cyclopentane-1,2-diamine,
(167) $N^1$-(4-azepan-1-yl-6,7-dihydro-5H-cyclopenta[d]pyrimidin-2-yl)-$N^2$-[(3-phenyl-1H-pyrazol-4-yl)methyl]cyclopentane-1,2-diamine,
(168) N-(4-azepan-1-yl-6,7-dihydro-5H-cyclopenta[d]pyrimidin-2-yl)cyclopentane-1,2-diamine,
(169) $N^1$-(4-azepan-1-yl-6,7,8,9-tetrahydro-5H-cyclohepta[d]pyrimidin-2-yl)-$N^2$,$N^2$-dimethylethane-1,2-diamine,
(170) $N^1$-(4-azepan-1-yl-6,7,8,9-tetrahydro-5H-cyclohepta[d]pyrimidin-2-yl)-$N^2$-(2-ethylbutyl)-$N^2$-methylethane-1,2-diamine,
(171) $N^1$-(4-azepan-1-yl-6,7,8,9-tetrahydro-5H-cyclohepta[d]pyrimidin-2-yl)-$N^2$-methyl-$N^2$-nonylethane-1,2-diamine,
(172) $N^1$-(4-azepan-1-yl-6,7,8,9-tetrahydro-5H-cyclohepta[d]pyrimidin-2-yl)-$N^2$-methyl-$N^2$-[2-(methylsulfanyl)ethyl]ethane-1,2-diamine,
(173) $N^1$-(4-azepan-1-yl-6,7,8,9-tetrahydro-5H-cyclohepta[d]pyrimidin-2-yl)-$N^2$-benzyl-$N^2$-methylethane-1,2-diamine,
(174) $N^1$-(4-azepan-1-yl-6,7,8,9-tetrahydro-5H-cyclohepta[d]pyrimidin-2-yl)-$N^2$-{4-[3-(dimethylamino)propoxy]benzyl}-$N^2$-methylethane-1,2-diamine, (175) N$^1$-(4-azepan-1-yl-6,7,8,9-tetrahydro-5H-cyclohepta[d]pyrimidin-2-yl)-N$^2$-methyl-N$^2$-[(3-phenyl-1H-pyrazol-4-yl)methyl]ethane-1,2-diamine,
(176) N$^1$-(4-azepan-1-yl-6,7,8,9-tetrahydro-5H-cyclohepta[d]pyrimidin-2-yl)-N$^2$-methylethane-1,2-diamine,
(177) 4-azepan-1-yl-N-[(1-methylpyrrolidin-2-yl)methyl]-6,7,8,9-tetrahydro-5H-cyclohepta[d]pyrimidin-2-amine,
(178) 4-azepan-1-yl-N-{[1-(2-ethylbutyl)pyrrolidin-2-yl]methyl}-6,7,8,9-tetrahydro-5H-cyclohepta[d]pyrimidin-2-amine,
(179) 4-azepan-1-yl-N-[(1-nonylpyrrolidin-2-yl)methyl]-6,7,8,9-tetrahydro-5H-cyclohepta[d]pyrimidin-2-amine,
(180) 4-azepan-1-yl-N-({1-[2-(methylsulfanyl)ethyl]pyrrolidin-2-yl}methyl)-6,7,8,9-tetrahydro-5H-cyclohepta[d]pyrimidin-2-amine,
(181) 4-azepan-1-yl-N-[(1-benzylpyrrolidin-2-yl)methyl]-6,7,8,9-tetrahydro-5H-cyclohepta[d]pyrimidin-2-amine,
(182) 4-azepan-1-yl-N-[(1-{4-[3-(dimethylamino)propoxy]benzyl}pyrrolidin-2-yl)methyl]-6,7,8,9-tetrahydro-5H-cyclohepta[d]pyrimidin-2-amine,
(183) 4-azepan-1-yl-N-({1-[(3-phenyl-1H-pyrazol-4-yl)methyl]pyrrolidin-2-yl}methyl)-6,7,8,9-tetrahydro-5H-cyclohepta[d]pyrimidin-2-amine,
(184) 4-azepan-1-yl-N-(pyrrolidin-2-ylmethyl)-6,7,8,9-tetrahydro-5H-cyclohepta[d]pyrimidin-2-amine,
(185) 4-azepan-1-yl-N-[(1-methylpiperidin-2-yl)methyl]-6,7,8,9-tetrahydro-5H-cyclohepta[d]pyrimidin-2-amine,
(186) 4-azepan-1-yl-N-{[1-(2-ethylbutyl)piperidin-2-yl]methyl}-6,7,8,9-tetrahydro-5H-cyclohepta[d]pyrimidin-2-amine,
(187) 4-azepan-1-yl-N-[(1-nonylpiperidin-2-yl)methyl]-6,7,8,9-tetrahydro-5H-cyclohepta[d]pyrimidin-2-amine,
(188) 4-azepan-1-yl-N-({1-[2-(methylsulfanyl)ethyl]piperidin-2-yl}methyl)-6,7,8,9-tetrahydro-5H-cyclohepta[d]pyrimidin-2-amine,
(189) 4-azepan-1-yl-N-[(1-benzylpiperidin-2-yl)methyl]-6,7,8,9-tetrahydro-5H-cyclohepta[d]pyrimidin-2-amine,
(190) 4-azepan-1-yl-N-[(1-{4-[3-(dimethylamino)propoxy]benzyl}piperidin-2-yl)methyl]-6,7,8,9-tetrahydro-5H-cyclohepta[d]pyrimidin-2-amine,
(191) 4-azepan-1-yl-N-({1-[(3-phenyl-1H-pyrazol-4-yl)methyl]piperidin-2-yl}methyl)-6,7,8,9-tetrahydro-5H-cyclohepta[d]pyrimidin-2-amine,
(192) 4-azepan-1-yl-N-(piperidin-2-ylmethyl)-6,7,8,9-tetrahydro-5H-cyclohepta[d]pyrimidin-2-amine,
(193) 4-azepan-1-yl-N-(1-methylpyrrolidin-3-yl)-6,7,8,9-tetrahydro-5H-cyclohepta[d]pyrimidin-2-amine,
(194) 4-azepan-1-yl-N-[1-(2-ethylbutyl)pyrrolidin-3-yl]-6,7,8,9-tetrahydro-5H-cyclohepta[d]pyrimidin-2-amine,
(195) 4-azepan-1-yl-N-(1-nonylpyrrolidin-3-yl)-6,7,8,9-tetrahydro-5H-cyclohepta[d]pyrimidin-2-amine,
(196) 4-azepan-1-yl-N-{1-[2-(methylsulfanyl)ethyl]pyrrolidin-3-yl}-6,7,8,9-tetrahydro-5H-cyclohepta[d]pyrimidin-2-amine,
(197) 4-azepan-1-yl-N-(1-benzylpyrrolidin-3-yl)-6,7,8,9-tetrahydro-5H-cyclohepta[d]pyrimidin-2-amine,
(198) 4-azepan-1-yl-N-(1-{4-[3-(dimethylamino)propoxy]benzyl}pyrrolidin-3-yl)-6,7,8,9-tetrahydro-5H-cyclohepta[d]pyrimidin-2-amine,
(199) 4-azepan-1-yl-N-{1-[(3-phenyl-1H-pyrazol-4-yl)methyl]pyrrolidin-3-yl}-6,7,8,9-tetrahydro-5H-cyclohepta[d]pyrimidin-2-amine,
(200) 4-azepan-1-yl-N-pyrrolidin-3-yl-6,7,8,9-tetrahydro-5H-cyclohepta[d]pyrimidin-2-amine,
(201) 4-azepan-1-yl-N-(1-methylpiperidin-3-yl)-6,7,8,9-tetrahydro-5H-cyclohepta[d]pyrimidin-2-amine,
(202) 4-azepan-1-yl-N-[1-(2-ethylbutyl)piperidin-3-yl]-6,7,8,9-tetrahydro-5H-cyclohepta[d]pyrimidin-2-amine,
(203) 4-azepan-1-yl-N-(1-nonylpiperidin-3-yl)-6,7,8,9-tetrahydro-5H-cyclohepta[d]pyrimidin-2-amine,
(204) 4-azepan-1-yl-N-{1-[2-(methylsulfanyl)ethyl]piperidin-3-yl}-6,7,8,9-tetrahydro-5H-cyclohepta[d]pyrimidin-2-amine,
(205) 4-azepan-1-yl-N-(1-benzylpiperidin-3-yl)-6,7,8,9-tetrahydro-5H-cyclohepta[d]pyrimidin-2-amine,
(206) 4-azepan-1-yl-N-(1-{4-[3-(dimethylamino)propoxy]benzyl}piperidin-3-yl)-6,7,8,9-tetrahydro-5H-cyclohepta[d]pyrimidin-2-amine,
(207) 4-azepan-1-yl-N-{1-[(3-phenyl-1H-pyrazol-4-yl)methyl]piperidin-3-yl}-6,7,8,9-tetrahydro-5H-cyclohepta[d]pyrimidin-2-amine,
(208) 4-azepan-1-yl-N-piperidin-3-yl-6,7,8,9-tetrahydro-5H-cyclohepta[d]pyrimidin-2-amine,
(209) N$^1$-(4-azepan-1-yl-6,7,8,9-tetrahydro-5H-cyclohepta[d]pyrimidin-2-yl)-N$^2$-methylcyclohexane-1,2-diamine,
(210) N$^1$-(4-azepan-1-yl-6,7,8,9-tetrahydro-5H-cyclohepta[d]pyrimidin-2-yl)-N$^2$-(2-ethylbutyl)cyclohexane-1,2-diamine,
(211) N$^3$-(4-azepan-1-yl-6,7,8,9-tetrahydro-5H-cyclohepta[d]pyrimidin-2-yl)-N$^2$-nonylpiperidine-2,3-diamine,
(212) N$^3$-(4-azepan-1-yl-6,7,8,9-tetrahydro-5H-cyclohepta[d]pyrimidin-2-yl)-N$^2$-[2-(methylsulfanyl)ethyl]piperidine-2,3-diamine,
(213) N$^3$-(4-azepan-1-yl-6,7,8,9-tetrahydro-5H-cyclohepta[d]pyrimidin-2-yl)-N$^2$-benzylpiperidine-2,3-diamine,
(214) N$^3$-(4-azepan-1-yl-6,7,8,9-tetrahydro-5H-cyclohepta[d]pyrimidin-2-yl)-N$^2$-{4-[3-(dimethylamino)propoxy]benzyl}piperidine-2,3-diamine,
(215) N$^3$-(4-azepan-1-yl-6,7,8,9-tetrahydro-5H-cyclohepta[d]pyrimidin-2-yl)-N$^2$-[(3-phenyl-1H-pyrazol-4-yl)methyl]piperidine-2,3-diamine,
(216) N-(4-azepan-1-yl-6,7,8,9-tetrahydro-5H-cyclohepta[d]pyrimidin-2-yl)cyclohexane-1,2-diamine,
(217) N$^1$-(4-azepan-1-yl-6,7,8,9-tetrahydro-5H-cyclohepta[d]pyrimidin-2-yl)-N$^2$-methylcyclopentane-1,2-diamine,
(218) N$^1$-(4-azepan-1-yl-6,7,8,9-tetrahydro-5H-cyclohepta[d]pyrimidin-2-yl)-N$^2$-(2-ethylbutyl)cyclopentane-1,2-diamine,
(219) N$^1$-(4-azepan-1-yl-6,7,8,9-tetrahydro-5H-cyclohepta[d]pyrimidin-2-yl)-N$^2$-nonylcyclopentane-1,2-diamine,
(220) N$^1$-(4-azepan-1-yl-6,7,8,9-tetrahydro-5H-cyclohepta[d]pyrimidin-2-yl)-N$^2$-[2-(methylsulfanyl)ethyl]cyclopentane-1,2-diamine,
(221) N$^1$-(4-azepan-1-yl-6,7,8,9-tetrahydro-5H-cyclohepta[d]pyrimidin-2-yl)-N$^2$-benzylcyclopentane-1,2-diamine,
(222) N$^1$-(4-azepan-1-yl-6,7,8,9-tetrahydro-5H-cyclohepta[d]pyrimidin-2-yl)-N$^2$-{4-[3-(dimethylamino)propoxy]benzyl}cyclopentane-1,2-diamine,
(223) N$^1$-(4-azepan-1-yl-6,7,8,9-tetrahydro-5H-cyclohepta[d]pyrimidin-2-yl)-N$^2$-[(3-phenyl-1H-pyrazol-4-yl)methyl]cyclopentane-1,2-diamine, and
(224) N-(4-azepan-1-yl-6,7,8,9-tetrahydro-5H-cyclohepta[d]pyrimidin-2-yl)cyclopentane-1,2-diamine.

Among the compounds represented by formula (I), more preferable are below-described compounds, salts thereof, N-oxides thereof or solvates thereof, or prodrugs thereof
(1) N-(4-azepan-1-ylpyrimidin-2-yl)ethane-1,2-diamine,
(2) N$^1$-(4-azepan-1-ylpyrimidin-2-yl)-N$^2$,N$^2$-dimethylethane-1,2-diamine,
(3) 4-azepan-1-yl-N-((3 S)-1-cyclohexylpyrrolidin-3-yl)pyrimidin-2-amine,
(4) 4-azepan-1-yl-N-((3 S)-1-benzylpyrrolidin-3-yl)pyrimidin-2-amine, (5) 4-azepan-1-yl-N-[(3S)-1-(2-ethylbutyl)piperidin-3-yl]pyrimidin-2-amine,
(6) 4-azepan-1-yl-N-[(3S)-1-cyclohexylpiperidin-3-yl]pyrimidin-2-amine,
(7) 4-azepan-1-yl-N-[(3S)-1-tetrahydro-2H-pyran-4-ylpiperidin-3-yl]pyrimidin-2-amine,
(8) 4-(3S)-3-[(4-azepan-1-ylpyrimidin-2-yl)amino]piperidin-1-ylcyclohexanol and
(9) (3 S)-N-(4-azepan-1-ylpyrimidin-2-yl)-1'-(cyclohexylcarbonyl)-1,4'-bipiperidin-3 -amine.

Moreover besides the above-described compounds, below-described compounds, salts thereof, N-oxides thereof or solvates thereof, or prodrugs thereof are included as compounds represented by formula (II).
(1) 5-[(3 -azetidin-1-ylphenyl)amino]-1-(2-hydroxycyclohexyl)piperidin-3-ol,
(2) 1-(3-hydroxycyclohexyl)-5-[(6-pyrrolidin-1-ylpyrazin-2-yl)amino]piperidin-3-carboxylic acid,
(3) 1-butyl-5-[(6-piperidin-1-ylpyridin-2-yl)amino]piperidin-2-carboxylic acid,
(4) 3-{[5-(3-hydroxyazepan-1-yl)-1-methyl-1H-pyrrol-2-yl]amino}-1-[4-(hydroxymethyl)cyclohexyl]piperidin-2-carboxylic acid,
(5) 1-[2-({4-hydroxy-1'-[(2-hydroxycyclohexyl)carbonyl]-1,4'-bipiperidin-3-yl}amino)-6-oxo-1,6-dihydropyrimidin-4-yl]proline,
(6) 3-{[1-(3-aminopyrrolidin-1-yl)-2-methyl-6-oxo-1,6-dihydropyrimidin-5-yl]amino}-1'-[(3-hydroxycyclohexyl)carbonyl]-1,3'-bipiperidin-4-carboxylic acid,
(7) 2-(3-{[(4-{3-[(methylamino)carbonyl]piperidin-1-yl}-1,3,5-triazi-2-yl)amino]methyl}piperidin-1-yl)cyclohexanecarboxylic acid,
(8) N-(1-{5-[(2-{1-[3-(hydroxymethyl)cyclohexyl]piperidin-3-yl}ethyl)amino]pyridazin-3-yl}piperidin-4-yl)acetamide,
(9) 3-(3-hydroxy-5-{[(5-{3-[(methylsulfonyl)amino]azetidin-1-yl}pyridazin-3-yl)amino]methyl}piperidin-1-yl)cyclohexanecarboxylic acid,
(10) 1-(2-aminocyclohexyl)-5-[({6-[2-(hydroxymethyl)pyrrolidin-1-yl]pyrimidin-4-yl}amino)methyl]piperidin-3-carboxylic acid,
(11) 2-amino-N-(3-{3-[(4-pyridin-2-ylquinolin-2-yl)amino]pyrrolidin-1-yl}cyclohexyl)cyclohexanecarboxamide,
(12) 1-phenyl-N-[(1-pyridin-3-ylisoquinolin-3-yl)methyl]piperidin-3-amine,
(13) [4-(7-{[6-(4-hydroxyphenyl)pyridin-3-yl]amino}-1H-indol-2-yl)piperidin-1-yl]acetic acid,
(14) 2-(3-{4-[({2-[4-(cyclohexylsulfonyl)-3-methoxyphenyl]pyridin-4-yl}methyl)amino]-1H-indol-3-yl}piperidin-1-yl)-N-methylacetamide,
(15) {5-[4-{[2-(1-methylpiperidin-2-yl)-1,3-benzoxazol-4-yl]amino}-3,4-dihydroisoquinolin-2(1H)-yl]thien-2-yl}(phenyl)methanone,
(16) (6-{[1-({[7-(1-adamantylamino)-1-benzothien-2-yl]amino}methyl)cyclohexyl]amino}pyridin-3-yl)(thien-2-yl)methanone,
(17) 4-[3-({6-[(1-hydroxycyclohexyl)methyl]-6-azaspiro[4.5]dec-8-yl}amino)-1-benzothien-4-yl]-N-methylpiperazine-1-carboxamide,
(18) 2-{2-[({5-[4-(methylsulfonyl)piperazin-1-yl]pyrimidin-2-yl}amino)methyl]pyrrolidin-1-yl}-6-phenylnicotinic acid,
(19) N-(1-{[[4-methoxy-4-(1,3-thiazol-2-yl)cyclohexyl](methyl)amino]methyl}cyclopropyl)-4-(5,6,7,8-tetrahydroquinolin-2-yl)-1H-imidazol-2-amine,
(20) 5-(1-methyl-1,2,3,4-tetrahydroquinolin-8-yl)-N-({5-[1-(3,4,5,6-tetrahydropyridin-2-yl)piperidin-4-yl]pyridin-3-yl}methyl)pyrazint-2-amine,
(21) 1-[3-(4-{[4-(3,4-dihydroquinolin-1(2H)-yl)-5-fluoropyrimidin-2-yl]amino}piperidin-1-yl)phenyl]-2,2-dimethylpropan-1-one,
(22) 1-(cyclohexylmethyl)-4-{[methyl(3-{[4-(3,4,5,6-tetrahydropyridin-2-ylamino)phenyl]amino~propyl)amino]methyl}cyclohexanol,
(23) 4-(4-{[4-(4,5,6,7-tetrahydro-1H-1,3-diazepin-2-yl)pyrimidin-2-yl]amino}azepan-1-yl)cyclohexylmethylcarbamate,
(24) 4-(3-{[4-(1-cyanocyclobutyl)pyrimidin-2-yl]amino}azetidin-1-yl)-2-(cyclopentyloxy)benzamide,
(25) 1-({4-[4-({[4-(1-hydroxycyclopentyl)pyrimidin-2-yl]amino}methyl)piperidin-1-yl]tetrahydro-2H-pyran-4-yl}acetyl)piperidin-4-ol,
(26) 1-(2-{[2-(2-tetrahydro-2H-pyran-4-ylpyridin-4-yl)-2-azabicyclo[2.2.2]oct-4-yl]amino}pyrimidin-4-yl)cycloheptanol,
(27) 3-({4-[3-({6-[benzyl(ethyl)amino]pyridazin-3-yl}amino)-8-azabicyclo[3.2.1]oct-8-yl]-4-methylpiperidin-1-yl}carbonyl)phenol,
(28) N-({4-[{2-[(4-azepan-1-yl-5-phenyl-1,3-thiazol-2-yl)amino]ethyl}(methyl)amino]-1-hydroxycyclohexyl}methyl)morpholine-4-carboxamide,
(29) 2-azepan-1-yl-5-{[1'-(pyridin-3-ylmethyl)-1,3'-bipiperidin-4-yl]amino}thiophene-3,4-dicarbonitrile,
(30) 4-({3-[(2-pyrrolidin-1-ylphenyl)amino]pyrrolidin-1-yl}methyl)cyclohexanol,
(31) methyl4-(3-{[6-(3-azabicyclo[3.1.1]hept-3-yl)pyrimidin-4-yl]amino}piperidin-1-yl)butanoate,
(32) [2-({3-[(4-azocan-1-ylpyrimidin-2-yl)amino]azetidin-1-yl}methyl)phenyl](1-methylpiperidin-4-yl)methanone,
(33) N-(6-azonan-1-ylpyrimidin-4-yl)-1-[4-(tetrahydro-2H-pyran-4-yloxy)phenyl]azepan-3-amine,
(34) 2-{(3-[(4-azepan-1-ylquinazolin-2-yl)amino]pyrrolidin-1-yl}-1,3-thiazol-4-carboxamide,
(35) $N^1$-(4-azepan-1-ylthieno[3,2-d]pyrimidin-2-yl)-$N^4$-cyclohexyl-$N^4$-methylbutane-1,4-diamine,
(36) 4-azepan-1-yl-N-(1-cyclopropylpiperidin-3-yl)-1,3-benzothiazol-2-amine,
(37) N-[1-(1-naphthylmethyl)azetidin-3-yl]-4-piperidin-1-yl-5,7-dihydrofuro[3,4-d]pyrimidin-2-amine,
(38) 6-azepan-1-yl-N-[1-(4-phenoxyphenyl)piperidin-4-yl]-9H-purin-2-amine,
(39) 4-azepan-1-yl-N-[1-(2-cyclopentylethyl)azepan-4-yl]-1-methyl-1H-pyrazolo[3,4-d]pyrimidin-6-amine and
(40) N-[4-({3-[(5-azepan-1-ylpyrazin-2-yl)amino]piperidin-1-yl}methyl)phenyl]acetamide.

Processes for the Preparation of the Compound of the Present Invention:

The compound of the present invention can be prepared by a method, such as a method described below, a method according to that, or a method described in Examples. In each method described below, a starting material can be used as a salt thereof. An example of the salt includes a salt of compound of formula (I) described above.

[1] Among a compound represented by formula (I)

(I)

(wherein all symbols have the same meanings as described above.), a compound in which Y is an amino group which may be protected, a hydroxyl group which may be protected or a mercapto group which may be protected, i.e., a compound represented by formula (I-a)

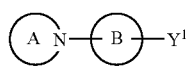
(I-a)

(wherein $Y^1$ is an amino group which may be protected, a hydroxyl group which may be protected or a mercapto group which may be protected and other symbols have the same meanings as described above.) can be prepared by reacting a compound represented formula (IIA)

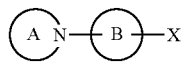
(IIA)

(wherein X is a leaving group such as halogen atom, methanesulfonyloxy (OMs), p-toluenesulfonyloxy (OTs), trifluoromethanesulfonyloxy (OTf), alkylthio, alkylsulfinyl, alkylsulfonyl or hydroxysulfonyl, and other symbols have the same meanings as described above.) with a compound represented formula (III)

(III)

(wherein all symbols have the same meanings as described above.), or reacting a compound represented by formula (IIB)

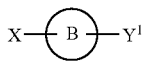
(IIB)

(wherein all symbols have the same meanings as described above.) with a compound represented by formula (IV)

(IV)

(wherein all symbols have the same meanings as described above.).

The reaction of a compound represented by formula (IIA) and a compound represented by formula (III) and the reaction of a compound represented by formula (IIB) and a compound represented by formula (IV) are known and the reactions can be carried out by below described (A) or (B).

(A) It may be carried out in an organic solvent (e.g. N,N-dimethylformamide, N,N-dimethylacetoamide, dimethylsulfoxide, alcohol solvent (methanol, ethanol, benzylalcohol etc.)) or without a solvent at −78 to 200° C.

(B) It may be carried out in an organic solvent (e.g. toluene, benzene) in the presence of a metallic salt (e.g. palladium acetate) and a ligand (e.g. tri(t-butyl)phosphine, dicyclohexyl (2-biphenyl)phosphine, 2,2-bis(diphenylphosphino)-1,1'binaphthyl (BINAP)) by addition of a base (potassium phosphate, potassium carbonate, sodium t-butoxide, sodium hydride, sodium amyl oxide etc.) at −78 to 200° C.

[2] Among a compound represented by formula (I-a), a compound having at least one primary or secondary amino group in ring A, ring B, $Y^1$ or substituents thereof, i.e., a compound represented by formula (I-a')

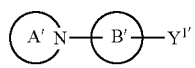
(I-a')

(wherein ring A', ring B' and $Y^{1\prime}$ have the same meanings as ring A, ring B and $Y^1$, respectively, with the proviso that any of those or substituents thereof has at least one primary or secondary amino group.) can be prepared by a deprotection of a compound having at least one primary or secondary amino group which is protected in ring A, ring B, $Y^1$ or substituents thereof among a compound represented by formula (I-a), i.e., a compound represented by formula (I-X)

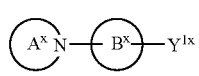
(I-X)

(wherein ring $A^X$, ring $B^X$ and $Y^{1X}$ have the same meanings as ring A, ring B and $Y^1$, respectively, with the proviso that any of those or substituents thereof has at least one primary or secondary amino group which is protected by protecting groups.) protected by protecting groups.

The protective group of amino includes such as benzyloxycarbonyi, tert-butoxycarbonyl, allyloxycarbonyl (Alloc), 1-methyl-1-(4-biphenyl)ethoxycarbonyl (Bpoc), trifluoroacetyl, 9-fluorenylmethoxycarbonyl, benzyl (Bn), p-methoxybenzyl, benzyloxymethyl (BOM) and 2-(trimethylsilyl) ethoxymethyl (SEM) and the like.

With regard to the protective group for amino, there is no particular limitation to the above ones so far as it is a group which is able to be easily and selectively detached. For example, a deprotection reaction may be carried out by a method mentioned in "T. W. Greene, *Protective Groups in Organic Synthesis*, John Wiley & Sons Inc, 1999".

Deprotection reaction of a protective group for amino is known and its examples are as follows.

(1) a hydrolyzing reaction with an alkali;
(2) a deprotection reaction under an acidic condition;
(3) a deprotection reaction by hydrogenolysis; and
(4) a deprotection reaction using metal complex.

Those methods will be specifically illustrated as follows.

(1) A deprotection reaction using an alkali is carried out, for example, at the temperature of 0 to 40° C. using a hydroxide of alkaline metal (such as sodium hydroxide, potassium hydroxide and lithium hydroxide), a hydroxide of alkaline earth metal (such as barium hydroxide and calcium hydroxide), a carbonate (such as sodium carbonate and potassium carbonate), an aqueous solution thereof or a mixture thereof in an organic solvent (such as methanol, tetrahydrofuran and 1,4-dioxane etc. alone, or a mixed solvent containing two or more solvents thereof at an optional ratio).

(2) A deprotection reaction under an acidic condition (e.g. a deprotection of t-butoxycarbonyl or trityl etc.) is carried out, for example, at the temperature of 0 to 100° C. in an organic acid (e.g. acetic acid, trifluoroacetic acid, methanesulfonic acid), an inorganic acid (e.g. hydrochloric acid and sulfuric acid) or a mixture thereof (such as hydrogen bromide/acetic acid) in water or an organic solvent (such as dichloromethane, chloroform, 1,4-dioxane, ethyl acetate and anisole etc.).

(3) A deprotection reaction by hydrogenolysis is carried out, for example, at the temperature of 0 to 200° C. in a hydrogen atmosphere of ordinary pressure or high pressure or in the presence of ammonium formate in the presence of a catalyst (such as palladium-carbon, palladium black, palladium hydroxide, platinum oxide and Raney nickel) in a solvent [such as an ether type (such as tetrahydrofuran, 1,4-dioxane, dimethoxyethane and diethyl ether), an alcohol type (such as methanol and ethanol), a benzene type (such as benzene and toluene), a ketone type (such as acetone and methyl ethyl ketone), a nitrile type (such as acetonitrile), an amide type (such as N,N-dimethylformamide), water, ethyl acetate, acetic acid or a mixed solvent comprising two or more thereof].

(4) A deprotection reaction using a metal complex (e.g. a deprotection of allyloxycarbonyl etc.) is carried out, for example, at the temperature of 0 to 40° C. using a metal complex [such as tetrakistriphenylphosphine palladium (0), bis(triphenylphosphine) palladium (II) dichloride, palladium (II) acetate and tris(triphenylphosphine) rhodium (I) chloride] in the presence or absence of a phosphine agent (such as triphenyl phosphine) in the presence of a trap reagent (such as tributyltin hydride, triethylsilane, dimedone, morpholine, diethylamine and pyrrolidine), an organic acid (such as acetic acid, formic acid and 2-ethylhexanoic acid) and/or an organic acid salt (such as sodium 2-ethylhexanoate and potassium 2-ethylhexanoate) in an organic solvent (such as dichloromethane, N,N-dimethylformamide, tetrahydrofuran, ethyl acetate, acetonitrile, dioxane and ethanol), water or a mixed solvent thereof.

Besides the above-mentioned method, for example, a deprotection reaction may be carried out by a method mentioned in "T. W. Greene, *Protective Groups in Organic Synthesis*, John Wiley & Sons Inc, 1999".

As persons skilled in the art can easily understand that the aimed compound of the present invention is able to be easily produced by using appropriate ones among those deprotection reactions.

The reaction can be followed by conversion to a desired non-toxic salt thereof by a known method, if necessary.

[3] A compound represented by formula (I-a) can be prepared by a reductive amination of a compound represented by formula (I-a') which prepared by the deprotection reaction of protecting groups of amino and corresponding aldehyde or ketone.

The reductive amination is conventionally known and carried out, for example, by reaction at a temperature of from 0 to 100° C. in an inert organic solvent (dichloroethane, dichloromethane, N,N-dimethylformamide, etc. alone, or a mixed solvent containing two or more solvents thereof at an optional ratio) using a reducing agent (sodium triacetoxy-borohydride, sodium cyano-borohydride, tetrabutylammonium borohydride, etc.), in the presence or absence of an organic acid (acetic acid, etc.) or in the presence or absence of a organic base (triethylamine, sodium hydrogencarbonate, etc.).

Among a compound represented by formula (I)

(wherein all symbols have the same meanings as described above.), a compound in which Y is hydrocarbon optionally having substituents or heterocyclic ring optionally having substituents, i.e., a compound represented by formula (I-b)

(wherein M is hydrocarbon optionally having substituents or heterocyclic ring optionally having substituents and other symbols have the same meaning as described above.) can be prepared by reacting a compound represented by formula (IIA)

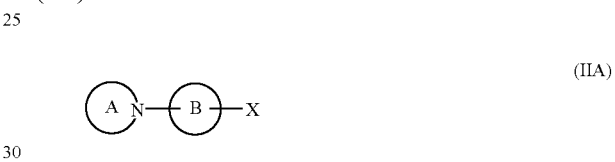

(wherein all symbols have the same meanings as described above.) with a compound represented by formula (V)

(wherein all symbols have the same meanings as described above.). The reaction is known. For example, it may be carried out in organic solvent (e:g. benzene, toluene, N,N-dimethylformamide, 1,4-dioxane, tetrahydrofuran, methanol, acetonitrile, dimethoxyethane, acetone) in presence of a base (sodium ethylate, sodium hydroxide, potassium hydroxide, triethylamine, sodium carbonate, sodium bicarbonate, potassium carbonate, cesium carbonate, thallium carbonate, tripotassium phosphate, cesium fluoride, barium hydroxide, tetrabutylammonium fluoride etc.)) or an aqueous solution thereof, or a mixture thereof, and catalyst (e.g. tetrakis(triphenylphosphine) palladium ($Pd(PPh_3)_4$), dichlorobis(triphenylphosphine) palladium ($PdCl_2(PPh_3)_2$), palladium acetate ($Pd(OAc)_2$), palladium black, 1,1'-bis(diphenylphosphinoferrocene)dichloropalladium ($PdCl_2(dppf)_2$), dichlorodiallyl palladium ($PdCl_2(allyl)_2$), iodophenylbis(triphenylphosphine)palladium ($PhPdI(PPh_3)_2$)) at room temperature to 120° C.

[5] As apparent for those skilled in the art, when a compound represented by formula (I-a) or a compound represented by formula (I-b) has hydroxy, carboxy, amino or mercapto which is not protected, those can be prepared by the reaction described from [1] to [4] and then by a deprotection of protective groups of hydroxy, carboxy, amino or mercapto.

The protective groups of amino are above-described.

The protective group of hydroxy includes, for example, methyl, trityl, methoxymethyl (MOM), 1-ethoxyethyl (EE), methoxyethoxymethyl (MEM), 2-tetrahydropyranyl (THP), trimethylsilyl (TMS), triethylsilyl (TES), t-butyldimethylsilyl (TBDMS), t-butyldiphenylsilyl (TBDPS), acetyl (Ac), pivaloyl, benzoyl, benzyl (Bn), p-methoxybenzyl, allyloxycarbonyl (Alloc), and 2,2,2-trichloroethoxycarbonyl (Troc) etc.

The protective group of mercapto includes, for example, benzyl, methoxybenzyl, methoxymethyl (MOM), 2-tetrahydropyranyl (THP), diphenylmethyl and acetyl (Ac) etc.

The carboxyl-protective group includes, for example, methyl, ethyl, t-butyl, allyl, phenacyl and benzyl etc.

With regard to the protective group for carboxyl, hydroxyl, amino and mercapto, there is no particular limitation to the above ones so far as it is a group which is able to be easily and selectively detached. For example, a deprotection reaction may be carried out by a method mentioned in "T. W. Greene, *Protective Groups in Organic Synthesis*, John Wiley & Sons Inc, 1999".

Deprotection reaction of a protective group for carboxyl, hydroxyl, amino or mercapto is known and its examples are as follows.

(1) a hydrolyzing reaction with an alkali;
(2) a deprotection reaction under an acidic condition;
(3) a deprotection reaction by hydrogenolysis;
(4) a deprotection reaction using metal complex;
(5) a deprotection reaction using an organic metal; and
(6) a deprotection reaction of silyl.

The methods from (1) to (4) can be carried out by above described method and the methods of (5) and (6) will be specifically illustrated as follows.

(5) A deprotection reaction using metal is carried out, for example, at the temperature of 0 to 40° C. with or without ultrasonic wave in the presence of powdery zinc in an acidic solvent (such as acetic acid, a buffer of pH 4.2 to 7.2 and a mixed solution of a solution thereof with an organic solvent such as tetrahydrofuran).

(6) A deprotection reaction of silyl is carried out, for example, at the temperature of 0 to 40° C. using tetrabutylammonium fluoride in an organic solvent miscible with water (such as tetrahydrofuran and acetonitrile etc.).

As persons skilled in the art can easily understand that the aimed compound of the present invention is able to be easily produced by using appropriate ones among those deprotection reactions.

The reaction can be followed by conversion to a desired non-toxic salt thereof by a known method, if necessary.

Besides the above-described methods, the compounds of the invention of formula (I) can be produced by using a combination of Examples described in this description, or the conventionally known methods, for example the methods described in *Comprehensive Organic Transformations: A Guide to Functional Group Preparations*, 2nd Edition (Richard C. Larock, John Willey & Sons Inc, 1999).

In the above-described processes for the preparation, a compound represented by formula (II) can be prepared using a compound represented by formula (VI)

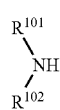

(VI)

(wherein all symbols have the same meanings as described above.) instead of a compound represented by formula (IV)

(wherein all symbols have the same meanings as described above.).

In the present invention, the compounds of formulae (IIA) and (IIB) which are used as the starting material can be prepared by the method described in reaction scheme.

reaction scheme

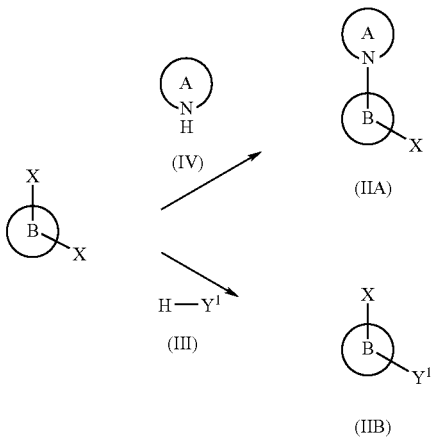

(in the reaction scheme, all symbols have the same meaning as described above.)

The compounds of formulae (III), (IV), (V), (VI) and (VII) used in the present invention are known compounds or can be prepared easily by known methods, for example the methods described in *Comprehensive Organic Transformations: A Guide to Functional Group Preparations,* 2nd Edition (Richard C. Larock, John Willey & Sons Inc, 1999).

In each reaction of the specification, the reactions with heating, as will be apparent to those skilled in the art, it may be carried with water bath, oil bath, sand bath and microwave.

In each reaction of the specification, it may be used a solid phase reagent which is supported by polymer (for example, polystyrene, polyacrylamide, polypropylene or polyethyleneglycol etc.).

In each reaction of the specification, the obtained products may be purified by conventional techniques. For example, the purification may be carried out by distillation at atmospheric or reduced pressure, by high performance liquid chromatography with silica gel or magnesium silicate, by thin layer chromatography, by ion-exchange resin, by scavenger resin, by column chromatography, by washing or by recrystallization. The purification may be done each reaction or after several reactions.

Toxicity:

The toxicity of the compounds of the present invention represented by formulae (I) and (II), salts thereof, N-oxides thereof or solvates thereof, or prodrugs thereof are very low and therefore the compounds may be considered safe for pharmaceutical use.

Application to Pharmaceuticals

Since the compounds of the present invention represented by formulae (I) and (II), salts, N-oxides or solvates thereof, or prodrugs thereof have a CXCR4-regulating effect, they are effective in treatment and prevention, for example, of an inflammatory/immune disease, allergic disease, infectious disease, especially HIV infection and accompanying diseases, psychoneurotic disease, cerebral disease, cardiovascular disease, metabolic disease and cancerous disease. In addition, it is also useful in the in vitro or in vivo amplification of stem cells for a gene therapy as well as in the regeneration medicine for the purpose of peripheral blood stem cell recruitment and tissue repair. Among such a regeneration medicine, it is useful as a transplantation medicine agent employed in bone marrow transplantation, peripheral blood stem cell transplantation and tissue repair.

The inflammatory/immune diseases include, for example, rheumatoid arthritis, arthritis, gout, transplanted organ rejection, graft versus host disease (GVHD), nephritis, psoriasis, rhinitis, conjunctivitis, multiple sclerosis, ulcerative colitis, Crohn's disease, shock accompanied with bacterial infection, pulmonary fibrosis, systemic response syndrome (SIRS), acute pulmonary disorder, diabetes and the like.

The allergic diseases include, for example, asthma, atopic dermatitis, rhinitis, conjunctivitis and the like.

The infectious diseases, especially HIV infection and accompanying diseases, include, for example, acquired immunodeficiency syndrome (AIDS), candidosis, carinii pneumonia, cytomegalovirus retinitis, Kaposi's sarcoma, malignant lymphoma, AIDS encephalopathy, bacterial sepsis and the like.

The psychoneurotic diseases and the cerebral diseases include, for example, dementia such as Alzheimer's disease, Parkinson's disease, cerebral stroke, cerebral infarction, epilepsy, schizophrenia, peripheral nervous disorder and the like.

The cardiovascular diseases include, for example, arteriosclerosis, ischemic reperfusion injury, hypertension, myocardial infarction, angina pectoris, cardiac insufficiency and the like.

The metabolic diseases include, for example, diabetes, osteoporosis, prostatic hypertrophy, pollakiuia and the like.

The cancerous diseases include, for example, mammary cancer, malignant tumor such as malignant lymphoma, cancer metastasis, post-radiotherapy/chemotherapy bone marrow suppression or thrombocytopenia and the like.

The compounds of the present invention of formulae (I) and (II), the salts thereof, the N-oxides thereof or the solvates thereof, or the prodrugs thereof may, be administered as a combined preparation by combining with other pharmaceuticals for the purpose of 1) supplementing and/or enhancing of prevention and/or treatment effect of the compound, 2) improvement in pharmacokinetics and absorption and reduction of dose of the compound, and/or 3) reduction of side effect of the compound.

The combined preparation of the compounds of the present invention of formulae (I) and (II), the salts thereof, the N-oxides thereof or the solvates thereof, or the prodrugs thereof with other pharmaceuticals may be administered in a form of a compounded agent in which both components are compounded in a preparation or may be in a form in which they are administered by means of separate preparations. The case of administration by means of separate preparations includes a simultaneous administration and administrations with time difference. In the case of administrations with time difference, the compound of the present invention of formulae (I) and (II) may be firstly administered followed by administering the other pharmaceutical or the other pharmaceutical may be administered firstly followed by administering the compound of the present invention of formulae (I) and (II). Methods for each of the administration are the same or different.

There is no particular limitation for the diseases showing prevention and/or treatment effect by the above-mentioned combined preparation, so far as it is a disease in which the prevention and/or treatment effect of the compound of present invention of formulae (I) and (II) are supplemented and/or enhanced.

Other agent for preventive and/or treating HIV infection and acquired immunodeficiency syndrome used for a combination with the compounds of the present invention of formulae (I) and (II), the salts thereof, the N-oxides thereof or the solvates thereof, or the prodrugs thereof are reverse transcriptase inhibitor, protease inhibitor, chemokine (such as CCR2, CCR3, CCR4, CCR5 and CXCR4) antagonist, fusion inhibitor, antibody to surface antigen of HIV-1 and vaccine of HIV-1 etc.

Reverse transcriptase inhibitors are concretely (1) nucleoside/nucleotide reverse transcriptase inhibitors: zidovudine (brand name: Retrovir), didanosine (brand name: Videx), zalcitabine (brand name: HIVID), stavudine (brand name: Zerit), lamivudine (brand name: Epivir), abacavir (brand name: Ziagen), adefovir, dipivoxil, emtricitabine (brand name: Coviracil) or Tenofovir (brand name: Viread) etc. and (2) nonnucleoside reverse transcriptase inhibitors: nevirapine (brand name: Viramune), delavirdine (brand name: Rescriptor), efavirenz (brand name: Sustiva, Stocklin) or capravirine (AG1549) etc.

Protease inhibitors are concretely indinavir (brand name: Crixivan), ritonavir (brand name: Norvir), nelfinavir (brand name: Viracept), saquinavir (brand name: Invirase, Fortovase), amprenavir (brand name: Agenerase), lopinavir (brand name: Kaletra) or tipranavir etc.

As chemokine antagonists, internal ligand of chemokine receptor, its derivatives, its non-peptide low molecular compound or antibody of chemokine receptor are included.

The examples of internal ligand of chemokine receptor are concretely, MIP-1α, MIP-1β, RANTES, SDF-1α, SDF-1β, MCP-1, MCP-2, MCP-4, Eotaxin and MDC etc.

The derivatives of internal ligand are concretely, AOP-RANTES, Met-SDF-1α, Met-SDF-1β etc.

Antibodies of chemokine receptor are concretely, Pro-140 etc.

CCR2 antagonists are concretely written in specification of WO99/07351, WO99/40913, WO00/46195, WO00/46196, WO00/46197, WO00/46198, WO00/46199, WO00/69432 or WO00/69815 or in Bioorg. Med. Chem. Lett., 10, 1803 (2000) etc.

CCR3 antagonists are concretely written in specification of DE19837386, WO99/55324, WO99/55330, WO00/04003, WO00/27800, WO00/27835, WO00/27843, WO00/29377, WO00/31032, WO00/31033, WO00/34278, WO00/35449, WO00/35451, WO00/35452, WO00/35453, WO00/35454, WO00/35876, WO00/35877, WO00/41685, WO00/51607, WO00/51608, WO00/51609, WO00/51610, WO00/53172, WO00/53600, WO00/58305, WO00/59497, WO00/59498, WO00/59502, WO00/59503, WO00/62814, WO00/73327 or WO01/09088 etc.

CCR4 antagonists are concretely written in specification of WO02/030357 or WO02/030358 etc.

CCR5 antagonists are concretely TAK-779, TAK-220, SCH-D, SCH-C, compounds written in specification of WO99/17773, WO99/32100, WO00/06085, WO00/06146, WO00/10965, WO00/06153, WO00/21916, WO00/37455, EP1013276, WO00/38680, WO00/39125, WO00/40239, WO00/42045, WO00/53175, WO00/42852, WO00/66551, WO00/66558, WO00/66559, WO00/66141, WO00/68203, JP-A-2000-309598, WO00/51607, WO00/51608, WO00/51609, WO00/51610, WO00/56729, WO00/59497, WO00/59498, WO00/59502, WO00/59503, WO00/76933, WO98/25605 or WO99/04794, WO99/38514 or in *Bioorg. Med. Chem. Lett.*, 10, 1803 (2000) etc.

CXCR4 antagonists are concretely AMD-3100, T-22, KRH-1120, KRH-1636, compounds written in specification of WO00/66112 etc.

Fusion Inhibitors are concretely, T-20 (Pentafuside) and T-1249 etc.

The examples of combination agents written above are intended to illustrate the present invention, but do not limit them.

The typical examples of the usual the dosage level in clinical trials of reverse transcriptase inhibitors or protease inhibitors written below are intended to illustrate the present invention, but do not limit them.

Zidovudine: 100 mg capsule, 200 mg per dose, 3 times per day; 300 mg tablet, 300 mg per dose, twice per day;
didanosine: 25-200 mg tablet, 125-200 mg per dose, twice per day;
zalcitabine: 0.375-0.75 mg tablet, 0.75 mg per dose, 3 times per day;
stavudine: 15-40 mg capsule, 30-40 mg per dose, twice per day;
lamivudine: 150 mg tablet, 150 mg per dose, twice per day;
abacavir: 300 mg tablet, 300 mg per dose, twice per day;
nevirapine: 200 mg tablet, 200 mg per dose, once per day for 14 days and then twice per day;
delavirdine: 100 mg tablet, 400 mg per dose, 3 times per day;
efavirenz: 50-200 mg capsule, 600 mg per dose, once per day;
indinavir: 200-400 mg capsule, 800 mg per dose, 3 times per day;
ritonavir: 100 mg capsule, 600 mg per dose, twice per day;
nelfinavir: 250 mg tablet, 750 mg per dose, 3 times per day;
saquinavir: 200 mg capsule, 1,200 mg per dose, 3 times per day;
amprenavir: 50-150 mg tablet, 1,200 mg per dose, twice per day.

Other drugs for supplementation and/or enhancement of the prophylactic and/or therapeutic effect of the compound represented by formula (I) or (II) on asthma include antihistamines, antiallergic agents (chemotaxis inhibitors, histamine antagonists, thromboxane synthetase inhibitors, thromboxane antagonists, Th2 cytokine inhibitors), steroids, bronchodilators (xanthine derivatives, sympathetic nerve stimulators, parasympathetic nerve blockers), vaccinating agents, gold formulations, Chinese herb medicines, basic nonsteroidal antiinflammatory agents, 5-lipoxygenase inhibitors, 5-lipoxygenase activating protein inhibitors, leukotriene synthesis inhibitors, prostaglandins, cannabinoid-2 receptor stimulators, antitussives, expectorants and the like.

The antihistamines include diphenhydramine, diphenylpyraline hydrochloride, diphenylpyraline teoclate, clemastine fumarate, dimenhydrinate, dl-chlorpheniramine maleate, d-chlorpheniramine maleate, triprolidine hydrochloride, promethazine hydrochloride, alimemazine tartarate, isothipendyl hydrochloride, homochlorcyclizine hydrochloride, hydroxyzine, cyproheptadine hydrochloride, levocabastine hydrochloride, astemizol, bepotastine, desloratadine, TAK-427, ZCR-2060, NIP-530, mometason furoate, mizolastin, BP-294, andolast, auranofin, acribastine and the like.

The chemotaxis inhibitors among antiallergic agents include sodium cromoglicate, tranilast, anlexanox, repirinast, ibudilast, pemirolast potassium, tazanolast, nedocromil, cromogricate, Israpafant and the like.

The histamine antagonists among antiallergic agent include ketotifen fumarate, azelastine hydrochloride, oxatomide, mequitazine, terfenadine, emedastine difumarate, epinastine hydrochloride, ebastine, cetirizine hydrochloride, olopatadine hydrochloride, loratadine, fexofenadine and the like.

The thromboxane synthetase inhibitors among antiallergic agents include, for example, ozagrel hydrochloride, and imitrodast sodium and the like.

Examples of the thromboxane receptor antagonist among antiallergic include seratrodast, ramatroban, domitroban calcium dihydrate, and KT-2-962 and the like.

The Th2 cytokine inhibitors among antiallergic agents include suplatast tosilate and the like.

Examples of the steroids for external application include clobetasol propionate, diflorasone acetate, fluocinonide, mometasone furoate, betamethasone dipropionate, betamethasone butyrate propionate, betamethasone valerate, difluprednate, budesonide, diflucortolone valerate, amcinonide, halcinonide, dexamethasone, dexamethasone propionate, dexamethasone valerate, dexamethasone acetate, hydrocortisone acetate, hydrocortisone butyrate, hydrocortisone butyrate propionate, deprodone propionate, prednisolone valerate acetate, fluocinolone acetonide, beclomethasone dipropionate, triamcinolone acetonide, flumethasone pivalate, alclometasone dipropionate, clobetasone butyrate, beclomethasone propionate, fludroxycortide and the like. The steroid preparations for internal use or injection include cortisone acetate, hydrocortisone, hydrocortisone sodium phosphate, hydrocortisone sodium succinate, fludrocortisone acetate, prednisolone, prednisolone acetate, prednisolone sodium succinate, prednisolone butylacetate, prednisolone sodium phosphate, halopredone acetate, methyl prednisolone, methyl prednisolone acetate, methyl prednisolone sodium succinate, triamcinolone, triamcinolone acetate, triamcinolone acetonide, dexamethasone, dexamethasone acetate, dexamethasone sodium phosphate, dexamethasone palmitate, paramethasone acetate, betamethasone and the like. The steroid preparations as an inhalant include beclomethasone propionate, fluticasone propionate, budesonide, flunisolide, triamcinolone, ST-126P, ciclesonide, dexamethasone palmitate, mometasone furoate, prasterone sulfate, deflazacort, methyl prednisolone sreptanate, methylprednisolone sodium succinate and the like.

The xanthine derivatives among bronchodilators include aminophylline, thoeophyline, doxophylline, cipamfylline, diprophilline, proxyphylline, cholinetheophylline and the like.

The sympathetic nerve stimulators among bronchodilators include epinephrine, ephedrine hydrochloride, 1-methylephedrine hydrochloride, methoxyphenamine hydrochloride, isoproterenol sulfate, isoproterenol hydrochloride, ciprenaline sulfate, clorprenaline hydrochloride, trimetoquinol hydrochloride, salbutamol sulfate, terbutaline sulfate, hexoprenaline sulfate, tulobuterol hydrochloride, procaterol hydrochloride, fenoterol hydrobromide, formoterol fumarate, clenbuterol hydrochloride, mabuterol hydrochloride, salmeterol xinafoate, R,R-formoterol, tulobuterol, pirbuterol hydrochloride, ritodrine hydrochloride, bambuterol, dopexamin hydrochloride, meluadrine tartrate, AR-C68397, levosalbutamol, KUR-1246, KUL-7211, AR-C89855, and S-1319 and the like.

The parasympathetic nerve blockers among bronchodilators include ipratropium bromide, flutropium bromide, oxitropium bromide, cimetropium bromide, temiverine, tiotropium bromide revatropate (UK-112166) and the like.

The vaccinating agents include paspat, asthremedin, broncasma berna, CS-560 and the like.

The gold formulations include sodium gold thiomalate and the like.

The basic nonsteroidal antiinflammatory agents include tiaramide hydrochloride, tinoridine hydrochloride, epirizole, emorfazone and the like.

The 5-lipoxygenase inhibitors include zileuton, docebenone, piripost, SCH-40120, WY-50295, E-6700, ML-3000, TMK-688, ZD-2138, darbufelone mesylate, R-68151, E-6080, DuP-654, SC-45662, CV-6504, NE-11740, CMI-977, NC-2000, E-3040, PD-136095, CMI-392, TZI-41078, Orf-20485, IDB-18024, BF-389, A-78773, TA-270, FLM-5011, CGS-23885, A-79175, ETH-615 etc.

The 5-lipoxygenase activating protein inhibitors include MK-591, MK-886 and the like.

The leukotriene synthesis inhibitors include auranofin, proglumetacin maleate, L-674636, A-81834, UPA-780, A-93178, MK-886, REV-5901A, SCH-40120, MK-591, Bay-x-1005, Bay-y-1015, DTI-0026, amlexanox, E-6700 and the like.

The prostaglandins (hereinafter abbreviated as "PG") include PG receptor agonist, PG receptor antagonist and the like.

The PG receptor include PGE receptors ($EP_1$, $EP_2$, $EP_3$, $EP_4$), PGD receptors (DP, CRTH2), PGF receptors (FP), PGI receptors (IP), TX receptors (TP) and the like.

The antitussive agents include codeine phosphate, dihydrocodeine phosphate, oxymetebanol, dextromethorphan hydrobromide, pentoxyverine citrate, dimemorfan phosphate, oxeladin citrate, cloperastine, benproberine phosphate, clofedanol hydrochloride, fominoben hydrochloride, noscapine, tipemidine hibenzate, eprazinone hydrochloride, plantago herb extract and the like.

The expectorants include foeniculated ammonia spirit, sodium hydrogen carbonate, potassium iodide, bromhexine hydrochloride, a cherry tree skin extract, carbocisteine, fudosteine, ambroxol hydrochloride, ambroxol hydrochloride sustained release capsule, methylcysteine hydrochloride, acetyl cysteine, ethyl L-cysteine hydrochloride, tyloxapol and the like.

Other drugs for supplementation and/or enhancement of the prophylactic and/or therapeutic effect of the compound represented by formulae (I) and (II) on atopic dermatitis (urticaria etc.) include steroids, nonsteroidal anti-inflammatory drugs (NSAID), immunosuppressant agents, prostaglandins, antiallergic agents, mediator releasing depressants, antihistamine drugs, forskolin preparations, phosphodiesterase inhibitors, cannabinoid-2 receptor stimulators and the like.

Other drugs for supplementation and/or enhancement of the prophylactic and/or therapeutic effect of the compound represented by formula (I) on allergic diseases (allergic bronchopulmonary aspergillosis, allergic eosinophilic gastroenteritis and the like) include antiasthmatic agents, inhalation steroids, inhalation β2 stimulants, methylxanthine-based antiasthmatic agents, antiallergic agents, antiinflammatory agents, anticholinergic agents and the like. Those which may also be exemplified include thromboxane antagonists, leukotriene antagonists, LTD4 antagonists, PAF antagonists, phosphodiesterase inhibitors, β2 agonists, steroids, mediator release inhibitors, eosionophile chemotaxis inhibitors, macrolide antibiotics, immunosuppressants, desensitizing (allergen) injection formulations and the like.

The antiasthmatic agents include theophylline, procaterol, ketotifen, azelastine and the like.

The inhalation steroids include beclometasone, fluticasone, budesonide and the like.

The inhalation β2 stimulants include fenoterol, sabutamol, formoterol, salmeterol and the like.

The methylxanthine-based antiasthmatic agents include teophylline and the like.

The antiallergic agents include ketotifen, terfenazine, azelastine, epinastine, suplatast, sodium cromoglicate and the like.

The antiinflammatory agents include diclofenac sodium, ibuprofen, indomethacin and the like.

The anticholinergic agents include ipratropium bromide, flutropium bromide, oxitropium bromide, thiotropium bromide and the like.

The thromboxane antagonists include ozagrel, seratrodast and the like.

The leukotriene antagonists include pranlukas, montelukast, zafirlukast, zileuton and the like.

The macrolide-based antibiotics include erythromycin, roxithromycin and the like.

The immunosuppressants include ciclosporin, tacroimus, FTY720 and the like.

Other drugs for supplementation and/or enhancement of the prophylactic and/or therapeutic effect of the compound represented by formulae (I) and (II) on hepatitis include liver hydrolysate formulations, polyene phosphatidylcholines, glycyrrizin formulations, protoporphyrin sodium, ursodesoxycholic acid, steroids, anticholinergic agents, antacids, propagermanium, lipid peroxidase inhibitors, mitochondorial benzodiazepine receptor antagonists and the like.

Other drugs for supplementation and/or enhancement of the prophylactic and/or therapeutic effect of the compound represented by formulae (I) and (II) on arthritis and rheumatoid arthritis include metalloproteinase inhibitors, immunosuppressants, nonsteroidal anti-inflammatory drugs (NSAID), steroids, prostaglandins, phosphodiesterase inhibitors, cannabinoid-2 receptor stimulants, disease modifying anti-rheumatic drugs (slow-acting anti-rheumatic drug), antiinflammatory enzyme preparations, chondroprotective agents, T-cell inhibitors, TNFα inhibitors, prostaglandin synthase inhibitors, IL-6 inhibitors, interferon gamma agonists, IL-1 inhibitors and the like.

Other drugs for supplementation and/or enhancement of the prophylactic and/or therapeutic effect of the compound represented by formulae (I) and (II) on psoriasis include steroids, vitamin D derivatives and the like.

Other drugs for supplementation and/or enhancement of the prophylactic and/or therapeutic effect of the compound represented by formulae (I) and (II) on rhinitis. include antihistamines, mediator release inhibitors, thoromboxane synthetase inhibitors, thromboxane $A_2$ receptor antagonists, leukotriene receptor antagonists, steroids, α adrenaline receptor stimulants, xanthine derivatives, anticholinergic agents, prostaglandins, nitrogen monoxide synthetase inhibitors, $β_2$ adrenaline receptor stimulants, phosphodiesterase inhibitors, cannabinoid-2 receptor stimulants and the like.

Other drugs for supplementation and/or enhancement of the prophylactic and/or therapeutic effect of the compound represented by formulae (I) and (II) on conjunctivitis include leukotriene receptor antagonists, antihistamines, mediator release inhibitors, nonsteroidal antiinflammatory agents, prostaglandins, steroids, nitrogen monoxide synthetase inhibitors, cannabinoid-2 receptor stimulants and the like.

Other drugs for supplementation and/or enhancement of the prophylactic and/or therapeutic effect of the compound represented by formulae (I) and (II) on multiple sclerosis include immunosuppressants, cannabinoid-2 receptor stimulants and the like.

Other drugs for supplementation and/or enhancement of the prophylactic and/or therapeutic effect of the compound represented by formulae (I) and (II) on ulcerative colitis include mesalazine, salazosulfapyridine, digestive tract ulcer agents, anticholinergic agents, steroids, 5-lipoxygenase inhibitors, antioxidants, LTB4 antagonists, local anesthetics, immunosuppressants, defensive factor promoters, MMP inhibitors, mitochondrual benzodiazepine receptor antagonists and the like.

Other drugs for supplementation and/or enhancement of the prophylactic and/or therapeutic effect of the compound represented by formulae (I) and (II) on complication of diabetes include sulfonylurea type hypoglycemic agents, biguanide preparations, alfa-glucosidase inhibitors, fast-acting insulin secretion accelerators, insulin preparations, PPAR agonists, insulin sensitizer without PPAR agonistic activity, beta-3 adrenaline receptor activators, aldose reductase inhibitors, dipeptidyl peptidase IV inhibitors and the like.

The sulfonylurea agents include acetohexamide, glibenclamide, gliclazide, glyclopyramide, chlorpropamide, tolazamide, tolbutamide, glimepiride and the like.

The biguanide preparations include buformin hydrochloride, metformin hydrochloride and the like.

The alfa-glucosidase inhibitors include acarbose, voglibose and the like.

The fast-acting insulin secretion accelerators include nateglinide, repaglinide and the like.

The PPAR agonists include pioglitazone, troglitazone, rosiglitazone, JTT-501 and the like.

The insulin sensitizers having no PPAR agonistic activity include ONO-5816, YM-440 and the like.

The beta-3 adrenaline receptor activators include AJ9677, L750355, CP331648 and the like.

The aldose reductase inhibitors include epalrestat, fidarestat, zenarestat and the like.

Other drugs for supplementation and/or enhancement of the prophylactic and/or therapeutic effect of the compound represented by formulae (I) and (II) on cancer (malignant tumor) or cancer metastasis include anticancer agents (MMP inhibitors, alkylating agents (cyclophosphamide, melphalan, thiotepa, mitomycin C, busulfan, procarbazine hydrochloride and the like), metabolism antagonists (methotrexate, mercaptopurine, azathipurine, fluorouracil, tegafur, cytarabine, azaserine and the like), antibiotics (mitomycin C, bleomycin, peplomycin, doxorubicin hydrochloride, aclarubicin, daunorubicin, actinomycin C), antimitotic agents, platinum complex (cisplatin), plant-derived antimalignant tumor agents (vincristine sulfate, vinblastin sulfate and the like), antitumor hormones (methyltestosterone, testosterone propionate, testosterone enanthate, mepitiostane, fosfestrol, chlormadinone acetate and the like), immunoactivators (picibanil, krestin and the like), interferons (IFNα, IFNα-2a, IFNα-2b, IFNβ, EFNγ-1a and the like) and the like.

Other drugs for supplementation and/or enhancement of the prophylactic and/or therapeutic effect of the compound represented by formulae (I) and (II) on immunological diseases (autoimmune diseases, transplantation organ rejections and the like) include immunosuppressants (ciclosporin, tacrolimus, FTY720 and the like).

Other drugs for supplementation and/or enhancement of the prophylactic and/or therapeutic effect of the compound represented by formulae (I) and (II) on dementia such as Alzheimer senile dementia include acetylcholine esterase inhibitors, nicotine receptor regulating agents, cerebral circulation and metabolism improving agents, monoamine oxidase inhibitors, vitamin E, aldose reductase inhibitors and the like.

Other drugs for supplementation and/or enhancement of the prophylactic and/or therapeutic effect of the compound represented by formulae (I) and (II) on epilepsy include phenytoin, trimetadione, ethosuximide, carbamazepine, phenobarbital, primidone, acetazolamide, sultiame, sodium valproate, clonazepam, diazepam, nitrazepam and the like.

Other drugs for supplementation and/or enhancement of the prophylactic and/or therapeutic effect of the compound represented by formulae (I) and (II) on arteriosclorosis include HMG-CoA reductase inhibitors, fibrate preparations, probucol preparations, anion-exchange resin, EPA preparations, nicotinic acid preparations, MTP inhibitors, other antihypercholesterolemic agents, EDG-2 antagonists and the like.

Other drugs for supplementation and/or enhancement of the effect of the compound represented by formulae (I) and (II) when employed in regenerative medicines include cytokines, various growth factors, such as various CSF (G-CSF, GM-CSF and the like), various interleukins (IL-3, 6, 7, 11, 12 and the like), EPO, TPO, SCF, FLT3 ligand, MIP-1α and the like.

The weight proportion of the compound represented by formulae (I) and (II) and the other pharmaceutical preparations is not specifically limited.

Arbitrary two or more of the other pharmaceutical preparations may be administered in combination.

Other drugs for supplementation and/or enhancement of the prophylactic and/or therapeutic effect of the compound represented by formulae (I) and (II) include not only those which have so far been found but also those which will be found on the basis of the aforementioned mechanism.

In order to use the compound of the present invention represented by formulae (I) and (II) or the compound represented by formulae (I) and (II) in combination with the other pharmaceutical preparations, these compounds are normally administered to the entire or local part of human body orally or parenterally. It is preferable to select the most effective administration route upon treatment.

The doses to be administered are determined depending upon, for example, age, body weight, symptom, the desired therapeutic effect, the route of administration, and the duration of the treatment. In the human adult, the doses per person are generally from 1 ng to 100 mg, by oral administration, up to several times per day, and from 0.1 ng to 10 mg, by parenteral administration, up to several times per day, or continuous administration from 1 to 24 hours per day from vein.

As mentioned above, the doses to be used depend upon various conditions. Therefore, there are cases in which doses lower than or greater than the ranges specified above may be used.

The compound represented by formulae (I) and (II) of the present invention, or concomitant drug combined the compound represented by formulae (I) and (II) with other drugs may be administered in the composition of, for example, solid compositions or liquid compositions, each for oral administration, or injections, external use, suppositories, each for parenteral administration.

Solid compositions for oral administration include compressed tablets, pills, capsules, dispersible powders and granules. Capsules include hard capsules and soft capsules.

In such solid forms, one or more of the active compound(s) may be admixed with vehicles (such as lactose, mannitol, glucose, microcrystalline cellulose, starch), binders (such as hydroxypropyl cellulose, polyvinylpyrrolidone or magnesium metasilicate aluminate), disintegrants (such as cellulose calcium glycolate), lubricants (such as magnesium stearate), stabilizing agents, and solution adjuvants (such as glutamic acid or aspartic acid) and prepared according to methods well known in normal pharmaceutical practice. The solid forms may, if desired, be coated with coating agents (such as sugar, gelatin, hydroxypropyl cellulose or hydroxypropylmethyl cellulose phthalate), or be coated with two or more films. And further, coating may include containment within capsules of absorbable materials such as gelatin.

Liquid forms for oral administration include pharmaceutically acceptable solutions, suspensions and emulsions, syrups and elixirs. In such forms, one or more of the active compound(s) may be dissolved, suspended or emulized into diluent(s) commonly used in the art (such as purified water, ethanol or a mixture thereof). Besides such liquid forms may also comprise some additives, such as wetting agents, suspending agents, emulsifying agents, sweetening agents, flavoring agents, aroma, preservative or buffering agent.

Injections for parenteral administration include sterile aqueous, suspensions, emulsions and solid forms which are dissolved or suspended into solvent(s) for injection immediately before use. In injections, one or more of the active compound(s) may be dissolved, suspended or emulized into solvent(s). The solvents may include distilled water for injection, physiological salt solution, vegetable oil, propylene glycol, polyethylene glycol, alcohol, e.g. ethanol, or a mixture thereof. Injections may comprise some additives, such as stabilizing agents, solution adjuvants (such as glutamic acid, aspartic acid or POLYSORBATE80 (registered trade mark)), suspending agents, emulsifying agents, soothing agent, buffering agents, preservative. They may be sterilized at a final step, or may be prepared by an aseptic manipulation. They may also be manufactured in the form of sterile solid forms, for example, freeze-dried products, which may be dissolved in sterile water or some other sterile diluent(s) for injection immediately before use.

In the parenteral administration, formulation of external use include, for example, ointment, ger, cream, poultice, patch, liniment, atomized agent, inhalation, spray, aerosol, eye drops and nasal drops, etc. They includes one or more of the active compound(s) and be prepared by known method or usual method.

Ointment is prepared by known method or usual method. For example, it is prepared by levigation or fusion of one or more of the active compound(s) and substrate. The substrate of ointment is selected from known or usual one. For example, higher fatty acid or higher fatty acid ester (adipic acid, myristic acid, palmitic acid, stearic acid, oleic acid, adipic acid ester, myristic acid ester, palmitic acid ester, stearic acid ester, oleic acid ester, etc.), wax (yellow beeswax, Spermaceti, ceresin, etc.), surfactant (polyoxyethylene alkyl ether phosphoric acid ester, etc.), higher alcohol (cetanol, stearil alcohol, cetostearyl alcohol, etc.), silicon oil (dimethyl polysiloxane, etc.), hydrocarbon (hydrophilic petrolatum, white petrolatum, purified lanolin, light liquid paraffin, etc.), glycol (ethylene glycol, diethylene glycol, propylene glycol, polyethylene glycol, macrogol, etc.), vegetable oil (castor oil, olive oil, sesame oil, turpentine oil, etc.), animal oil (mink oil, egg yolk oil, squalane, squalene, etc.), water, absorption accelerator, skin fit inhibitor, etc. are used as single substance selected from them or mixture which consists of two or more kinds that is selected from them. Moreover, humectant, preservative agent, stabilizer, antioxidative agent, fragrant materials, etc. may be contained.

Ger is prepared by known method or usual method. For example, it is prepared by fusion of one or more of the active compound(s) and substrate. The substrate of gel is selected from known or usual one. For example, lower alcohol (ethanol, isopropylalcohol, etc.), gelling agent (carboxy methyl cellulose, hydroxy ethyl cellulose, hydroxy propyl cellulose, ethyl cellulose, etc.), neutralizing agent, (triethanolamine, diisopropanolamine, etc.), surfactant, (polyethylene glycol monostearate, etc.), gum, water, absorption accelerator, skin fit inhibitor, etc. are used as single substance selected from them or mixture which consists of two or more kinds that is selected from them. Moreover, preservative agent, antioxidative agent, fragrant materials, etc. may be contained.

Cream is prepared by known method or usual method. For example, it is prepared by fusion or emulsification of one or more of the active compound(s) and substrate. The substrate of cream is selected from known or usual one. For example, higher fatty acid ester, lower alcohol, hydrocarbon, polyalcohol (propylene glycol, 1,3-butylene glycol, etc.), higher alcohol (2-hexyldecanol, cetanol, etc.), emulsifying agent (polyoxyethylene alkyl ether, fatty acid ester, etc.), water, absorption accelerator, skin fit inhibitor, etc. are used as single substance selected from them or mixture which consists of two or more kinds that is selected from them. Moreover, preservative agent, antioxidative agent, fragrant materials, etc. may be contained.

Poultice is prepared by known method or usual method. For example, it is prepared by fusion of one or more of the active compound(s) and substrate, and then the kneaded one is laid over support medium. The substrate for poultice is selected from known or usual one. For example, thickening agent (polyacrylic acid, polyvinylpyrolidone, gum acacia, starch, gelatin, methyl cellulose, etc.), bulking agent (kaolin, zinc oxide, talc, calcium, magnesium, etc.), water, solubilizing agent, thickener, skin fit inhibitor, etc. are used as single substance selected from them or mixture which consists of two or more kinds that is selected from them. Moreover, preservative agent, antioxidative agent, fragrant materials, etc. may be contained.

Patch is prepared by known method or usual method. For example, it is prepared by fusion of one or more of the active compound(s) and substrate, and then laid over support medium. The substrate for patch is selected from known or usual one. For example, polymer substrate, fat, higher fatty acid, thickener, skin fit inhibitor, etc. are used as single substance selected from them or mixture which consists of two or more kinds that is selected from them. Moreover, preservative agent, antioxidative agent, fragrant materials, etc. may be contained.

Liniment is prepared by known method or usual method. For example, one or more of the active compound(s) may be dissolved, suspended or emulsified in water, alcohol (ethanol, polyethylene glycol, etc.), higher fatty acid, glycerin, soap, emulsifying agent, suspending agent, etc. as single substance selected from them or mixture which consists of two or more kinds that is selected from them. Moreover, preservative agent, antioxidative agent, fragrant materials, etc. may be contained.

Atomized agent, inhalation and spray may comprise in addition to a diluent, a stabilizer such as sodium bisulfite and an isotonization buffer such as sodium chloride, sodium citrate or citric acid. The preparation process of sprays is described in detail in, for example, U.S. Pat. Nos. 2,868,691 and 3,095,355.

In case of administration of nasal drops, they may be usually sprayed intranasally in the form of liquid or powder comprising drugs with a special apparatus for nasal drops or nebulizer quantitatively.

The eye drops for parenteral administration may be in the form of liquid, suspension, emulsion or ointment or may be dissolved in a solvent in use.

These eye drops are prepared by any known method. For example, one or more active materials are dissolved, suspended or emulsified in a solvent. As such a solvent for eye drops there may be used sterilized purified water, physiological saline and other aqueous or nonaqueous solvents (e.g., vegetable oil), singly or in combination. The eye drops may comprise an isotonic agent (e.g., sodium chloride, concentrated glycerin), a buffering agent (e.g., sodium phosphate, sodium acetate), a surface active agent (e.g., Polysolvate 80 (trade name), polyoxyl stearate 40, polyoxyethylene-hardened castor oil), a stabilizer (sodium citrate, sodium edetate), a preservative (e.g., benzalconium chloride, Paraben), etc. properly selectively as necessary. The eye drops are sterilized at the final step or prepared by an aseptic manipulation. Alternatively, an aseptic solid agent such as freeze-dried product which has previously been prepared may be rendered aseptic or dissolved in an aseptic distilled water for injection or other solvent before use.

The dosage of inhalations for parenreral administration include aerosol, powders for inhalation or liquids for inhalation. The liquids for inhalation may be dissolved or suspended in water or the other appropriate solvent as needed.

Such inhalations are prepared in a known method.

For example, a liquid for inhalation is prepared by selecting proper additives from an antiseptic (such as benzalkonium chloride or p-aminobenzonic acid), a coloring agent, a buffering agent (such as sodium phosphate or sodium acetate), an isotonizing agent (such as sodium chloride or concentrated glycerin), thickening agent (such as carboxyvinylpolymer), or an accelerator of absorption, etc., if necessary.

A powder for inhalation is prepared by selecting proper additives from a lubricant agent (such as stearin acid and the salt thereof), a binding agent, (such as starch, dextrin), a diluting agent (such as lactose, cellulose), a coloring agent, an antiseptic (such as benzalkonium chloride or p-aminobenzonic acid), an accelerator of absorption, etc., if necessary.

In case of administration of liquid for inhalation, spray (atomizer, nebulizer) is usually used and in case of administration of powder for inhalation, inhalation administration apparatus for powder agents is usually used.

The other compositions for parenteral administration include suppositories for intrarectal administration and pessaries for vaginal administration which comprise one or more of the active substance(s) and may be prepared by methods known per se.

BEST MODE FOR CARRYING OUT THE INVENTION

The present invention is explained below in detail based on Reference Examples and Examples, but the present invention is not limited thereto.

All the compounds described in the present specification were named according to IUPAC nomenclature system or named using ACD/Name (ver. 6.0, Advanced Chemistry Development Inc.).

The solvents in the parentheses show the developing solvents or eluting solvents and the ratios of the solvents used are by volume in chromatographic separations or TLC. The solvents in the parentheses in NMR show the solvents for measurement. Electrospray ionization (ESI, condition: Pos., 20 V) was used as a method of Mass measurement.

HPLC condition is outlined below.

(1) Condition A (Analysis)
Used equipment: Waters LC/MS
Column: Xterra (registered trade name) MS $C_{18}$, 5 μm, 4.6× 50 mm I.D.
Flow rate: 3 mL/min
Solvent:Liquid A:0.1% trifluoroacetic acid aqueous solution
Liquid B:0.1% trifluoroacetic acid—acetonitrile solution

| Time (min.) | liquid A | Liquid B |
|---|---|---|
| 0 | 95 | 5 |
| 0.5 | 95 | 5 |
| 3 | 0 | 100 |
| 3.5 | 0 | 100 |
| 3.51 | 95 | 5 |
| 5 | 95 | 5 |

(2) Condition B (Analysis)
Used equipment: Waters LC/MS
Column: Xterra (registered trade name) MS $C_{18}$, 5 μm, 4.6× 50 mm I.D.
Flow rate: 3 mL/min
Solvent: Liquid A: 0.1% triethylamine aqueous solution
Liquid B: 0.1% triethylamine—acetonitrile solution

| Time (min.) | Liquid A | Liquid B |
|---|---|---|
| 0 | 95 | 5 |
| 0.5 | 95 | 5 |
| 3 | 0 | 100 |
| 3.5 | 0 | 100 |
| 3.51 | 95 | 5 |
| 7 | 95 | 5 |

REFERENCE EXAMPLE 1

2-chloro-4-(perhydroazepin-1-yl)pyrimidine

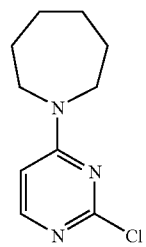

To a solution of 2,4-dichloropyrimidine (3.0 g) in tetrahydrofuran (50 mL) were added triethylamine (4.2 mL) and perhydroazepine (2.5 mL) with ice cooling and the mixture was stirred for 1 hour at room temperature. To the reaction mixture was added water (30 mL) and the resulting mixture was concentrated. The residue was extracted with methylene chloride three times. The organic layer was washed with brine, dried over anhydrous magnesium sulfate and concentrated. The residue was purified by column chromatography on silica gel (hexane:ethyl acetate=5:1→2:1) to give the title compound (3.03 g) having the following physical data.

TLC:Rf 0.18 (hexane:ethyl acetate=3:1);

NMR (CDCl$_3$): δ 1.53 (m, 4H), 1.78 (m, 4H), 3.44 (m, 2H), 3.83 (m, 2H), 6.29 (d, J=6.32 Hz, 1H), 7.96 (d, J=6.32 Hz, 1H).

EXAMPLE 1

2-(2-dimethylaminoethylamino)-4-(perhydroazepin-1-yl)pyrimidine

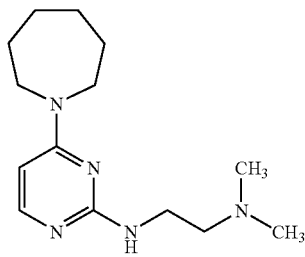

A mixture of the compound prepared in Reference Example 1 (1.5 g) and N,N-dimethylethylenediamine (1.56 mL) was stirred for 16 hour at 90° C. The reaction mixture was cooled and purified by column chromatography on silica gel (ethyl acetate: methanol:triethylamine=10:1:0→10:1:0.2) to give the title compound (1.44 g) having the following physical data.

crystalline powder: melting point 53.0-54.5° C.;

TLC:Rf 0.30 (chloroform:methanol:28% ammonia water=80:10:1);

NMR (DMSO-d$_6$, 363.1K): δ 1.50 (m, 4H), 1.70 (m, 4H), 2.19 (s, 6H), 2.42 (t, J=6.00 Hz, 2H), 3.33 (q, J=6.00 Hz, 2H), 3.56 (m, 4H), 5.74 (m, 1H), 5.83 (d, J=6.00 Hz, 1H), 7.72 (d, J=6.00 Hz, 1H).

Example 1(1) TO Example 1(47)

By the same procedure as described in Reference Example 1→Example 1 using corresponding compounds, the compounds of the present invention having the following physical data were given.

Example 1(1)

2-[3-(imidazol-1-yl)propylamino]-4-(perhydroazepin-1-yl)pyrimidine

TLC:Rf 0.66 (chloroform:methanol:28% ammonia water=80:10:1);

NMR (DMSO-d$_6$): δ 1.49 (m, 4H), 1.69 (m, 4H), 1.97 (m, 2H), 3.24 (m, 2H), 3.54 (m, 4H), 4.01 (t, J=7.00 Hz, 2H), 5.84 (d, J=6.04 Hz, 1H), 6.12 (m, 1H), 6.86 (d, J=1.24 Hz, 1H), 7.10 (d, J=1.24 Hz, 1H), 7.56 (s, 1H), 7.73 (d, J=6.04 Hz, 1H).

Example 1(2)

2-(2-dimethylaminopropylamino)-4-(perhydroazepin-1-yl)pyrimidine

TLC:Rf 0.57 (chloroform:methanol:28% ammonia water=80:10:1);

NMR (DMSO-d$_6$, 363.1K): δ 0.91 (d, J=6.59 Hz, 3H), 1.50 (m, 4H), 1.69 (m, 4H), 2.20 (s, 6H), 2.72 (m, 1H), 3.20 (m, 2H), 3.55 (t, J=6.00 Hz, 4H), 5.67 (m, 1H), 5.83 (d, J=5.77 Hz, 1H), 7.72 (d, J=5.77 Hz, 1H).

Example 1(3)

4-(2-dimethylaminoethylamino)-2-pyrrolidinopyrimidine

TLC:Rf 0.29 (chloroform:methanol:28% ammonia water=80:10:1);

NMR (DMSO-d$_6$): δ 1.84 (m, 4H), 2.17 (s, 6H), 2.38 (t, J=6.73 Hz, 2H), 3.37 (m, 6H), 5.70 (d, J=5.50 Hz, 1H), 6.77 (m, 1H), 7.64 (d, J=5.50 Hz, 1H).

Example 1(4)

4-(2-dimethylaminoethylamino)-2-(perhydroazocin-1-yl)pyrimidine

TLC:Rf 0.38 (chloroform:methanol:28% ammonia water=80:10:1);

NMR (DMSO-d$_6$): δ 1.43 (m, 6H), 1.69 (m, 4H), 2.15 (s, 6H), 2.36 (t, J=6.73 Hz, 2H), 3.32 (m, 2H), 3.58 (m, 4H), 5.68 (d, J=5.50 Hz, 1H), 6.77 (m, 1H), 7.65 (d, J=5.50 Hz, 1H).

Example 1(5)

4-(2-dimethylaminoethylamino)-2-piperidinopyrimidine

TLC:Rf 0.44 (chloroform:methanol:28% ammonia water=80:10:1);

NMR (DMSO-d$_6$): δ 1.44 (m, 4H), 1.56 (m, 2H), 2.15 (s, 6H), 2.35 (t, J=6.00 Hz, 2H), 3.33 (m, 2H), 3.63 (t, J=6.00 Hz, 4H), 5.70 (d, J=5.77 Hz, 1H), 6.76 (s, 1H), 7.66 (d, J=5.77 Hz, 1H).

Example 1(6)

2-(2-dimethylamino-1-methylethylamino)-4-(perhydroazepin-1-yl)pyrimidine

TLC:Rf 0.52 (chloroform:methanol:28% ammonia water=80:10:1);

NMR (CD$_3$OD): δ 1.18 (d, J=6.32 Hz, 3H), 1.55 (m, 4H), 1.76 (m, 4H), 2.28 (m, 7H), 2.51 (m, 1H), 3.58 (m, 4H), 4.15 (m, 1H), 5.90 (d, J=6.04 Hz, 1H), 7.67 (d, J=6.04 Hz, 1H).

Example 1(7)

4-(2-dimethylaminoethylamino)-2-(4-methylpiperazin-1-yl)pyrimidine

NMR (DMSO-d$_6$): δ 2.20 (s, 3H), 2.26 (s, 6H), 2.32 (m, 4H), 3.30 (m, 4H), 3.63 (m, 4H), 5.76 (d, J=5.20 Hz, 1H), 6.91 (m, 1H), 7.69 (d, J=5.20 Hz, 1H);

MS (m/z): 265 (M+H)$^+$;

HPLC retention time (min): 2.83; HPLC condition: B.

Example 1(8)

4-(2-dimethylaminoethylamino)-2-(4-phenylpiperazin-1-yl)pyrimidine

MS (m/z): 327 (M+H)$^+$;

HPLC retention time (min): 3.51; HPLC condition: B.

Example 1(9)

2-(4-benzylpiperazin-1-yl)-4-(2-dimethylaminoethylamino)pyrimidine

MS (m/z): 341 (M+H)$^+$;
HPLC retention time (min): 3.42; BPLC condition: B.

Example 1(10)

2-(4-acetylpiperazin-1-yl)-4-(2-dimethylaminoethylamino)pyrimidine

MS (m/z): 293 (M+H)$^+$;
HPLC retention time (min): 2.78; HPLC condition: B.

Example 1(11)

4-(2-dimethylaminoethylamino)-2-(4-hydroxypiperidin-1-yl)pyrimidine

MS (m/z): 266 (M+H)$^+$;
HPLC retention time (min): 2.76; HPLC condition: B.

Example 1(12)

4-(2-dimethylaminoethylamino)-2-(4-methylpiperidin-1-yl)pyrimidine

MS (m/z): 264 (M+H)$^{30}$ ;
HPLC retention time (min): 3.49; HPLC condition: B.

Example 1(13)

4-(2-dimethylaminoethylamino)-2-(3-methylpiperidin-1-yl)pyrimidine

MS (m/z): 264 (M+H)$^+$;
HPLC retention time (min): 3.46; HPLC condition: B.

Example 1(14)

4-(2-dimethylaminoethylamino)-2-(2-methylpiperidin-1-yl)pyrimidine

MS (m/z): 264 (M+H)$^+$;
HPLC retention time (min): 2.89; HPLC condition: B.

Example 1 (15)

2-(3-hydroxypyrrolidin-1-yl)-4-(2-dimethylaminoethylamino)pyrimidine

MS (m/z): 252 (M+H)$^+$;
HPLC retention time (min): 2.70; HPLC condition: B.

Example 1(16)

2-(4-ethoxycarbonylpiperidin-1-yl)-4-(2-dimethylaminoethylamino)pyrimidine

MS (m/z): 322 (M+H)$^+$;
HPLC retention time (min): 3.31; HPLC condition: B.

Example 1(17)

2-(3-ethoxycarbonylpiperidin-1-yl)-4-(2-dimethylaminoethylamino)pyrimidine

MS (m/z): 322 (M+H)$^+$;
HPLC retention time (min): 3.33; HPLC condition: B.

Example 1(18)

2-thiomorpholino-4-(2-dimethylaminoethylamino)pyrimidine

MS (m/z): 268 (M+H)$^+$;
HPLC retention time (min): 3.18; HPLC condition: B.

Example 1(19)

4-(2-dimethylaminoethylamino)-2-morpholinopyrimidine

MS (m/z): 252 (M+H)$^+$;
HPLC retention time (min): 2.83; HPLC condition: B.

Example 1(20)

2-(4-carbamoylpiperidin-1-yl)-4-(2-dimethylaminoethylamino)pyrimidine

MS (m/z): 585 (2M+H)$^+$, 293 (M+H)$^+$;
HPLC retention time (min): 2.72; HPLC condition: B.

Example 1(21)

2-(3-carbamoylpiperidin-1-yl)-4-(2-dimethylaminoethylamino)pyrimidine

MS (m/z): 293 (M+H)$^+$;
HPLC retention time (min): 2.78; HPLC condition: B.

Example 1(22)

2-(4-benzyloxycarbonyl-1,4-perhydrodiazepin-1-yl)-4-(2-imethylaminoethylamino)pyrimidine

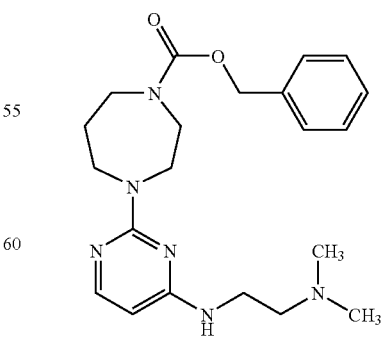

MS (m/z): 797 (2M+H)$^+$, 399 (M+H)$^+$;
HPLC retention time (min): 3.44; HPLC condition: B.

Example 1(23)

2-(4-benzyl-1,4-perhydrodiazepin-1-yl)-4-(2-dimethylaminoethylamino)pyrimidine

MS (m/z): 355 (M+H)$^+$;
HPLC retention time (min): 3.47; HPLC condition: B.

Example 1(24)

4-(2-dimethylaminoethylamino)-2-(perhydroquinolin-1-yl)pyrimidine

MS (m/z): 304 (M+H)$^+$;
HPLC retention time (min): 3.84; HPLC condition: B.

Example 1(25)

4-(2-dimethylaminoethylamino)-2-(perhydroisoquinolin-2-yl)pyrimidine

MS (m/z): 304 (M+H)$^+$;
HPLC retention time (min): 3.86; HPLC condition: B.

Example 1(26)

4-(2-dimethylaminoethylamino)-2-(4-methyl-1,4-perhydrodiazepin-1-yl)pyrimidine

MS (m/z): 279 (M+H)$^+$;
HPLC retention time (min): 2.90; HPLC condition: B.

Example 1(27)

4-(2-dimethylaminoethylamino)-2-(4-propylpiperidin-1-yl)pyrimidine

MS (m/z): 292 (M+H)$^+$;
HPLC retention time (min): 3.89; BPLC condition: B.

Example 1(28)

2-(4-butylpiperazin-1-yl)-4-(2-dimethylaminoethylamino)pyrimidine

MS (m/z): 307 (M+H)$^+$;
HPLC retention time (min): 3.34; HPLC condition: B.

Example 1(29)

4-(2-dimethylaminoethylamino)-2-(1,2,3,6-tetrahydropyridin-1-yl)pyrimidine

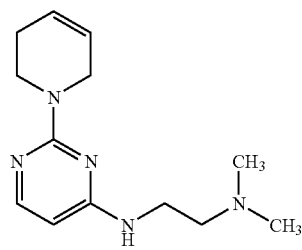

MS (m/z): 248 (M+H)$^+$;
HPLC retention time (min): 3.25; HPLC condition: B.

Example 1(30)

4-(2-dimethylaminoethylamino)-2-(3,5-dimethylpiperidin-1-yl)pyrimidine

MS (m/z): 278 (M+H)$^+$;
HPLC retention time (min): 3.67; BPLC condition: B.

Example 1(31)

4-(2-dimethylaminoethylamino)-2-(perhydroazepin-1-yl)pyrimidine

TLC: Rf 0.41 (chloroform: methanol: 28% ammonia water=80:10:1);
NMR (DMSO-d$_6$): δ 7.65 (brd, J=5.7 Hz, 1H), 6.72 (br, 1H), 5.68 (d, J=5.7 Hz, 1H), 3.61 (m, 4H), 3.30 (m, 2H), 2.36 (t, J=6.9 Hz, 2H), 2.15 (s, 6H), 1.65 (m, 4H), 1.44 (m, 4H).

Example 1(32)

2-(3-dimethylaminopropylamino)-4-pyrrolidinopyrimidine

TLC:Rf 0.19 (chloroform: methanol: 28% ammonia water=80:10:1);
NMR (DMSO-d$_6$): δ 1.60 (m, 2H), 1.87 (m, 4H), 2.10 (s, 6H), 2.22 (t, J=7.14 Hz, 2H), 3.20 (m, 2H), 3.38 (m, 4H), 5.66 (d, J=5.77 Hz, 1H), 6.37 (m, 1H), 7.70 (d, J=5.77 Hz, 1H).

Example 1(33)

2-(3-dimethylaminopropylamino)-4-piperidinopyrimidine

TLC: Rf 0.28 (chloroform: methanol: 28% ammonia water=80:10:1);
NMR (DMSO-d$_6$): δ 1.46 (m, 4H), 1.60 (m, 4H), 2.11 (s, 6H), 2.22 (t, J=7.14 Hz, 2H), 3.18 (m, 2H), 3.49 (m, 4H), 5.95 (d, J=6.04 Hz, 1H), 6.41 (m, 1H), 7.72 (d, J=6.04 Hz, 1H).

Example 1(34)

2-(3-dimethylaminopropylamino)-4-(perhydroazepin-1-yl)pyrimidine

TLC:Rf 0.19 (chloroform: methanol: 28% ammonia water=80:10:1);
NMR (DMSO-d$_6$): δ 1.44 (m, 4H), 1.61 (m, 6H), 2.09 (s, 6H), 2.21 (t, J=7.14 Hz, 2H), 3.18 (q, J=6.59 Hz, 2H), 3.51 (m, 4H), 5.81 (d, J=6.04 Hz, 1H), 6.41 (m, 1H), 7.70 (d, J=6.04 Hz, 1H).

Example 1(35)

2-(2-dimethylaminoethylamino)-4-pyrrolidinopyrimidine

TLC: Rf 0.20 (chloroform: methanol: 28% ammonia water=80:10:1);
NMR (DMSO-d$_6$): δ 1.87 (m, 4H), 2.15 (s, 6H), 2.36 (t, J=6.73 Hz, 2H), 3.35 (m, 6H), 5.68 (d, J=5.77 Hz, 1H), 6.14 (m, 1H), 7.71 (d, J=5.77 Hz, 1H).

Example 1(36)

2-(2-dimethylaminoethylamino)-6-methyl-4-(perhydroazepin-1-yl)pyrimidine

TLC: Rf 0.30 (chloroform: methanol: triethylamine=80:10:1);
NMR (DMSO-$d_6$): δ 1.45 (m, 4H), 1.67 (m, 4H), 2.05 (s, 3H), 2.19 (s, 6H), 2.41 (t, J=6.90 Hz, 2H), 3.29 (m, 2H), 3.65 (m, 4H), 5.73 (s, 1H), 6.15 (m, 1H).

Example 1(37)

2-(2-dimethylaminoethylamino)-5-methyl-4-(perhydroazepin-1-yl)pyrimidine

TLC:Rf 0.32 (chloroform: methanol: triethylamine=80:10:1);
NMR (DMSO-$d_6$): δ 1.47 (m, 4H), 1.69 (m, 4H), 2.08 (s, 3H), 2.14 (s, 6H), 2.34 (t, J=6.60 Hz, 2H), 3.25 (td, J=6.60, 6.00 Hz, 2H), 3.60 (t, J=6.00 Hz, 4H), 6.00 (m, 1H), 7.52 (s, 1H).

Example 1(38)

2-(1-benzylpiperidin-4-ylamino)-4-(perhydroazepin-1-yl)pyrimidine

TLC: Rf 0.52 (chloroform: methanol: 28% ammonia water=80:10:1);
NMR (DMSO-$d_6$, 363.1K): δ 1.49 (m, 6H), 1.68 (m, 4H), 1.87 (m, 2H), 2.07 (td, J=11.47, 2.61 Hz, 2H), 2.77 (m, 2H), 3.46 (s, 2H), 3.54 (t, J=6.00 Hz, 4H), 3.66 (m, 1H), 5.74 (m, 1H), 5.82 (d, J=6.04 Hz, 1H), 7.25 (m, 5H), 7.72 (d, J=6.04 Hz, 1H).

Example 1(39)

2-(2-morpholinoethylamino)-4-(perhydroazepin-1-yl)pyrimidine

TLC:Rf 0.41 (chloroform: methanol: 28% ammonia water=80:10:1);
NMR (DMSO-$d_6$): δ 1.45 (m, 4H), 1.68 (m, 4H), 2.38 (m, 6H), 3.30 (q, J=6.00 Hz, 2H), 3.57 (m, 8H), 5.83 (d, J=5.70 Hz, 1H), 6.19 (m, 1H), 7.71 (d, J=5.70 Hz, 1H).

Example 1(40)

4-(perhydroazepin-1-yl)-2-(2-pyrrolidinoethylamino)pyrimidine

TLC: Rf 0.23 (chloroform: methanol: 28% ammonia water=80:10:1);
NMR (DMSO-$d_6$, 363.1K): δ 1.51 (m, 4H), 1.74 (m, 8H), 2.69 (m, 2H), 2.75 (t, J=6.60 Hz, 2H), 3.42 (m, 2H), 3.56 (m, 4H), 5.86 (d, J=6.00 Hz, 1H), 5.99 (m, 1H), 7.73 (d, J=6.00 Hz, 1H).

Example 1(41)

2-(2-aminoethylamino)-4-(perhydroazepin-1-yl)pyrimidine dihydrochloride crystalline powder: melting point 100-102° C.;
TLC: Rf 0.16 (chloroform: methanol: 28% ammonia water=80:10:1);
NMR (CD$_3$OD): δ 1.61 (m, 4H), 1.85 (m, 4H), 3.22 (t, J=6.00 Hz, 2H), 3.70 m, 2H), 3.75 (t, J=6.00 Hz, 2H), 3.93 (m, 2H), 6.44 (d, J=7.70 Hz, 1H), 7.72 (d, J=7.70 Hz, 1H).

Example 1(42)

(±)-2-[(1R*,2R*)-2-aminocyclohexylamino]-4-(perhydroazepin-1-yl)pyrimidine

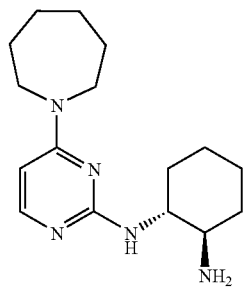

TLC: Rf 0.23 (chloroform: methanol: 28% ammonia water=80:10:1);
NMR (DMSO-$d_6$): δ 1.11 (m, 4H), 1.45 (m, 4H), 1.62 (m, 6H), 1.81 (m, 1H), 1.97 (m, 1H), 3.37 (m, 6H), 5.82 (d, J=5.80 Hz, 1H), 6.19 (m, 1H), 7.70 (d, J=5.80 Hz, 1H).

Example 1(43)

(±)-2-[(1S*,2R*)-2-aminocyclohexylamino]-4-(perhydroazepin-1-yl)pyrimidine

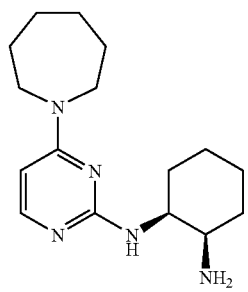

TLC: Rf 0.19 (chloroform: methanol: 28% ammonia water=80:10:1);
NMR (DMSO-$d_6$): δ 1.25 (m, 2H), 1.47 (m, 10H), 1.68 (m, 4H), 2.96 (m, 1H), 3.37 (m, 4H), 3.73 (m, 1H), 5.83 (d, J=5.80 Hz, 1H), 5.91 (m, 1H), 7.71 (d, J=5.80 Hz, 1H).

Example 1(44)

2-(2-dimethylaminoethylamino)-4-(perhydroquinolin-1-yl)pyrimidine

TLC: Rf 0.50 (chloroform: methanol: 28% ammonia water=80:10:1);
NMR (DMSO-$d_6$, 373.1K): δ 1.37 (m, 6H), 1.60 (m, 2H), 1.80 (m, 5H), 2.62 (s, 6H), 2.84 (m, 1H), 2.98 (m, 2H), 3.54

(m, 2H), 4.16 (m, 1H), 4.36 (m, 1H), 6.08 (d, J=6.32 Hz 1H), 6.74 (m, 1H), 7.77 (d, J=6.32 Hz, 1H).

Example 1(45)

4-(4-acetylpiperazin-1-yl)-2-(2-dimethylaminoethylamino)pyrimidine

TLC: Rf 0.40 (chloroform: methanol: 28% ammonia water=80:10:1)
NMR (DMSO-$d_6$): δ 2.02 (s, 3H), 2.54 (s, 6H), 2.87 (t, J=6.32 Hz, 2H), 3.40 (m, 10H), 6.09 (d, J=6.04 Hz, 1H), 6.64 (m, 1H), 7.83 (d, J=6.04 Hz, 1H).

Example 1(46)

2-(2-dimethylaminoethylamino)-4-(3-methylpiperidin-1-yl)pyrimidine

TLC: Rf 0.50 (chloroform: methanol: 28% ammonia water=80:10:1);
NMR (DMSO-$d_6$): δ 0.86 (d, J=6.60 Hz, 3H), 1.14 (m, 1H), 1.34 (m, 1), 1.48 (m, 1H), 1.62 (m, 1H), 1.78 (m, 1H), 2.14 (s, 6H), 2.34 (t, J=6.90 Hz, 2H), 2.44 (m, 1H), 2.76 (m, 1H), 3.27 (m, 2H), 4.16 (m, 2H), 5.98 (d, J=5.80 Hz, 1H), 6.20 (m, 1H), 7.73 (d, J=5.80 Hz, 1H).

Example 1(47)

2-(2-aminoethylamino)-5-bromo-4-(perhydroazepin-1-yl)pyrimidine dihydrochloride

TLC: Rf 0.60 (chloroform: methanol: 28% ammonia water=80:10:1);
NMR (CD$_3$OD): δ 1.65 (m, 4H), 1.90 (m, 4H), 3.21 (t, J=6.00 Hz, 2H), 3.73 (t, J600 Hz, 2H), 4.11 (m, 4H), 8.06 (s, 1H).

REFERENCE EXAMPLE 2

2-chloro-4-(perhydroazepin-1-yl)quinazoline

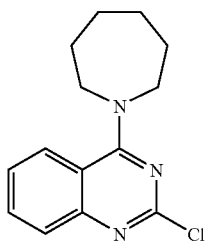

To a solution of 2,4-dichloroquinazoline (1.0 g) in tetrahydrofuran (10 mL) were added triethylamine (2.1 mL) and perhydroazepine (0.745 mL) with ice cooling and the mixture was stirred for 1 hour at room temperature. To the reaction mixture was added water (20 mL) and the resulting mixture was concentrated. The residue was extracted with methylene chloride three times. The organic layer was washed with brine, dried over anhydrous magnesium sulfate and concentrated. The residue was washed with hexane-diethyl ether (10:1) to give the title compound (991 mg) having the following physical data.
TLC: Rf 0.31 (hexane: ethyl acetate=3: 1); MS (m/z): 264, 262 (M+H)$^+$;
HPLC retention time (min) 3.34; HPLC condition: A.

EXAMPLE 2

2-(2-diethylaminoethylamino)-4-(perhydroazepin-1-yl)quinazoline

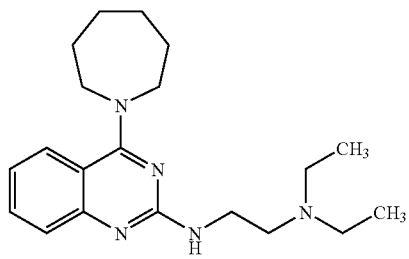

To a solution of the compound prepared in Reference Example 2 (300 mg) in 2-propanol (3 mL) was added N,N-diethylethylenediamine (0.49 m) and the mixture was stirred for 16 hours at 80° C. The reaction mixture was cooled and the residue was purified by column chromatography on silica gel (ethyl acetate:methanol:triethylamine=10:1:0→10:1:0.3) to give the compound (267 mg) of the present invention having the following physical data.
TLC:Rf 0.43 (chloroform: methanol: 28% ammonia water=80:10:1);
NMR (CDCl$_3$): δ 7.80 (d, J=7.5 Hz, 1H), 7.45 (m, 2H), 6.98 (m, 1H), 5.26 (br, 1H), 3.87 (m, 4H), 3.53 (m, 2H), 2.66 (t, J=6.3 Hz, 2H), 2.58 (q, J=6.9 Hz, 4H), 1.97 (m, 4H), 1.66 (m, 4H), 1.04 (t, J=6.9 Hz, 6H); MS (m/z): 342 (M+H)$^+$, 171;
HPLC retention time (min): 2.96 min.; HPLC condition: A.

Example 2(1) TO Example 2(95)

By the same procedure as described in Reference Example 2→Example 2 using corresponding compounds, the compounds of the present invention having the following physical data were given.

Example 2(1)

2-[2-[N,N-bis(2-hydroxyethyl)amino]ethylamino]-4-pyrrolidinoquinazoline

HPLC retention time (min): 2.78; MS (m/z): 346 (M+H)$^+$, 242; HPLC condition: A.

Example 2(2)

2-[3-(imidazol-1-yl)propylamino]-4-pyrrolidinoquinazoline

HPLC retention time (min): 2.96; MS (m/z): 323 (M+H)$^+$, 215; HPLC condition: A.

Example 2(3)

2-(2-morpholinoethylamino)-4-pyrrolidinoquinazoline

HPLC retention time (min): 2.77; MS (m/z): 328 (M+H)$^+$, 242; BPLC condition: A.

Example 2(4)

2-[3-(2-methylpiperidin-1-yl)propylamino]-4-pyrrolidinoquinazoline

MPLC retention time (min): 2.98; MS (m/z): 354 (M+H)$^+$; HPLC condition: A.

Example 2(5)

2-[2-[N,N-bis(2-hydroxyethyl)amino]ethylamino]-4-piperidinoquinazoline

HPLC retention time (min): 2.87; MS (m/z): 719(2M+H)$^+$, 360 (M+H)$^+$; HPLC condition: A.

Example 2(6)

2-[3-(imidazol-1-yl)propylamino]-4-piperidinoquinazoline

HPLC retention time (min): 3.01; MS (m/z): 337 (M+H)$^+$, 229; BPLC condition: A.

Example 2(7)

2-(2-morpholinoethylamino)-4-piperidinoquinazoline

HPLC retention time (min): 2.90; MS (m/z): 342 (M+H)$^+$; HPLC condition: A.

Example 2(8)

2-(3-pyrrolidinopropylamino)-4-piperidinoquinazoline

HPLC retention time (min): 2.98; MS (m/z): 340 (M+H)$^+$, 229; HPLC condition: A.

Example 2(9)

2-[2-(1-methylpyrrolidin-2-yl)ethylamino]-4-piperidinoquinazoline

HPLC retention time (min): 2.98; MS (m/z): 340 (M+H)$^+$, 170.5; HPLC condition: A.

Example 2(10)

2-(1-ethylpyrrolidin-2-ylmethylamino)-4-piperidinoquinazoline

HPLC retention time (min): 2.96; MS (m/z): 340 (M+H)$^+$; HPLC condition: A.

Example 2(11)

2-(2,2-dimethyl-3-dimethylaminopropylamino)-4-piperidinoquinazoline
HPLC retention time (min): 3.00; MS (m/z): 342 (M+H)$^+$; HPLC condition: A.

Example 2(12)

2-(2-dimethylaminopropylamino)-4-piperidinoquinazoline

HPLC retention time (min): 2.94; MS (m/z): 314 (M+H)$^+$; HPLC condition: A.

Example 2(13)

2-(2-diethylaminoethylamino)-4-piperidinoquinazoline

HPLC retention time (min): 2.94; MS (m/z): 328 (M+H)$^+$; HPLC condition: A.

Example 2(14)

2-(3-diethylaminopropylamino)-4-piperidinoquinazoline

HPLC retention time (min): 2.98; MS (m/z): 342 (M+H)$^+$, 314, 229; HPLC condition: A.

Example 2(15)

2-(3-morpholinopropylamino)-4-piperidinoquinazoline

HPLC retention time (min): 2.96; MS (m/z): 356 (M+H)$^+$, 178.5; HPLC condition: A.

Example 2(16)

2-[3-[N,N-bis(2-hydroxyethyl)amino]propylamino]-4-piperidinoquinazoline

HPLC retention time (min): 2.92; MS (m/z): 374 (M+H)$^+$, 356, 314; HPLC condition A.

Example 2(17)

2-(3-dimethylaminopropylamino)-4-piperidinoquinazoline

HPLC retention time (min): 2.96; MS (m/z): 314 (M+H)$^+$; HPLC condition: A.

Example 2(18)

2-(2-dimethylamino-1-methylethylamino)-4-piperidinoquinazoline

HPLC retention time (min): 2.92; MS (m/z): 314 (M+H)$^+$; HPLC condition: A.

Example 2(19)

2-[3-(2-methylpiperidin-1-yl)propylamino]-4-piperidinoquinazoline

HPLC retention time (min): 3.03; MS (m/z): 368 (M+H)$^+$, 229; HPLC condition: A.

Example 2(20)

2-[2-[N,N-bis(2-hydroxyethyl)amino]ethylamino]-4-(perhydroazepin-1-yl)quinazoline HPLC retention time (min): 2.90; MS (m/z): 747 (2M+H)$^+$, 374 (M+H)$^+$; HPLC condition: A.

Example 2(21)

2-[3-(imidazol-1-yl)propylamino]-4-(perhydroazepin-1-yl)quinazoline

HPLC retention time (min): 3.09; MS (m/z): 351 (M+H)$^+$; HPLC condition: A.

Example 2(22)

2-(2-morpholinoethylamino)-4-(perhydroazepin-1-yl)quinazoline

HPLC retention time (min): 2.96; MS (m/z): 711 (2M+H)$^+$, 356 (M+H)$^+$; HPLC condition: A.

Example 2(23)

2-(3-pyrrolidinopropylamino)-4-(perhydroazepin-1-yl)quinazoline

HPLC retention time (min): 3.05; MS (m/z): 354 (M+H)$^+$; HPLC condition: A.

Example 2(24)

2-[2-(1-methylpyrrolidin-2-yl)ethylamino]-4-(perhydroazepin-1-yl)quinazoline

HPLC retention time (min): 3.03; MS (m/z): 707 (2M+H)$^+$, 354 (M+H)$^+$; HPLC condition: A.

Example 2(25)

2-(1-ethylpyrrolidin-2-ylmethylamino)-4-(perhydroazepin-1-yl)quinazoline

HPLC retention time (min): 3.03; MS (m/z): 354 (M+H)$^+$; HPLC condition: A.

Example 2(26)

2-(2,2-dimethyl-3-dimethylaminopropylamino)-4-(perhydroazepin-1-yl)quinazoline

HPLC retention time (min): 3.05; MS (m/z): 711 (2M+H)$^+$, 356 (M+H)$^+$; HPLC condition: A.

Example 2(27)

2-(2-dimethyl aminopropylamino)-4-(perhydroazepin-1-yl)quinazoline

HPLC retention time (min): 3.01; MS (m/z): 328 (M+H)$^+$; HPLC condition: A.

Example 2(28)

2-(3-diethylaminopropylamino)-4-(perhydroazepin-1-yl)quinazoline

HPLC retention time (min): 3.05; MS (m/z): 356 (M+H)$^+$; HPLC condition: A.

Example 2(29)

2-(3-morpholinopropylamino)-4-(perhydroazepin-1-yl)quinazoline

HPLC retention time (min): 3.00; MS (m/z): 370 (M+H)$^+$; HPLC condition: A.

Example 2(30)

2-[3-[N,N-bis(2-hydroxyethyl)amino]propylamino]-4-(perhydroazepin-1-yl)quinazoline HPLC retention time (min): 2.96; MS (m/z): 388(M+H)$^+$; RPLC condition: A.

Example 2(31)

2-(2-dimethylamino-1-methylethylamino)-4-(perhydroazepin-1-yl)quinazoline

HPLC retention time (min): 2.98; MS (m/z): 328 (M+H)$^+$; HPLC condition: A.

Example 2(32)

2-[3-(2-methylpiperidin-1-yl)propylamino]-4-(perhydroazepin-1-yl)quinazoline

HPLC retention time (min): 3.11; MS (m/z): 382 (M+H)$^+$, 243; HPLC condition: A.

Example 2(33)

2-(2-dimethylaminoethylamino)-4-pyrrolidinoquinazoline

HPLC retention time (min): 2.83; MS (m/z): 286 (M+H)$^+$, 241; HPLC condition: A.

Example 2(34)

2-(2-pyrrolidinoethylamino)-4-pyrrolidinoquinazoline

HPLC retention time (min): 3.11; MS (m/z): 312 (M+H)$^+$, 241; HPLC condition: A.

Example 2(35)

2-(3-pyrrolidinopropylamino)-4-pyrrolidinoquinazoline

HPLC retention time (min): 2.89; MS (m/z): 326 (M+H)$^+$, 215; BPLC condition: A.

Example 2(36)

2-(2-piperidinoethylamino)-4-pyrrolidinoquinazoline

HPLC retention time (min): 2.90; MS (m/z): 326 (M+H)$^+$; HPLC condition: A.

Example 2(37)

2-(2-(1-methylpyrrolidin-2-yl)ethylamino)-4-pyrrolidinoquinazoline

HPLC retention time (min): 2.90; MS (m/z): 651 (2M+H)$^+$, 326 (M+H)$^+$; HPLC condition: A.

Example 2(38)

2-(1-ethylpyrrolidin-2-ylmethylamino)-4-pyrrolidinoquinazoline

HPLC retention time (min): 2.89; MS (m/z): 326 (M+H)$^+$; HPLC condition: A.

Example 2(39)

2-(2,2-dimethyl-3-dimethylaminopropylamino)-4-pyrrolidinoquinazoline

HPLC retention time (min): 2.94; MS (m/z): 328 (M+H)$^+$; HPLC condition: A.

Example 2(40)

2-(2-dimethylaminopropylamino)-4-pyrrolidinoquinazoline

HPLC retention time (min): 2.89; MS (m/z): 300 (M+H)$^+$, 150.5; HPLC condition: A.

Example 2(41)

2-(2-diethylaminoethylamino)-4-pyrrolidinoquinazoline

HPLC retention time (min): 2.89; MS (m/z): 314 (M+H)$^+$, 241; HPLC condition: A.

Example 2(42)

2-(3-diethylaminopropylamino)-4-pyrrolidinoquinazoline

HPLC retention time (min): 2.92; MS (m/z): 328 (M+H)$^+$; HPLC condition: A.

Example 2(43)

2-(3-morpholinopropylamino)-4-pyrrolidinoquinazoline

HPLC retention time (min): 2.89; MS (m/z): 342 (M+H)$^+$; HPLC condition: A.

Example 2(44)

2-[3-[N,N-bis(2-hydroxyethyl)amino]propylamino]-4-pyrrolidinoquinazoline

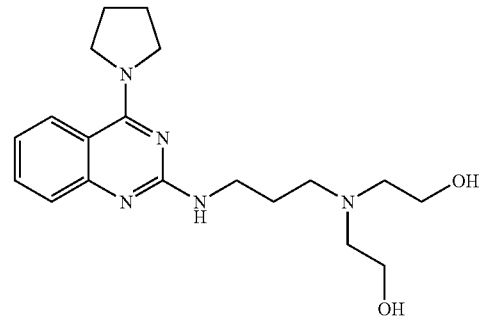

HPLC retention time (min): 2.89; MS (m/z): 360 (M+H)$^+$; HPLC condition: A.

Example 2(45)

2-(3-dimethylaminopropylamino)-4-pyrrolidinoquinazoline

HPLC retention time (min): 2.89; MS (m/z): 300 (M+H)$^+$, 255; HPLC condition: A.

Example 2(46)

2-(2-dimethylamino-1-methylethylamino)-4-pyrrolidinoquinazoline

HPLC retention time (min): 2.87; MS (m/z): 300 (M+H)$^+$; HPLC condition: A.

Example 2(47)

2-(1-methylpyrrolidin-2-ylmethylamino)-4-pyrrolidinoquinazoline

HPLC retention time (min): 2.91; MS (m/z): 312 (M+H)$^+$; HPLC condition: A.

Example 2(48)

2-[2-[N,N-bis(2-hydroxyethyl)amino]ethylamino]-4-(perhydroazocin-1-yl)quinazoline HPLC retention time (min): 3.00; MS (m/z): 775 (2M+H)$^+$, 388 (M+H)$^+$; HPLC condition: A.

Example 2(49)

2-(2-pyrrolidinoethylamino)-4-(perhydroazocin-1-yl)quinazoline

HPLC retention time (min): 3.02; MS (m/z): 354 (M+H)$^+$; HPLC condition: A.

Example 2(50)

2-(3-imidazol-1-ylpropylamino)-4-(perhydroazocin-1-yl)quinazoline

HPLC retention time (min): 3.07; MS (m/z): 729 (2M+H)$^+$, 365 (M+H)$^+$; HPLC condition: A.

Example 2(51)

2-(2-morpholinoethylamino)-4-(perhydroazocin-1-yl)quinazoline

HPLC retention time (min): 3.01; MS (m/z): 739 (2M+H)$^+$, 370 (M+H)$^+$; HPLC condition: A.

Example 2(52)

2-(3-pyrrolidinopropylamino)-4-(perhydroazocin-1-yl)quinazoline

HPLC retention time (min): 3.11; MS (m/z): 368 (M+H)$^+$, 184.5; HPLC condition: A.

Example 2(53)

2-(2-piperidinoethylamino)-4-(perhydroazocin-1-yl)quinazoline

HPLC retention time (min): 3.07; MS (m/z): 368 (M+H)$^+$, 184.5; HPLC condition: A.

Example 2(54)

2-[2-(1-methylpyrrolidin-2-yl)ethylamino]-4-(perhydroazocin-1-yl)quinazoline

HPLC retention time (min): 3.09; MS (m/z): 735 (2M+H)$^+$, 368 (M+H)$^+$; HPLC condition: A.

Example 2(55)

2-(1-ethylpyrrolidin-2-ylmethylamino)-4-(perhydroazocin-1-yl)quinazoline

HPLC retention time (min): 3.09; MS (m/z): 368 (M+H)$^+$, 207; HPLC condition: A.

Example 2(56)

2-(3-dimethylamino-2,2-dimethylpropylamino)-4-(perhydroazocin-1-yl)quinazoline

HPLC retention time (min): 3.11; MS (m/z): 370 (M+H)$^+$; HPLC condition: A.

Example 2(57)

2-(2-dimethylaminopropylamino)-4-(perhydroazocin-1-yl)quinazoline

HPLC retention time (min): 3.07; MS (m/z): 342 (M+H)$^+$; HPLC condition: A.

Example 2(58)

2-(2-diethylaminoethylamino)-4-(perhydroazocin-1-yl)quinazoline

HPLC retention time (min): 3.05; MS (m/z): 356 (M+H)$^+$; HPLC condition: A.

Example 2(59)

2-(3-diethylaminopropylamino)-4-(perhydroazocin-1-yl)quinazoline

HPLC retention time (min): 3.11; MS (m/z): 370 (M+H)$^+$, 185.5; HPLC condition: A.

Example 2(60)

2-(3-morpholinopropylamino)-4-(perhydroazocin-1-yl)quinazoline

HPLC retention time (min): 3.07; MS (m/z): 384 (M+H)$^+$; HPLC condition: A.

Example 2(61)

2-[3-[N,N-bis(2-hydroxyethyl)amino]propylamino]-4-(perhydroazocin-1-yl)quinazoline HPLC retention time (min): 3.03; MS (m/z): 402 (M+H)$^+$; HPLC condition: A.

Example 2(62)

2-(3-dimethylaminopropylamino)-4-(perhydroazocin-1-yl)quinazoline

HPLC retention time (min): 3.07; MS (m/z): 342 (M+H)$^+$, 297; HPLC condition: A.

Example 2(63)

2-(2-dimethylamino-1-methylethylamino)-4-(perhydroazocin-1-yl)quinazoline

HPLC retention time (min): 3.02; MS (m/z): 342 (M+H)$^+$; HPLC condition: A.

Example 2(64)

2-[3-(2-methylpiperidin-1-yl)propylamino]-4-(perhydroazocin-1-yl)quinazoline

HPLC retention time (min): 3.14; MS (m/z): 396 (M+H)$^+$, 198.5; HPLC condition: A.

Example 2(65)

2-(1-methylpyrrolidin-2-ylmethylamino)-4-(perhydroazocin-1-yl)quinazoline

HPLC retention time (min): 3.07; MS (m/z): 354 (M+H)$^+$; HPLC condition: A.

Example 2(66)

2-[2-[N,N-bis(2-hydroxyethyl)amino]ethylamino]-4-(3-azabicyclo[3.2.2]nonan-3-yl)quinazoline

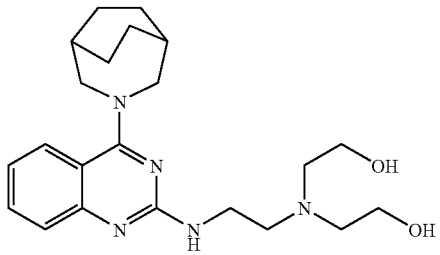

HPLC retention time (min): 3.01; MS (m/z): 799 (2M+H)$^+$, 400 (M+H)$^+$; HPLC condition: A.

Example 2(67)

2-(2-pyrrolidinoethylamino)-4-(3-azabicyclo[3.2.2]nonan-3-yl)quinazoline

HPLC retention time (min): 3.09; MS (m/z): 366 (M+H)$^+$, 207; HPLC condition: A.

Example 2(68)

2-[3-(imidazol-1-ylamino)propyl]-4-(3-azabicyclo[3.2.2]nonan-3-yl)quinazoline

HPLC retention time (min): 3.11; MS (m/z): 753 (2M+H)$^+$, 377 (M+H)$^+$; HPLC condition: A.

Example 2(69)

2-(2-morpholinoethylamino)-4-(3-azabicyclo[3.2.2]nonan-3-yl)quinazoline

HPLC retention time (min): 3.05; MS (m/z): 763(2M+H)$^+$, 382 (M+H)$^+$; HPLC condition: A.

Example 2(70)

2-(3-pyrrolidinopropylamino)-4-(3-azabicyclo[3.2.2]nonan-3-yl)quinazoline

HPLC retention time (min): 3.11; MS (m/z): 380 (M+H)$^+$, 190.5; HPLC condition: A.

Example 2(71)

2-(2-piperidinoethylamino)-4-(3-azabicyclo[3.2.2]nonan-3-yl)quinazoline

HPLC retention time (min): 3.11; MS (m/z): 380 (M+H)$^+$; HPLC condition: A.

Example 2(72)

2-[2-(1-methylpyrrolidin-2-yl)ethylamino]-4-(3-azabicyclo[3.2.2]nonan-3-yl)quinazoline HPLC retention time (min): 3.11; MS (m/z): 380 (M+H)$^+$; HPLC condition: A.

Example 2(73)

2-(1-ethylpyrrolidin-2-ylmethylamino)-4-(3-azabicyclo[3.2.2]nonan-3-yl)quinazoline HPLC retention time (min): 3.11; MS (m/z): 380 (M+H)$^+$; HPLC condition: A.

Example 2(74)

2-[3-dimethylamino-2,2-dimethylpropylamino]-4-(3-azabicyclo[3.2.2]nonan-3-yl)quinazoline HPLC retention time (min): 3.14; MS (m/z): 382 (M+H)$^+$; HPLC condition: A.

Example 2(75)

2-(2-dimethylaminopropylamino)-4-(3-azabicyclo[3.2.2]nonan-3-yl)quinazoline

HPLC retention time (min): 3.09; MS (m/z): 354 (M+H)$^+$; HPLC condition: A.

Example 2(76)

2-(2-diethylaminoethylamino)-4-(3-azabicyclo[3.2.2]nonan-3-yl)quinazoline

HPLC retention time (min): 3.06; MS (m/z): 368 (M+H)$^+$; HPLC condition: A.

Example 2(77)

2-(3-diethylaminopropylamino)-4-(3-azabicyclo[3.2.2]nonan-3-yl)quinazoline

HPLC retention time (min): 3.14; MS (m/z): 382 (M+H)$^+$, 191.5; HPLC condition: A.

Example 2(78)

2-(3-morpholinopropylamino)-4-(3-azabicyclo[3.2.2]nonan-3-yl)quinazoline

HPLC retention time (min): 3.08; MS (m/z): 791 (2M+H)$^+$, 396 (M+H)$^+$; HPLC condition: A.

Example 2(79)

2-[3-[N,N-bis(2-hydroxyethyl)amino]propylamino]-4-(3-azabicyclo[3.2.2]nonan-3-yl)quinazoline HPLC retention time (min): 3.05; MS (m/z): 414 (M+H)$^+$; HPLC condition: A.

Example 2(80)

2-(3-dimethylaminopropylamino)-4-(3-azabicyclo[3.2.2]nonan-3-yl)quinazoline

HPLC retention time (min): 3.09; MS (m/z): 354 (M+H)$^+$; HPLC condition: A.

Example 2(81)

2-(2-dimethylamino-1-methylethylamino)-4-(3-azabicyclo[3.2.2]nonan-3-yl)quinazoline HPLC retention time (min): 3.07; MS (m/z): 354 (M+H)$^+$; HPLC condition: A.

Example 2(82)

2-[3-(2-methylpiperidin-1-yl)propylamino]-4-(3-azabicyclo[3.2.2]nonan-3-yl)quinazolin HPLC retention time (min): 3.18; MS (m/z): 408 (M+H)$^+$; HPLC condition: A.

Example 2(83)

2-(1-methylpyrrolidin-2-ylmethylamino)-4-(3-azabicyclo[3.2.2]nonan-3-yl)quinazoline HPLC retention time (min): 3.09; MS (m/z): 731 (2M+H)$^+$, 366 (M+H)$^+$; HPLC condition: A.

Example 2(84)

2-(2-dimethylaminoethylamino)-4-piperidinoquinazoline

MS (m/z): 300 (M+H)$^+$;
HPLC retention time (min): 3.83; HPLC condition: B.

Example 2(85)

2-(2-pyrrolidinoethylamino)-4-piperidinoquinazoline

NMR (DMSO-d$_6$): δ 7.66 (d, J=7.2 Hz, 1H), 7.48 (m, 1H), 7.30 (d, J=8.4 Hz, 1H), 7.04 (t, J=7.2 Hz, 1H), 6.51 (m, 1H), 3.50 (m, 4H), 3.43 (m, 2H), 3.25 (m, 2H), 3.15 (m, 2H), 2.57 (t, J=6.9 Hz, 2H), 1.66 (m, 10H);
MS (m/z): 326 (M+H)$^+$, 283;
HPLC retention time (min): 4.16; HPLC condition: B.

Example 2(86)

2-(2-piperidinoethylamino)-4-piperidinoquinazoline

NMR (DMSO-d$_6$): δ 7.66 (dd, J=8.4, 0.9 Hz, 1H), 7.49 (m, 1H), 7.30 (d, J=8.1 Hz, 1H), 7.04 (t, J=7.2 Hz, 1H), 6.45 (m, 1H), 3.40 (m, 4H), 3.43 (m, 2H), 2.45 (t, J=7.2 Hz, 2H), 2.37 (m, 4H), 1.66 (m, 6H), 1.49 (m, 4H), 1.38 (m, 2H);
MS (m/z): 340 (M+H)$^+$;
HPLC retention time (min): 4.16; HPLC condition: B.

Example 2(87)

2-(2-pyrrolidinoethylamino)-4-(perhydroazepin-1-yl)quinazoline

NMR (DMSO-d$_6$): δ 7.81 (d, J=8.4 Hz, 1H), 7.44 (m, 1H), 7.25 (d, J=7.8 Hz, 1H), 6.96 (t, J=7.5 Hz, 1H), 6.29 (m, 1H), 3.81 (m, 4H), 3.39 (m, 2H), 2.56 (t, J=6.9 Hz, 2H), 2.37 (m, 4H), 1.86 (m, 4H), 1.67 (m, 4H), 1.56 (m, 4H);
MS (m/z): 340 (M+H)$^+$, 215;
HPLC retention time (min): 4.41; HPLC condition: B.

Example 2(88)

2-(2-piperidinoethylamino)-4-(perhydroazepin-1-yl)quinazoline

NMR (DMSO-d$_6$): δ 7.81 (d, J=8.4 Hz, 1H), 7.44 (m, 1H), 7.25 (d, J=8.4 Hz, 1H), 6.92 (t, J=8.4 Hz, 1H), 6.23 (m, 1H), 3.86 (m, 4H), 3.38 (m, 2H), 2.43 (m, 2H), 2.36 (m, 4H), 1.86 (m, 4H), 1.56 (m, 4H), 1.48 (m, 4H), 1.37 (m, 2H);
MS (m/z): 354 (M+H)$^+$;
HPLC retention time (min): 3.96; HPLC condition: B.

Example 2(89)

2-(3-dimethylaminopropylamino)-4-(perhydroazepin-1-yl)quinazoline

NMR (DMSO-d$_6$): δ 7.80 (d, J=7.5 Hz, 1H), 7.48 (m, 1H), 7.24 (d, J=7.8 Hz, 1H), 6.95 (t, J=7.5 Hz, 1H), 6.49 (m, 1H), 3.80 (m, 4H), 3.30 (m, 2H), 2.24 (t, J=6.9 Hz, 2H), 2.11 (s, 6H), 1.86 (m, 4H), 1.62 (m, 2H), 1.56 (m, 4H);
MS (m/z): 328 (M+H)$^+$;
HPLC retention time (min): 2.96; HPLC condition: A.

Example 2(90)

2-(4-dimethylaminobutylamino)-4-(perhydroazepin-1-yl)quinazoline

NMR (DMSO-d$_6$): δ 7.81 (d, J=8.1 Hz, 1H), 7.44 (t, J=8.1 Hz, 1H), 7.24 (d, J=8.1 Hz, 1H), 6.96 (t, J=8.1 Hz, 1H), 6.57 (m, 1H), 3.81 (m, 4H), 3.30 (m, 2H), 2.37 (m, 2H), 2.21 (s, 6H), 1.86 (m, 4H), 1.56-(m, 4H), 1.50 (m, 4H);
MS (m/z): 342 (M+H)$^+$;
HPLC retention time (min): 3.00; HPLC condition: A.

Example 2(91)

4-(2-dimethylaminoethylamino)-2-(perhydroazepin-1-yl)quinazoline

TLC: Rf 0.31 (chloroform:methanol:28% ammoniawater=80:10:1);
NMR (DMSO-d$_6$): δ 7.89 (d, J=6.9 Hz, 1H), 7.83 (t, J=6.3 Hz, 1H), 7.43 (dd, J=8.4, 6.9 Hz, 1H), 7.21 (d, J=7.8 Hz, 1H), 6.98 (dd, J=8.4, 7.8 Hz, 1H), 3.74 (t, J=6.0 Hz, 4H), 3.57 (dt, J=6.3, 6.3 Hz, 2H), 2.54 (t, J=6.3 Hz, 2H), 2.22 (s, 6H), 1.7 (m, 4H), 1.46 (m, 4H).

Example 2(92)

2-(2-aminoethylamino)-4-(perhydroazepin-1-yl)quinazoline

TLC: Rf 0.14 (chloroform:methanol:28% ammonia water=80:10:1);
NMR (DMSO-d$_6$): δ 7.81 (d, J=8.4 Hz, 1H), 7.43 (dd, J=8.4, 7.2 Hz, 1H), 7.25 (d, J=8.4 Hz, 1H), 6.96 (dd, J=8.4, 7.2 Hz, 1H), 6.46 (br, 1H), 3.79 (m, 4H), 3.29 (m, 2H), 2.69 (t, J=6.0 Hz, 2H), 1.85 (m, 4H), 1.56 (m, 4H).

Example 2(93)

2-(2-dimethylaminoethylamino)-4-(perhydroazocin-1-yl)quinazoline

TLC: Rf 0.31 (chloroform:methanol:28% ammonia water=80:10:1);
NMR (DMSO-d$_6$): δ 1.61 (m, 6H), 1.90 (m, 4H), 2.60 (s, 6H), 2.98 (t, J=6.18 Hz, 2H), 3.65 (t, J=6.18 Hz, 2H), 3.94 (m, 4H), 7.17 (m, 1H), 7.42 (m, 1H), 7.57 (m, 1H), 7.96 (d, J=8.24 Hz, 1H).

Example 2(94)

4-(3-azabicyclo[3.2.2]nonan-3-yl)-2-(2-dimethylaminoethylamino)quinazoline

TLC: Rf 0.34 (chloroform:methanol:28% ammonia water=80:10:1);
NMR (DMSO-d$_6$): δ 2.01 (m, 10H), 2.56 (s, 6H), 2.77 (t, J=6.73 Hz, 2H), 3.74 (m, 2H), 4.17 (m, 4H), 6.71 (m, 1H), 7.37 (t, J=8.1 Hz, 1H), 7.65 (d, J=8.1 Hz, 1H) 7.83 (t, J=8.1 Hz, 1H), 8.09 (d, J=8.10 Hz, 1H).

Example 2(95)

2-(2-dimethylaminoethylamino)-4-(perhydroazepin-1-yl)quinazoline

TLC: Rf 0.45 (chloroform:methanol:28% ammonia water=80:10:1);
NMR (DMSO-d$_6$): δ 1.56 (m, 4H), 1.85 (m, 4H), 2.16 (s, 6H), 2.39 (t, J=6.87 Hz, 2H), 3.37 (m, 2H), 3.80 (m, 4H), 6.23 (m, 1H), 6.96 (m, 1H), 7.25 (d, J=8.24 Hz, 1H), 7.44 (m, 1H), 7.81 (d, J=8.52 Hz, 1H).

REFERENCE EXAMPLE 3

2-[1-(t-butoxycarbonyl)pyrrolidin-2-ylmethylamino]-4-(perhydroazepin-1-yl)pyrimidine The title compound having the following physical data was given by substituting N,N-dimethylethylenediamine in example 1 with 1-(t-butoxycarbonyl)pyrrolidin-2-ylmethylamine.
TLC: Rf 0.45 (chloroform: methanol=9:1);
NMR (CDCl$_3$): δ 7.65 (m, 1H), 5.81 (d, J=6.3 Hz, 1H), 4.01 (m, 1H), 3.52 (m, 8H), 1.89 (m, 4H), 1.75 (m, 4H), 1.55 (m, 4H), 1.46 (s, 9H);
MS (m/z): 376 (M+H)$^+$.

EXAMPLE 3

2-(pyrrolidin-2-yllmethylamino)-4-(perhydroazepin-1-yl)pyrimidine

To the compound prepared in Reference Example 3 (1.06 g) was added a 95% aqueous solution of trifluoroacetic acid (20 mL) with ice cooling and the mixture was stirred for 2 hours at 0° C. The reaction mixture was concentrated and the residue was purified by column chromatography on silica gel (chloroform:methanol=9:1→chloroform:methanol:28% ammonia water=80:10:1) to give the compound of the present invention (0.72 g) having the following physical data.

TLC: Rf 0.08 (chloroform:methanol:28% ammonia water =80:10:1);
NMR (CDCl$_3$): δ 1.48 (m, 6H), 1.73 (m, 4H), 2.07 (m, 2H), 2.76 (m, 2H), 3.02 (m, 2H), 3.14 (m, 2H), 3.55 (m, 3H), 3.89 (m, 1H), 4.84 (d, J=6.30 Hz, 1H), 5.78 (d, J=6.30 Hz, 1H), 7.79 (d, J=6.30 Hz, 1H);
MS (FAB, Pos., Glycerin+m-NBA) (m/z): 276 (M+H)$^+$.

EXAMPLE 4

2-(1-benzylpyrrolidin-3-ylamino)-4-(perhydroazepin-1-yl)pyrimidine

A mixture of the compound prepared in Reference Example 1 (4.00 g) and 1-benzyl -3-aminopyrrolidine (4.33 g) was stirred for 16 hours at 90° C. The resulting solution was cooled and purified by column chromatography on silica gel (ethyl acetate:hexane=1:2→chloroform:methanol:28% ammonia water=80:10:0.6) to give the title compound (4.85 g) having the following physical data.
TLC: Rf 0.45 (chloroform:methanol:28% ammonia water =80:10:1);
NMR (DMSO-d$_6$): δ 1.50 (m, 4H), 1.74 (m, 5H), 2.21 (m, 1H), 2.60 (dd, J=9.89, 5.22 Hz, 1H), 2.70 (m, 1H), 2.83 (m, 1H), 3.00 (dd, J=9.89, 6.87 Hz, 1H), 3.55 (m, 4H), 3.78 (s, 2H), 4.33 (m, 1H), 5.93 (d, J=6.32 Hz, 1H), 6.35 (m, 1H), 7.31 (m, 5H), 7.73 (d, J=6.04 Hz, 1H).

EXAMPLE 5

4-(perhydroazepin-1-yl)-2-(pyrrolidin-3-ylamino)pyrimidine

Under atmosphere of argon to a solution of the compound prepared in Example 4 (4.5 g) in ethanol (150 mL) was added palladium hydroxide (0.97 g), and under atmosphere of hydrogen the mixture was stirred for 4 hours at 75° C. The reaction mixture was cooled and filtered, and the filtrate was concentrated. The residue was purified by column chromatography on silica gel (methylene chloride:methanol:28% ammonia water=80:10:0.5→80:10:1) to give the compound of the present invention (2.96 g) having the following physical data.
TLC: Rf 0.15 (chloroform:methanol:28% ammonia water=80:10:1);
NMR (DMSO-d$_6$): δ1.45 (m, 4H), 1.62 (m, 6H), 1.93 (m, 1H), 2.66 (dd, J=11.26, 4.40 Hz, 1H), 2.76 (m, 1H), 2.94 (m, 2H), 3.59 (m, 4H), 4.16 (m, 1H), 5.85 (d, J=6.04 Hz, 1H), 6.42 (m, 1H), 7.72 (d, J=6.04 Hz, 1H).

REFERENCE EXAMPLE 4

2-(1-benzyloxycarbonylpiperidin-3-ylamino)-4-(perhydroazepin-1-yl)pyrimidine

A mixture of the compound prepared in Reference Example 1 (5.74 g) and 1-benzyloxycarbonyl-3-aminopiperidine (6.35 g) was stirred for 16 hours at 90° C. The reaction mixture was cooled and purified by column chromatography on silica gel (ethyl acetate:hexane=1:2→chloroform:methanol:28% ammonia water=80:10:0.5) to give the title compound (3.40 g) having the following physical data.
TLC: Rf 0.68 (chloroform:methanol:28% ammonia water=80:10:1)
NMR (CDCl$_3$): δ 1.40 (m, 2H), 1.55 (m, 4H), 1.69 (m, 4H), 2.05 (m, 2H), 3.05 (m, 2H), 3.55 (m, 4H), 3.91 (m, 1H), 4.12

(m, 2H), 4.73 (m, 1H), 5.13 (s, 2H), 5.80 (d, J=600 Hz, 1H), 7.34 (m, 5H), 7.80 (d, J=6.00 Hz, 1H).

EXAMPLE 6

2-(piperidin-3-ylamino)-4-(perhydroazepin-1-yl)pyrimidine

Under atmosphere of argon, to a solution of the compound prepared in Reference Example 4 (5.06 g) in methanol (150 mL) was added palladium-carbon (1.0 g) and under atmosphere of hydrogen the mixture was stirred for 4 hours at room temperature. The reaction mixture was filtered and the filtrate was concentrated. The residue was purified by column chromatography on silica gel (methylene chloride:methanol: 28% ammonia water=80:10:0.5→80:10:1) to give the compound of the present invention (3.02 g) having the following physical data.

TLC: Rf 0.18 (chloroform:methanol:28% ammonia water=80:10:1);
NMR (CDCl$_3$): δ 1.48 (m, 6H), 1.73 (m, 4H), 2.07 (m, 2H), 2.76 (m, 2H), 3.02 (m, 2H), 3.14 (m, 2H), 3.55 (m, 3H), 3.89 (m, 1H), 4.84 (d, J=6.30 Hz, 1H), 5.78 (d, J=6.30 Hz, 1H), 7.79 (d, J=6.30 Hz, 1H).

Example 6(1)

4-(perhydroazepin-1-yl)-2-(piperidin-4-ylamino)pyrimidine

By the same procedure as described in Example 6 using corresponding compounds, the compound of the present invention having the following physical data was given.

TLC: Rf 0.15 (chloroform:methanol:28% ammonia water=80:10:1);
NMR (DMSO-d$_6$): δ 1.27 (m, 2H), 1.45 (m, 4H), 1.65 (m, 4H), 1.76 (m, 2H), 2.47 (m, 2H), 2.92 (m, 2H), 3.63 (m, 5H), 5.81 (d, J=6.04 Hz, 1H), 6.19 (m, 1H), 7.70 (d, J=6.04 Hz, 1H).

EXAMPLE 7

2-[1-(3-methylbutyl)pyrrolidin-2-ylmethylamino]-4-(perhydroazepin-1-yl)pyrimidine To a solution of the compound prepared in Example 3 (200 mg) in a 1% solution of acetic acid in N,N-dimethylformamide (3 mL) were added 3-methylbutanal (93.4 mg) and sodium triacetoxyborohydride (462 mg) and the mixture was stirred for 8 hours at room temperature. To the reaction mixture was added acetic acid (0.5 mL). The resulting solution was poured into PS-sulfonic acid resin (prewashed with methanol (5 mL×3 times), Argonaut Inc. product ID:800287, lot. No. 00819, 1.43 mmol/g, 2.06 g). The resin was washed with methanol (5 mL×3 times). Subsequently, the resin was eluted with 5% triethylamine-methanol solution (30 mL) and the eluted solution was concentrated. The resin was dissolved in methylene chloride (10 mL) and thereto was added isocyanate resin (Argonaut Inc., product ID:800262, lot. No. 00814, 1.43 mmol/g, 1.00 g) and the resulting mixture was subjected to a reaction. The reaction mixture was filtered and the filtrate was concentrated to give the compound of the present invention (85 mg) having the following physical data.

TLC: Rf 0.43 (dichloromethane:methanol:28% ammonia water=80:10:1);
NMR (DMSO-d$_6$, 373 K): δ 0.79 (d, J=6.60 Hz, 3H), 0.80 (m, J=6.60 Hz, 3H), 1.34 (m, 2H), 1.43 (m, 4H), 1.63 (m, 7H), 1.82 (m, 2H), 2.45 (m, 2H), 2.89 (m, 2H) 3.16 (m, 2H), 3.42 (m, 1H), 3.50 (t, J=5.70 Hz, 4H), 5.83 (d, J=6.20 Hz, 1H), 6.02 (m, 1H), 7.66 (d, J=6.20 Hz, 1H);

HPLC retention time (min): 4.53; MS (m/z): 346 (M+H)$^+$; HPLC condition: B.

Example 7(1) TO Example 7(375)

By the same procedure as described in Reference Example 1→Reference Example 3→Example 3→Example 7, Reference Example 1→Example 4→Example 5→Example 7 or Reference Example 1→Reference Example 4→Example 6→Example 7 using corresponding compounds, the compounds of the present invention having the following compounds were given.

Example 7(1)

2-[1-(4-methylbenzyl)pyrrolidin-3-ylamino]-4-(perhydroazepin-1-yl)pyrimidine

TLC: Rf 0.54 (chloroform:methanol:28% ammonia water=80:10:1);
NMR (CD$_3$OD): δ 1.53 (m, 4H), 1.69 (m, 6H), 2.30 (s, 3H), 2.43 (dd, J=10.03, 5.08 Hz, 1H), 2.57 (m, 1H), 2.70 (m, 1H), 2.92 (dd, J=9.89, 7.14 Hz, 1H), 3.61 (m, 4H), 4.37 (m, 1H), 4.86 (s, 2H), 5.90 (d, J=6.32 Hz, 1H), 7.16 (m, 4H), 7.65 (d, J=6.32 Hz, 1H).

Example 7(2)

2-[1-(3-methoxybenzyl)pyrrolidin-3-ylamino]-4-(perhydroazepin-1-yl)pyrimidine

TLC: Rf 0.85 (chloroform:methanol:28% ammonia water=80:10:1);
NMR (DMSO-d$_6$): δ 1.43 (m, 4H), 1.68 (m, 6H), 2.10 (m, 1H), 2.28 (dd, J=9.34, 5.49 Hz, 1H), 2.48 (m, 1H), 2.79 (t, J=8.10 Hz, 1H), 3.33 (s, 3H), 3.51 (m, 4H), 3.71 (s, 2H), 4.21 (m, 1H), 5.81 (m, 1H), 6.44 (s, 1H), 6.81 (m, 3H), 7.19 (m, 1H), 7.69 (m, 1H).

Example 7(3)

2-(1-cyclohexylmethylpyrrolidin-3-ylamino)-4-(perhydroazepin-1-yl)pyrimidine

TLC: Rf 0.77 (chloroform:methanol:28% ammonia water=80:10:1);
NMR (DMSO-d$_6$, 373.1K): δ 0.94 (m, 2H), 1.20 (m, 3H), 1.46 (m, 5H), 1.67 (m, 10H), 2.10 (m, 1H), 2.24 (m, 2H), 2.37 (dd, J=9.34, 5.22 Hz, 1H), 2.48 (m, 1H), 2.59 (m, 1H), 2.80 (dd, J=9.07, 6.87 Hz, 1H), 3.56 (t, J=6.00 Hz, 4H), 4.26 (m, 1H), 5.77 (m, 1H), 5.84 (d, J=6.04 Hz, 1H), 7.72 (d, J=6.04 Hz, 1H).

Example 7(4)

2-[(3S)-1-isobutylpyrrolidin-3-ylamino]-4-(perhydroazepin-1-yl)pyrimidine

TLC: Rf 0.70 (chloroform:methanol:28% ammonia water=80:10:1);
NMR (DMSO-d$_6$): δ 0.84 (d, J=6.59 Hz, 6H), 1.44 (m, 4H), 1.62 (m, 5H), 2.09 (m, 4H), 2.25 (dd, J=9.34, 5.49 Hz, 1H), 2.45 (m, 2H), 2.77 (t, J=9.00 Hz, 1H), 3.38 (m, 4H), 4.19 (m, 1H), 5.83 (d, J=6.04 Hz, 1H), 6.37 (m, 1H), 7.71 (d, J=6.04 Hz, 1H).

Example 7(5)

2-[(3R)-1-isobutylpyrrolidin-3-ylamino]-4-(perhydroazepin-1-yl)pyrimidine

TLC: Rf 0.70 (chloroform:methanol:28% ammonia water=80:10:1);
NMR (DMSO-$d_6$): δ 0.84 (d, J=6.59 Hz, 6H), 1.44 (m, 4H), 1.62 (m, 5H), 2.09 (m, 4H), 2.25 (dd, J=9.34, 5.49 Hz, 1H), 2.45 (m, 2H), 2.77 (t, J=9.00 Hz, 1H), 3.38 (m, 4H), 4.19 (m, 1H), 5.83 (d, J=6.04 Hz, 1H), 6.37 (m, 1H), 7.71 (d, J=6.04 Hz, 1H).

Example 7(6)

2-[1-(2,4,6-trimethoxybenzyl)piperidin-3-ylamino]-4-(perhydroazepin-1-yl)pyrimidine HPLC retention time (min):4.13; MS (m/z): 911 (2M+H)$^+$, 456 (M+H)$^+$; HPLC condition: B.

Example 7(7)

2-[1-(3-cyanobenzyl)piperidin-3-ylamino]-4-(perhydroazepin-1-yl)pyrimidine

HPLC retention time (min): 3.94; MS (m/z): 781 (2M+H)$^+$, 391 (M+H)$^+$; HPLC condition: B.

Example 7(8)

2-[1-(3-methylbutyl)piperidin-3-ylamino]-4-(perhydroazepin-1-yl)pyrimidine

HPLC retention time (min): 4.34; MS (m/z): 346 (M+H)$^+$; HPLC condition: B.

Example 7(9)

2-[1-(2-carboxymethyloxybenzyl)piperidin-3-ylamino]-4-(perhydroazepin-1-yl)pyrimidine

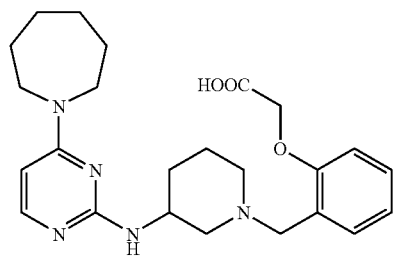

HPLC retention time (min): 3.04; MS (m/z): 879 (2M+H)$^+$, 440 (M+H)$^+$; HPLC condition: B.

Example 7(10)

2-[1-(4-dimethylaminobenzyl)piperidin-3-ylamino]-4-(perhydroazepin-1-yl)pyrimidine HPLC retention time (min): 4.20; MS (m/z): 817 (2M+H)$^+$, 409 (M+H)$^+$, 134; HPLC condition: B.

Example 7(11)

2-[1-(3-phenoxybenzyl)piperidin-3-ylamino]-4-(perhydroazepin-1-yl)pyrimidine

HPLC retention time (min): 4.50; MS (m/z): 915 (2M+H)$^+$, 458 (M+H)$^+$; HPLC condition: B.

Example 7(12)

2-(1-carboxymethylpiperidin-3-ylamino)-4-(perhydroazepin-1-yl)pyrimidine

HPLC retention time (min): 2.81; MS (m/z): 667 (2M+H)$^+$, 334 (M+H)$^+$; HPLC condition: B.

Example 7(13)

2-[1-(cyclopropylmethyl)piperidin-3-ylamino]-4-(perhydroazepin-1-yl)pyrimidine

HPLC retention time (min): 3.98; MS (m/z): 659 (2M+H)$^+$, 330 (M+H)$^+$; HPLC condition: B.

Example 7(14)

2-[1-(3-methylthiopropyl)piperidin-3-ylamino]-4-(perhydroazepin-1-yl)pyrimidine

HPLC retention time (min): 3.93; MS (m/z): 364 (M+H)$^+$; HPLC condition: B.

Example 7(15)

2-[1-(quinolin-2-ylmethyl)piperidin-3-ylamino]-4-(perhydroazepin-1-yl)pyrimidine HPLC retention time (min): 3.92; MS (m/z): 833 (2M+H)$^+$, 417 (M+H)$^+$; HPLC condition: B.

Example 7(16)

2-[1-[(Z)-dec-4-enyl]piperidin-3-ylamino]-4-(perhydroazepin-1-yl)pyrimidine

HPLC retention time (min): 3.53; MS (m/z): 827 (2M+H)$^+$, 414 (M+H)$^+$, 207.5; HPLC condition: A.

Example 7(17)

2-[1-(3-phenylpropyl)piperidin-3-ylamino]-4-(perhydroazepin-1-yl)pyrimidine

HPLC retention time (min): 4.34; MS (m/z): 787 (2M+H)$^+$, 394 (M+H)$^+$; HPLC condition: B.

Example 7(18)

2-(1-butylpiperidin-3-ylamino)-4-(perhydroazepin-1-yl)pyrimidine

HPLC retention time (min): 4.23; MS (m/z): 332 (M+H)$^+$; HPLC condition: B.

Example 7(19)

2-(1-benzylpiperidin-3-ylamino)-4-(perhydroazepin-1-yl)pyrimidine

HPLC retention time (min): 4.13; MS (m/z): 731 (2M+H)$^+$, 366 (M+H)$^+$; HPLC condition: B.

Example 7(20)

2-[1-[(E)-3-(4-dimethylaminophenyl)-2-propenyl]piperidin-3-ylamino]-4-(perhydroazepin-1-yl)pyrimidine HPLC retention time (min): 4.36; MS (m/z): 869 (2M+H)$^+$, 435 (M+H)$^+$, 160; HPLC condition: B.

Example 7(21)

2-[1-[(E)-3-(2-furyl)-2-propenyl]piperidin-3-ylamino]-4-(perhydroazepin-1-yl)pyrimidine HPLC retention time (min): 4.03; MS (m/z): 763 (2M+H)$^+$, 382 (M+H)$^+$; HPLC condition: B.

Example 7(22)

2-[1-(3-hydroxybenzyl)piperidin-3-ylamino]-4-(perhydroazepin-1-yl)pyrimidine

HPLC retention time (min): 3.43; MS (m/z): 763 (2M+H)$^+$, 382 (M+H)$^+$; HPLC condition: B.

Example 7(23)

2-[1-(2-hydroxybenzyl)piperidin-3-ylamino]-4-(perhydroazepin-1-yl)pyrimidine

HPLC retention time (min): 4.11; MS (m/z): 763 (2M+H)$^+$, 382 (M+H)$^+$; HPLC condition: B.

Example 7(24)

2-[1-(4-dihydroxyborylbenzyl)piperidin-3-ylamino]-4-(perhydroazepin-1-yl)pyrimidine

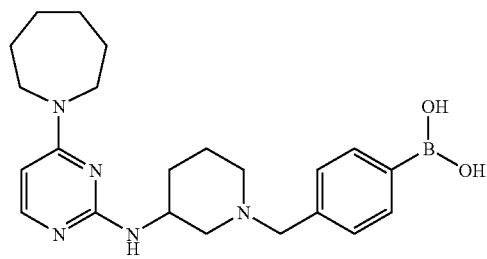

HPLC retention time (min): 3.09; MS (m/z): 410 (M+H)$^+$; HPLC condition: B.

Example 7(25)

2-[1-(4-heptyloxybenzyl)piperidin-3-ylamino]-4-(perhydroazepin-1-yl)pyrimidine

HPLC retention time (min): 3.70; MS (m/z): 959 (2M+H)$^+$, 480 (M+H)$^+$; HPLC condition: A.

Example 7(26)

2-[1-(benzo[b]fulran-2-ylmethyl)piperidin-3-ylamino]-4-(perhydroazepin-1-yl)pyrimidine HPLC retention time (min): 4.14; MS (m/z): 811 (2M+H)$^+$, 406 (M+H)$^+$; HPLC condition: B.

Example 7(27)

2-[1-(3-methylbenzo[b]thiophen-2-ylmethyl)piperidin-3-ylamino]-4-(perhydroazepin-1-yl)pyrimidine HPLC retention time (min): 4.56; MS (m/z): 871 (2M+H)$^+$, 436 (M+H)$^+$; HPLC condition: B.

Example 7(28)

2-[1-(3,7-dimethyloct-6-enyl)piperidin-3-ylamino]-4-(perhydroazepin-1-yl)pyrimidine HPLC retention time (min): 3.48; MS (m/z): 827 (2M+H)$^+$, 414 (M+H)$^+$, 207.5; HPLC condition: A.

Example 7(29)

2-[1-(4-pyrrolidinobenzyl)piperidin-3-ylamino]-4-(perhydroazepin-1-yl)pyrimidine HPLC retention time (min): 4.56; MS (m/z): 869 (2M+H)$^+$, 435 (M+H)$^+$, 160; HPLC condition: B.

Example 7(30)

2-[1-[3-(4-t-butylphenyl)-2-methylpropyl]piperidin-3-ylamino]-4-(perhydroazepin-1-yl)pyrimidine HPLC retention time (min): 3.58; MS (m/z): 927 (2M+H)$^+$, 464 (M+H)$^+$, 232.5; HPLC condition: A.

Example 7(31)

2-[1-(2-benzyloxybenzyl)piperidin-3-ylamino]-4-(perhydroazepin-1-yl)pyrimidine

HPLC retention time (min): 4.48; MS (m/z): 943 (2M+H)$^+$, 472 (M+H)$^+$; HPLC condition: B.

Example 7(32)

2-[1-[3,5-di-(t-butyl)-4-hydroxybenzyl]piperidin-3-ylamino]-4-(perhydroazepin-1-yl)pyrimidine HPLC retention time (min): 4.76; MS (m/z): 987 (2M+H)$^+$, 494 (M+H)$^+$; HPLC condition: B.

Example 7(33)

2-[1-[3-(4-isopropylphenyl)-2-methylpropyl]piperidin-3-ylamino]-4-(perhydroazepin-1-yl)pyrimidine HPLC retention time (min): 5.06; MS (m/z): 899 (2M+H)$^+$, 450 (M+H)$^+$; HPLC condition: B.

Example 7(34)

2-[1-[3,4-bis(benzyloxy)benzyl]piperidin-3-ylamino]-4-(perhydroazepin-1-yl)pyrimidine HPLC retention time (min): 4.52; MS (m/z): 578 (M+H)$^+$; HPLC condition: B.

Example 7(35)

2-[1-(3-octyloxybenzyl)piperidin-3-ylamino]-4-(perhydroazepin-1-yl)pyrimidine

HPLC retention time (min): 3.81; MS (m/z): 987 (2M+H)$^+$, 494 (M+H)$^+$, 276, 219; HPLC condition: A.

Example 7(36)

2-[1-(3,5,5-trimethylhexyl)piperidin-3-ylamino]-4-(perhydroazepin-1-yl)pyrimidine HPLC retention time (min): 3.43; MS (m/z): 803 (2M+H)$^+$, 402 (M+H)$^+$, 201.5; HPLC condition: A.

Example 7(37)

2-[1-[5-(4-hydroxy-4-methylpentyl)-1,2,3,4-tetrahydrobenzen-2-ylmethyl]piperidin-3-ylamino]-4-(perhydroazepin-1-yl)pyrimidine

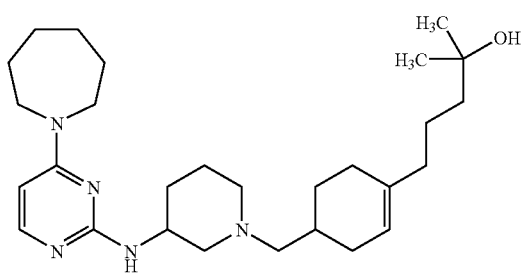

HPLC retention time (min): 4.42; MS (mn/z): 939 (2M+H)$^+$, 470 (M+H)$^+$; HPLC condition: B.

Example 7(38)

2-[1-(5-hydroxypentyl)piperidin-3-ylamino]-4-(perhydroazepin-1-yl)pyrimidine

HPLC retention time (min): 3.50; MS (m/z): 362 (M+H)$^+$; HPLC condition: B.

Example 7(39)

2-[1-[(1R,2S,3R,5R)-2-hydroxy-4,6,8-trioxaspiro[bicyclo[3.3.0]octane-7,1'-cyclohexane]-3-ylmethyl]piperidin-3-ylamino]-4-(perhydroazepin-1-yl)pyrimidine

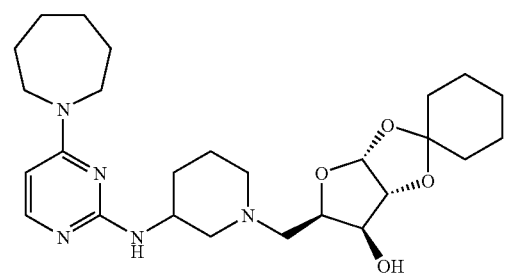

HPLC retention time (min): 3.81; MS (m/z): 975 (2M+H)$^+$, 488 (M+H)$^+$, 290; HPLC condition: B.

Example 7(40)

2-[1-(3-phenylpyrazol-4-ylmethyl)piperidin-3-ylamino]-4-(perhydroazepin-1-yl)pyrimidine HPLC retention time (min): 3.76; MS (m/z): 863 (2M+H)$^+$, 432 (M+H)$^+$, 290; HPLC condition: B.

Example 7(41)

2-[1-(4-t-butylbenzyl)piperidin-3-ylamino]-4-(perhydroazepin-1-yl)pyrimidine

HPLC retention time (min): 4.68; MS (m/z): 843 (2M+H)$^+$, 422 (M+H)$^+$; HPLC condition: B.

Example 7(42)

2-[1-(benzo-1,4-dioxan-6-ylmethyl)piperidin-3-ylamino]-4-(perhydroazepin-1-yl)pyrimidine HPLC retention time (min): 3.98; MS (m/z): 847 (2M+H)$^+$, 424 (M+H)$^+$; HPLC condition: B.

Example 7(43)

2-[1-[2-(1,1,5-trimethyl-1,2,3,4-tetrahydrobenzen-6-yl)ethyl]piperidin-3-ylamino]-4-(perhydroazepin-1-yl)pyrimidine

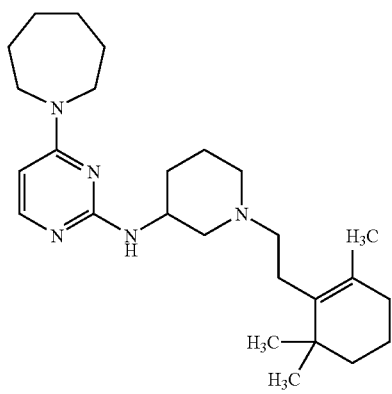

HPLC retention time (min): 3.48; MS (m/z): 851 (2M+H)$^+$, 426 (M+H)$^+$; HPLC condition: A.

Example 7(44)

2-[1-[4-(3-dimethylaminopropyloxy)benzyl]piperidin-3-ylamino]-4-(perhydroazepin-1-yl)pyrimidine HPLC retention time (min): 4.17; MS (m/z): 933 (2M+H)$^+$, 467 (M+H)$^+$; HPLC condition: B.

Example 7(45)

2-[1-(2-furylmethyl)piperidin-3-ylamino]-4-(perhydroazepin-1-yl)pyrimidine

HPLC retention time (min): 3.82; MS (m/z): 711 (2M+H)$^+$, 356 (M+H)$^+$; HPLC condition: B.

Example 7(46)

2-(1-isobutylpiperidin-3-ylamino)-4-(perhydroazepin-1-yl)pyrimidine

HPLC retention time (min): 4.29; MS (m/z): 663 (2M+H)$^+$, 332 (M+H)$^+$; HPLC condition: B.

Example 7(47)

2-(1-cyclohexylmethylpiperidin-3-ylamino)-4-(perhydroazepin-1-yl)pyrimidine

HPLC retention time (min): 4.86; MS (m/z): 743 (2M+H)$^+$, 372 (M+H)$^+$; HPLC condition: B.

Example 7(48)

2-[1-(2-thiazolylmethyl)piperidin-3-ylamino]-4-(perhydroazepin-1-yl)pyrimidine

HPLC retention time (min): 3.65; MS (m/z): 745 (2M+H)$^+$, 373 (M+H)$^+$; HPLC condition: B.

Example 7(49)

2-[1-(4-acetylaminobenzyl)piperidin-3-ylamino]-4-(perhydroazepin-1-yl)pyrimidine HPLC retention time (min): 3.56; MS (m/z): 845 (2M+H)$^+$, 423 (M+H)$^+$; HPLC condition: B.

Example 7(50)

2-[1-(2-methoxybenzyl)piperidin-3-ylamino]-4-(perhydroazepin-1-yl)pyrimidine

HPLC retention time (min): 4.13; MS (m/z): 791 (2M+H)$^+$, 396 (M+H)$^+$; HPLC condition: B.

Example 7(51)

2-[1-(4-methoxybenzyl)piperidin-3-ylamino]-4-(perhydroazepin-1-yl)pyrimidine

HPLC retention time (min): 4.06; MS (m/z): 791 (2M+H)$^+$, 396 (M+H)$^+$; HPLC condition: B.

Example 7(52)

2-[1-(4-phenylbenzyl)piperidin-3-ylamino]-4-(perhydroazepin-1-yl)pyrimidine

HPLC retention time (min): 4.55; MS (m/z): 883 (2M+H)$^+$, 442 (M+H)$^+$; HPLC condition: B.

Example 7(53)

2-[1-[(2E)-3,7-dimethylocta-2,6-dienyl]piperidin-3-ylamino]-4-(perhydroazepin-1-yl)pyrimidine

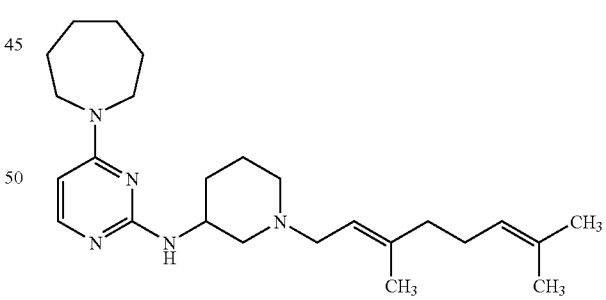

HPLC retention time (min): 4.95; MS (m/z): 823 (2M+H)$^+$, 412 (M+H)$^+$; HPLC condition: B.

Example 7(54)

2-[1-(4-diethylaminobenzyl)piperidin-3-ylamino]-4-(perhydroazepin-1-yl)pyrimidine HPLC retention time (min): 4.55; MS (m/z): 873 (2M+H)$^+$, 437 (M+H)$^+$, 162; HPLC condition: B.

Example 7(55)

2-[1-(2-ethylhexyl)piperidin-3-ylamino]-4-(perhydroazepin-1-yl)pyrimidine

HPLC retention time (min): 3.36; MS (m/z): 775 (2M+H)$^+$, 388 (M+H)$^+$, 276, 194; HPLC condition: A.

Example 7(56)

2-[1-(3-fluorobenzyl)piperidin-3-ylamino]-4-(perhydroazepin-1-yl)pyrimidine

HPLC retention time (min): 4.18; MS (m/z): 767 (2M+H)$^+$, 384 (M+H)$^+$; HPLC condition: B.

Example 7(57)

2-[1-(2-hydroxyethyl)piperidin-3-ylamino]-4-(perhydroazepin-1-yl)pyrimidine

HPLC retention time (min): 3.29; MS (m/z): 320 (M+H)$^+$; HPLC condition: B.

Example 7(58)

2-[1-(1-naphthylmethyl)piperidin-3-ylamino]-4-(perhydroazepin-1-yl)pyrimidine

HPLC retention time (min): 4.54; MS (mn/z): 831 (2M+H)$^+$, 416 (M+H)$^+$; HPLC condition: B.

Example 7(59)

2-[1-(3-nitrobenzyl)piperidin-3-ylamino]-4-(perhydroazepin-1-yl)pyrimidine

HPLC retention time (min): 4.08; MS (m/z): 821 (2M+H)$^+$, 411 (M+H)$^+$; HPLC condition: B.

Example 7(60)

2-(1-propylpiperidin-3-ylamino)-4-(perhydroazepin-1-yl)pyrimidine

HPLC retention time (min): 4.01; MS (m/z): 635 (2M+H)$^+$, 318 (M+H)$^+$; HPLC condition: B.

Example 7(61)

2-[1-[(2S,3S,4R)-2,3,4,5-tetrahydroxypentyl]piperidin-3-ylamino]-4-(perhydroazepin-1-yl)pyrimidine

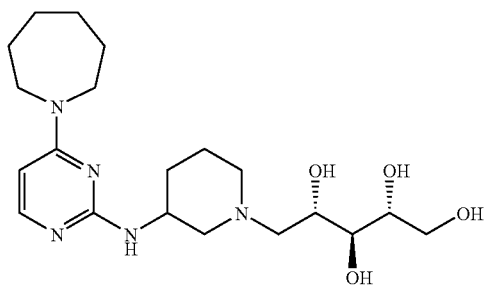

HPLC retention time (min): 3.11; MS (m/z): 819 (2M+H)$^+$, 410 (M+H)$^+$; HPLC condition: B.

Example 7(62)

2-[1-(2-thienomethyl)piperidin-3-ylamino]-4-(perhydroazepin-1-yl)pyrimidine

HPLC retention time (min): 4.05; MS (m/z): 743 (2M+H)$^+$, 372 (M+H)$^+$; HPLC condition: B.

Example 7(63)

2-[1-(4-chlorobenzyl)piperidin-3-ylamino]-4-(perhydroazepin-1-yl)pyrimidine

HPLC retention time (min): 4.35; MS (m/z): 801 (2M+H)$^+$, 400 (M+H)$^+$; HPLC condition: B.

Example 7(64)

2-[1-(2,3-dimethoxybenzyl)piperidin-3-ylamino]-4-(perhydroazepin-1-yl)pyrimidine HPLC retention time (min): 4.08; MS (m/z): 426 (M+H)$^+$; HPLC condition: B.

Example 7(65)

2-[1-[(3S,4R)-3,4,5-trihydroxypentyl]piperidin-3-ylamino]-4-(perhydroazepin-1-yl)pyrimidine

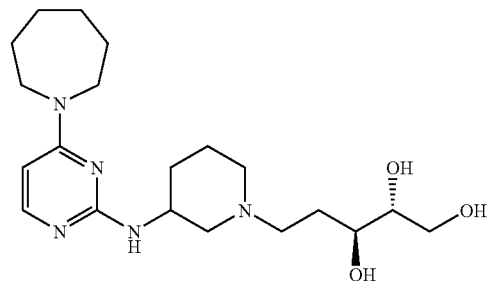

HPLC retention time (min): 3.18; MS (m/z): 787 (2M+H)$^+$, 394 (M+H)$^+$; HPLC condition: B.

Example 7(66)

2-[1-(1,5-dimethyl-2-phenyl-3-oxo-2,3-dihydro-1H-pyrazol-4-ylmethyl)piperidin-3-ylamino]-4-(perhydroazepin-1-yl)pyrimidine

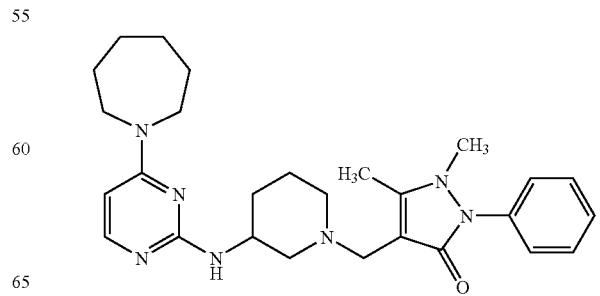

HPLC retention time (min): 3.52; MS (m/z): 951 (2M+H)+, 476 (M+H)+; HPLC condition: B.

Example 7(67)

2-[1-[5-[(E)-4-methylpent-2-enyl]-1,2,3,4-tetrahydrobenzen-2-ylmethyl]piperidin-3-ylamino]-4-(perhydroazepin-1-yl)pyrimidine

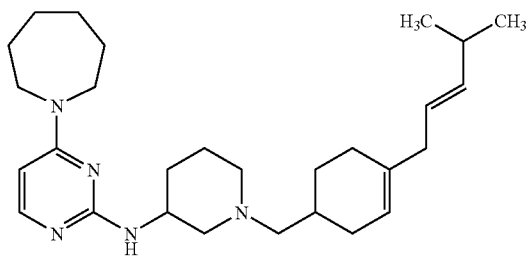

HPLC retention time (min) 3.57; MS (m/z): 903 (2M+H)+, 452 (M+H)+, 276; HPLC condition: A.

Example 7(68)

2-[1-(4-hexyloxy-3-methoxybenzyl)piperidin-3-ylamino]-4-(perhydroazepin-1-yl)pyrimidine HPLC retention time (min): 4.76; MS (m/z): 991 (2M+H)+, 496 (M+H)+; HPLC condition: B.

Example 7(69)

2-[1-(4-fluorobenzyl)piperidin-3-ylamino]-4-(perhydroazepin-1-yl)pyrimidine

HPLC retention time (min): 4.16; MS (m/z): 767 (2M+H)+, 384 (M+H)+; HPLC condition: B.

Example 7(70)

2-[1-(1,2,5-trimethyl-1,2,3,4-tetrahydrobenzen-3-ylmethyl)piperidin-3-ylamino]-4-(perhydroazepin-1-yl)pyrimidine

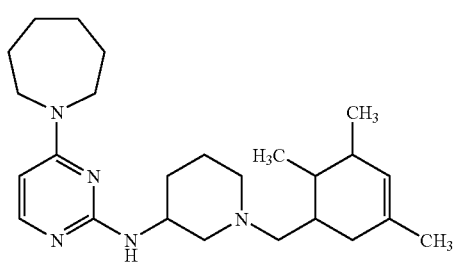

HPLC retention time (min): 5.11; MS (m/z): 823 (2M+H)+, 412 (M+H)+; HPLC condition: B.

Example 7(71)

2-[1-(3,5-dimethyl-1-phenylpyrazol-4-ylmethyl)piperidin-3-ylamino]-4-(perhydroazepin-1-yl)pyrimidine HPLC retention time (min): 4.04; MS (m/z): 919 (2M+H)+, 460 (M+H)+; HPLC condition: B.

Example 7(72)

2-[1-(2-benzyloxyethyl)piperidin-3-ylamino]-4-(perhydroazepin-1-yl)pyrimidine

HPLC retention time (min): 4.06; MS (m/z): 410 (M+H)+; HPLC condition: B.

Example 7(73)

2-[1-(4-benzyloxy-3-methoxybenzyl)piperidin-3-ylamino]-4-(perhydroazepin-1-yl)pyrimidine HPLC retention time (min): 4.29; MS (m/z): 502 (M+H)+; HPLC condition: B.

Example 7(74)

2-[1-(3-benzyloxybenzyl)piperidin-3-ylamino]-4-(perhydroazepin-1-yl)pyrimidine

HPLC retention time (min): 4.45; MS (m/z): 943 (2M+H)+, 472 (M+H)+; HPLC condition: B.

Example 7(75)

2-[1-(4-benzyloxybenzyl)piperidin-3-ylamino]-4-(perhydroazepin-1-yl)pyrimidine

HPLC retention time (min): 4.44; MS (m/z): 943 (2M+H)+, 472 (M+H)+; HPLC condition: B.

Example 7(76)

2-[1-(4-phenoxybenzyl)piperidin-3-ylamino]-4-(perhydroazepin-1-yl)pyrimidine

HPLC retention time (min): 4.51; MS (m/z): 915 (2M+H)+, 458 (M+H)+; HPLC condition: B.

Example 7(77)

2-[2-[N-methyl-N-(2,4,6-trimethoxybenzyl)amino]ethylamino]-4-(perhydroazepin-1-yl)pyrimidine HPLC retention time (min): 4.16; MS (m/z): 430 (M+H)+, 416; HPLC condition: B.

Example 7(78)

2-[2-[N-methyl-N-(3-methylbutyl)amino]ethylamino]-4-(perhydroazepin-1-yl)pyrimidine HPLC retention time (min): 4.26; MS (m/z): 320 (M+H)+; HPLC condition: B.

Example 7(79)

2-[2-[N-(2-carboxymethyloxybenzyl)-N-methylamino]ethylamino]-4-(perhydroazepin-1-yl)pyrimidine HPLC retention time (min): 2.97; MS (m/z): 827 (2M+H)$^+$, 414 (M+H)$^+$; HPLC condition: B.

Example 7(80)

2-[2-[N-(4-dimethylaminobenzyl)-N-methylamino]ethylamino]-4-(perhydroazepin-1-yl)pyrimidine HPLC retention time (min): 4.11; MS (m/z): 383 (M+H)$^+$, 134; HPLC condition: B.

Example 7(81)

2-[2-(N-carboxymethyl-N-methylamino)ethylamino]-4-(perhydroazepin-1-yl)pyrimidine HPLC retention time (min): 2.77; MS (m/z): 615 (2M+H)$^+$, 308 (M+H)$^+$; HPLC condition: B.

Example 7(82)

2-[2-(N-cyclopropylmethyl-N-methylamino)ethylamino]-4-(perhydroazepin-1-yl)pyrimidine HPLC retention time (min): 3.88; MS (m/z): 304 (M+H)$^+$; HPLC condition: B.

Example 7(83)

2-[2-[N-methyl-N-(3-methylthiopropyl)amino]ethylamino]-4-(perhydroazepin-1-yl)pyrimidine HPLC retention time (min): 3.86; MS (m/z): 338 (M+H)$^+$; HPLC condition: B.

Example 7(84)

2-[2-[N-(3-carboxypropyl)-N-methylamino]ethylamino]-4-(perhydroazepin-1-yl)pyrimidine HPLC retention time (min): 2.81; MS (m/z): 671 (2M+H)$^+$, 336 (M+H)$^+$; HPLC condition: B.

Example 7(85)

2-[2-[N-(2,6-dimethylhept-5-enyl)-N-methylamino]ethylamino]-4-(perhydroazepin-1-yl)pyrimidine HPLC retention time (min): 4.84; MS (m/z): 374 (M+H)$^+$; HPLC condition: B.

Example 7(86)

2-[2-[N-(2,2-dimethylpropyl)-N-methylamino]ethylamino]-4-(perhydroazepin-1-yl)pyrimidine HPLC retention time (min): 4.41; MS (m/z): 320 (M+H)$^+$; HPLC condition: B.

Example 7(87)

2-[2-[N-[(Z)-dec-4-enyl]-N-methylamino]ethylamino]-4-(perhydroazepin-1-yl)pyrimidine HPLC retention time (min): 5.13; MS (m/z): 388 (M+H)$^+$; HPLC condition: B.

Example 7(88)

2-[2-[N-methyl-N-(3-phenylpropyl)amino]ethylamino]-4-(perhydroazepin-1-yl)pyrimidine HPLC retention time (min): 4.22; MS (m/z): 368 (M+H)$^+$; HPLC condition: B.

Example 7(89)

2-[2-(N-butyl-N-methylamino)ethylamino]-4-(perhydroazepin-1-yl)pyrimidine

HPLC retention time (min): 4.11; MS (m/z): 306 (M+H)$^+$; HPLC condition: B.

Example 7(90)

2-[2-(N-benzyl-N-methylamino)ethylamino]-4-(perhydroazepin-1-yl)pyrimidine

HPLC retention time (min): 4.05; MS (m/z): 340 (M+H)$^+$; HPLC condition: B.

Example 7(91)

2-[2-[N-[(E)-3-(4-dimethylaminophenyl)-2-propenyl]-N-methylamino]ethylamino]-4-(perhydroazepin-1-yl)pyrimidine HPLC retention time (min): 4.26; MS (m/z): 817 (2M+H)$^+$, 409 (M+H)$^+$; HPLC condition: B.

Example 7(92)

2-[2-[N-[(E)-3-(2-furyl)-2-propenyl]-N-methylamino]ethylamino]-4-(perhydroazepin-1-yl)pyrimidine

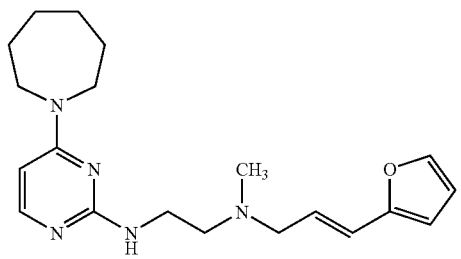

HPLC retention time (min): 3.95; MS (m/z): 356 (M+H)$^+$; HPLC condition: B.

Example 7(93)

2-[2-[N-(3-hydroxybenzyl)-N-methylamino]ethylamino]-4-(perhydroazepin-1-yl)pyrimidine HPLC retention time (min): 3.44; MS (m/z): 356 (M+H)$^+$, 262; HPLC condition: B.

Example 7(94)

2-[2-[N-(2-hydroxybenzyl)-N-methylaminoethylamino]-4-(perhydroazepin-1-yl)pyrimidine HPLC retention time (min): 3.95; MS (m/z): 711 (2M+H)$^+$, 356 (M+H)$^+$; HPLC condition: B.

Example 7(95)

2-[2-[3-N-(4-heptyloxybenzyl)-N-methylaminoethylamino]-4-(perhydroazepin-1-yl)pyrimidine HPLC retention time (min): 5.11; MS (m/z): 454 (M+H)$^+$; HPLC condition: B.

Example 7(96)

2-[2-[N-(3,7-dimethyloct-6-enyl)-N-methylamino]ethylamino]-4-(perhydroazepin-1-yl)pyrimidine HPLC retention time (min): 4.98; MS (m/z): 388 (M+H)$^+$; HPLC condition: B.

Example 7(97)

2-[2-[N-methyl-N-(4-pyrrolidinobenzyl)amino]ethylamino]-4-(perhydroazepin-1-yl)pyrimidine HPLC retention time (min): 4.46; MS (m/z): 409 (M+H)$^+$, 160; HPLC condition: B.

Example 7(98)

2-[2-[N-[3-(4-t-butylphenyl)-2-methylpropyl]-N-methylamino]ethylamino]-4-(perhydroazepin-1-yl)pyrimidine HPLC retention time (min): 4.99; MS (m/z): 438 (M+H)$^+$; HPLC condition: B.

Example 7(99)

2-[2-[N-(2-benzyloxybenzyl)-N-methylamino]ethylamino]-4-(perhydroazepin-1-yl)pyrimidine HPLC retention time (min): 4.37; MS (m/z): 446 (M+H)$^+$; HPLC condition: B.

Example 7(100)

2-[2-[N-[3-(4-isopropylphenyl)-2-methylpropyl]-N-methylamino]ethylamino]-4-(perhydroazepin-1-yl)pyrimidine HPLC retention time (min): 4.89; MS (m/z): 424 (M+H)$^+$; HPLC condition: B.

Example 7(101)

2-[2-[N-[3,4-bis(benzyloxy)benzyl]-N-methylamino]ethylamino]-4-(perhydroazepin-1-yl)pyrimidine HPLC retention time (min): 4.10; MS (m/z): 552 (M+H)$^+$; HPLC condition: B.

Example 7(102)

2-[2-[N-(4-octyloxybenzyl)-N-methylamino]ethylamino]-4-(perhydroazepin-1-yl)pyrimidine HPLC retention time (min): 3.71; MS (m/z): 468 (M+H)$^+$, 219; HPLC condition: A.

Example 7(103)

2-[2-[N-methyl-N-(3,5,5-trimethylhexyl)amino]ethylamino]-4-(perhydroazepin-1-yl)pyrimidine HPLC retention time (min): 4.98; MS (m/z): 376 (M+H)$^+$; HPLC condition: B.

Example 7(104)

2-[2-[N-[5-(4-hydroxy-4-methylpentyl)-1,2,3,4-tetrahydrobenzen-2-ylmethyl]-N-methylamino]ethylamino]-4-(perhydroazepin-1-yl)pyrimidine HPLC retention time (min): 4.27; MS (m/z): 444 (M+H)$^+$; HPLC condition: B.

Example 7(105)

2-[2-[N-(5-hydroxypentyl)-N-methylamino]ethylamino]-4-(perhydroazepin-1-yl)pyrimidine HPLC retention time (min): 3.43; MS (m/z): 336 (M+H)$^+$; HPLC condition: B.

Example 7(106)

2-[2-[N-methyl-N-(3-phenylpyrazol-4-ylmethyl)amino]ethylamino]-4-(perhydroazepin-1-yl)pyrimidine HPLC retention time (min): 3.68; MS (m/z): 811 (2M+H)$^+$, 406 (M+H)$^+$, 278; HPLC condition: B.

Example 7(107)

2-[2-[N-(4-t-butylbenzyl)-N-methylamino]ethylamino]-4-(perhydroazepin-1-yl)pyrimidine HPLC retention time (min): 4.57; MS (m/z): 396 (M+H)$^+$; HPLC condition: B.

Example 7(108)

2-[2-[N-(benzo-1,4-dioxan-6-ylmethyl)-N-methylamino]ethylamino]-4-(perhydroazepin-1-yl)pyrimidine HPLC retention time (min): 3.91; MS (m/z): 795 (2M+H)$^+$, 398 (M+H)$^+$, 292; HPLC condition: B.

Example 7(109)

2-[2-[N-methyl-N-[2-(1,1,5-trimethyl-1,2,3,4-tetrahydrobenzen-6-yl)ethyl]amino]ethylamino]-4-(perhydroazepin-1-yl)pyrimidine

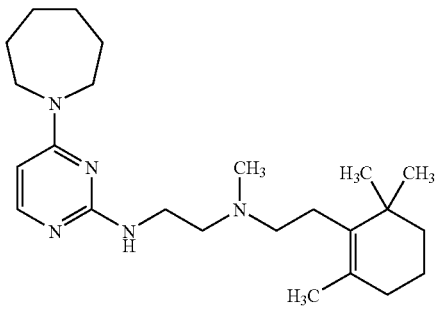

HPLC retention time (min): 5.03; MS (m/z): 400 (M+H)$^+$, 118; HPLC condition: B.

Example 7(110)

2-[2-[N-(2-furylmethyl)-N-methylamino]ethylamino]-4-(perhydroazepin-1-yl)pyrimidine HPLC retention time (min): 3.78; MS (m/z): 330 (M+H)$^+$, 250; HPLC condition: B.

Example 7(111)

2-[2-N-(4-diethylaminobenzyl)-N-methylamino]ethylamino]-4-(perhydroazepin-1-yl)pyrimidine HPLC retention time (min): 4.45; MS (m/z): 411 (M+H)$^+$, 162; HPLC condition: B.

Example 7(112)

2-[2-[N-(2-ethylhexyl)-N-methylamino]ethylamino]-4-(perhydroazepin-1-yl)pyrimidine HPLC retention time (min): 4.94; MS (m/z): 362 (M+H)$^+$; HPLC condition: B.

Example 7(113)

2-[2-[N-methyl-N-(naphthalen-1-ylmethyl)amino]ethylamino]-4-(perhydroazepin-1-yl)pyrimidine HPLC retention time (min): 4.36; MS (m/z): 390 (M+H)$^+$; HPLC condition: B.

Example 7(114)

2-[2-(N-methyl-N-propylamino)ethylamino]-4-(perhydroazepin-1-yl)pyrimidine

HPLC retention time (min): 3.92; MS (m/z): 292 (M+H)$^+$; HPLC condition: B.

Example 7(115)

4-(perhydroazepin-1-yl)-2-[2-[N-methyl-N-[(2S,3S,4R)-2,3,4,5-tetrahydroxypentyl]amino]ethylamino]pyrimidine HPLC retention time (min): 3.08; MS (m/z): 384 (M+H)$^+$; HPLC condition: B.

Example 7(116)

2-[2-[N-(2,3-dimethoxybenzyl)-N-methylamino]ethylamino]-4-(perhydroazepin-1-yl)pyrimidine HPLC retention time (min): 4.00; MS (m/z): 400 (M+H)$^+$, 118; HPLC condition: B.

Example 7(117)

2-[2-[N-methyl-N-[(3S,4R)-3,4,5-trihydroxypentyl]amino]ethylamino]-4-(perhydroazepin-1-yl)pyrimidine HPLC retention time (min): 3.13; MS (m/z): 735 (2M+H)$^+$, 368 (M+H)$^+$; HPLC condition: B.

Example 7(118)

2-[2-[N-(1,5-dimethyl-2-phenyl-3-oxo-2,3-dihydro-1H-pyrazol-4-ylmethyl)-N-methylamino]ethylamino]-4-(perhydroazepin-1-yl)pyrimidine HPLC retention time (min): 3.48; MS (m/z): 450 (M+H)$^+$; HPLC condition: B.

Example 7(119)

2-[2-[N-[5-[(E)-4-methylpent-2-enyl]-1,2,3,4-tetrahydrobenzen-2-ylmethyl]-N-methylamino]ethylamino]-4-(perhydroazepin-1-yl)pyrimidine HPLC retention time (min): 3.50; MS (m/z): 426 (M+H)$^+$, 358, 208; HPLC condition: A.

Example 7(120)

2-[2-[N-methyl-N-(1,2,5-trimethyl-1,2,3,4-tetrahydrobenzen-3-ylmethyl)amino]ethylamino]-4-(perhydroazepin-1-yl)pyrimidine HPLC retention time (min): 4.88; MS (m/z): 386 (M+H)$^+$; HPLC condition: B.

Example 7(121)

2-[2-[N-(3,5-dimethyl-1-phenylpyrazol-4-ylmethyl)-N-methylamino]ethylamino]-4-(perhydroazepin-1-yl)pyrimidine HPLC retention time (min): 3.95; MS (m/z): 867 (2M+H)$^+$, 434 (M+H)$^+$; HPLC condition: B.

Example 7(122)

2-[2-[N-(4-benzyloxy-3-methoxybenzyl)-N-methylamino]ethylamino]-4-(perhydroazepin-1-yl)pyrimidine HPLC retention time (min): 4.21; MS (m/z): 951 (2M+H)$^+$, 476 (M+H)$^+$; HPLC condition: B.

Example 7(123)

2-[2-[N-(4-benzyloxybenzyl)-N-methylamino]ethylamino]-4-(perhydroazepin-1-yl)pyrimidine HPLC retention time (min): 4.35; MS (m/z): 446 (M+H)$^+$; HPLC condition: B.

Example 7(124)

2-[1-(2,4,6-trimethoxybenzyl)pyrrolidin-2-ylmethylamino]-4-(perhydroazepin-1-yl)pyrimidine HPLC retention time (min): 4.86; MS (m/z): 456 (M+H)$^+$; HPLC condition: B.

Example 7(125)

2-[1-(2-carboxymethyloxybenzyl)pyrrolidin-2-ylmethylamino]-4-(perhydroazepin-1-yl)pyrimidine HPLC retention time (min): 3.04; MS (m/z): 879 (2M+H)$^+$, 440 (M+H)$^+$; HPLC condition: B.

Example 7(126)

2-[1-(4-dimethyl aminobenzyl)pyrrolidin-2-ylmethylamino]-4-(perhydroazepin-1-yl)pyrimidine HPLC retention time (min): 4.38; MS (m/z): 409 (M+H)$^+$, 134; HPLC condition: B.

Example 7(127)

2-[1-(3-phenoxybenzyl)pyrrolidin-2-ylmethylamino]-4-(perhydroazepin-1-yl)pyrimidine HPLC retention time (min): 4.58; MS (m/z): 458 (M+H)$^+$; HPLC condition: B.

Example 7(128)

2-[1-[(E)-2-methyl-2-butenyl]pyrrolidin-2-ylmethylamino]-4-(perhydroazepin-1-yl)pyrimidine HPLC retention time (min): 4.50; MS (m/z): 344 (M+H)$^+$; HPLC condition: B.

Example 7(129)

2-(1-carboxymethylpyrrolidin-2-ylmethylamino)-4-(perhydroazepin-1-yl)pyrimidine

HPLC retention time (min): 2.83; MS (m/z): 667 (2M+H)$^+$, 334 (M+H)$^+$; HPLC condition: B.

Example 7(130)

2-(1-cyclopropylmethylpyrrolidin-2-ylmethylamino)-4-(perhydroazepin-1-yl)pyrimidine HPLC retention time (min): 4.11; MS (m/z): 330 (M+H)$^+$; HPLC condition: B.

Example 7(131)

2-[1-(3-methylthiopropyl)pyrrolidin-2-ylmethylamino]-4-(perhydroazepin-1-yl)pyrimidine HPLC retention time (min): 4.06; MS (m/z): 364 (M+H)$^+$, 276; HPLC condition: B.

Example 7(132)

2-[1-(2,6-dimethyl-hept-5-enyl)pyrrolidin-2-ylmethylamino]-4-(perhydroazepin-1-yl)pyrimidine HPLC retention time (min): 3.34; MS (m/z): 400 (M+H)$^+$, 276, 200.5; HPLC condition: A.

Example 7(133)

2-(1-neopentylpyrrolidin-2-ylmethylamino)-4-(perhydroazepin-1-yl)pyrimidine

HPLC retention time (min): 4.71; MS (m/z): 346 (M+H)$^+$; HPLC condition: B.

Example 7(134)

2-[1-[(Z)-dec-4-enyl]pyrrolidin-2-ylmethylamino]-4-(perhydroazepin-1-yl)pyrimidine HPLC retention time (min): 3.49; MS (m/z): 414 (M+H)$^+$, 207.5; HPLC condition: A.

Example 7(135)

2-[1-(3-phenylpropyl)pyrrolidin-2-ylmethylamino]-4-(perhydroazepin-1-yl)pyrimidine HPLC retention time (min): 4.46; MS (m/z): 394 (M+H)$^+$; HPLC condition: B.

Example 7(136)

2-(1-butylpyrrolidin-2-ylmethylamino)-4-(perhydroazepin-1-yl)pyrimidine

HPLC retention time (min): 4.36; MS (m/z): 332 (M+H)$^+$; HPLC condition: B.

Example 7(137)

2-(1-benzylpyrrolidin-2-ylmethylamino)-4-(perhydroazepin-1-yl)pyrimidine

HPLC retention time (min): 4.26; MS (m/z): 366 (M+H)$^+$; HPLC condition: B.

Example 7(138)

2-[1-[(E)-3-(4-dimethylaminophenyl)-2-propenyl]pyrrolidin-2-ylmethylamino]-4-(perhydroazepin-1-yl)pyrimidine HPLC retention time (min): 4.54; MS (m/z): 435 (M+H)$^+$, 160; HPLC condition: B.

Example 7(139)

2-[1-[(E)-3-(2-furyl)-2-propenyl]pyrrolidin-2-ylmethylamino]-4-(perhydroazepin-1-yl)pyrimidine HPLC retention time (min): 4.15; MS (m/z): 382 (M+H)$^+$; HPLC condition: B.

Example 7(140)

2-[1-(3-hydroxybenzyl)pyrrolidin-2-ylmethylamino]-4-(perhydroazepin-1-yl)pyrimidine HPLC retention time (min): 3.62; MS (m/z): 763 (2M+H)$^+$, 382 (M+H)$^+$; HPLC condition: B.

Example 7(141)

2-[1-(2-hydroxybenzyl)pyrrolidin-2-ylmethylamino]-4-(perhydroazepin-1-yl)pyrimidine HPLC retention time (min): 4.12; MS (m/z): 382 (M+H)$^+$, 276; HPLC condition: B.

Example 7(142)

2-[1-(4-dihydroxyborylbenzyl)pyrrolidin-2-ylmethylamino]-4-(perhydroazepin-1-yl)pyrimidine

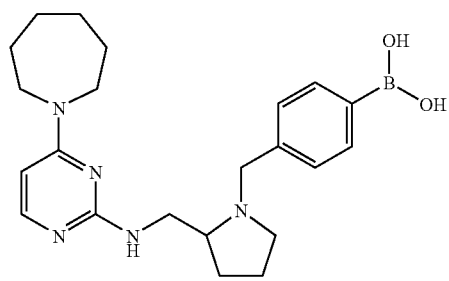

HPLC retention time (min): 3.20; MS (m/z): 410 (M+H)$^+$; HPLC condition: B.

Example 7(143)

2-[1-(4-heptyloxybenzyl)pyrrolidin-2-ylmethylamino]-4-(perhydroazepin-1-yl)pyrimidine HPLC retention time (min): 3.62; MS (m/z): 480 (M+H)$^+$, 276; HPLC condition: A.

Example 7(144)

2-[1-(3-methylbenzo[b]thiophen-2-ylmethyl)pyrrolidin-2-ylmethylamino]-4-(perhydroazepin-1-yl)pyrimidine HPLC retention time (min): 4.63; MS (m/z): 436 (M+H)$^+$; HPLC condition: B.

Example 7(145)

2-[1-(3,7-dimethyloct-6-enyl)pyrrolidin-2-ylmethylamino]-4-(perhydroazepin-1-yl)pyrimidine HPLC retention time (min): 3.43; MS (m/z): 414 (M+H)$^+$, 207.5; HPLC condition: A.

Example 7(146)

2-[1-(4-pyrrolidinobenzyl)pyrrolidin-2-ylmethylamino]-4-(perhydroazepin-1-yl)pyrimidine HPLC retention time (min): 4.83; MS (m/z): 435 (M+H)$^+$; HPLC condition: B.

Example 7(147)

2-[1-[3-(4-t-butylphenyl)-2-methylpropyl]pyrrolidin-2-ylmethylamino]-4-(perhydroazepin-1-yl)pyrimidine HPLC retention time (min): 3.53; MS (m/z): 464 (M+H)$^+$, 232.5; HPLC condition: A.

Example 7(148)

2-[1-(2-benzyloxybenzyl)pyrrolidin-2-ylmethylamino]-4-(perhydroazepin-1-yl)pyrimidine HPLC retention time (min): 4.58; MS (m/z): 472 (M+H)$^+$; HPLC condition: B.

Example 7(149)

2-[1-[3-(4-isopropylphenyl)-2-methylpropyl]pyrrolidin-2-ylmethylamino]-4-(perhydroazepin-1-yl)pyrimidine HPLC retention time (min): 3.46; MS (m/z): 450 (M+H)$^+$, 225.5; HPLC condition: A.

Example 7(150)

2-[1-[3,4-bis(benzyloxy)benzyl]pyrrolidin-2-ylmethylamino]-4-(perhydroazepin-1-yl)pyrimidine HPLC retention time (min): 4.72; MS (m/z): 578 (M+H)$^+$; HPLC condition: B.

Example 7(151)

2-[1-[5-(4-hydroxy-4-methylpentyl)-1,2,3,4-tetrahydrobenzen-2-ylmethyl]pyrrolidin-2-ylmethylamino]-4-(perhydroazepin-1-yl)pyrimidine HPLC retention time (min): 4.58; MS (m/z): 470 (M+H)$^+$; HPLC condition: B.

Example 7(152)

2-[1-(5-hydroxypentyl)pyrrolidin-2-ylmethylamino]-4-(perhydroazepin-1-yl)pyrimidine HPLC retention time (min): 3.58; MS (m/z): 362 (M+H)$^+$; HPLC condition: B.

Example 7(153)

2-[1-[(1R,2S,3R,5R)-2-hydroxy-4,6,8-trioxaspiro[bicyclo[3.3.0]octane-7,1'-cyclohexane]-3-ylmethyl]pyrrolidin-2-ylamino]-4-(perhydroazepin-1-yl)pyrimidine

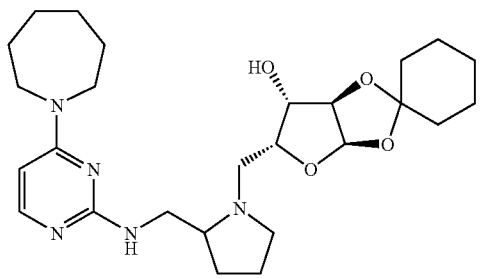

HPLC retention time (min): 3.99; MS (m/z): 488 (M+H)$^+$, 276; HPLC condition: B.

Example 7(154)

2-[1-(3-phenylpyrazol-4-ylmethyl)pyrrolidin-2-ylmethylamino]-4-(perhydroazepin-1-yl)pyrimidine HPLC retention time (min): 3.79; MS (m/z): 863 (2M+H)$^+$, 432 (M+H)$^+$, 290; HPLC condition: B.

Example 7(155)

2-[1-(4-t-butylbenzyl)pyrrolidin-2-ylmethylamino]-4-(perhydroazepin-1-yl)pyrimidine HPLC retention time (min): 4.83; MS (m/z): 422 (M+H)$^+$; HPLC condition: B.

Example 7(156)

2-[1-(1,4-benzodioxan-6-ylmethyl)pyrrolidin-2-ylamino]4-(perhydroazepin-1-yl)pyrimidine HPLC retention time (min): 4.13; MS (m/z): 424 (M+H)$^+$, 276; HPLC condition: B.

Example 7(157)

2-[1-[2-(1,1,5-trimethyl-1,2,3,4-tetrahydrobenzen-6-yl)ethyl]pyrrolidin-2-ylmethylamino]-4-(perhydroazepin-1-yl)pyrimidine HPLC retention time (min): 3.41; MS (m/z): 426 (M+H)$^+$, 276, 213.5; HPLC condition: A.

Example 7(158)

2-[1-[4-(3,3-dimethylaminopropyloxy)benzyl]pyrrolidin-2-ylmethylamino]-4-(perhydroazepin-1-yl)pyrimidine HPLC retention time (min): 4.36; MS (m/z): 467 (M+H)$^+$, 234; HPLC condition: B.

Example 7(159)

2-[1-(2-firylmethyl)pyrrolidin-2-ylmethylamino]-4-(perhydroazepin-1-yl)pyrimidine HPLC retention time (min): 3.94; MS (m/z): 356 (M+H)$^+$; HPLC condition: B.

Example 7(160)

2-(1-isobutylpyrrolidin-2-ylmethylamino)-4-(perhydroazepin-1-yl)pyrimidine

HPLC retention time (min): 4.48; MS (m/z): 332 (M+H)$^+$; HPLC condition: B.

Example 7(161)

2-(1-cyclohexylmethylpyrrolidin-2-ylmethylamino)-4-(perhydroazepin-1-yl)pyrimidine HPLC retention time (min): 5.06; MS (m/z): 372 (M+H)$^+$; HPLC condition: B.

Example 7(162)

2-[1-(4-acetylaminobenzyl)pyrrolidin-2-ylmethylamino]-4-(perhydroazepin-1-yl)pyrimidine HPLC retention time (min): 3.65; MS (m/z): 845 (2M+H)$^+$, 423 (M+H)$^+$; HPLC condition: B.

Example 7(163)

2-[1-(2-methoxybenzyl)pyrrolidin-2-ylmethylamino]-4-(perhydroazepin-1-yl)pyrimidine HPLC retention time (min): 4.32; MS (m/z): 396 (M+H)$^+$; HPLC condition: B.

Example 7(164)

2-[1-(4-methoxybenzyl)pyrrolidin-2-ylmethylamino]-4-(perhydroazepin-1-yl)pyrimidine HPLC retention time (min): 4.19; MS (m/z): 396 (M+H)$^+$; HPLC condition: B.

Example 7(165)

2-[1-(4-phenylbenzyl)pyrrolidin-2-ylmethylamino]-4-(perhydroazepin-1-yl)pyrimidine HPLC retention time (min): 4.66; MS (m/z): 442 (M+H)+; HPLC condition: B.

Example 7(166)

2-[1-[(2E)-3,7-dimethyloct-2,6-dienyl]pyrrolidin-2-ylmethylamino]-4-(perhydroazepin-1-yl)pyrimidine HPLC retention time (min): 3.40; MS (m/z): 412 (M+H)$^+$, 276; HPLC condition: A.

Example 7(167)

2-[1-(4-diethylaminobenzyl)pyrrolidin-2-ylmethylamino]-4-(perhydroazepin-1-yl)pyrimidine HPLC retention time (min): 4.78; MS (m/z): 437 (M+H)$^+$, 162; HPLC condition: B.

Example 7(168)

2-[1-(2-ethylhexyl)pyrrolidin-2-ylmethylamino]-4-(perhydroazepin-1-yl)pyrimidine HPLC retention time (min): 3.31; MS (m/z): 388 (M+H)$^+$, 194.5; HPLC condition: A.

Example 7(169)

2-[1-(naphthalen-1-ylmethyl)pyrrolidin-2-ylmethylamino]-4-(perhydroazepin-1-yl)pyrimidine HPLC retention time (min): 4.56; MS (m/z): 416 (M+H)$^+$; HPLC condition: B.

Example 7(170)

2-(1-propylpyrrolidin-2-ylmethylamino)-4-(perhydroazepin-1-yl)pyrimidine

HPLC retention time (min): 4.14; MS (m/z): 318 (M+H)$^+$; HPLC condition: B.

Example 7(171)

4-(perhydroazepin-1-yl)-2-[1-[(2S,3S,4R)-2,3,4,5-tetrahydroxypentyl]pyrrolidin-2-ylmethylamino]pyrimidine HPLC retention time (min): 3.18; MS (m/z): 410 (M+H)$^+$; HPLC condition: B.

Example 7(172)

2-[1-(2-thienylmethyl)pyrrolidin-2-ylmethylamino]-4-(perhydroazepin-1-yl)pyrimidine HPLC retention time (min): 4.15; MS (m/z): 372 (M+H)$^+$, 276; HPLC condition: B.

Example 7(173)

2-[1-(4-chlorobenzyl)pyrrolidin-2-ylmethylamino]-4-(perhydroazepin-1-yl)pyrimidine HPLC retention time (min): 4.47; MS (m/z): 400 (M+H)$^+$; HPLC condition: B.

Example 7(174)

2-[1-(2,3-dimethoxybenzyl)pyrrolidin-2-ylmethylamino]-4-(perhydroazepin-1-yl)pyrimidine HPLC retention time (min): 4.25; MS (m/z): 426 (M+H)$^+$; HPLC condition: B.

Example 7(175)

4-(perhydroazepin-1-yl)-2-[1-[(3S,4R)-3,4,5-trihydroxypentyl]pyrrolidin-2-ylmethylamino]pyrimidine HPLC retention time (min): 3.21; MS (m/z): 787 (2M+H)$^+$, 394 (M+H)$^+$; HPLC condition: B.

Example 7(176)

2-[1-(1,5-dimethyl-2-phenyl-3-oxo-2,3-dihydro-1H-pyrazol-4-ylmethyl)pyrrolidin-2-ylmethylamino]-4-(perhydroazepin-1-yl)pyrimidine

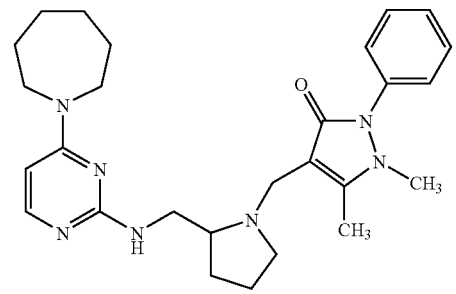

HPLC retention time (min): 3.68; MS (m/z): 476 (M+H)$^+$; HPLC condition: B.

Example 7(177)

2-[1-[5-[(E)-4-methyl-2-pentenyl]-1,2,3,4-tetrahydrobenzen-2-ylmethyl]pyrrolidin-2-ylmethylamino]-4-(perhydroazepin-1-yl)pyrimidine HPLC retention time (min): 3.53; MS (m/z): 452 (M+H)$^+$, 384, 226.5; HPLC condition: A.

Example 7(178)

2-[1-(4-hexyloxy-3-methoxybenzyl)pyrrolidin-2-ylmethylamino]-4-(perhydroazepin-1-yl)pyrimidine HPLC retention time (min): 4.86; MS (m/z): 496 (M+H)$^+$; HPLC condition: B.

Example 7(179)

2-[1-(4-fluorobenzyl)pyrrolidin-2-ylmethylamino]-4-(perhydroazepin-1-yl)pyrimidine HPLC retention time (min): 4.27; MS (m/z): 384 (M+H)$^+$; HPLC condition: B.

Example 7(180)

2-[1-(1,2,5-trimethyl-1,2,3,4-tetrahydrobenzen-3-ylmethyl)pyrrolidin-2-ylmethylamino]-4-(perhydroazepin-1-yl)pyrimidine HPLC retention time (min): 3.32; MS (m/z): 412 (M+H)$^+$, 206.5; HPLC condition: A.

Example 7(181)

2-[1-(3,5-dimethyl-1-phenylpyrazol-4-ylmethyl)pyrrolidin-2-ylmethylamino]-4-(perhydroazepin-1-yl)pyrimidine HPLC retention time (min): 4.15; MS (m/z): 460 (M+H)$^+$; HPLC condition: B.

Example 7(182)

2-[1-(4-benzyloxy-3-methoxybenzyl)pyrrolidin-2-ylmethylamino]-4-(perhydroazepin-1-yl)pyrimidine HPLC retention time (min): 4.40; MS (m/z): 502 (M+H)$^+$; HPLC condition: B.

Example 7(183)

2-[1-(3-benzyloxybenzyl)pyrrolidin-2-ylmethylamino]-4-(perhydroazepin-1-yl)pyrimidine HPLC retention time (min): 4.56; MS (m/z): 472 (M+H)$^+$; HPLC condition: B.

Example 7(184)

2-[1-(4-benzyloxybenzyl)pyrrolidin-2-ylmethylamino]-4-(perhydroazepin-1-yl)pyrimidine HPLC retention time (min): 4.57; MS (m/z): 472 (M+H)$^+$; HPLC condition: B.

Example 7(185)

2-[1-(4-phenoxybenzyl)pyrrolidin-2-ylmethylamino]-4-(perhydroazepin-1-yl)pyrimidine HPLC retention time (min): 4.63; MS (m/z): 458 (M+H)$^+$; HPLC condition: B.

Example 7(186)

2-[2-[N-[(E)-2-butenyl]-N-methyl]ethylamino]-4-(perhydroazepin-1-yl)pyrimidine

HPLC retention time (min): 3.98; MS (m/z): 304 (M+H)$^+$; HPLC condition: B.

Example 7(187)

2-[2-(N-methyl-N-pentyl)ethylamino]-4-(perhydroazepin-1-yl)pyrimidine

HPLC retention time (min): 4.35; MS (m/z): 320 (M+H)$^+$; HPLC condition: B.

Example 7(188)

2-[2-[N-methyl-N-[(E)-2-pentenyl]amino]ethylamino]-4-(perhydroazepin-1-yl)pyrimidine HPLC retention time (min): 4.18; MS (m/z): 318 (M+H)$^+$; HPLC condition: B.

Example 7(189)

2-[2-[N-(2-ethylbutyl)-N-methyl]ethylamino]-4-(perhydroazepin-1-yl)pyrimidine

HPLC retention time (min): 4.55; MS (m/z): 334 (M+H)$^+$; HPLC condition: B.

Example 7(190)

2-[2-(N-hexyl-N-methyl)ethylamino]-4-(perhydroazepin-1-yl)pyrimidine

HPLC retention time (min): 4.56; MS (m/z): 334 (M+H)$^+$; HPLC condition: B.

Example 7(191)

2-[2-[N-methyl-N-(2-methylpentyl)amino]ethylamino]-4-(perhydroazepin-1-yl)pyrimidine HPLC retention time (min): 4.56; MS (m/z): 334 (M+H)$^+$; HPLC condition: B.

Example 7(192)

2-[2-[N-[(E)-2-hexenyl]-N-methylamino]ethylamino]-4-(perhydroazepin-1-yl)pyrimidine HPLC retention time (min): 4.37; MS (m/z): 332 (M+H)$^+$; HPLC condition: B.

Example 7(193)

2-[2-[N-(3,3-dimethylbutyl)-N-methylamino]ethylamino]-4-(perhydroazepin-1-yl)pyrimidine HPLC retention time (min): 4.37; MS (m/z): 334 (M+H)$^+$; HPLC condition: B.

Example 7(194)

2-[2-[N-(1,2,3,4-tetrahydrobenzen-2-ylmethyl)-N-methylamino]ethylamino]-4-(perhydroazepin-1-yl)pyrimidine

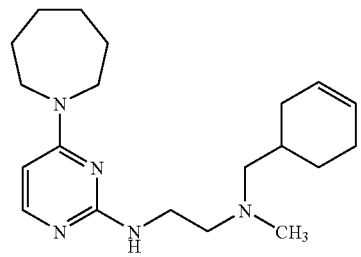

HPLC retention time (min): 4.37; MS (m/z): 344 (M+H)$^+$; HPLC condition: B.

Example 7(195)

2-[2-[N-(2,3-dimethylpentyl)-N-methylamino]ethylamino]-4-(perhydroazepin-1-yl)pyrimidine HPLC retention time (min): 4.71; MS (m/z): 348 (M+H)$^+$; HPLC condition: B.

Example 7(196)

2-[2-[N-methyl-(N-2-octynyl)amino]ethylamino]-4-(perhydroazepin-1-yl)pyrimidine

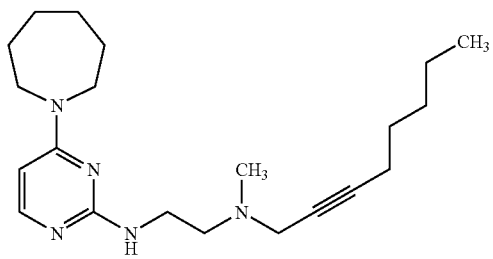

HPLC retention time (min): 4.47; MS (m/z): 358 (M+H)$^+$; HPLC condition: B.

Example 7(197)

2-[2-[N-methyl-N-(2-propylpentyl)amino]ethylamino]-4-(perhydroazepin-1-yl)pyrimidine HPLC retention time (min): 4.96; MS (m/z): 362 (M+H)$^+$; HPLC condition: B.

Example 7(198)

2-[1-(2-methoxyethyl)pyrrolidin-2-ylmethylamino]-4-(perhydroazepin-1-yl)pyrimidine HPLC retention time (min): 3.68; MS (m/z): 334 (M+H)$^+$; HPLC condition: B.

Example 7(199)

2-[1-[(E)-2-butenyl]pyrrolidin-2-ylmethylamino]-4-(perhydroazepin-1-yl)pyrimidine HPLC retention time (min): 4.23; MS (m/z): 330 (M+H)$^+$; HPLC condition: B.

Example 7(200)

2-(1-pentylpyrrolidin-2-ylmethylamino)-4-(perhydroazepin-1-yl)pyrimidine

HPLC retention time (min): 4.62; MS (m/z): 346 (M+H)$^+$; HPLC condition B.

Example 7(201)

2-[1-[(E)-2-pentenyl]pyrrolidin-2-ylmethylamino]-4-(perhydroazepin-1-yl)pyrimidine HPLC retention time (min): 4.45; MS (m/z): 344 (M+H)$^+$; HPLC condition: B.

Example 7(202)

2-[1-(2-ethylbutyl)pyrrolidin-2-ylmethylamino]-4-(perhydroazepin-1-yl)pyrimidine HPLC retention time (min): 4.91; MS (m/z): 360 (M+H)$^+$; HPLC condition: B.

Example 7(203)

2-(1-hexylpyrrolidin-2-ylmethylamino)-4-(perhydroazepin-1-yl)pyrimidine

HPLC retention time (min): 4.91; MS (m/z): 360 (M+H)$^+$; HPLC condition B.

Example 7(204)

2-[1-(2-methylpentyl)pyrrolidin-2-ylmethylamino]-4-(perhydroazepin-1-yl)pyrimidine HPLC retention time (min): 4.93; MS (m/z): 360 (M+H)$^+$; HPLC condition: B.

Example 7(205)

2-[1-[(E)-2-hexenyl]pyrrolidin-2-ylmethylamino]-4-(perhydroazepin-1-yl)pyrimidine HPLC retention time (min): 4.68; MS (m/z): 358 (M+H)$^+$; HPLC condition: B.

Example 7(206)

2-[1-(3,3-dimethylbutyl)pyrrolidin-2-ylmethylamino]-4-(perhydroazepin-1-yl)pyrimidine HPLC retention time (min): 4.65; MS (m/z): 360 (M+H)$^+$; HPLC condition: B.

Example 7(207)

2-[1-(1,2,3,4-tetrahydrobenzen-2-ylmethyl)pyrrolidin-2-ylmethylamino]-4-(perhydroazepin-1-yl)pyrimidine HPLC retention time (min): 4.71; MS (m/z): 370 (M+H)$^+$; HPLC condition: B.

Example 7(208)

2-[1-(2,3-dimethylpentyl)pyrrolidin-2-ylmethylamino]-4-(perhydroazepin-1-yl)pyrimidine HPLC retention time (min): 5.11; MS (m/z): 374 (M+H)$^+$; HPLC condition: B.

Example 7(209)

2-[1-(2-octynyl)pyrrolidin-2-ylmethylamino]-4-(perhydroazepin-1-yl)pyrimidine

HPLC retention time (min): 4.68; MS (m/z): 384 (M+H)$^+$; HPLC condition: B.

Example 7(210)

2-[1-(2-propylpentyl)pyrrolidin-2-ylmethylamino]-4-(perhydroazepin-1-yl)pyrimidine HPLC retention time (min): 4.94; MS (m/z): 388 (M+H)$^+$; HPLC condition: B.

Example 7(211)

2-[1-(2-methoxyethyl)pyrrolidin-3-ylamino]-4-(perhydroazepin-1-yl)pyrimidine

HPLC retention time (min): 3.53; MS (m/z): 320 (M+H)$^+$; HPLC condition: B.

Example 7(212)

2-[1-[(E)-2-butenyl]pyrrolidin-3-ylamino]-4-(perhydroazepin-1-yl)pyrimidine

HPLC retention time (min): 4.06; MS (m/z): 316 (M+H)$^+$; HPLC condition: B.

Example 7(213)

2-[1-(2,2-dimethoxyethyl)pyrrolidin-3-ylamino]-4-(perhydroazepin-1-yl)pyrimidine HPLC retention time (min): 3.51; MS (m/z): 350 (M+H)$^+$; HPLC condition: B.

Example 7(214)

2-(1-pentylpyrrolidin-3-ylamino)-4-(perhydroazepin-1-yl)pyrimidine

HPLC retention time (min): 4.39; MS (m/z): 332 (M+H)$^+$; HPLC condition: B.

Example 7(215)

2-[1-[(E)-2-pentenyl]pyrrolidin-3-ylamino]-4-(perhydroazepin-1-yl)pyrimidine

HPLC retention time (min): 4.24; MS (m/z): 330 (M+H)$^+$; HPLC condition: B.

Example 7(216)

2-[1-(2-ethylbutyl)pyrrolidin-3-ylamino]-4-(perhydroazepin-1-yl)pyrimidine

HPLC retention time (min): 4.56; MS (m/z): 346 (M+H)$^+$; HPLC condition: B.

Example 7(217)

2-(1-hexylpyrrolidin-3-ylamino)-4-(perhydroazepin-1-yl)pyrimidine

HPLC retention time (min): 4.63; MS (m/z): 346 (M+H)$^+$; HPLC condition: B.

Example 7(218)

2-[1-(2-methylpentyl)pyrrolidin-3-ylamino]-4-(perhydroazepin-1-yl)pyrimidine

HPLC retention time (min): 4.56; MS (m/z): 346 (M+H)$^+$; HPLC condition: B.

Example 7(219)

2-[1-[(E)-2-hexenyl]pyrrolidin-3-ylamino]-4-(perhydroazepin-1-yl)pyrimidine

HPLC retention time (min): 4.45; MS (m/z): 344 (M+H)$^+$; HPLC condition: B.

Example 7(220)

2-[1-(3,3-dimethylbutyl)pyrrolidin-3-ylamino]-4-(perhydroazepin-1-yl)pyrimidine

HPLC retention time (min): 4.44; MS (m/z): 346 (M+H)$^+$; HPLC condition: B.

Example 7(221)

2-[1-(1,2,3,4-tetrahydrobenzen-2-ylmethyl)pyrrolidin-3-ylamino]-4-(perhydroazepin-1-yl)pyrimidine HPLC retention time (min): 4.39; MS (m/z): 356 (M+H)$^+$; HPLC condition: B.

Example 7(222)

2-[1-(2,3-dimethylpentyl)pyrrolidin-3-ylamino]-4-(perhydroazepin-1-yl)pyrimidine HPLC retention time (min): 4.70; MS (m/z): 360 (M+H)$^+$; HPLC condition: B.

Example 7(223)

2-[1-(2,2-dimethyl-4-pentenyl)pyrrolidin-3-ylamino]-4-(perhydroazepin-1-yl)pyrimidine HPLC retention time (min): 4.62; MS (m/z): 358 (M+H)$^+$; HPLC condition: B.

Example 7(224)

2-[1-(2-octynyl)pyrrolidin-3-ylamino]-4-(perhydroazepin-1-yl)pyrimidine

HPLC retention time (min): 4.53; MS (m/z): 370 (M+H)$^+$; HPLC condition: B.

Example 7(225)

2-[1-(2-propylpentyl)pyrrolidin-3-ylamino]-4-(perhydroazepin-1-yl)pyrimidine

HPLC retention time (min): 4.97; MS (m/z): 374 (M+H)$^+$; HPLC condition: B.

Example 7(226)

2-[1-(2-methoxyethyl)piperidin-3-ylamino]-4-(perhydroazepin-1-yl)pyrimidine

HPLC retention time (min): 3.56; MS (m/z): 334 (M+H)$^+$; HPLC condition: B.

Example 7(227)

2-[1-[(E)-2-butenyl]piperidin-3-ylamino]-4-(perhydroazepin-1-yl)pyrimidine

HPLC retention time (min): 4.10; MS (m/z): 659 (2M+H)$^+$, 330 (M+H)$^+$; HPLC condition: B.

Example 7(228)

2-[1-(2,2-dimethoxyethyl)piperidin-3-ylamino]-4-(perhydroazepin-1-yl)pyrimidine

HPLC retention time (min): 3.56; MS (m/z): 364 (M+H)$^+$; HPLC condition: B.

Example 7(229)

2-(1-pentylpiperidin-3-ylamino)-4-(perhydroazepin-1-yl)pyrimidine

HPLC retention time (min): 4.45; MS (m/z): 346 (M+H)$^+$; HPLC condition: B.

Example 7(230)

2-[1-[(E)-2-pentenyl]piperidin-3-ylamino]-4-(perhydroazepin-1-yl)pyrimidine

HPLC retention time (min): 4.29; MS (m/z): 344 (M+H)$^+$; HPLC condition: B.

Example 7(231)

2-[1-(2-ethylbutyl)piperidin-3-ylamino]-4-(perhydroazepin-1-yl)pyrimidine

TLC: Rf 0.60 (chloroform:methanol:28% ammonia water=80:10:1);
NMR (CDCl$_3$): δ 0.84 (t, J=7.5 Hz, 6H), 1.31 (m, 5H), 1.54 (m, 6H), 1.75 (m, 6H), 2.11 (d, J=7.0 Hz, 2H), 2.22 (m, 1H), 2.32 (m, 2H), 2.67 (m, 1H), 3.56 (m, 4H), 4.02 (m, 1H), 5.32 (m, 1H), 5.77 (d, J=6.0 Hz, 1H), 7.77 (d, J=6.0 Hz, 1H);
HPLC retention time (min): 4.77; MS (m/z): 719 (2M+H)$^+$, 360 (M+H)$^+$; HPLC condition: B.

Example 7(232)

2-(1-hexylpiperidin-3-ylamino)-4-(perhydroazepin-1-yl)pyrimidine

HPLC retention time (min): 4.73; MS (m/z): 719 (2M+H)$^+$, 360 (M+H)$^+$; HPLC condition: B.

Example 7(233)

2-[1-(2-methylpentyl)piperidin-3-ylamino]-4-(perhydroazepin-1-yl)pyrimidine

HPLC retention time (min): 4.77; MS (m/z): 719 (2M+H)$^+$, 360 (M+H)$^+$; HPLC condition: B.

Example 7(234)

2-[1-[(E)-2-hexenyl]piperidin-3-ylamino]-4-(perhydroazepin-1-yl)pyrimidine

HPLC retention time (min): 4.51; MS (m/z): 358 (M+H)$^+$; HPLC condition: B.

Example 7(235)

2-[1-(3,3-dimethylbutyl)piperidin-3-ylamino]-4-(perhydroazepin-1-yl)pyrimidine

HPLC retention time (min): 4.50; MS (m/z): 360 (M+H)$^+$; HPLC condition: B.

Example 7(236)

2-[1-(1,2,3,4-tetrahydrobenzen-2-ylmethyl)piperidin-3-ylamino]-4-(perhydroazepin-1-yl)pyrimidine HPLC retention time (min): 4.54; MS (m/z): 739 (2M+H)$^+$, 370 (M+H)$^+$; HPLC condition: B.

Example 7(237)

2-[1-(2,3-dimethylpentyl)piperidin-3-ylamino]-4-(perhydroazepin-1-yl)pyrimidine

HPLC retention time (min): 4.96; MS (m/z): 747 (2M+H)$^+$, 374 (M+H)$^+$; HPLC condition: B.

Example 7(238)

2-[1-(2-octynyl)piperidin-3-ylamino]-4-(perhydroazepin-1-yl)pyrimidine

HPLC retention time (min): 4.59; MS (m/z): 384 (M+H)$^+$; HPLC condition: B.

Example 7(239)

2-[1-(2-propylpentyl)piperidin-3-ylamino]-4-(perhydroazepin-1-yl)pyrimidine

HPLC retention time (min): 5.09; MS (m/z): 775 (2M+H)$^+$, 388 (M+H)$^+$; HPLC condition: B.

Example 7(240)

4-(perhydroazepin-1-yl)-2-[1-(2,4,6-trimethoxybenzyl)pyrrolidin-3-ylamino]pyrimidine HPLC retention time (min): 4.19; MS (m/z): 442 (M+H)$^+$; HPLC condition: B.

Example 7(241)

2-[1-(3-cyanobenzyl)pyrrolidin-3-ylamino]-4-(perhydroazepin-1-yl)pyrimidine

HPLC retention time (min): 3.86; MS (m/z): 753 (2M+H)$^+$, 377 (M+H)$^+$; HPLC condition: B.

Example 7(242)

2-[1-(3-methylbutyl)pyrrolidin-3-ylamino]-4-(perhydroazepin-1-yl)pyrimidine

HPLC retention time (min): 4.33; MS (m/z): 332 (M+H)$^+$; HPLC condition: B.

Example 7(243)

2-[1-(2-carboxymethyloxybenzyl)pyrrolidin-3-ylamino]-4-(perhydroazepin-1-yl)pyrimidine HPLC retention time (min): 3.00; MS (m/z): 851 (2M+H)$^+$, 426 (M+H)$^+$; HPLC condition: B.

Example 7(244)

2-[1-(4-dimethylaminobenzyl)pyrrolidin-3-ylamino]-4-(perhydroazepin-1-yl)pyrimidine HPLC retention time (min): 4.00; MS (m/z): 395 (M+H)$^+$; HPLC condition: B.

Example 7(245)

4-(perhydroazepin-1-yl)-2-[1-(3-phenoxybenzyl)pyrrolidin-3-ylamino]pyrimidine

HPLC retention time (min): 4.37; MS (m/z): 444 (M+H)$^+$; HPLC condition: B.

Example 7(246)

2-[1-[(E)-2-methyl-2-butenyl]pyrrolidin-3-ylamino]-4-(perhydroazepin-1-yl)pyrimidine

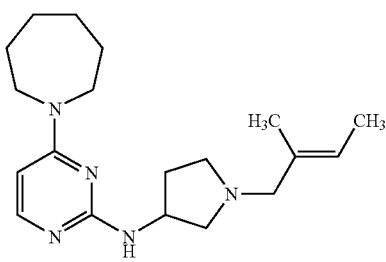

HPLC retention time (min): 4.21; MS (m/z): 330 (M+H)$^+$; HPLC condition: B.

Example 7(247)

2-[1-[(1R)-6,6-dimethylbicyclo[3.1.1]hept-2-en-2-ylmethyl]pyrrolidin-3-ylamino]-4-(perhydroazepin-1-yl)pyrimidine

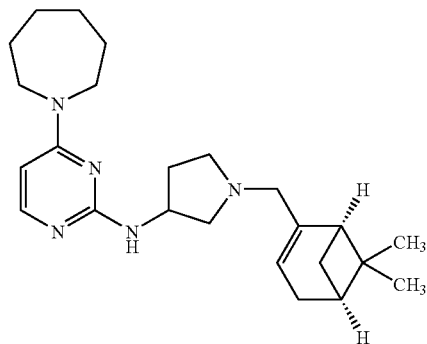

HPLC retention time (min): 4.87; MS (m/z): 396 (M+H)$^+$; HPLC condition: B.

Example 7(248)

2-[1-[(Z)-4-decenyl]pyrrolidin-3-ylamino]-4-(perhydroazepin-1-yl)pyrimidine

HPLC retention time (min): 5.34; MS (m/z): 400 (M+H)$^+$; HPLC condition: B.

Example 7(249)

4-(perhydroazepin-1-yl)-2-[1-(3-phenylpropyl)pyrrolidin-3-ylamino]pyrimidine

HPLC retention time (min): 4.30; MS (m/z): 380 (M+H)$^+$; HPLC condition: B.

Example 7(250)

2-(1-butylpyrrolidin-3-ylamino)-4-(perhydroazepin-1-yl)pyrimidine

HPLC retention time (min): 4.19; MS (m/z): 318 (M+H)$^+$; HPLC condition: B.

Example 7(251)

2-[1-[(E)-3-(4-dimethylaminophenyl)-2-propenyl]pyrrolidin-3-ylamino]-4-(perhydroazepin-1-yl)pyrimidine HPLC retention time (min): 4.01; MS (m/z): 421 (M+H)$^+$; HPLC condition: B.

Example 7(252)

2-[1-(3-hydroxybenzyl)pyrrolidin-3-ylamino]-4-(perhydroazepin-1-yl)pyrimidine

HPLC retention time (min): 3.38; MS (m/z): 735 (2M+H)$^+$, 368 (M+H)$^+$; HPLC condition: B.

Example 7(253)

2-[1-(2-hydroxybenzyl)pyrrolidin-3-ylamino]-4-(perhydroazepin-1-yl)pyrimidine

HPLC retention time (min): 3.97; MS (m/z): 735 (2M+H)$^+$, 368 (M+H)$^+$; HPLC condition: B.

Example 7(254) 2-[1-(4-dihydroxyborylbenzyl)pyrrolidin-3-ylamino]-4-(perhydroazepin-1-yl)pyrimidine

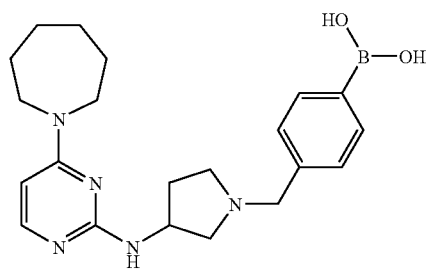

HPLC retention time (min): 3.03; MS (m/z): 396 (M+H)$^+$; HPLC condition: B.

Example 7(255)

2-[1-(4-heptyloxybenzyl)pyrrolidin-3-ylamino]-4-(perhydroazepin-1-yl)pyrimidine

HPLC retention time (min): 5.16; MS (m/z): 466 (M+H)$^+$, 398; HPLC condition: B.

Example 7(256)

2-[1-(benzo[b]furan-2-ylmethyl)pyrrolidin-3-ylamino]-4-(perhydroazepin-1-yl)pyrimidine HPLC retention time (min): 4.08; MS (m/z): 392 (M+H)$^+$; HPLC condition: B.

Example 7(257)

2-[1-(3-methylbenzo[b]thiophen-2-ylmethyl)pyrrolidin-3-ylamino]-4-(perhydroazepin-1-yl)pyrimidine HPLC retention time (min): 4.37; MS (m/z): 843 (2M+H)$^+$, 422 (M+H)$^+$; HPLC condition: B.

Example 7(258)

2-[1-[2-(4-chlorophenylthio)benzyl]pyrrolidin-3-ylamino]-4-(perhydroazepin-1-yl)pyrimidine HPLC retention time (min): 4.85; MS (m/z): 496, 494(M+H)$^+$, 398; HPLC condition: B.

Example 7(259)

2-[1-(3,7-dimethyl-6-octenyl)pyrrolidin-3-ylamino]-4-(perhydroazepin-1-yl)pyrimidine HPLC retention time (min): 5.10; MS (m/z): 400 (M+H)$^+$; HPLC condition: B.

Example 7(260)

4-(perhydroazepin-1-yl)-2-[1-(4-pyrrolidinobenzyl)pyrrolidin-3-ylamino]pyrimidine HPLC retention time (min): 4.46; MS (m/z): 421 (M+H)$^+$; HPLC condition: B.

Example 7(261)

2-[1-[2-methyl-3-(4-t-butylphenyl)propyl]pyrrolidin-3-ylamino]-4-(perhydroazepin-1-yl)pyrimidine HPLC retention time (min): 5.03; MS (m/z): 450 (M+H)$^+$; HPLC condition: B.

Example 7(262)

2-[1-(2-benzyloxybenzyl)pyrrolidin-3-ylamino]-4-(perhydroazepin-1-yl)pyrimidine

HPLC retention time (min): 4.37; MS (m/z): 458 (M+H)$^+$; HPLC condition: B.

Example 7(263)

2-[1-[3,5-di-(t-butyl)-4-hydroxybenzyl]pyrrolidin-3-ylamino]-4-(perhydroazepin-1-yl)pyrimidine HPLC retention time (min): 4.63; MS (m/z): 480 (M+H)$^+$; HPLC condition: B.

Example 7(264)

2-[1-[3-(4-isopropylphenyl)-2-methylpropyl]pyrrolidin-3-ylamino]-4-(perhydroazepin-1-yl)pyrimidine HPLC retention time (min): 4.94; MS (m/z): 436 (M+H)$^+$; HPLC condition: B.

Example 7(265)

2-[1-[3,4-bis(benzyloxy)benzyl]pyrrolidin-3-ylamino]-4-(perhydroazepin-1-yl)pyrimidine HPLC retention time (min): 4.48; MS (m/z): 564 (M+H)$^+$; HPLC condition: B.

Example 7(266)

4-(perhydroazepin-1-yl)-2-[1-(3,5,5-trimethylhexyl) pyrrolidin-3-ylamino]pyrimidine HPLC retention time (min): 5.11; MS (m/z): 388 (M+H)$^+$; HPLC condition: B.

Example 7(267)

2-[1-(butoxycarbonylmethyl)pyrrolidin-3-ylamino]-4-(perhydroazepin-1-yl)pyrimidine HPLC retention time (min): 3.91; MS (m/z): 376 (M+H)$^+$, 260; HPLC condition: B.

Example 7(268)

2-[1-[5-(4-hydroxy-4-methylpentyl)-1,2,3,4-tetrahydrobenzen-2-ylmethyl]pyrrolidin-3-ylamino]-4-(perhydroazepin-1-yl)pyrimidine HPLC retention time (min): 4.26; MS (m/z): 456 (M+H)$^+$; HPLC condition: B.

Example 7(269)

2-[1-(5-hydroxypentyl)pyrrolidin-3-ylamino]-4-(perhydroazepin-1-yl)pyrimidine

HPLC retention time (min): 3.45; MS (m/z): 348 (M+H)$^+$; HPLC condition: B.

Example 7(270)

2-[1-[(1R,2S,3R,5R)-2-hydroxy-4,6,8-trioxaspiro[bicyclo[3.3.0]octane-7,1'-cyclohexane]-3-ylmethyl]pyrrolidin-3-ylamino]-4-(perhydroazepin-1-yl)pyrimidine

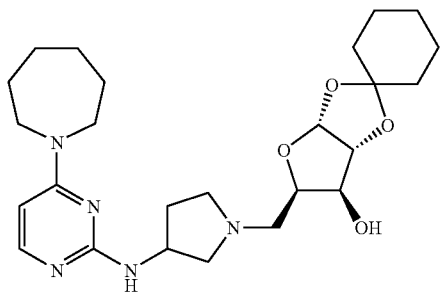

HPLC retention time (min): 3.77; MS (m/z): 474 (M+H)$^+$; HPLC condition: B.

Example 7(271)

4-(perhydroazepin-1-yl)-2-[1-(3-phenylpyrazol-4-ylmethyl)pyrrolidin-3-ylamino]pyrimidine HPLC retention time (min): 3.69; MS (m/z): 835 (2M+H)$^+$, 418 (M+H)$^+$; HPLC condition: B.

Example 7(272)

2-[1-(4-t-butylbenzyl)pyrrolidin-3-ylamino]-4-(perhydroazepin-1-yl)pyrimidine

HPLC retention time (min): 4.54; MS (m/z): 408 (M+H)$^+$; HPLC condition: B.

Example 7(273)

2-[1-(1,4-benzodioxan-6-ylmethyl)pyrrolidin-3-ylamino]-4-(perhydroazepin-1-yl)pyrimidine HPLC retention time (min): 3.88; MS (m/z): 410 (M+H)$^+$; HPLC condition: B.

Example 7(274)

4-(perhydroazepin-1-yl)-2-[1-[2-(1,1,5-trimethyl-1,2,3,4-tetrahydrobenzen-6-yl)ethyl]pyrrolidin-3-ylamino]pyrimidine

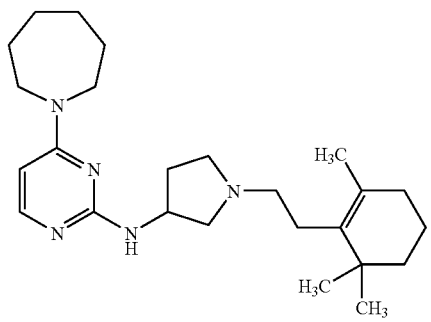

HPLC retention time (min): 5.23; MS (m/z): 412 (M+H)$^+$; HPLC condition B.

Example 7(275)

4-(perhydroazepin-1-yl)-2-[1-[4-(3-dimethylaminopropyloxy)benzyl]pyrrolidin-3-ylamino]pyrimidine HPLC retention time (min): 4.08; MS (m/z): 453 (M+H)$^+$; HPLC condition: B.

Example 7(276)

2-[1-(2-furylmethyl)pyrrolidin-3-ylamino]-4-(perhydroazepin-1-yl)pyrimidine

HPLC retention time (min): 3.78; MS (m/z): 342 (M+H)$^+$; HPLC condition: B.

Example 7(277)

4-(perhydroazepin-1-yl)-2-[1-(2-thiazolylmethyl)pyrrolidin-3-ylamino]pyrimidine

HPLC retention time (min): 3.56; MS (m/z): 359 (M+H)$^+$; HPLC condition: B.

Example 7(278)

2-[1-(4-acetylaminobenzyl)pyrrolidin-3-ylamino]-4-(perhydroazepin-1-yl)pyrimidine HPLC retention time (min): 3.47; MS (m/z): 817 (2M+H)$^+$, 409 (M+H)$^+$; HPLC condition: B.

Example 7(279)

2-[1-(2-methoxybenzyl)pyrrolidin-3-ylamino]-4-(perhydroazepin-1-yl)pyrimidine

HPLC retention time (min): 4.06; MS (m/z): 382 (M+H)$^+$; HPLC condition: B.

Example 7(280)

2-[1-(4-methoxybenzyl)pyrrolidin-3-ylamino]-4-(perhydroazepin-1-yl)pyrimidine

HPLC retention time (min): 3.95; MS (m/z): 382 (M+H)$^+$; HPLC condition: B.

Example 7(281)

4-(perhydroazepin-1-yl)-2-[1-(4-phenylbenzyl)pyrrolidin-3-ylamino]pyrimidine

HPLC retention time (min): 4.41; MS (m/z): 855 (2M+H)$^+$, 428 (M+H)$^+$; HPLC condition: B.

Example 7(282)

2-[1-((2E)-3,7-dimethyl-2,6-octadienyl)pyrrolidin-3-ylamino]-4-(perhydroazepin-1-yl)pyrimidine HPLC retention time (min): 4.94; MS (m/z): 398 (M+H)$^+$; HPLC condition: B.

Example 7(283)

2-[1-(4-diethylaminobenzyl)pyrrolidin-3-ylamino]-4-(perhydroazepin-1-yl)pyrimidine HPLC retention time (min): 4.44; MS (m/z): 423 (M+H)$^+$; HPLC condition: B.

Example 7(284)

2-[1-(2-ethylhexyl)pyrrolidin-3-ylamino]-4-(perhydroazepin-1-yl)pyrimidine

HPLC retention time (min): 4.99; MS (m/z): 374 (M+H)$^+$; HPLC condition: B.

Example 7(285)

2-[1-(3-fluorobenzyl)pyrrolidin-3-ylamino]-4-(perhydroazepin-1-yl)pyrimidine

HPLC retention time (min): 4.04; MS (m/z): 370 (M+H)$^+$; HPLC condition: B.

Example 7(286)

2-[1-(2-hydroxyethyl)pyrrolidin-3-ylamino]-4-(perhydroazepin-1-yl)pyrimidine

HPLC retention time (min): 3.27; MS (m/z): 306 (M+H)$^+$; HPLC condition: B.

Example 7(287)

2-[1-(1-naphthylmethyl)pyrrolidin-3-ylamino]-4-(perhydroazepin-1-yl)pyrimidine

HPLC retention time (min): 4.33; MS (m/z): 402 (M+H)$^+$; HPLC condition: B.

Example 7(288)

2-[1-(3-nitrobenzyl)pyrrolidin-3-ylamino]-4-(perhydroazepin-1-yl)pyrimidine

HPLC retention time (min): 3.93; MS (m/z): 793 (2M+H)$^+$, 397 (M+H)$^+$; HPLC condition: B.

Example 7(289)

4-(perhydroazepin-1-yl)-2-[1-[(2S,3S,4R)-2,3,4,5-tetrahydroxypentyl]pyrrolidin-3-ylamino]pyrimidine HPLC retention time (min): 3.07; MS (m/z): 791 (2M+H)$^+$, 396 (M+H)$^+$; HPLC condition: B.

Example 7(290)

4-(perhydroazepin-1-yl)-2-[1-(2-thienylmethyl)pyrrolidin-3-ylamino]pyrimidine

HPLC retention time (min): 3.95; MS (m/z): 358 (M+H)$^+$; HPLC condition: B.

Example 7(291)

2-[1-(4-chlorobenzyl)pyrrolidin-3-ylamino]-4-(perhydroazepin-1-yl)pyrimidine

HPLC retention time (min): 4.21; MS (m/z): 388, 386 (M+H)$^+$; HPLC condition B.

Example 7(292)

2-[1-(1,3-benzodioxol-4-ylmethyl)pyrrolidin-3-ylamino]-4-(perhydroazepin-1-yl)pyrimidine HPLC retention time (min): 3.93; MS (m/z): 396 (M+H)$^+$; HPLC condition: B.

Example 7(293)

4-(perhydroazepin-1-yl)-2-[1-((3S,4R)-3,4,5-trihydroxypentyl)pyrrolidin-3-ylamino]pyrimidine HPLC retention time (min): 3.14; MS (m/z): 759 (2M+H)$^+$, 380 (M+H)$^+$; HPLC condition: B.

Example 7(294)

2-[1-(1,5-dimethyl-2-phenyl-3-oxo-2,3-dihydro-1H-pyrazol-4-ylmethyl)piperidin-3-ylamino]-4-(perhydroazepin-1-yl)pyrimidine

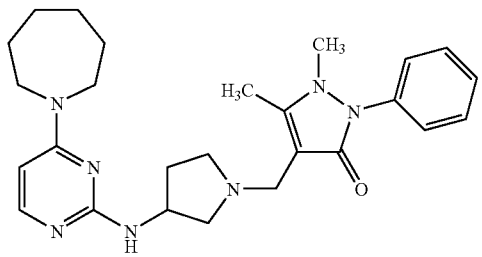

HPLC retention time (min): 3.49; MS (m/z): 923 (2M+H)⁺, 462 (M+H)⁺; HPLC condition: B.

Example 7(295)

4-(perhydroazepin-1-yl)-2-[1-[5-[(E)-4-methyl-2-pentenyl]-1,2,3,4-tetrahydrobenzen-2-yl]pyrrolidin-3-ylamino]pyrimidine

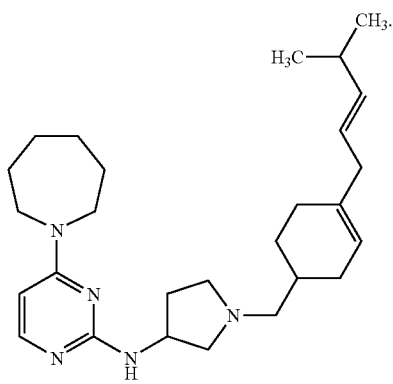

HPLC retention time (min): 5.43; MS (m/z): 438 (M+H)⁺; HPLC condition: B.

Example 7(296)

2-[1-(3-methoxy-4-hexyloxybenzyl)pyrrolidin-3-ylamino]4-(perhydroazepin-1-yl)pyrimidine HPLC retention time (min): 4.59; MS (m/z): 963 (2M+H)⁺, 482 (M+H)⁺; HPLC condition: B.

Example 7(297)

4-(perhydroazepin-1-yl)-2-[1-(4-fluorobenzyl)pyrrolidin-3-ylamino]pyrimidine

HPLC retention time (min): 4.02; MS (m/z): 370 (M+H)⁺; HPLC condition: B.

Example 7(298)

4-(perhydroazepin-1-yl)-2-[1-(1,2,5-trimethyl-1,2,3,4-tetrahydrobenzen-3-ylmethyl)pyrrolidin-3-ylamino]pyrimidine

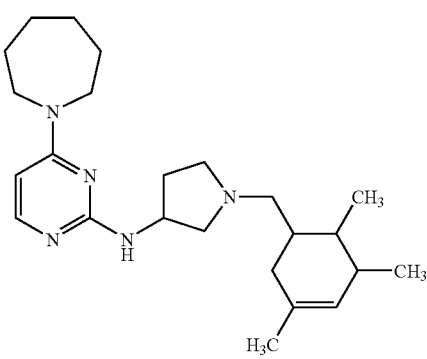

HPLC retention time (min): 4.98; MS (m/z): 398 (M+H)⁺; HPLC condition: B.

Example 7(299)

4-(perhydroazepin-1-yl)-2-[1-(3,5-dimethyl-1-phenylpyrazol-4-ylmethyl)pyrrolidin-3-ylamino]pyrimidine HPLC retention time (min): 3.91; MS (m/z): 891 (2M+H)⁺, 446 (M+H)⁺; HPLC condition: B.

Example 7(300)

2-[1-(4-benzyloxy-3-methoxybenzyl)pyrrolidin-3-ylamino]4-(perhydroazepin-1-yl)pyrimidine HPLC retention time (min): 4.19; MS (m/z): 975 (2M+H)⁺, 488 (M+H)⁺; HPLC condition: B.

Example 7(301)

2-[1-(3-benzyloxybenzyl)pyrrolidin-3-ylamino]-4-(perhydroazepin-1-yl)pyrimidine

HPLC retention time (min): 4.33; MS (m/z): 458 (M+H)⁺; HPLC condition: B.

Example 7(302)

2-[1-(4-benzyloxybenzyl)pyrrolidin-3-ylamino]-4-(perhydroazepin-1-yl)pyrimidine

HPLC retention time (min): 4.32; MS (m/z): 915 (2M+H)⁺, 458 (M+H)⁺; HPLC condition: B.

Example 7(303)

4-(perhydroazepin-1-yl)-2-[1-(4-phenoxybenzyl)pyrrolidin-3-ylamino]pyrimidine

HPLC retention time (min): 4.41; MS (m/z): 887 (2M+H)⁺, 444 (M+H)⁺; HPLC condition: B.

Example 7(304)

4-(perhydroazepin-1-yl)-2-[1-(2,4,6-trimethoxybenzyl)piperidin-4-ylamino]pyrimidine HPLC retention time (min): 4.13; MS (m/z): 911 (2M+H)⁺, 456 (M+H)⁺; HPLC condition: B.

Example 7(305)

2-[1-(3-cyanobenzyl)piperidin-4-ylamino]-4-(perhydroazepin-1-yl)pyrimidine

HPLC retention time (min): 3.95; MS (m/z): 781 (2M+H)⁺, 391 (M+H)⁺; HPLC condition: B.

Example 7(306)

2-[1-(3-methylbutyl)piperidin-4-ylamino]-4-(perhydroazepin-1-yl)pyrimidine

HPLC retention time (min): 4.33; MS (m/z): 346 (M+H)⁺; HPLC condition: B.

Example 7(307)

2-[1-(2-carboxymethoxybenzyl)piperidin-4-ylamino]-4-(perhydroazepin-1-yl)pyrimidine HPLC retention time (min): 3.03; MS (m/z): 879 (2M+H)⁺, 440 (M+H)⁺; HPLC condition: B.

Example 7(308)

2-[1-(4-dimethylaminobenzyl)piperidin-4-ylamino]-4-(perhydroazepin-1-yl)pyrimidine HPLC retention time (min): 4.19; MS (m/z): 817 (2M+H)⁺, 409 (M+H)⁺; HPLC condition: B.

Example 7(309)

4-(perhydroazepin-1-yl)-2-[1-(3-phenoxybenzyl)piperidin-4-ylamino]pyrimidine

HPLC retention time (min): 4.50; MS (m/z): 915 (2M+H)⁺, 458 (M+H)⁺; HPLC condition: B.

Example 7(310)

2-[1-[(E)-2-methyl-2-butenyl]piperidin-4-ylamino]-4-(perhydroazepin-1-yl)pyrimidine HPLC retention time (min): 4.37; MS (m/z): 687 (2M+H)⁺, 344 (M+H)⁺; HPLC condition: B.

Example 7(311)

2-[(1R)-1-(6,6-dimethylbicyclo[3.1.1]hept-2-en-2-ylmethyl)piperidin-4-ylamino]-4-(perhydroazepin-1-yl)pyrimidine

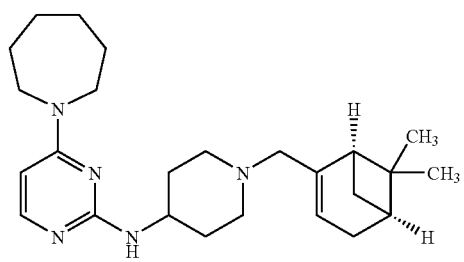

HPLC retention time (min): 5.09; MS (m/z) 819 (2M+H)⁺, 410 (M+H)⁺; HPLC condition: B.

Example 7(312)

2-[1-carboxymethylpiperidin-4-ylamino]-4-(perhydroazepin-1-yl)pyrimidine

HPLC retention time (min) 2.78; MS (m/z): 667 (2M+H)⁺, 334 (M+H)⁺; HPLC condition: B.

Example 7(313)

2-(1-cyclopropylmethylpiperidin-4-ylamino)-4-(perhydroazepin-1-yl)pyrimidine

HPLC retention time (min): 3.97; MS (m/z): 659 (2M+H)⁺, 330 (M+H)⁺; HPLC condition: B.

Example 7(314)

2-[1-(3-methylthiopropyl)piperidin-4-ylamino]-4-(perhydroazepin-1-yl)pyrimidine

HPLC retention time (min): 3.95; MS (m/z): 364 (M+H)⁺; HPLC condition: B.

Example 7(315)

2-[1-(2,6-dimethyl-5-heptenyl)piperidin-4-ylamino]-4-(perhydroazepin-1-yl)pyrimidine HPLC retention time (min): 5.03; MS (m/z): 799 (2M+H)⁺, 400 (M+H)⁺; HPLC condition: B.

Example 7(316)

4-(perhydroazepin-1-yl)-2-[1-(quinolin-2-ylmethyl)piperidin-4-ylamino]pyrimidine HPLC retention time (min): 3.93; MS (m/z): 833 (2M+H)⁺, 417 (M+H)⁺; HPLC condition: B.

Example 7(317)

2-(1-neopentylpiperidin-4-ylamino)-4-(perhydroazepin-1-yl)pyrimidine

HPLC retention time (min): 4.76; MS (m/z): 691 (2M+H)$^+$, 346 (M+H)$^+$; HPLC condition: B.

Example 7(318)

2-[1-[(Z)-4-decenyl]piperidin-4-ylamino]-4-(perhydroazepin-1-yl)pyrimidine

HPLC retention time (min): 5.34; MS (m/z): 414 (M+H)$^+$; HPLC condition: B.

Example 7(319)

4-(perhydroazepin-1-yl)-2-[1-(3-phenylpropyl)piperidin-4-ylamino]pyrimidine

HPLC retention time (min): 4.32; MS (m/z): 787 (2M+H)$^+$, 394 (M+H)$^+$; HPLC condition: B.

Example 7(320)

2-[1-butylpiperidin-4-ylamino]-4-(perhydroazepin-1-yl)pyrimidine

HPLC retention time (min): 4.21; MS (m/z): 332 (M+H)$^+$; HPLC condition: B.

Example 7(321)

2-[1-[(E)-3-(4-dimethylaminophenyl)-2-propenyl]piperidin-4-ylamino]-4-(perhydroazepin-1-yl)pyrimidine HPLC retention time (min): 4.33; MS (m/z): 869 (2M+H)$^+$, 435 (M+H)$^+$; HPLC condition: B.

Example 7(322)

2-[1-(3-hydroxybenzyl)piperidin-4-ylamino]-4-(perhydroazepin-1-yl)pyrimidine

HPLC retention time (min): 3.44; MS (m/z): 763 (2M+H)$^+$, 382 (M+H)$^+$; HPLC condition: B.

Example 7(323)

2-[1-(2-hydroxybenzyl)piperidin-4-ylamino]-4-(perhydroazepin-1-yl)pyrimidine

HPLC retention time (min): 4.10; MS (m/z): 763 (2M+H)$^+$, 382 (M+H)$^+$; HPLC condition: B.

Example 7(324)

2-[1-(4-dihydroxyborylbenzyl)piperidin-4-ylamino]-4-(perhydroazepin-1-yl)pyrimidine

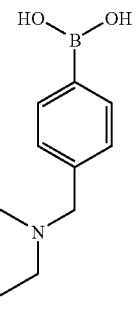

HPLC retention time (min): 3.11; MS (m/z): 410 (M+H)$^+$; HPLC condition: B.

Example 7(325)

2-[1-(4-heptyloxybenzyl)piperidin-4-ylamino]-4-(perhydroazepin-1-yl)pyrimidine

HPLC retention time (min): 5.31; MS (m/z): 480 (M+H)$^+$; HPLC condition: B.

Example 7(326)

2-[1-(benzo[b]furan-2-ylmethyl)piperidin-4-ylamino]-4-(perhydroazepin-1-yl)pyrimidine HPLC retention time (min): 4.17; MS (m/z): 811 (2M+H)$^+$, 406 (M+H)$^+$; HPLC condition: B.

Example 7(327)

2-[1-(3-methylbenzo[b]thiophen-2-yl)piperidin-4-ylamino]-4-(perhydroazepin-1-yl)pyrimidine HPLC retention time (min): 4.54; MS (m/z): 871 (2M+H)$^+$, 436 (M+H)$^+$; HPLC condition: B.

Example 7(328)

2-[1-[2-(4-chlorophenylthio)benzyl]piperidin-4-ylamino]-4-(perhydroazepin-1-yl)pyrimidine HPLC retention time (min): 5.03; MS (m/z): 510, 508 (M+H)$^+$; HPLC condition: B.

Example 7(329)

2-[1-(3,7-dimethyl-6-octenyl)piperidin-4-ylamino]-4-(perhydroazepin-1-yl)pyrimidine HPLC retention time (min): 5.12; MS (m/z): 414 (M+H)$^+$; HPLC condition: B.

Example 7(330)

4-(perhydroazepin-1-yl)-2-[1-(4-pyrrolidinobenzyl)piperidin-4-ylamino]pyrimidine HPLC retention time (min): 4.57; MS (m/z): 869 (2M+H)$^+$, 435 (M+H)$^+$; HPLC condition: B.

Example 7(331)

2-[1-[2-methyl-3-(4-t-butylphenyl)propyl]piperidin-4-ylamino]-4-(perhydroazepin-1-yl)pyrimidine HPLC retention time (min): 5.21; MS (m/z): 464 (M+H)$^+$; HPLC condition: B.

Example 7(332)

2-[1-(2-benzyloxybenzyl)piperidin-4-ylamino]-4-(perhydroazepin-1-yl)pyrimidine

HPLC retention time (min): 4.44; MS (m/z): 472 (M+H)$^+$; HPLC condition: B.

Example 7(333)

2-[1-(3,5-di-t-butyl-4-hydroxybenzyl)piperidin-4-ylamino]-4-(perhydroazepin-1-yl)pyrimidine HPLC retention time (min): 4.72; MS (m/z): 494 (M+H)$^+$; HPLC condition: B.

Example 7(334)

2-[1-[3-(4-isopropylphenyl)-2-methylpropyl]piperidin-4-ylamino]-4-(perhydroazepin-1-yl)pyrimidine HPLC retention time (min): 5.09; MS (m/z): 450 (M+H)$^+$; HPLC condition: B.

Example 7(335)

2-[1-[3,4-bis(benzyloxy)benzyl]piperidin-4-ylamino]-4-(perhydroazepin-1-yl)pyrimidine HPLC retention time (min): 4.57; MS (m/z): 578 (M+H)$^+$; HPLC condition: B.

Example 7(336)

2-[1-(4-octyloxybenzyl)piperidin-4-ylamino]-4-(perhydroazepin-1-yl)pyrimidine

HPLC retention time (min): 5.64; MS (m/z): 494 (M+H)$^+$; HPLC condition: B.

Example 7(337)

4-(perhydroazepin-1-yl)-2-[1-(3,5,5-trimethylhexyl)piperidin-4-ylamino]pyrimidine HPLC retention time (min): 5.16; MS (m/z): 402 (M+H)$^+$; HPLC condition: B.

Example 7(338)

2-(1-butoxycarbonylmethylpiperidin-4-ylamino)-4-(perhydroazepin-1-yl)pyrimidine

HPLC retention time (min): 3.99; MS (m/z): 779 (2M+H)$^+$, 390 (M+H)$^+$; HPLC condition: B.

Example 7(339)

2-[1-[5-(4-hydroxy-4-methylpentyl)-1,2,3,4-tetrahydrobenzen-2-ylmethyl]piperidin-4-ylamino]-4-(perhydroazepin-1-yl)pyrimidine

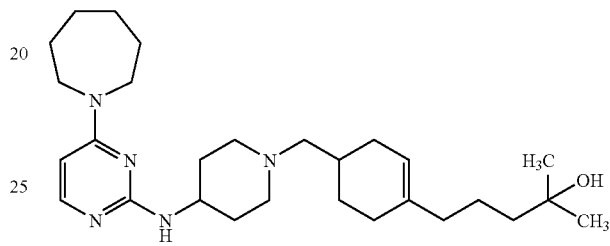

HPLC retention time (min): 4.41; MS (m/z): 470 (M+H)$^+$; HPLC condition: B.

Example 7(340)

2-[1-(5-hydroxypentyl)piperidin-4-ylamino]-4-(perhydroazepin-1-yl)pyrimidine

HPLC retention time (min): 3.49; MS (m/z): 723 (2M+H)$^+$, 362 (M+H)$^+$; HPLC condition: B.

Example 7(341)

2-[1-[(1R,2S,3R,5R)-2-hydroxy-4,6,8-trioxaspiro[bicyclo[3.3.0]octane-7,1'-cyclohexane]-3-ylmethyl]piperidin-4-ylamino]-4-(perhydroazepin-1-yl)pyrimidine

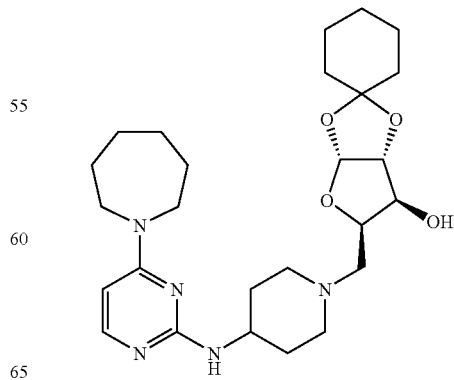

HPLC retention time (min): 3.80; MS (m/z): 488 (M+H)⁺; HPLC condition: B.

Example 7(342)

4-(perhydroazepin-1-yl)-2-[1-(3-phenylpyrazol-4-ylmethyl)piperidin-4-ylamino]pyrimidine HPLC retention time (min): 3.77; MS (m/z): 863 (2M+H)⁺, 432 (M+H)⁺; HPLC condition: B.

Example 7(343)

2-[1-(4-t-butylbenzyl)piperidin-4-ylamino]-4-(perhydroazepin-1-yl)pyrimidine

HPLC retention time (min): 4.68; MS (m/z): 843 (2M+H)⁺, 422 (M+H)⁺; HPLC condition: B.

Example 7(344)

2-[1-(1,4-benzodioxan-6-ylmethyl)piperidin-4-ylamino]4-(perhydroazepin-1-yl)pyrimidine HPLC retention time (min): 3.99; MS (m/z): 847 (2M+H)⁺, 424 (M+H)⁺; HPLC condition: B.

Example 7(345)

4-(perhydroazepin-1-yl)-2-[1-[2-(1,1,5-trimethyl-1,2,3,4-tetrahydrobenzen-6-yl)ethyl]piperidin-4-ylamino]pyrimidine

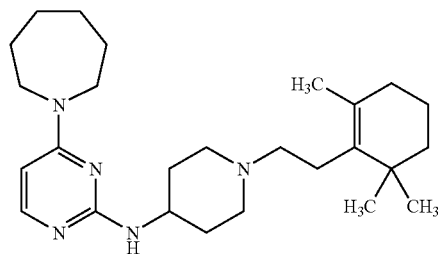

HPLC retention time (min): 5.18; MS (m/z): 426 (M+H)⁺; HPLC condition: B.

Example 7(346)

2-[1-[4-(3-dimethylaminopropyloxy)benzyl]piperidin-4-ylamino]-4-(perhydroazepin-1-yl)pyrimidine HPLC retention time (min): 4.22; MS (m/z): 467 (M+H)⁺; HPLC condition: B.

Example 7(347)

2-[1-(2-furylmethyl)piperidin-4-ylamino]-4-(perhydroazepin-1-yl)pyrimidine

HPLC retention time (min): 3.82; MS (m/z): 711 (2M+H)⁺, 356 (M+H)⁺; HPLC condition: B.

Example 7(348)

2-(1-isobutylpiperidin-4-ylamino)-4-(perhydroazepin-1-yl)pyrimidine

HPLC retention time (min): 4.30; MS (m/z): 663 (2M+H)⁺, 332 (M+H)⁺; HPLC condition: B.

Example 7(349)

2-(1-cyclohexylmethylpiperidin-4-ylamino)-4-(perhydroazepin-1-yl)pyrimidine

HPLC retention time (min): 4.85; MS (m/z): 743 (2M+H)⁺, 372 (M+H)⁺; HPLC condition: B.

Example 7(350)

4-(perhydroazepin-1-yl)-2-[1-(2-thiazolylmethyl)piperidin-4-ylamino]pyrimidine

HPLC retention time (min): 3.64; MS (m/z): 745 (2M+H)⁺, 373 (M+H)⁺; HPLC condition: B.

Example 7(351)

2-[1-(4-acetylaminobenzyl)piperidin-4-ylamino]-4-(perhydroazepin-1-yl)pyrimidine HPLC retention time (min) 3.55; MS (m/z): 845 (2M+H)⁺, 423 (M+H)⁺; HPLC condition: B.

Example 7(352)

2-[1-(2-methoxybenzyl)piperidin-4-ylamino]-4-(perhydroazepin-1-yl)pyrimidine

HPLC retention time (min): 4.13; MS (m/z): 791 (2M+H)⁺, 396 (M+H)⁺; HPLC condition: B.

Example 7(353)

2-[1-(4-methoxybenzyl)piperidin-4-ylamino]-4-(perhydroazepin-1-yl)pyrimidine

HPLC retention time (min): 4.06; MS (m/z): 791 (2M+H)⁺, 396 (M+H)⁺; HPLC condition: B.

Example 7(354)

4-(perhydroazepin-1-yl)-2-[1-(4-phenylbenzyl)piperidin-4-ylamino]pyrimidine

HPLC retention time (min): 4.54; MS (m/z): 883 (2M+H)⁺, 442 (M+H)⁺; HPLC condition: B.

Example 7(355)

2-[1-[(2E)-3,7-dimethyl-2,6-octadienyl]piperidin-4-ylamino]-4-(perhydroazepin-1-yl)pyrimidine HPLC retention time (min): 4.89; MS (m/z): 823 (2M+H)⁺, 412 (M+H)⁺; HPLC condition: B.

Example 7(356)

2-[1-(4-diethylaminobenzyl)piperidin-4-ylamino]-4-(perhydroazepin-1-yl)pyrimidine HPLC retention time (min): 4.57; MS (m/z): 873 (2M+H)⁺, 437 (M+H)⁺; HPLC condition: B.

Example 7(357)

2-[1-(3-fluorobenzyl)piperidin-4-ylamino]-4-(perhydroazepin-1-yl)pyrimidine

HPLC retention time (min): 4.15; MS (m/z): 767 (2M+H)$^+$, 384 (M+H)$^+$; HPLC condition: B.

Example 7(358)

2-[1-(1-naphthylmethyl)piperidin-4-ylamino]-4-(perhydroazepin-1-yl)pyrimidine

HPLC retention time (min): 4.54; MS (m/z): 831 (2M+H)$^+$, 416 (M+H)$^+$; HPLC condition: B.

Example 7(359)

2-[1-(3-nitrobenzyl)piperidin-4-ylamino]-4-(perhydroazepin-1-yl)pyrimidine

HPLC retention time (min): 4.04; MS (m/z): 821 (2M+H)$^+$, 411 (M+H)$^+$; HPLC condition: B.

Example 7(360)

4-(perhydroazepin-1-yl)-2-(1-propylpiperidin-4-ylamino)pyrimidine

HPLC retention time (min): 4.02; MS (m/z): 635 (2M+H)$^+$, 318 (M+H)$^+$; HPLC condition: B.

Example 7(361)

4-(perhydroazepin-1-yl)-2-[1-[(2S,3S,4R)-2,3,4,5-tetrahydroxypentyl]piperidin-4-ylamino]pyrimidine HPLC retention time (min): 3.14; MS (m/z): 410 (M+H)$^+$; HPLC condition: B.

Example 7(362)

4-(perhydroazepin-1-yl)-2-[1-(2-thienylmethyl)piperidin-4-ylamino]pyrimidine

HPLC retention time (min): 4.06; MS (m/z): 743 (2M+H)$^+$, 372 (M+H)$^+$; HPLC condition: B.

Example 7(363)

2-[1-(4-chlorobenzyl)piperidin-4-ylamino]-4-(perhydroazepin-1-yl)pyrimidine

HPLC retention time (min): 4.35; MS (m/z): 799 (2M+H)$^+$, 402, 400 (M+H)$^+$; HPLC condition: B.

Example 7(364)

2-[1-(1,3-benzodioxol-4-yl)piperidin-4-ylamino]-4-(perhydroazepin-1-yl)pyrimidine HPLC retention time (min): 4.02; MS (m/z): 819 (2M+H)$^+$, 410 (M+H)$^+$; HPLC condition: B.

Example 7(365)

4-(perhydroazepin-1-yl)-2-[1-[(3S,4R)-3,4,5-trihydroxypentyl]piperidin-4-ylamino]pyrimidine HPLC retention time (min): 3.18; MS (m/z): 787 (2M+H)$^+$, 394 (M+H)$^+$; HPLC condition: B.

Example 7(366)

2-[1-(1,5-dimethyl-2-phenyl-3-oxo-2,3-dihydro-1H-pyrazol-4-ylmethyl)piperidin-4-ylamino]-4-(perhydroazepin-1-yl)pyrimidine

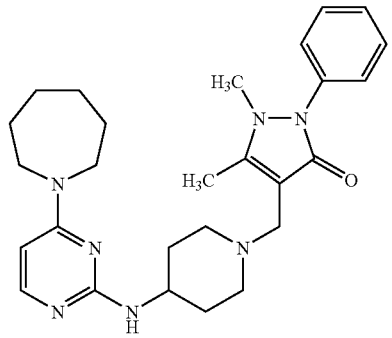

HPLC retention time (min): 3.51; MS (m/z): 951 (2M+H)$^+$, 476 (M+H)$^+$; HPLC condition: B.

Example 7(367)

2-[1-(3-methoxy-4-hexyloxybenzyl)piperidin-4-ylamino]-4-(perhydroazepin-1-yl)pyrimidine HPLC retention time (min): 4.72; MS (m/z): 496 (M+H)$^+$; HPLC condition: B.

Example 7(368)

2-[1-(4-fluorobenzyl)piperidin-4-ylamino]-4-(perhydroazepin-1-yl)pyrimidine

HPLC retention time (min): 4.13; MS (m/z): 767 (2M+H)$^+$, 384 (M+H)$^+$; HPLC condition: B.

Example 7(369)

4-(perhydroazepin-1-yl)-2-[1-(1,2,5-trimethyl-1,2,3,4-tetrahydrobenzen-3-ylmethyl)piperidin-4-ylamino]pyrimidine

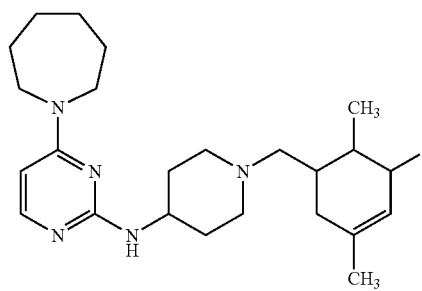

HPLC retention time (min): 5.18; MS (m/z): 823 (2M+H)$^+$, 412 (M+H)$^+$; HPLC condition: B.

Example 7(370)

2-[1-(3,5-dimethyl-1-phenylpyrazol-4-ylmethyl)piperidin-4-ylamino]-4-(perhydroazepin-1-yl)pyrimidine HPLC retention time (min): 4.02; MS (m/z): 919 (2M+H)$^+$, 460 (M+H))$^+$; HPLC condition: B.

Example 7(371)

2-[1-(2-benzyloxyethyl)piperidin-4-ylamino]-4-(perhydroazepin-1-yl)pyrimidine

HPLC retention time (min): 4.06; MS (m/z): 410 (M+H)$^+$; HPLC condition: B.

Example 7(372)

2-[1-(4-benzyloxy-3-methoxybenzyl)piperidin-4-ylamino]-4-(perhydroazepin-1-yl)pyrimidine HPLC retention time (min): 4.30; MS (m/z): 502 (M+H)$^+$; HPLC condition: B.

Example 7(373)

2-[1-(3-benzyloxybenzyl)piperidin-4-ylamino]-4-(perhydroazepin-1-yl)pyrimidine

HPLC retention time (min): 4.44; MS (m/z): 943 (2M+H)$^+$, 472 (M+H)$^+$; HPLC condition: B.

Example 7(374)

2-[1-(4-benzyloxybenzyl)piperidin-4-ylamino]-4-(perhydroazepin-1-yl)pyrimidine

HPLC retention time (min): 4.44; MS (m/z): 943 (2M+H)$^+$, 472 (M+H)$^+$; HPLC condition: B.

Example 7(375)

4-(perhydroazepin-1-yl)-2-[1-(4-phenoxybenzyl)piperidin-4-ylamino]pyrimidine

HPLC retention time (min): 4.51; MS (m/z): 915 (2M+H)$^+$, 458 (M+H)$^+$; HPLC condition: B.

EXAMPLE 8

4-(perhydroazepin-1-yl)-2-[(1-benzyl)azetidin-3-ylamino]pyrimidine

By the same procedure as described in Example 4 using the compound prepared in Reference Example 1 and 1-benzyl-3-aminoazetidine, the compound of the present invention having the following physical data was given.

TLC: Rf 0.40 (ethyl acetate:methanol:triethylamine=20:2:1);
MS (m/z): 338 (M+H)$^+$, 248, 190;
HPLC retention time (min): 3.01; HPLC condition: A.

Example 8(1) TO Example 8(2)

By the same procedure as described in Example 8 using the compound prepared in Reference Example 1 and corresponding amine compounds, the compounds of the present invention having the following physical data were given.

Example 8(1)

4-(perhydroazepin-1-yl)-2-[(3S)-(1-benzyl)piperidin-3-ylamino]pyrimidine

TLC: Rf 0.50 (ethyl acetate:methanol:triethylamine=20:2:1);
NMR (DMSO-d$_6$, 323K): δ 1.33 (m, 1H), 1.45 (m, 4H), 1.51 (m, 1H), 1.65 (m, 5H), 1.76 (m, 1H), 1.90 (m, 1H), 2.04 (m, 1H), 2.60 (m, 1H), 2.85 (m, 1H), 3.28 (m, 2H), 3.49 (m, 4H), 3.84 (m, 1H), 5.83 (d, J=6.0 Hz, 1H), 5.94 (m, 1H), 7.23 (m, 1H), 7.29 (m, 4H), 7.70 (d, J=6.0 Hz, 1H);
MS (m/z): 366 (M+H)$^+$, 276;
HPLC retention time (min): 3.03; HPLC condition: A.

Example 8(2)

4-(perhydroazepin-1-yl)-2-[(3S)-(1-benzyl)perhydroazepin-3-ylamino]pyrimidine

TLC: Rf 0.45 (chloroform:methanol:28% ammonia water=80:10:1);
NMR (DMSO-d$_6$): δ 1.41 (m, 5H), 1.64 (m, 9H), 2.56 (m, 3H), 2.81 (m, 1H), 3.49 (m, 4H), 3.63 (s, 2H), 3.97 (m, 1H), 5.80 (d, J=6.0 Hz, 1H), 6.06 (m, 1H), 7.24 (m, 5H), 7.68 (d, J=6.0 Hz, 1H);
MS (m/z): 380 (M+H)$^+$, 290;
HPLC retention time (min): 3.03; HPLC condition: A.

EXAMPLE 9

4-(perhydroazepin-1-yl)-2-(azetidin-3-ylamino)pyrimidine

By the same procedure as described in Example 5 using the compound prepared in Example 8, the compound of the present invention having the following physical data was given.

TLC: Rf 0.65 (chloroform:methanol:28% ammonia water=80:20:4);
NMR (CDCl$_3$): δ 1.52 (m, 4H), 1.73 (m, 4H), 3.54 (m, 4H), 3.61 (m, 2H), 3.89 (m, 2H), 4.85 (m, 1H), 5.41 (m, 1H), 5.80 (d, J=6.0 Hz, 1H), 7.77 (d, J=6.0 Hz, 1H);
MS (m/z): 248 (M+H)$^+$, 124.5 (M+2H)$^{2+}$;
HPLC retention time (min): 2.81; HPLC condition: A.

Example 9(1) TO Example 9(3)

By the same procedure as described in Example 9 using corresponding benzylamine derivatives, the compounds of the present invention having the following physical data were given.

Example 9(1)

4-(perhydroazepin-1-yl)-2-[(3S)-piperidin-3-ylamino]pyrimidine

TLC: Rf 0.70 (chloroform:methanol:28% ammonia water=80:20:4);
NMR (DMSO-d$_6$): δ 1.43 (m, 6H), 1.62 (m, 5H), 1.82 (m, 1H), 2.34 (m, 2H), 2.73 (m, 1H), 3.00 (m, 1H), 3.45 (m, 4H), 3.75 (m, 1H), 5.82 (d, J=6.0 Hz, 1H), 6.21 (m, 1H), 7.70 (d, J=6.0 Hz, 1H);
MS (m/z): 276 (M+H)$^+$, 138.5 (M+2H)$^{2+}$;
HPLC retention time (min): 2.85; HPLC condition: A.

Example 9(2)

4-(perhydroazepin-1-yl)-2-[(3S)-perhydroazepin-3-ylamino]pyrimidine

TLC: Rf 0.33 (chloroform:methanol:28% ammonia water=80:10:1);
NMR (DMSO-$d_6$): δ 1.34 (m, 5H), 1.70 (m, 9H), 2.60 (dd, J=13.5, 7.0 Hz, 1H), 2.72 (t, J=5.5 Hz, 2H), 2.90 (dd, J=13.5, 4.0 Hz, 1H), 3.57 (m, 4H), 3.90 (m, 1H), 5.81 (d, J=6.0 Hz, 1H), 6.10 (m, 1H), 7.70 (d, J=6.0 Hz, 1H);
MS (m/z): 290 (M+H)$^+$, 145.5 (M+2H)$^{2+}$;
HPLC retention time (min): 2.92; HPLC condition: A.

Example 9(3)

4-(perhydroazepin-1-yl)-2-[(3S)-perhydroazepin-3-ylamino]-5,6,7,8-tetrahydroquinazoline TLC: Rf 0.32 (chloroform:methanol:28% ammonia water=80:10:1);
NMR (DMSO-$d_6$): δ 1.43 (m, 6H), 1.56 (m, 5H), 1.73 (m, 7H), 2.43 (m, 4H), 2.57 (m, 1H), 2.71 (t, J=6.0 Hz, 2H), 2.87 (m, 1H), 3.50 (t, J=6.0 Hz, 4H), 3.85 (m, 1H), 5.85 (m, 1H);
MS (m/z): 344(M+H)$^+$, 172.5 (M+2H)$^{2+}$;
HPLC retention time (min): 3.09; HPLC condition: A.

EXAMPLE 10

4-(perhydroazepin-1-yl)-2-[(1-isobutyl)azetidin-3-ylamino]pyrimidine

By the same procedure as described in Example 7 using the compound prepared in Example 9 and isobutylaldehyde, the compound of the present invention having the following physical data was given.

TLC: Rf 0.40 (ethyl acetate:methanol:triethylamine=20:2:1);
NMR (DMSO-$d_6$, 323K): δ 0.84 (d, J=7.0 Hz, 6H), 1.47 (m, 4H), 1.52 (m, 1H), 1.69 (m, 4H), 2.19 (d, J=7.0 Hz, 2H), 2.80 (t, J=7.0 Hz, 2H), 3.54 (m, 6H), 4.33 (m, 1H), 5.87 (d, J=6.0 Hz, 1H), 6.62 (m, 1H), 7.73 (d, J=6.0 Hz, 1H);
MS (m/z): 304 (M+H)$^+$, 248, 152.5 (M+2H)$^{2+}$;
HPLC retention time (min): 2.96; HPLC condition: A.

Example 10(1) TO Example 10(12)

By the same procedure as described in Example 10 using corresponding amine compounds and corresponding aldehyde compounds, the compounds of the present invention having the following physical data were given.

Example 10(1)

4-(perhydroazepin-1-yl)-2-[1-(2-ethylbutyl)azetidin-3-ylamino]pyrimidine

TLC: Rf 0.40 (ethyl acetate:methanol:triethylamine=20:2:1);
NMR (DMSO-$d_6$, 323K): δ 0.82 (t, J=7.5 Hz, 6H), 1.15 (m, 1H), 1.25 (m, 2H), 1.30 (m, 2H), 1.48 (m, 4H), 1.69 (m, 4H), 2.27 (d, J=6.5 Hz, 2H), 2.79 (t, J=7.0 Hz, 2H), 3.53 (m, 6H), 4.32 (m, 1H), 5.87 (d, J=6.0 Hz, 1H), 6.62 (m, 1H), 7.73 (d, J=6.0 Hz, 1H);
MS (m/z): 332 (M+H)$^+$, 248, 166.5 (M+2H)$^{2+}$;
HPLC retention time (min): 3.09; HPLC condition: A.

Example 10(2)

4-(perhydroazepin-1-yl)-2-[(1-cyclohexyl)azetidin-3-ylamino]pyrimidine

TLC: Rf 0.40 (ethyl acetate:methanol:triethylamine=20:2:1);
MS (m/z): 330 (M+H)$^+$, 248, 165.5 (M+2H)$^{2+}$;
HPLC retention time (min): 3.03; HPLC condition: A.

Example 10(3)

4-(perhydroazepin-1-yl)-2-[1-(2-pyridinylmethyl)azetidin-3-ylamino]pyrimidine

TLC: Rf 0.33 (ethyl acetate:methanol:triethylamine=20:2:1);
MS (m/z): 339 (M+H)$^+$, 170 (M+2H)$^{2+}$;
HPLC retention time (min): 2.94; HPLC condition: A.

Example 10(4)

4-(perhydroazepin-1-yl)-2-[(3S)-(1-isobutyl)piperidin-3-ylamino]pyrimidine

TLC: Rf 0.50 (ethyl acetate:methanol:triethylamine=20:2:1);
NMR (DMSO-$d_6$, 323K): δ 0.85 (d, J=6.5 Hz, 3H), 0.87 (d, J=6.5 Hz, 3H), 1.33 (m, 1H), 1.48 (m, 5H), 1.69 (m, 7H), 1.88 (m, 1H), 2.05 (m, 3H), 2.57 (m, 1H), 2.88 (m, 1H), 3.55 (m, 4H), 3.83 (m, 1H), 5.87 (d, J=6.0 Hz, 1H), 5.97 (m, 1H), 7.73 (d, J=6.0 Hz, 1H);
MS (m/z): 332 (M+H)$^+$, 276, 166.5 (M+2H)$^{2+}$;
HPLC retention time (min): 2.98; HPLC condition: A.

Example 10(5)

4-(perhydroazepin-1-yl)-2-[(3S)-1-(2-ethylbutyl)piperidin-3-ylamino]pyrimidine oil;

TLC: Rf 0.60 (chloroform:methanol:28% ammonia water=80:10:1);
NMR (CDCl$_3$): δ 0.84 (t, J=7.5 Hz, 6H), 1.31 (m, 5H), 1.54 (m, 5H), 1.75 (m, 5H), 1.88 (m, 2H), 2.10 (d, J=7.0 Hz, 2H), 2.31 (m, 3H), 2.65 (m, 1H), 3.56 (m, 4H), 4.02 (m, 1H), 5.17 (m, 1H), 5.76 (d, J=6.0 Hz, 1H), 7.80 (d, J=6.0 Hz, 1H).
MS (m/z): 360 (M+H)$^+$, 276, 180.5 (M+2H)$^{2+}$;
HPLC retention time (min): 3.11; HPLC condition: A.

Example 10(6)

4-(perhydroazepin-1-yl)-2-[(3S)-1-(2-pyridinylmethyl)piperidin-3-ylamino]pyrimidine TLC: Rf 0.35 (ethyl acetate:methanol:triethylamine=20:2:1);
NMR (DMSO-$d_6$, 323K): δ 1.34 (m, 1H), 1.45 (m, 4H), 1.54 (m, 1H), 1.65 (m, 5H), 1.77 (m, 1H), 1.99 (m, 1H), 2.13 (m, 1H), 2.65 (m, 1H), 2.89 (m, 1H), 3.50 (m, 4H), 3.55 (d, J=13.65 Hz, 1H), 3.63 (d, J=13.5 Hz, 1H), 3.86 (m, 1H), 5.84

(d, J=6.0 Hz, 1H), 5.99 (m, 1H), 7.23 (m, 1H), 7.44 (d, J=8.0 Hz, 1H), 7.71 (d, J=6.0 Hz, 1H), 7.74 (dd, J=8.0, 2.0 Hz, 1H), 8.47 (m, 1H);

MS (m/z): 367 (M+H)$^+$, 184 (M+2H)$^{2+}$;

HPLC retention time (min): 2.92; HPLC condition: A.

Example 10(7)

4-(perhydroazepin-1-yl)-2-[(3S)-(1-cyclohexyl)piperidin-3-ylamino]pyrimidine oil;

TLC: Rf 0.48 (chloroform:methanol:28% ammonia water=80:10:1);

NMR (CDCl$_3$): δ 1.06 (m, 1H), 1.22 (m, 4H), 1.55 (m, 5H), 1.76 (m, 12H), 2.28 (m, 2H), 2.45 (m, 1H), 2.56 (m, 1H), 2.95 (m, 1H), 3.57 (m, 4H), 3.98 (m, 1H), 5.06 (m, 1H), 5.75 (d, J=6.0 Hz, 1H), 7.79 (d, J=6.0 Hz, 1H).

MS (m/z): 358 (M+H)$^+$, 276, 179.5 (M+2H)$^{2+}$;

HPLC retention time (min): 2.94; HPLC condition: A.

Example 10(8)

4-(perhydroazepin-1-yl)-2-[(3S)-1-(tetrahydro-2H-pyran-4-yl)piperidin-3-ylamino]pyrimidine oil;

TLC: Rf 0.45 (chloroform:methanol:28% ammonia water=80:10:1);

NMR (CDCl$_3$): δ 1.55 (m, 8H), 1.75 (m, 8H), 1.91 (m, 1H), 2.28 (m, 1H), 2.45 (m, 2H), 2.58 (m, 1H), 2.96 (m, 1H), 3.36 (m, 2H), 3.57 (m, 4H), 4.01 (m, 2H), 5.11 (m, 1H), 5.77 (d, J=6.0 Hz, 1H), 7.79 (d, J=6.0 Hz, 1H).

MS (m/z): 719 (2M+H)$^+$, 360 (M+H)$^+$, 276;

HPLC retention time (min): 2.78; HPLC condition: A.

Example 10(9)

4-(perhydroazepin-1-yl)-2-[(3S)-(1-isobutyl)perhydroazepin-3-ylamino]pyrimidine

TLC: Rf 0.50 (ethyl acetate:methanol:triethylamine=20:2:1);

NMR (DMSO-d$_6$, 323K): δ 0.87 (d, J=6.5 Hz, 3H), 0.88 (d, J=6.5 Hz, 3H), 1.48 (m, 4H), 1.62 (m, 5H), 1.68 (m, 4H), 1.76 (m, 2H), 2.21 (dd, J=12.0, 7.5 Hz, 1H), 2.26 (dd, J=12.0, 7.0 Hz, 1H), 2.60 (m, 3H), 2.77 (dd, J=13.5, 4.0 Hz, 1H), 3.55 (m, 4H), 3.94 (m, 1H), 5.84 (d, J=6.0 Hz, 1H), 5.87 (m, 1H), 7.72 (d, J=6.0 Hz, 1H);

MS (m/z): 346 (M+H)$^+$, 290, 173.5 (M+2H)$^{2+}$;

HPLC retention time (min): 3.00; HPLC condition: A.

Example 10(10)

4-(perhydroazepin-1-yl)-2-[(3S)-1-(2-ethylbutyl)perhydroazepin-3-ylamino]pyrimidine TLC: Rf 0.60 (chloroform:methanol:28% ammonia water=80:10:1);

NMR (DMSO-d$_6$, 323K): δ 0.83 (t, J=7.5 Hz, 3H), 0.85 (t, J=7.5 Hz, 3H), 1.30 (m, 6H), 1.48 (m, 4H), 1.62 (m, 3H), 1.69 (m, 4H), 1.75 (m, 2H), 2.29 (m, 2H), 2.58 (m, 3H), 2.76 (dd, J=13.5, 4.0 Hz, 1H), 3.55 (m, 4H), 3.95 (m, 1H), 5.84 (m, 2H), 7.72 (d, J=6.0 Hz, 1H);

MS (m/z): 374 (M+H)$^+$, 290, 187.5 (M+2H)$^{2+}$;

HPLC retention time (min): 3.12; HPLC condition: A.

Example 10(11)

4-(perhydroazepin-1-yl)-2-[(3S)-(1-cyclohexyl)pyrrolidin-3-ylamino]pyrimidine oil;

TLC: Rf 0.35 (ethyl acetate:methanol:triethylamine=20:2:1);

NMR (DMSO-d$_6$): δ 1.15 (m, 6H), 1.44 (m, 6H), 1.66 (m, 7H), 1.78 (m, 1H), 2.01 (m, 2H), 2.34 (dd, J=9.0, 5.5 Hz, 1H), 2.55 (m, 1H), 2.87 (t, J=8.5 Hz, 1H), 3.52 (m, 4H), 4.17 (m, 1H), 5.83 (d, J=6.0 Hz, 1H), 6.38 (m, 1H), 7.71 (d, J=6.0 Hz, 1H);

MS (m/z): 344 (M+H)$^+$, 262, 182;

HPLC retention time (min): 3.05; HPLC condition: A.

EXAMPLE 11-0001 TO EXAMPLE 11-1035

By the same procedure as described in Reference Example 1→Example 1 using corresponding compounds, the compounds of the present invention having the following physical data were given.

Example 11-0001

$N^1$-[4-(3,4-dihydroisoquinolin-2(1H)-yl)pyrimidin-2-yl]-$N^3$,$N^3$-dimethylpropane-1,3-diamine NMR (DMSO-d$_6$): δ 1.63 (m, 2H), 2.11 (s, 6H), 2.23 (t, J=7.0 Hz, 2H), 2.83 (t, J=6.0 Hz, 2H), 3.23 (q, J=6.5 Hz, 2H), 3.76 (t, J=6.0 Hz, 2H), 4.66 (s, 2H), 6.04 (d, J=6.0 Hz, 1H), 6.53 (m, 1H), 7.19 (m, 4H), 7.80 (d, J=6.0 Hz, 1H);

MS (ESI, Pos. 20 V): 312 (M+H)$^+$, 278, 156;

TLC: Rf 0.19 (CHCl$_3$:MeOH:NH$_4$OH=80:10:1).

Example 11-0002

$N^1$-[4-(3,4-dihydroisoquinolin-2(1H)-yl)pyrimidin-2-yl]-$N^2$,$N^2$-dimethylethane-1,2-diamine NMR (DMSO-d$_6$): δ 2.16 (s, 6H), 2.36 (t, J=6.9 Hz, 2H), 2.84 (t, J=5.7 Hz, 2H), 3.32 (m, 2H), 3.76 (t, J=5.7 Hz, 2H), 4.67 (s, 2H), 6.06 (d, J=6.0 Hz, 1H), 6.28 (m, 1H), 7.17 (m, 4 H) 7.80 (d, J=6.0 Hz, 1H);

MS (ESI, Pos. 20 V): 298 (M+H)$^+$, 149;

TLC: Rf 0.34 (CHCl$_3$:MeOH:NH$_4$OH=80:10:1).

Example 11-0003

N-2-[(4-azepan-1-ylpyrimidin-2-yl)amino]ethylacetamide

NMR (DMSO-d$_6$, 373.1K): δ 1.51 (m, 4H), 1.70 (m, 4H), 1.80 (s, 3H), 3.22 (m, 2H), 3.32 (m, 2H), 3.56 (t, J=6.0 Hz, 4H), 5.85 (d, J=6.0 Hz, 1H), 5.97 (m, 1H), 7.52 (m, 1H), 7.73 (d, J=6.0 Hz, 1H);

MS (ESI, Pos. 20 V): 278 (M+H)$^+$;

TLC: Rf 0.44 (CHCl$_3$:MeOH:NH$_4$OH=80:10:1).

Example 11-0004

(1R*,2R*)—N-[4-(3,4-dihydroisoquinolin-2(1H)-yl)pyrimidin-2-yl]cyclohexane-1,2-diamine NMR (DMSO-d$_6$): δ 1.15 (m, 4H), 1.66 (m, 2H), 1.82 (m, 1H), 1.97 (m, 1H), 2.84 (t, J=6.0 Hz, 2H), 3.37 (m, 2H), 3.76

(t, J=6.0 Hz, 2H), 4.67 (s, 2H), 6.05 (d, J=6.0 Hz, 1H), 6.35 (m, 1H), 7.17 (m, 4H), 7.80 (d, J=6.0 Hz, 1H);
MS (MALDI-TOF, Pos.): 324 (M+H)$^+$;
TLC: Rf 0.41 (CHCl$_3$:MeOH:NH$_4$OH=80:10:1).

Example 11-0005

(1S*,2R*)—N-[4-(3,4-dihydroisoquinolin-2(1H)-yl) pyrimidin-2-yl]cyclohexane-1,2-diamine NMR (DMSO-d$_6$): δ 1.27 (m, 2H), 1.51 (m, 6H), 2.83 (t, J=6.0 Hz, 2H), 2.98 (m, 1H), 3.77 (m, 3H), 4.66 (s, 2H), 6.04 (m, 2H), 7.18 (m, 4H), 7.80 (d, J=6.0 Hz, 1H);
MS (MALDI-TOF, Pos.): 324 (M+H)$^+$;
TLC: Rf 0.36 (CHCl$_3$:MeOH:NOH=80:10:1).

Example 11-0006

3-[(4-azepan-1-ylpyrimidin-2-yl)amino]azepane-2-one
NMR (DMSO-d$_6$, 373K): δ 1.32 (m, 2H), 1.49 (m, 4H), 1.72 (m, 6H), 1.92 (m, 1H), 2.08 (m, 1H), 3.18 (m, 2H), 3.57 (m, 4H), 4.44 (m, 1H), 5.88 (m, 2H), 7.47 (m, 1H), 7.76 (d, J=6.0 Hz, 1H);
MS (ESI, Pos. 20 V): 607 (2M+H)$^+$, 304 (M+H)$^+$;
TLC: Rf 0.50 (CHCl$_3$:MeOH:NH$_4$OH=80:10:1).

Example 11-0007

(3S)—N-(4-azepan-1-ylpyrimidin-2-yl)-1,3'-bipiperidin-3-amine

NMR (DMSO-d$_6$): δ 1.25 (m, 3H), 1.44 (m, 5H), 1.68 (m, 8H), 2.02 (m, 1H), 2.38 (m, 4H), 2.65 (m, 1H), 2.81 (d, J=12.30 Hz, 1H), 2.98 (m, 2H), 3.52 (m, 4H), 3.77 (m, 2H), 5.83 (d, J=6.0 Hz, 1H), 6.10 (m, 1H), 7.70 (d, J=6.0 Hz, 1H);
MS (ESI, Pos. 20 V): 359 (M+H)$^+$, 276;
TLC: Rf 0.21 (CHCl$_3$:MeOH:NHOH=80:10:1).

Example 11-0008

(3S)—N-(4-azepan-1-ylpyrimidin-2-yl)-1,4'-bipiperidin-3-amine

NMR (DMSO-d$_6$): δ 1.29 (m, 3H), 1.46 (m, 5H), 1.70 (m, 8H), 1.95 (m, 1H), 2.16 (m, 1H), 2.30 (m, 1H), 2.42 (m, 2H), 2.64 (m, 1H), 2.97 (m, 3H), 3.52 (m, 4H), 3.78 (m, 2H), 5.83 (d, J=6.0 Hz, 1H), 6.12 (m, 1H), 7.70 (d, J=6.0 Hz, 1H);
MS (ESI, Pos. 20 V): 359 (M+H)$^+$, 276, 180 (M+2H)$^{2+}$;
TLC: Rf 0.18 (CHCl$_3$:MeOH:NH$_4$OH=80:10:1).

Example 11-0009

2-[4-((1S*,2S*)-2-[4-(3,4-dihydroisoquinolin-2(1H)-yl)pyrimidin-2-yl]aminocyclohexyl)piperazin-1-yl] ethanol NMR (DMSO-d$_6$): δ 1.22 (m, 4H), 1.74 (m, 4H), 2.26 (m, 6H), 2.40 (m, 2H), 2.66 (m, 2H), 3.05 (m, 2H), 3.35 (m, 2H), 3.84 (m, 3H), 4.32 (m, 1H), 4.76 (s, 2H), 6.23 (m, 1H), 7.07 (t, J=7.3 Hz, 1H), 7.19 (m, 4H), 7.32 (d, J=8.2 Hz, 1H), 7.51 (t, J=7.30 Hz, 1H), 7.81 (d, J=8.2 Hz, 1H);
MS (ESI, Pos. 20 V): 487 (M+H)$^+$, 244;
TLC: Rf 0.47 (CHCl$_3$:MeOH:NH$_4$OH=80:10:1).

Example 11-0010

4-azepan-1-yl-N-[(1-ethylpyrrolidin-2-yl)methyl] pyrimidin-2-amine

NMR (CDCl$_3$): δ 1.24 (t, J=7.10 Hz, 3H), 1.54 (m, 4H), 1.75 (m, 4H), 1.80 (m, 2H), 2.01 (m, 2H), 2.50 (m, 2H), 3.07 (m, 1H), 3.56 (m, 8H), 5.83 (d, J=6.30 Hz, 1H), 6.16 (m, 1H), 7.72 (d, J=6.30 Hz, 1H);
MS (ESI, Pos. 20 V): 304 (M+H)$^+$;
TLC: Rf 0.33 (CHCl$_3$:MeOH:NH$_4$OH=80:10:1).

Example 11-0011

N$^1$-(4-azepan-1-ylpyrimidin-2-yl)-N$^2$,N$^2$-diisopropylethane-1,2-diamine

NMR (CDCl$_3$): δ 1.10 (d, J=6.6 Hz, 12H), 1.53 (m, 4H), 1.74 (m, 4H), 2.75 (t, J=6.3 Hz, 2H), 3.14 (m, 2H), 3.46 (m, 2H), 3.57 (m, 4H), 5.79 (d, J=6.3 Hz, 1H), 5.90 (m, 1H), 7.73 (d, J=6.3 Hz, 1H);
MS (ESI, Pos. 20 V): 320 (M+H)$^+$;
TLC: Rf 0.33 (CHCl$_3$:MeOH:NH$_4$OH=80:10:1).

Example 11-0012

4-azepan-1-yl-N-(3-pyrrolidin-1-ylpropyl)pyrimidin-2-amine

NMR (CDCl$_3$): δ 1.52 (m, 4H), 1.74 (m, 4H), 1.83 (m, 4H), 2.60 (m, 6H), 2.92 (m, 2H), 3.42 (t, J=6.6 Hz, 2H), 3.54 (m, 4H), 5.25 (m, 1H), 5.76 (d, J=6.3 Hz, 1H), 7.76 (d, J=6.3 Hz, 1H);
MS (ESI, Pos. 20 V): 304 (M+H)$^+$;
TLC: Rf 0.35 (CHCl$_3$:MeOH=9:1).

Example 11-0013

4-azepan-1-yl-N-(3-morpholin-4-ylpropyl)pyrimidin-2-amine

NMR (CDCl$_3$): δ 1.49 (m, 4H), 1.70 (m, 6H), 2.37 (m, 6H), 3.37 (q, J=6.60 Hz, 2H), 3.54 (m, 4H), 3.64 (t, J=4.70 Hz, 4H), 4.82 (m, 1H), 5.77 (d, J=6.60 Hz, 1H), 7.59 (d, J=6.60 Hz, 1H);
MS (ESI, Pos. 20 V): 320 (M+H)$^+$, 233;
TLC: Rf 0.33 (CHCl$_3$:MeOH=9:1).

Example 11-0014

1-3-[(4-azepan-1-ylpyrimidin-2-yl)amino]propyl ピロリ)di ジン-2-オン

NMR (CDCl$_3$): δ 1.53 (m, 4H), 1.76 (m, 4H), 1.80 (m, 2H), 1.99 (m, 2H), 2.35 (t, J=7.90 Hz, 2H), 3.36 (m, 4H), 3.63 (m, 6H), 5.82 (d, J=6.60 Hz, 1H), 6.39 (m, 1H), 7.65 (d, J=6.60 Hz, 1H);
MS (ESI, Pos. 20 V): 318 (M+H)$^+$;
TLC: Rf 0.50 (CHCl$_3$:MeOH=9:1).

Example 11-0015

4-azepan-1-yl-N-[3-(4-methylpiperazin-1-yl)propyl]pyrimidin-2-amine

NMR (CDCl$_3$): δ 1.53 (m, 4H), 1.75 (m, 6H), 2.27 (s, 3H), 2.45 (m, 8H), 2.64 (m, 2H), 3.40 (m, 2H), 3.55 (m, 4H), 5.48 (m, 1H), 5.77 (d, J=6.30 Hz, 1H), 7.76 (d, J=6.30 Hz, 1H);
MS (ESI, Pos. 20 V): 333 (M+H)$^+$, 233;
TLC: Rf 0.25 (CHCl$_3$:MeOH=9:1).

Example 11-0016

4-azepan-1-yl-N-[(3S)-1-cyclopentylpiperidin-3-yl]pyrimidin-2-amine

NMR (CDCl$_3$): δ 1.41 (m, 2H), 1.52 (m, 6H), 1.65 (m, 2H), 1.79 (m, 8H), 1.96 (m, 2H), 2.06 (m, 1H), 2.22 (m, 1H), 2.51 (m, 1H), 2.63 (m, 1H), 3.00 (m, 1H), 3.56 (m, 4H), 4.02 (m, 1H), 5.01 (m, 1H), 5.76 (d, J=6.20 Hz, 1H), 7.78 (d, J=6.20 Hz, 1H);
MS (ESI, Pos. 20 V): 344 (M+H)$^+$, 247, 172.5 (M+2H)$^{2+}$;
TLC: Rf 0.60 (AcOEt:MeOH:TEA=20:10:1).

Example 11-0017

N$^1$-(4-azepan-1-ylpyrimidin-2-yl)-N$^2$-phenylethane-1,2-diamine

NMR (CDCl$_3$): δ 1.55 (s, 4H), 1.76 (m, 4H), 3.35 (t, J=5.70 Hz, 2H), 3.60 (m, 4H), 3.64 (q, J=5.70 Hz, 2H), 4.29 (m, 1H), 5.27 (m, 1H), 5.82 (d, J=6.30 Hz, 1H), 6.63 (m, 3H), 7.15 (dd, J=8.50, 7.10 Hz, 2H), 7.79 (d, J=6.30 Hz, 1H);
MS (ESI, Pos. 20 V): 312 (M+H)$^+$;
TLC: Rf 0.45 (CHCl$_3$:MeOH=9:1).

Example 11-0018

1-[2-(3-phenylimidazolidin-1-yl)pyrimidin-4-yl]azepane

NMR (CDCl$_3$): δ 1.54 (m, 4H), 1.77 (m, 4H), 3.58 (t, J=6.80 Hz, 2H), 3.59 (m, 4H), 3.92 (t, J=6.60 Hz, 2H), 4.87 (s, 2H), 5.85 (d, J=6.00 Hz, 1H), 6.69 (d, J=8.50 Hz, 2H), 6.79 (t, J=7.10 Hz, 1H), 7.27 (dd, J=8.50, 7.10 Hz, 2H), 7.91 (d, J=6.00 Hz, 1H);
MS (ESI, Pos. 20 V): 324 (M+H)$^+$;
TLC: Rf 0.35 (AcOEt:hexane=1:2).

Example 11-0019

N-[4-(2,3-dihydro-1H-indol-1-yl)pyrimidin-2-yl]ethane-1,2-diamine dihydrochloride NMR (300 MHz, CD$_3$OD): δ 8.42 (brd, J=8.1 Hz, 1H), 7.92 (d, J=7.2 Hz, 1H), 7.45-7.27 (m, 2H), 7.18 (m, 1H), 6.51 (d, J=7.2 Hz, 1H), 4.26 (t, J=8.1 Hz, 2H), 3.94-3.78 (m, 2H), 3.50-3.25 (m, 4H);
MS (FAB, Pos., Glycerin+m-NBA): 256 (M+H)$^+$, 239, 213;
TLC: Rf 0.13 (n-BuOH:AcOH:H$_2$O=4:2:1).

Example 11-0020

N-[4-(3,4-dihydroquinolin-1(2H)-yl)pyrimidin-2-yl]ethane-1,2-diamine dihydrochloride NMR (300 MHz, CD$_3$OD): δ 7.72 (brd, J=7.2 Hz, 1H), 7.48-7.22 (m, 4H), 6.64 (d, J=7.2 Hz, 1H), 4.20-4.00 (m, 2H), 3.94-3.70 (m, 2H), 3.36-3.18 (m, 2H), 2.79 (t, J=6.6 Hz, 2H), 2.12-2.00 (m, 2H);
MS (FAB, Pos., Glycerin+m-NBA): 270 (M+H)$^+$, 253, 227;
TLC: Rf 0.22 (n-BuOH:AcOH:H$_2$O=4:2:1).

Example 11-0021

4-azepan-1-yl-N-(pyridin-2-ylmethyl)pyrimidin-2-amine

NMR (DMSO-d$_6$): δ 1.34 (m, 4H), 1.63 (m, 4H), 3.52 (m, 4H), 4.48 (d, J=5.90 Hz, 2H), 5.86 (d, J=5.90 Hz, 1H), 6.97 (m, 1H), 7.17 (m, 1H), 7.24 (d, J=7.70 Hz, 1H), 7.67 (td, J=7.70, 1.80 Hz, 1H), 7.72 (d, J=5.90 Hz, 1H), 8.45 (m, 1H);
MS (ESI, Pos. 20 V): 284 (M+J)$^+$;
TLC: Rf 0.53 (CHCl$_3$:MeOH:NH$_4$OH=80:10:1).

Example 11-0022

N$^1$-(4-azepan-1-ylpyrimidin-2-yl)-N$^2$-(pyridin-2-ylmethyl)ethane-1,2-diamine NMR (CD$_3$OD): δ 1.52 (m, 4H), 1.74 (m, 4H), 2.83 (t, J=6.20 Hz, 2H), 3.47 (t, J=6.20 Hz, 2H), 3.53 (m, 4H), 3.90 (s, 2H), 5.91 (d, J=6.20 Hz, 1H), 7.27 (m, 1H), 7.44 (m, 1H), 7.66 (d, J=6.20 Hz, 1H), 7.76 (m, 1H), 8.46 (m, 1H);
MS (ESI, Pos. 20 V): 327 (M+H)$^+$;
TLC: Rf 0.50 (CHCl$_3$:MeOH:NH$_4$OH=80:10:1).

Example 11-0023

N-2-[(4-azepan-1-ylpyrimidin-2-yl)amino]ethylguanidine dihydrochloride

NMR (DMSO-d$_6$): δ 1.46 (m, 4H), 1.71 (m, 4H), 3.35 (m, 2H), 3.47 (m, 2H), 3.63 (m, 2H), 3.79 (t, J=6.00 Hz, 2H), 6.40 (d, J=7.30 Hz, 1H), 7.34 (m, 4H), 7.83 (d, J=7.30 Hz, 1H), 7.99 (m, 1H), 8.21 (m, 1H), 12.63 (m, 1H);
MS (ESI, Pos. 20 V): 555 (2M+H)$^+$, 278 (M+H)$^+$, 261;
TLC: Rf 0.26 (AcOEt:AcOH:H$_2$O=3:1:1).

Example 11-0024

2-[(4-azepan-1-ylpyrimidin-2-yl)amino]-N,N,N-trimethylethanaminium iodide

NMR (DMSO-d$_6$): δ 1.46 (m, 4H), 1.69 (m, 4H), 3.11 (s, 9H), 3.41 (m, 2H), 3.51 (m, 4H), 3.68 (m, 2H), 5.94 (d, J=6.00 Hz, 1H), 6.72 (m, 1H), 7.77 (d, J=6.00 Hz, 1H);
MS (MALDI-TOF, Pos.): 278 (M$^+$), 233, 219;
TLC: Rf 0.10 (AcOEt:AcOH: H$_2$O=3:1:1).

Example 11-0025

N-[4-(3,6-dihydropyridin-1(2H)-yl)pyrimidin-2-yl]ethane-1,2-diamine dihydrochloride NMR (DMSO-d$_6$): δ 2.19 (m, 2H), 2.98 (m, 2H), 3.64 (m, 2H), 3.77 (m, 1H), 3.98 (m, 1H), 4.12 (m, 1H), 4.34 (m, 1H), 5.77 (d, J=7.30 Hz, 1H), 5.94 (m, 1H), 6.58 (m, 1H), 7.88 (d, J=7.30 Hz, 1H), 8.40 (m, 4H), 12.64 (m, 1H);

MS (MALDI-TOF, Pos.): 220 (M+H)$^+$;

TLC: Rf 0.49 (CHCl$_3$:MeOH:NH$_4$OH=80:20:4).

Example 11-0026

N-[4-(1,4'-bipiperidin-1'-yl)pyrimidin-2-yl]ethane-1,2-diamine trihydrochloride

NMR (DMSO-d$_6$): δ 1.39 (m, 1H), 1.73 (m, 5H), 1.95 (m, 2H), 2.26 (m, 2H), 2.93 (m, 5H), 3.18 (m, 1H), 3.38 (m, 2H), 3.46 (m, 1H), 3.64 (q, J=6.00 Hz, 2H), 4.35 (m, 2H), 5.10 (m, 1H), 6.61 (d, J=7.30 Hz, 1H), 7.90 (d, J=7.30 Hz, 1H), 8.28 (m, 3H), 11.04 (m, 1H), 12.68 (m, 1H);

MS (MALDI-TOF, Pos.): 305 (M+H)$^+$;

TLC: Rf 0.39 (CHCl$_3$:MeOH:NH$_4$OH=80:20:4).

Example 11-0027

N-(4-piperidin-1-ylpyrimidin-2-yl)ethane-1,2-diamine

NMR (DMSO-d$_6$): δ 1.44 (m, 4H), 1.63 (m, 2H), 2.91 (t, J=6.00 Hz, 2H), 3.41 (m, 2H), 3.52 (m, 4H), 6.06 (d, J=5.90 Hz, 1H), 6.59 (m, 1H), 7.80 (m, 3H);

MS(LC-MS, APCI, Pos. 20 V): 222 (M+H)$^+$, 179;

TLC: Rf 0.48 (CHCl$_3$:MeOH:NH$_4$OH=80:20:4).

Example 11-0028

N$^1$-(4-azepan-1-ylpyrimidin-2-yl)-N$^2$-isopropylethane-1,2-diamine

NMR (DMSO-d$_6$): δ 0.94 (d, J=6.20 Hz, 6H), 1.42 (m, 4H), 1.67 (m, 4H), 2.62 (m, 2H), 2.68 (m, 1H), 3.24 (m, 2H), 3.62 (m, 4H), 5.83 (d, J=6.00 Hz, 1H), 6.26 (m, 1H), 7.71 (d, J=6.00 Hz, 1H);

MS (ESI, Pos. 20 V): 555 (2M+H)$^+$, 278 (M+H)$^+$;

TLC: Rf 0.53 (CHCl$_3$:MeOH:NH$_4$OH=80:20:4).

Example 11-0029

4-azepan-1-yl-N-(1-isopropylpyrrolidin-3-yl)pyrimidin-2-amine

NMR (DMSO-d$_6$): δ 0.98 (m, 6H), 1.45 (m, 5H), 1.62 (m, 5H), 2.05 (m, 1H), 2.30 (m, 2H), 2.54 (m, 1H), 2.84 (t, J=7.90 Hz, 1H), 3.60 (m, 4H), 4.16 (m, 1H), 5.83 (d, J=5.90 Hz, 1H), 6.39 (m, 1H), 7.71 (d, J=5.90 Hz, 1H);

MS (ESI, Pos. 20 V): 304 (M+H)$^+$, 262;

TLC: Rf 0.19 (CHCl$_3$:MeOH:NH$_4$OH=80:10:1).

Example 11-0030

4-azepan-1-yl-N-[1-(1-ethylpropyl)pyrrolidin-3-yl]pyrimidin-2-amine

NMR (DMSO-d$_6$): δ 0.80 (m, 6H), 1.33 (m, 4H), 1.47 (m, 5H), 1.64 (m, 4H), 2.03 (m, 2H), 2.30 (dd, J=9.00, 5.70 Hz, 1H), 2.55 (m, 2H), 2.88 (t, J=7.90 Hz, 1H), 3.60 (m, 4H), 4.17 (m, 1H), 5.83 (d, J=6.20 Hz, 1H), 6.39 (m, 1H), 7.71 (d, J=6.20 Hz, 1H),

MS (ESI, Pos. 20 V): 332 (M+H)$^+$, 262, 193;

TLC: Rf 0.26 (CHCl$_3$:MeOH:NH$_4$OH=80:10:1).

Example 11-0031

4-azepan-1-yl-N-(1-cyclohexylpyrrolidin-3-yl)pyrimidin-2-amine

NMR (DMSO-d$_6$): δ 1.15 (m, 5H), 1.47 (m, 5H), 1.60 (m, 7H), 1.79 (m, 2H), 2.02 (m, 2H), 2.32 (dd, J=9.20, 5.50 Hz, 1H), 2.55 (m, 2H), 2.86 (t, J=8.10 Hz, 1H), 3.59 (m, 4H), 4.17 (m, 1H), 5.83 (d, J=6.20 Hz, 1H), 6.38 (m, 1H), 7.71 (d, J=6.20 Hz, 1H);

MS (ESI, Pos. 20 V): 344 (M+H)$^+$, 262;

TLC: Rf 0.26 (CHCl$_3$:MeOH:NH$_4$OH=80:10:1).

Example 11-0032

4-azepan-1-yl-N-[(3R)-1-benzylpyrrolidin-3-yl]pyrimidin-2-amine

NMR (CDCl$_3$): δ 1.53 (m, 4H), 1.73 (m, 5H), 2.31 (m, 1H), 2.49 (m, 2H), 2.70 (m, 1H), 2.90 (m, 1H), 3.55 (m, 4H), 3.63 (s, 2H), 4.45 (m, 1H), 5.44 (m, 1H), 5.79 (d, J=6.20 Hz, 1H), 7.30 (m, 5H), 7.74 (d, J=6.20 Hz, 1H);

MS (ESI, Pos. 20 V): 352 (M+H)$^+$, 262, 192;

TLC: Rf 0.55 (CHCl$_3$:MeOH:NH$_4$OH=80:10:1).

Example 11-0033 4-azepan-1-yl-N-[(3S)-1-benzylpyrrolidin-3-yl]pyrimidin-2-amine oil;

NMR (CDCl$_3$): δ 1.53 (m, 4H), 1.72 (m, 5H), 2.33 (m, 1H), 2.51 (m, 2H), 2.70 (m, 1H), 2.90 (dd, J=9.50, 6.60 Hz, 1H), 3.58 (m, 4H), 3.63 (s, 2H), 4.46 (m, 1H), 5.37 (m, 1H), 5.79 (d, J=6.20 Hz, 1H), 7.32 (m, 5H), 7.75 (d, J=6.20 Hz, 1H);

MS (ESI, Pos. 20 V): 352 (M+H)$^+$, 262, 192;

TLC: Rf 0.55 (CHCl$_3$:MeOH:NH$_4$OH=80:10:1).

Example 11-0034

4-azepan-1-yl-N-[(3S)-1-(pyridin-2-ylmethyl)pyrrolidin-3-yl]pyrimidin-2-amine

NMR (CDCl$_3$): δ 1.54 (m, 4H), 1.74 (m, 5H), 2.33 (m, 1H), 2.59 (m, 2H), 2.78 (m, 1H), 2.96 (m, 1H), 3.57 (m, 4H), 3.76 (d, J=13.60 Hz, 1H), 3.82 (d, J=13.60 Hz, 1H), 4.50 (m, 1H), 5.80 (d, J=6.20 Hz, 1H), 5.81 (m, 1H), 7.15 (m, 1H), 7.43 (d, J=7.70 Hz, 1H), 7.65 (td, J=7.70, 1.80 Hz, 1H), 7.72 (d, J=6.20 Hz, 1H), 8.54 (m, 1H);

MS (ESI, Pos. 20 V): 353 (M+H)$^+$, 177 (M+2H)$^{2+}$;

TLC: Rf 0.30 (AcOEt:MeOH:TEA=20:2:1).

Example 11-0035

4-azepan-1-yl-N-[(3S)-1-(2-ethylbutyl)pyrrolidin-3-yl]pyrimidin-2-amine

NMR (CDCl$_3$): δ 0.86 (t, J=7.30 Hz, 6H), 1.36 (m, 5H), 1.54 (m, 4H), 1.75 (m, 5H), 2.29 (m, 3H), 2.46 (m, 2H), 2.67

(m, 1H), 2.83 (m, 1H), 3.57 (m, 4H), 4.45 (m, 1H), 5.26 (m, 1H), 5.79 (d, J=6.20 Hz, 1H), 7.78 (d, J=6.20 Hz, 1H);
MS (ESI, Pos. 20 V): 346 (M+H)$^+$, 289, 262;
TLC: Rf 0.50 (AcOEt:MeOH:TEA=20:2:1).

Example 11-0036

4-azepan-1-yl-N-[(3S)-1-(cyclohexylmethyl)pyrrolidin-3-yl]pyrimidin-2-amine

NMR (CDCl$_3$): δ 0.88 (m, 2H), 1.20 (m, 4H), 1.45 (m, 1H), 1.54 (m, 4H), 1.75 (m, 9H), 2.27 (m, 3H), 2.47 (m, 2H), 2.68 (m, 1H), 2.87 (m, 1H), 3.58 (m, 4H), 4.46 (m, 1H), 5.28 (m, 1H), 5.80 (d, J=6.20 Hz, 1H), 7.77 (d, J=6.20 Hz, 1H);
MS (ESI, Pos. 20 V): 358 (M+H)$^+$, 262;
TLC: Rf 0.50 (AcOEt:MeOH:TEA=20:2:1).

Example 11-0037

4-azepan-1-yl-N-[(3R)-1-(2-ethylbutyl)pyrrolidin-3-yl]pyrimidin-2-amine

NMR (DMSO-d$_6$): δ 0.81 (m, 6H), 1.26 (m, 6H), 1.45 (m, 4H), 1.63 (m, 4H), 2.07 (m, 1H), 2.21 (m, 3H), 2.43 (m, 2H), 2.79 (m, 1H), 3.43 (m, 4H), 4.19 (m, 1H), 5.84 (d, J=5.90 Hz, 1H), 6.40 (m, 1H), 7.71 (d, J=5.90 Hz, 1H);
MS (ESI, Pos. 20 V): 346 (M+H)$^+$, 262, 173.5 (M+2H)$^+$;
TLC: Rf 0.28 (CHCl$_3$:MeOH:NH$_4$OH=80:10:1).

Example 11-0038

4-azepan-1-yl-N-[(3R)-1-(cyclohexylmethyl)pyrrolidin-3-yl]pyrimidin-2-amine

NMR (DMSO-d$_6$): δ 0.82 (m, 2H), 1.14 (m, 3H), 1.35 (m, 1H), 1.43 (m, 4H), 1.65 (m, 10H), 2.05 (m, 1H), 2.15 (m, 2H), 2.24 (m, 1H), 2.40 (m, 2H), 2.74 (m, 1H), 3.52 (m, 4H), 4.19 (m, 1H), 5.84 (d, J=5.90 Hz, 1H), 6.45 (m, 1H), 7.71 (d, J=5.90 Hz, 1H);
MS (ESI, Pos. 20 V): 358 (M+H)$^+$, 179.5 (M+2H)$^+$;
TLC: Rf 0.37 (CHCl$_3$: MeOH: NH$_4$OH=80:10:1).

Example 11-0040

4-azepan-1-yl-N-(1-tetrahydro-2H-pyran-4-ylpyrrolidin-3-yl)pyrimidin-2-amine

NMR (DMSO-d$_6$): δ 1.28 (m, 2H), 1.47 (m, 4H), 1.69 (m, 6H), 2.07 (m, 2H), 2.33 (m, 1H), 2.61 (m, 1H), 2.86 (m, 1H), 3.31 (m, 4H), 3.39 (m, 4H), 3.84 (m, 2H), 4.21 (m, 1H), 5.84 (d, J=5.90 Hz, 1H), 6.39 (m, 1H), 7.71 (d, J=5.90 Hz, 1H);
MS (ESI, Pos. 20 V): 346 (M+H)$^+$, 290;
TLC: Rf 0.44 (CHCl$_3$: MeOH: NH$_4$OH=80:10:1).

Example 11-0041

4-azepan-1-yl-N-[(3R)-1-cyclohexylpyrrolidin-3-yl]pyrimidin-2-amine

NMR (DMSO-d$_6$): δ 1.16 (m, 5H), 1.50 (m, 5H), 1.67 (m, 7H), 1.83 (m, 2H), 2.07 (m, 3H), 2.70 (m, 2H), 2.98 (m, 1H), 3.63 (m, 4H), 4.22 (m, 1H), 5.86 (d, J=5.90 Hz, 1H), 6.43 (m, 1H), 7.72 (d, J=5.90 Hz, 1H);
MS (ESI, Pos. 20 V): 344 (M+H)$^+$, 262;
TLC: Rf 0.39 (CHCl$_3$: MeOH: NH$_4$OH=80:10:1).

Example 11-0042

4-azepan-1-yl-N-[(3S)-pyrrolidin-3-yl]pyrimidin-2-amine

NMR (DMSO-d$_6$): δ 1.42 (m, 4H), 1.67 (m, 5H), 1.93 (m, 1H), 2.66 (dd, J=11.10, 4.50 Hz, 1H), 2.76 (m, 1H), 2.94 (m, 2H), 3.81 (m, 4H), 4.23 (m, 1H), 5.85 (d, J=6.00 Hz, 1H), 6.48 (m, 1H), 7.72 (d, J=6.00 Hz, 1H);
MS (ESI, Pos. 20 V): 262 (M+H)$^+$, 131.5 (M+2H)$^{2+}$;
TLC: Rf 0.20 (CHCl$_3$: MeOH: NH$_4$OH=80:10:1).

Example 11-0043

(3S)—N-(4-azepan-1-ylpyrimidin-2-yl)-1-cyclohexylazepan-3-amine

NMR (DMSO-d$_6$): δ 1.18 (m, 4H), 1.40 (m, 5H), 1.56 (m, 5H), 1.72 (m, 8H), 2.33 (m, 2H), 2.69 (m, 5H), 3.57 (m, 4H), 3.86 (m, 1H), 5.81 (d, J=6.20 Hz, 1H), 5.95 (m, 1H), 7.70 (d, J=6.20 Hz, 1H);
MS (ESI, Pos. 20 V): 372 (M+H)$^+$, 290, 186.5 (M+2H)$^{2+}$;
TLC: Rf 0.47 (CHCl$_3$: MeOH: NH$_4$OH=80:10:1).

Example 11-0044

(3 S)—N-(4-azepan-1-ylpyrimidin-2-yl)-1-tetrahydro-2H-pyran-4-ylazepan-3-amine

NMR (DMSO-d$_6$): δ 1.37 (m, 7H), 1.68 (m, 11H), 2.70 (m, 5H), 3.17 (m, 2H), 3.55 (m, 4H), 3.85 (m, 3H), 5.82 (d, J=6.00 Hz, 1H), 6.01 (m, 1H), 7.70 (d, J=6.00 Hz, 1H);
MS (ESI, Pos. 20 V): 374 (M+H)$^+$, 316, 290, 187.5 (M+2H)$^{2+}$;
TLC: Rf 0.50 (CHCl$_3$: MeOH: NH$_4$OH=80:10:1).

Example 11-0045

4-azepan-1-yl-N-cycloheptylpyrimidin-2-amine

NMR (DMSO-d$_6$): δ 1.46 (m, 12H), 1.69 (m, 6H), 1.85 (m, 2H), 3.52 (m, 4H), 3.77 (m, 1H), 5.80 (d, J=6.00 Hz, 1H), 6.26 (m, 1H), 7.70 (d, J=6.00 Hz, 1H);
MS (ESI, Pos. 20 V): 577 (2M+H)$^+$, 289 (M+H)$^+$;
TLC: Rf 0.41 (CHCl$_3$: MeOH=10:1).

Example 11-0046

(3S)-1'-acetyl-N-(4-azepan-1-ylpyrimidin-2-yl)-1,3'-bipiperidin-3-amine

NMR (DMSO-d$_6$): δ 1.30 (m, 8H), 1.71 (m, 8H), 1.94 (m, 3H), 2.04 (m, 1H), 2.24 (m, 2H), 2.48 (m, 1H), 2.69 (m, 1H), 2.96 (m, 2H), 3.48 (m, 4H), 3.76 (m, 2H), 4.33 (m, 1H), 5.84 (d, J=6.00 Hz, 1H), 6.19 (m, 1H), 7.71 (d, J=6.00 Hz, 1H);
MS (ESI, Pos. 20 V): 401 (M+H)$^+$, 276, 201 (M+2H)$^{2+}$;
TLC: Rf 0.52 (CHCl$_3$: MeOH: NH$_4$OH=80:10:1).

Example 11-0047

(3 S)-1'-acetyl-N-(4-azepan-1-ylpyrimidin-2-yl)-1,4'-bipiperidin-3-amine

NMR (DMSO-d$_6$): δ 1.22 (m, 3H), 1.46 (m, 5H), 1.71 (m, 8H), 1.95 (s, 3H), 2.02 (m, 1H), 2.21 (m, 1H), 2.42 (m, 2H), 2.66 (m, 1H), 2.96 (m, 2H), 3.52 (m, 4H), 3.80 (m, 2H), 4.38 (m, 1H), 5.83 (d, J=6.00 Hz, 1H), 6.09 (m, 1H), 7.71 (d, J=6.00 Hz, 1H);
MS (ESI, Pos. 20 V): 401 (M+H)$^+$, 201 (M+2H)$^{2+}$;
TLC: Rf 0.46 (CHCl$_3$: MeOH: NH$_4$OH=80:10:1).

Example 11-0048

(3 S)—N-(4-azepan-1-ylpyrimidin-2-yl)-1'-(methylsulfonyl)-1,3'-bipiperidin-3-amine NMR (DMSO-d$_6$): δ 1.28 (m, 3H), 1.47 (m, 5H), 1.64 (m, 5H), 1.82 (m, 3H), 2.04 (m, 1H), 2.25 (m, 1H), 2.48 (m, 4H), 2.71 (m, 1H), 2.82 (s, 3H), 2.98 (m, 1H), 3.50 (m, 5H), 3.78 (m, 1H), 5.84 (d, J=6.00 Hz, 1H), 6.14 (m, 1H), 7.71 (d, J=6.00 Hz, 1H);
MS (ESI, Pos. 20 V): 437 (M+H)$^+$, 276, 219 (M+2H)$^{2+}$;
TLC: Rf 0.54 (CHCl$_3$: MeOH: NH$_4$OH=80:10:1).

Example 11-0049

(3S)—N-(4-azepan-1-ylpyrimidin-2-yl)-1'-(methylsulfonyl)-1,4'-bipiperidin-3-amine NMR (DMSO-d$_6$): δ 1.27 (m, 3H), 1.44 (m, 6H), 1.63 (m, 5H), 1.79 (m, 3H), 1.99 (m, 1H), 2.18 (m, 1H), 2.35 (t, J=11.10 Hz, 1H), 2.67 (t, J=11.10 Hz, 3H), 2.82 (s, 3H), 2.98 (m, 1H), 3.52 (m, 5H), 3.80 (m, 1H), 5.83 (d, J=6.00 Hz, 1H), 6.09 (m, 1H), 7.71 (d, J=6.00 Hz, 1H);
MS (ESI, Pos. 20 V): 873 (2M+H)$^+$, 437 (M+H)$^+$, 219 (M+2H)$^{2+}$;
TLC: Rf 0.63 (CHCl$_3$: MeOH: NH$_4$OH=80:10:1).

Example 11-0050

1-(3 S)-3-[(4-azepan-1-ylpyrimidin-2-yl)amino]piperidin-1-ylcyclohexanecarbonitrile NMR (DMSO-d$_6$): δ 1.29 (m, 3H), 1.47 (m, 6H), 1.69 (m, 9H), 1.88 (m, 1H), 2.07 (m, 3H), 2.90 (m, 1H), 3.15 (m, 3H), 3.53 (m, 4H), 3.83 (m, 1H), 5.84 (d, J=6.00 Hz, 1H), 6.25 (m, 1H), 7.71 (d, J=6.00 Hz, 1H);
MS (ESI, Pos. 20 V): 765 (2M+H)$^+$, 383 (NM+H)$^+$, 356, 276;
TLC: Rf 0.26 (AcOEt).

Example 11-0051

4-azepan-1-yl-N-[(3S)-1-(1-methylcyclohexyl)piperidin-3-yl]pyrimidin-2-amine

NMR (DMSO-d$_6$): δ 0.77 (s, 3H), 1.18 (m, 6H), 1.44 (m, 7H), 1.67 (m, 9H), 1.88 (m, 1H), 2.07 (m, 1H), 2.70 (m, 1H), 2.99 (m, 1H), 3.53 (m, 4H), 3.81 (m, 1H), 5.82 (d, J=5.90 Hz, 1H), 6.08 (m, 1H), 7.70 (d, J=5.90 Hz, 1H);
MS (ESI, Pos. 20 V): 3 72 (M+H)$^+$, 276;
TLC: Rf 0.67 (CHCl$_3$: MEOH: NH$_4$OH=80:10:1).

Example 11-0052

4-(3 S)-3-[(4-azepan-1-ylpyrimidin-2-yl)amino]piperidin-1-ylcyclohexanone

NMR (D)MSO-d$_6$): δ 1.41 (m, 6H), 1.63 (m, 5H), 1.83 (m, 4H), 2.00 (m, 4H), 2.22 (m, 2H), 2.38 (m, 3H), 2.96 (m, 4H), 3.60 (m, 4H), 3.98 (m, 1H), 6.05 (m, 1H), 6.98 (m, 1H), 7.76 (d, J=6.60 Hz, 1H);
MS (ESI, Pos. 20 V): 372 (M+H)$^+$, 290, 186.5 (M+2H)$^{2+}$;
TLC: Rf 0.67 (CHCl$_3$: MEOH: NHOH=80:10:1).

Example 11-0053

4-azepan-1-yl-N-[(3S)-1-(3-methylcyclohexyl)piperidin-3-yl]pyrimidin-2-amine

NMR (DMSO-d$_6$, 373 K): δ 0.88 (m, 3H), 1.16 (m, 1H), 1.27 (m, 1H), 1.38 (m, 4H), 1.50 (m, 8H), 1.63 (m, 2H), 1.70 (m, 4H), 1.92 (m, 1H), 2.09 (m, 1H), 2.22 (m, 1H), 2.36 (m, 1H), 2.59 (m, 1H), 2.89 (m, 1H), 3.55 (t, J=6.00 Hz, 4H), 3.83 (m, 1H), 5.54 (d, J=8.40 Hz, 1H), 5.83 (d, J=6.00 Hz, 1H), 7.72 (d, J=6.00 Hz, 1H);
MS (ESI, Pos. 20 V): 372 (M+H)$^+$, 276, 186.5 (M+2H)$^{2+}$;
TLC: Rf 0.42 (AcOEt: MeOH: TEA=20:2:1).

Example 11-0054

4-azepan-1-yl-N-[(3S)-1-(3,5-dimethylcyclohexyl)piperidin-3-yl]pyrimidin-2-amine NMR (DMSO-d$_6$): δ 0.53 (m, 2H), 0.80 (m, 6H), 1.45 (m, 8H), 1.65 (m, 8H), 1.83 (m, 2H), 2.17 (m, 1H), 2.48 (m, 2H), 2.70 (m, 1H), 2.93 (m, 1H), 3.50 (m, 4H), 3.77 (m, 1H), 5.82 (d, J=6.00 Hz, 1H), 6.03 (m, 1H), 7.70 (d, J=6.00 Hz, 1H);
MS (ESI, Pos. 20 V): 386 (M+H)$^+$, 276, 193.5 (M+2H)$^{2+}$;
TLC: Rf 0.47 (AcOEt: MeOH: TEA=20:2:1).

Example 11-0055

4-azepan-1-yl-N-[(3S)-1-(3,4-dimethylcyclopentyl)piperidin-3-yl]pyrimidin-2-amine NMR (DMSO-d$_6$): δ 0.86 (m, 6H), 1.05 (m, 2H), 1.29 (m, 4H), 1.45 (m, 4H), 1.66 (m, 8H), 1.89 (m, 2H), 2.58 (m, 2H), 2.96 (m, 1H), 3.49 (m, 4H), 3.73 (m, 1H), 5.82 (d, J=6.00 Hz, 1H) 6.06 (m, 1H), 7.70 (d, J=6.00 Hz, 1H);
MS (ESI, Pos. 20 V): 372 (M+H)$^+$, 276, 186.5 (M+2H)$^{2+}$;
TLC: Rf 0.42 (AcOEt: MeOH: TEA=20:2:1).

Example 11-0056

4-azepan-1-yl-N-[(3S)-1-cycloheptylpiperidin-3-yl]pyrimidin-2-amine

NMR (DMSO-d$_6$): δ 1.44 (m, 14H), 1.66 (m, 10H), 1.97 (m, 1H), 2.18 (m, 1H), 2.45 (m, 2H), 2.86 (m, 1H), 3.51 (m, 4H), 3.71 (m, 1H), 5.82 (d, J=6.00 Hz, 1H), 6.00 (m, 1H), 7.70 (d, J=6.00 Hz, 1H);
MS (ESI, Pos. 20 V): 372 (M+H)$^+$, 276, 186.5 (M+2H)$^{2+}$;
TLC: Rf 0.42 (AcOEt: MeOH: TEA=20:2:1).

Example 11-0057

4-azepan-1-yl-N-[(3S)-1-(3,5-dimethylcyclohexyl)pyrrolidin-3-yl]pyrimidin-2-amine NMR (DMSO-d$_6$): δ 0.47 (m, 2H), 0.81 (m, 6H), 1.45 (m, 6H), 1.67 (m, 10H), 2.04 (m, 1H), 2.21 (m, 1H), 2.36 (m, 1H), 2.58 (m, 1H), 2.90 (m, 1H), 3.50 (m, 4H), 4.17 (m, 1H), 5.83 (d, J=6.00 Hz, 1H), 6.35 (m, 1H), 7.71 (d, J=6.00 Hz, 1H);
MS (ESI, Pos. 20 V): 372 (M+H)$^+$, 262;
TLC: Rf 0.42 (AcOEt: MeOH: TEA=20:2:1).

Example 11-0058

4-azepan-1-yl-N-[(3 S)-1-ethylpiperidin-3-yl]pyrimidin-2-amine

NMR (DMSO-d$_6$): δ 0.96 (t, J=7.00 Hz, 3H), 1.28 (m, 1H), 1.44 (m, 5H), 1.66 (m, 6H), 1.91 (m, 1H), 2.28 (m, 2H), 2.48 (m, 1H), 2.58 (m, 1H), 2.89 (m, 1H), 3.51 (m, 4H), 3.77 (m, 1H) 5.83 (d, J=5.90 Hz, 1H), 6.05 (m, 1H), 7.71 (d, J=5.90 Hz, 1H);

MS (ESI, Pos. 20 V): 304 (M+H)$^+$, 152.5 (M+2H)$^{2+}$;

TLC: Rf 0.40 (AcOEt: MeOH: TEA=20:2:1).

Example 11-0059

4-azepan-1-yl-N-[1-(1-ethylcyclohexyl)piperidin-3-yl]pyrimidin-2-amine

NMR (DMSO-d$_6$): δ 0.75 (t, J=7.50 Hz, 3H), 1.30 (m, 9H), 1.45 (m, 6H), 1.69 (m, 9H), 1.96 (m, 1H), 2.16 (m, 1H), 2.73 (m, 1H), 2.99 (m, 1H), 3.50 (m, 4H), 3.74 (m, 1H), 5.81 (d, J=6.00 Hz, 1H), 6.04 (m, 1H), 7.69 (d, J=6.00 Hz, 1H);

MS (ESI, Pos. 20 V): 386 (M+1H)$^+$, 276, 111;

TLC: Rf 0.38 (CHCl$_3$: MeOH=10:1).

Example 11-0060

4-azepan-1-yl-N-[-(1-phenylcyclohexyl)piperidin-3-yl]pyrimidin-2-amine

NMR (DMSO-d$_6$): δ 1.04 (m, 1H), 1.29 (m, 5H), 1.46 (m, 5H), 1.65 (m, 9H), 1.87 (m, 2H), 2.12 (m, 2H), 2.69 (m, 1H), 2.98 (m, 1H), 3.50 (m, 4H), 3.77 (m, 1H), 5.82 (d, J=6.00 Hz, 1H), 6.03 (m, 1H), 7.19 (m, 1H), 7.29 (m, 4H), 7.69 (d, J=6.00 Hz, 1H);

MS (ESI, Pos. 20 V): 434 (M+H)$^+$, 276, 159;

TLC: Rf 0.38 (CHCl$_3$: MeOH=10:1).

Example 11-0061

N-(1-cyclohexylpiperidin-3-yl)-4-(1,4-oxazepan-4-yl)pyrimidin-2-amine

NMR (CDCl$_3$): δ 1.02 (m, 1H), 1.20 (m, 2H), 1.50 (m, 3H), 1.78 (m, 8H), 1.96 (m, 2H), 2.26 (m, 2H), 2.46 (m, 1H), 2.53 (m, 1H), 2.89 (m, 1H), 3.68 (m, 4H), 3.76 (m, 4H), 3.95 (m, 1H), 5.10 (d, J=9.30 Hz, 1H), 5.76 (d, J=6.00 Hz, 1H), 7.82 (d, J=6.00 Hz, 1H);

MS (ESI, Pos. 20 V): 360 (M+H)$^+$, 278, 180.5 (M+2H)$^+$;

TLC: Rf 0.38 (AcOEt: MeOH: TEA=20:2:1).

Example 11-0062

N-(4-azepan-1-ylpyrimidin-2-yl)-1'-(cyclopentylacetyl)-1,4'-bipiperidin-3-amine

NMR (DMSO-d$_6$): δ 1.11 (m, 3H), 1.26 (m, 2H), 1.51 (m, 9H), 1.71 (m, 10H), 1.93 (m, 1H), 2.06 (m, 1H), 2.18 (m, 1H), 2.27 (m, 2H), 2.41 (m, 2H), 2.68 (m, 1H), 2.93 (m, 2H), 3.50 (m, 4H), 3.72 (m, 1H), 3.89 (m, 1H), 4.43 (m, 1H), 5.83 (d, J=6.00 Hz, 1H), 6.10 (m, 1H), 7.70 (d, J=6.00 Hz, 1H);

MS (ESI, Pos. 20 V): 469 (M+H)$^+$, 359, 235 (M+2H)$^{2+}$, 180;

TLC: Rf 0.66 (CHCl$_3$: MeOH: NH$_4$OH=80:10:1).

Example 11-0063

3-[(4-azepan-1-ylpyrimidin-2-yl)amino]-N-(tert-butyl)-1,4'-bipiperidin-1'-carboxamide NMR (DMSO-d$_6$): δ 1.21 (s, 9H), 1.30 (m, 3H), 1.45 (m, 5H), 1.67 (m, 8H), 1.96 (m, 1H), 2.15 (m, 1H), 2.37 (m, 3H), 2.68 (m, 1H), 2.96 (m, 1H), 3.52 (m, 4H), 3.76 (m, 1H), 3.98 (m, 2H), 5.68 (s, 1H), 5.84 (d, J=6.00 Hz, 1H), 6.13 (m, 1H), 7.71 (d, J=6.00 Hz, 1H);

MS (ESI, Pos. 20 V): 458 (M+H)$^+$, 276, 180;

TLC: Rf 0.53 (CHCl$_3$: MeOH: NH$_4$OH=80:10:1).

Example 11-0064 isopropyl 3-[(4-azepan-1-ylpyrimidin-2-yl)amino]-1,4'-bipiperidine-1'-carboxylate NMR (DMSO-d$_6$): δ 1.15 (d, J=6.20 Hz, 6H), 1.27 (m, 3H), 1.45 (m, 5H), 1.69 (m, 8H), 1.97 (m, 1H), 2.19 (m, 1H), 2.38 (m, 1H), 2.72 (m, 3H), 3.00 (m, 1H), 3.50 (m, 4H), 3.74 (m, 1H), 3.99 (m, 2H), 4.74 (m, 1H), 5.84 (d, J=6.20 Hz, 1H), 6.15 (m, 1H), 7.70 (d, J=6.20 Hz, 1H);

MS (ESI, Pos. 20 V): 445 (M+H)$^+$, 359, 276, 202;

TLC: Rf 0.57 (CHCl$_3$: MeOH: NH$_4$OH=80:10:1).

Example 11-0065

(3 S)—N-(4-azepan-1-ylpyrimidin-2-yl)-1'-(cyclohexylcarbonyl)-1,4'-bipiperidin-3-amine noncrystalline material;

NMR (CDCl$_3$): δ 1.24 (m, 4H), 1.52 (m, 8H), 1.71 (m, 15H), 2.25 (m, 1H), 2.47 (m, 4H), 2.95 (m, 2H), 3.55 (m, 4H), 3.96 (m, 2H), 4.64 (m, 1H), 5.01 (m, 1H), 5.75 (d, J=6.00 Hz, 1H), 7.77 (d, J=6.00 Hz, 1H);

MS (ESI, Pos. 20 V): 469 (M+H)$^+$, 359, 318, 212, 111;

TLC: Rf 0.48 (AcOEt: MeOH: TEA=20:2:1).

Example 11-0066

(3S)—N-(4-azepan-1-ylpyrimidin-2-yl)-1'-(cyclopentylcarbonyl)-1,4'-bipiperidin-3-amine NMR (DMSO-d$_6$): δ 1.20 (m, 4H), 1.44 (m, 7H), 1.69 (m, 14H), 1.96 (m, 1H), 2.20 (m, 1H), 2.40 (m, 1H), 2.68 (m, 1H), 2.96 (m, 3H), 3.51 (m, 4H), 3.76 (m, 1H), 4.03 (m, 1H), 4.45 (m, 1H), 5.84 (d, J=6.00 Hz, 1H), 6.16 (m, 1H), 7.71 (d, J=6.00 Hz, 1H);

MS (ESI, Pos. 20 V): 455 (M+H)$^+$, 359;

TLC: Rf 0.53 (CHCl$_3$: MeOH: NH$_4$OH=80:10:1).

Example 11-0067

(3 S)—N-(4-azepan-1-ylpyrimidin-2-yl)-1'-(2-methylbutanoyl)-1,4'-bipiperidin-3-amine NMR (DMSO-d$_6$): δ 0.77 (t, J=7.40 Hz, 3H), 0.94 (m, 3H), 1.19 (m, 5H), 1.46 (m, 6H), 1.71 (m, 8H), 1.97 (m, 1H), 2.20 (m, 1H), 2.39 (m, 1H), 2.66 (m, 2H), 3.00 (m, 2H), 3.50 (m, 4H) 3.75 (m, 1H), 4.01 (m, 1H), 4.46 (m, 1H), 5.84 (d, J=6.00 Hz, 1H), 6.15 (m, 1H), 7.71 (d, J=6.00 Hz, 1H);

MS (ESI, Pos. 20 V): 443 (M+H)$^+$, 359;

TLC: Rf 0.51 (CHCl$_3$: MeOH: NH$_4$OH=80:10:1).

Example 11-0068

(3S)—N-(4-azepan-1-ylpyrimidin-2-yl)-1'-(cyclopentylacetyl)-1,4'-bipiperidin-3-amine NMR (DMSO-$d_6$): δ 1.05 (m, 3H), 1.28 (m, 3H), 1.47 (m, 8H), 1.71 (m, 11H), 1.95 (m, 1H), 2.08 (m, 1H), 2.19 (m, 1H), 2.28 (m, 2H), 2.41 (m, 1H), 2.68 (m, 1H), 2.96 (m, 2H), 3.51 (m, 4H), 3.73 (m, 1H), 3.93 (m, 1H), 4.39 (m, 1H), 5.84 (d, J=6.00 Hz, 1H), 6.12 (m, 1H), 7.71 (d, J=6.00 Hz, 1H);

MS (ESI, Pos. 20 V): 469 (M+H)$^+$, 359, 180;

TLC: Rf 0.53 (CHCl$_3$: MeOH: NH$_4$OH=80:10:1).

Example 11-0069

(3S)—N-(4-azepan-1-ylpyrimidin-2-yl)-1'-(3-fluorobenzoyl)-1,4'-bipiperidin-3-amine NMR (DMSO-$d_6$): δ 1.36 (m, 9H), 1.67 (m, 8H), 2.01 (m, 1H), 2.24 (m, 2H), 2.71 (m, 2H), 3.02 (m, 2H), 3.51 (m, 4H), 3.79 (m, 1H), 4.50 (m, 1H), 5.85 (d, J=6.00 Hz, 1H), 6.22 (m, 1H), 7.22 (m, 3H), 7.47 (m, 1H), 7.71 (d, J=6.00 Hz, 1H);

MS (ESI, Pos. 20 V): 481 (M+H)$^+$, 359, 241 (M+2H)$^{2+}$, 123;

TLC: Rf 0.62 (CHCl$_3$: MeOH: NH$_4$OH=80:10:1).

Example 11-0070

N-(4-azepan-1-ylpyrimidin-2-yl)-1'-(piperidin-1-ylcarbonyl)-1,4'-bipiperidin-3-amine NMR (DMSO-$d_6$): δ 1.23 (m, 3H), 1.47 (m, 11H), 1.70 (m, 8H), 1.96 (m, 1H), 2.21 (m, 1H), 2.38 (m, 2H), 2.63 (m, 3H), 2.91 (m, 1H), 3.10 (m, 4H), 3.52 (m, 5H), 3.79 (m, 1H), 5.84 (d, J=6.00 Hz, 1H), 6.14 (m, 1H), 7.71 (d, J=6.00 Hz, 1H);

MS (ESI, Pos. 20 V): 470 (M+H)$^+$, 359, 112;

TLC: Rf 0.65 (CHCl$_3$: MeOH: NH$_4$OH=80:10:1).

Example 11-0071

4-azepan-1-yl-N-(3-piperidin-1-ylcyclohexyl)pyrimidin-2-amine

NMR (DMSO-$d_6$): δ 1.31 (m, 3H), 1.49 (m, 13H), 1.69 (m, 6H), 2.38 (m, 5H), 3.54 (m, 4H), 4.10 (m, 1H), 5.81 (d, J=6.00 Hz, 1H), 6.07 (m, 1H), 7.70 (d, J=6.00 Hz, 1H);

MS (ESI, Pos. 20 V): 358 (M+H)$^+$, 179.5 (M+2H)$^{2+}$;

TLC: Rf 0.74 (CHCl$_3$: MeOH: NH OH=80:10:1).

Example 11-0072

4-azepan-1-yl-N-(1,4-trans-4-piperidin-1-ylcyclohexyl)pyrimidin-2-amine

NMR (DMSO-$d_6$): δ 1.18 (m, 3H), 1.33 (m, 3H), 1.47 (m, 8H), 1.69 (m, 6H), 1.94 (m, 2H), 2.20 (m, 1H), 2.42 (m, 4H), 3.57 (m, 5H), 5.81 (d, J=6.00 Hz, 1H), 6.14 (m, 1H), 7.70 (d, J=6.00 Hz, 1H);

MS (ESI, Pos. 20 V): 715 (2M+H)$^+$, 358 (M+H)$^+$, 179.5 (M+2H)$^{2+}$;

TLC: Rf 0.45 (CHCl$_3$: MeOH: NH$_4$OH=80:10:1).

Example 11-0073

4-(3S)-3-[(4-azepan-1-ylpyrimidin-2-yl)amino]piperidin-1-ylcyclohexanecarboxylic acid dihydrochloride NMR (CD$_3$OD): δ 1.61 (m, 8H), 1.86 (m, 5H), 2.23 (m, 7H), 2.69 (m, 1H), 2.84 (m, 1H), 3.05 (m, 1H), 3.51 (m, 1H), 3.72 (m, 4H), 3.96 (m, 2H), 4.47 (m, 1H), 6.43 (d, J=7.50 Hz, 1H), 7.69 (d, J=7.50 Hz, 1H);

MS (ESI, Pos. 20 V): 402 (M+H)$^+$, 304, 276, 201.5 (M+2H)$^{2+}$;

TLC: Rf 0.64 (CHCl$_3$: MeOH: NH$_4$OH=80:10:1).

Example 11-0074

1,4-trans-4-(3S)-3-[(4-azepan-1-ylpyrimidin-2-yl)amino]piperidin-1-ylcyclohexanol NMR (DMSO-$d_6$): δ 1.12 (m, 5H), 1.42 (m, 5H), 1.63 (m, 8H), 1.79 (m, 2H), 1.94 (m, 1H), 2.22 (m, 2H), 2.64 (m, 1H), 2.92 (m, 1H), 3.50 (m, 4H), 3.77 (m, 2H), 4.44 (d, J=4.20 Hz, 1H), 5.82 (d, J=6.00 Hz, 1H) 6.10 (m, 1H), 7.70 (d, J=6.00 Hz, 1H);

MS (FAB, Pos.): 374 (M+H)$^+$;

TLC: Rf 0.33 (CHCl$_3$: MeOH: NH$_4$OH=80:10:1).

Example 11-0075

4-azepan-1-yl-N-[(1R*,2R*)-2-piperidin-1-ylcyclohexyl]pyrimidin-2-amine

NMR (DMSO-$d_6$): δ 1.09 (m, 5H), 1.32 (m, 6H), 1.45 (m, 4H), 1.63 (m, 6H), 1.83 (m, 1H), 2.31 (m, 5H), 3.57 (m, 5H), 5.74 (d, J=4.80 Hz, 1H), 5.84 (d, J=6.00 Hz, 1H), 7.71 (d, J=6.00 Hz, 1H);

MS (ESI, Pos. 20 V): 358 (M+H)$^+$, 179.5 (M+2H)$^{2+}$;

TLC: Rf 0.43 (CHCl$_3$: MeOH: NH$_4$OH=80:10:1).

Example 11-0076

1,4-シス-4-(3S)-3-[(4-azepan-1-ylpyrimidin-2-yl)amino]piperidin-1-ylcyclohexanol noncrystalline material NMR (DMSO-$d_6$): δ 1.29 (m, 7H), 1.46 (m, 4H), 1.68 (m, 9H), 1.95 (m, 1H), 2.22 (m, 2H), 2.64 (m, 1H), 2.95.(m, 1H), 3.49 (m, 4H), 3.77 (m, 2H), 4.22 (d, J=3.30 Hz, 1H), 5.83 (d, J=6.00 Hz, 1H), 6.13 (m, 1H) 7.70 (d, J=6.00 Hz, 1H);

MS (FAB, Pos.): 374 (M+H)$^+$;

TLC: Rf 0.33 (CHCl$_3$: MeOH: NH H=80:10:1).

Example 11-0077

1-2-[(1-cyclohexylpiperidin-3-yl)amino]pyrimidin-4-ylazepan-4-ol

NMR (DMSO-$d_6$): δ 1.08 (m, 6H), 1.49 (m, 7H), 1.72 (m, 5H), 1.84 (m, 2H), 2.01 (m, 1H), 2.24 (m, 2H), 2.63 (m, 1H), 2.98 (m, 1H), 3.48 (m, 4H), 3.64 (m, 1H), 3.79 (m, 1H), 4.49 (d, J=3.80 Hz, 1H), 5.82 (d, J=6.00 Hz, 1H), 6.10 (m, 1H), 7.71 (d, J=6.00 Hz, 1H);

MS (ESI, Pos. 20 V): 374 (M+H)$^+$, 292, 187.5 (M+2H)$^{2+}$;

TLC: Rf 0.46 (CHCl$_3$: MeOH: NH$_4$OH=80:10:1).

Example 11-0078

(4-(3S)-3-[(4-azepan-1-ylpyrimidin-2-yl)amino]piperidin-1-ylcyclohexyl)(cyclohexyl)methanone NMR (CDCl$_3$): δ 1.27 (m, 4H), 1.53 (m, 10H), 1.74 (m, 11H), 1.92 (m, 4H), 2.04 (m, 1H), 2.26 (m, 2H), 2.46 (m, 4H), 2.91 (m, 1H), 3.55 (m, 4H), 3.98 (m, 1H), 5.05 (m, 1H), 5.75 (m, 1H), 7.78 (m, 1H);
MS (ESI, Pos. 20 V): 468 (M+H)$^+$, 276, 234.5 (M+2H)$^{2+}$, 193;
TLC: Rf 0.45 (AcOEt: MeOH: TEA=20:2:1).

Example 11-0079

N'-(4-azepan-1-ylpyrimidin-2-yl)-N$^2$-cyclohexyl-N$^2$-ethylethane-1,2-diamine

NMR (DMSO-d$_6$): δ 0.95 (t, J=7.00 Hz, 3H), 1.16 (m, 5H), 1.41 (m, 4H), 1.54 (m, 1H), 1.74 (m, 8H), 2.37 (m, 5H), 3.17 (m, 2H), 3.62 (m, 4H), 5.81 (d, J=6.00 Hz, 1H), 6.17 (m, 1H), 7.69 (d, J=6.00 Hz, 1H);
MS (ESI, Pos. 20 V): 346 (M+H)$^+$, 264, 173.5 (M+2H)$^{2+}$;
TLC: Rf 0.44 (CHCl$_3$: MeOH: NH$_4$OH=80:10:1).

Example 11-0080

N'-(4-azepan-1-ylpyrimidin-2-yl)-N$^2$-cyclohexylethane-1,2-diamine

NMR (DMSO-d$_6$): δ 0.92 (m, 2H), 1.19 (m, 3H), 1.45 (m, 5H), 1.63 (m, 6H), 1.79 (m, 2H), 2.27 (m, 1H), 2.65 (t, J=6.50 Hz, 2H), 3.20 (m, 2H), 3.62 (m, 4H), 5.83 (d, J=6.00 Hz, 1H), 6.25 (m, 1H), 7.70 (d, J=6.00 Hz, 1H);
MS (FAB, Pos.): 318 (M+H)$^+$, 219, 206, 193;
TLC: Rf 0.49 (CHCl$_3$: NH$_4$OH=80:10:1).

Example 11-0081

N'-(4-azepan-1-ylpyrimidin-2-yl)-N$^2$-cyclohexyl-N$^2$-methylethane-1,2-diamine NMR (DMSO-d$_6$): δ 1.14 (m, 5H), 1.44 (m, 4H), 1.54 (m, 1H), 1.71 (m, 8H), 2.19 (s, 3H), 2.30 (m, 2H), 2.42 (m, 1H), 3.18 (m, 2H), 3.62 (m, 4H), 5.82 (d, J=6.00 Hz, 1H), 6.11 (m, 1H), 7.70 (d, J=6.00 Hz, 1H);
MS (ESI, Pos. 20 V): 332 (M+H)$^+$, 250;
TLC: Rf 0.42 (CHCl$_3$: MeOH: NH$_4$OH=80:10:1).

Example 11-0082

N'-(4-azepan-1-ylpyrimidin-2-yl)-N$^2$-methyl-N$^2$-tetrahydro-2H-pyran-4-ylethane-1,2-diamine NMR (DMSO-d$_6$): δ 1.38 (dd, J=12.40, 4.50 Hz, 1H), 1.45 (m, 5H), 1.65 (m, 6H), 2.20 (s, 3H), 2.42 (m, 1H), 2.53 (m, 2H), 3.23 (m, 4H), 3.55 (m, 4H), 3.85 (dd, J=11.10, 4.10 Hz, 2H), 5.83 (d, J=6.00 Hz, 1H), 6.15 (m, 1H), 7.70 (d, J=6.00 Hz, 1H);
MS (ESI, Pos. 20 V): 334 (M+H)$^+$, 276, 250;
TLC: Rf 0.52 (CHCl$_3$: MeOH: NH$_4$OH=80:10:1).

Example 11-0083

(1R*,2S*)-N'-(4-azepan-1-ylpyrimidin-2-yl)-N$^2$-cyclohexylcyclohexane-1,2-diamine NMR (DMSO-d$_6$): δ 0.83 (m, 1H), 1.09 (m, 4H), 1.25 (m, 3H), 1.44 (m, 8H), 1.70 (m, 10H), 2.34 (m, 1H), 2.87 (m, 1H), 3.55 (m, 4H), 3.83 (m, 1H), 5.78 (m, 1H), 5.83 (d, J=6.00 Hz, 1H), 7.70 (d, J=6.00 Hz, 1H);
MS (ESI, Pos. 20 V): 372 (M+H)$^+$, 290, 186.5 (M+2H)$^{2+}$;
TLC: Rf 0.54 (CHCl$_3$: MeOH: NH$_4$OH=80:10:1).

Example 11-0084

(1R*,2R*)-N'-(4-azepan-1-ylpyrimidin-2-yl)-N$^2$-cyclohexylcyclohexane-1,2-diamine NMR (DMSO-d$_6$): δ 0.99 (m, 8H), 1.42 (m, 6H), 1.64 (m, 10H), 1.86 (m, 2H), 2.41 (m, 3H), 3.49 (m, 4H), 5.82 (d, J=6.00 Hz, 1H), 6.10 (m, 1H), 7.70 (d, J=6.00 Hz, 1H);
MS (ESI, Pos. 20 V): 372 (M+H)$^+$, 290, 186.5 (M+2H)$^{2+}$;
TLC: Rf 0.54 (CHCl$_3$: MeOH: NH$_4$H=80:10:1).

Example 11-0085

3-[(4-azepan-1-ylpyrimidin-2-yl)amino]-1,4'-bipiperidin-1'-ylacetic acid dihydrochloride NMR (CD$_3$OD): δ 1.61 (m, 4H), 1.86 (m, 5H), 2.14 (m, 3H), 2.24 (m, 2H), 2.49 (m, 2H), 2.92 (m, 1H), 3.06 (m, 1H), 3.23 (m, 1H), 3.65 (m, 5H), 3.81 (m, 3H), 4.00 (m, 1H), 4.09 (m, 1H), 4.14 (s, 2H), 4.59 (m, 1H), 6.43 (d, J=7.70 Hz, 1H), 7.69 (d, J=7.70 Hz, 1H);
MS (ESI, Pos. 20 V): 833 (2M+H)$^+$, 417 (M+H)$^+$, 276, 209 (M+2H)$^{2+}$;
TLC: Rf 0.22 (CHCl$_3$: MeOH: NH$_4$OH=20:5:1).

Example 11-0086

3-3-[(4-azepan-1-ylpyrimidin-2-yl)amino]-1,4'-bipiperidin-1'-ylpropionic acid dihydrochloride NMR (CD$_3$OD): δ 1.61 (m, 4H), 1.83 (m, 5H), 2.12 (m, 3H), 2.24 (m, 2H), 2.49 (m, 2H), 2.88 (t, J=6.80 Hz, 2H), 3.17 (m, 2H), 3.44 (t, J=6.80 Hz, 2H), 3.69 (m, 8H), 3.98 (m, 2H), 4.07 (m, 1H), 4.56 (m, 1H), 6.43 (d, J=7.50 Hz, 1H), 7.69 (d, J=7.50 Hz, 1H);
MS (ESI, Pos. 20 V): 431 (M+H)$^+$, 304, 276, 216 (M+2H)$^{2+}$, 156;
TLC: Rf 0.22 (CHCl$_3$: MeOH: NH$_4$OH=20:5:1).

Example 11-0087

4-3-[(4-azepan-1-ylpyrimidin-2-yl)amino]-1,4'-bipiperidin-1'-ylbutyric acid dihydrochloride NMR (CD$_3$OD): δ 1.62 (m, 4H), 1.86 (m, 5H), 2.14 (m, 5H), 2.48 (m, 4H), 2.90 (m, 1H), 3.12 (m, 4H), 3.72 (m, 9H), 3.99 (m, 2H), 4.07 (m, 1H), 4.56 (m, 1H), 6.43 (d, J=8.10 Hz, 1H), 7.69 (d, J=8.10 Hz, 1H);
MS (ESI, Pos. 20 V): 445 (M+H)$^+$, 276, 223 (M+2H)$^{2+}$, 170;
TLC: Rf 0.22 (CHCl$_3$: MeOH: NH$_4$OH=20:5:1).

Example 11-0088 methyl (4-3-[(4-azepan-1-ylpyrimidin-2-yl)amino]piperidin-1-ylcyclohexyl)acetate NMR (CDCl$_3$): δ 1.01 (m, 1H), 1.28 (m, 1H), 1.54 (m, 9H), 1.74 (m, 8H), 1.92 (m, 2H), 2.10 (m, 1H), 2.24 (m, 3H), 2.49

(m, 2H), 2.90 (m, 1H), 3.57 (m, 4H), 3.66 (s, 3H), 3.99 (m, 1H), 5.15 (m, 1H), 5.76 (m, 1H), 7.79 (m, 1H);
MS (ESI, Pos. 20 V): 430 (M+H)+, 276, 215.5 (M+2H)2+, 123;
TLC: Rf 0.48 (AcOEt: MeOH: TEA=20:2:1).

Example 11-0089 methyl 3-(4-3-[(4-azepan-1-ylpyrimidin-2-yl)amino] piperidin-1-ylcyclohexyl)propanoate NMR (CDCl$_3$): δ 0.93 (m, 1H), 1.24 (m, 1H), 1.54 (m, 11H), 1.74 (m, 8H), 2.00 (m, 2H), 2.28 (m, 4H), 2.48 (m, 2H), 2.91 (m, 1H), 3.58 (m, 4H), 3.67 (s, 3H), 3.99 (m, 1H), 5.12 (m, 1H), 5.76 (m, 1H), 7.79 (m, 1H);
MS (ESI, Pos. 20 V): 444 (M+H)+, 276, 222.5 (M+2H)2+, 137;
TLC: Rf 0.48 (AcOEt: MeOH: TEA=20:2:1).

Example 11-0090

(4-3-[(4-azepan-1-ylpyrimidin-2-yl)amino]piperidin-1-ylcyclohexyl)acetic acid hydrochloride NMR (CD$_3$OD): δ 1.18 (m, 1H), 1.61 (m, 4H), 1.85 (m, 6H), 1.97 (m, 2H), 2.17 (m, 6H), 2.42 (m, 2H), 2.86 (m, 1H), 3.04 (m, 1H), 3.24 (m, 1H), 3.53 (m, 1H), 3.70 (m, 3H), 3.83 (m, 1H), 3.92 (m, 1H), 4.05 (m, 1H), 4.52 (m, 1H), 5.00 (d, J=4.80 Hz, 1H), 6.43 (d, J=7.70 Hz, 1H), 7.70 (d, J=7.70 Hz, 1H);
MS (ESI, Pos. 20 V): 416 (M+H)+, 276, 208.5 (M+2H)2+, 123;
TLC: Rf 0.53 (CHCl$_3$: MeOH: NH$_4$OH=20:5:1).

Example 11-0091

3-(4-3-[(4-azepan-1-ylpyrimidin-2-yl)amino]piperidin-1-ylcyclohexyl)propionic acid hydrochloride NMR (CD$_3$OD): δ 1.10 (m, 1H), 1.62 (m, 4H), 1.86 (m, 10H), 2.23 (m, 6H), 2.49 (t, J=8.20 Hz, 2H), 2.85 (m, 1H), 3.04 (m, 1H), 3.24 (m, 1H), 3.56 (m, 1H), 3.72 (m, 2H), 3.84 (m, 2H), 3.97 (m, 3H), 4.48 (m, 1H), 6.43 (d, J=7.70 Hz, 1H), 7.69 (d, J=7.70 Hz, 1H);
MS (ESI, Pos. 20 V): 430 (M+H)+, 276, 215.5 (M+2H)2+, 138;
TLC: Rf 0.53 (CHCl$_3$: MeOH: NH$_4$OH=20:5:1).

Example 11-0092

3-[(4-azepan-1-ylpyrimidin-2-yl)amino]-N,N-dimethyl-1,4'-bipiperidine-1'-sulfonamide NMR (CDCl$_3$): δ 1.55 (m, 8H), 1.75 (m, 8H), 2.27 (m, 1H), 2.38 (m, 1H), 2.47 (m, 1H), 2.57 (m, 1H), 2.79 (m, 2H), 2.80 (s, 6H), 2.93 (m, 1H), 3.59 (m, 4H), 3.73 (m, 2H), 4.00 (m, 1H), 5.38 (m, 1H), 5.78 (d, J=6.20 Hz, 1H), 7.77 (d, J=6.20 Hz, 1H);
MS (ESI, Pos. 20 V): 931 (2M+H)+, 466 (M+H)+, 276, 211;
TLC: Rf 0.35 (CHCl$_3$: MeOH=10:1).

Example 11-0093

4-3-[(4-azepan-1-ylpyrimidin-2-yl)amino]piperidin-1-ylcyclohexanone O-(cyclohexylmethyl)oxime NMR (CDCl$_3$): δ 0.95 (m, 2H), 1.23 (m, 3H), 1.54 (m, 8H), 1.72 (m, 12H), 1.92 (m, 2H), 2.08 (m, 1H), 2.28 (m, 1H), 2.49 (m, 4H), 2.92 (m, 1H), 3.21 (m, 1H), 3.56 (m, 5H), 3.80 (d, J=6.40 Hz, 2H), 4.00 (m, 1H), 5.08 (m, 1H), 5.76 (d, J=6.00 Hz, 1H), 7.79 (d, J=6.00 Hz, 1H);
MS (ESI, Pos. 20 V): 966 (2M+H)+, 483 (M+H)+, 242 (M+2H)2+;
TLC: Rf 0.45 (AcOEt: MeOH: TEA=20:2:1).

Example 11-0094

4-3-[(4-azepan-1-ylpyrimidin-2-yl)amino]piperidin-1-ylcyclohexanone O-cycloheptyloxime NMR (CDCl$_3$): δ 1.54 (m, 18H), 1.75 (m, 5H), 1.85 (m, 2H), 1.94 (m, 3H), 2.07 (m, 1H), 2.28 (m, 1H), 2.50 (m, 4H), 2.92 (m, 1H), 3.22 (m, 1H), 3.56 (m, 4H), 3.74 (m, 1H), 3.99 (m, 1H), 4.16 (m, 1H), 5.08 (m, 1H), 5.76 (d, J=6.00 Hz, 1H), 7.79 (d, J=6.00 Hz, 1H);
MS (ESI, Pos. 20 V): 966 (2M+H)+, 483 (M+H)+, 276, 194;
TLC: Rf 0.45 (AcOEt: MeOH: TEA=20:2:1).

Example 11-0095

4-3-[(4-azepan-1-ylpyrimidin-2-yl)amino]piperidin-1-ylcyclohexanone O-cyclohexyloxime NMR (CDCl$_3$): δ 1.33 (m, 5H), 1.54 (m, 8H), 1.74 (m, 8H), 1.82 (m, 2H), 1.90 (m, 3H), 2.08 (m, 1H), 2.28 (m, 1H), 2.49 (m, 4H), 2.93 (m, 1H), 3.25 (m, 1H), 3.56 (m, 5H), 3.98 (m, 2H), 5.07 (m, 1H), 5.76 (d, J=6.00 Hz, 1H), 7.79 (d, J=6.00 Hz, 1H);
MS (ESI, Pos. 20 V): 469 (M+H)+, 276, 194;
TLC: Rf 0.50 (AcOEt: MeOH: TEA=20:2:1).

Example 11-0096

4-azepan-1-yl-N-[1,4-trans-1-(4-phenoxycyclohexyl)piperidin-3-yl]pyrimidin-2-amine NMR (CDCl$_3$): δ 0.85 (m, 1H), 1.42 (m, 4H), 1.54 (m, 4H), 1.75 (m, 8H), 1.92 (m, 2H), 2.18 (m, 2H), 2.28 (m, 1H), 2.43 (m, 2H), 2.58 (m, 1H), 2.96 (m, 1H), 3.58 (m, 4H), 4.00 (m, 1H), 4.12 (m, 1H), 5.34 (m, 1H), 5.78 (d, J=6.00 Hz, 1H), 6.88 (d, J=7.50 Hz, 2H), 6.92 (t, J=7.50 Hz, 1H), 7.26 (t, J=7.50 Hz, 2H), 7.77 (d, J=6.00 Hz, 1H);
MS (ESI, Pos. 20 V): 899 (2M+H)+, 450 (M+H)+, 276;
TLC: Rf 0.23 (CHCl$_3$: MeOH=10:1).

Example 11-0097 benzyl 4-3-[(4-azepan-1-ylpyrimidin-2-yl)amino]piperidin-1-ylcyclohexylcarbamate NMR (CDCl$_3$): δ 1.12 (m, 1H), 1.53 (m, 10H), 1.74 (m, 8H), 2.05 (m, 1H), 2.24 (m, 2H), 2.47 (m, 2H), 2.88 (m, 1H), 3.56 (m, 4H), 3.78 (m, 1H), 3.99 (m, 1H), 4.98 (m, 1H), 5.09 (s, 2H), 5.37 (m, 1H), 5.76 (d, J=6.20 Hz, 1H), 7.36 (m, 5H), 7.76 (d, J=6.20 Hz, 1H);
MS (ESI, Pos. 20 V): 507 (M+H)+, 415, 373, 276;
TLC: Rf 0.45 (AcOEt: MeOH: TEA=20:2:1).

Example 11-0098 benzyl (4-3-[(4-azepan-1-ylpyrimidin-2-yl)amino]piperidin-1-ylcyclohexyl)methylcarbamate NMR (CDCl$_3$): δ 0.96 (m, 1H), 1.53 (m, 11H), 1.74 (m, 8H), 2.09 (m, 1H), 2.26 (m, 2H), 2.46 (m, 2H), 2.84 (m, 1H), 3.09 (m, 2H), 3.56 (m, 4H), 3.99 (m, 1H), 4.81 (m, 1H), 5.10 (s, 2H), 5.21 (m, 1H), 5.76 (d, J=6.20 Hz, 1H), 7.35 (m, 5H), 7.78 (d, J=6.20 Hz, 1H);

MS (ESI, Pos. 20 V): 521 (M+H)$^+$, 431, 387, 276;

TLC: Rf 0.45 (AcOEt: MeOH: TEA=20:2:1).

Example 11-0099

N-(4-azepan-1-ylpyrimidin-2-yl)-1-methylpiperidine-3-carboxamide

NMR (DMSO-d$_6$): δ 1.41 (m, 6H), 1.68 (m, 6H), 1.87 (m, 1H), 2.00 (m, 1H), 2.14 (s, 3H), 2.61 (m, 1H), 2.74 (m, 1H), 2.97 (m, 1H), 3.48 (m, 2H), 3.70 (m, 2H), 6.31 (d, J=6.2 Hz, 1 H) 7.96 (d, J=6.2 Hz, 1H), 9.90 (s, 1H);

MS (FAB, Pos.): 318 (M+H)$^+$;

TLC: Rf 0.52 (CHCl$_3$: MeOH: NH$_4$OH=80:10:1).

Example 11-0100

N-[1-(4-aminocyclohexyl)piperidin-3-yl]-4-azepan-1-ylpyrimidin-2-amine

NMR (CDCl$_3$): δ 1.22 (m, 1H), 1.55 (m, 7H), 1.76 (m, 12H), 2.25 (m, 1H), 2.44 (m, 1H), 2.59 (m, 1H), 2.75 (m, 0.5H), 2.96 (m, 0.5H), 3.14 (m, 2H), 3.57 (m, 4H), 4.02 (m, 1H), 5.30 (m, 0.5H), 5.79 (m, 1.5H), 7.75 (m, 1H);

MS (ESI, Pos. 20 V): 373 (M+H)$^+$, 178;

TLC: Rf 0.55 (CHCl$_3$: MeOH: NH$_4$OH=80:20:2).

Example 11-0101

N-1-[4-(aminomethyl)cyclohexyl]piperidin-3-yl-4-azepan-1-ylpyrimidin-2-amine

NMR (CDCl$_3$): δ 0.93 (m, 1H), 1.24 (m, 2H), 1.54 (m, 8H), 1.65 (m, 3H), 1.75 (m, 5H), 1.86 (m, 2H), 2.26 (m, 2H), 2.50 (m, 2H), 2.63 (m, 2H), 2.85 (m, 0.5H), 2.97 (m, 0.5H), 3.57 (m, 4H), 4.00 (m, 1H), 5.18 (m, 1H), 5.76 (d, J=6.20 Hz, 1H), 7.79 (m, 1H);

MS (ESI, Pos. 20 V): 387 (M+H)$^+$, 276, 194 (M+2H)$^{2+}$, 185;

TLC: Rf 0.55 (CHCl$_3$: MeOH: NH$_4$OH=80:20:2).

Example 11-0102

4-(3S)-3-[(4-azepan-1-ylpyrimidin-2-yl)amino]piperidin-1-yl-1-methylcyclohexanol NMR (CDCl$_3$): δ 1.22 (m, 3H), 1.42 (m, 3H), 1.54 (m, 5H), 1.64 (m, 4H), 1.75 (m, 8H), 2.28 (m, 2H), 2.47 (m, 1H), 2.57 (m, 1H), 2.95 (m, 1H), 3.58 (m, 4H), 3.77 (m, 1H), 4.00 (m, 1H), 5.16 (m, 1H), 5.76 (m, 1H), 7.79 (m, 1H);

MS (ESI, Pos. 20 V): 388 (M+H)$^+$, 304, 276, 193;

TLC: Rf 0.45 (AcOEt: MeOH: TEA=20:2:1).

Example 11-0103

N-(4-3-[(4-azepan-1-ylpyrimidin-2-yl)amino]piperidin-1-ylcyclohexyl)methanesulfonamide NMR (CDCl$_3$): δ 1.30 (m, 2H), 1.54 (m, 5H), 1.61 (m, 3H), 1.74 (m, 6H), 1.85 (m, 2H), 2.11 (m, 1H), 2.25 (m, 1H), 2.42 (m, 2H), 2.52 (m, 2H), 2.76 (m, 1H), 2.89 (m, 0.5H), 2.97 (s, 3H), 3.21 (m, 0.5H), 3.57 (m, 4H), 4.02 (m, 1H), 4.60 (m, 0.5H), 4.93 (m, 0.5H), 5.20 (m, 1H), 5.76 (m, 1H), 7.78 (m, 1H);

MS (ESI, Pos. 20 V): 451 (M+H)$^+$, 356, 276, 226 (M+2H)$^{2+}$, 178;

TLC: Rf 0.50 (AcOEt: MeOH: TEA=20:2:1).

Example 11-0104

N-[(4-3-[(4-azepan-1-ylpyrimidin-2-yl)amino]piperidin-1-ylcyclohexyl)methyl]methanesulfonamide NMR (CDCl$_3$): δ 0.98 (m, 1H), 1.26 (m, 1H), 1.54 (m, 10H), 1.74 (m, 8H), 1.87 (m, 1H), 2.03 (m, 1H), 2.36 (m, 3H), 2.56 (m, 0.5H), 2.75 (m, 0.5H), 2.95 (m, 4H), 3.08 (m, 1H) 3.56 (m, 4H), 4.02 (m, 1H), 4.43 (m, 0.5H), 4.69 (m, 0.5H), 5.21 (m, 1H), 5.76 (d, J=6.00 Hz, 1H), 7.78 (d, J=6.00 Hz, 1H);

MS (ESI, Pos. 20 V): 465 (M+H)$^+$, 276, 233 (M+2H)$^{2+}$, 138;

TLC: Rf 0.50 (AcOEt: MeOH: TEA=20:2:1).

Example 11-0105

N-(4-3-[(4-azepan-1-ylpyrimidin-2-yl)amino]piperidin-1-ylcyclohexyl)cyclohexanecarboxamide NMR (CDCl$_3$): δ 1.11 (m, 1H), 1.25 (m, 2H), 1.54 (m, 10H), 1.75 (m, 15H), 2.04 (m, 2H), 2.23 (m, 1H), 2.41 (m, 3H), 2.87 (m, 1H), 3.56 (m, 5H), 4.00 (m, 2H), 5.13 (m, 1.5H), 5.61 (m, 0.5H), 5.77 (m, 1H), 7.79 (d, J=6.20 Hz, 1H);

MS (FAB, Pos., matrix=Glycerin+m-NBA): 483 (M+H)$^+$, 193;

TLC: Rf 0.50 (AcOEt: TEA=20:10:1).

Example 11-0106

N-[(4-3-[(4-azepan-1-ylpyrimidin-2-yl)amino]piperidin-1-ylcyclohexyl)methyl]cyclohexanecarboxamide NMR (CDCl$_3$): δ 0.97 (m, 1H), 1.25 (m, 4H), 1.54 (m, 11H), 1.75 (m, 15H), 2.06 (m, 1H), 2.29 (m, 2H), 2.47 (m, 2H), 2.89 (m, 1H), 3.08 (m, 1H), 3.21 (m, 1H), 3.57 (m, 4H), 4.02 (m, 1H), 5.46 (m, 1H), 5.63 (m, 1H), 5.78 (m, 1H), 7.76 (m, 1H);

MS (FAB, Pos., matrix=Glycerin+m-NBA): 497 (M+H)$^+$, 193;

TLC: Rf 0.50 (AcOEt: MeOH: TEA=20:2:1).

Example 11-0107

N-(4-3-[(4-azepan-1-ylpyrimidin-2-yl)amino]piperidin-1-ylcyclohexyl)acetamide

NMR (CDCl$_3$): δ 1.13 (m, 1H), 1.55 (m, 11H), 1.74 (m, 8H), 1.96 (m, 3H), 2.33 (m, 3.5H), 2.55 (m, 0.5H), 2.72 (m, 0.5H), 2.92 (m, 0.5H), 3.58 (m, 4H), 4.01 (m, 2H), 5.15 (m, 0.5H), 5.32 (m, 1H), 5.76 (m, 1H), 5.94 (m, 0.5H), 7.78 (m, 1H);

MS (ESI, Pos. 20 V): 415 (M+H)$^+$, 276, 208 (M+2H)$^{2+}$, 140;
TLC: Rf 0.45 (AcOEt: MeOH: TEA=20:2:1).

Example 11-0108

N-[(4-3-[(4-azepan-1-ylpyrimidin-2-yl)amino]piperidin-1-ylcyclohexyl)methyl]acetamide NMR (CDCl$_3$): δ 0.97 (m, 1H), 1.25 (m, 1H), 1.54 (m, 9H), 1.74 (m, 6H), 1.86 (m, 4H), 1.99 (m, 3H), 2.24 (m, 1H), 2.43 (m, 3H), 2.74 (m, 0.5H), 2.94 (m, 0.5H), 3.17 (m, 2H), 3.56 (m, 4H), 4.02 (m, 1H), 5.20 (m, 1H), 5.49 (m, 0.5H), 5.76 (m, 1H), 5.81 (m, 0.5H), 7.78 (m, 1H);
MS (ESI, Pos. 20 V): 429 (M+H)$^+$, 276, 215 (M+2H)$^{2+}$, 154;
TLC: Rf 0.45 (AcOEt: MeOH: TEA=20:2:1).

Example 11-0109

N-(4-azepan-1-ylpyrimidin-2-yl)-1-methylpiperidine-2-carboxamide

NMR (CDCl$_3$): δ 1.68 (m, 12H), 2.08 (m, 3H), 2.29 (s, 3H), 2.64 (m, 1H), 2.97 (m, 1H), 3.63 (m, 4H), 6.14 (d, J=6.2 Hz, 1H), 8.09 (d, J=6.2 Hz, 1H), 8.84 (s, 1H);
MS (FAB, Pos.): 318 (M+H)$^+$;
TLC: Rf 0.50 (CHCl$_3$: MeOH: NH$_4$OH=80:10:1).

Example 11-0110

N'-(4-3-[(4-azepan-1-ylpyrimidin-2-yl)amino]piperidin-1-ylcyclohexyl)-N,N-dimethylsulfamide NMR (CDCl$_3$): δ 1.26 (m, 2H), 1.57 (m, 8H), 1.75 (m, 8H), 2.07 (m, 2H), 2.29 (m, 2H), 2.47 (m, 2H), 2.79 (m, 6H), 2.97 (m, 1H), 3.54 (m, 4.5H), 4.01 (m, 1.5H), 4.47 (m, 1H), 5.18 (m, 1H), 5.76 (m, 1H), 7.78 (m, 1H);
MS (FAB, pos. matrix=Glycerin+m-NBA): 480 (M+H)$^+$, 371, 287, 243, 217, 193, 122;
TLC: Rf 0.45 (AcOEt: MeOH: TEA=20:2:1).

Example 11-0111

N'-[(4-3-[(4-azepan-1-ylpyrimidin-2-yl)amino]piperidin-1-ylcyclohexyl)methyl]-N,N-dimethylsulfamide NMR (CDCl$_3$): δ 0.97 (m, 1H), 1.26 (m, 1H), 1.54 (m, 10H), 1.74 (m, 4H), 1.87 (m, 3H), 2.26 (m, 2H), 2.45 (m, 2H), 2.57 (m, 1H), 2.81 (m, 6H), 2.88 (m, 1H), 3.00 (m, 1H), 3.57 (m, 5H), 4.01 (m, 1.5H), 4.13 (m, 0.5H), 4.31 (m, 0.5H), 4.81 (m, 0.5H), 5.16 (m, 1H), 5.76 (d, J=6.20 Hz, 1H), 7.78 (d, J=6.20 Hz, 1H);
MS (FAB, Pos., matrix=Glycerin+m-NBA): 494 (M+H)$^+$, 301, 257, 217, 193, 122;
TLC: Rf 0.45 (AcOEt: MeOH: TEA=20:2:1).

Example 11-0112

N-(4-azepan-1-ylpyrimidin-2-yl)-1'-(cycloheptylcarbonyl)-1,4'-bipiperidin-3-amine NMR (CDCl$_3$): δ 1.55 (m, 13H), 1.75 (m, 15H), 2.26 (m, 1H), 2.53 (m, 5H), 2.97 (m, 2H), 3.56 (m, 4H), 3.95 (m, 2H), 4.65 (m, 1H), 5.08 (m, 1H), 5.77 (d, J=6.20 Hz, 1H), 7.79 (d, J=6.20 Hz, 1H);
MS (ESI, Pos. 20 V): 483 (M+H)$^+$, 359;
TLC: Rf 0.50 (AcOEt: MeOH: TEA=20:2:1).

Example 11-0113

N-(4-azepan-1-ylpyrimidin-2-yl)-1'-(tetrahydro-2H-pyran-4-ylcarbonyl)-1,4'-bipiperidin-3-amine NMR (CDCl$_3$): δ 1.55 (m, 9H), 1.74 (m, 6H), 1.84 (m, 5H), 2.27 (m, 1H), 2.52 (m, 4H), 2.73 (m, 1H), 2.96 (m, 2H), 3.44 (m, 2H), 3.57 (m, 4H), 3.99 (m, 4H), 4.65 (m, 1H), 5.18 (m, 1H), 5.77 (d, J=6.20 Hz, 1H), 7.78 (d, J=6.20 Hz, 1H);
MS (ESI, Pos. 20 V): 471 (M+H)$^+$, 359, 3.04;
TLC: Rf 0.33 (AcOEt: MeOH: TEA=20:2:1).

Example 11-0114

4-(3S)-3-[(4-azepan-1-ylpyrimidin-2-yl)amino]piperidin-1-yl-1-phenylcyclohexanol NMR (CDCl$_3$): δ 1.54 (m, 7H), 1.80 (m, 13H), 2.43 (m, 4H), 2.64 (m, 1H), 3.03 (m, 1H), 3.55 (m, 4H), 4.01 (m, 1H), 5.13 (m, 1H), 5.75 (m, 1H), 7.24 (m, 1H), 7.34 (m, 2H), 7.51 (m, 2H), 7.77 (m, 1H);
MS (FAB, pos. matrix=Glycerin+m-NBA): 450 (M+H)$^+$;
TLC: Rf 0.50 (AcOEt: MeOH: TEA=20:2:1).

Example 11-0115

N'-(4-azepan-1-ylpyrimidin-2-yl)-N$^2$-methylethane-1,2-diamine

NMR (CDCl$_3$): δ 1.54 (m, 4H), 1.74 (m, 4H), 2.71 (s, 3H), 3.24 (t, J=5.20 Hz, 2H), 3.43 (m, 3H), 3.77 (m, 4H), 5.81 (d, J=6.60 Hz, 1H), 7.54 (m, 1H), 7.65 (d, J=6.60 Hz, 1H);
MS (ESI, Pos. 20 V): 250 (M+H)$^+$, 125;
TLC: Rf 0.33 (CHCl$_3$: MeOH: NH$_4$OH=80:10:1).

Example 11-0116

4-azepan-1-yl-N-[(3S)-1-(1,4-dioxaspiro[4.5]dec-8-yl)piperidin-3-yl]pyrimidin-2-amine NMR (CDCl$_3$): δ 1.53 (m, 8H), 1.72 (m, 12H), 2.30 (m, 2H), 2.55 (m, 2H), 2.95 (m, 1H), 3.58 (m, 4H), 3.92 (s, 4H), 4.02 (m, 1H), 5.09 (m, 1H), 5.76 (d, J=6.00 Hz, 7.79 (d, J=6.00 Hz, 1H);
MS (ESI, Pos. 20 V): 416 (M+H)$^+$, 276, 208.5 (M+2H)$^{2+}$;
TLC: Rf 0.55 (CHCl$_3$: MeOH: NH$_4$OH=80:10:1).

Example 11-0117

N-(1-benzylpiperidin-3-yl)-4-(1,4-oxazepan-4-yl)pyrimidin-2-amine

NMR (CDCl$_3$): δ 1.55 (m, 1H), 1.71 (m, 3H), 1.95 (m, 2H), 2.29 (m, 1H), 2.39 (m, 2H), 2.72 (m, 1H), 3.46 (d, J=13.00 Hz, 1H), 3.52 (d, J=13.00 Hz, 1H), 3.68 (m, 4H), 3.74 (m, 4H), 4.02 (m, 1H), 5.15 (m, 1H), 5.77 (d, J=6.00 Hz, 1H), 7.28 (m, 5H), 7.83 (d, J=6.00 Hz, 1H);
MS (ESI, Pos. 20 V): 368 (M+H)$^+$, 278;
TLC: Rf 0.45 (AcOEt: MeOH: TEA=20:2:1).

Example 11-0118

4-(1,4-oxazepan-4-yl)-N-piperidin-3-ylpyrimidin-2-amine

NMR (CDCl$_3$): δ 1.50 (m, 1H), 1.71 (m, 1H), 1.86 (m, 2H), 1.96 (m, 2H), 2.53 (m, 1H), 2.66 (m, 1H), 2.86 (m, 1H), 3.21 (m, 1H), 3.69 (m, 4H), 3.76 (m, 4H), 3.85 (m, 1H), 4.93 (m, 1H), 5.78 (d, J=6.00 Hz, 1H), 7.82 (d, J=6.00 Hz, 1H);
MS (ESI, Pos. 20 V): 278 (M+H)$^+$, 139.5 (M+2H)$^{2+}$;
TLC: Rf 0.44 (CHCl$_3$: MeOH: NH$_4$OH=80:20:4).

Example 11-0119 ethyl 4-(3S)-3-[(4-azepan-1-ylpyrimidin-2-yl)amino]piperidin-1-ylcyclohexanecarboxylate NMR (CDCl$_3$): δ 1.24 (m, 3H), 1.52 (m, 11H), 1.72 (m, 7H), 1.89 (m, 1H), 2.03 (m, 2H), 2.21 (m, 2H), 2.40 (m, 1H), 2.51 (m, 1H), 2.91 (m, 1H), 3.55 (m, 4H), 3.97 (m, 1H), 4.11 (m, 2H), 5.17 (m, 1H), 5.74 (m, 1H), 7.76 (d, J=6.20 Hz, 1H);
MS (ESI, Pos. 20 V): 430 (M+H)$^+$, 276, 215.5 (M+2H)$^{2+}$;
TLC: Rf 0.52 (AcOEt: MeOH: TEA=20:2:1).

Example 11-0120

4-(3S)-3-[(4-azepan-1-ylpyrimidin-2-yl)amino]piperidin-1-yl-N-methoxy-N-methylcyclohexanecarboxamide NMR (CDCl$_3$): δ 1.51 (m, 9H), 1.71 (m, 6H), 1.90 (m, 4H), 2.24 (m, 1H), 2.37 (m, 2H), 2.54 (m, 2H), 2.79 (m, 1H), 2.91 (m, 1H), 3.13 (m, 3H), 3.56 (m, 4H), 3.65 (m, 3H), 3.98 (m, 1H), 5.10 (m, 1H), 5.73 (m, 1H), 7.75 (m, 1H);
MS (ESI, Pos. 20 V): 445 (M+H)$^+$, 384, 276, 223 (M+2H)$^{2+}$, 170;
TLC: Rf 0.45 (AcOEt: MeOH: TEA=20:2:1).

Example 11-0121

4-(3S)-3-[(4-azepan-1-ylpyrimidin-2-yl)amino]piperidin-1-ylcyclohexanecarboaldehyde NMR (CDCl$_3$): δ 1.29 (m, 4H), 1.54 (m, 6H), 1.74 (m, 6H), 2.01 (m, 4H), 2.28 (m, 3H), 2.53 (m, 2H), 2.95 (m, 1H), 3.56 (m, 4H), 3.98 (m, 1H), 5.16 (m, 1H), 5.76 (d, J=6.00 Hz, 1H), 7.78 (d, J=6.00 Hz, 1H), 9.61 (s, 1H);
MS (ESI, Pos. 20 V): 386 (M+H)$^+$, 276, 193.5 (M+2H)$^{2+}$;
TLC: Rf 0.48 (AcOEt: MeOH: TEA=20:2:1).

Example 11-0122

(4-(3S)-3-[(4-azepan-1-ylpyrimidin-2-yl)amino]piperidin-1-ylcyclohexyl)(cyclohexyl)methanol NMR (CDCl$_3$): δ 1.23 (m, 6H), 1.54 (m, 12H), 1.75 (m, 12H), 2.04 (m, 2H), 2.25 (m, 2H), 2.40 (m, 2H), 2.56 (m, 2H), 2.97 (m, 1H), 3.55 (m, 4H), 4.02 (m, 1H), 5.39 (m, 1H), 5.76 (d, J=6.20 Hz, 1H), 7.77 (m, 1H);
MS (ESI, Pos. 20 V): 470 (M+H)$^+$, 276, 235.5 (M+2H)$^{2+}$;
TLC: Rf 0.48 (AcOEt: MeOH: TEA=20:2:1).

Example 11-0123

4-azepan-1-yl-N-(1-benzylpyrrolidin-3-yl)pyrimidin-2-amine

NMR (DMSO-d$_6$, 363.1K): δ 1.48 (m, 4H), 1.68 (m, 6H), 2.13 (m, 1H), 2.38 (dd, J=9.3, 5.2 Hz, 1H), 2.58 (m, 1H), 2.84 (dd, J=9.3, 6.9 Hz, 1H), 3.53 (t, J=6.00 Hz, 4H), 3.59 (s, 2H), 4.27 (m, 1H), 5.83 (d, J=6.04 Hz, 1H), 5.94 (m, 1H), 7.24 (m, 5 H). 7.71 (d, J=6.04 Hz, 1H);
MS (ESI, Pos. 20 V): 352 (M+H)$^+$;
HPLC condition: A; HPLC retention time (min): 3.00;
TLC: Rf 0.16 (CH$_3$Cl: MeOH: NH$_4$OH=80:10:1).

Example 11-0124

1-[2-(4-phenylpiperazin-1-yl)pyrimidin-4-yl]azepane

NMR (DMSO-d$_6$, 363.1K): δ 1.52 (m, 4H), 1.72 (m, 4H), 3.20 (t, J=5.10 Hz, 4H), 3.60 (t, J=6.00 Hz, 4H), 3.83 (t, J=5.10 Hz, 4H), 5.93 (d, J=6.04 Hz, 1H), 6.79 (t, J=7.3 Hz, 1H), 6.97 (d, J=7.7 Hz, 2H), 7.23 (m, 2H), 7.86 (d, J=6.04 Hz, 1H);
MS (ESI, Pos. 20 V): 338 (M+H)$^+$;
HPLC condition: A; HPLC retention time (min): 3.40;
TLC: Rf 0.18 (Hexane: AcOEt=3:1).

Example 11-0125

1-[2-(4-methylpiperazin-1-yl)pyrimidin-4-yl]azepane

NMR (DMSO-d$_6$, 363.1K): δ 1.49 (m, 4H), 1.71 (m, 4H), 2.20 (s, 3H), 2.32 (t, J=5.10 Hz, 4H), 3.56 (t, J=6.00 Hz, 4H), 3.65 (t, J=5.10 Hz, 4H), 5.88 (d, J=6.0 Hz, 1H), 7.80 (d, J=6.0 Hz, 1H);
MS (ESI, Pos. 20 V): 276 (M+H)$^+$;
HPLC condition: A; HPLC retention time (min): 2.76;
TLC: Rf 0.18 (CHCl$_3$: MeOH: NH$_4$OH=80:10:1).

Example 11-0126

1-[2-(4-benzylpiperazin-1-yl)pyrimidin-4-yl]azepane

NMR (DMSO-d$_6$, 363.1K): δ 1.48 (m, 4H), 1.68 (m, 4H), 2.40 (t, J=5.10 Hz, 4H), 3.50 (s, 2H), 3.54 (t, J=5.70 Hz, 4H), 3.65 (t, J=5.10 Hz, 4H), 5.87 (d, J=6.0 Hz, 7.26 (m, 5H), 7.79 (d, J=6.0 Hz, 1H);
MS (ESI, Pos. 20 V): 352 (M+H)$^+$;
HPLC condition: A; HPLC retention time (min): 2.96;
TLC: Rf 0.41 (CHCl$_3$: MeOH: NH$_4$OH=80:10:1).

Example 11-0127

3-[(4-azepan-1-ylpyrimidin-2-yl)amino]pyrrolidin-1-ylacetic acid

Example 11-0128

4-azepan-1-yl-N-[1-(cyclopropylmethyl)pyrrolidin-3-yl]pyrimidin-2-amine

Example 11-0129

4-azepan-1-yl-N-1-[3-(methylsulfanyl)propyl]pyrrolidin-3-ylpyrimidin-2-amine

Example 11-0130

4-3-[(4-azepan-1-ylpyrimidin-2-yl)amino]pyrrolidin-1-ylbutyric acid

Example 11-0131

4-azepan-1-yl-N-[1-(2,6-dimethylhept-5-enyl)pyrrolidin-3-yl]pyrimidin-2-amine

Example 11-0132

4-azepan-1-yl-N-[1-(quinolin-2-ylmethyl)pyrrolidin-3-yl]pyrimidin-2-amine

Example 11-0133

2-(acetylamino)-1-3-[(4-azepan-1-ylpyrimidin-2-yl)amino]pyrrolidin-1-yl-1,2-dideoxy-D-galactitol

Example 11-0134

4-azepan-1-yl-N-(1-neopentylpyrrolidin-3-yl)pyrimidin-2-amine

Example 11-0135

4-azepan-1-yl-N-1-[(2E)-3-(2-furyl)prop-2-enyl]pyrrolidin-3-ylpyrimidin-2-amine

MS (ESI, Pos.20V): 368 (M+H)$^+$;
HPLC condition: B; HPLC retention time (min): 3.97.

Example 11-0136

4-azepan-1-yl-N-1-[4-(octyloxy)benzyl]pyrrolidin-3-ylpyrimidin-2-amine

Example 11-0137

4-azepan-1-yl-N-(1-isobutylpyrrolidin-3-yl)pyrimidin-2-amine

MS (ESI, Pos.20V): 318 (M+H)$^+$;
HPLC condition: B; HPLC retention time (min): 4.15.

Example 11-0138

4-azepan-1-yl-N-(1-propylpyrrolidin-3-yl)pyrimidin-2-amine

Example 11-0139

4-azepan-1-yl-N-1-[(2E)-dec-2-enyl]pyrrolidin-3-ylpyrimidin-2-amine

Example 11-0140

4-azepan-1-yl-N-1-[2-(benzyloxy)ethyl]pyrrolidin-3-ylpyrimidin-2-amine

Example 11-0141

4-4-[(4-azepan-1-ylpyrimidin-2-yl)amino]piperidin-1-ylbutyric acid

Example 11-0142

2-(acetylamino)-1-4-[(4-azepan-1-ylpyrimidin-2-yl)amino]piperidin-1-yl-1,2-dideoxy-D-galactitol

Example 11-0143

4-azepan-1-yl-N-(1-benzylpiperidin-4-yl)pyrimidin-2-amine

MS (ESI, Pos.20V): 731 (2M+H)$^+$, 366 (M+H)$^+$;
HPLC condition: B; HPLC retention time (min): 4.11.

Example 11-0144

4-azepan-1-yl-N-1-[(2E)-3-(2-furyl)prop-2-enyl]piperidin-4-ylpyrimidin-2-amine

Example 11-0145

4-azepan-1-yl-N-[1-(2-ethylhexyl)piperidin-4-yl]pyrimidin-2-amine

Example 11-0146

2-4-[(4-azepan-1-ylpyrimidin-2-yl)amino]piperidin-1-ylethanol

Example 11-0147

4-azepan-1-yl-N-1-[(2E)-dec-2-enyl]piperidin-4-ylpyrimidin-2-amine

Example 11-0148

4-azepan-1-yl-N-[1-(4-[(2E)-4-methylpent-2-enyl]cyclohex-3-en-1-ylmethyl)piperidin-yl]pyrimidin-2-amine

Example 11-0149

5-methyl-3-phenyl-N-2-[(4-pyrrolidin-1-ylpyrimidin-2-yl)amino]ethylisoxazole-4-carboxamide MS (ESI, Pos.20V): 785 (2M+H)$^+$, 393 (M+H)$^+$;
HPLC condition: A; HPLC retention time (min): 3.22.

Example 11-0150

N-2-[(4-piperidin-1-ylpyrimidin-2-yl)amino]ethylbenzamide

MS (ESI, Pos.20V): 326 (M+H)$^+$;
HPLC condition: A; HPLC retention time (min): 3.16.

Example 11-0151

5-methyl-3-phenyl-N-2-[(4-piperidin-1-ylpyrimidin-2-yl)amino]ethylisoxazole-4-carboxamide MS (ESI, Pos.20V): 813 (2M+H)$^+$, 407 (M+H)$^+$;
HPLC condition: A; HPLC retention time (min): 3.27.

Example 11-0152

N-2-[(4-azepan-1-ylpyrimidin-2-yl)amino]ethyl-2,2-diphenylacetamide

MS (ESI, Pos.20V): 859 (2M+H)$^+$, 430 (M+H)$^+$;
HPLC condition: A; HPLC retention time (min): 3.49.

Example 11-0153

N-2-[(4-azepan-1-ylpyrimidin-2-yl)amino]ethyl-5-methyl-3-phenylisoxazole-4-carboxamide MS (ESI, Pos.20V): 841 (2M+H)$^+$, 421 (M+H);
HPLC condition: A; HPLC retention time (min): 3.34.

Example 11-0154

N-2-[(4-azepan-1-ylpyrimidin-2-yl)amino]ethylacrylamide

MS (ESI, Pos.20V): 290 (M+H)$^+$;
HPLC condition: A; HPLC retention time (min): 3.05.

Example 11-0155

N-2-[(4-azepan-1-ylpyrimidin-2-yl)amino]ethylcyclohexanecarboxamide

MS (ESI, Pos.20V): 346 (M+H)$^+$, 267;
HPLC condition: A; HPLC retention time (min): 3.31.

Example 11-0156

N-2-[(4-azepan-1-ylpyrimidin-2-yl)amino]ethyl-3-cyclopentylpropanamide

MS (ESI, Pos.20V): 719 (2M+H)$^+$, 360 (M+H)$^+$;
HPLC condition: A; HPLC retention time (min): 3.42.

Example 11-0157

N-(2-[4-(3,4-dihydroisoquinolin-2(1H)-yl)pyrimidin-2-yl]aminoethyl)-2,2-diphenylacetamide MS (ESI, Pos.20V): 927 (2M+H)$^+$, 464 (M+H)$^+$;
HPLC condition: A; HPLC retention time (min): 3.56.

Example 11-0158

N-(2-[4-(3,4-dihydroisoquinolin-2(1H)-yl)pyrimidin-2-yl]aminoethyl)-5-methyl-3-phenylisoxazole-4-carboxamide MS (ESI, Pos.20V): 455 (M+H)$^+$;
HPLC condition: A; HPLC retention time (min): 3.42.

Example 11-0159

$N^1$-(4-azepan-1-ylpyrimidin-2-yl)-$N^2$-methyl-$N^2$-(quinolin-2-ylmethyl)ethane-1,2-diamine

Example 11-0160 butyl N-2-[(4-azepan-1-ylpyrimidin-2-yl)amino]ethyl-N-methylglycinate

Example 11-0161

$N^1$-(4-azepan-1-ylpyrimidin-2-yl)-$N^2$-[(2E)-3,7-dimethyloct-2,6-dienyl]-$N^2$-methylethane-1,2-diamine

Example 11-0162 butyl (2-[(4-azepan-1-ylpyrimidin-2-yl)amino]methylpyrrolidin-1-yl)acetate

Example 11-0163 ethyl N-2-[(4-azepan-1-ylpyrimidin-2-yl)amino]ethyl-N-methylglycinate

Example 11-0164 ethyl (2-[(4-azepan-1-ylpyrimidin-2-yl)amino]methylpyrrolidin-1-yl)acetate

Example 11-0165

N-(4-pyrrolidin-1-ylpyrimidin-2-yl)ethane-1,2-diamine

MS (ESI, Pos.20V): 208 (M+H);
HPLC condition: B; HPLC retention time (min): 2.86.

Example 11-0166

1-2-[(2-aminoethyl)amino]pyrimidin-4-ylpyrrolidin-3-ol

Example 11-0167

N-[4-(4-phenylpiperazin-1-yl)pyrimidin-2-yl]ethane-1,2-diamine

MS (ESI, Pos.20V): 299 (M+H);
HPLC condition: A; HPLC retention time (min): 2.94.

Example 11-0168

N-[4-(4-methylpiperazin-1-yl)pyrimidin-2-yl]ethane-1,2-diamine

MS (ESI, Pos.20V): 237 (M+H);
HPLC condition: B; HPLC retention time (min): 2.59.

Example 11-0169

N-(4-morpholin-4-ylpyrimidin-2-yl)ethane-1,2-diamine

Example 11-0170

N-(4-thiomorpholin-4-ylpyrimidin-2-yl)ethane-1,2-diamine

MS (ESI, Pos.20V): 240 (M+H);
HPLC condition: B; HPLC retention time (min): 2.89.

Example 11-0171

2-(1-2-[(2-aminoethyl)amino]pyrimidin-4-ylpiperidin-2-yl)ethanol

MS (ESI, Pos.20V): 266 (M+H);
HPLC condition: A; HPLC retention time (min): 2.73.

Example 11-0172

(1-2-[(2-aminoethyl)amino]pyrimidin-4-ylpiperidin-3-yl)methanol

MS (ESI, Pos.20V): 252 (M+H);
HPLC condition: B; HPLC retention time (min): 2.74.

Example 11-0173

1-2-[(2-aminoethyl)amino]pyrimidin-4-ylpiperidin-4-ol

MS (ESI, Pos.20V): 238 (M+H);
HPLC condition: B; HPLC retention time (min): 2.41.

Example 11-0174

N-[4-(4-phenyl-3,6-dihydropyridin-1(2H)-yl)pyrimidin-2-yl]ethane-1,2-diamine

MS (ESI, Pos.20V): 296 (M+H);
HPLC condition: A; HPLC retention time (min): 3.08.

Example 11-0175

2-(1-2-[(2-aminoethyl)amino]pyrimidin-4-ylpiperidin-4-yl)ethanol

MS (ESI, Pos.20V): 266 (M+H);
HPLC condition: A; HPLC retention time (min): 2.63.

Example 11-0176

1-2-[(2-aminoethyl)amino]pyrimidin-4-ylpiperidin-3-ol

MS (ESI, Pos.20V): 238 (M+H);
HPLC condition: B; HPLC retention time (min): 2.57.

Example 11-0177

N-[4-(3,6-dihydropyridin-1(2H)-yl)pyrimidin-2-yl]ethane-1,2-diamine

MS (ESI, Pos.20V): 220 (M+H);
HPLC condition: A; HPLC retention time (min): 2.70.

Example 11-0178

4-2-[(2-aminoethyl)amino]pyrimidin-4-ylpiperazine-1-carboaldehyde

Example 11-0179

2-(4-2-[(2-aminoethyl)amino]pyrimidin-4-ylpiperazin-1-yl)ethanol

Example 11-0180

N-[4-(3,5-dimethylpiperidin-1-yl)pyrimidin-2-yl]ethane-1,2-diamine

MS (ESI, Pos.20V): 250 (M+H);
HPLC condition: A; HPLC retention time (min): 2.98.

Example 11-0181

N-(4-azepan-1-ylpyrimidin-2-yl)ethane-1,2-diamine

MS (ESI, Pos.20V): 236 (M+H);
HPLC condition: A; HPLC retention time (min): 2.84.

Example 11-0182

N-[4-(4-methyl-1,4-diazepan-1-yl)pyrimidin-2-yl]ethane-1,2-diamine

MS (ESI, Pos.20V): 251 (M+H);
HPLC condition: B; HPLC retention time (min): 2.68.

Example 11-0183

N-[4-(2,6-dimethylmorpholin-4-yl)pyrimidin-2-yl]ethane-1,2-diamine

MS (ESI, Pos.20V): 252 (M+H);
HPLC condition: A; HPLC retention time (min): 2.68.

Example 11-0184

N-4-[(2S)-2-(methoxymethyl)pyrrolidin-1-yl]pyrimidin-2-ylethane-1,2-diamine

MS (ESI, Pos.20V): 252 (M+H);
HPLC condition: A; HPLC retention time (min): 2.71.

Example 11-0185 ethyl 1-2-[(2-aminoethyl)amino]pyrimidin-4-ylpiperidine-3-carboxylate

MS (ESI, Pos.20V): 294 (M+H);
HPLC condition: A; HPLC retention time (min): 2.85.

Example 11-0186 ethyl 1-2-[(2-aminoethyl)amino]pyrimidin-4-ylpiperidine-4-carboxylate

MS (ESI, Pos.20V): 294 (M+H);
HPLC condition: A; HPLC retention time (min): 2.85.

Example 11-0187

N-[4-(4-phenylpiperidin-1-yl)pyrimidin-2-yl]ethane-1,2-diamine

MS (ESI, Pos.20V): 298 (M+H);
HPLC condition: A; HPLC retention time (min): 3.08.

Example 11-0188

N-[4-(4-benzylpiperidin-1-yl)pyrimidin-2-yl]ethane-1,2-diamine

MS (ESI,.Pos.20V): 312 (M+H);
HPLC condition: A; HPLC retention time (min): 3.16.

Example 11-0189

N-[4-(1,4'-bipiperidin-1'-yl)pyrimidin-2-yl]ethane-1,2-diamine

MS (ESI, Pos.20V): 305 (M+H);
HPLC condition: B; HPLC retention time (min): 3.14.

Example 11-0190

N-4-[4-(4-methoxyphenyl)piperazin-1-yl]pyrimidin-2-ylethane-1,2-diamine

MS (ESI, Pos.20V): 329 (M+H);
HPLC condition: A; HPLC retention time (min): 2.81.

Example 11-0191

N-(4-4-[4-(trifluoromethyl)phenyl]piperazin-1-ylpyrimidin-2-yl)ethane-1,2-diamine MS (ESI, Pos.20V): 367 (M+H);
HPLC condition: A; HPLC retention time (min): 3.20.

Example 11-0192

N-[4-(4-cyclohexylpiperazin-1-yl)pyrimidin-2-yl]ethane-1,2-diamine

MS (ESI, Pos.20V): 305 (M+H);
HPLC condition: B; HPLC retention time (min): 3.29.

Example 11-0193

N-[4-(4-benzylpiperazin-1-yl)pyrimidin-2-yl]ethane-1,2-diamine

MS (ESI, Pos.20V): 313 (M+H);
HPLC condition: B; HPLC retention time (min): 3.27.

Example 11-0194

N-4-[4-(2,4-dimethylphenyl)piperazin-1-yl]pyrimidin-2-ylethane-1,2-diamine

MS (ESI, Pos.20V): 327 (M+H);
HPLC condition: A; HPLC retention time (min): 3.12.

Example 11-0195

N-(4-4-[(2E)-3-phenylprop-2-enyl]piperazin-1-ylpyrimidin-2-yl)ethane-1,2-diamine MS (ESI, Pos.20V): 339 (M+H);
HPLC condition: A; HPLC retention time (min): 2.86.

Example 11-0196

N-4-[4-(2-oxo-2-pyrrolidin-1-ylethyl)piperazin-1-yl]pyrimidin-2-ylethane-1,2-diamine MS (ESI, Pos.20V): 334 (M+H);
HPLC condition: B; HPLC retention time (min): 2.77.

Example 11-0197 ethyl 4-2-[(2-aminoethyl)amino]pyrimidin-4-ylpiperazine-1-carboxylate

MS (ESI, Pos.20V): 295 (M+H);
HPLC condition: A; HPLC retention time (min): 2.78.

Example 11-0198

N-(4-4-[5-(trifluoromethyl)pyridin-2-yl]-1,4-diazepan-1-ylpyrimidin-2-yl)ethane-1,2-diamine MS (ESI, Pos.20V): 382 (M+H);
HPLC condition: A; HPLC retention time (min): 3.00.

Example 11-0199

N-(1-2-[(2-aminoethyl)amino]pyrimidin-4-ylpyrrolidin-3-yl)-N-methylacetamide

MS (ESI, Pos.20V): 279 (M+H);
HPLC condition: B; HPLC retention time (min): 2.57.

Example 11-0200

N-[4-(2-pyridin-2-ylazepan-1-yl)pyrimidin-2-yl]ethane-1,2-diamine

MS (ESI, Pos.20V): 313 (M+H);
HPLC condition: A; HPLC retention time (min): 2.74.

Example 11-0201

(3R)-N-(4-azepan-1-ylpyrimidin-2-yl)-1-benzylazepan-3-amine

NMR (DMSO-$d_6$): 1.36 (m, 5H), 1.59 (m, 8H), 1.82 (m, 1H), 2.56 (m, 3H), 2.80 (m, 1H), 3.48 (m, 4H), 3.63 (s, 2H), 3.95 (m, 1H), 5.80 (d, J=5.90 Hz, 1H), 6.08 (m, 1H), 7.24 (m, 5H), 7.68 (d, J=5.90 Hz, 1H);
MS (ESI, Pos. 20 V): 380 (M+H)$^+$, 290, 193;
HPLC condition: A; HPLC retention time (min): 3.03;
TLC: Rf 0.55 ($CHCl_3$: MeOH: $NH_4OH$=80:10:1).

Example 11-0202

(3R)-N-(4-azepan-1-ylpyrimidin-2-yl)azepan-3-amine

NMR (DMSO-$d_6$): δ 1.44 (m, 5H), 1.61 (m, 9H), 2.60 (dd, J=13.50, 7.10 Hz, 1H), 2.72 (t, J=6.00 Hz, 2H), 2.89 (dd, J=13.50, 4.30 Hz, 1H), 3.56 (m, 4H), 3.87 (m, 1H), 5.81 (d, J=6.00 Hz, 1H), 6.09 (m, 1H), 7.70 (d, J=6.00 Hz, 1H);
MS (ESI, Pos. 20 V): 290 (M+H)$^+$, 145.5 (M+2H)$^{2+}$;
HPLC condition: A; HPLC retention time (min): 2.92;
TLC: Rf 0.20 ($CHCl_3$: MeOH: $NH_4OH$=80:10:1).

Example 11-0203

(3S)—N-(4-azepan-1-ylpyrimidin-2-yl)-1-(pyridin-2-ylmethyl)azepan-3-amine

Example 11-0204

(3R)-N-(4-azepan-1-ylpyrimidin-2-yl)-1-(pyridin-2-ylmethyl)azepan-3-amine

Example 11-0205

(3R)-N-(4-azepan-1-ylpyrimidin-2-yl)-1-(2-ethylbutyl)azepan-3-amine

MS (ESI, Pos. 20 V): 374 (M+H)$^+$, 290, 187.5 N+2H)$^{2+}$;
HPLC condition: A; HPLC retention time (min): 3.12.

Example 11-0206

(3R)-N-(4-azepan-1-ylpyrimidin-2-yl)-1-isobutylazepan-3-amine

MS (ESI, Pos. 20 V): 346 (M+H)$^+$, 290, 173.5 (M+2H)$^{2+}$;
HPLC condition: A; HPLC retention time (min): 3.00.

Example 11-0207

(3R)-N-(4-azepan-1-ylpyrimidin-2-yl)-1-cyclohexylazepan-3-amine

MS (ESI, Pos. 20 V): 372 (M+H)$^+$, 346, 290, 186.5 (M+2H)$^{2+}$;
HPLC condition: A; HPLC retention time (min): 3.07.

Example 11-0208

4-azepan-1-yl-N-[(3R)-1-benzylpiperidin-3-yl]pyrimidin-2-amine

MS (ESI, Pos.20V): 366 (M+H)$^+$, 276;
HPLC condition: A; HPLC retention time (min): 3.03.

Example 11-0209

4-azepan-1-yl-N-[(3R)-1-(pyridin-2-ylmethyl)piperidin-3-yl]pyrimidin-2-amine

MS (ESI, Pos.20V): 367 (M+H)$^+$, 184 (M+2H)$^{2+}$;
HPLC condition: A; HPLC retention time (min): 2.92.

Example 11-0210

4-azepan-1-yl-N-[(3R)-1-(2-ethylbutyl)piperidin-3-yl]pyrimidin-2-amine

MS (ESI, Pos.20V): 360 (M+H)$^+$, 276, 180.5 (M+2H)$^{2+}$;
HPLC condition: A; HPLC retention time (min): 3.11.

Example 11-0211

4-azepan-1-yl-N-[(3R)-1-isobutylpiperidin-3-yl]pyrimidin-2-amine

MS (ESI, Pos.20V): 332 (M+H)$^+$, 276, 166.5 (M+2H)$^{2+}$;
HPLC condition: A; HPLC retention time (min): 2.96.

Example 11-0212

4-azepan-1-yl-N-[(3R)-1-cyclohexylpiperidin-3-yl]pyrimidin-2-amine

MS (ESI, Pos.20V): 358 (M+H)$^+$, 276, 179.5 (M+2H)$^{2+}$;
HPLC condition: A; HPLC retention time (min): 3.05.

Example 11-0213

4-azepan-1-yl-N-[1-(3,3-dimethylcyclohexyl)pyrrolidin-3-yl]pyrimidin-2-amine

MS (ESI, Pos.20V): 372 (M+H)$^+$, 262, 186.5 (M+2H)$^{2+}$;
HPLC condition: A; HPLC retention time (min): 3.18.

Example 11-0214

4-azepan-1-yl-N-[1-(2-methoxy-1-methylethyl)pyrrolidin-3-yl]pyrimidin-2-amine

MS (ESI, Pos.20V): 334 (M+H)$^+$, 193;
HPLC condition: A; HPLC retention time (min): 2.92.

Example 11-0215

4-azepan-1-yl-N-(1-cyclobutylpyrrolidin-3-yl)pyrimidin-2-amine

MS (ESI, Pos.20V): 316 (M+H)$^+$, 262, 193;
HPLC condition: A; HPLC retention time (min): 2.94.

Example 11-0216

4-azepan-1-yl-N-(1-tetrahydro-2H-thiopyran-4-ylpyrrolidin-3-yl)pyrimidin-2-amine MS (ESI, Pos.20V): 362 (M+H)$^+$, 262, 193;
HPLC condition: A; HPLC retention time (min): 3.00.

Example 11-0217

4-azepan-1-yl-N-(1-cyclopentylpyrrolidin-3-yl)pyrimidin-2-amine

MS (ESI, Pos.20V): 330 (M+H)$^+$, 262, 193, 165.5 (M+2H)$^{2+}$;
HPLC condition: A; HPLC retention time (min): 2.98.

Example 11-0218

4-azepan-1-yl-N-[1-(1-methylbutyl)pyrrolidin-3-yl]pyrimidin-2-amine

MS (ESI, Pos.20V): 332 (M+H)$^+$, 262, 166.5 (M+2H)$^{2+}$;
HPLC condition: A; HPLC retention time (min): 3.03.

Example 11-0219

4-azepan-1-yl-N-[1-(1,2-dimethylpropyl)pyrrolidin-3-yl]pyrimidin-2-amine

MS (ESI, Pos.20V): 332 (M+H)$^+$, 262, 193;
HPLC condition: A; HPLC retention time (min): 3.00.

Example 11-0220

4-azepan-1-yl-N-[1-(2,2-dimethoxy-1-methylethyl)pyrrolidin-3-yl]pyrimidin-2-amine MS (ESI, Pos.20V): 364 (M+H)$^+$, 193;
HPLC condition: A; HPLC retention time (min): 2.96.

Example 11-0221

4-azepan-1-yl-N-[1-(1,3-dimethylbutyl)pyrrolidin-3-yl]pyrimidin-2-amine

MS (ESI, Pos.20V): 346 (M+H)$^+$, 262, 173.5 (M+2H)$^{2+}$;
HPLC condition: A; HPLC retention time (min): 3.11.

Example 11-0222

4-azepan-1-yl-N-[1-(1-methylpentyl)pyrrolidin-3-yl]
pyrimidin-2-amine

MS (ESI, Pos.20V): 346 (M+H)$^+$, 262, 173.5 (M+2H)$^{2+}$;
HPLC condition: A; HPLC retention time (min): 3.12.

Example 11-0223

4-azepan-1-yl-N-[1-(3,3-dimethoxy-1-methylpropyl)
pyrrolidin-3-yl]pyrimidin-2-amine MS (ESI, Pos.20V): 378 (M+H)$^+$;
HPLC condition: A; HPLC retention time (min): 2.98.

Example 11-0224

4-azepan-1-yl-N-[1-(1-methylpent-4-enyl)pyrrolidin-
3-yl]pyrimidin-2-amine

MS (ESI, Pos.20V): 344 (M+H)$^+$, 262, 172.5 (M+2H)$^{2+}$;
HPLC condition: A; HPLC retention time (min): 3.07.

Example 11-0225

4-azepan-1-yl-N-(1-cyclohex-2-en-1-ylpyrrolidin-3-
yl)pyrimidin-2-amine

MS (ESI, Pos.20V): 342 (M+H)$^+$, 262, 193;
HPLC condition: A; HPLC retention time (min): 3.03.

Example 11-0226

4-azepan-1-yl-N-[1-(2-methylcyclopentyl)pyrroli-
din-3-yl]pyrimidin-2-amine

MS (ESI, Pos.20V): 344 (M+H)$^+$, 262, 193;
HPLC condition: A; HPLC retention time (min): 3.03.

Example 11-0227

4-azepan-1-yl-N-[1-(3-methylcyclopentyl)pyrroli-
din-3-yl]pyrimidin-2-amine

MS (ESI, Pos.20V): 344 (M+H)$^+$, 262, 172.5 (M+2H)$^{2+}$;
HPLC condition: A; HPLC retention time (min): 3.07.

Example 11-0228

4-azepan-1-yl-N-[1-(1-ethylbutyl)pyrrolidin-3-yl]
pyrimidin-2-amine

MS (ESI, Pos.20V): 346 (M+H)$^+$, 262, 173.5 (M+2H)$^{2+}$;
HPLC condition: A; HPLC retention time (min): 3.09.

Example 11-0229

4-azepan-1-yl-N-[1-(2-methylcyclopent-2-en-1-yl)
pyrrolidin-3-yl]pyrimidin-2-amine MS (ESI, Pos.20V): 342 (M+H)$^+$, 193;
HPLC condition: A;-HPLC retention time (min): 3.03.

Example 11-0230

4-azepan-1-yl-N-[1-(1-methylpiperidin-4-yl)pyrroli-
din-3-yl]pyrimidin-2-amine

MS (ESI, Pos.20V): 359 (M+H)$^+$, 262, 180 (M+2H)$^{2+}$;
HPLC condition: A; HPLC retention time (min): 2.83.

Example 11-0231

4-azepan-1-yl-N-[1-(1-methylhexyl)pyrrolidin-3-yl]
pyrimidin-2-amine

MS (ESI, Pos.20V): 360 (M+H)$^+$, 262, 180.5 (M+2H)$^{2+}$;
HPLC condition: A; HPLC retention time (min): 3.22.

Example 11-0232

4-azepan-1-yl-N-[1-(1-ethylpentyl)pyrrolidin-3-yl]
pyrimidin-2-amine

MS (ESI, Pos.20V): 360 (M+H)$^+$, 262, 180.5 (M+2H)$^{2+}$;
HPLC condition: A; HPLC retention time (min): 3.18.

Example 11-0233

4-azepan-1-yl-N-[1-(2-methylcyclohexyl)pyrrolidin-
3-yl]pyrimidin-2-amine

MS (ESI, Pos.20V): 358 (M+H)$^+$, 262, 179.5 (M+2H)$^{2+}$;
HPLC condition: A; HPLC retention time (min): 3.09.

Example 11-0234

4-azepan-1-yl-N-[1-(3-methylcyclohexyl)pyrrolidin-
3-yl]pyrimidin-2-amine

MS (ESI, Pos.20V): 358 (M+H)$^+$, 262, 179.5 (M+2H)$^{2+}$;
HPLC condition: A; HPLC retention time (min): 3.14.

Example 11-0235

4-azepan-1-yl-N-[1-(4-methylcyclohexyl)pyrrolidin-
3-yl]pyrimidin-2-amine

MS (ESI, Pos.20V): 358 (M+H)$^+$, 262, 179.5 (M+2H)$^{2+}$;
HPLC condition: A; HPLC retention time (min): 3.12.

Example 11-0236

4-azepan-1-yl-N-[1-(3,4-dimethylcyclopentyl)pyrro-
lidin-3-yl]pyrimidin-2-amine

MS (ESI, Pos.20V): 358 (M+H)$^+$, 262, 179.5 (M+2H)$^{2+}$;
HPLC condition: A; HPLC retention time (min): 3.14.

Example 11-0237

4-azepan-1-yl-N-[1-(2-methoxycyclohexyl)pyrroli-
din-3-yl]pyrimidin-2-amine

MS (ESI, Pos.20V): 374 (M+H)$^+$, 262;
HPLC condition: A; HPLC retention time (min): 3.05.

Example 11-0238

4-azepan-1-yl-N-[1-(1-propylbutyl)pyrrolidin-3-yl]
pyrimidin-2-amine

MS (ESI, Pos.20V): 360 (M+H)$^+$, 262, 180.5 (M+2H)$^{2+}$;
HPLC condition: A; HPLC retention time (min): 3.18.

Example 11-0239

4-azepan-1-yl-N-(1-cycloheptylpyrrolidin-3-yl)pyrimidin-2-amine

MS (ESI, Pos.20V): 358 (M+H)$^+$, 262, 179.5 (M+2H)$^{2+}$;
HPLC condition: A; HPLC retention time (min): 3.11.

Example 11-0240

4-azepan-1-yl-N-(1-tricyclo[2.2.1.0$^{2,6}$]hept-3-ylpyrrolidin-3-yl)pyrimidin-2-amine MS (ESI, Pos.20V): 354 (M+H)$^+$, 262, 193;
HPLC condition: A; HPLC retention time (min): 3.03.

Example 11-0241

4-azepan-1-yl-N-[1-(1-isopropylpiperidin-4-yl)pyrrolidin-3-yl]pyrimidin-2-amine

MS (ESI, Pos.20V): 387 (M+H)$^+$, 262, 194 (M+2H)$^{2+}$;
HPLC condition: A; HIPLC retention time (min): 2.85.

Example 11-0242

4-azepan-1-yl-N-[1-(1-methylheptyl)pyrrolidin-3-yl]
pyrimidin-2-amine

MS (ESI, Pos.20V): 374 (M+H)$^+$, 262, 187.5 (M+2H)$^{2+}$;
HPLC condition: A; HPLC retention time (min): 3.31.

Example 11-0243

4-azepan-1-yl-N-[1-(1-cyclohexylethyl)pyrrolidin-3-yl]pyrimidin-2-amine

MS (ESI, Pos.20V): 372 (M+H)$^+$, 262, 186.5 (M+2H)$^{2+}$;
HPLC condition: A; HPLC retention time (min): 3.18.

Example 11-0244

4-azepan-1-yl-N-[1-(1-propylpiperidin-4-yl)pyrrolidin-3-yl]pyrimidin-2-amine

MS (ESI, Pos.20V): 387 (M+H)$^+$, 262, 194 (M+2H)$^{2+}$;
HPLC condition: A; HPLC retention time (min): 2.87.

Example 11-0245

4-azepan-1-yl-N-[1-(1,4-dioxaspiro[4.5]dec-8-yl)
pyrrolidin-3-yl]pyrimidin-2-amine MS (ESI, Pos.20V): 402 (M+H)$^+$, 262, 193;
HPLC condition: A; HPLC retention time (min): 2.98.

Example 11-0246

4-azepan-1-yl-N-(1-cyclooctylpyrrolidin-3-yl)pyrimidin-2-amine

MS (ESI, Pos.20V): 372 (M+H)$^+$, 262;
HPLC condition: A; HPLC retention time (min): 3.18.

Example 11-0247

4-azepan-1-yl-N-[1-(3,5-dimethylcyclohexyl)pyrrolidin-3-yl]pyrimidin-2-amine

MS (ESI, Pos.20V): 372 (M+H)$^+$, 262, 186.5 (M+2H)$^{2+}$;
HPLC condition: A; HPLC retention time (min): 3.20.

Example 11-0248

4-azepan-1-yl-N-1-[3-(diethylamino)-1-methylpropyl]pyrrolidin-3-ylpyrimidin-2-amine MS (ESI, Pos.20V): 389 (M+H)$^+$, 262, 195 (M+2H)$^{2+}$;
HPLC condition: A; HPLC retention time (min): 2.87.

Example 11-0249

4-azepan-1-yl-N-[1-(1-ethylhexyl)pyrrolidin-3-yl]
pyrimidin-2-amine

MS (ESI, Pos.20V): 374 (M+H)$^+$, 262;
HPLC condition: A; HPLC retention time (min): 3.27.

Example 11-0250

4-azepan-1-yl-N-[1-(2,3-dihydro-1H-inden-2-yl)
pyrrolidin-3-yl]pyrimidin-2-amine MS (ESI, Pos.20V): 378 (M+H)$^+$, 262, 189.5 (M+2H)$^{2+}$;
HPLC condition: A; HPLC retention time (min): 3.11.

Example 11-0251

4-azepan-1-yl-N-1-[4-(trifluoromethyl)cyclohexyl]
pyrrolidin-3-ylpyrimidin-2-amine MS (ESI, Pos.20V): 412 (M+H)$^+$, 262, 206.5 (M+2H)$^{2+}$;
HPLC condition: A; HPLC retention time (min): 3.18.

Example 11-0252

4-azepan-1-yl-N-[1-(2-propylcyclohexyl)pyrrolidin-3-yl]pyrimidin-2-amine

MS (ESI, Pos.20V): 386 (M+H)$^+$, 262, 193.5 (M+2H)$^{2+}$;
HPLC condition: A; HPLC retention time (min): 3.23.

Example 11-0253

4-azepan-1-yl-N-[1-(1-cyclohexylpropyl)pyrrolidin-3-yl]pyrimidin-2-amine

MS (ESI, Pos.20V): 386 (M+H)$^+$, 262;
HPLC condition: A; HPLC retention time, (min): 3.23.

Example 11-0254

4-azepan-1-yl-N-[1-(1-butylpentyl)pyrrolidin-3-yl]
pyrimidin-2-amine

MS (ESI, Pos.20V): 388 (M+H)$^+$, 262;
HPLC condition: A; HPLC retention time (min): 3.33.

Example 11-0255

4-azepan-1-yl-N-[1-(1-methyl-3-phenylpropyl)pyr-
rolidin-3-yl]pyrimidin-2-amine

MS (ESI, Pos.20V): 394 (M+H)$^+$, 262, 197.5 (M+2H)$^{2+}$;
HPLC condition: A; HPLC retention time (min): 3.22.

Example 11-0256

4-azepan-1-yl-N-(1-decahydronaphthalen-2-ylpyrro-
lidin-3-yl)pyrimidin-2-amine

MS (ESI, Pos.20V): 398 (M+H)$^+$, 262, 199.5 (M+2H)$^{2+}$;
HPLC condition: A; HPLC retention time (min): 3.27.

Example 11-0257

4-azepan-1-yl-N-(1-cyclodecylpyrrolidin-3-yl)pyri-
midin-2-amine

MS (ESI, Pos.20V): 400 (M+H)$^+$, 262;
HPLC condition: A; HPLC retention time (min): 3.31.

Example 11-0258

4-azepan-1-yl-N-[1-(1,2,3,4-tetrahydronaphthalen-2-
yl)pyrrolidin-3-yl]pyrimidin-2-amine MS (ESI, Pos.20V): 392 (M+H)$^+$, 262;
HPLC condition: A; HPLC retention time (min): 3.18.

Example 11-0259

4-azepan-1-yl-N-[1-(1-pentylhexyl)pyrrolidin-3-yl]
pyrimidin-2-amine

MS (ESI, Pos.20V): 416 (M+H)$^+$, 262, 208.5 (M+2H)$^{2+}$;
HPLC condition: A; HPLC retention time (min): 3.51.

Example 11-0260

4-azepan-1-yl-N-[1-(6-methoxy-1,2,3,4-tetrahy-
dronaphthalen-2-yl)pyrrolidin-3-yl]pyrimidin-2-
amine MS (ESI, Pos.20V): 422 (M+H)$^+$, 262;
HPLC condition: A; HPLC retention time (min): 3.16.

Example 11-0261

4-azepan-1-yl-N-[1-(7-methoxy-1,2,3,4-tetrahy-
dronaphthalen-2-yl)pyrrolidin-3-yl]pyrimidin-2-
amine MS (ESI, Pos.20V): 422 (M+H)$^+$, 262;
HPLC condition: A; HPLC retention time (min): 3.16.

Example 11-0262

4-azepan-1-yl-N-[1-(1-benzylpiperidin-4-yl)pyrroli-
din-3-yl]pyrimidin-2-amine

MS (ESI, Pos.20V): 435 (M+H)$^+$, 193;
HPLC condition: A; HPLC retention time (min): 2.96.

Example 11-0263

4-azepan-1-yl-N-(1-cyclododecylpyrrolidin-3-yl)
pyrimidin-2-amine

MS (ESI, Pos.20V): 428 (M+H)$^+$, 262, 214.5 (M+2H)$^{2+}$;
HPLC condition: A; HPLC retention time (min): 3.45.

Example 11-0264

4-azepan-1-yl-N-[1-(4-phenylcyclohexyl)pyrrolidin-
3-yl]pyrimidin-2-amine

MS (ESI, Pos.20V): 420 (M+H)$^+$, 262, 210.5 (M+2H)$^{2+}$;
HPLC condition: A; HPLC retention time (min): 3.29.

Example 11-0265

4-azepan-1-yl-N-[1-(2-phenylcyclohexyl)pyrrolidin-
3-yl]pyrimidin-2-amine

MS (ESI, Pos.20V): 420 (M+H)$^+$, 262, 210.5 (M+2H)$^{2+}$;
HPLC condition: A; HPLC retention time (min): 3.22.

Example 11-0266

4-azepan-1-yl-N-1-[1-(2-phenylethyl)piperidin-4-yl]
pyrrolidin-3-ylpyrimidin-2-amine MS (ESI, Pos.20V): 449 (M+H)$^+$, 262, 225 (M+2H)$^{2+}$;
HPLC condition: A; HPLC retention time (min): 3.00.

Example 11-0267

4-azepan-1-yl-N-[1-(1-methyl-2,2-diphenylethyl)
pyrrolidin-3-yl]pyrimidin-2-amine MS (ESI, Pos.20V): 456 (M+H)$^+$, 262;
HPLC condition: A; HPLC retention time (min): 3.29.

Example 11-0268

4-azepan-1-yl-N-[1-(1-benzyl-2-phenylethyl)pyrroli-
din-3-yl]pyrimidin-2-amine

MS (ESI, Pos.20V): 456 (M+H)$^+$, 262;
HPLC condition: A; HPLC retention time (min): 3.36.

Example 11-0269

4-azepan-1-yl-N-(1-tetrahydrothien-3-ylpiperidin-3-
yl)pyrimidin-2-amine

MS (ESI, Pos.20V): 362 (M+H)$^+$, 276, 193;
HPLC condition: A; HPLC retention time (min): 2.96.

Example 11-0270

4-azepan-1-yl-N-[1-(3,3-dimethylcyclohexyl)piperidin-3-yl]pyrimidin-2-amine

MS (ESI, Pos.20V): 386 (M+H)$^+$, 276, 193.5 (M+2H)$^{2+}$;
HPLC condition: A; HPLC retention time (min): 3.18.

Example 11-0271

4-azepan-1-yl-N-(1-cyclobutylpiperidin-3-yl)pyrimidin-2-amine

MS (ESI, Pos.20V): 330 (M+H)$^+$, 276, 193, 165.5 (M+2H)$^{2+}$;
HPLC condition: A; HPLC retention time (min): 2.94.

Example 11-0272

4-azepan-1-yl-N-(1-tetrahydro-2H-thiopyran-4-ylpiperidin-3-yl)pyrimidin-2-amine

MS (ESI, Pos.20V): 376 (M+H)$^+$, 276, 188.5 (M+2H)$^{2+}$;
HPLC condition: A; HPLC retention time (min): 3.00.

Example 11-0273

4-azepan-1-yl-N-(1-cyclopentylpiperidin-3-yl)pyrimidin-2-amine

MS (ESI, Pos.20V): 344 (M+H)$^+$, 276, 172.5 (M+2H)$^{2+}$;
HPLC condition: A; HPLC retention time (min): 3.00.

Example 11-0274

4-azepan-1-yl-N-[1-(1-methylbutyl)piperidin-3-yl]pyrimidin-2-amine

MS (ESI, Pos.20V): 346 (M+H)$^+$, 276, 193;
HPLC condition: A; HPLC retention time (min): 3.03.

Example 11-0275

4-azepan-1-yl-N-[1-(3-methylcyclopentyl)piperidin-3-yl]pyrimidin-2-amine

MS (ESI, Pos.20V): 358 (M+H)$^+$, 276, 179.5 (M+2H)$^{2+}$;
HPLC condition: A; HPLC retention time (min): 3.05.

Example 11-0276

4-azepan-1-yl-N-[1-(1-ethylbutyl)piperidin-3-yl]pyrimidin-2-amine

MS (ESI, Pos.20V): 360 (M+H)$^+$, 318;
HPLC condition: A; HPLC retention time (min): 3.09.

Example 11-0277

N-(4-azepan-1-ylpyrimidin-2-yl)-1'-methyl-1,4'-bipiperidin-3-amine

MS (ESI, Pos.20V): 373 (M+H)$^+$, 276, 187 (M+2H)$^{2+}$;
HPLC condition: A; HPLC retention time (min): 2.83.

Example 11-0278

4-azepan-1-yl-N-(1-cyclohept-2-en-1-ylpiperidin-3-yl)pyrimidin-2-amine

MS (ESI, Pos.20V): 370 (M+H)$^+$, 276;
HPLC condition: A; HPLC retention time (min): 3.07.

Example 11-0279

4-azepan-1-yl-N-[1-(1-methylhexyl)piperidin-3-yl]pyrimidin-2-amine

MS (ESI, Pos.20V): 374 (M+H)$^+$, 276, 187.5 (M+2H)$^{2+}$;
HPLC condition: A; HPLC retention time (min): 3.20.

Example 11-0280

4-azepan-1-yl-N-[1-(3-methylcyclohexyl)piperidin-3-yl]pyrimidin-2-amine

MS (ESI, Pos.20V): 372 (M+H)$^+$, 276, 186.5 (M+2H)$^{2+}$;
HPLC condition: A; HPLC retention time (min): 3.11.

Example 11-0281

4-azepan-1-yl-N-[1-(3,4-dimethylcyclopentyl)piperidin-3-yl]pyrimidin-2-amine

MS (ESI, Pos.20V): 372 (M+H)$^+$;
HPLC condition: A; HPLC retention time (min): 3.14.

Example 11-0282

4-azepan-1-yl-N-(1-cycloheptylpiperidin-3-yl)pyrimidin-2-amine

MS (ESI, Pos.20V): 372 (M+H)$^+$, 276, 186.5 (M+2H)$^{2+}$;
HPLC condition: A; HPLC retention time (min): 3.11.

Example 11-0283

4-azepan-1-yl-N-(1-tricyclo[2.2.1.0$^{2,6}$]hept-3-ylpiperidin-3-yl)pyrimidin-2-amine MS (ESI, Pos.20V): 368 (M+H)$^+$, 276, 184.5 (M+2H)$^{2+}$;
HPLC condition: A; HPLC retention time (min): 3.01.

Example 11-0284

N-(4-azepan-1-ylpyrimidin-2-yl)-1'-isopropyl-1,4'-bipiperidin-3-amine

MS (ESI, Pos.20V): 401 (M+H)$^+$, 276, 201 (M+2H)$^{2+}$;
HPLC condition: A; HPLC retention time (min): 2.85.

Example 11-0285

4-azepan-1-yl-N-[1-(1-methylheptyl)piperidin-3-yl]pyrimidin-2-amine

MS (ESI, Pos.20V): 388 (M+H)$^+$, 276, 194.5 (M+2H)$^{2+}$;
HPLC condition: A; HPLC retention time (min): 3.29.

Example 11-0286

N-(4-azepan-1-ylpyrimidin-2-yl)-1'-propyl-1,4'-bipiperidin-3-amine

MS (ESI, Pos.20V): 401 (M+H)$^+$, 276, 201 (M+2H)$^{2+}$;
HPLC condition: A; HPLC retention time (min): 2.87.

Example 11-0287

4-azepan-1-yl-N-[1-(1,4-dioxaspiro[4.5]dec-8-yl)piperidin-3-yl]pyrimidin-2-amine MS (ESI, Pos.20V): 416 (M+H)$^+$, 276, 208.5 (M+2H)$^{2+}$;
HPLC condition: A; HPLC retention time (min): 2.96.

Example 11-0288

4-azepan-1-yl-N-(1-cyclooctylpiperidin-3-yl)pyrimidin-2-amine

MS (ESI, Pos.20V): 386 (M+H)$^+$, 276, 193.5 (M+2H)$^{2+}$;
HPLC condition: A; HPLC retention time (min): 3.16.

Example 11-0289

4-azepan-1-yl-N-[1-(3,5-dimethylcyclohexyl)piperidin-3-yl]pyrimidin-2-amine

MS (ESI, Pos.20V): 386 (M+H)$^+$, 276, 193.5 (M+2H)$^{2+}$;
HPLC condition: A; HPLC retention time (min): 3.20.

Example 11-0290

4-azepan-1-yl-N-1-[3-(diethylamino)-1-methylpropyl]piperidin-3-ylpyrimidin-2-amine MS (ESI, Pos.20V): 403 (M+H)$^+$, 276, 202 (M+2H)$^{2+}$;
HPLC condition: A; HPLC retention time (min): 2.87.

Example 11-0291

4-azepan-1-yl-N-[1-(1-ethylhexyl)piperidin-3-yl]pyrimidin-2-amine

MS (ESI, Pos.20V): 388 (M+H)$^+$, 276, 194.5 (M+2H)$^{2+}$;
HPLC condition: A; HPLC retention time (min): 3.27.

Example 11-0292

4-azepan-1-yl-N-[1-(2,3-dihydro-1H-inden-2-yl)piperidin-3-yl]pyrimidin-2-amine

MS (ESI, Pos.20V): 392 (M+H)$^+$, 276, 196.5 (M+2H)$^{2+}$;
HPLC condition: A; HPLC retention time (min): 3.11.

Example 11-0293

4-azepan-1-yl-N-1-[4-(trifluoromethyl)cyclohexyl]piperidin-3-ylpyrimidin-2-amine MS (ESI, Pos.20V): 426 (M+H)$^+$, 276, 213.5 (M+2H)$^{2+}$;
HPLC condition: A; 1HPLC retention time (min): 3.14.

Example 11-0294

4-azepan-1-yl-N-[1-(1-methyl-3-phenylpropyl)piperidin-3-yl]pyrimidin-2-amine

MS (ESI, Pos.20V): 408 (M+H)$^+$, 276, 204.5 (M+2H)$^{2+}$;
HPLC condition: A; HPLC retention time (min): 3.20.

Example 11-0295

4-azepan-1-yl-N-(1-decahydronaphthalen-2-ylpiperidin-3-yl)pyrimidin-2-amine

MS (ESI, Pos.20V): 412 (M+H)$^+$, 276, 206.5 (M+2H)$^{2+}$;
HPLC condition: A; HPLC retention time (min): 3.27.

Example 11-0296

4-azepan-1-yl-N-[1-(1,2,3,4-tetrahydronaphthalen-2-yl)piperidin-3-yl]pyrimidin-2-amine MS (ESI, Pos.20V): 406 (M+H)$^+$, 276;
HPLC condition: A; HPLC retention time (min): 3.16.

Example 11-0297

4-azepan-1-yl-N-[1-(1-pentylhexyl)piperidin-3-yl]pyrimidin-2-amine

MS (ESI, Pos.20V): 430 (M+H)$^+$, 276, 215.5 (M+2H)$^{2+}$;
HPLC condition: A; HPLC retention time (min): 3.49.

Example 11-0298

4-azepan-1-yl-N-[1-(7-methoxy-1,2,3,4-tetrahydronaphthalen-2-yl)piperidin-3-yl]pyrimidin-2-amine MS (ESI, Pos.20V): 436 (M+H)$^+$, 276;
HPLC condition: A; HPLC retention time (min): 3.16.

Example 11-0299

N-(4-azepan-1-ylpyrimidin-2-yl)-1'-benzyl-1,4'-bipiperidin-3-amine

MS (ESI, Pos.20V): 449 (M+H)$^+$, 276, 225 (M+2H)$^{2+}$;
HPLC condition: A; HPLC retention time (min): 2.96.

Example 11-0300

4-azepan-1-yl-N-[1-(4-phenylcyclohexyl)piperidin-3-yl]pyrimidin-2-amine

MS (ESI, Pos.20V): 434 (M+H)$^+$, 276, 217.5 (M+2H)$^{2+}$;
HPLC condition: A; HPLC retention time (min): 3.23.

Example 11-0301

N-(4-azepan-1-ylpyrimidin-2-yl)-1'-(2-phenylethyl)-1,4'-bipiperidin-3-amine

MS (ESI, Pos.20V): 463 (M+H)$^+$, 276, 232 (M+2H)$^{2+}$;
HPLC condition: A; HPLC retention time (min): 3.00.

Example 11-0302

N-(4-azepan-1-ylpyrimidin-2-yl)-1'-ethyl-1,4'-bipiperidin-3-amine

MS (ESI, Pos.20V): 387 (M+H)$^+$, 276, 194 (M+2H)$^{2+}$;
HPLC condition: A; HPLC retention time (min): 2.83.

Example 11-0303

N-(4-azepan-1-ylpyrimidin-2-yl)-1'-benzyl-3'-methyl-1,4'-bipiperidin-3-amine

MS (ESI, Pos.20V): 463 (M+H)$^+$, 232 (M+2H)$^{2+}$;
HPLC condition: A; HPLC retention time (min): 2.94.

Example 11-0304

4-azepan-1-yl-N-(1-cyclopent-3-en-1-ylpiperidin-3-yl)pyrimidin-2-amine

MS (ESI, Pos.20V): 342 (M+H)$^+$;
HPLC condition: A; HPLC retention time (min): 3.00.

Example 11-0305

4-azepan-1-yl-N-[1-(1-propylheptyl)piperidin-3-yl]pyrimidin-2-amine

MS (ESI, Pos.20V): 416 (M+H)$^+$, 276, 208.5 (M+2H)$^{2+}$;
HPLC condition: A; HPLC retention time (min): 3.42.

Example 11-0306

4-azepan-1-yl-N-1-[2-(benzyloxy)-1-methylethyl]piperidin-3-ylpyrimidin-2-amine

MS (ESI, Pos.20V): 424 (M+H)$^+$, 334;
HPLC condition: A; HPLC retention time (min): 3.16.

Example 11-0307

N-(4-azepan-1-ylpyrimidin-2-yl)-1'-isobutyl-1,4'-bipiperidin-3-amine

MS (ESI, Pos.20V): 415 (M+H)$^+$, 276, 208 (M+2H)$^{2+}$;
HPLC condition: A; HPLC retention time (min): 2.89.

Example 11-0308

N-(4-azepan-1-ylpyrimidin-2-yl)-1-tetrahydrothien-3-ylazepan-3-amine

MS (ESI, Pos.20V): 376 (M+H)$^+$, 290, 193;
HPLC condition: A; HPLC retention time (min): 3.01.

Example 11-0309

N-(4-azepan-1-ylpyrimidin-2-yl)-1-(3,3-dimethylcyclohexyl)azepan-3-amine

MS (ESI, Pos.20V): 400 (M+H)$^+$, 332, 200.5 (M+2H)$^{2+}$;
HPLC condition: A; HPLC retention time (min): 3.20.

Example 11-0310

N-(4-azepan-1-ylpyrimidin-2-yl)-1-(2-methoxy-1-methylethyl)azepan-3-amine

MS (ESI, Pos.20V): 362 (M+H)$^+$;
HPLC condition: A; HPLC retention time (min): 2.98.

Example 11-0311

N-(4-azepan-1-ylpyrimidin-2-yl)-1-cyclobutylazepan-3-amine

MS (ESI, Pos.20V): 344 (M+H)$^+$, 290, 172.5 (M+2H)$^{2+}$;
HPLC condition: A; HPLC retention time (min): 3.00.

Example 11-0312

N-(4-azepan-1-ylpyrimidin-2-yl)-1-tetrahydro-2H-thiopyran-4-ylazepan-3-amine

MS (ESI, Pos.20V): 390 (M+H)$^+$, 290, 195.5 (M+2H)$^{2+}$;
HPLC condition: A; HPLC retention time (min): 3.03.

Example 11-0313

N-(4-azepan-1-ylpyrimidin-2-yl)-1-cyclopentylazepan-3-amine

MS (ESI, Pos.20V): 358 (M+H)$^+$, 290, 179.5 (M+2H)$^{2+}$;
HPLC condition: A; HPLC retention time (min): 3.01.

Example 11-0314

N-(4-azepan-1-ylpyrimidin-2-yl)-1-(1-methylbutyl)azepan-3-amine

MS (ESI, Pos.20V): 360 (M+H)$^+$, 290, 180.5 (M+2H)$^{2+}$;
HPLC condition: A; HPLC retention time (min): 3.07.

Example 11-0315

N-(4-azepan-1-ylpyrimidin-2-yl)-1-(2,2-dimethoxy-1-methylethyl)azepan-3-amine

MS (ESI, Pos.20V): 392 (M+H)$^+$, 180;
HPLC condition: A; HPLC retention time (min): 3.01.

Example 11-0316

N-(4-azepan-1-ylpyrimidin-2-yl)-1-(1,3-dimethylbutyl)azepan-3-amine

MS (ESI, Pos.20V): 374 (M+H)$^+$, 187.5 (M+2H)$^{2+}$;
HPLC condition: A; HPLC retention time (min): 3.14.

Example 11-0317

N-(4-azepan-1-ylpyrimidin-2-yl)-1-(1-methylpentyl)azepan-3-amine

MS (ESI, Pos.20V): 374 (M+H)$^+$, 187.5 (M+2H)$^{2+}$;
HPLC condition: A; HPLC retention time (min): 3.14.

Example 11-0318

N-(4-azepan-1-ylpyrimidin-2-yl)-1-(3,3-dimethoxy-1-methylpropyl)azepan-3-amine

MS (ESI, Pos.20V): 406 (M+H)$^+$;
HPLC condition: A; HPLC retention time (min): 3.01.

Example 11-0319

N-(4-azepan-1-ylpyrimidin-2-yl)-1-(1-methylpent-4-enyl)azepan-3-amine

MS (ESI, Pos.20V): 372 (M+H)$^+$, 186.5 (M+2H)$^{2+}$;
HPLC condition: A; HPLC retention time (min): 3.12.

Example 11-0320

N-(4-azepan-1-ylpyrimidin-2-yl)-1-(2-methylcyclopentyl)azepan-3-amine

MS (ESI, Pos.20V): 372 (M+H)$^+$, 290, 186.5 (M+2H)$^{2+}$;
HPLC condition: A; HPLC retention time (min): 3.05.

Example 11-0321

N-(4-azepan-1-ylpyrimidin-2-yl)-1-(3-methylcyclopentyl)azepan-3-amine

MS (ESI, Pos.20V): 372 (M+H)$^+$, 290, 186.5 (M+2H)$^{2+}$;
HPLC condition: A; HPLC retention time (min): 3.11.

Example 11-0322

N-(4-azepan-1-ylpyrimidin-2-yl)-1-(1-methylpiperidin-4-yl)azepan-3-amine

MS (ESI, Pos.20V): 387 (M+H)$^+$, 290, 194 (M+2H)$^{2+}$;
HPLC condition: A; HPLC retention time (min): 2.87.

Example 11-0323

N-(4-azepan-1-ylpyrimidin-2-yl)-1-cyclohept-2-en-1-ylazepan-3-amine

MS (ESI, Pos.20V): 384 (M+H)$^+$;
HPLC condition: A; HPLC retention time (min): 3.11.

Example 11-0324

N-(4-azepan-1-ylpyrimidin-2-yl)-1-(1-methylhexyl)azepan-3-amine

MS (ESI, Pos.20V): 388 (M+H)$^+$, 290, 194.5 (M+2H)$^{2+}$;
HPLC condition: A; HPLC retention time (min): 3.23.

Example 11-0325

N-(4-azepan-1-ylpyrimidin-2-yl)-1-(1-ethylpentyl)azepan-3-amine

MS (ESI, Pos.20V): 388 (M+H)$^+$, 290, 194.5 (M+2H)$^{2+}$;
HPLC condition: A; HPLC retention time (min): 3.20.

Example 11-0326

N-(4-azepan-1-ylpyrimidin-2-yl)-1-(2-methylcyclohexyl)azepan-3-amine

MS (ESI, Pos.20V): 386 (M+H)$^+$;
HPLC condition: A; HPLC retention time (min): 3.14.

Example 11-0327

N-(4-azepan-1-ylpyrimidin-2-yl)-1-(3-methylcyclohexyl)azepan-3-amine

MS (ESI, Pos.20V): 386 (M+H)$^+$, 290, 193.5 (M+2H)$^{2+}$;
HPLC condition: A; HPLC retention time (min): 3.14.

Example 11-0328

N-(4-azepan-1-ylpyrimidin-2-yl)-1-(4-methylcyclohexyl)azepan-3-amine

MS (ESI, Pos.20V): 386 (M+H)$^+$, 290, 193.5 (M+2H)$^{2+}$;
HPLC condition: A; HPLC retention time (min): 3.14.

Example 11-0329

N-(4-azepan-1-ylpyrimidin-2-yl)-1-(3,4-dimethylcyclopentyl)azepan-3-amine

MS (ESI, Pos.20V): 386 (M+H)$^+$, 290, 193.5 (M+2H)$^{2+}$;
HPLC condition: A; HPLC retention time (min): 3.16.

Example 11-0330

N-(4-azepan-1-ylpyrimidin-2-yl)-1-(2-methoxycyclohexyl)azepan-3-amine

MS (ESI, Pos.20V): 402 (M+H)$^+$, 290, 201.5 (M+2H)$^{2+}$;
HPLC condition: A; HPLC retention time (min): 3.12.

Example 11-0331

N-(4-azepan-1-ylpyrimidin-2-yl)-1-(1-propylbutyl)azepan-3-amine

MS (ESI, Pos.20V): 388 (M+H)$^+$;
HPLC condition: A; HPLC retention time (min): 3.23.

Example 11-0332

N-(4-azepan-1-ylpyrimidin-2-yl)-1-cycloheptylazepan-3-amine

MS (ESI, Pos.20V): 386 (M+H)$^+$, 290, 193.5 (M+2H)$^{2+}$;
HPLC condition: A; HPLC retention time (min): 3.14.

Example 11-0333

N-(4-azepan-1-ylpyrimidin-2-yl)-1-tricyclo[2.2.1.0$^{2,6}$]hept-3-ylazepan-3-amine MS (ESI, Pos.20V): 382 (M+H)$^+$, 290, 191.5 (M+2H)$^{2+}$;
HPLC condition: A; HPLC retention time (min): 3.05.

Example 11-0334

N-(4-azepan-1-ylpyrimidin-2-yl)-1-[(1R,5S)-8-methyl-8-azabicyclo[3.2.1]oct-3yl]azepan-3-amine

Example 11-0335

N-(4-azepan-1-ylpyrimidin-2-yl)-1-(1-isopropylpiperidin-4-yl)azepan-3-amine

MS (ESI, Pos.20V): 415 (M+H)$^+$, 290, 208 (M+2H)$^{2+}$;
HPLC condition: A; HPLC retention time (min): 2.89.

Example 11-0336

N-(4-azepan-1-ylpyrimidin-2-yl)-1-(1-methylheptyl)azepan-3-amine

MS (ESI, Pos.20V): 402 (M+H)$^+$, 290, 201.5 (M+2H)$^{2+}$;
HPLC condition: A; HPLC retention time (min): 3.33.

Example 11-0337

N-(4-azepan-1-ylpyrimidin-2-yl)-1-(1-cyclohexylethyl)azepan-3-amine

MS (ESI, Pos.20V): 400 (M+H)$^+$;
HPLC condition: A; HPLC retention time (min): 3.23.

Example 11-0338

N-(4-azepan-1-ylpyrimidin-2-yl)-1-(1-propylpiperidin-4-yl)azepan-3-amine

MS (ESI, Pos.20V): 415 (M+H)$^+$, 290, 208 (M+2H)$^{2+}$;
HPLC condition: A; HPLC retention time (min): 2.90.

Example 11-0339

N-(4-azepan-1-ylpyrimidin-2-yl)-1-(1,4-dioxaspiro[4.5]dec-8-yl)azepan-3-amine

MS (ESI, Pos.20V): 430 (M+H)$^+$, 215.5 (M+2H)$^{2+}$;
HPLC condition: A; HPLC retention time (min): 3.00.

Example 11-0340

N-(4-azepan-1-ylpyrimidin-2-yl)-1-cyclooctylazepan-3-amine

MS (ESI, Pos.20V): 400 (M+H)$^+$, 290;
HPLC condition: A; HPLC retention time (min): 3.20.

Example 11-0341

N-(4-azepan-1-ylpyrimidin-2-yl)-1-[3-(diethylamino)-1-methylpropyl]azepan-3-amine MS (ESI, Pos.20V): 417 (M+H)$^+$, 193;
HPLC condition: A; HPLC retention time (min): 2.90.

Example 11-0342

N-(4-azepan-1-ylpyrimidin-2-yl)-1-(1-ethylhexyl)azepan-3-amine

MS (ESI, Pos.20V): 402 (M+H)$^+$, 290, 201.5 (M+2H)$^{2+}$;
HPLC condition: A; HPLC retention time (min): 3.31.

Example 11-0343

N-(4-azepan-1-ylpyrimidin-2-yl)-1-(2,3-dihydro-1H-inden-2-yl)azepan-3-amine

MS (ESI, Pos.20V): 406 (M+H)$^+$, 203.5 (M+2H)$^{2+}$;
HPLC condition: A; HPLC retention time (min): 3.12.

Example 11-0344

N-(4-azepan-1-ylpyrimidin-2-yl)-1-[4-(trifluoromethyl)cyclohexyl]azepan-3-amine

MS (ESI, Pos.20V): 440 (M+H)$^+$, 220.5 (M+2H)$^{2+}$;
HPLC condition: A; HPLC retention time (min): 3.18.

Example 11-0345

N-(4-azepan-1-ylpyrimidin-2-yl)-1-(2-propylcyclohexyl)azepan-3-amine

MS (ESI, Pos.20V): 414 (M+H)$^+$;
HPLC condition: A; HPLC retention time (min): 3.23.

Example 11-0346

N-(4-azepan-1-ylpyrimidin-2-yl)-1-(1-methyl-3-phenylpropyl)azepan-3-amine

MS (ESI, Pos.20V): 422 (M+H)$^+$, 290, 211.5 (M+2H)$^{2+}$;
HPLC condition: A; HPLC retention time (min): 3.20.

Example 11-0347

N-(4-azepan-1-ylpyrimidin-2-yl)-1-decahydronaphthalen-2-ylazepan-3-amine

MS (ESI, Pos.20V): 426 (M+H)$^+$, 213.5 (M+2H)$^{2+}$;
HPLC condition: A; HPLC retention time (min): 3.29.

Example 11-0348

N-(4-azepan-1-ylpyrimidin-2-yl)-1-(1,2,3,4-tetrahydronaphthalen-2-yl)azepan-3-amine MS (ESI, Pos.20V): 420 (M+H)$^+$, 290;
HPLC condition: A; HPLC retention time (min): 3.20.

Example 11-0349

N-(4-azepan-1-ylpyrimidin-2-yl)-1-(6-methoxy-1,2,3,4-tetrahydronaphthalen-2-yl)azepan-3-amine MS (ESI, Pos.20V): 450 (M+H)$^+$, 290;
HPLC condition: A; HPLC retention time (min): 3.18.

Example 11-0350

N-(4-azepan-1-ylpyrimidin-2-yl)-1-(7-methoxy-1,2,3,4-tetrahydronaphthalen-2-yl)azepan-3-amine MS (ESI, Pos.20V): 450 (M+H)$^+$, 290;
HPLC condition: A; HPLC retention time (min): 3.18.

Example 11-0351

N-(4-azepan-1-ylpyrimidin-2-yl)-1-(1-benzylpiperidin-4-yl)azepan-3-amine

MS (ESI, Pos.20V): 463 (M+H)$^+$, 290, 232 (M+2H)$^{2+}$;
HPLC condition: A; HPLC retention time (min): 2.98.

Example 11-0352

N-(4-azepan-1-ylpyrimidin-2-yl)-1-cyclododecylazepan-3-amine

MS (ESI, Pos.20V): 456 (M+H)$^+$, 290, 228.5 (M+2H)$^{2+}$;
HPLC condition: A; HPLC retention time (min): 3.47.

Example 11-0353

N-(4-azepan-1-ylpyrimidin-2-yl)-1-(4-phenylcyclohexyl)azepan-3-amine

MS (ESI, Pos.20V): 448 (M+H)$^+$, 224.5 (M+2H)$^{2+}$;
HPLC condition: A; HPLC retention time (min): 3.27.

Example 11-0354

N-(4-azepan-1-ylpyrimidin-2-yl)-1-[1-(2-phenylethyl)piperidin-4-yl]azepan-3-amine MS (ESI, Pos.20V): 477 (M+H)$^+$, 290;
HPLC condition: A; HPLC retention time (min): 3.05.

Example 11-0355

N-(4-azepan-1-ylpyrimidin-2-yl)-1-(1-ethylpiperidin-4-yl)azepan-3-amine

MS (ESI, Pos.20V): 401 (M+H)$^+$, 290, 201 (M+2H)$^{2+}$;
HPLC condition: A; HPLC retention time (min): 2.89.

Example 11-0356

N-(4-azepan-1-ylpyrimidin-2-yl)-1-(1-benzyl-3-methylpiperidin-4-yl)azepan-3-amine MS (ESI, Pos.20V): 477 (M+H)$^+$, 239 (M+2H)$^{2+}$;
HPLC condition: A; HPLC retention time (min): 2.98.

Example 11-0357

N-(4-azepan-1-ylpyrimidin-2-yl)-1-[2-(benzyloxy)-1-methylethyl]azepan-3-amine

MS (ESI, Pos.20V): 438 (M+H)$^+$;
HPLC condition: A; HPLC retention time (min): 3.20.

Example 11-0358

N-(4-azepan-1-ylpyrimidin-2-yl)-1-(1-isobutylpiperidin-4-yl)azepan-3-amine

MS (ESI, Pos.20V): 429 (M+H)$^+$, 290,215 (M+2H)$^{2+}$;
HPLC condition: A; HPLC retention time (min): 2.92.

Example 11-0359

1-(2-adamantyl)-N-(4-azepan-1-ylpyrimidin-2-yl)azepan-3-amine

MS (ESI, Pos.20V): 424 (M+H)$^+$, 290;
HPLC condition: A; HPLC retention time (min): 3.20.

Example 11-0360

4-azepan-1-yl-N-[1-(1-isobutyrylpiperidin-3-yl)pyrrolidin-3-yl]pyrimidin-2-amine MS (ESI, Pos.20V): 415 (M+H)$^+$, 345, 208 (M+2H)$^{2+}$;
HPLC condition: A; HPLC retention time (min): 3.00.

Example 11-0361

4-azepan-1-yl-N-[1-(1-butyrylpiperidin-3-yl)pyrrolidin-3-yl]pyrimidin-2-amine

MS (ESI, Pos.20V): 415 (M+H)$^+$, 345, 262, 208 (M+2H)$^{2+}$;
HPLC condition: A; HPLC retention time (min): 3.00.

Example 11-0362

4-azepan-1-yl-N-1-[1-(3-methylbenzoyl)piperidin-3-yl]pyrrolidin-3-ylpyrimidin-2-amine MS (ESI, Pos.20V): 463 (M+H)$^+$, 345, 232 (M+2H)$^{2+}$;
HPLC condition: A; HPLC retention time (min): 3.12.

Example 11-0363

N-[1-(1-acetylpiperidin-3-yl)pyrrolidin-3-yl]-4-azepan-1-ylpyrimidin-2-amine

MS (ESI, Pos.20V): 387 (M+H)$^+$, 345, 194 (M+2H)$^{2+}$;
HPLC condition: A; HPLC retention time (min): 2.90.

Example 11-0364

4-azepan-1-yl-N-1-[1-(4-fluorobenzoyl)piperidin-3-yl]pyrrolidin-3-ylpyrimidin-2-amine MS (ESI, Pos.20V): 467 (M+H)$^+$, 345, 234 (M+2H)$^{2+}$;
HPLC condition: A; HPLC retention time (min): 3.07.

Example 11-0365

4-azepan-1-yl-N-1-[1-(4-methylbenzoyl)piperidin-3-yl]pyrrolidin-3-ylpyrimidin-2-amine MS (ESI, Pos.20V): 463 (M+H)$^+$, 345, 232 (M+2H)$^{2+}$;
HPLC condition: A; HPLC retention time (min): 3.12.

Example 11-0366

4-azepan-1-yl-N-[1-(1-heptanoylpiperidin-3-yl)pyrrolidin-3-yl]pyrimidin-2-amine

MS (ESI, Pos.20V): 457 (M+H)$^+$, 345, 229 (M+2H)$^{2+}$;
HPLC condition: A; HPLC retention time (min): 3.23.

Example 11-0367

4-azepan-1-yl-N-1-[1-(2-methoxybenzoyl)piperidin-3-yl]pyrrolidin-3-ylpyrimidin-2-amine MS (ESI, Pos.20V): 479 (M+H)$^+$, 345, 240 (M+2H)$^{2+}$;
HPLC condition: A; HPLC retention time (min): 3.05.

Example 11-0368

4-azepan-1-yl-N-1-[1-(2-methylbenzoyl)piperidin-3-yl]pyrrolidin-3-ylpyrimidin-2-amine MS (ESI, Pos.20V): 463 (M+H)$^+$, 345;
HPLC condition: A; HPLC retention time (min): 3.09.

Example 11-0369

4-azepan-1-yl-N-[1-(1-hexanoylpiperidin-3-yl)pyrrolidin-3-yl]pyrimidin-2-amine

MS (ESI, Pos.20V): 443 (M+H)$^+$, 345, 222 (M+2H)$^{2+}$;
HPLC condition: A; HPLC retention time (min): 3.16.

Example 11-0370

4-azepan-1-yl-N-1-[1-(phenylacetyl)piperidin-3-yl]pyrrolidin-3-ylpyrimidin-2-amine MS (ESI, Pos.20V): 463 (M+H)$^+$, 232 (M+2H)$^{2+}$;
HPLC condition: A; HPLC retention time (min): 3.09.

Example 11-0371

4-azepan-1-yl-N-1-[1-(4-methoxybenzoyl)piperidin-3-yl]pyrrolidin-3-ylpyrimidin-2-amine MS (ESI, Pos.20V): 479 (M+H)$^+$, 345, 135;
HPLC condition: A; HPLC retention time (min): 3.06.

Example 11-0372

4-azepan-1-yl-N-(1-1-[(2E)-3-phenylprop-2-enoyl]piperidin-3-ylpyrrolidin-3-yl)pyrimidin-2-amine MS (ESI, Pos.20V): 949 (2M+H)$^+$, 475 (M+H)$^+$, 131;
HPLC condition: A; HPLC retention time (min): 3.16.

Example 11-0373

4-azepan-1-yl-N-[1-(1-propionylpiperidin-3-yl)pyrrolidin-3-yl]pyrimidin-2-amine

MS (ESI, Pos.20V): 401 (M+H)$^+$, 262, 201 (M+2H)$^{2+}$;
HPLC condition: A; HPLC retention time (min): 2.94.

Example 11-0374

4-azepan-1-yl-N-1-[1-(cyclopropylcarbonyl)piperidin-3-yl]pyrrolidin-3-ylpyrimidin-2-amine MS (ESI, Pos.20V): 413 (M+H)$^+$, 345, 207 (M+2H)$^{2+}$;
HPLC condition: A; HPLC retention time (min): 2.98.

Example 11-0375

4-azepan-1-yl-N-1-[1-(2-chlorobenzoyl)piperidin-3-yl]pyrrolidin-3-ylpyrimidin-2-amine MS (ESI, Pos.20V): 483 (M+H)$^+$, 345, 242 (M+2H)$^{2+}$;
HPLC condition: A; HPLC retention time (min): 3.11.

Example 11-0376

4-azepan-1-yl-N-1-[1-(cyclohexylcarbonyl)piperidin-3-yl]pyrrolidin-3-ylpyrimidin-2-amine MS (ESI, Pos.20V): 455 (M+H)$^+$, 345, 228 (M+2H)$^{2+}$;
HPLC condition: A; HPLC retention time (min): 3.16.

Example 11-0377

4-azepan-1-yl-N-1-[1-(2-furoyl)piperidin-3-yl]pyrrolidin-3-ylpyrimidin-2-amine

MS (ESI, Pos.20V): 439 (M+H)$^+$, 262, 220 (M+2H)$^{2+}$;
HPLC condition: A; HPLC retention time (min): 3.00.

Example 11-0378

4-azepan-1-yl-N-[1-(1-pentanoylpiperidin-3-yl)pyrrolidin-3-yl]pyrimidin-2-amine

MS (ESI, Pos.20V): 429 (M+H)$^+$, 345, 215 (M+2H)$^{2+}$;
HPLC condition: A; HPLC retention time (min): 3.07.

Example 11-0379

4-azepan-1-yl-N-1-[1-(phenoxyacetyl)piperidin-3-yl]pyrrolidin-3-ylpyrimidin-2-amine MS (ESI, Pos.20V): 479 (M+H)$^+$, 240 (M+2H)$^{2+}$;
HPLC condition: A; HPLC retention time (min): 3.11.

Example 11-0380

4-azepan-1-yl-N-[1-(1-octanoylpiperidin-3-yl)pyrrolidin-3-yl]pyrimidin-2-amine

MS (ESI, Pos.20V): 471 (M+H)$^+$, 345, 236 (M+2H)$^{2+}$;
HPLC condition: A; HPLC retention time (min): 3.34.

Example 11-0381

4-azepan-1-yl-N-1-[1-(3-phenylpropanoyl)piperidin-3-yl]pyrrolidin-3-ylpyrimidin-2-amine MS (ESI, Pos.20V): 477 (M+H)$^+$, 345, 239 (M+2H)$^{2+}$;
HPLC condition: A; HPLC retention time (min): 3.18.

Example 11-0382

4-azepan-1-yl-N-(1-1-[2-(trifluoromethyl)benzoyl]
piperidin-3-ylpyrrolidin-3-yl)pyrimidin-2-amine MS (ESI, Pos.20V): 517 (M+H)$^+$, 259 (M+2H)$^{2+}$;
HPLC condition: A; HPLC retention time (min): 3.16.

Example 11-0383

4-azepan-1-yl-N-1-[1-(2-naphthoyl)piperidin-3-yl]
pyrrolidin-3-ylpyrimidin-2-amine MS (ESI, Pos.20V): 997 (2M+H)$^+$, 499 (M+H)$^+$, 155;
HPLC condition: A; HPLC retention time (min): 3.18.

Example 11-0384

4-azepan-1-yl-N-1-[1-(thien-2-ylacetyl)piperidin-3-
yl]pyrrolidin-3-ylpyrimidin-2-amine MS (ESI, Pos.20V): 469 (M+H)$^+$, 235 (M+2H)$^{2+}$;
HPLC condition: A; HPLC retention time (min): 3.09.

Example 11-0385

4-azepan-1-yl-N-1-[1-(3,3-dimethylbutanoyl)piperi-
din-3-yl]pyrrolidin-3-ylpyrimidin-2-amine MS (ESI, Pos.20V): 443 (M+H)$^+$, 345, 222 (M+2H)$^{2+}$;
HPLC condition: A; HPLC retention time (min): 3.12.

Example 11-0386

4-azepan-1-yl-N-1-[1-(3-methoxybenzoyl)piperidin-
3-yl]pyrrolidin-3-ylpyrimidin-2-amine MS (ESI, Pos.20V): 479 (M+H)$^+$, 345, 240 (M+2H)$^{2+}$;
HPLC condition: A; HPLC retention time (min): 3.07.

Example 11-0387

4-azepan-1-yl-N-1-[1-(2-ethylhexanoyl)piperidin-3-
yl]pyrrolidin-3-ylpyrimidin-2-amine MS (ESI, Pos.20V): 471 (M+H)$^+$, 345, 236 (M+2H)$^{2+}$;
HPLC condition: A; HPLC retention time (min): 3.27.

Example 11-0388

4-azepan-1-yl-N-1-[1-(3-fluorobenzoyl)piperidin-3-
yl]pyrrolidin-3-ylpyrimidin-2-amine MS (ESI, Pos.20V): 467 (M+H)$^+$, 345, 234 (M+2H)$^{2+}$;
HPLC condition: A; HPLC retention time (min): 3.09.

Example 11-0389

4-azepan-1-yl-N-1-[1-(3-chlorobenzoyl)piperidin-3-
yl]pyrrolidin-3-ylpyrimidin-2-amine MS (ESI, Pos.20V): 483 (M+H)$^+$, 345, 242 (M+2H)$^{2+}$, 139;
HPLC condition: A; HPLC retention time (min): 3.14.

Example 11-0390

4-azepan-1-yl-N-1-[1-(4-tert-butylbenzoyl)piperidin-
3-yl]pyrrolidin-3-ylpyrimidin-2-amine MS (ESI, Pos.20V): 505 (M+H)$^+$, 345, 161;
HPLC condition: A; HPLC retention time (min): 3.31.

Example 11-0391

4-azepan-1-yl-N-1-[1-(thien-2-ylcarbonyl)piperidin-
3-yl]pyrrolidin-3-ylpyrimidin-2-amine MS (ESI, Pos.20V): 455 (M+H)$^+$, 345, 228 (M+2H)$^{2+}$;
HPLC condition: A; HPLC retention time (min): 3.03.

Example 11-0392

4-azepan-1-yl-N-(1-1-[(4-chlorophenyl)acetyl]pip-
eridin-3-ylpyrrolidin-3-yl)pyrimidin-2-amine MS (ESI, Pos.20V): 499, 497 (M+H)$^+$, 249 (M+2H)$^{2+}$;
HPLC condition: A; HPLC retention time (min): 3.22.

Example 11-0393

4-azepan-1-yl-N-1-[1-(3-methylbutanoyl)piperidin-
3-yl]pyrrolidin-3-ylpyrimidin-2-amine MS (ESI, Pos.20V): 429 (M+H)$^+$, 345; 215 (M+2H)$^{2+}$;
HPLC condition: A; HPLC retention time (min): 3.07.

Example 11-0394

4-azepan-1-yl-N-(1-1-[4-(trifluoromethyl)benzoyl]
piperidin-3-ylpyrrolidin-3-yl)pyrimidin-2-amine MS (ESI, Pos.20V): 517 (M+H)$^+$, 259 (M+2H)$^{2+}$;
HPLC condition: A; HPLC retention time (min): 3.23.

Example 11-0395

4-azepan-1-yl-N-[1-(1-benzoylpiperidin-3-yl)pyrro-
lidin-3-yl]pyrimidin-2-amine

MS (ESI, Pos.20V): 449 (M+H)$^+$, 345, 225 (M+2H)$^{2+}$;
HPLC condition: A; IPLC retention time (min): 3.05.

Example 11-0396

4-azepan-1-yl-N-1-[1-(2-fluorobenzoyl)piperidin-3-
yl]pyrrolidin-3-ylpyrimidin-2-amine MS (ESI, Pos.20V): 467 (M+H)$^+$, 345, 234 (M+2H)$^{2+}$, 123;
HPLC condition: A; HPLC retention time (min): 3.05.

Example 11-0397

4-azepan-1-yl-N-1-[1-(diphenylacetyl)piperidin-3-
yl]pyrrolidin-3-ylpyrimidin-2-amine MS (ESI, Pos.20V): 539 (M+H)$^+$, 345, 270 (M+2H)$^{2+}$;
HPLC condition: A; HPLC retention time (min): 3.31.

Example 11-0398

4-azepan-1-yl-N-1-[1-(2-phenoxypropanoyl)piperidin-3-yl]pyrrolidin-3-ylpyrimidin-2-amine MS (ESI, Pos.20V): 493 (M+H)$^+$, 247(M+2H)$^{2+}$, 121;
HPLC condition: A; HPLC retention time (min): 3.16.

Example 11-0399

4-azepan-1-yl-N-1-[1-(2-methylpentanoyl)piperidin-3-yl]pyrrolidin-3-ylpyrimidin-2-amine MS (ESI, Pos.20V): 443 (M+H)$^+$, 345, 222 (M+2H)$^{2+}$;
HPLC condition: A; HPLC retention time (min): 3.11.

Example 11-0400

4-azepan-1-yl-N-1-[1-(methoxyacetyl)piperidin-3-yl]pyrrolidin-3-ylpyrimidin-2-amine MS (ESI, Pos.20V): 417 (M+H)$^+$, 345, 262, 209 (M+2H)$^{2+}$;
HPLC condition: A; HPLC retention time (min): 2.89.

Example 11-0401 ethyl 4-(3-3-[(4-azepan-1-ylpyrimidin-2-yl)amino]pyrrolidin-1-ylpiperidin-1-yl)-4-oxobutanoate MS (ESI, Pos.20V): 473 (M+H)$^+$, 237 (M+2H)$^{2+}$, 214;
HPLC condition: A;
HPLC retention time (min): 3.01.

Example 11-0402

4-azepan-1-yl-N-1-[1-(3-cyclopentylpropanoyl)piperidin-3-yl]pyrrolidin-3-ylpyrimidin-2-amine MS (ESI, Pos.20V): 469 (M+H)$^+$, 345, 235 (M+2H)$^{2+}$;
HPLC condition: A;
HPLC retention time (min): 3.25.

Example 11-0403

4-azepan-1-yl-N-1-[1-(2-propylpentanoyl)piperidin-3-yl]pyrrolidin-3-ylpyrimidin-2-amine MS (ESI, Pos.20V): 471 (M+H)$^+$, 345, 236 (M+2H)$^{2+}$;
HPLC condition: A;
HPLC retention time (min): 3.27.

Example 11-0404

Methyl 5-(3-3-[(4-azepan-1-ylpyrimidin-2-yl)amino]pyrrolidin-1-ylpiperidin-1-yl)-5-oxopentanoate MS (ESI, Pos.20V): 473 (M+H)$^+$, 237 (M+2H)$^{2+}$, 221, 193;
HPLC condition: A; HPLC retention time (min): 3.00.

Example 11-0405

4-azepan-1-yl-N-(1-1-[(4-chlorophenoxy)acetyl]piperidin-3-ylpyrrolidin-3-yl)pyrimidin-2-amine MS (ESI, Pos.20V): 515, 513 (M+H)$^+$, 257 (M+2H)$^{2+}$;
HPLC condition: A; HPLC retention time (min): 3.22.

Example 11-0407

4-azepan-1-yl-N-1-[1-(cyclopentylacetyl)piperidin-3-yl]pyrrolidin-3-ylpyrimidin-2-amine MS (ESI, Pos.20V): 455 (M+H)$^+$, 345, 228 (M+2H)$^{2+}$, 173;
HPLC condition: A; HPLC retention time (min): 3.16.

Example 11-0408

4-azepan-1-yl-N-1-[1-(cyclopentylcarbonyl)piperidin-3-yl]pyrrolidin-3-ylpyrimidin-2-amine MS (ESI, Pos.20V): 441 (M+H)$^+$, 345, 221 (M+2H)$^{2+}$;
HPLC condition: A; HPLC retention time (min): 3.11.

Example 11-0409

4-azepan-1-yl-N-1-[1-(mesitylcarbonyl)piperidin-3-yl]pyrrolidin-3-ylpyrimidin-2-amine MS (ESI, Pos.20V): 491 (M+H)$^+$, 345, 147;
HPLC condition: A; HPLC retention time (min): 3.23.

Example 11-0410

4-azepan-1-yl-N-(1-1-[(3-methoxyphenyl)acetyl]piperidin-3-ylpyrrolidin-3-yl)pyrimidin-2-amine MS (ESI, Pos.20V): 493 (M+H)$^+$, 247 (M+2H)$^{2+}$, 121;
HPLC condition: A; HPLC retention time (min): 3.12.

Example 11-0411 ethyl 3-(3-3-[(4-azepan-1-ylpyrimidin-2-yl)amino]pyrrolidin-1-ylpiperidin-1-yl)-3-oxopropanoate MS (ESI, Pos.20V): 459 (M+H)$^+$, 262, 230 (M+2H)$^{2+}$;
HPLC condition: A; HPLC retention time (min): 3.01.

Example 11-0412

4-azepan-1-yl-N-1-[1-(4-butoxybenzoyl)piperidin-3-yl]pyrrolidin-3-ylpyrimidin-2-amine MS (ESI, Pos.20V): 521 (M+H)$^+$, 345, 177;
HPLC condition: A; HPLC retention time (min): 3.31.

Example 11-0413

4-azepan-1-yl-N-(1-1-[(benzyloxy)acetyl]piperidin-3-ylpyrrolidin-3-yl)pyrimidin-2-amine MS (ESI, Pos.20V): 493 (M+H)$^+$, 403;
HPLC condition: A; HPLC retention time (min): 3.12.

Example 11-0414

4-azepan-1-yl-N-1-[1-(2-methylbutanoyl)piperidin-3-yl]pyrrolidin-3-ylpyrimidin-2-amine MS (ESI, Pos.20V): 429 (M+H)$^+$, 345, 215 (M+2H)$^{2+}$;
HPLC condition: A; HPLC retention time (min): 3.05.

Example 11-0415

4-azepan-1-yl-N-(1-1-[(4-methoxyphenyl)acetyl]piperidin-3-ylpyrrolidin-3-yl)pyrimidin-2-amine MS (ESI, Pos.20V): 493 (M+H)$^+$, 345, 247 (M+2H)$^{2+}$, 121;
HPLC condition: A; HPLC retention time (min): 3.11.

Example 11-0416 ethyl 5-(3-3-[(4-azepan-1-ylpyrimidin-2-yl)amino]pyrrolidin-1-ylpiperidin-1-yl)-5-oxopentanoate MS (ESI, Pos.20V): 487 (M+H)$^+$, 393, 244 (M+2H)$^{2+}$, 221;
HPLC condition: A; HPLC retention time (min): 3.05.

Example 11-0417

4-azepan-1-yl-N-1-[1-(cyclobutylcarbonyl)piperidin-3-yl]pyrrolidin-3-ylpyrimidin-2-amine MS (ESI, Pos.20V): 427 (M+H)$^+$, 345, 193;
HPLC condition: A; HPLC retention time (min): 3.03.

Example 11-0418

4-azepan-1-yl-N-1-[1-(2-ethylbutanoyl)piperidin-3-yl]pyrrolidin-3-ylpyrimidin-2-amine MS (ESI, Pos.20V): 443 (M+H)$^+$, 345, 222 (M+2H)$^{2+}$;
HPLC condition: A; HPLC retention time (min): 3.12.

Example 11-0419

4-azepan-1-yl-N-(1-1-[4-(trifluoromethoxy)benzoyl]piperidin-3-ylpyrrolidin-3-yl)pyrimidin-2-amine MS (ESI, Pos.20V): 533 (M+H)$^+$, 345, 267 (M+2H)$^{2+}$;
HPLC condition.: A; HPLC retention time (min): 3.23.

Example 11-0420

4-azepan-1-yl-N-1-[1-(methylsulfonyl)piperidin-3-yl]pyrrolidin-3-ylpyrimidin-2-amine MS (ESI, Pos.20V): 423 (M+H)$^+$, 345, 262 (M+2H)$^{2+}$, 212;
HPLC condition: A; HPLC retention time (min): 2.94.

Example 11-0421

4-azepan-1-yl-N-1-[1-(pentylsulfonyl)piperidin-3-yl]pyrrolidin-3-ylpyrimidin-2-amine MS (ESI, Pos.20V): 479 (M+H)$^+$, 262, 240 (M+2H)$^{2+}$, 212;
HPLC condition: A; HPLC retention time (min): 3.22.

Example 11-0422

4-azepan-1-yl-N-1-[1-(propylsulfonyl)piperidin-3-yl]pyrrolidin-3-ylpyrimidin-2-amine MS (ESI, Pos.20V): 451 (M+H)$^+$, 262, 226 (M+2H)$^{2+}$, 190;
HPLC condition: A; HPLC retention time (min): 3.05.

Example 11-0423

4-azepan-1-yl-N-1-[1-(isopropylsulfonyl)piperidin-3-yl]pyrrolidin-3-ylpyrimidin-2-amine MS (ESI, Pos.20V): 451 (M+H)$^+$, 345, 262, 193;
HPLC condition: A; HPLC retention time (min): 3.03.

Example 11-0424

4-azepan-1-yl-N-(1-piperidin-3-ylpyrrolidin-3-yl)pyrimidin-2-amine

MS (ESI, Pos.20V): 345 (M+H)$^+$, 262;
HPLC condition: A; HPLC retention time (min): 2.80.

Example 11-0425

4-azepan-1-yl-N-1-[1-(butylsulfonyl)piperidin-3-yl]pyrrolidin-3-ylpyrimidin-2-amine MS (ESI, Pos.20V): 465 (M+H)$^+$, 262, 233(M+2H)$^{2+}$, 204;
HPLC condition: A; HPLC retention time (min): 3.12.

Example 11-0426

4-azepan-1-yl-N-1-[1-(phenylsulfonyl)piperidin-3-yl]pyrrolidin-3-ylpyrimidin-2-amine MS (ESI, Pos.20V): 485 (M+H)$^+$, 262, 243 (M+2H)$^{2+}$, 224;
HPLC condition: A; HPLC retention time (min): 3.14.

Example 11-0427

4-azepan-1-yl-N-[1-(1-[4-(trifluoromethyl)phenyl]sulfonylpiperidin-3-yl)pyrrolidin-3-yl]pyrimidin-2-amine MS (ESI, Pos.20V): 553 (M+H)$^+$, 277(M+2H)$^{2+}$;
HPLC condition: A; HPLC retention time (min): 3.31.

Example 11-0428

4-azepan-1-yl-N-(1-1-[(4-methoxyphenyl)sulfonyl]piperidin-3-ylpyrrolidin-3-yl)pyrimidin-2-amine MS (ESI, Pos.20V): 515 (M+H)$^+$ 345, 258 (M+2H)$^{2+}$, 171;
HPLC condition: A; HPLC retention time (min): 3.16.

Example 11-0429

4-azepan-1-yl-N-1-[1-(benzylsulfonyl)piperidin-3-yl]pyrrolidin-3-ylpyrimidin-2-amine MS (ESI, Pos.20V): 499 (M+H)$^+$, 345, 250 (M+2H)$^{2+}$;
HPLC condition: A; HPLC retention time (min): 3.16.

Example 11-0430

4-azepan-1-yl-N-(1-1-[(4-methylphenyl)sulfonyl]piperidin-3-ylpyrrolidin-3-yl)pyrimidin-2-amine MS (ESI, Pos.20V): 499 (M+H)$^+$, 262, 250 (M+2H)$^{2+}$, 238;
HPLC condition: A; HPLC retention time (min): 3.20.

Example 11-0431

4-azepan-1-yl-N-(1-1-[(3-methylphenyl)sulfonyl]piperidin-3-ylpyrrolidin-3-yl)pyrimidin-2-amine MS (ESI, Pos.20V): 499 (M+H)$^+$, 262, 250 (M+2H)$^{2+}$;
HPLC condition: A; HPLC retention time (min): 3.22.

Example 11-0432

4-azepan-1-yl-N-(1-1-[(2-methylphenyl)sulfonyl]piperidin-3-ylpyrrolidin-3-yl)pyrimidin-2-amine MS (ESI, Pos.20V): 499 (M+H)$^+$, 262, 250 (M+2H)$^{2+}$;
HPLC condition: A; HPLC retention time (min): 3.20.

Example 11-0433

4-azepan-1-yl-N-[1-(1-[4-(trifluoromethoxy)phenyl]sulfonylpiperidin-3-yl)pyrrolidin-3-yl]pyrimidin-2-amine MS (ESI, Pos.20V): 569 (M+H)$^+$, 308, 285 (M+2H)$^{2+}$;
HPLC condition: A; HPLC retention time (min): 3.34.

Example 11-0434

4-azepan-1-yl-N-(1-1-[(4-butoxyphenyl)sulfonyl]piperidin-3-ylpyrrolidin-3-yl)pyrimidin-2-amine MS (ESI, Pos.20V): 557 (M+H)$^+$, 345, 279 (M+2H)$^{2+}$;
HPLC condition: A; HPLC retention time (min): 3.44.

Example 11-0435

4-azepan-1-yl-N-(1-1-[(4-tert-butylphenyl)sulfonyl]piperidin-3-ylpyrrolidin-3-yl)pyrimidin-2-amine MS (ESI, Pos.20V): 541 (M+H)$^+$, 271 (M+2H)$^{2+}$;
HPLC condition: A; HPLC retention time (min): 3.40.

Example 11-0436

4-azepan-1-yl-N-(1-[(4-nitrophenyl)sulfonyl]piperidin-3-ylpyrolidin-3-yl)pyrimidin-2-amine MS (ESI, Pos.20V): 530 (M+H)$^+$, 265 (M+2H)$^{2+}$;
HPLC condition: A; HPLC retention time (min): 3.22.

Example 11-0437

4-[(3-3-[(4-azepan-1-ylpyrimidin-2-yl)amino]pyrrolidin-1-ylpiperidin-1-yl)sulfonyl]benzonitrile MS (ESI, Pos.20V): 510 (M+H)$^+$, 255(M+2H)$^{2+}$;
HPLC condition: A; HPLC retention time (min): 3.16.

Example 11-0438

4-azepan-1-yl-N-1-[1-(2-naphthylsulfonyl)piperidin-3-yl]pyrrolidin-3-ylpyrimidin-2-amine MS (ESI, Pos.20V): 535 (M+H)$^+$, 268 (M+2H)$^{2+}$;
HPLC condition: A; HPLC retention time (min): 3.29.

Example 11-0439

4-azepan-1-yl-N-[1-(1-isobutyrylpiperidin-4-yl)pyrrolidin-3-yl]pyrimidin-2-amine MS (ESI, Pos.20V): 415 (M+H)$^+$, 193;
HPLC condition: A; HPLC retention time (min): 2.98.

Example 11-0440

4-azepan-1-yl-N-[1-(1-butyrylpiperidin-4-yl)pyrrolidin-3-yl]pyrimidin-2-amine

MS (ESI, Pos.20V): 415 (M+H)$^+$, 193;
HPLC condition: A; HPLC retention time (min): 2.98.

Example 11-0441

4-azepan-1-yl-N-1-[1-(3-methylbenzoyl)piperidin-4-yl]pyrrolidin-3-ylpyrimidin-2-amine MS (ESI, Pos.20V): 463 (M+H)$^+$, 345, 119;
HPLC condition: A; HPLC retention time (min): 3.09.

Example 11-0442

N-[1-(1-acetylpiperidin-4-yl)pyrrolidin-3-yl]-4-azepan-1-ylpyrimidin-2-amine

MS (ESI, Pos.20V): 387 (M+H)$^+$, 345, 193;
HPLC condition: A; HPLC retention time (min): 2.90.

Example 11-0443

4-azepan-1-yl-N-1-[1-(4-fluorobenzoyl)piperidin-4-yl]pyrrolidin-3-ylpyrimidin-2-amine MS (ESI, Pos.20V): 467 (M+H)$^+$, 345, 193, 123;
HPLC condition: A;-HPLC retention time (min): 3.07.

Example 11-0444

4-azepan-1-yl-N-1-[1-(4-methylbenzoyl)piperidin-4-yl]pyrrolidin-3-ylpyrimidin-2-amine MS (ESI, Pos.20V): 463 (M+H)$^+$, 345, 119;
HPLC condition: A; HPLC retention time (min): 3.09.

Example 11-0445

4-azepan-1-yl-N-[1-(1-heptanoylpiperidin-4-yl)pyrrolidin-3-yl]pyrimidin-2-amine

MS (ESI, Pos.20V): 457 (M+H)$^+$, 345, 229 (M+2H)$^{2+}$, 173;
HPLC condition: A; HPLC retention time (min): 3.2.

Example 11-0446

4-azepan-1-yl-N-1-[1-(2-methoxybenzoyl)piperidin-4-yl]pyrrolidin-3-ylpyrimidin-2-amine MS (ESI, Pos.20V): 479 (M+H)$^+$, 345, 193, 135;
HPLC condition: A; HPLC retention time (min): 3.03.

Example 11-0447

4-azepan-1-yl-N-1-[1-(2-methylbenzoyl)piperidin-4-yl]pyrrolidin-3-ylpyrimidin-2-amine MS (ESI, Pos.20V): 463 (M+H)$^+$, 345, 119;
HPLC condition: A; HPLC retention time (min): 3.07.

Example 11-0448

4-azepan-1-yl-N-[1-(1-hexanoylpiperidin-4-yl)pyrrolidin-3-yl]pyrimidin-2-amine

MS (ESI, Pos.20V): 443 (M+H)$^+$, 345, 173;
HPLC condition: A; HPLC retention time (min): 3.12.

Example 11-0449

4-azepan-1-yl-N-1-[1-(phenylacetyl)piperidin-4-yl]pyrrolidin-3-ylpyrimidin-2-amine MS (ESI, Pos.20V): 463 (M+H)$^+$, 232 (M+2H)$^{2+}$;
HPLC condition: A; HPLC retention time (min): 3.09.

Example 11-0450

4-azepan-1-yl-N-1-[1-(4-methoxybenzoyl)piperidin-4-yl]pyrrolidin-3-ylpyrimidin-2-amine MS (ESI, Pos.20V): 479 (M+H)$^+$, 345, 193, 135;
HPLC condition: A; HPLC retention time (min): 3.03.

Example 11-0451

4-azepan-1-yl-N-(1-1-[(2E)-3-phenylprop-2-enoyl]piperidin-4-ylpyrrolidin-3-yl)pyrimidin-2-amine MS (ESI, Pos.20V): 949 (2M+H)$^+$, 475 (M+H)$^+$, 345;
HPLC condition: A; HPLC retention time (min): 3.14.

Example 11-0452

4-azepan-1-yl-N-1-[1-(1-propionylpiperidin-4-yl)pyrrolidin-3-yl]pyrimidin-2-amine MS (ESI, Pos.20V): 401 (M+H)$^+$, 345, 173;
HPLC condition: A; HPLC retention time (min): 2.90.

Example 11-0453

4-azepan-1-yl-N-1-[1-(cyclopropylcarbonyl)piperidin-4-yl]pyrrolidin-3-ylpyrimidin-2-amine MS (ESI, Pos.20V): 413 (M+H)$^+$, 345;
HPLC condition: A; HPLC retention time (min): 2.94.

Example 11-0454

4-azepan-1-yl-N-1-[1-(2-chlorobenzoyl)piperidin-4-yl]pyrrolidin-3-ylpyrimidin-2-amine MS (ESI, Pos.20V): 485, 483 (M+H)$^+$, 345, 139;
HPLC condition: A; HPLC retention time (min): 3.07.

Example 11-0455

4-azepan-1-yl-N-1-[1-(cyclohexylcarbonyl)piperidin-4-yl]pyrrolidin-3-ylpyrimidin-2-amine MS (ESI, Pos.20V): 455 (M+H)$^+$, 345;
HPLC condition: A; HPLC retention time (min): 3.11.

Example 11-0456

4-azepan-1-yl-N-1-[1-(2-furoyl)piperidin-4-yl]pyrrolidin-3-ylpyrimidin-2-amine

MS (ESI, Pos.20V): 439 (M+H)$^+$, 220 (M+2H)$^{2+}$;
HPLC condition: A; HPLC retention time (min): 2.96.

Example 11-0457

4-azepan-1-yl-N-[1-(1-pentanoylpiperidin-4-yl)pyrrolidin-3-yl]pyrimidin-2-amine

MS (ESI, Pos.20V): 429 (M+H)$^+$, 345, 193;
HPLC condition: A; HPLC retention time (min): 3.05.

Example 11-0458

4-azepan-1-yl-N-1-[1-(phenoxyacetyl)piperidin-4-yl]pyrrolidin-3-ylpyrimidin-2-amine MS (ESI, Pos.20V): 479 (M+H)$^+$, 429, 240 (M+2H)$^{2+}$;
HPLC condition: A; HPLC retention time (min): 3.09.

Example 11-0459

4-azepan-1-yl-N-[1-(1-octanoylpiperidin-4-yl)pyrrolidin-3-yl]pyrimidin-2-amine

MS (ESI, Pos.20V): 471 (M+H)$^+$, 345, 236 (M+2H)$^{2+}$, 173;
HPLC condition: A; HPLC retention time (min): 3.28.

Example 11-0460

4-azepan-1-yl-N-1-[1-(3-phenylpropanoyl)piperidin-4-yl]pyrrolidin-3-ylpyrimidin-2-amine MS (ESI, Pos.20V): 477 (M+H)$^+$, 345, 239 (M+2H)$^{2+}$, 173;
HPLC condition: A; HPLC retention time (min): 3.14.

Example 11-0461

4-azepan-1-yl-N-(1-1-[2-(trifluoromethyl)benzoyl]
piperidin-4-ylpyrrolidin-3-yl)pyrimidin-2-amine MS (ESI, Pos.20V): 517 (M+H)$^+$, 259 (M+2H)$^{2+}$;
HPLC condition: A; HPLC retention time (min): 3.12.

Example 11-0462

4-azepan-1-yl-N-1-[1-(2-naphthoyl)piperidin-4-yl]
pyrrolidin-3-ylpyrimidin-2-amine MS (ESI, Pos.20V): 997 (2M+H)$^+$, 499 (M+H)$^+$, 155;
HPLC condition: A; HPLC retention time (min): 3.18.

Example 11-0463

4-azepan-1-yl-N-1-[1-(thien-2-ylacetyl)piperidin-4-
yl]pyrrolidin-3-ylpyrimidin-2-amine MS (ESI, Pos.20V): 469 (M+H)$^+$, 235 (M+2H)$^{2+}$, 193;
HPLC condition: A; HPLC retention time (min): 3.05.

Example 11-0464

4-azepan-1-yl-N-1-[1-(3,3-dimethylbutanoyl)piperi-
din-4-yl]pyrrolidin-3-ylpyrimidin-2-amine MS (ESI, Pos.20V): 443 (M+H)$^+$, 345, 173;
HPLC condition: A; HPLC retention time (min): 3.07.

Example 11-0465

4-azepan-1-yl-N-1-[1-(3-methoxybenzoyl)piperidin-
4-yl]pyrrolidin-3-ylpyrimidin-2-amine MS (ESI, Pos.20V): 479 (M+H)$^+$, 345, 135;
HPLC condition: A; HPLC retention time (min): 3.07.

Example 11-0466

4-azepan-1-yl-N-1-[1-(2-ethylhexanoyl)piperidin-4-
yl]pyrrolidin-3-ylpyrimidin-2-amine MS (ESI, Pos.20V): 471 (M+H)$^+$, 345;
HPLC condition: A; HPLC retention time (min): 3.22.

Example 11-0467

4-azepan-1-yl-N-1-[1-(3-fluorobenzoyl)piperidin-4-
yl]pyrrolidin-3-ylpyrimidin-2-amine MS (ESI, Pos.20V): 467 (M+H)$^+$, 345, 234 (M+2H)$^{2+}$, 123;
HPLC condition: A; HPLC retention time (min): 3.07.

Example 11-0468

4-azepan-1-yl-N-1-[1-(3-chlorobenzoyl)piperidin-4-
yl]pyrrolidin-3-ylpyrimidin-2-amine MS (ESI, Pos.20V): 483 (M+H)$^+$, 345, 138;
HPLC condition: A; HPLC retention time (min): 3.12.

Example 11-0469

4-azepan-1-yl-N-1-[1-(4-tert-butylbenzoyl)piperidin-
4-yl]pyrrolidin-3-ylpyrimidin-2-amine MS (ESI, Pos.20V): 505 (M+H)$^+$, 345, 161;
HPLC condition: A; HPLC retention time (min): 3.29.

Example 11-0470

4-azepan-1-yl-N-1-[1-(thien-2-ylcarbonyl)piperidin-
4-yl]pyrrolidin-3-ylpyrimidin-2-amine MS (ESI, Pos.20V): 455 (M+H)$^+$, 345, 193;
HPLC condition: A; HPLC retention time (min): 3.03.

Example 11-0471

4-azepan-1-yl-N-(1-1-[(4-chlorophenyl)acetyl]pip-
eridin-4-ylpyrrolidin-3 yl)pyrimidin-2-amine MS (ESI, Pos.20V): 499, 497 (M+H)$^+$, 249 (M+2H)$^{2+}$;
HPLC condition: A; HPLC retention time (min): 3.18.

Example 11-0472

4-azepan-1-yl-N-1-[1-(3-methylbutanoyl)piperidin-
4-yl]pyrrolidin-3-ylpyrimidin-2-amine MS (ESI, Pos.20V): 429 (M+H)$^+$, 345, 193;
HPLC condition: A; HPLC retention time (min): 3.03.

Example 11-0473

4-azepan-1-yl-N-(1-1-[4-(trifluoromethyl)benzoyl]
piperidin-4-ylpyrrolidin-3-yl)pyrimidin-2-amine MS (ESI, Pos.20V): 517 (M+H)$^+$;
HPLC condition: A; HPLC retention time (min): 3.20.

Example 11-0474

4-azepan-1-yl-N-[1-(1-benzoylpiperidin-4-yl)pyrro-
lidin-3-yl]pyrimidin-2-amine

MS (ESI, Pos.20V): 449 (M+H)$^+$, 345, 193;
HPLC condition: A; HPLC retention time (min): 3.03.

Example 11-0475

4-azepan-1-yl-N-1-[1-(2-fluorobenzoyl)piperidin-4-
yl]pyrrolidin-3-ylpyrimidin-2-amine MS (ESI, Pos.20V): 467 (M+H)$^+$, 345, 234 (M+2H)$^{2+}$, 193;
HPLC condition: A; HPLC retention time (min): 3.03.

Example 11-0476

4-azepan-1-yl-N-1-[1-(diphenylacetyl)piperidin-4-
yl]pyrrolidin-3-ylpyrimidin-2-amine MS (ESI, Pos.20V): 539 (M+H)$^+$, 345, 167;
HPLC condition: A; HPLC retention time (min): 3.27.

Example 11-0477

4-azepan-1-yl-N-1-[1-(2-phenoxypropanoyl)piperidin-4-yl]pyrrolidin-3-ylpyrimidin-2-amine MS (ESI, Pos.20V): 493 (M+H)$^+$, 345, 247 (M+2H)$^{2+}$, 121;
HPLC condition: A; HPLC retention time (min): 3.11.

Example 11-0478

4-azepan-1-yl-N-1-[1-(2-methylpentanoyl)piperidin-4-yl]pyrrolidin-3-ylpyrimidin-2-amine MS (ESI, Pos.20V): 443 (M+H)$^+$, 345;
HPLC condition: A; HPLC retention time (min): 3.09.

Example 11-0479

4-azepan-1-yl-N-1-[1-(methoxyacetyl)piperidin-4-yl]pyrrolidin-3-ylpyrimidin-2-amine MS (ESI, Pos.20V): 417 (M+H)$^+$, 345, 262 (M+2H)$^{2+}$, 209;
HPLC condition: A; HPLC retention time (min): 2.86.

Example 11-0480 ethyl 4-(4-3-[(4-azepan-1-ylpyrimidin-2-yl)amino]pyrrolidin-1-ylpiperidin-1-yl)-4-oxobutanoate MS (ESI, Pos.20V): 473 (M+H)$^+$, 214;
HPLC condition: A; HPLC retention time (min): 3.00.

Example 11-0481

4-azepan-1-yl-N-1-[1-(3-cyclopentylpropanoyl)piperidin-4-yl]pyrrolidin-3-ylpyrimidin-2-amine MS (ESI, Pos.20V): 469 (M+H)$^+$, 345, 235 (M+2H)$^{2+}$, 173;
HPLC condition: A; HPLC retention time (min): 3.22.

Example 11-0482

4-azepan-1-yl-N-1-[1-(2-propylpentanoyl)piperidin-4-yl]pyrrolidin-3-ylpyrimidin-2-amine MS (ESI, Pos.20V): 471 (M+H)$^+$, 345;
HPLC condition: A; HPLC retention time (min): 3.22.

Example 11-0483 methyl 5-(4-3-[(4-azepan-1-ylpyrimidin-2-yl)amino]pyrrolidin-1-ylpiperidin-1-yl)-5-oxopentanoate MS (ESI, Pos.20V): 473 (M+H)$^+$, 221;
HPLC condition: A; HPLC retention time (min): 3.00.

Example 11-0484

4-azepan-1-yl-N-(1-1-[(4-chlorophenoxy)acetyl]piperidin-4-ylpyrrolidin-3-yl)pyrimidin-2-amine MS (ESI, Pos.20V): 513 (M+H)$^+$, 257 (M+2H)$^{2+}$;
HPLC condition: A; HPLC retention time (min): 3.20.

Example 11-0486

4-azepan-1-yl-N-1-[1-(cyclopentylacetyl)piperidin-4-yl]pyrrolidin-3-ylpyrimidin-2-amine MS (ESI, Pos.20V): 455 (M+H)$^+$, 345, 173;
HPLC condition: A; HPLC retention time (min): 3.11.

Example 11-0487

4-azepan-1-yl-N-1-[1-(cyclopentylcarbonyl)piperidin-4-yl]pyrrolidin-3-ylpyrimidin-2-amine MS (ESI, Pos.20V): 441 (M+H)$^+$, 345, 193;
HPLC condition: A; HPLC retention time (min): 3.05.

Example 11-0488

4-azepan-1-yl-N-1-[1-(mesitylcarbonyl)piperidin-4-yl]pyrrolidin-3-ylpyrimidin-2-amine MS (ESI, Pos.20V): 491 (M+H)$^+$, 345, 147;
HPLC condition: A; HPLC retention time (min): 3.18.

Example 11-0489

4-azepan-1-yl-N-(1-1-[(3-methoxyphenyl)acetyl]piperidin-4-ylpyrrolidin-3-yl)pyrimidin-2-amine MS (ESI, Pos.20V): 493 (M+H)$^+$, 247 (M+2H)$^{2+}$, 173;
HPLC condition: A; HPLC retention time (min): 3.09.

Example 11-0490 ethyl 3-(4-3-[(4-azepan-1-ylpyrimidin-2-yl)amino]pyrrolidin-1-ylpiperidin-1-yl)-3-oxopropanoate MS (ESI, Pos.20V): 459 (M+H)$^+$, 193;
HPLC condition: A; HPLC retention time (min): 2.96.

Example 11-0491

4-azepan-1-yl-N-1-[1-(4-butoxybenzoyl)piperidin-4-yl]pyrrolidin-3-ylpyrimidin-2-amine MS (ESI, Pos.20V): 521 (M+H)$^+$, 345, 177;
HPLC condition: A; HPLC retention time (min): 3.29.

Example 11-0492

4-azepan-1-yl-N-(1-1-[(benzyloxy)acetyl]piperidin-4-ylpyrrolidin-3-yl)pyrimidin-2-amine MS (ESI, Pos.20V): 493 (M+H)$^+$, 403;
HPLC condition: A; HPLC retention time (min): 3.11.

Example 11-0493

4-azepan-1-yl-N-1-[1-(2-methylbutanoyl)piperidin-4-yl]pyrrolidin-3-ylpyrimidin-2-amine MS (ESI, Pos.20V): 429 (M+H)$^+$, 345, 193;
HPLC condition: A; HPLC retention time (min): 3.01.

Example 11-0494

4-azepan-1-yl-N-(1-1-[(4-methoxyphenyl)acetyl]piperidin-4-ylpyrrolidin-3-yl)pyrimidin-2-amine MS (ESI, Pos.20V): 493 (M+H)$^+$, 247 (M+2H)$^{2+}$, 121;
HPLC condition: A; HPLC retention time (min): 3.07.

Example 11-0495 ethyl 5-(4-3-[(4-azepan-1-ylpyrimidin-2-yl)amino]pyrrolidin-1-ylpiperidin-1-yl)-5-oxopentanoate MS (ESI, Pos.20V): 487 (M+H)$^+$, 393, 221;
HPLC condition: A; HPLC retention time (min): 3.03.

Example 11-0496

4-azepan-1-yl-N-1-[1-(cyclobutylcarbonyl)piperidin-4-yl]pyrrolidin-3-ylpyrimidin-2-amine MS (ESI, Pos.20V): 427 (M+H)$^+$, 345, 193;
HPLC condition: A; HPLC retention time (min): 3.02.

Example 11-0497

4-azepan-1-yl-N-1-[1-(2-ethylbutanoyl)piperidin-4-yl]pyrrolidin-3-ylpyrimidin-2-amine MS (ESI, Pos.20V): 443 (M+H)$^+$, 345;
HPLC condition: A; HPLC retention time (min): 3.07.

Example 11-0498

4-azepan-1-yl-N-(1-1-[4-(trifluoromethoxy)benzoyl]piperidin-4-ylpyrrolidin-3-yl)pyrimidin-2-amine MS (ESI, Pos.20V): 533 (M+H)$^+$, 189;
HPLC condition: A; HPLC retention time (min): 3.22.

Example 11-0499

4-azepan-1-yl-N-1-[1-(methylsulfonyl)piperidin-4-yl]pyrrolidin-3-ylpyrimidin-2-amine MS (ESI, Pos.20V): 423 (M+H)$^+$, 262 (M+2H)$^{2+}$, 212;
HPLC condition: A; HPLC retention time (min): 2.94.

Example 11-0500

4-azepan-1-yl-N-1-[1-(pentylsulfonyl)piperidin-4-yl]pyrrolidin-3-ylpyrimidin-2-amine MS (ESI, Pos.20V): 957 (2M+H)$^+$, 479 (M+H)$^+$, 240(M+2H)$^{2+}$;
HPLC condition: A; HPLC retention time (min): 3.22.

Example 11-0501

4-azepan-1-yl-N-1-[1-(propylsulfonyl)piperidin-4-yl]pyrrolidin-3-ylpyrimidin-2-amine MS (ESI, Pos.20V): 901 (2M+H)$^+$, 451 (M+H)$^+$, 226 (M+2H)$^{2+}$;
HPLC condition: A; HPLC retention time (min): 3.03.

Example 11-0502

4-azepan-1-yl-N-1-[1-(isopropylsulfonyl)piperidin-4-yl]pyrrolidin-3-ylpyrimidin-2-amine MS (ESI, Pos.20V): 901 (2M+H)$^+$, 451 (M+H)$^+$, 226 (M+2H)$^{2+}$;
HPLC condition: A; HPLC retention time (min): 3.03.

Example 11-0503

4-azepan-1-yl-N-(1-piperidin-4-ylpyrrolidin-3-yl)pyrimidin-2-amine

MS (ESI, Pos.20V): 345 (M+H)$^+$, 262, 173 (M+2H)$^{2+}$;
HPLC condition: A; HPLC retention time (min): 2.79.

Example 11-0504

4-azepan-1-yl-N-1-[1-(butylsulfonyl)piperidin-4-yl]pyrrolidin-3-ylpyrimidin-2-amine MS (ESI, Pos.20V): 929 (2M+H)$^+$, 465 (M+H)$^+$, 233 (M+2H)$^{2+}$;
HPLC condition: A; HPLC retention time (min): 3.12.

Example 11-0505

4-azepan-1-yl-N-1-[1-(phenylsulfonyl)piperidin-4-yl]pyrrolidin-3-ylpyrimidin-2-amine MS (ESI, Pos.20V): 969 (2M+H)$^+$, 485 (M+H)$^+$, 243 (M+2H)$^{2+}$;
HPLC condition: A; HPLC retention time (min): 3.13.

Example 11-0506

4-azepan-1-yl-N-(1-1-[(4-chlorophenyl)sulfonyl]piperidin-4-ylpyrrolidin-3-yl)pyrimidin-2-amine MS (ESI, Pos.20V): 521, 519 (M+H)$^+$, 260(M+2H)$^{2+}$;
HPLC condition: A; HPLC retention time (min): 3.23.

Example 11-0507

4-azepan-1-yl-N-[1-(1-[4-(trifluoromethyl)phenyl]sulfonylpiperidin-4-yl)pyrrolidin-3-yl]pyrimidin-2-amine MS (ESI, Pos.20V): 553 (M+H)$^+$, 277 (M+2H)$^{2+}$;
HPLC condition: A; HPLC retention time (min): 3.33.

Example 11-0508

4-azepan-1-yl-N-(1-1-[(4-methoxyphenyl)sulfonyl]piperidin-4-ylpyrrolidin-3-yl)pyrimidin-2-amine MS (ESI, Pos.20V): 515 (M+H)$^+$, 345, 258 (M+2H)$^{2+}$;
HPLC condition: A; HPLC retention time (min): 3.16.

Example 11-0509

4-azepan-1-yl-N-1-[1-(benzylsulfonyl)piperidin-4-yl]pyrrolidin-3-ylpyrimidin-2-amine MS (ESI, Pos.20V): 997 (2M+H)$^+$, 499 (M+H)$^+$, 345;
HPLC condition: A; HPLC retention time (min): 3.16.

Example 11-0510

4-azepan-1-yl-N-(1-1-[(4-methylphenyl)sulfonyl]piperidin-4-ylpyrrolidin-3-yl)pyrimidin-2-amine MS (ESI, Pos.20V): 997 (2M+H)$^+$, 499 (M+H)$^+$, 250 (M+2H)$^{2+}$;
HPLC condition: A; HPLC retention time (min): 3.22.

Example 11-0511

4-azepan-1-yl-N-(1-1-[(3-methylphenyl)sulfonyl]piperidin-4-ylpyrrolidin-3-yl)pyrimidin-2-amine MS (ESI, Pos.20V): 997 (2M+H)$^+$, 499 (M+H)$^+$, 250 (M+2H)$^{2+}$;
HPLC condition: A; HPLC retention time (min): 3.20.

Example 11-0512

4-azepan-1-yl-N-(1-1-[(2-methylphenyl)sulfonyl]piperidin-4-ylpyrrolidin-3-yl)pyrimidin-2-amine MS (ESI, Pos.20V): 997 (2M+H)$^+$, 499 (M+H)$^+$, 250 (M+2H)$^{2+}$;
HPLC condition: A; HPLC retention time (min): 3.20.

Example 11-0513

4-azepan-1-yl-N-[1-(1-[4-(trifluoromethoxy)phenyl]sulfonylpiperidin-4-yl)pyrrolidin-3-yl]pyrimidin-2-amine MS (ESI, Pos.20V): 569 (M+H)$^+$, 285 (M+2H)$^{2+}$;
HPLC condition: A; HPLC retention time (min): 3.34.

Example 11-0514

4-azepan-1-yl-N-(1-1-[(4-butoxyphenyl)sulfonyl]piperidin-4-ylpyrrolidin-3-yl)pyrimidin-2-amine MS (ESI, Pos.20V): 557 (M+H)$^+$, 345, 279 (M+2H)$^{2+}$;
HPLC condition: A; HPLC retention time (min): 3.42.

Example 11-0515

4-azepan-1-yl-N-(1-1-[(4-tert-butylphenyl)sulfonyl]piperidin-4-ylpyrrolidin-3-yl)pyrimidin-2-amine MS (ESI, Pos.20V): 541 (M+H)$^+$, 271 (M+2H)$^{2+}$;
HPLC condition: A; HPLC retention time (min): 3.42.

Example 11-0516

4-azepan-1-yl-N-(1-1-[(4-nitrophenyl)sulfonyl]piperidin-4-ylpyrrolidin-3-yl)pyrimidin-2-amine MS (ESI, Pos.20V): 530 (M+H)$^+$, 278;
HPLC condition: A; HPLC retention time (min): 3.22.

Example 11-0517

4-[(4-3-[(4-azepan-1-ylpyrimidin-2-yl)amino]pyrrolidin-1-ylpiperidin-1-yl)sulfonyl]benzonitrile MS (ESI, Pos.20V): 510 (M+H)$^+$, 255.5 (M+2H)$^{2+}$, 186;
HPLC condition: A; HPLC retention time (min): 3.18.

Example 11-0518

4-azepan-1-yl-N-1-[1-(2-naphthylsulfonyl)piperidin-4-yl]pyrrolidin-3-ylpyrimidin-2-amine MS (ESI, Pos.20V): 535 (M+H)$^+$, 268 (M+2H)$^{2+}$;
HPLC condition: A; HPLC retention time (min): 3.31.

Example 11-0519

N-(4-azepan-1-ylpyrimidin-2-yl)-1'-isobutyryl-1,3'-bipiperidin-3-amine

MS (ESI, Pos.20V): 429 (M+H)$^+$, 359, 276, 215 (M+2H)$^{2+}$;
HPLC condition: A; HPLC retention time (min): 3.01.

Example 11-0520

N-(4-azepan-1-ylpyrimidin-2-yl)-1'-butyryl-1,3'-bipiperidin-3-amine

MS (ESI, Pos.20V): 429 (M+H)$^+$, 359, 276, 215 (M+2H)$^{2+}$;
HPLC condition: A; HPLC retention time (min): 3.00.

Example 11-0521

N-(4-azepan-1-ylpyrimidin-2-yl)-1'-(3-methylbenzoyl)-1,3'-bipiperidin-3-amine

MS (ESI, Pos.20V): 477 (M+H)$^+$, 359, 239 (M+2H)$^{2+}$, 119;
HPLC condition: A; HPLC retention time (min): 3.11.

Example 11-0522

1'-acetyl-N-(4-azepan-1-ylpyrimidin-2-yl)-1,3'-bipiperidin-3-amine

MS (ESI, Pos.20V): 401 (M+H)$^+$, 359, 276, 201 (M+2H)$^{2+}$;
HPLC condition: A; HPLC retention time (min): 2.90.

Example 11-0523

N-(4-azepan-1-ylpyrimidin-2-yl)-1'-(4-fluorobenzoyl)-1,3'-bipiperidin-3-amine

MS (ESI, Pos.20V): 481 (M+H)$^+$, 359, 241 (M+2H)$^{2+}$, 123;
HPLC condition: A; HPLC retention time (min): 3.09.

Example 11-0524

N-(4-azepan-1-ylpyrimidin-2-yl)-1'-(4-methylbenzoyl)-1,3'-bipiperidin-3-amine

MS (ESI, Pos.20V): 477 (M+H)$^+$, 359, 239 (M+2H)$^{2+}$, 119;
HPLC condition: A; HPLC retention time (min): 3.11.

Example 11-0525

N-(4-azepan-1-ylpyrimidin-2-yl)-1'-heptanoyl-1,3'-bipiperidin-3-amine

MS (ESI, Pos.20V): 471 (M+H)$^+$, 359, 236 (M+2H)$^{2+}$, 180;
HPLC condition: A; HPLC retention time (min): 3.25.

Example 11-0526

N-(4-azepan-1-ylpyrimidin-2-yl)-1'-(2-methoxybenzoyl)-1,3'-bipiperidin-3-amine

MS (ESI, Pos.20V): 493 (M+H)$^+$, 359, 247 (M+2H)$^{2+}$, 135;
HPLC condition: A; HPLC retention time (min): 3.05.

Example 11-0527

N-(4-azepan-1-ylpyrimidin-2-yl)-1'-(2-methylbenzoyl)-1,3'-bipiperidin-3-amine

MS (ESI, Pos.20V): 477 (M+H)$^+$, 359, 239 (M+2H)$^{2+}$, 119;
HPLC condition: A; HPLC retention time (min): 3.09.

Example 11-0528

N-(4-azepan-1-ylpyrimidin-2-yl)-1'-hexanoyl-1,3'-bipiperidin-3-amine

MS (ESI, Pos.20V): 457 (M+H)$^+$, 359, 276, 229 (M+2H)$^{2+}$;
HPLC condition: A; HPLC retention time (min): 3.16.

Example 11-0529

N-(4-azepan-1-ylpyrimidin-2-yl)-1'-(phenylacetyl)-1,3'-bipiperidin-3-amine

MS (ESI, Pos.20V): 477 (M+H)$^+$, 239 (M+2H)$^{2+}$;
HPLC condition: A; HPLC retention time (min): 3.07.

Example 11-0530

N-(4-azepan-1-ylpyrimidin-2-yl)-1'-(4-methoxybenzoyl)-1,3'-bipiperidin-3-amine

MS (ESI, Pos.20V): 493 (M+H)$^+$, 359, 247 (M+2H)$^{2+}$, 135;
HPLC condition: A; HPLC retention time (min): 3.07.

Example 11-0531

N-(4-azepan-1-ylpyrimidin-2-yl)-1'-[(2E)-3-phenylprop-2-enoyl]-1,3'-bipiperidin-3-amine MS (ESI, Pos.20V): 489 (M+H)$^+$, 359, 245 (M+2H)$^{2+}$, 204;
HPLC condition: A; HPLC retention time (min): 3.16.

Example 11-0532

N-(4-azepan-1-ylpyrimidin-2-yl)-1'-propionyl-1,3'-bipiperidin-3-amine

MS (ESI, Pos.20V): 415 (M+H)$^+$, 359, 276, 208 (M+2H)$^{2+}$;
HPLC condition: A; HPLC retention time (min): 2.94.

Example 11-0533

N-(4-azepan-1-ylpyrimidin-2-yl)-1'-(cyclopropylcarbonyl)-1,3'-bipiperidin-3-amine MS (ESI, Pos.20V): 427 (M+H)$^+$, 359, 276, 214 (M+2H)$^{2+}$;
HPLC condition: A; HPLC retention time (min): 2.98.

Example 11-0534

N-(4-azepan-1-ylpyrimidin-2-yl)-1'-(2-chlorobenzoyl)-1,3'-bipiperidin-3-amine

MS (ESI, Pos.20V): 499, 497 (M+H)$^+$, 359, 249 (M+2H)$^{2+}$;
HPLC condition: A; HPLC retention time (min): 3.09.

Example 11-0535

N-(4-azepan-1-ylpyrimidin-2-yl)-1'-(cyclohexylcarbonyl)-1,3'-bipiperidin-3-amine MS (ESI, Pos.20V): 469 (M+H)$^+$, 359, 235 (M+2H)$^{2+}$, 111;
HPLC condition: A; HPLC retention time (min): 3.16.

Example 11-0536

N-(4-azepan-1-ylpyrimidin-2-yl)-1'-(2-furoyl)-1,3'-bipiperidin-3-amine

MS (ESI, Pos.20V): 453 (M+H)$^+$, 276, 227 (M+2H)$^{2+}$;
HPLC condition: A; HPLC retention time (min): 3.01.

Example 11-0537

N-(4-azepan-1-ylpyrimidin-2-yl)-1'-pentanoyl-1,3'-bipiperidin-3-amine

MS (ESI, Pos.20V): 443 (M+H)$^+$, 359, 222(M+2H)$^{2+}$;
HPLC condition: A; HPLC retention time (min): 3.07.

Example 11-0538

N-(4-azepan-1-ylpyrimidin-2-yl)-1'-(phenoxyacetyl)-1,3'-bipiperidin-3-amine

MS (ESI, Pos.20V): 493 (M+H)$^+$, 276, 247 (M+2H)$^{2+}$;
HPLC condition: A; HPLC retention time (min): 3.11.

Example 11-0539

N-(4-azepan-1-ylpyrimidin-2-yl)-1'-octanoyl-1,3'-bipiperidin-3-amine

MS (ESI, Pos.20V): 485 (M+H)$^+$, 359, 243 (M+2H)$^{2+}$;
HPLC condition: A; HPLC retention time (min): 3.33.

Example 11-0540

N-(4-azepan-1-ylpyrimidin-2-yl)-1'-(3-phenylpropanoyl)-1,3'-bipiperidin-3-amine

MS (ESI, Pos.20V): 491 (M+H)$^+$, 359, 246 (M+2H)$^{2+}$;
HPLC condition: A; HPLC retention time (min): 3.16.

Example 11-0541

N-(4-azepan-1-ylpyrimidin-2-yl)-1'-[2-(trifluoromethyl)benzoyl]-1,3'-bipiperidin-3-amine MS (ESI, Pos.20V): 531 (M+H)$^+$, 266 (M+2H)$^{2+}$;
HPLC condition: A; HPLC retention time (min): 3.14.

Example 11-0542

N-(4-azepan-1-ylpyrimidin-2-yl)-1'-(2-naphthoyl)-1,3'-bipiperidin-3-amine

MS (ESI, Pos.20V): 513 (M+H)$^+$, 359, 257 (M+2H)$^{2+}$, 155;
HPLC condition: A; HPLC retention time (min): 3.20.

Example 11-0543

N-(4-azepan-1-ylpyrimidin-2-yl)-1'-(thien-2-ylacetyl)-1,3'-bipiperidin-3-amine

MS (ESI, Pos.20V): 483 (M+H)$^+$, 276, 242 (M+2H)$^{2+}$;
HPLC condition: A; HPLC retention time (min): 3.09.

Example 11-0544

N-(4-azepan-1-ylpyrimidin-2-yl)-1'-(3,3-dimethylbutanoyl)-1,3'-bipiperidin-3-amine MS (ESI, Pos.20V): 457 (M+H)$^+$, 359, 229 (M+2H)$^{2+}$;
HPLC condition: A; HPLC retention time (min): 3.12.

Example 11-0545

N-(4-azepan-1-ylpyrimidin-2-yl)-1'-(3-methoxybenzoyl)-1,3'-bipiperidin-3-amine

MS (ESI, Pos.20V): 493 (M+H)$^+$, 359, 247 (M+2H)$^{2+}$, 135;
HPLC condition: A; HPLC retention time (min): 3.09.

Example 11-0546

N-(4-azepan-1-ylpyrimidin-2-yl)-1'-(2-ethylhexanoyl)-1,3'-bipiperidin-3-amine

MS (ESI, Pos.20V): 485 (M+H)$^+$, 359, 243 (M+2H)$^{2+}$;
HPLC condition: A; HPLC retention time (min): 3.25.

Example 11-0547

N-(4-azepan-1-ylpyrimidin-2-yl)-1'-(3-fluorobenzoyl)-1,3'-bipiperidin-3-amine

MS (ESI, Pos.20V): 481 (M+H)$^+$, 359, 241 (M+2H)$^{2+}$, 123;
HPLC condition: A; HPLC retention time (min): 3.09.

Example 11-0548

N-(4-azepan-1-ylpyrimidin-2-yl)-1'-(3-chlorobenzoyl)-1,3'-bipiperidin-3-amine

MS (ESI, Pos.20V): 499, 497 (M+H)$^+$, 359, 249 (M+2H)$^{2+}$;
HPLC condition: A; HPLC retention time (min): 3.14.

Example 11-0549

N-(4-azepan-1-ylpyrimidin-2-yl)-1'-(4-tert-butylbenzoyl)-1,3'-bipiperidin-3-amine MS (ESI, Pos.20V): 519 (M+H)$^+$, 359, 260 (M+2H)$^{2+}$;
HPLC condition: A; HPLC retention time (min): 3.31.

Example 11-0550

N-(4-azepan-1-ylpyrimidin-2-yl)-1'-(thien-2-ylcarbonyl)-1,3'-bipiperidin-3-amine MS (ESI, Pos.20V): 469 (M+H)$^+$, 359, 235 (M+2H)$^{2+}$, 111;
HPLC condition: A; HPLC retention time (min): 3.03.

Example 11-0551

N-(4-azepan-1-ylpyrimidin-2-yl)-1'-[(4-chlorophenyl)acetyl]-1,3'-bipiperidin-3-amine MS (ESI, Pos.20V): 513, 511 (M+H)$^+$, 256 (M+2H)$^{2+}$;
HPLC condition: A; HPLC retention time (min): 3.20.

Example 11-0552

N-(4-azepan-1-ylpyrimidin-2-yl)-1'-(3-methylbutanoyl)-1,3'-bipiperidin-3-amine

MS (ESI, Pos.20V): 443 (M+H)$^+$, 359, 222 (M+2H)$^{2+}$;
HPLC condition: A; HPLC retention time (min): 3.07.

Example 11-0553

N-(4-azepan-1-ylpyrimidin-2-yl)-1'-[4-(trifluoromethyl)benzoyl]-1,3'-bipiperidin-3-amine MS (ESI, Pos.20V): 531 (M+H)$^+$, 266 (M+2H)$^{2+}$;
HPLC condition: A; HPLC retention time (min): 3.22.

Example 11-0554

N-(4-azepan-1-ylpyrimidin-2-yl)-1'-benzoyl-1,3'-bipiperidin-3-amine

MS (ESI, Pos.20V): 463 (M+H)$^+$, 359, 232 (M+2H)$^{2+}$;
HPLC condition: A; HPLC retention time (min): 3.05.

Example 11-0555

N-(4-azepan-1-ylpyrimidin-2-yl)-1'-(2-fluorobenzoyl)-1,3'-bipiperidin-3-amine

MS (ESI, Pos.20V): 481 (M+H)$^+$, 359, 241 (M+2H)$^{2+}$;
HPLC condition: A; HPLC retention time (min): 3.05.

Example 11-0556

N-(4-azepan-1-ylpyrimidin-2-yl)-1'-(diphenylacetyl)-1,3'-bipiperidin-3-amine

MS (ESI, Pos.20V): 553 (M+H)$^+$, 359, 277 (M+2H)$^{2+}$, 167;
HPLC condition: A; HPLC retention time (min): 3.27.

Example 11-0557

N-(4-azepan-1-ylpyrimidin-2-yl)-1'-(2-phenoxypropanoyl)-1,3'-bipiperidin-3-amine MS (ESI, Pos.20V): 507 (M+H)$^+$, 254 (M+2H)$^{2+}$, 121;
HPLC condition: A; HPLC retention time (min): 3.14.

Example 11-0558

N-(4-azepan-1-ylpyrimidin-2-yl)-1'-(2-methylpentanoyl)-1,3'-bipiperidin-3-amine

MS (ESI, Pos.20V): 457 (M+H)$^+$, 359, 229 (M+2H)$^{2+}$;
HPLC condition: A; HPLC retention time (min): 3.12.

Example 11-0559

N-(4-azepan-1-ylpyrimidin-2-yl)-1'-(methoxyacetyl)-1,3'-bipiperidin-3-amine

MS (ESI, Pos.20V): 431 (M+H)$^+$, 359, 216 (M+2H)$^{2+}$;
EPLC condition: A; HPLC retention time (min): 2.90.

Example 11-0560 ethyl 4-3-[(4-azepan-1-ylpyrimidin-2-yl)amino]-1,3'-bipiperidin-1'-yl-4-oxobutanoate MS (ESI, Pos.20V): 487 (M+H)$^+$, 359, 244 (M+2H)$^{2+}$, 211;
HPLC condition: A; HPLC retention time (min): 3.02.

Example 11-0561

N-(4-azepan-1-ylpyrimidin-2-yl)-1'-(3-cyclopentylpropanoyl)-1,3'-bipiperidin-3-amine MS (ESI, Pos.20V): 483 (M+H)$^+$, 359, 242 (M+2H)$^{2+}$;
HPLC condition: A; HPLC retention time (min): 3.23.

Example 11-0562

N-(4-azepan-1-ylpyrimidin-2-yl)-1'-(2-propylpentanoyl)-1,3'-bipiperidin-3-amine

MS (ESI, Pos.20V): 485 (M+H)$^+$, 359, 243 (M+2H)$^{2+}$;
HPLC condition: A; HPLC retention time (min): 3.27.

Example 11-0563 methyl 5-3-[(4-azepan-1-ylpyrimidin-2-yl)amino]-1,3'-bipiperidin-1'-yl-5-oxopentanoate MS (ESI, Pos.20V): 487 (M+H)$^+$, 228;
HPLC condition: A; HPLC retention time (min): 3.01.

Example 11-0564

N-(4-azepan-1-ylpyrimidin-2-yl)-1'-[(4-chlorophenoxy)acetyl]-1,3'-bipiperidin-3-amine MS (ESI, Pos.20V): 529, 527 (M+H)$^+$, 264 (M+2H)$^{2+}$;
HPLC condition: A; HPLC retention time (min): 3.22.

Example 11-0566

N-(4-azepan-1-ylpyrimidin-2-yl)-1'-(cyclopentylacetyl)-1,3'-bipiperidin-3-amine

MS (ESI, Pos.20V): 469 (M+H)$^+$, 359, 235 (M+2H)$^{2+}$, 180;
HPLC condition: A; HPLC retention time (min): 3.14.

Example 11-0567

N-(4-azepan-1-ylpyrimidin-2-yl)-1'-(cyclopentylcarbonyl)-1,3'-bipiperidin-3-amine MS (ESI, Pos.20V): 455 (M+H)$^+$, 359, 228 (M+2H)$^{2+}$;
HPLC condition: A; HPLC retention time (min): 3.09.

Example 11-0568

N-(4-azepan-1-ylpyrimidin-2-yl)-1'-(mesitylcarbonyl)-1,3'-bipiperidin-3-amine

MS (ESI, Pos.20V): 505 (M+H)$^+$, 359, 147;
HPLC condition: A; HPLC retention time (min): 3.23.

Example 11-0569

N-(4-azepan-1-ylpyrimidin-2-yl)-1'-[(3-methoxyphenyl)acetyl]-1,3'-bipiperidin-3-amine MS (ESI, Pos.20V): 507 (M+H)$^+$, 359, 254 (M+2H)$^{2+}$, 121;
HPLC condition: A; HPLC retention time (min): 3.09.

Example 11-0570 ethyl 3-3-[(4-azepan-1-ylpyrimidin-2-yl)amino]-1,3'-bipiperidin-1'-yl-3-oxopropanoate MS (ESI, Pos.20V): 473 (M+H)$^+$, 276, 237 (M+2H)$^{2+}$;
HPLC condition: A; HPLC retention time (min): 3.00.

Example 11-0571

N-(4-azepan-1-ylpyrimidin-2-yl)-1'-(4-butoxybenzoyl)-1,3'-bipiperidin-3-amine

MS (ESI, Pos.20V): 535 (M+H)$^+$, 359, 177;
HPLC condition: A; HPLC retention time (min): 3.33.

Example 11-0572

N-(4-azepan-1-ylpyrimidin-2-yl)-1'-[(benzyloxy)acetyl]-1,3'-bipiperidin-3-amine

MS (ESI, Pos.20V): 507 (M+H)$^+$, 417;
HPLC condition: A; HPLC retention time (min): 3.12.

Example 11-0573

N-(4-azepan-1-ylpyrimidin-2-yl)-1'-(2-methylbutanoyl)-1,3'-bipiperidin-3-amine

MS (ESI, Pos.20V): 465 (M+Na)+, 443 (M+H)$^+$;
HPLC condition: A; HPLC retention time (min): 3.05.

Example 11-0574

N-(4-azepan-1-ylpyrimidin-2-yl)-1'-[(4-methoxyphenyl)acetyl]-1,3'-bipiperidin-3-amine MS (ESI, Pos.20V): 507 (M+H)$^+$, 359, 254(M+2H)$^{2+}$;
HPLC condition: A; HPLC retention time (min): 3.11.

Example 11-0575 ethyl 5-3-[(4-azepan-1-ylpyrimidin-2-yl)amino]-1,3'-bipiperidin-1'-yl-5-oxopentanoate MS (ESI, Pos.20V): 501 (M+H)$^+$, 228;
HPLC condition: A; HPLC retention time (min): 3.07.

Example 11-0576

N-(4-azepan-1-ylpyrimidin-2-yl)-1'-(cyclobutylcarbonyl)-1,3'-bipiperidin-3-amine MS (ESI, Pos.20V): 441 (M+H)$^+$, 359, 221 (M+2H)$^{2+}$;
HPLC condition: A; HPLC retention time (min): 3.03.

Example 11-0577

N-(4-azepan-1-ylpyrimidin-2-yl)-1'-(2-ethylbutanoyl)-1,3'-bipiperidin-3-amine

MS (ESI, Pos.20V): 457 (M+H)$^+$, 359, 229 (M+2H)$^{2+}$;
HPLC condition: A; HPLC retention time (min): 3.12.

Example 11-0578

N-(4-azepan-1-ylpyrimidin-2-yl)-1'-[4-(trifluoromethoxy)benzoyl]-1,3'-bipiperidin-3-amine MS (ESI, Pos.20V): 547 (M+H)$^+$, 359, 274 (M+2H)$^{2+}$;
HPLC condition: A; HPLC retention time (min): 3.25.

Example 11-0579

N-(4-azepan-1-ylpyrimidin-2-yl)-1'-(methylsulfonyl)-1,3'-bipiperidin-3-amine

MS (ESI, Pos.20V): 437 (M+H)$^+$, 359, 276;
HPLC condition: A; HPLC retention time (min): 2.96.

Example 11-0580

N-(4-azepan-1-ylpyrimidin-2-yl)-1'-(pentylsulfonyl)-1,3'-bipiperidin-3-amine

MS (ESI, Pos.20V): 493 (M+H)$^+$, 276, 247 (M+2H)$^{2+}$;
HPLC condition: A; HPLC retention time (min): 3.22.

Example 11-0581

N-(4-azepan-1-ylpyrimidin-2-yl)-1'-(propylsulfonyl)-1,3'-bipiperidin-3-amine

MS (ESI, Pos.20V): 465 (M+H)$^+$, 276, 233 (M+2H)$^{2+}$;
HPLC condition: A; HPLC retention time (min): 3.07.

Example 11-0582

N-(4-azepan-1-ylpyrimidin-2-yl)-1'-(isopropylsulfonyl)-1,3'-bipiperidin-3-amine

MS (ESI, Pos.20V): 465 (M+H)$^+$, 359, 276, 233 (M+2H)$^{2+}$;
HPLC condition: A; HPLC retention time (min): 3.05.

Example 11-0583

N-(4-azepan-1-ylpyrimidin-2-yl)-1,3'-bipiperidin-3-amine

MS (ESI, Pos.20V): 359 (M+H)$^+$, 276;
HPLC condition: A; HPLC retention time (min): 2.83.

Example 11-0584

N-(4-azepan-1-ylpyrimidin-2-yl)-1'-(butylsulfonyl)-1,3'-bipiperidin-3-amine

MS (ESI, Pos.20V): 479 (M+H)$^+$, 276, 240 (M+2H)$^{2+}$;
HPLC condition: A; HPLC retention time (min): 3.12.

Example 11-0585

N-(4-azepan-1-ylpyrimidin-2-yl)-1'-(phenylsulfonyl)-1,3'-bipiperidin-3-amine

MS (ESI, Pos.20V): 499 (M+H)$^+$, 276, 250 (M+2H)$^{2+}$;
HPLC condition: A; HPLC retention time (min): 3.14.

Example 11-0586

N-(4-azepan-1-ylpyrimidin-2-yl)-1'-[(4-chlorophenyl)sulfonyl]-1,3'-bipiperidin-3-amine MS (ESI, Pos.20V): 535, 533 (M+H)$^+$, 267 (M+2H)$^{2+}$;
HPLC condition: A; HPLC retention time (min): 3.23.

Example 11-0587

N-(4-azepan-1-ylpyrimidin-2-yl)-1'-[4-(trifluoromethyl)phenyl]sulfonyl-1,3'-bipiperidin-3-amine MS (ESI, Pos.20V): 567 (M+H)$^+$, 284 (M+2H)$^{2+}$;
HPLC condition: A; HPLC retention time (min): 3.31.

Example 11-0588

N-(4-azepan-1-ylpyrimidin-2-yl)-1'-[(4-methoxyphenyl)sulfonyl]-1,3'-bipiperidin-3-amine MS (ESI, Pos.20V): 529 (M+H)$^+$, 265 (M+2H)$^{2+}$;
HPLC condition: A; HPLC retention time (min): 3.18.

Example 11-0589

N-(4-azepan-1-ylpyrimidin-2-yl)-1'-(benzylsulfonyl)-1,3'-bipiperidin-3-amine

MS (ESI, Pos.20V): 513 (M+H)$^+$, 359, 257 (M+2H)$^{2+}$;
HPLC condition: A; HPLC retention time (min): 3.18.

Example 11-0590

N-(4-azepan-1-ylpyrimidin-2-yl)-1'-[(4-methylphenyl)sulfonyl]-1,3'-bipiperidin-3-amine MS (ESI, Pos.20V): 513 (M+H)$^+$, 276, 257 (M+2H)$^{2+}$;
HPLC condition: A; HPLC retention time (min): 3.22.

Example 11-0591

N-(4-azepan-1-ylpyrimidin-2-yl)-1'-[(3-methylphenyl)sulfonyl]-1,3'-bipiperidin-3-amine MS (ESI, Pos.20V): 513 (M+H)$^+$, 276, 257 (M+2H)$^{2+}$;
HPLC condition: A; HPLC retention time (min): 3.20.

Example 11-0592

N-(4-azepan-1-ylpyrimidin-2-yl)-1'-[(2-methylphenyl)sulfonyl]-1,3'-bipiperidin-3-amine MS (ESI, Pos.20V): 513 (M+H)$^+$, 276, 257 (M+2H)$^{2+}$;
HPLC condition: A; HPLC retention time (min): 3.20.

Example 11-0593

N-(4-azepan-1-ylpyrimidin-2-yl)-1'-[4-(trifluoromethoxy)phenyl]sulfonyl-1,3'-bipiperidin-3-amine MS (ESI, Pos.20V): 583 (M+H)$^+$, 292 (M+2H)$^{2+}$;
HPLC condition: A; HPLC retention time (min): 3.33.

Example 11-0594

N-(4-azepan-1-ylpyrimidin-2-yl)-1'-[(4-butoxyphenyl)sulfonyl]-1,3'-bipiperidin-3-amine MS (ESI, Pos.20V): 571 (M+H)$^+$, 286 (M+2H)$^{2+}$;
HPLC condition: A; HPLC retention time (min): 3.42.

Example 11-0595

N-(4-azepan-1-ylpyrimidin-2-yl)-1'-[(4-tert-butylphenyl)sulfonyl]-1,3'-bipiperidin-3-amine MS (ESI, Pos.20V): 555 (M+H)$^+$, 278 (M+2H)$^{2+}$;
HPLC condition: A; HPLC retention time (min): 3.38.

Example 11-0596

N-(4-azepan-1-ylpyrimidin-2-yl)-1'-[(4-nitrophenyl)sulfonyl]-1,3'-bipiperidin-3-amine MS (ESI, Pos.20V): 544 (M+H)$^+$, 272.5 (M+2H)$^{2+}$;
HPLC condition: A; HPLC retention time (min): 3.20.

Example 11-0597

4-(3-[(4-azepan-1-ylpyrimidin-2-yl)amino]-1,3'-bipiperidin-1'-ylsulfonyl)benzonitrile MS (ESI, Pos.20V): 524 (M+H)$^+$, 262.5 (M+2H)$^{2+}$;
HPLC condition: A; HPLC retention time (min): 3.16.

Example 11-0598

N-(4-azepan-1-ylpyrimidin-2-yl)-1'-(2-naphthylsulfonyl)-1,3'-bipiperidin-3-amine MS (ESI, Pos.20V): 549 (M+H)$^+$, 275 (M+2H)$^{2+}$;
HPLC condition: A; HPLC retention time (min): 3.29.

Example 11-0599

N-(4-azepan-1-ylpyrimidin-2-yl)-1'-isobutyryl-1,4'-bipiperidin-3-amine

MS (ESI, Pos.20V): 429 (M+H)$^+$, 359;
HPLC condition: A; HPLC retention time (min) 2.98.

Example 11-0600

N-(4-azepan-1-ylpyrimidin-2-yl)-1'-butyryl-1,4'-bipiperidin-3-amine

MS (ESI, Pos.20V): 429 (M+H)$^+$, 359, 193;
HPLC condition: A; HPLC retention time (min): 2.96.

Example 11-0601

N-(4-azepan-1-ylpyrimidin-2-yl)-1'-(3-methylbenzoyl)-1,4'-bipiperidin-3-amine

MS (ESI, Pos.20V): 477 (M+H)$^+$, 359, 119;
HPLC condition: A; HPLC retention time (min): 3.09.

Example 11-0602

1'-acetyl-N-(4-azepan-1-ylpyrimidin-2-yl)-1,4'-bipiperidin-3-amine

MS (ESI, Pos.20V): 401 (M+H)$^+$, 359, 276, 201 (M+2H)$^{2+}$;
HPLC condition: A; HPLC retention time (min): 2.87.

Example 11-0603

N-(4-azepan-1-ylpyrimidin-2-yl)-1'-(4-fluorobenzoyl)-1,4'-bipiperidin-3-amine

MS (ESI, Pos.20V): 481 (M+H)$^+$, 359, 123;
HPLC condition: A; HPLC retention time (min): 3.05.

Example 11-0604

N-(4-azepan-1-ylpyrimidin-2-yl)-1'-(4-methylbenzoyl)-1,4'-bipiperidin-3-amine

MS (ESI, Pos.20V): 477 (M+H)$^+$, 359, 119;
HPLC condition: A; HPLC retention time (min): 3.07.

Example 11-0605

N-(4-azepan-1-ylpyrimidin-2-yl)-1'-heptanoyl-1,4'-bipiperidin-3-amine

MS (ESI, Pos.20V): 471 (M+H)$^+$, 236 (M+2H)$^{2+}$, 180;
HPLC condition: A; HPLC retention time (min): 3.20.

Example 11-0606

N-(4-azepan-1-ylpyrimidin-2-yl)-1'-(2-methoxybenzoyl)-1,4'-bipiperidin-3-amine

MS (ESI, Pos.20V): 493 (M+H)$^+$, 359, 193, 135;
HPLC condition: A; HPLC retention time (min): 3.01.

Example 11-0607

N-(4-azepan-1-ylpyrimidin-2-yl)-1'-(2-methylbenzoyl)-1,4'-bipiperidin-3-amine

MS (ESI, Pos.20V): 477 (M+H)$^+$, 359, 193;
HPLC condition: A; HPLC retention time (min): 3.05.

Example 11-0608

N-(4-azepan-1-ylpyrimidin-2-yl)-1'-hexanoyl-1,4'-bipiperidin-3-amine

MS (ESI, Pos.20V): 457 (M+H)$^+$, 359, 229 (M+2H)$^{2+}$, 180;
HPLC condition: A; HPLC retention time (min): 3.11.

Example 11-0609

N-(4-azepan-1-ylpyrimidin-2-yl)-1'-(phenylacetyl)-1,4'-bipiperidin-3-amine

MS (ESI, Pos.20V): 477 (M+H)$^+$, 359, 239 (M+2H)$^{2+}$;
HPLC condition: A; HPLC retention time (min): 3.05.

Example 11-0610

N-(4-azepan-1-ylpyrimidin-2-yl)-1'-(4-methoxybenzoyl)-1,4'-bipiperidin-3-amine

MS (ESI, Pos.20V): 493 (M+H)$^+$, 359, 193, 135;
HPLC condition: A; HPLC retention time (min): 3.03.

Example 11-0611

N-(4-azepan-1-ylpyrimidin-2-yl)-1'-[(2E)-3-phenylprop-2-enoyl]-1,4'-bipiperidin-3-amine MS (ESI, Pos.20V): 977 (2M+H)$^+$, 489 (M+H)$^+$, 359;
HPLC condition: A; HPLC retention time (min): 3.11.

Example 11-0612

N-(4-azepan-1-ylpyrimidin-2-yl)-1'-propionyl-1,4'-bipiperidin-3-amine

MS (ESI, Pos.20V): 415 (M+H)$^+$, 359, 180;
HPLC condition: A; HPLC retention time (min): 2.90.

Example 11-0613

N-(4-azepan-1-ylpyrimidin-2-yl)-1'-(cyclopropylcarbonyl)-1,4'-bipiperidin-3-amine MS (ESI, Pos.20V): 427 (M+H)$^+$, 359;
HPLC condition: A; HPLC retention time (min): 2.94.

Example 11-0614

N-(4-azepan-1-ylpyrimidin-2-yl)-1'-(2-chlorobenzoyl)-1,4'-bipiperidin-3-amine

MS (ESI, Pos.20V): 499, 497 (M+H)$^+$, 359, 249 (M+2H)$^{2+}$;
HPLC condition: A; HPLC retention time (min): 3.05.

Example 11-0615

N-(4-azepan-1-ylpyrimidin-2-yl)-1'-(cyclohexylcarbonyl)-1,4'-bipiperidin-3-amine MS (ESI, Pos.20V): 469 (M+H)$^+$, 359;
HPLC condition: A; HPLC retention time (min): 3.11.

Example 11-0616

N-(4-azepan-1-ylpyrimidin-2-yl)-1'-(2-fuiroyl)-1,4'-bipiperidin-3-amine

MS (ESI, Pos.20V): 453 (M+H)$^+$, 359, 227 (M+2H)$^{2+}$;
HPLC condition: A; HPLC retention time (min): 2.96.

Example 11-0617

N-(4-azepan-1-ylpyrimidin-2-yl)-1'-pentanoyl-1,4'-bipiperidin-3-amine

MS (ESI, Pos.20V): 443 (M+H)$^+$, 359, 222 (M+2H)$^{2+}$, 193;
HPLC condition: A; HPLC retention time (min): 3.03.

Example 11-0618

N-(4-azepan-1-ylpyrimidin-2-yl)-1'-(phenoxyacetyl)-1,4'-bipiperidin-3-amine

MS (ESI, Pos.20V): 493 (M+H)$^+$, 443, 247 (M+2H)$^{2+}$;
HPLC condition: A; HPLC retention time (min): 3.07.

Example 11-0619

N-(4-azepan-1-ylpyrimidin-2-yl)-1'-octanoyl-1,4'-bipiperidin-3-amine

MS (ESI, Pos.20V): 485 (M+H)$^+$, 359, 243 (M+2H)$^{2+}$;
HPLC condition: A; HPLC retention time (min): 3.25.

Example 11-0620

N-(4-azepan-1-ylpyrimidin-2-yl)-1'-(3-phenylpropanoyl)-1,4'-bipiperidin-3-amine

MS (ESI, Pos.20V): 491 (M+H)$^+$, 359, 246 (M+2H)$^{2+}$;
HPLC condition: A; HPLC retention time (min): 3.11.

Example 11-0621

N-(4-azepan-1-ylpyrimidin-2-yl)-1'-[2-(trifluoromethyl)benzoyl]-1,4'-bipiperidin-3-amine MS (ESI, Pos.20V): 531 (M+H)$^+$, 359, 266 (M+2H)$^{2+}$;
HPLC condition: A; HPLC-retention time (min): 3.09.

Example 11-0622

N-(4-azepan-1-ylpyrimidin-2-yl)-1'-(2-naphthoyl)-1,4'-bipiperidin-3-amine

MS (ESI, Pos.20V): 513 (M+H)$^+$, 359, 155;
HPLC condition: A; HPLC retention time (min): 3.14.

Example 11-0623

N-(4-azepan-1-ylpyrimidin-2-yl)-1'-(thien-2-ylacetyl)-1,4'-bipiperidin-3-amine

MS (ESI, Pos.20V): 483 (M+H)$^+$, 242 (M+2H)$^{2+}$, 193;
HPLC condition: A; HPLC retention time (min): 3.05.

Example 11-0624

N-(4-azepan-1-ylpyrimidin-2-yl)-1'-(3,3-dimethylbutanoyl)-1,4'-bipiperidin-3-amine MS (ESI, Pos.20V): 457 (M+H)$^+$, 359, 180;
HPLC condition: A; HPLC retention time (min): 3.07.

Example 11-0625

N-(4-azepan-1-ylpyrimidin-2-yl)-1'-(3-methoxybenzoyl)-1,4'-bipiperidin-3-amine

MS (ESI, Pos.20V): 493 (M+H)$^+$, 359, 193, 135;
HPLC condition: A; HPLC retention time (min): 3.05.

Example 11-0626

N-(4-azepan-1-ylpyrimidin-2-yl)-1'-(2-ethylhexanoyl)-1,4'-bipiperidin-3-amine

MS (ESI, Pos.20V): 485 (M+H)$^+$, 359;
HPLC condition: A; HPLC retention time (min): 3.20.

Example 11-0627

N-(4-azepan-1-ylpyrimidin-2-yl)-1'-(3-fluorobenzoyl)-1,4'-bipiperidin-3-amine

MS (ESI, Pos.20V): 481 (M+H)$^+$, 359, 241 (M+2H)$^{2+}$, 123;
HPLC condition: A; HPLC retention time (min): 3.05.

Example 11-0628

N-(4-azepan-1-ylpyrimidin-2-yl)-1'-(3-chlorobenzoyl)-1,4'-bipiperidin-3-amine

MS (ESI, Pos.20V): 499, 497 (M+H)$^+$, 359, 249 (M+2H)$^{2+}$, 139
HPLC condition: A; HPLC retention time (min): 3.11.

Example 11-0629

N-(4-azepan-1-ylpyrimidin-2-yl)-1'-(4-tert-butylbenzoyl)-1,4'-bipiperidin-3-amine MS (ESI, Pos.20V): 519 (M+H)$^+$, 359, 161;
HPLC condition: A; HPLC retention time (min): 3.25.

Example 11-0630

N-(4-azepan-1-ylpyrimidin-2-yl)-1'-(thien-2-ylcarbonyl)-1,4'-bipiperidin-3-amine MS (ESI, Pos.20V): 469 (M+H)$^+$, 359, 193;
HPLC condition: A; HPLC retention time (min): 3.01.

Example 11-0631

N-(4-azepan-1-ylpyrimidin-2-yl)-1'-[(4-chlorophenyl)acetyl]-1,4'-bipiperidin-3-amine MS (ESI, Pos.20V): 513, 511 (M+H)$^+$, 359, 256 (M+2H)$^{2+}$;
HPLC condition: A; HPLC retention time (min): 3.14.

Example 11-0632

N-(4-azepan-1-ylpyrimidin-2-yl)-1'-(3-methylbutanoyl)-1,4'-bipiperidin-3-amine

MS (ESI, Pos.20V): 443 (M+H)$^+$, 359, 193;
HPLC condition: A; HPLC retention time (min): 3.01.

Example 11-0633

N-(4-azepan-1-ylpyrimidin-2-yl)-1'-[4-(trifluoromethyl)benzoyl]-1,4'-bipiperidin-3-amine MS (ESI, Pos.20V): 531 (M+H)$^+$, 266 (M+2H)$^{2+}$;
HPLC condition: A; HPLC retention time (min): 3.18.

Example 11-0634

N-(4-azepan-1-ylpyrimidin-2-yl)-1'-benzoyl-1,4'-bipiperidin-3-amine

MS (ESI, Pos.20V): 463 (M+H)$^+$, 359, 193
HPLC condition: A; HPLC retention time (min): 3.01.

Example 11-0635

N-(4-azepan-1-ylpyrimidin-2-yl)-1'-(2-fluorobenzoyl)-1,4'-bipiperidin-3-amine

MS (ESI, Pos.20V): 481 (M+H)$^+$, 359, 241 (M+2H)$^{2+}$, 193;
HPLC condition: A; HPLC retention time (min): 3.01.

Example 11-0636

N-(4-azepan-1-ylpyrimidin-2-yl)-1'-(diphenylacetyl)-1,4'-bipiperidin-3-amine

MS (ESI, Pos.20V): 553 (M+H)$^+$, 359, 277 (M+2H)$^{2+}$, 167;
HPLC condition: A; HPLC retention time (min): 3.25.

Example 11-0637

N-(4-azepan-1-ylpyrimidin-2-yl)-1'-(2-phenoxypropanoyl)-1,4'-bipiperidin-3-amine MS (ESI, Pos.20V): 507 (M+H)$^+$, 359, 254 (M+2H)$^{2+}$, 121;
HPLC condition: A; HPLC retention time (min): 3.11.

Example 11-0638

N-(4-azepan-1-ylpyrimidin-2-yl)-1'-(2-methylpentanoyl)-1,4'-bipiperidin-3-amine

MS (ESI, Pos.20V): 457 (M+H)$^+$, 359;
HPLC condition: A; HPLC retention time (min): 3.09.

Example 11-0639

N-(4-azepan-1-ylpyrimidin-2-yl)-1'-(methoxyacetyl)-1,4'-bipiperidin-3-amine

MS (ESI, Pos.20V): 431 (M+H)$^+$, 359, 276, 216 (M+2H)$^{2+}$;
HPLC condition: A; HPLC retention time (min): 2.87.

Example 11-0640 ethyl 4-3-[(4-azepan-1-ylpyrimidin-2-yl)amino]-1,4'-bipiperidin-1'-yl-4-oxobutanoate MS (ESI, Pos.20V): 487 (M+H)$^+$, 244 (M+2H)$^{2+}$, 221;
HPLC condition: A; HPLC retention time (min): 3.00.

Example 11-0641

N-(4-azepan-1-ylpyrimidin-2-yl)-1'-(3-cyclopentylpropanoyl)-1,4'-bipiperidin-3-amine MS (ESI, Pos.20V): 483 (M+H)$^+$, 359, 242 (M+2H)$^{2+}$;
HPLC condition: A; HPLC retention time (min): 3.20.

Example 11-0642

N-(4-azepan-1-ylpyrimidin-2-yl)-1'-(2-propylpentanoyl)-1,4'-bipiperidin-3-amine

MS (ESI, Pos.20V): 485 (M+H)$^+$, 359;
HPLC condition: A; 1HPLC retention time (min): 3.20.

Example 11-0643 methyl 5-3-[(4-azepan-1-ylpyrimidin-2-yl)amino]-1,4'-bipiperidin-1'-yl-5-oxopentanoate MS (ESI, Pos.20V): 487 (M+H)$^+$, 228;
HPLC condition: A; HPLC retention time (min): 2.96.

Example 11-0644

N-(4-azepan-1-ylpyrimidin-2-yl)-1'-[(4-chlorophenoxy)acetyl]-1,4'-bipiperidin-3-amine MS (ESI, Pos.20V): 529, 527 (M+H)$^+$, 264 (M+2H)$^{2+}$;
HPLC condition: A; HPLC retention time (min): 3.16.

Example 11-0646

N-(4-azepan-1-ylpyrimidin-2-yl)-1'-(cyclopentylcarbonyl)-1,4'-bipiperidin-3-amine MS (ESI, Pos.20V): 455 (M+H)$^+$, 359, 193;
HPLC condition: A; HPLC retention time (min): 3.05.

Example 11-0647

N-(4-azepan-1-ylpyrimidin-2-yl)-1'-(mesitylcarbonyl)-1,4'-bipiperidin-3-amine

MS (ESI, Pos.20V): 505 (M+H)$^+$, 359, 267, 147;
HPLC condition: A; HPLC retention time (min): 3.14.

Example 11-0648

N-(4-azepan-1-ylpyrimidin-2-yl)-1'-[(3-methoxyphenyl)acetyl]-1,4'-bipiperidin-3-amine MS (ESI, Pos.20V): 507 (M+H)$^+$, 359, 254 (M+2H)$^{2+}$, 180;
HPLC condition: A; HPLC retention time (min): 3.05.

Example 11-0649 ethyl 3-3-[(4-azepan-1-ylpyrimidin-2-yl)amino]-1,4'-bipiperidin-1'-yl-3-oxopropanoate MS (ESI, Pos.20V): 473 (M+H)$^+$, 359, 237 (M+2H)$^{2+}$;
HPLC condition: A; HPLC retention time (min): 2.94.

Example 11-0650

N-(4-azepan-1-ylpyrimidin-2-yl)-1'-(4-butoxybenzoyl)-1,4'-bipiperidin-3-amine

MS (ESI, Pos.20V): 535 (M+H)$^+$, 359, 177;
HPLC condition: A; HPLC retention time (min): 3.27.

Example 11-0651

N-(4-azepan-1-ylpyrimidin-2-yl)-1'-[(benzyloxy)acetyl]-1,4'-bipiperidin-3-amine

MS (ESI, Pos.20V): 507 (M+H)$^+$, 417;
HPLC condition: A; HPLC retention time (min): 3.09.

Example 11-0652

N-(4-azepan-1-ylpyrimidin-2-yl)-1'-(2-methylbutanoyl)-1,4'-bipiperidin-3-amine

MS (ESI, Pos.20V): 443 (M+H)$^+$, 359, 193;
HPLC condition: A; HPLC retention time (min): 3.01.

Example 11-0653

N-(4-azepan-1-ylpyrimidin-2-yl)-1'-[(4-methoxyphenyl)acetyl]-1,4'-bipiperidin-3-amine MS (ESI, Pos.20V): 507 (M+H)$^+$, 359, 254 (M+2H)$^{2+}$, 121;
HPLC condition: A; HPLC retention time (min): 3.07.

Example 11-0654 ethyl 5-3-[(4-azepan-1-ylpyrimidin-2-yl)amino]-1,4'-bipiperidin-1'-yl-5-oxopentanoate MS (ESI, Pos.20V): 501 (M+H)$^+$, 251 (M+2H)$^{2+}$, 228;
HPLC condition: A; HPLC retention time (min): 3.01.

Example 11-0655

N-(4-azepan-1-ylpyrimidin-2-yl)-1'-(cyclobutylcarbonyl)-1,4'-bipiperidin-3-amine MS (ESI, Pos.20V): 441 (M+H)$^+$, 359, 193;
HPLC condition: A; HPLC retention time (min): 3.00.

Example 11-0656

N-(4-azepan-1-ylpyrimidin-2-yl)-1'-(2-ethylbutanoyl)-1,4'-bipiperidin-3-amine

MS (ESI, Pos.20V): 457 (M+H)$^+$, 359;
HPLC condition: A; HPLC retention time (min): 3.05.

Example 11-0657

N-(4-azepan-1-ylpyrimidin-2-yl)-1'-[4-(trifluoromethoxy)benzoyl]-1,4'-bipiperidin-3-amine MS (ESI, Pos.20V): 547 (M+H)$^+$, 359, 189;
HPLC condition: A; HPLC retention time (min): 3.22.

Example 11-0658

N-(4-azepan-1-ylpyrimidin-2-yl)-1'-(methylsulfonyl)-1,4'-bipiperidin-3-amine

MS (ESI, Pos.20V): 437 (M+H)$^+$, 276, 219 (M+2H)$^{2+}$;
HPLC condition: A; HPLC retention time (min): 2.92.

Example 11-0659

N-(4-azepan-1-ylpyrimidin-2-yl)-1'-(pentylsulfonyl)-1,4'-bipiperidin-3-amine

MS (ESI, Pos.20V): 985 (2M+H)$^+$, 493 (M+H)$^+$, 247 (M+2H)$^{2+}$;
HPLC condition: A; HPLC retention time (min): 3.20.

Example 11-0660

N-(4-azepan-1-ylpyrimidin-2-yl)-1'-(propylsulfonyl)-1,4'-bipiperidin-3-amine

MS (ESI, Pos.20V): 929 (2M+H)$^+$, 465 (M+H)$^+$, 233 (M+2H)$^{2+}$;
HPLC condition: A; HPLC retention time (min): 3.05.

Example 11-0661

N-(4-azepan-1-ylpyrimidin-2-yl)-1'-(isopropylsulfonyl)-1,4'-bipiperidin-3-amine

MS (ESI, Pos.20V): 929 (2M+H)$^+$, 465 (M+H)$^+$, 233 (M+2H)$^{2+}$;
HPLC condition: A; HPLC retention time (min): 3.01.

Example 11-0662

N-(4-azepan-1-ylpyrimidin-2-yl)-1,4'-bipiperidin-3-amine

MS (ESI, Pos.20V): 359 (M+H)$^+$, 276, 180 (M+2H)$^{2+}$;
HPLC condition: A; HPLC retention time (min): 2.83.

Example 11-0663

N-(4-azepan-1-ylpyrimidin-2-yl)-1'-(butylsulfonyl)-1,4'-bipiperidin-3-amine

MS (ESI, Pos.20V): 957 (2M+H)$^+$, 479 (M+H)$^+$, 240 (M+2H)$^{2+}$;
HPLC condition: A; HPLC retention time (min): 3.12.

Example 11-0664

N-(4-azepan-1-ylpyrimidin-2-yl)-1'-(phenylsulfonyl)-1,4'-bipiperidin-3-amine

MS (ESI, Pos.20V): 997 (2M+H)$^+$, 499 (M+H)$^+$, 250 (M+2H)$^{2+}$;
HPLC condition: A; HPLC retention time (min): 3.12.

Example 11-0665

N-(4-azepan-1-ylpyrimidin-2-yl)-1'-[(4-chlorophenyl)sulfonyl]-1,4'-bipiperidin-3-amine MS (ESI, Pos.20V): 535, 533 (M+H)$^+$, 267 (M+2H)$^{2+}$;
HPLC condition: A; HPLC retention time (min): 3.22.

Example 11-0666

N-(4-azepan-1-ylpyrimidin-2-yl)-1'-[4-(trifluoromethyl)phenyl]sulfonyl-1,4'-bipiperidin-3-amine MS (ESI, Pos.20V): 567 (M+H)$^+$, 284 (M+2H)$^{2+}$;
HPLC condition: A; HPLC retention time (min): 3.29.

Example 11-0667

N-(4-azepan-1-ylpyrimidin-2-yl)-1'-[(4-methoxyphenyl)sulfonyl]-1,4'-bipiperidin-3-amine MS (ESI, Pos.20V): 529 (M+H)$^+$, 359, 265 (M+2H)$^{2+}$;
HPLC condition: A; HPLC retention time (min): 3.16.

Example 11-0668

N-(4-azepan-1-ylpyrimidin-2-yl)-1'-(benzylsulfonyl)-1,4'-bipiperidin-3-amine

MS (ESI, Pos.20V): 513 (M+H)$^+$, 359;
HPLC condition: A; HPLC retention time (min): 3.14.

Example 11-0669

N-(4-azepan-1-ylpyrimidin-2-yl)-1'-[(4-methylphenyl)sulfonyl]-1,4'-bipiperidin-3-amine MS (ESI, Pos.20V): 513 (M+H)$^+$, 276, 257 (M+2H)$^{2+}$, 238;
HPLC condition: A; HPLC retention time (min): 3.20.

Example 11-0670

N-(4-azepan-1-ylpyrimidin-2-yl)-1'-[(3-methylphenyl)sulfonyl]-1,4'-bipiperidin-3-amine MS (ESI, Pos.20V): 513 (M+H)$^+$, 276, 257 (M+2H)$^{2+}$;
HPLC condition: A; HPLC retention time (min): 3.18.

Example 11-0671

N-(4-azepan-1-ylpyrimidin-2-yl)-1'-[(2-me-thylphenyl)sulfonyl]-1,4'-bipiperidin-3-amine MS (ESI, Pos.20V): 513 (M+H)$^+$, 276, 257 (M+2H)$^{2+}$, 238;
HPLC condition: A; HPLC retention time (min): 3.20.

Example 11-0672

N-(4-azepan-1-ylpyrimidin-2-yl)-1'-[4-(trifluoromethoxy)phenyl]sulfonyl-1,4'-bipiperidin-3-amine MS (ESI, Pos.20V): 583 (M+H)$^+$, 292 (M+2H)$^{2+}$;
HPLC condition: A; HPLC retention time (min): 3.33.

Example 11-0673

N-(4-azepan-1-ylpyrimidin-2-yl)-1'-[(4-butoxyphenyl)sulfonyl]-1,4'-bipiperidin-3-amine MS (ESI, Pos.20V): 571 (M+H)$^+$, 359, 286 (M+2H)$^{2+}$;
HPLC condition: A; HPLC retention time (min): 3.38.

Example 11-0674

N-(4-azepan-1-ylpyrimidin-2-yl)-1'-[(4-tert-butylphenyl)sulfonyl]-1,4'-bipiperidin-3-amine MS (ESI, Pos.20V): 555 (M+H)$^+$, 278 (M+2H)$^{2+}$;
HPLC condition: A; HPLC retention time (min): 3.38.

Example 11-0675

N-(4-azepan-1-ylpyrimidin-2-yl)-1'-[(4-nitrophenyl)sulfonyl]-1,4'-bipiperidin-3-amine MS (ESI, Pos.20V): 544 (M+H)$^+$, 292;
HPLC condition: A; HPLC retention time (min): 3.20.

Example 11-0676

4-(3-[(4-azepan-1-ylpyrimidin-2-yl)amino]-1,4'-bipiperidin-1'-ylsulfonyl)benzonitrile MS (ESI, Pos.20V): 524 (M+H)$^+$, 262.5 (M+2H)$^{2+}$;
HPLC condition: A; HPLC retention time (min): 3.14.

Example 11-0677

N-(4-azepan-1-ylpyrimidin-2-yl)-1'-(2-naphthylsulfonyl)-1,4'-bipiperidin-3-amine MS (ESI, Pos.20V): 549 (M+H)$^+$, 275 (M+2H)$^{2+}$;
HPLC condition: A; HPLC retention time (min): 3.27.

Example 11-0678

N-(4-azepan-1-ylpyrimidin-2-yl)-1-(1-isobutyrylpiperidin-3-yl)azepan-3-amine

MS (ESI, Pos.20V): 443 (M+H)$^+$, 373, 290, 222(M+2H)$^{2+}$;
HPLC condition: A; HPLC retention time (min): 3.03.

Example 11-0679

N-(4-azepan-1-ylpyrimidin-2-yl)-1-(1-butyrylpiperidin-3-yl)azepan-3-amine

MS (ESI, Pos.20V): 443 (M+H)$^+$, 290, 222(M+2H)$^{2+}$;
HPLC condition: A; HPLC retention time (min): 3.03.

Example 11-0680

N-(4-azepan-1-ylpyrimidin-2-yl)-1-[1-(3-methylbenzoyl)piperidin-3-yl]azepan-3-amine MS (ESI, Pos.20V): 491 (M+H)$^+$, 373, 246 (M+2H)$^{2+}$, 119;
HPLC condition: A; HPLC retention time (min): 3.12.

Example 11-0681

1-(1-acetylpiperidin-3-yl)-N-(4-azepan-1-ylpyrimidin-2-yl)azepan-3-amine

MS (ESI, Pos.20V): 415 (M+H)$^+$, 373, 290, 208 (M+2H)$^{2+}$;
HPLC condition: A; HPLC retention time (min): 2.92.

Example 11-0682

N-(4-azepan-1-ylpyrimidin-2-yl)-1-[1-(4-fluorobenzoyl)piperidin-3-yl]azepan-3-amine MS (ESI, Pos.20V): 495 (M+H)$^+$, 373, 248 (M+2H)$^{2+}$, 130;
HPLC condition: A; HPLC retention time (min): 3.11.

Example 11-0683

N-(4-azepan-1-ylpyrimidin-2-yl)-1-[1-(4-methylbenzoyl)piperidin-3-yl]azepan-3-amine MS (ESI, Pos.20V): 491 (M+H)$^+$, 373, 246 (M+2H)$^{2+}$, 119;
HPLC condition: A; HPLC retention time (min): 3.14.

Example 11-0684

N-(4-azepan-1-ylpyrimidin-2-yl)-1-(1-heptanoylpiperidin-3-yl)azepan-3-amine

MS (ESI, Pos.20V): 485 (M+H)$^+$, 290, 243 (M+2H)$^{2+}$;
HPLC condition: A; HPLC retention time (min): 3.27.

Example 11-0685

N-(4-azepan-1-ylpyrimidin-2-yl)-1-[1-(2-methoxybenzoyl)piperidin-3-yl]azepan-3-amine MS (ESI, Pos.20V): 507 (M+H)$^+$, 373, 254 (M+2H)$^{2+}$, 135;
HPLC condition: A; HPLC retention time (min): 3.09.

Example 11-0686

N-(4-azepa-1-ylpyrimidin-2-yl)-1-[1-(2-methylbenzoyl)piperidin-3-yl]azepan-3-amine MS (ESI, Pos.20V): 491 (M+H)$^+$, 373, 246 (M+2H)$^{2+}$, 119;
HPLC condition: A; HPLC retention time (min): 3.11.

Example 11-0687

N-(4-azepan-1-ylpyrimidin-2-yl)-1-(1-hexanoylpiperidin-3-yl)azepan-3-amine

MS (ESI, Pos.20V): 471 (M+H)$^+$, 373, 290, 236 (M+2H)$^{2+}$;
HPLC condition: A; HPLC retention time (min): 3.16.

Example 11-0688

N-(4-azepan-1-ylpyrimidin-2-yl)-1-[1-(phenylacetyl)piperidin-3-yl]azepan-3-amine MS (ESI, Pos.20V): 491 (M+H)$^+$, 290, 246 (M+2H)$^{2+}$;
HPLC condition: A; HPLC retention time (min): 3.12.

Example 11-0689

N-(4-azepan-1-ylpyrimidin-2-yl)-1-[1-(4-methoxybenzoyl)piperidin-3-yl]azepan-3-amine MS (ESI, Pos.20V): 507 (M+H)$^+$, 373, 254 (M+2H)$^{2+}$, 135;
HPLC condition: A; HPLC retention time (min): 3.11.

Example 11-0690

N-(4-azepan-1-ylpyrimidin-2-yl)-1-1-[(2E)-3-phenylprop-2-enoyl]piperidin-3-ylazepan-3-amine MS (ESI, Pos.20V): 503 (M+H)$^+$, 373, 252 (M+2H)2, 131;
HPLC condition: A; HPLC retention time (min): 3.18.

Example 11-0691

N-(4-azepan-1-ylpyrimidin-2-yl)-1-(1-propionylpiperidin-3-yl)azepan-3-amine

MS (ESI, Pos.20V): 429 (M+H)$^+$, 290, 215 (M+2H)$^{2+}$;
HPLC condition: A; HPLC retention time (min): 2.98.

Example 11-0692

N-(4-azepan-1-ylpyrimidin-2-yl)-1-[1-(cyclopropylcarbonyl)piperidin-3-yl]azepan-3-amine MS (ESI, Pos.20V): 441 (M+H)$^+$, 373, 290, 221 (M+2H)$^{2+}$;
HPLC condition: A; HPLC retention time (min): 3.00.

Example 11-0693

N-(4-azepan-1-ylpyrimidin-2-yl)-1-[1-(2-chlorobenzoyl)piperidin-3-yl]azepan-3-amine MS (ESI, Pos.20V): 513, 511 (M+H)$^+$, 256 (M+2H)$^{2+}$;
HPLC condition: A; HPLC retention time (min): 3.11.

Example 11-0694

N-(4-azepan-1-ylpyrimidin-2-yl)-1-[1-(cyclohexylcarbonyl)piperidin-3-yl]azepan-3-amine MS (ESI, Pos.20V): 483 (M+H)$^+$, 373, 242 (M+2H)$^{2+}$, 111;
HPLC condition: A; HPLC retention time (min): 3.16.

Example 11-0695

N-(4-azepan-1-ylpyrimidin-2-yl)-1-[1-(2-furoyl)piperidin-3-yl]azepan-3-amine

MS (ESI, Pos.20V): 467 (M+H)$^+$, 290, 234 (M+2H)$^{2+}$;
HPLC condition: A; HPLC retention time (min): 3.01.

Example 11-0696

N-(4-azepan-1-ylpyrimidin-2-yl)-1-(1-pentanoylpiperidin-3-yl)azepan-3-amine

MS (ESI, Pos.20V): 457 (M+H)$^+$, 290, 229 (M+2H)$^{2+}$;
HPLC condition: A; HPLC retention time (min): 3.11.

Example 11-0697

N-(4-azepan-1-ylpyrimidin-2-yl)-1-[1-(phenoxyacetyl)piperidin-3-yl]azepan-3-amine MS (ESI, Pos.20V): 507, (M+H)$^+$, 457, 290, 254 (M+2H)$^{2+}$;
HPLC condition: A; HPLC retention time (min): 3.16.

Example 11-0698

N-(4-azepan-1-ylpyrimidin-2-yl)-1-(1-octanoylpiperidin-3-yl)azepan-3-amine

MS (ESI, Pos.20V): 499 (M+H)$^+$, 373, 250 (M+2H)$^{2+}$;
HPLC condition: A; HPLC retention time (min): 3.36.

Example 11-0699

N-(4-azepan-1-ylpyrimidin-2-yl)-1-[1-(3-phenylpropanoyl)piperidin-3-yl]azepan-3-amine MS (ESI, Pos.20V): 505 (M+H)$^+$, 253 (M+2H)$^{2+}$;
HPLC condition: A; HPLC retention time (min): 3.18.

Example 11-0700

N-(4-azepan-1-ylpyrimidin-2-yl)-1-1-[2-(trifluoromethyl)benzoyl]piperidin-3-ylazepan-3-amine MS (ESI, Pos.20V): 545 (M+H)$^+$, 273 (M+2H)$^{2+}$;
HPLC condition: A; HPLC retention time (min): 3.18.

Example 11-0701

N-(4-azepan-1-ylpyrimidin-2-yl)-1-[1-(2-naphthoyl)piperidin-3-yl]azepan-3-amine

MS (ESI, Pos.20V): 527 (M+H)$^+$, 373, 264 (M+2H)$^{2+}$, 155;
HPLC condition: A; HPLC retention time (min): 3.22.

Example 11-0702

N-(4-azepan-1-ylpyrimidin-2-yl)-1-[1-(thien-2-ylacetyl)piperidin-3-yl]azepan-3-amine MS (ESI, Pos.20V): 497 (M+H)$^+$, 290, 249 (M+2H)$^{2+}$;
HPLC condition: A; HPLC retention time (min): 3.11.

Example 11-0703

N-(4-azepan-1-ylpyrimidin-2-yl)-1-[1-(3,3-dimethylbutanoyl)piperidin-3-yl]azepan-3-amine MS (ESI, Pos.20V): 471 (M+H)$^+$, 373, 236 (M+2H)$^{2+}$;
HPLC condition: A; HPLC retention time (min): 3.14.

Example 11-0704

N-(4-azepan-1-ylpyrimidin-2-yl)-1-[1-(3-methoxybenzoyl)piperidin-3-yl]azepan-3-amine MS (ESI, Pos.20V): 507 (M+H)$^+$, 373, 254 (M+2H)$^{2+}$, 135;
HPLC condition: A; HPLC retention time (min): 3.11.

Example 11-0705

N-(4-azepan-1-ylpyrimidin-2-yl)-1-[1-(2-ethylhexanoyl)piperidin-3-yl]azepan-3-amine MS (ESI, Pos.20V): 499 (M+H)$^+$, 373, 250 (M+2H)$^{2+}$;
HPLC condition: A; HPLC retention time (min): 3.29.

Example 11-0706

N-(4-azepan-1-ylpyrimidin-2-yl)-1-[1-(3-fluorobenzoyl)piperidin-3-yl]azepan-3-amine MS (ESI, Pos.20V): 495 (M+H)$^+$, 290, 248 (M+2H)$^{2+}$, 206;
HPLC condition: A; HPLC retention time (min): 3.11.

Example 11-0707

N-(4-azepan-1-ylpyrimidin-2-yl)-1-[1-(3-chlorobenzoyl)piperidin-3-yl]azepan-3-amine MS (ESI, Pos.20V): 513, 511 (M+H)$^+$, 290, 256 (M+2H)$^{2+}$;
HPLC condition: A; HPLC retention time (min): 3.18.

Example 11-0708

N-(4-azepan-1-ylpyrimidin-2-yl)-1-[1-(4-tert-butylbenzoyl)piperidin-3-yl]azepan-3-amine MS (ESI, Pos.20V): 533 (M+H)$^+$, 373, 267 (M+2H)$^{2+}$;
HPLC condition: A; HPLC retention time (min): 3.34.

Example 11-0709

N-(4-azepan-1-ylpyrimidin-2-yl)-1-[1-(thien-2-ylcarbonyl)piperidin-3-yl]azepan-3-amine MS (ESI, Pos.20V): 483 (M+H)$^+$, 373, 242 (M+2H)$^{2+}$, 111;
HPLC condition: A; HPLC retention time (min): 3.07.

Example 11-0710

N-(4-azepan-1-ylpyrimidin-2-yl)-1-1-[(4-chlorophenyl)acetyl]piperidin-3-ylazepan-3-amine MS (ESI, Pos.20V): 527, 525 (M+H)$^+$, 263 (M+2H)$^{2+}$;
HPLC condition: A; HPLC retention time (min): 3.22.

Example 11-0711

N-(4-azepan-1-ylpyrimidin-2-yl)-1-[1-(3-methylbutanoyl)piperidin-3-yl]azepan-3-amine MS (ESI, Pos.20V): 457 (M+H)$^+$, 373, 290, 229 (M+2H)$^{2+}$;
HPLC condition: A; HPLC retention time (min): 3.09.

Example 11-0712

N-(4-azepan-1-ylpyrimidin-2-yl)-1-1-[4-(trifluoromethyl)benzoyl]piperidin-3-ylazepan-3-amine MS (ESI, Pos.20V): 545 (M+H)$^+$, 273 (M+2H)$^{2+}$;
HPLC condition: A; HPLC retention time (min): 3.25.

Example 11-0713

N-(4-azepan-1-ylpyrimidin-2-yl)-1-(1-benzoylpiperidin-3-yl)azepan-3-amine

MS (ESI, Pos.20V): 477 (M+H)$^+$, 373, 239 (M+2H)$^{2+}$;
HPLC condition: A; HPLC retention time (min): 3.07.

Example 11-0714

N-(4-azepan-1-ylpyrimidin-2-yl)-1-[1-(2-fluorobenzoyl)piperidin-3-yl]azepan-3-amine MS (ESI, Pos.20V): 495 (M+H)$^+$, 290,248 (M+2H)$^{2+}$, 206;
HPLC condition: A; HPLC retention time (min): 3.07.

Example 11-0715

N-(4-azepan-1-ylpyrimidin-2-yl)-1-[1-(diphenylacetyl)piperidin-3-yl]azepan-3-amine MS (ESI, Pos.20V): 567 (M+H)$^+$, 373, 284, (M+2H)$^{2+}$, 167;
HPLC condition: A; HPLC retention time (min): 3.31.

Example 11-0716

N-(4-azepan-1-ylpyrimidin-2-yl)-1-[1-(2-phenoxypropanoyl)piperidin-3-yl]azepan-3-amine MS (ESI, Pos.20V): 521 (M+H)$^+$, 261 (M+2H)$^{2+}$;
HPLC condition: A; HPLC retention time (min): 3.18.

Example 11-0717

N-(4-azepan-1-ylpyrimidin-2-yl)-1-[1-(2-methylpentanoyl)piperidin-3-yl]azepan-3-amine MS (ESI, Pos.20V): 471 (M+H)$^+$, 373, 236 (M+2H)$^{2+}$;
HPLC condition: A; HPLC retention time (min): 3.16.

Example 11-0718

N-(4-azepan-1-ylpyrimidin-2-yl)-1-[1-(methoxyacetyl)piperidin-3-yl]azepan-3-amine MS (ESI, Pos.20V): 445 (M+H)$^+$, 373, 290, 223 (M+2H)$^{2+}$;
HPLC condition: A; HPLC retention time (min): 2.92.

Example 11-0719 ethyl 4-(3-3-[(4-azepan-1-ylpyrimidin-2-yl)amino]azepan-1-ylpiperidin-1-yl)-4-oxobutanoate MS (ESI, Pos.20V): 501 (M+H)$^+$, 251 (M+2H)$^{2+}$, 228;
HPLC condition: A; HPLC retention time (min): 3.05.

Example 11-0720

N-(4-azepan-1-ylpyrimidin-2-yl)-1-[1-(3-cyclopentylpropanoyl)piperidin-3-yl]azepan-3-amine MS (ESI, Pos.20V): 497 (M+H)$^+$, 373, 249 (M+2H)$^{2+}$;
HPLC condition: A; HPLC retention time (min): 3.27.

Example 11-0721

N-(4-azepan-1-ylpyrimidin-2-yl)-1-[1-(2-propylpentanoyl)piperidin-3-yl]azepan-3-amine MS (ESI, Pos.20V): 499 (M+H)$^+$, 373, 250 (M+2H)$^{2+}$;
HPLC condition: A; HPLC retention time (min): 3.29.

Example 11-0722 methyl 5-(3-3-[(4-azepan-1-ylpyrimidin-2-yl)amino]azepan-1-ylpiperidin-1-yl)-5-oxopentanoate MS (ESI, Pos.20V): 501 (M+H)$^+$, 235;
HPLC condition: A; HPLC retention time (min): 3.03.

Example 11-0723

N-(4-azepan-1-ylpyrimidin-2-yl)-1-1-[(4-chlorophenoxy)acetyl]piperidin-3-ylazepan-3-amine MS (ESI, Pos.20V): 543, 541 (M+H)$^+$, 271 (M+2H)$^{2+}$;
HPLC condition: A; HPLC retention time (min): 3.23.

Example 11-0725

N-(4-azepan-1-ylpyrimidin-2-yl)-1-[1-(cyclopentylacetyl)piperidin-3-yl]azepan-3-amine MS (ESI, Pos.20V): 483 (M+H)$^+$, 373, 242 (M+2H)$^{2+}$, 111;
HPLC condition: A; HPLC retention time (min): 3.20.

Example 11-0726

N-(4-azepan-1-ylpyrimidin-2-yl)-1-[1-(cyclopentylcarbonyl)piperidin-3-yl]azepan-3-amine MS (ESI, Pos.20V): 469 (M+H)$^+$, 373, 235 (M+2H)$^{2+}$;
HPLC condition: A; HPLC retention time (min): 3.12.

Example 11-0727

N-(4-azepan-1-ylpyrimidin-2-yl)-1-[1-(mesitylcarbonyl)piperidin-3-yl]azepan-3-amine MS (ESI, Pos.20V): 519 (M+H)$^+$, 373, 147;
HPLC condition: A; HPLC retention time (min): 3.25.

Example 11-0728

N-(4-azepan-1-ylpyrimidin-2-yl)-1-1-[(3-methoxyphenyl)acetyl]piperidin-3-ylazepan-3-amine MS (ESI, Pos.20V): 521 (M+H)$^+$, 261 (M+2H)$^{2+}$;
HPLC condition: A; HPLC retention time (min): 3.12.

Example 11-0729 ethyl 3-(3-3-[(4-azepan-1-ylpyrimidin-2-yl)amino]azepan-1-ylpiperidin-1-yl)-3-oxopropanoate MS (ESI, Pos.20V): 487 (M+H)$^+$, 290, 244 (M+2H)$^{2+}$;
HPLC condition: A; HPLC retention time (min): 3.03.

Example 11-0730

N-(4-azepan-1-ylpyrimidin-2-yl)-1-[1-(4-butoxybenzoyl)piperidin-3-yl]azepan-3-amine MS (ESI, Pos.20V): 549 (M+H)$^+$, 373, 177;
HPLC condition: A; HPLC retention time (min): 3.34.

Example 11-0731

N-(4-azepan-1-ylpyrimidin-2-yl)-1-1-[(benzyloxy)acetyl]piperidin-3-ylazepan-3-amine MS (ESI, Pos.20V): 521 (M+H)$^+$, 431;
HPLC condition: A; HPLC retention time (min): 3.16.

Example 11-0732

N-(4-azepan-1-ylpyrimidin-2-yl)-1-[1-(2-methylbutanoyl)piperidin-3-yl]azepan-3-amine MS (ESI, Pos.20V): 457 (M+H)$^+$, 373, 290, 229 (M+2H)$^{2+}$;
HPLC condition: A; HPLC retention time (min): 3.09.

Example 11-0733

N-(4-azepan-1-ylpyrimidin-2-yl)-1-1-[(4-methoxyphenyl)acetyl]piperidin-3-ylazepan-3-amine MS (ESI, Pos.20V): 521 (M+H)$^+$, 261 (M+2H)$^{2+}$, 121;
HPLC condition: A; HPLC retention time (min): 3.11.

Example 11-0734 ethyl 5-(3-3-[(4-azepan-1-ylpyrimidin-2-yl)amino]azepan-1-ylpiperidin-1-yl)-5-oxopentanoate MS (ESI, Pos.20V): 515 (M+H)$^+$, 235;
HPLC condition: A; HPLC retention time (min): 3.09.

Example 11-0735

N-(4-azepan-1-ylpyrimidin-2-yl)-1-[1-(cyclobutylcarbonyl)piperidin-3-yl]azepan-3-amine MS (ESI, Pos.20V): 455 (M+H)$^+$, 373, 290, 228 (M+2H)$^{2+}$;
HPLC condition: A; HPLC retention time (min): 3.05.

Example 11-0736

N-(4-azepan-1-ylpyrimidin-2-yl)-1-[1-(2-ethylbutanoyl)piperidin-3-yl]azepan-3-amine MS (ESI, Pos.20V): 471 (M+H)$^+$, 373, 236 (M+2H)$^{2+}$;
HPLC condition: A; HPLC retention time (min): 3.14.

Example 11-0737

N-(4-azepan-1-ylpyrimidin-2-yl)-1-1-[4-(trifluoromethoxy)benzoyl]piperidin-3-ylazepan-3-amine MS (ESI, Pos.20V): 561 (M+H)$^+$, 373, 281 (M+2H)$^{2+}$;
HPLC condition: A; HPLC retention time (min): 3.27.

Example 11-0738

N-(4-azepan-1-ylpyrimidin-2-yl)-1-[1-(methylsulfonyl)piperidin-3-yl]azepan-3-amine MS (ESI, Pos.20V): 451 (M+H)$^+$, 373, 290, 226 (M+2H)$^{2+}$;
HPLC condition: A; HPLC retention time (min): 2.98.

Example 11-0739

N-(4-azepan-1-ylpyrimidin-2-yl)-1-[1-(pentylsulfonyl)piperidin-3-yl]azepan-3-amine MS (ESI, Pos.20V): 507 (M+H)$^+$, 290, 254 (M+2H)$^{2+}$;
HPLC condition: A; HPLC retention time (min): 3.25.

Example 11-0740

N-(4-azepan-1-ylpyrimidin-2-yl)-1-[1-(propylsulfonyl)piperidin-3-yl]azepan-3-amine MS (ESI, Pos.20V): 479 (M+H)$^+$, 290, 240 (M+2H)$^{2+}$;
HPLC condition: A; HPLC retention time (min): 3.09.

Example 11-0741

N-(4-azepan-1-ylpyrimidin-2-yl)-1-[1-(isopropylsulfonyl)piperidin-3-yl]azepan-3-amine MS (ESI, Pos.20V): 479 (M+H)$^+$, 290, 240 (M+2H)$^{2+}$;
HPLC condition: A; HPLC retention time (min): 3.07.

Example 11-0742

N-(4-azepan-1-ylpyrimidin-2-yl)-1-piperidin-3-ylazepan-3-amine

MS (ESI, Pos.20V): 745 (2M+H)$^+$, 373 (M+H)$^+$, 290;
HPLC condition: A; HPLC retention time (min): 2.89.

Example 11-0743

N-(4-azepan-1-ylpyrimidin-2-yl)-1-[1-(butylsulfonyl)piperidin-3-yl]azepan-3-amine MS (ESI, Pos.20V): 493 (M+H)$^+$, 290, 247 (M+2H)$^{2+}$;
HPLC condition: A; HPLC retention time (min): 3.16.

Example 11-0744

N-(4-azepan-1-ylpyrimidin-2-yl)-1-[1-(phenylsulfonyl)piperidin-3-yl]azepan-3-amine MS (ESI, Pos.20V): 513 (M+H)$^+$, 290, 257 (M+2H)$^{2+}$;
HPLC condition: A; HPLC retention time (min): 3.18.

Example 11-0745

N-(4-azepan-1-ylpyrimidin-2-yl)-1-1-[(4-chlorophenyl)sulfonyl]piperidin-3-ylazepan-3-amine MS (ESI, Pos.20V): 549, 547 (M+H)$^+$, 274 (M+2H)$^{2+}$;
HPLC condition: A; HPLC retention time (min): 3.27.

Example 11-0746

N-(4-azepan-1-ylpyrimidin-2-yl)-1-(1-[4-(trifluoromethyl)phenyl]sulfonylpiperidin-3-yl)azepan-3-amine MS (ESI, Pos.20V): 581 (M+H)$^+$, 291 (M+2H)$^{2+}$;
HPLC condition: A; HPLC retention time (min): 3.33.

Example 11-0747

N-(4-azepan-1-ylpyrimidin-2-yl)-1-1-[(4-methoxyphenyl)sulfonyl]piperidin-3-ylazepan-3-amine MS (ESI, Pos.20V): 543 (M+H)$^+$, 272 (M+2H)$^{2+}$;
HPLC condition: A; HPLC retention time (min): 3.20.

Example 11-0748

N-(4-azepan-1-ylpyrimidin-2-yl)-1-[1-(benzylsulfonyl)piperidin-3-yl]azepan-3-amine MS (ESI, Pos.20V): 527 (M+H)$^+$, 373, 264 (M+2H)$^{2+}$;
HPLC condition: A; HPLC retention time (min): 3.20.

Example 11-0749

N-(4-azepan-1-ylpyrimidin-2-yl)-1-1-[(4-methylphenyl)sulfonyl]piperidin-3-ylazepan-3-amine MS (ESI, Pos.20V): 527 (M+H)$^+$, 290, 264 (M+2H)$^{2+}$;
HPLC condition: A; HPLC retention time (min): 3.21.

Example 11-0750

N-(4-azepan-1-ylpyrimidin-2-yl)-1-1-[(3-methylphenyl)sulfonyl]piperidin-3-ylazepan-3-amine MS (ESI, Pos.20V): 527 (M+H)$^+$, 290, 264 (M+2H)$^{2+}$;
HPLC condition: A; HPLC retention time (min): 3.23.

Example 11-0751

N-(4-azepan-1-ylpyrimidin-2-yl)-1-1-[(2-methylphenyl)sulfonyl]piperidin-3-ylazepan-3-amine MS (ESI, Pos.20V): 527 (M+H)$^+$, 290, 264 (M+2H)$^{2+}$;
HPLC condition: A; HPLC retention time (min): 3.22.

Example 11-0752

N-(4-azepan-1-ylpyrimidin-2-yl)-1-(1-[4-(trifluoromethoxy)phenyl]sulfonylpiperidin-3-yl)azepan-3-amine MS (ESI, Pos.20V): 597 (M+H)$^+$, 299(M+2H)$^{2+}$;
HPLC condition: A; HPLC retention time (min): 3.36.

Example 11-0753

N-(4-azepan-1-ylpyrimidin-2-yl)-1-1-[(4-butoxyphenyl)sulfonyl]piperidin-3-ylazepan-3-amine MS (ESI, Pos.20V): 585 (M+H)$^+$, 293 (M+2H)$^{2+}$;
HPLC condition: A; HPLC retention time (min): 3.44.

Example 11-0754

N-(4-azepan-1-ylpyrimidin-2-yl)-1-1-[(4-tert-butylphenyl)sulfonyl]piperidin-3-ylazepan-3-amine MS (ESI, Pos.20V): 569 (M+H)$^+$, 285 (M+2H)$^{2+}$;
HPLC condition: A; HPLC retention time (min): 3.42.

Example 11-0755

N-(4-azepan-1-ylpyrimidin-2-yl)-1-1-[(4-nitrophenyl)sulfonyl]piperidin-3-ylazepan-3-amine MS (ESI, Pos.20V): 558 (M+H)$^+$, 279.5 (M+2H)$^{2+}$;
HPLC condition: A; HPLC retention time (min): 3.25.

Example 11-0756

4-[(3-3-[(4-azepan-1-ylpyrimidin-2-yl)amino]azepan-1-ylpiperidin-1-yl)sulfonyl]benzonitrile MS (ESI, Pos.20V): 538 (M+H)$^+$, 269.5 (M+2H)$^{2+}$;
HPLC condition: A; HPLC retention time (min): 3.20.

Example 11-0757

N-(4-azepan-1-ylpyrimidin-2-yl)-1-[1-(2-naphthylsulfonyl)piperidin-3-yl]azepan-3-amine MS (ESI, Pos.20V): 563 (M+H)$^+$, 282 (M+2H)$^{2+}$;
HPLC condition: A; HPLC retention time (min): 3.31.

Example 11-0758

N-(4-azepan-1-ylpyrimidin-2-yl)-1-(1-isobutyrylpiperidin-4-yl)azepan-3-amine

MS (ESI, Pos.20V): 443 (M+H)$^+$, 373;
HPLC condition: A; HPLC retention time (min): 2.98.

Example 11-0759

N-(4-azepan-1-ylpyrimidin-2-yl)-1-(1-butyrylpiperidin-4-yl)azepan-3-amine

MS (ESI, Pos.20V): 443 (M+H)$^+$, 373, 187;
HPLC condition: A; HPLC retention time (min): 3.00.

Example 11-0760

N-(4-azepan-1-ylpyrimidin-2-yl)-1-[(3-methylbenzoyl)piperidin-4-yl]azepan-3-amine MS (ESI, Pos.20V): 491 (M+H)$^+$, 373, 119;
HPLC condition: A; HPLC retention time (min): 3.09.

Example 11-0761

1-(1-acetylpiperidin-4-yl)-N-(4-azepan-1-ylpyrimidin-2-yl)azepan-3-amine

MS (ESI, Pos.20V): 415 (M+H)$^+$, 373, 290, 187;
HPLC condition: A; HPLC retention time (min): 2.89.

Example 11-0762

N-(4-azepan-1-ylpyrimidin-2-yl)-1-[1-(4-fluorobenzoyl)piperidin-4-yl]azepan-3-amine MS (ESI, Pos.20V): 495 (M+H)$^+$, 373, 123;
HPLC condition: A; HPLC retention time (min): 3.07.

Example 11-0763

N-(4-azepan-1-ylpyrimidin-2-yl)-1-[1-(4-methylbenzoyl)piperidin-4-yl]azepan-3-amine MS (ESI, Pos.20V): 491 (M+H)$^+$, 373, 119;
HPLC condition: A; HPLC retention time (min): 3.09.

Example 11-0764

N-(4-azepan-1-ylpyrimidin-2-yl)-1-(1-heptanoylpiperidin-4-yl)azepan-3-amine

MS (ESI, Pos.20V): 485 (M+H)$^+$, 373, 243 (M+2H)$^{2+}$, 187;
HPLC condition: A; HPLC retention time (min): 3.22.

Example 11-0765

N-(4-azepan-1-ylpyrimidin-2-yl)-1-[1-(2-methoxybenzoyl)piperidin-4-yl]azepan-3-amine MS (ESI, Pos.20V): 507 (M+H)$^+$, 373, 135;
HPLC condition: A; HPLC retention time (min): 3.05.

Example 11-0766

N-(4-azepan-1-ylpyrimidin-2-yl)-1-[1-(2-methylbenzoyl)piperidin-4-yl]azepan-3-amine MS (ESI, Pos.20V): 981 (2M+H)$^+$, 491 (M+H)$^+$, 373, 119;
HPLC condition: A; HPLC retention time (min): 3.07.

Example 11-0767

N-(4-azepan-1-ylpyrimidin-2-yl)-1-(1-hexanoylpiperidin-4-yl)azepan-3-amine

MS (ESI, Pos.20V): 471 (M+H)$^+$, 373, 236 (M+2H)$^{2+}$;
HPLC condition: A; HPLC retention time (min): 3.12.

Example 11-0768

N-(4-azepan-1-ylpyrimidin-2-yl)-1-[1-(phenylacetyl)piperidin-4-yl]azepan-3-amine MS (ESI, Pos.20V): 491 (M+H)$^+$, 373, 246 (M+2H)$^{2+}$;
HPLC condition: A; HPLC retention time (min): 3.07.

Example 11-0769

N-(4-azepan-1-ylpyrimidin-2-yl)-1-[1-(4-methoxybenzoyl)piperidin-4-yl]azepan-3-amine MS (ESI, Pos.20V): 507 (M+H)$^+$, 373, 135;
HPLC condition: A; HPLC retention time (min): 3.05.

Example 11-0770

N-(4-azepan-1-ylpyrimidin-2-yl)-1-1-[(2E)-3-phenylprop-2-enoyl]piperidin-4-ylazepan-3-amine MS (ESI, Pos.20V): 503 (M+H)$^+$, 373, 131;
HPLC condition: A; HPLC retention time (min): 3.14.

Example 11-0771

N-(4-azepan-1-ylpyrimidin-2-yl)-1-(1-propionylpiperidin-4-yl)azepan-3-amine

MS (ESI, Pos.20V): 429 (M+H)$^+$, 373, 215 (M+2H)$^{2+}$;
HPLC condition: A; HPLC retention time (min): 2.94.

Example 11-0772

N-(4-azepan-1-ylpyrimidin-2-yl)-1-[1-(cyclopropylcarbonyl)piperidin-4-yl]azepan-3-amine MS (ESI, Pos.20V): 441 (M+H)$^+$, 373;
HPLC condition: A; HPLC retention time (min): 2.96.

Example 11-0773

N-(4-azepan-1-ylpyrimidin-2-yl)-1-[1-(2-chlorobenzoyl)piperidin-4-yl]azepan-3-amine MS (ESI, Pos.20V): 513, 511 (M+H)$^+$, 373, 256 (M+2H)$^{2+}$, 139;
HPLC condition: A; HPLC retention time (min): 3.07.

Example 11-0774

N-(4-azepan-1-ylpyrimidin-2-yl)-1-[1-(cyclohexylcarbonyl)piperidin-4-yl]azepan-3-amine MS (ESI, Pos.20V): 483 (M+H)$^+$, 373;
HPLC condition: A; HPLC retention time (min): 3.11.

Example 11-0775

N-(4-azepan-1-ylpyrimidin-2-yl)-1-[1-(2-furoyl)piperidin-4-yl]azepan-3-amine

MS (ESI, Pos.20V): 467 (M+H)$^+$, 234 (M+2H)$^{2+}$;
HPLC condition: A; HPLC retention time (min): 2.96.

Example 11-0776

N-(4-azepan-1-ylpyrimidin-2-yl)-1-(1-pentanoylpiperidin-4-yl)azepan-3-amine

MS (ESI, Pos.20V): 457 (M+H)$^+$, 373, 187;
HPLC condition: A; HPLC retention time (min): 3.07.

Example 11-0777

N-(4-azepan-1-ylpyrimidin-2-yl)-1-[1-(phenoxyacetyl)piperidin-4-yl]azepan-3-amine MS (ESI, Pos.20V): 507 (M+H)$^+$, 254 (M+2H)$^{2+}$;
HPLC condition: A; HPLC retention time (min): 3.11.

Example 11-0778

N-(4-azepan-1-ylpyrimidin-2-yl)-1-(1-octanoylpiperidin-4-yl)azepan-3-amine

MS (ESI, Pos.20V): 499 (M+H)$^+$, 373, 250 (M+2H)$^{2+}$;
HPLC condition: A; HPLC retention time (min) 3.31.

Example 11-0779

N-(4-azepan-1-ylpyrimidin-2-yl)-1-[1-(3-phenylpropanoyl)piperidin-4-yl]azepan-3-amine MS (ESI, Pos.20V): 505 (M+H)$^+$, 373, 253 (M+2H)$^{2+}$;
HPLC condition: A; HPLC retention time (min): 3.14.

Example 11-0780

N-(4-azepan-1-ylpyrimidin-2-yl)-1-1-[2-(trifluoromethyl)benzoyl]piperidin-4-ylazepan-3-amine MS (ESI, Pos.20V): 545 (M+H)$^+$, 373, 273 (M+2H)$^{2+}$;
HPLC condition: A; HPLC retention time (min): 3.11.

Example 11-0781

N-(4-azepan-1-ylpyrimidin-2-yl)-1-[1-(2-naphthoyl)piperidin-4-yl]azepan-3-amine

MS (ESI, Pos.20V): 527 (M+H)$^+$, 373, 155;
HPLC condition: A; HPLC retention time (min): 3.18.

Example 11-0782

N-(4-azepan-1-ylpyrimidin-2-yl)-1-[1-(thien-2-ylacetyl)piperidin-4-yl]azepan-3-amine MS (ESI, Pos.20V): 497 (M+H)$^+$, 249 (M+2H)$^{2+}$;
HPLC condition: A; HPLC retention time (min): 3.05.

Example 11-0783

N-(4-azepan-1-ylpyrimidin-2-yl)-1-[1-(3,3-dimethylbutanoyl)piperidin-4-yl]azepan-3-amine MS (ESI, Pos.20V): 471 (M+H)$^+$, 373, 187;
HPLC condition: A; HPLC retention time (min): 3.09.

Example 11-0784

N-(4-azepan-1-ylpyrimidin-2-yl)-1-[1-(3-methoxybenzoyl)piperidin-4-yl]azepan-3-amine MS (ESI, Pos.20V): 507 (M+H)$^+$, 373, 135;
HPLC condition: A; HPLC retention time (min): 3.07.

Example 11-0785

N-(4-azepan-1-ylpyrimidin-2-yl)-1-[1-(2-ethylhexanoyl)piperidin-4-yl]azepan-3-amine MS (ESI, Pos.20V): 499 (M+H)$^+$, 373;
HPLC condition: A; HPLC retention time (min): 3.22.

Example 11-0786

N-(4-azepan-1-ylpyrimidin-2-yl)-1-[1-(3-fluorobenzoyl)piperidin-4-yl]azepan-3-amine MS (ESI, Pos.20V): 495 (M+H)$^+$, 373, 248 (M+2H)$^{2+}$, 123;
HPLC condition: A; HPLC retention time (min): 3.07.

Example 11-0787

N-(4-azepan-1-ylpyrimidin-2-yl)-1-[1-(3-chlorobenzoyl)piperidin-4-yl]azepan-3-amine MS (ESI, Pos.20V): 513, 511 (M+H)$^+$, 373, 256 (M+2H)$^{2+}$;
HPLC condition: A; HPLC retention time (min): 3.12.

Example 11-0788

N-(4-azepan-1-ylpyrimidin-2-yl)-1-[1-(4-tert-butylbenzoyl)piperidin-4-yl]azepan-3-amine MS (ESI, Pos.20V): 533 (M+H)$^+$, 373, 161;
HPLC condition: A; HPLC retention time (min): 3.27.

Example 11-0789

N-(4-azepan-1-ylpyrimidin-2-yl)-1-[1-(thien-2-ylcarbonyl)piperidin-4-yl]azepan-3-amine MS (ESI, Pos.20V): 483 (M+H)$^+$, 373, 111;
HPLC condition: A; HPLC retention time (min): 3.03.

Example 11-0790

N-(4-azepan-1-ylpyrimidin-2-yl)-1-1-[(4-chlorophenyl)acetyl]piperidin-4-ylazepan-3-amine MS (ESI, Pos.20V): 527, 525 (M+H)$^+$, 263 (M+2H)$^{2+}$;
HPLC condition: A; HPLC retention time (min): 3.18.

Example 11-0791

N-(4-azepan-1-ylpyrimidin-2-yl)-1-[1-(3-methylbutanoyl)piperidin-4-yl]azepan-3-amine MS (ESI, Pos.20V): 457 (M+H)$^+$, 373, 187;
HPLC condition: A; HPLC retention time (min): 3.03.

Example 11-0792

N-(4-azepan-1-ylpyrimidin-2-yl)-1-1-[4-(trifluoromethyl)benzoyl]piperidin-4-ylazepan-3-amine MS (ESI, Pos.20V): 545 (M+H)$^+$, 273 (M+2H)$^{2+}$;
HPLC condition: A; HPLC retention time (min): 3.19.

Example 11-0793

N-(4-azepan-1-ylpyrimidin-2-yl)-1-(1-benzoylpiperidin-4-yl)azepan-3-amine

MS (ESI, Pos.20V): 477 (M+H)$^+$, 373;
HPLC condition: A; HPLC retention time (min): 3.03.

Example 11-0794

N-(4-azepan-1-ylpyrimidin-2-yl)-1-[1-(2-fluorobenzoyl)piperidin-4-yl]azepan-3-amine MS (ESI, Pos.20V): 495 (M+H)$^+$, 373, 248 (M+2H)$^{2+}$, 123;
HPLC condition: A; HPLC retention time (min): 3.05.

Example 11-0795

N-(4-azepan-1-ylpyrimidin-2-yl)-1-[1-(diphenylacetyl)piperidin-4-yl]azepan-3-amine MS (ESI, Pos.20V): 567 (M+H)$^+$, 373, 284 (M+2H)$^{2+}$, 167;
HPLC condition: A; HPLC retention time (min): 3.27.

Example 11-0796

N-(4-azepan-1-ylpyrimidin-2-yl)-1-[1-(2-phenoxypropanoyl)piperidin-4-yl]azepan-3-amine MS (ESI, Pos.20V): 521 (M+H)$^+$, 373, 261 (M+2H)$^{2+}$, 121;
HPLC condition: A; HPLC retention time (min): 3.12.

Example 11-0797

N-(4-azepan-1-ylpyrimidin-2-yl)-1-[1-(2-methylpentanoyl)piperidin-4-yl]azepan-3-amine MS (ESI, Pos.20V): 471 (M+H)$^+$, 373;
HPLC condition: A; HPLC retention time (min): 3.11.

Example 11-0798

N-(4-azepan-1-ylpyrimidin-2-yl)-1-[1-(methoxyacetyl)piperidin-4-yl]azepan-3-amine MS (ESI, Pos.20V): 445 (M+H)$^+$, 373, 290, 223 (M+2H)$^{2+}$;
HPLC condition: A; HPLC retention time (min): 2.90.

Example 11-0799 ethyl 4-(4-3-[(4-azepan-1-ylpyrimidin-2-yl)amino]azepan-1-ylpiperidin-1-yl)-4-oxobutanoate MS (ESI, Pos.20V): 501 (M+H)$^+$, 251 (M+2H)$^{2+}$, 228;
HPLC condition: A;
HPLC retention time (min): 3.01.

Example 11-0800

N-(4-azepan-1-ylpyrimidin-2-yl)-1-[1-(3-cyclopentylpropanoyl)piperidin-4-yl]azepan-3-amine MS (ESI, Pos.20V): 497 (M+H)$^+$, 373, 249 (M+2H)$^{2+}$;
HPLC condition: A; HPLC retention time (min): 3.22.

Example 11-0801

N-(4-azepan-1-ylpyrimidin-2-yl)-1-[1-(2-propylpentanoyl)piperidin-4-yl]azepan-3-amine MS (ESI, Pos.20V): 499 (M+H)$^+$, 373;
HPLC condition: A; HPLC retention time (min): 3.22.

Example 11-0802 methyl 5-(4-3-[(4-azepan-1-ylpyrimidin-2-yl)amino]azepan-1-ylpiperidin-1-yl)-5-oxopentanoate MS (ESI, Pos.20V): 501 (M+H)$^+$, 235;
HPLC condition: A; HPLC retention time (min): 2.98.

Example 11-0803

N-(4-azepan-1-ylpyrimidin-2-yl)-1-1-[(4-chlorophenoxy)acetyl]piperidin-4-ylazepan-3-amine MS (ESI, Pos.20V): 543, 541 (M+H)$^+$, 271 (M+2H)$^{2+}$;
HPLC condition: A; HPLC retention time (min): 3.22.

Example 11-0805

N-(4-azepan-1-ylpyrimidin-2-yl)-1-[1-(cyclopentylacetyl)piperidin-4-yl]azepan-3-amine MS (ESI, Pos.20V): 483 (M+H)$^+$, 373, 242 (M+2H)$^{2+}$, 187;
HPLC condition: A; HPLC retention time (min): 3.12.

Example 11-0806

N-(4-azepan-1-ylpyrimidin-2-yl)-1-[1-(cyclopentylcarbonyl)piperidin-4-yl]azepan-3-amine MS (ESI, Pos.20V): 469 (M+H)$^+$, 373;
HPLC condition: A; HPLC retention time (min): 3.07.

Example 11-0807

N-(4-azepan-1-ylpyrimidin-2-yl)-1-[1-(mesitylcarbonyl)piperidin-4-yl]azepan-3-amine MS (ESI, Pos.20V): 519 (M+H)$^+$, 373, 147;
HPLC condition: A; HPLC retention time (min): 3.16.

Example 11-0808

N-(4-azepan-1-ylpyrimidin-2-yl)-1-1-[(3-methoxyphenyl)acetyl]piperidin-4-ylazepan-3-amine MS (ESI, Pos.20V): 521 (M+H)$^+$, 261 (M+2H)$^{2+}$, 121;
HPLC condition: A; HPLC retention time (min): 3.09.

Example 11-0809 ethyl 3-(4-3-[(4-azepan-1-ylpyrimidin-2-yl)amino]azepan-1-ylpiperidin-1-yl)-3-oxopropanoate MS (ESI, Pos.20V): 487 (M+H)$^+$, 373, 244 (M+2H)$^{2+}$;
HPLC condition: A; HPLC retention time (min): 3.00.

Example 11-0810

N-(4-azepan-1-ylpyrimidin-2-yl)-1-[1-(4-butoxybenzoyl)piperidin-4-yl]azepan-3-amine MS (ESI, Pos.20V): 549 (M+H)$^+$, 373, 177;
HPLC condition: A; HPLC retention time (min): 3.31.

Example 11-0811

N-(4-azepan-1-ylpyrimidin-2-yl)-1-1-[(benzyloxy)acetyl]piperidin-4-ylazepan-3-amine MS (ESI, Pos.20V): 521 (M+H)$^+$, 431;
HPLC condition: A; HPLC retention time (min): 3.12.

Example 11-0812

N-(4-azepan-1-ylpyrimidin-2-yl)-1-[1-(2-methylbutanoyl)piperidin-4-yl]azepan-3-amine MS (ESI, Pos.20V): 457 (M+H)$^+$, 373;
HPLC condition: A; HPLC retention time (min): 3.03.

Example 11-0813

N-(4-azepan-1-ylpyrimidin-2-yl)-1-1-[(4-methoxyphenyl)acetyl]piperidin-4-ylazepan-3-amine MS (ESI, Pos.20V): 521 (M+H)$^+$, 373, 261 (M+2H)$^{2+}$, 121;
HPLC condition: A; HPLC retention time (min): 3.09.

Example 11-0814 ethyl 5-(4-3-[(4-azepan-1-ylpyrimidin-2-yl)amino]azepan-1-ylpiperidin-1-yl)-5-oxopentanoate MS (ESI, Pos.20): 515 (4 +H)$^+$, 235;
HPLC condition: A; HPLC retention time (min): 3.05.

Example 11-0815

N-(4-azepan-1-ylpyrimidin-2-yl)-1-[1-(cyclobutylcarbonyl)piperidin-4-yl]azepan-3-amine MS (ESI, Pos.20V): 455 (M+H)$^+$, 373;
HPLC condition: A; HPLC retention time (min): 3.01.

Example 11-0816

N-(4-azepan-1-ylpyrimidin-2-yl)-1-[1-(2-ethylbutanoyl)piperidin-4-yl]azepan-3-amine MS (ESI, Pos.20V): 471 (M+H)$^+$, 373;
HPLC condition: A; HPLC retention time (min): 3.09.

Example 11-0817

N-(4-azepan-1-ylpyrimidin-2-yl)-1-1-[4-(trifluoromethoxy)benzoyl]piperidin-4-ylazepan-3-amine MS (ESI, Pos.20V): 561 (M+H)$^+$, 373, 274;
HPLC condition: A; HPLC retention time (min): 3.22.

Example 11-0818

N-(4-azepan-1-ylpyrimidin-2-yl)-1-[1-(methylsulfonyl)piperidin-4-yl]azepan-3-amine MS (ESI, Pos.20V): 901 (2M+H)$^+$, 451(M+H)$^+$, 226 (M+2H)$^{2+}$;
HPLC condition: A; HPLC retention time (min): 2.96.

Example 11-0819

N-(4-azepan-1-ylpyrimidin-2-yl)-1-[1-(pentylsulfonyl)piperidin-4-yl]azepan-3-amine MS (ESI, Pos.20V): 507 (M+H)$^+$, 373, 254 (M+2H)$^{2+}$;
HPLC condition: A; HPLC retention time (min): 3.23.

Example 11-0820

N-(4-azepan-1-ylpyrimidin-2-yl)-1-[1-(propylsulfonyl)piperidin-4-yl]azepan-3-amine MS (ESI, Pos.20V): 957 (2M+H)$^+$, 479 (M+H)$^+$, 240 (M+2H)$^{2+}$;
HPLC condition: A; HPLC retention time (min): 3.07.

Example 11-0821

N-(4-azepan-1-ylpyrimidin-2-yl)-1-[1-(isopropylsulfonyl)piperidin-4-yl]azepan-3-amine MS (ESI, Pos.20V): 957 (2M+H)$^+$, 479 (M+H)$^+$, 240 (M+2H)$^{2+}$;
HPLC condition: A; HPLC retention time (min): 3.05.

Example 11-0822

N-(4-azepan-1-ylpyrimidin-2-yl)-1-piperidin-4-ylazepan-3-amine

MS (ESI, Pos.20V): 373 (M+H)$^+$, 290, 187 (M+2H)$^{2+}$;
HPLC condition: A; HPLC retention time (min): 2.87.

Example 11-0823

N-(4-azepan-1-ylpyrimidin-2-yl)-1-[1-(butylsulfonyl)piperidin-4-yl]azepan-3-amine MS (ESI, Pos.20V): 985 (2M+H)$^+$, 493 (M+H)$^+$, 247 (M+2H)$^{2+}$;
HPLC condition: A; HPLC retention time (min): 3.14.

Example 11-0824

N-(4-azepan-1-ylpyrimidin-2-yl)-1-[1-(phenylsulfonyl)piperidin-4-yl]azepan-3-amine MS (ESI, Pos.20V): 513 (M+H)$^+$, 290, 257 (M+2H)$^{2+}$;
HPLC condition: A; HPLC retention time (min): 3.16.

Example 11-0825

N-(4-azepan-1-ylpyrimidin-2-yl)-1-1-[(4-chlorophenyl)sulfonyl]piperidin-4-ylazepan-3-amine MS (ESI, Pos.20V): 549, 547 (M+H)$^+$, 274 (M+2H)$^{2+}$;
HPLC condition: A; HPLC retention time (min): 3.27.

Example 11-0826

N-(4-azepan-1-ylpyrimidin-2-yl)-1-(1-[4-(trifluoromethyl)phenyl]sulfonylpiperidin-4-yl)azepan-3-amine MS (ESI, Pos.20V): 581 (M+H)$^+$, 291 (M+2H)$^{2+}$;
HPLC condition: A; HPLC retention time (min): 3.33.

Example 11-0827

N-(4-azepan-1-ylpyrimidin-2-yl)-1-1-[(4-methoxyphenyl)sulfonyl]piperidin-4-ylazepan-3-amine MS (ESI, Pos.20V): 543 (M+H)$^+$, 373, 272 (M+2H)$^{2+}$;
HPLC condition: A; HPLC retention time (min): 3.18.

Example 11-0828

N-(4-azepan-1-ylpyrimidin-2-yl)-1-[1-(benzylsulfonyl)piperidin-4-yl]azepan-3-amine MS (ESI, Pos.20V): 527 (M+H)$^+$, 373;
HPLC condition: A; HPLC retention time (min): 3.16.

Example 11-0829

N-(4-azepan-1-ylpyrimidin-2-yl)-1-1-[(4-methylphenyl)sulfonyl]piperidin-4-ylazepan-3-amine MS (ESI, Pos.20V): 527 (M+H)$^+$, 264 (M+2H)$^{2+}$;
HPLC condition: A; HPLC retention time (min): 3.22.

Example 11-0830

N-(4-azepan-1-ylpyrimidin-2-yl)-1-1-[(3-methylphenyl)sulfonyl]piperidin-4-ylazepan-3-amine MS (ESI, Pos.20V): 527 (M+H)$^+$, 264 (M+2H)$^{2+}$;
HPLC condition: A; HPLC retention time (min): 3.22.

Example 11-0831

N-(4-azepan-1-ylpyrimidin-2-yl)-1-1-[(2-methylphenyl)sulfonyl]piperidin-4-ylazepan-3-amine MS (ESI, Pos.20V): 527 (M+H)$^+$, 290, 264 (M+2H)$^{2+}$;
HPLC condition: A; HPLC retention time (min): 3.20.

Example 11-0832

N-(4-azepan-1-ylpyrimidin-2-yl)-1-(1-[4-(trifluoromethoxy)phenyl]sulfonylpiperidin-4-yl)azepan-3-amine MS (ESI, Pos.20V): 597 (M+H)$^+$, 299 (M+2H)$^{2+}$;
HPLC condition: A; HPLC retention time (min): 3.34.

Example 11-0833

N-(4-azepan-1-ylpyrimidin-2-yl)-1-1-[(4-butoxyphenyl)sulfonyl]piperidin-4-ylazepan-3-amine MS (ESI, Pos.20V): 585 (M+H)$^+$, 373, 293 (M+2H)$^{2+}$;
HPLC condition: A; HPLC retention time (min): 3.42.

Example 11-0834

N-(4-azepan-1-ylpyrimidin-2-yl) 1-1-[(4-tert-butylphenyl)sulfonyl]piperidin-4-ylazepan-3-amine MS (ESI, Pos.20V): 569 (M+H)$^+$, 285 (M+2H)$^{2+}$;
HPLC condition: A; HPLC retention time (min): 3.42.

Example 11-0835

N-(4-azepan-1-ylpyrimidin-2-yl)-1-1-[(4-nitrophenyl)sulfonyl]piperidin-4-ylazepan-3-amine MS (ESI, Pos.20V): 558 (M+H)$^+$, 279.5 (M+2H)$^{2+}$;
HPLC condition: A; HPLC retention time (min): 3.22.

Example 11-0836

4-[(4-3-[(4-azepan-1-ylpyrimidin-2-yl)amino]azepan-1-ylpiperidin-1-yl)sulfonyl]benzonitrile MS (ESI, Pos.20V): 538 (M+H)$^+$, 269.5 (M+2H)$^{2+}$;
HPLC condition: A; HPLC retention time (min): 3.16.

Example 11-0837

N-(4-azepan-1-ylpyrimidin-2-yl)-1-[1-(2-naphthylsulfonyl)piperidin-4-yl]azepan-3-amine MS (ESI, Pos.20V): 563 (M+H)$^+$, 282 (M+2H)$^{2+}$;
HPLC condition: A; HPLC retention time (min): 3.31.

Example 11-0838

4-azepan-1-yl-N-1-[(1-methyl-1H-pyrrol-2-yl)methyl]azetidin-3-ylpyrimidin-2-amine MS (ESI, Pos. 20 V): 341 (M+H)$^+$, 248;
HPLC condition: A; HPLC retention time (min): 2.98.

Example 11-0839

4-(3-[(4-azepan-1-ylpyrimidin-2-yl)amino]azetidin-1-ylmethyl)-1,5-dimethyl-2-phenyl-1,2-dihydro-3H-pyrazole-3-one MS (ESI, Pos. 20 V): 895 (2M+H)$^+$, 448 (M+H)$^+$, 290, 201;
HPLC condition: A; HPLC retention time (min): 2.98.

Example 11-0840

4-azepan-1-yl-N-[1-(2-furylmethyl)azetidin-3-yl]pyrimidin-2-amine

MS (ESI, Pos. 20 V): 328 (M+H)$^+$, 193;
HPLC condition: A; HPLC retention time (min): 2.94.

Example 11-0841

4-azepan-1-yl-N-1-[(5-methyl-2-furyl)methyl]azetidin-3-ylpyrimidin-2-amine

MS (ESI, Pos. 20 V): 342 (M+H)$^+$, 248;
HPLC condition: A; HPLC retention time (min): 3.00.

Example 11-0842

[5-(3-[(4-azepan-1-ylpyrimidin-2-yl)amino]azetidin-1-ylmethyl)-2-furyl]methyl acetate MS (ESI, Pos. 20 V): 400 (M+H)$^+$, 290, 193;
HPLC condition: A; HPLC retention time (min): 2.94.

Example 11-0843

[5-(3-[(4-azepan-1-ylpyrimidin-2-yl)amino]azetidin-1-ylmethyl)-2-furyl]methanol

MS (ESI, Pos. 20 V): 358 (M+H)$^+$, 248;
HPLC condition: A; HPLC retention time (min): 2.83.

Example 11-0844

4-azepan-1-yl-N-1-[(2E)-3-(2-furyl)prop-2-enyl]azetidin-3-ylpyrimidin-2-amine

MS (ESI, Pos. 20 V): 354 (M+H)$^+$;
HPLC condition: A; HPLC retention time (min): 3.00.

Example 11-0845

4-azepan-1-yl-N-(1-benzylazetidin-3-yl)pyrimidin-2-amine

MS (ESI, Pos. 20 V): 338 (M+H)$^+$, 290, 248, 193;
HPLC condition: A; HPLC retention time (min): 3.01.

Example 11-0846

4-azepan-1-yl-N-[1-(2-methoxybenzyl)azetidin-3-yl]pyrimidin-2-amine

MS (ESI, Pos. 20 V): 368 (M+H)$^+$, 248, 193;
HPLC condition: A; HPLC retention time (min): 3.00.

Example 11-0847

4-azepan-1-yl-N-[1-(2,3-dimethoxybenzyl)azetidin-3-yl]pyrimidin-2-amine

MS (ESI, Pos. 20 V): 795 (2M+H)$^+$, 398 (M+H)$^+$, 248;
HPLC condition: A; HPLC retention time (min): 3.01.

Example 11-0848

4-azepan-1-yl-N-[1-(2,4-dimethoxybenzyl)azetidin-3-yl]pyrimidin-2-amine

MS (ESI, Pos. 20 V): 795 (2M+H)$^+$, 398 (M+H)$^+$, 151;
HPLC condition: A; HPLC retention time (min): 3.03.

Example 11-0849

4-azepan-1-yl-N-[1-(2,4,6-trimethoxybenzyl)azetidin-3-yl]pyrimidin-2-amine

MS (ESI, Pos. 20 V): 855 (2M+H)$^+$, 428 (M+H)$^+$;
HPLC condition: A; HPLC retention time (min): 3.07.

Example 11-0850

4-azepan-1-yl-N-[1-(2,5-dimethoxybenzyl)azetidin-3-yl]pyrimidin-2-amine

MS (ESI, Pos. 20 V): 795 (2M+H)$^+$, 398 (M+H)$^+$, 248;
HPLC condition: A; HPLC retention time (min): 3.01.

Example 11-0851

[2-(3-[(4-azepan-1-ylpyrimidin-2-yl)amino]azetidin-1-ylmethyl)phenoxy]acetic acid MS (ESI, Pos. 20 V): 412 (M+H)$^+$, 290, 193;
HPLC condition: A; HPLC retention time (min): 2.94.

Example 11-0852

4-azepan-1-yl-N-1-[2-(trifluoromethyl)benzyl]azetidin-3-ylpyrimidin-2-amine

MS (ESI, Pos. 20 V): 406 (M+H)$^+$;
HPLC condition: A; HPLC retention time (min): 3.11.

Example 11-0853

4-azepan-1-yl-N-[1-(2-methylbenzyl)azetidin-3-yl]pyrimidin-2-amine

MS (ESI, Pos. 20 V): 352 (M+H)$^+$, 276, 193;
HPLC condition: A; HPLC retention time (min): 3.01.

Example 11-0854

3-(3-[(4-azepan-1-ylpyrimidin-2-yl)amino]azetidin-1-ylmethyl)benzonitrile

MS (EST, Pos. 20 V): 363 (M+H)$^+$, 290, 193;
HPLC condition: A; HPLC retention time (min): 3.00.

Example 11-0855

4-azepan-1-yl-N-[1-(3-fluorobenzyl)azetidin-3-yl]pyrimidin-2-amine

MS (ESI, Pos. 20 V): 356 (M+H)$^+$, 290, 193;
HPLC condition: A; HPLC retention time (min): 3.00.

Example 11-0856

4-azepan-1-yl-N-[1-(3-fluoro-4-methoxybenzyl)azetidin-3-yl]pyrimidin-2-amine

MS (ESI, Pos. 20 V): 771 (2M+H)$^+$, 386 (M+H)$^+$, 248;
HPLC condition: A; HPLC retention time (min): 3.05.

Example 11-0857

4-azepan-1-yl-N-[1-(3-phenoxybenzyl)azetidin-3-yl]pyrimidin-2-amine

MS (ESI, Pos. 20 V): 859 (2M+H)$^+$, 430 (M+H)$^+$, 183;
HPLC condition: A; HPLC retention time (min): 3.27.

Example 11-0858

4-azepan-1-yl-N-[1-(3-methoxybenzyl)azetidin-3-yl]pyrimidin-2-amine

MS (ESI, Pos. 20 V): 368 (M+H)$^+$;
HPLC condition: A; HPLC retention time (min): 3.05.

Example 11-0859

4-azepan-1-yl-N-[1-(3,4-dimethoxybenzyl)azetidin-3-yl]pyrimidin-2-amine

MS (ESI, Pos. 20 V): 795 (2M+H)$^+$, 398 (M+H)$^+$, 248, 193;
HPLC condition: A; HPLC retention time (min): 3.00.

Example 11-0860

4-azepan-1-yl-N-[1-(3,4,5-trimethoxybenzyl)azetidin-3-yl]pyrimidin-2-amine

MS (ESI, Pos. 20 V): 855 (2M+H)$^+$, 428 (M+H)$^+$, 181;
HPLC condition: A; HPLC retention time (min): 3.03.

Example 11-0861

4-azepan-1-yl-N-1-[4-(benzyloxy)-3-methoxybenzyl]azetidin-3-ylpyrimidin-2-amine

MS (ESI, Pos. 20 V): 947 (2M+H)$^+$, 474 (M+H)$^+$, 248;
HPLC condition: A; HPLC retention time (min): 3.27.

Example 11-0862

4-azepan-1-yl-N-1-[3-(benzyloxy)benzyl]azetidin-3-ylpyrimidin-2-amine

MS (ESI, Pos. 20 V): 887 (2M+H)$^+$, 444 (M+H)$^+$, 197;
HPLC condition: A; HPLC retention time (min): 3.23.

Example 11-0863

3-(3-[(4-azepan-1-ylpyrimidin-2-yl)amino]azetidin-1-ylmethyl)phenol

MS (ESI, Pos. 20 V): 354 (M+H)$^+$, 290, 193;
HPLC condition: A; HPLC retention time (min): 2.94.

Example 11-0864

5-(3-[(4-azepan-1-ylpyrimidin-2-yl)amino]azetidin-1-ylmethyl)-2-methoxyphenol

MS (ESI, Pos. 20 V): 384 (M+H)$^+$, 290, 248, 137;
HPLC condition: A; HPLC retention time (min): 2.90.

Example 11-0865

4-azepan-1-yl-N-1-[3-(trifluoromethyl)benzyl]azetidin-3-ylpyrimidin-2-amine

MS (ESI, Pos. 20 V): 406 (M+H)$^+$;
HPLC condition: A; HPLC retention time (min): 3.16.

Example 11-0866

4-azepan-1-yl-N-[1-(3-methylbenzyl)azetidin-3-yl]pyrimidin-2-amine

MS (ESI, Pos. 20 V): 352 (M+H)$^+$, 248;
HPLC condition: A; HPLC retention time (min): 3.07.

Example 11-0867

4-(3-[(4-azepan-1-ylpyrimidin-2-yl)amino]azetidin-1-ylmethyl)benzonitrile

MS (ESI, Pos. 20 V): 363 (M+H)$^+$, 290, 193;
HPLC condition: A; HPLC retention time (min): 2.96.

Example 11-0868

4-azepan-1-yl-N-[1-(4-fluorobenzyl)azetidin-3-yl]pyrimidin-2-amine

MS (ESI, Pos. 20 V): 356 (M+H)$^+$, 263;
HPLC condition: A; HPLC retention time (min): 3.03.

Example 11-0869

N-[4-(3-[(4-azepan-1-ylpyrimidin-2-yl)amino]azetidin-1-ylmethyl)phenyl]acetamide MS (ESI, Pos. 20 V): 789 (2M+H)$^+$, 395 (M+H)$^+$, 193;
HPLC condition: A; HPLC retention time (min): 2.89.

Example 11-0870

4-azepan-1-yl-N-1-[4-(dimethylamino)benzyl]azetidin-3-ylpyrimidin-2-amine

MS (ESI, Pos. 20 V): 381 (M+H)$^+$, 248, 191 (M+2H)$^{2+}$, 134;
HPLC condition: A; HPLC retention time (min): 2.89.

Example 11-0871

4-azepan-1-yl-N-1-[4-(diethylamino)benzyl]azetidin-3-ylpyrimidin-2-amine

MS (ESI, Pos. 20 V): 817 (2M+H)$^+$, 409 (M+H)$^+$, 205 (M+2H)$^{2+}$;
HPLC condition: A; HPLC retention time (min): 2.85.

Example 11-0872

4-azepan-1-yl-N-[1-(4-phenoxybenzyl)azetidin-3-yl]pyrimidin-2-amine

MS (ESI, Pos. 20 V): 859 (2M+H)$^+$, 430 (M+H)$^+$, 248;
HPLC condition: A; HPLC retention time (min): 3.27.

Example 11-0873

4-azepan-1-yl-N-[1-(4-methoxybenzyl)azetidin-3-yl]pyrimidin-2-amine

MS (ESI, Pos. 20 V): 368 (M+H)$^+$, 248;
HPLC condition: A; HPLC retention time (min): 3.03.

Example 11-0874

4-azepan-1-yl-N-1-[4-(benzyloxy)benzyl]azetidin-3-ylpyrimidin-2-amine

MS (ESI, Pos. 20 V): 887 (2M+H)$^+$, 444 (M+H)$^+$, 248;
HPLC condition: A; HPLC retention time (min): 3.29.

Example 11-0875

4-azepan-1-yl-N-[1-(1H-imidazol-2-ylmethyl)azetidin-3-yl]pyrimidin-2-amine

MS (ESI, Pos. 20 V): 328 (M+H)$^+$, 248, 164.5 (M+2H)$^{2+}$;
HPLC condition: A; HPLC retention time (min): 2.79.

Example 11-0876

4-azepan-1-yl-N-[1-(1-naphthylmethyl)azetidin-3-yl]pyrimidin-2-amine

MS (ESI, Pos. 20 V): 775 (2M+H)$^+$, 388 (M+H)$^+$, 248;
HPLC condition: A; HPLC retention time (min): 3.07.

Example 11-0877

4-azepan-1-yl-N-1-[(4-methoxy-1-naphthyl)methyl]azetidin-3-ylpyrimidin-2-amine

MS (ESI, Pos. 20 V): 418 (M+H)$^+$, 248, 171;
HPLC condition: A; HPLC retention time (min): 3.18.

Example 11-0878

4-azepan-1-yl-N-1-[3,4-bis(benzyloxy)benzyl]azetidin-3-ylpyrimidin-2-amine

MS (ESI, Pos. 20 V): 550 (M+H)$^+$, 248;
HPLC condition: A; HPLC retention time (min): 3.45.

Example 11-0879

4-azepan-1-yl-N-[1-(1H-pyrrol-2-ylmethyl)azetidin-3-yl]pyrimidin-2-amine

MS (ESI, Pos. 20 V): 327 (M+H)$^+$, 248, 193;
HPLC condition: A; HPLC retention time (min): 2.96.

Example 11-0880

4-azepan-1-yl-N-[1-(thien-2-ylmethyl)azetidin-3-yl]pyrimidin-2-amine

MS (ESI, Pos. 20 V): 344 (M+H)$^+$, 290, 248, 193;
HPLC condition: A; HPLC retention time (min): 2.98.

Example 11-0881

4-azepan-1-yl-N-1-[(3-methylthien-2-yl)methyl]azetidin-3-ylpyrimidin-2-amine

MS (ESI, Pos. 20 V): 358 (M+H)$^+$, 248;
HPLC condition: A; HPLC retention time (min): 3.03.

Example 11-0882

4-azepan-1-yl-N-1-[(4-bromothien-2-yl)methyl]azetidin-3-ylpyrimidin-2-amine

MS (ESI, Pos. 20 V): 424, 422 (M+H)$^+$, 248;
HPLC condition: A; HPLC retention time (min): 3.07.

Example 11-0883

4-azepan-1-yl-N-1-[(5-bromothien-2-yl)methyl]azetidin-3-ylpyrimidin-2-amine

MS (ESI, Pos. 20 V): 424, 422 (M+H)$^+$, 248;
HPLC condition: A; HPLC retention time (min): 3.09.

Example 11-0884

4-azepan-1-yl-N-[1-(1H-indol-3-ylmethyl)azetidin-3-yl]pyrimidin-2-amine

MS (ESI, Pos. 20 V): 377 (M+H)$^+$, 248, 130;
HPLC condition: A; HPLC retention time (min): 3.05.

Example 11-0885

4-azepan-1-yl-N-[1-(pyridin-4-ylmethyl)azetidin-3-yl]pyrimidin-2-amine

MS (ESI, Pos. 20 V): 339 (M+H)$^+$, 262, 170 (M+2H)$^{2+}$;
HPLC condition: A; HPLC retention time (min): 2.74.

Example 11-0886

4-(3-[(4-azepan-1-ylpyrimidin-2-yl)amino]azetidin-1-ylmethyl)phenol

MS (ESI, Pos. 20 V): 354 (M+H)$^+$, 248, 193;
HPLC condition: A; HPLC retention time (min): 2.89.

Example 11-0887

4-azepan-1-yl-N-[1-(1,1'-biphenyl-4-ylmethyl)azetidin-3-yl]pyrimidin-2-amine

MS (ESI, Pos. 20 V): 827 (2M+H)$^+$, 414 (M+H)$^+$, 248;
HPLC condition: A; HPLC retention time (min): 3.25.

Example 11-0888 methyl 4-(3-[(4-azepan-1-ylpyrimidin-2-yl)amino]azetidin-1-ylmethyl)benzoate

MS (ESI, Pos. 20 V): 791 (2M+H)$^+$, 396 (M+H)$^+$, 193;
HPLC condition: A; HPLC retention time (min): 3.03.

Example 11-0889

4-(3-[(4-azepan-1-ylpyrimidin-2-yl)amino]azetidin-1-ylmethyl)benzoic acid

MS (ESI, Pos. 20 V): 763 (2M+H)$^+$, 382 (M+H)$^+$, 193;
HPLC condition: A; HPLC retention time (min): 2.89.

Example 11-0890

4-azepan-1-yl-N-1-[4-(trifluoromethyl)benzyl]azetidin-3-ylpyrimidin-2-amine

MS (ESI, Pos. 20 V): 406 (M+H)$^+$;
HPLC condition: A; HPLC retention time (min): 3.18.

Example 11-0891

4-azepan-1-yl-N-[1-(4-methylbenzyl)azetidin-3-yl]pyrimidin-2-amine

MS (ESI, Pos. 20 V): 352 (M+H)$^+$, 248;
HPLC condition: A; HPLC retention time (min): 3.07.

Example 11-0892

4-azepan-1-yl-N-(1-neopentylazetidin-3-yl)pyrimidin-2-amine

MS (ESI, Pos. 20 V): 318 (M+H)$^+$, 290, 193;
HPLC condition: A; HPLC retention time (min): 2.92.

Example 11-0893

4-azepan-1-yl-N-1-[(2E)-2-methylbut-2-enyl]azetidin-3-ylpyrimidin-2-amine

MS (ESI, Pos. 20 V): 316 (M+H)$^+$, 282;
HPLC condition: A; HPLC retention time (min): 2.98.

Example 11-0894

4-azepan-1-yl-N-(1-isobutylazetidin-3-yl)pyrimidin-2-amine

MS (ESI, Pos. 20 V): 304 (M+H)$^+$, 290, 248, 193;
HPLC condition: A; HPLC retention time (min): 2.87.

Example 11-0895

4-azepan-1-yl-N-[1-(2-ethylhexyl)azetidin-3-yl]pyrimidin-2-amine

MS (ESI, Pos. 20 V): 719 (2M+H)$^+$, 360 (M+H)$^+$, 248;
HPLC condition: A; HPLC retention time (min): 3.20.

Example 11-0896

4-azepan-1-yl-N-1-[(2E)-3,7-dimethyloct-2,6-dienyl]azetidin-3-ylpyrimidin-2-amine MS (ESI, Pos. 20 V): 384 (M+H)$^+$, 248;
HPLC condition: A; HPLC retention time (min): 3.31.

Example 11-0897

4-azepan-1-yl-N-(1-(2E)-3-[4-(dimethylamino)phenyl]prop-2-enylazetidin-3-yl)pyrimidin-2-amine MS (ESI, Pos. 20 V): 407 (M+H)$^+$, 276, 204 (M+2H)$^{2+}$;
HPLC condition: A; HPLC retention time (min): 2.89.

Example 11-0898

4-azepan-1-yl-N-(1-isopentylazetidin-3-yl)pyrimidin-2-amine

MS (ESI, Pos. 20V): 318 (M+H)$^+$, 159.5 (M+2H)$^{2+}$;
HPLC condition: A; HPLC retention time (min): 3.01.

Example 11-0899

4-azepan-1-yl-N-(1-propylazetidin-3-yl)pyrimidin-2-amine

MS (ESI, Pos. 20 V): 290 (M+H)$^+$, 248, 145.5 (M+2H)$^{2+}$;
HPLC condition: A; HPLC retention time (min): 2.89.

Example 11-0900

4-azepan-1-yl-N-1-[3-(methylsulfanyl)propyl]azetidin-3-ylpyrimidin-2-amine

MS (ESI, Pos. 20 V): 336 (M+H)$^+$, 290, 193;
HPLC condition: A; HPLC retention time (min): 2.90.

Example 11-0901

4-azepan-1-yl-N-(1-butylazetidin-3-yl)pyrimidin-2-amine

MS (ESI, Pos. 20 V): 304 (M+H)$^+$, 290, 248, 193;
HPLC condition: A; HPLC retention time (min): 2.96.

Example 11-0902

4-azepan-1-yl-N-[1-(quinolin-2-ylmethyl)azetidin-3-yl]pyrimidin-2-amine

MS (ESI, Pos. 20 V): 389 (M+H)$^+$, 290, 195 (M+2H)$^{2+}$;
HPLC condition: A; HPLC retention time (min): 3.02.

Example 11-0903

4-azepan-1-yl-N-[1-(3-nitrobenzyl)azetidin-3-yl]pyrimidin-2-amine

MS (ESI, Pos. 20 V): 765 (2M+H)$^+$, 383 (M+H)$^+$, 290;
HPLC condition: A; HPLC retention time (min): 3.03.

Example 11-0904

4-(3-[(4-azepan-1-ylpyrimidin-2-yl)amino]azetidin-1-ylmethyl)-2,6-ditert-butylphenol MS (ESI, Pos. 20 V): 931 (2M+H)$^+$, 466 (M+H)$^+$, 219;
HPLC condition: A; HPLC retention time (min): 3.40.

Example 11-0905

4-azepan-1-yl-N-[1-(2,3-dihydro-1,4-benzodioxin-6-ylmethyl)azetidin-3-yl]pyrimidin-2-amine MS (ESI, Pos. 20 V): 791 (2M+H)$^+$, 396 (M+H)$^+$, 248;
HPLC condition: A; HPLC retention time (min): 2.98.

Example 11-0906

4-azepan-1-yl-N-[1-(3-furylmethyl)azetidin-3-yl]pyrimidin-2-amine

MS (ESI, Pos. 20 V): 328 (M+H)$^+$, 193;
HPLC condition: A; HPLC retention time (min): 2.89.

Example 11-0907

4-azepan-1-yl-N-[1-(2,6-dimethoxybenzyl)azetidin-3-yl]pyrimidin-2-amine

MS (ESI, Pos. 20 V): 795 (2M+H)$^+$, 398 (M+H)$^+$, 248;
HPLC condition: A; HPLC retention time (min): 3.03.

Example 11-0908

4-azepan-1-yl-N-(1-4-[3-(dimethylamino)propoxy]benzylazetidin-3-yl)pyrimidin-2-amine MS (ESI, Pos. 20 V): 439 (M+H)$^+$, 354, 220 (M+2H)$^{2+}$;
HPLC condition: A; HPLC retention time (min): 2.85.

Example 11-0909

4-azepan-1-yl-N-1-[(2-methyl-1H-indol-3-yl)methyl]azetidin-3-ylpyrimidin-2-amine MS (ESI, Pos. 20 V): 781 (2M+H)$^+$, 391 (M+H)$^+$, 248;
HPLC condition: A; HPLC retention time (min): 3.03.

Example 11-0910

4-azepan-1-yl-N-[1-(cyclopropylmethyl)azetidin-3-yl]pyrimidin-2-amine

MS (ESI, Pos. 20 V): 302 (M+H)$^+$, 290, 193;
HPLC condition: A; HPLC retention time (min): 2.94.

Example 11-0911

N-1-[4-(allyloxy)benzyl]azetidin-3-yl-4-azepan-1-ylpyrimidin-2-amine

MS (ESI, Pos. 20 V): 787 (2M+H)$^+$, 394 (M+H)$^+$, 248;
HPLC condition: A; HPLC retention time (min): 3.11.

Example 11-0912

4-azepan-1-yl-N-1-[4-(octyloxy)benzyl]azetidin-3-ylpyrimidin-2-amine

MS (ESI, Pos. 20 V): 931 (2M+H)$^+$, 466 (M+H)$^+$, 248, 144;
HPLC condition: A; HPLC retention time (min): 3.58.

Example 11-0913

4-azepan-1-yl-N-1-[(1-methyl-1H-indol-3-yl)methyl]azetidin-3-ylpyrimidin-2-amine MS (ESI, Pos. 20 V): 781 (2M+H)$^+$, 391 (M+H)$^+$, 248, 144;
HPLC condition: A; HPLC retention time (min): 3.09.

Example 11-0914

4-azepan-1-yl-N-[1-(1-benzofuran-2-ylmethyl)azetidin-3-yl]pyrimidin-2-amine

MS (ESI, Pos. 20 V): 755 (2M+H)$^+$, 378 (M+H)$^+$, 248;
HPLC condition: A; HPLC retention time (min): 3.05.

Example 11-0915

4-azepan-1-yl-N-1-[2-(benzyloxy)benzyl]azetidin-3-ylpyrimidin-2-amine

MS (ESI, Pos. 20 V): 444 (M+H)$^+$, 354, 248;
HPLC condition: A; HPLC retention time (min): 3.22.

Example 11-0916

4-azepan-1-yl-N-1-[4-(heptyloxy)benzyl]azetidin-3-ylpyrimidin-2-amine

MS (ESI, Pos. 20 V): 903 (2M+H)$^+$, 452 (M+H)$^+$, 248;
HPLC condition: A; HPLC retention time (min): 3.51.

Example 11-0917

4-azepan-1-yl-N-[1-(1,3-benzodioxol-4-ylmethyl)azetidin-3-yl]pyrimidin-2-amine

MS (ESI, Pos. 20 V): 382 (M+H)$^+$, 290, 248, 135;
HPLC condition: A; HPLC retention time (min): 3.00.

Example 11-0918

4-azepan-1-yl-N-1-[(3,5,6-trimethylcyclohex-3-en-1-yl)methyl]azetidin-3-ylpyrimidin-2-amine MS (ESI, Pos. 20 V): 767 (2M+H)$^+$, 384 (M+H)$^+$, 260, 130;
HPLC condition: A; HPLC retention time (min): 3.20.

Example 11-0919

4-azepan-1-yl-N-1-[4-(hexyloxy)-3-methoxybenzyl]azetidin-3-ylpyrimidin-2-amine

MS (ESI, Pos. 20 V): 935 (2M+H)$^+$, 468 (M+H)$^+$, 248;
HPLC condition: A; HPLC retention time (min): 3.38.

Example 11-0920

4-azepan-1-yl-N-1-[(6-chloro-1,3-benzodioxol-5-yl)methyl]azetidin-3-ylpyrimidin-2-amine MS (ESI, Pos. 20 V): 418, 416 (M+H)$^+$, 290, 248, 169;
HPLC condition: A; HPLC retention time (min): 3.03.

Example 11-0921

4-azepan-1-yl-N-1-[(5-ethyl-2-furyl)methyl]azetidin-3-ylpyrimidin-2-amine

MS (ESI, Pos. 20 V): 356 (M+H)$^+$, 290, 248, 193;
HPLC condition: A; HPLC retention time (min): 3.03.

Example 11-0922

4-azepan-1-yl-N-[1-(4-tert-butylbenzyl)azetidin-3-yl]pyrimidin-2-amine

MS (ESI, Pos. 20 V): 787 (2M+H)$^+$, 394 (M+H)$^+$, 248;
HPLC condition: A; HPLC retention time (min): 3.23.

Example 11-0923

4-azepan-1-yl-N-[1-(3,7-dimethyloct-6-enyl)azetidin-3-yl]pyrimidin-2-amine

MS (ESI, Pos. 20 V): 771 (2M+H)$^+$, 386 (M+H)$^+$, 260, 130;
HPLC condition: A; HPLC retention time (min): 3.31.

Example 11-0924

4-azepan-1-yl-N-1-[2-(tert-butylsulfanyl)benzyl]azetidin-3-ylpyrimidin-2-amine

MS (ESI, Pos. 20 V): 426 (M+H)$^+$, 370;
HPLC condition: A; HPLC retention time (min): 3.22.

Example 11-0925

4-azepan-1-yl-N-1-[4-(trifluoromethoxy)benzyl]azetidin-3-ylpyrimidin-2-amine

MS (ESI, Pos. 20 V): 843 (2M+H)$^+$, 422 (M+H)$^+$, 175;
HPLC condition: A; HPLC retention time (min): 3.18.

Example 11-0926

4-azepan-1-yl-N-1-[(3,5-dimethyl-1-phenyl-1H-pyrazol-4-yl)methyl]azetidin-3-ylpyrimidin-2-amine MS (ESI, Pos. 20 V): 432 (M+H)$^+$, 216.5 (M+2H)$^{2+}$;
HPLC condition: A; HPLC retention time (min): 3.07.

Example 11-0927

4-azepan-1-yl-N-(1-2-[(4-chlorophenyl)sulfanyl]benzylazetidin-3-yl)pyrimidin-2-amine MS (ESI, Pos. 20 V): 482, 480 (M+H)$^+$, 248;
HPLC condition: A; HPLC retention time (min): 3.33.

Example 11-0928

4-azepan-1-yl-N-1-[(3-methyl-1-benzothien-2-yl)methyl]azetidin-3-ylpyrimidin-2-amine MS (ESI, Pos. 20 V): 815 (2M+H)$^+$, 408 (M+H)$^+$, 248;
HPLC condition: A; HPLC retention time (min): 3.14.

Example 11-0929

4-(3-[(4-azepan-1-ylpyrimidin-2-yl)amino]azetidin-1-ylmethyl)-1-naphthol

MS (ESI, Pos. 20 V): 404 (M+H)$^+$, 290, 157;
HPLC condition: A; HPLC retention time (min): 3.05.

Example 11-0930

4-azepan-1-yl-N-(1-4-[2-(diethylamino)ethoxy]benzylazetidin-3-yl)pyrimidin-2-amine MS (ESI, Pos. 20 V): 453 (M+H)$^+$, 227 (M+2H)$^{2+}$;
HPLC condition: A; HPLC retention time (min): 2.89.

Example 11-0931

4-azepan-1-yl-N-(1-[(1R,5S)-6,6-dimethylbicyclo[3.1.1]hept-2-en-2-yl]methylazetidin-3-yl)pyrimidin-2-amine MS (ESI, Pos. 20 V): 763 (2M+H)$^+$, 382 (M+H)$^+$, 248;
HPLC condition: A; HPLC retention time (min): 3.20.

Example 11-0932

4-azepan-1-yl-N-1-[(6-methoxy-2-naphthyl)methyl]azetidin-3-ylpyrimidin-2-amine

MS (ESI, Pos. 20 V): 835 (2M+H)$^+$, 418 (M+H)$^+$, 171;
HPLC condition: A; HPLC retention time (min): 3.14.

Example 11-0933

4-azepan-1-yl-N-[1-(4-[(2E)-4-methylpent-2-enyl]cyclohex-3-en-1-ylmethyl)azetidin-3-yl]pyrimidin-2-amine MS (ESI, Pos. 20 V): 847 (2M+H)$^+$, 424 (M+H)$^+$, 356;
HPLC condition: A; HPLC retention time (min): 3.42.

Example 11-0934

4-azepan-1-yl-N-1-[(5-chloro-3-methyl-1-phenyl-1H-pyrazol-4-yl)methyl]azetidin-3-ylpyrimidin-2-amine MS (ESI, Pos. 20 V): 903 (2M+H)$^+$, 454, 452 (M+H)$^+$, 248;
HPLC condition: A; HPLC retention time (min): 3.11.

Example 11-0935

4-azepan-1-yl-N-1-[(2-chloroquinolin-3-yl)methyl]azetidin-3-ylpyrimidin-2-amine

MS (ESI, Pos. 20 V): 845 (2M+H)$^+$, 425, 423 (M+H)$^+$, 290;
HPLC condition: A; HPLC retention time (min): 3.05.

Example 11-0936

(3a'R,5'R,6'S,6a'R)-5'-[(3-[4-(1-azepanyl)-2-pyrimidinyl]amino-1-azetidinyl)methyl]tetrahydrospiro[cyclohexane-1,2'-furo[2,3-d][1,3]dioxol]-6'-ol MS (ESI, Pos. 20 V): 919 (2M+H)$^+$, 460 (M+H)$^+$, 181;
HPLC condition: A; HPLC retention time (min): 3.07.

Example 11-0937

4-azepan-1-yl-N-[1-(1,3-thiazol-2-ylmethyl)azetidin-3-yl]pyrimidin-2-amine

MS (ESI, Pos. 20 V): 345 (M+H)$^+$, 248;
HPLC condition: A; HPLC retention time (min): 2.85.

Example 11-0938

4-azepan-1-yl-N-1-[(5-ethylthien-2-yl)methyl]azetidin-3-ylpyrimidin-2-amine

MS (ESI, Pos. 20 V): 372 (M+H)$^+$, 248, 125;
HPLC condition: A; HPLC retention time (min): 3.09.

Example 11-0939

2-(3-[(4-azepan-1-ylpyrimidin-2-yl)amino]azetidin-1-ylmethyl)quinolin-8-ol

MS (ESI, Pos. 20 V): 809 (2M+H)$^+$, 405 (M+H)$^+$, 290, 203 (M+2H)$^{2+}$;
HPLC condition: A; HPLC retention time (min): 3.03.

Example 11-0940

4-azepan-1-yl-N-1-[(2-phenyl-1H-imidazol-4-yl)methyl]azetidin-3-ylpyrimidin-2-amine MS (ESI, Pos. 20 V): 404 (M+H)$^+$, 290, 248, 157;
HPLC condition: A; HPLC retention time (min): 2.96.

Example 11-0941

4-azepan-1-yl-N-[1-(5-[3,5-bis(trifluoromethyl)phenyl]-2-furylmethyl)azetidin-3-yl]pyrimidin-2-amine MS (ESI, Pos. 20 V): 540 (M+H)$^+$, 248;
HPLC condition: A; HPLC retention time (min): 3.44.

Example 11-0942 methyl 3-(3-[(4-azepan-1-ylpyrimidin-2-yl)amino]azetidin-1-ylmethyl)benzoate

MS (ESI, Pos. 20 V): 791 (2M+H)$^+$, 396 (M+H)$^+$, 193;
HPLC condition: A; HPLC retention time (min): 3.02.

Example 11-0943

4-azepan-1-yl-N-1-[2-(benzyloxy)ethyl]azetidin-3-ylpyrimidin-2-amine

MS (ESI, Pos. 20 V): 382 (M+H)$^+$, 292, 234;
HPLC condition: A; HPLC retention time (min): 3.07.

Example 11-0944

4-azepan-1-yl-N-(1-[5-(4-chlorophenyl)-2-furyl]methylazetidin-3-yl)pyrimidin-2-amine MS (ESI, Pos. 20 V): 440, 438 (M+H)$^+$, 248;
HPLC condition: A; HPLC retention time (min): 3.25.

Example 11-0945

4-azepan-1-yl-N-1-[3-(5-methyl-2-furyl)butyl]azetidin-3-ylpyrimidin-2-amine

MS (ESI, Pos. 20 V): 384 (M+H)$^+$, 248, 163;
HPLC condition: A; HPLC retention time (min): 3.12.

Example 11-0946

4-azepan-1-yl-N-(1-[5-(3-chlorophenyl)-2-furyl]methylazetidin-3-yl)pyrimidin-2-amine MS (ESI, Pos. 20 V): 875 (2M+H)$^+$, 440, 438 (M+H)$^+$, 248;
HPLC condition: A; HPLC retention time (min): 3.25.

Example 11-0947 methyl 3-(3-[(4-azepan-1-ylpyrimidin-2-yl)amino]azetidin-1-ylmethyl)-1H-indole-6-carboxylate MS (ESI, Pos. 20 V): 869 (2M+H)$^+$, 435 (M+H)$^+$, 290;
HPLC condition: A; HPLC retention time (min): 3.03.

Example 11-0948

4-azepan-1-yl-N-1-[4-(methylsulfonyl)benzyl]azeti-
din-3-ylpyrimidin-2-amine

MS (ESI, Pos. 20 V): 831 (2M+H)$^+$, 416 (M+H)$^+$, 193;
HPLC condition: A; HPLC retention time (min): 2.90.

Example 11-0949

4-azepan-1-yl-N-(1-[5-(2-chlorophenyl)-2-furyl]
methylazetidin-3-yl)pyrimidin-2-amine MS (ESI, Pos. 20 V): 440, 438 (M+H)$^+$, 248;
HPLC condition: A; HPLC retention time (min): 3.22.

Example 11-0950

4-azepan-1-yl-N-1-[(3-phenyl-1H-pyrazol-4-yl)me-
thyl]azetidin-3-ylpyrimidin-2-amine MS (ESI, Pos. 20 V): 807 (2M+H)$^+$, 404 (M+H)$^+$, 248, 202.5 (M+2H)$^{2+}$;
HPLC condition: A; HPLC retention time (min): 2.98.

Example 11-0951

4-azepan-1-yl-N-[1-(5-[2-(trifluoromethyl)phenyl]-
2-furylmethyl)azetidin-3-yl]pyrimidin-2-amine MS (ESI, Pos. 20 V): 472 (M+H)$^+$, 225;
HPLC condition: A; HPLC retention time (min): 3.25.

Example 11-0952

4-azepan-1-yl-N-[-(5-[3-(trifluoromethyl)phenyl]-2-
furylmethyl)azetidin-3-yl]pyrimidin-2-amine MS (ESI, Pos. 20 V): 943 (2M+H)$^+$, 472 (M+H)$^+$, 225;
HPLC condition: A; HPLC retention time (min): 3.31.

Example 11-0953

4-azepan-1-yl-N-[1-(5-[2-chloro-5-(trifluoromethyl)
phenyl]-2-furylmethyl)azetidin-3-yl]pyrimidin-2-
amine MS (ESI, Pos. 20 V): 508, 506 (M+H)$^+$, 248;
HPLC condition: A; HPLC retention time (min): 3.33.

Example 11-0954

4-azepan-1-yl-N-[1-(5-[2-(trifluoromethoxy)phenyl]-
2-furylmethyl)azetidin-3-yl]pyrimidin-2-amine MS (ESI, Pos. 20 V): 975 (2M+H)$^+$, 488 (M+H)$^+$, 241;
HPLC condition: A; HPLC retention time (min): 3.29.

Example 11-0955

4-3-[(4-azepan-1-ylpyrimidin-2-yl)amino]piperidin-
1-ylcyclohexanone O-methyloxime MS (ESI, Pos. 20 V): 401 (M+H)$^+$, 276, 177;
HPLC condition: A; HPLC retention time (min): 2.98.

Example 11-0956

4-3-[(4-azepan-1-ylpyrimidin-2-yl)amino]piperidin-
1-ylcyclohexanone O-ethyloxime MS (ESI, Pos. 20 V): 415 (M+H)$^+$, 276, 208 (M+2H)$^{2+}$, 177;
HPLC condition: A; HPLC retention time (min): 3.03.

Example 11-0957

4-3-[(4-azepan-1-ylpyrimidin-2-yl)amino]piperidin-
1-ylcyclohexanone O-allyloxime MS (ESI, Pos. 20 V): 427 (M+H)$^+$, 276, 214 (M+2H)$^{2+}$, 177;
HPLC condition: A; HPLC retention time (min): 3.09.

Example 11-0958

4-3-[(4-azepan-1-ylpyrimidin-2-yl)amino]piperidin-
1-ylcyclohexanone O-(tert-butyl)oxime MS (ESI, Pos. 20 V): 443 (M+H)$^+$, 276, 194, 112;
HPLC condition: A; HPLC retention time (min): 3.20.

Example 11-0959

4-3-[(4-azepan-1-ylpyrimidin-2-yl)amino]piperidin-
1-ylcyclohexanone O-tetrahydro-2H-pyran-2-
yloxime MS (ESI, Pos. 20 V): 471 (M+H)$^+$, 387, 276, 194;
HPLC condition: A; HPLC retention time (min): 3.05.

Example 11-0960

[(4-3-[(4-azepan-1-ylpyrimidin-2-yl)amino]piperi-
din-1-ylcyclohexylidene)amino]oxyacetic acid MS (ESI, Pos. 20 V): 445 (M+H)$^+$, 416, 304, 185, 171;
HPLC condition: A; HPLC retention time (min): 2.90.

Example 11-0961

4-3-[(4-azepan-1-ylpyrimidin-2-yl)amino]piperidin-
1-ylcyclohexanone O-isobutyloxime MS (ESI, Pos. 20 V): 443 (M+H)$^+$, 276, 222 (M+2H)$^{2+}$, 177;
HPLC condition: A; HPLC retention time (min): 3.20.

Example 11-0962

4-3-[(4-azepan-1-ylpyrimidin-2-yl)amino]piperidin-
1-ylcyclohexanone O-[2-(trimethylsilyl)ethyl]oxime MS (ESI, Pos. 20 V): 487 (M+H)$^+$, 387, 276, 230;
HPLC condition: A; HPLC retention time (min): 3.40.

Example 11-0963

4-3-[(4-azepan-1-ylpyrimidin-2-yl)amino]piperidin-1-ylcyclohexanone O-phenyloxime MS (ESI, Pos. 20 V): 925 (2M+H)$^+$, 463 (M+H)$^+$, 193, 177;
HPLC condition: A; HPLC retention time (min): 3.25.

Example 11-0964

4-3-[(4-azepan-1-ylpyrimidin-2-yl)amino]piperidin-1-ylcyclohexanone O-benzyloxime MS (ESI, Pos. 20 V): 477 (M+H)$^+$, 387, 239 (M+2H)$^{2+}$;
HPLC condition: A; HPLC retention time (min): 3.23.

Example 11-0965

4-3-[(4-azepan-1-ylpyrimidin-2-yl)amino]piperidin-1-ylcyclohexanone O-trityloxime MS (ESI, Pos. 20 V): 629 (M+H)$^+$, 387, 243;
HPLC condition: A; HPLC retention time (min): 3.60.

Example 11-0966

3-[(4-azepan-1-ylpyrimidin-2-yl)amino]-N-phenyl-1,4'-bipiperidin-1'-carboxamide

MS (ESI, Pos.20V): 478 (M+H)$^+$, 239.5 (M+2H)$^{2+}$, 180;
HPLC condition: A; HPLC retention time (min): 3.05.

Example 11-0967

3-[(4-azepan-1-ylpyrimidin-2-yl)amino]-N-butyl-1,4'-bipiperidin-1'-carboxamide

MS (ESI, Pos.20V): 458 (M+H)$^+$, 276, 180;
HPLC condition: A; HPLC retention time (min): 3.00.

Example 11-0968

3-[(4-azepan-1-ylpyrimidin-2-yl)amino]-N-(4-chlorophenyl)-1,4'-bipiperidin-1'-carboxamide MS (ESI, Pos.20V): 514, 512 (M+H)$^+$, 256.5 (M+2H)$^{2+}$, 180;
HPLC condition: A; HPLC retention time (min): 3.16.

Example 11-0969

3-[(4-azepan-1-ylpyrimidin-2-yl)amino]-N-(3-methylphenyl)-1,4'-bipiperidin-1'-carboxamide MS (ESI, Pos.20V): 492 (M+H)$^+$, 246.5 (M+2H)$^{2+}$, 180;
HPLC condition: A; HPLC retention time (min): 3.11.

Example 11-0970

3-[(4-azepan-1-ylpyrimidin-2-yl)amino]-N-(3-chlorophenyl)-1,4'-bipiperidin-1'-carboxamide MS (ESI, Pos.20V): 514, 512 (M+H)$^+$, 256.5 (M+2H)$^{2+}$, 193;
HPLC condition: A; HPLC retention time (min): 3.16.

Example 11-0971

3-[(4-azepan-1-ylpyrimidin-2-yl)amino]-N-cyclohexyl-1,4'-bipiperidin-1'-carboxamide MS (ESI, Pos.20V): 484 (M+H)$^+$, 276, 180;
HPLC condition: A; HPLC retention time (min): 3.09.

Example 11-0972

3-[(4-azepan-1-ylpyrimidin-2-yl)amino]-N-(2-chlorophenyl)-1,4'-bipiperidin-1'-carboxamide MS (ESI, Pos.20V): 514, 512 (M+H)$^+$, 256.5(M+2H)$^{2+}$, 180;
HPLC condition: A; HPLC retention time (min): 3.09.

Example 11-0973

3-[(4-azepan-1-ylpyrimidin-2-yl)amino]-N-(4-methylphenyl)-1,4'-bipiperidin-1'-carboxamide MS (ESI, Pos.20V): 492 (M+H)$^+$, 246.5 (M+2H)$^{2+}$, 180;
HPLC condition: A; HPLC retention time (min): 3.11.

Example 11-0974

3-[(4-azepan-1-ylpyrimidin-2-yl)amino]-N-ethyl-1,4'-bipiperidin-1'-carboxamide

MS (ESI, Pos.20V): 430 (M+H)$^+$, 276, 180;
HPLC condition: A; HPLC retention time (min): 2.90.

Example 11-0975

3-[(4-azepan-1-ylpyrimidin-2-yl)amino]-N-(3,4-dichlorophenyl)-1,4'-bipiperidin-1'-carboxamide MS (ESI, Pos.20V): 548, 546 (M+H)$^+$, 466, 273.5 (M+2H)$^{2+}$;
HPLC condition: A; HPLC retention time (min): 3.23.

Example 11-0976

3-[(4-azepan-1-ylpyrimidin-2-yl)amino]-N-[3-(trifluoromethyl)phenyl]-1,4'-bipiperidin-1-carboxamide MS (ESI, Pos.20V): 546 (M+H)$^+$, 466, 273.5 (M+2H)$^{2+}$;
HPLC condition: A; HPLC retention time (min): 3.22.

Example 11-0977

3-[(4-azepan-1-ylpyrimidin-2-yl)amino]-N-(2-methoxyphenyl)-1,4'-bipiperidin-1'-carboxamide MS (ESI, Pos.20V): 508 (M+H)$^+$, 254.5 (M+2H)$^{2+}$, 180;
HPLC condition: A; HPLC retention time (min): 3.07.

Example 11-0978

3-[(4-azepan-1-ylpyrimidin-2-yl)amino]-N-hexyl-1,4'-bipiperidin-1'-carboxamide

MS (ESI, Pos.20V): 486 (M+H)$^+$, 276, 180;
HPLC condition: A; HPLC retention time (min): 3.18.

Example 11-0979

3-[(4-azepan-1-ylpyrimidin-2-yl)amino]-N-(3-methoxyphenyl)-1,4'-bipiperidin-1'-carboxamide MS (ESI, Pos.20V): 508 (M+H)$^+$, 254.5 (M+2H)$^{2+}$, 180;
HPLC condition: A; HPLC retention time (min): 3.03.

Example 11-0980

3-[(4-azepan-1-ylpyrimidin-2-yl)amino]-N-(4-ethoxyphenyl)-1,4'-bipiperidin-1'-carboxamide MS (ESI, Pos.20V): 522 (M+H)$^+$, 261.5 (M+2H)$^{2+}$, 180;
HPLC condition: A; HPLC retention time (min): 3.11.

Example 11-0981

3-[(4-azepan-1-ylpyrimidin-2-yl)amino]-N-(4-methoxyphenyl)-1,4'-bipiperidin-1'-carboxamide MS (ESI, Pos.20V): 508 (M+H)$^+$, 254.5 (M+2H)$^{2+}$, 180;
HPLC condition: A; HPLC retention time (min): 3.03.

Example 11-0982

3-[(4-azepan-1-ylpyrimidin-2-yl)amino]-N-(1-naphthyl)-1,4'-bipiperidin-1'-carboxamide MS (ESI, Pos.20V): 528 (M+H)$^+$, 264.5 (M+2H)$^{2+}$, 180;
HPLC condition: A; HPLC retention time (min): 3.12.

Example 11-0983

3-[(4-azepan-1-ylpyrimidin-2-yl)amino]-N-(2-ethoxyphenyl)-1,4'-bipiperidin-1'-carboxamide MS (ESI, Pos.20V): 522 (M+H)$^+$, 261.5 (M+2H)$^{2+}$, 180;
HPLC condition: A; HPLC retention time (min): 3.14.

Example 11-0984

3-[(4-azepan-1-ylpyrimidin-2-yl)amino]-N-[2-(trifluoromethyl)phenyl]-1,4'-bipiperidin-1'-carboxamide MS (ESI, Pos.20V): 546 (M+H)$^+$, 253.5 (M+2H)$^{2+}$;
HPLC condition: A; HPLC retention time (min): 3.11.

Example 11-0985

3-[(4-azepan-1-ylpyrimidin-2-yl)amino]-N-(2,4-dichlorophenyl)-1,4'-bipiperidin-1'-carboxamide MS (ESI, Pos.20V): 548, 546 (M+H)$^+$, 465, 273.5 (M+2H)$^{2+}$, 193;
HPLC condition: A; HPLC retention time (min): 3.17.

Example 11-0986 ethyl N-(3-[(4-azepan-1-ylpyrimidin-2-yl)amino]-1,4'-bipiperidin-1'-ylcarbonyl)glycinate MS (ESI, Pos.20V): 488 (M+H)$^+$, 221, 193;
HPLC condition: A; HPLC retention time (min): 2.94.

Example 11-0987

3-[(4-azepan-1-ylpyrimidin-2-yl)amino]-N-(2-methylphenyl)-1,4'-bipiperidin-1'-carboxamide MS (ESI, Pos.20V): 492 (M+H)$^+$, 246.5 (M+2H)$^{2+}$, 180;
HPLC condition: A; HPLC retention time (min): 3.03.

Example 11-0988

3-[(4-azepan-1-ylpyrimidin-2-yl)amino]-N-(2-fluorophenyl)-1,4'-bipiperidin-1'-carboxamide MS (ESI, Pos.20V): 496 (M+H)$^+$, 248.5 (M+2H)$^{2+}$, 193;
HPLC condition: A; HPLC retention time (min): 3.03.

Example 11-0989

3-[(4-azepan-1-ylpyrimidin-2-yl)amino]-N-(3-fluorophenyl)-1,4'-bipiperidin-1'-carboxamide MS (ESI, Pos.20V): 991 (2M+H)$^+$, 496 (M+H)$^+$, 248.5 (M+2H)$^{2+}$;
HPLC condition: A; HPLC retention time (min): 3.09.

Example 11-0990

3-[(4-azepan-1-ylpyrimidin-2-yl)amino]-N-(2,4-difluorophenyl)-1,4'-bipiperidin-1'-carboxamide MS (ESI, Pos.20V): 514 (M+H)$^+$, 257.5 (M+2H)$^{2+}$;
HPLC condition: A; HPLC retention time (min): 3.05.

Example 11-0991

3-[(4-azepan-1-ylpyrimidin-2-yl)amino]-N-(4-isopropylphenyl)-1,4'-bipiperidin-1'-carboxamide MS (ESI, Pos.20V): 520 (M+H)$^+$, 260.5 (M+2H)$^{2+}$, 180;
HPLC condition: A; HPLC retention time (min): 3.23.

Example 11-0992

3-[(4-azepan-1-ylpyrimidin-2-yl)amino]-N-(2-ethylphenyl)-1,4'-bipiperidin-1'-carboxamide MS (ESI, Pos.20V): 506 (M+H)$^+$, 253.5 (M+2H)$^{2+}$, 180;
HPLC condition: A; HPLC retention time (min): 3.11.

Example 11-0993

3-[(4-azepan-1-ylpyrimidin-2-yl)amino]-N-benzyl-1,4'-bipiperidin-1'-carboxamide

MS (ESI, Pos.20V): 492 (M+H)$^+$, 372, 180;
HPLC condition: A; HPLC retention time (min): 3.07.

Example 11-0994

3-[(4-azepan-1-ylpyrimidin-2-yl)amino]-N-(4-fluorophenyl)-1,4'-bipiperidin-1'-carboxamide MS (ESI, Pos.20V): 496 (M+H)$^+$, 248.5 (M+2H)$^{2+}$;
HPLC condition: A; HPLC retention time (min): 3.05.

Example 11-0995

3-[(4-azepan-1-ylpyrimidin-2-yl)amino]-N-[4-(trifluoromethyl)phenyl]-1,4'-bipiperidin-1'-carboxamide MS (ESI, Pos.20V): 546 (M+H)$^+$, 466, 273.5 (M+2H)$^{2+}$;
HPLC condition: A; HPLC retention time (min): 3.23.

Example 11-0996

3-[(4-azepan-1-ylpyrimidin-2-yl)amino]-N-(2,5-dimethylphenyl)-1,4'-bipiperidin-1'-carboxamide MS (ESI, Pos.20V): 506 (M+H)$^+$, 253.5 (M+2H)$^{2+}$, 180;
HPLC condition: A; HPLC retention time (min): 3.11.

Example 11-0997

3-[(4-azepan-1-ylpyrimidin-2-yl)amino]-N-[3-(methylsulfanyl)phenyl]-1,4'-bipiperidin-1'-carboxamide MS (ESI, Pos.20V): 524 (M+H)$^+$, 262.5 (M+2H)$^{2+}$, 180;
HPLC condition: A; HPLC retention time (min): 3.14.

Example 11-0998

N-(1-adamantyl)-3-[(4-azepan-1-ylpyrimidin-2-yl)amino]-1,4'-bipiperidin-1'-carboxamide MS (ESI, Pos.20V): 536 (M+H)$^+$, 461, 180;
HPLC condition: A; HPLC retention time (min): 3.23.

Example 11-0999

3-[(4-azepan-1-ylpyrimidin-2-yl)amino]-N-(2,4-dimethoxyphenyl)-1,4'-bipiperidin-1'-carboxamide MS (ESI, Pos.20V): 538 (M+H)$^+$, 269.5 (M+2H)$^{2+}$, 180;
HPLC condition: A; HPLC retention time (min): 3.03.

Example 11-1000

3-[(4-azepan-1-ylpyrimidin-2-yl)amino]-N-(3,5-dimethylphenyl)-1,4'-bipiperidin-1'-carboxamide MS (ESI, Pos.20V): 506 (M+H)$^+$, 446, 253.5 (M+2H)$^{2+}$, 180;
HPLC condition: A; HPLC retention time (min): 3.14.

Example 11-1001

N-(3-acetylphenyl)-3-[(4-azepan-1-ylpyrimidin-2-yl)amino]-1,4'-bipiperidin-1'-carboxamide MS (ESI, Pos.20V): 520 (M+H)$^+$, 372, 193;
HPLC condition: A; HPLC retention time (min): 3.01.

Example 11-1002

3-[(4-azepan-1-ylpyrimidin-2-yl)amino]-N-(3,5-dichlorophenyl)-1,4'-bipiperidin-1'-carboxamide MS (ESI, Pos.20V): 548, 546 (M+H)$^+$, 466, 273.5 (M+2H)$^{2+}$;
HPLC condition: A; HPLC retention time (min): 3.27.

Example 11-1003

3-[(4-azepan-1-ylpyrimidin-2-yl)amino]-N-(2,5-dichlorophenyl)-1,4'-bipiperidin-1'-carboxamide MS (ESI, Pos.20V): 548, 546 (M+H)$^+$, 466, 273.5 (M+2H)$^{2+}$;
HPLC condition: A; HPLC retention time (min): 3.15.

Example 11-1004

3-[(4-azepan-1-ylpyrimidin-2-yl)amino]-N-pentyl-1,4'-bipiperidin-1'-carboxamide

MS (ESI, Pos.20V): 472 (M+H)$^+$, 276, 180;
HPLC condition: A; HPLC retention time (min): 3.09.

Example 11-1005

3-[(4-azepan-1-ylpyrimidin-2-yl)amino]-N-(1,1'-biphenyl-2-yl)-1,4'-bipiperidin-1'-carboxamide MS (ESI, Pos.20V): 554 (M+H)$^+$, 496, 277.5 (M+2H)$^{2+}$, 180;
HPLC condition: A; HPLC retention time (min): 3.18.

Example 11-1006

3-[(4-azepan-1-ylpyrimidin-2-yl)amino]-N-(2,6-dichlorophenyl)-1,4'-bipiperidin-1'-carboxamide MS (ESI, Pos.20V): 548, 546 (M+H)$^+$, 273.5 (M+2H)$^{2+}$, 180;
HPLC condition: A; HPLC retention time (min): 3.05.

Example 11-1007

3-[(4-azepan-1-ylpyrimidin-2-yl)amino]-N-(2-phenylethyl)-1,4'-bipiperidin-1'-carboxamide MS (ESI, Pos.20V): 506 (M+H)$^+$, 180;
HPLC condition: A; HPLC retention time (min): 3.11.

Example 11-1008

3-[(4-azepan-1-ylpyrimidin-2-yl)amino]-N-(2,4-dimethylphenyl)-1,4'-bipiperidin-1'-carboxamide MS (ESI, Pos.20V): 506 (M+H)$^+$, 253.5 (M+2H)$^{2+}$, 180;
HPLC condition: A; HPLC retention time (min): 3.11.

Example 11-1009

3-[(4-azepan-1-ylpyrimidin-2-yl)amino]-N-(2,3-dichlorophenyl)-1,4'-bipiperidin-1'-carboxamide MS (ESI, Pos.20V): 548, 546 (M+H)$^+$, 273.5 (M+2H)$^{2+}$;
HPLC condition: A; HPLC retention time (min): 3.16.

Example 11-1010

N-(4-acetylphenyl)-3-[(4-azepan-1-ylpyrimidin-2-yl)amino]-1,4'-bipiperidin-1'-carboxamide MS (ESI, Pos.20V): 520 (M+H)$^+$, 372, 193;
HPLC condition: A; HPLC retention time (min): 3.01.

Example 11-1011

3-[(4-azepan-1-ylpyrimidin-2-yl)amino]-N-(3-cyanophenyl)-1,4'-bipiperidin-1'-carboxamide MS (ESI, Pos.20V): 503 (M+H)$^+$, 252 (M+2H)$^{2+}$;
HPLC condition: A; HPLC retention time (min): 3.05.

Example 11-1012 ethyl 4-[(3-[(4-azepan-1-ylpyrimidin-2-yl)amino]-1,4'-bipiperidin-1'-ylcarbonyl)amino]benzoate MS (ESI, Pos.20V): 550 (M+H)$^+$, 472, 275 5 (M+2H)$^{2+}$;
HPLC condition: A; HPLC retention time (min): 3.14.

Example 11-1013

3-[(4-azepan-1-ylpyrimidin-2-yl)amino]-N-[4-(methylsulfanyl)phenyl]-1,4'-bipiperidin-1'-carboxamide MS (ESI, Pos.20V): 524 (M+H)$^+$, 262.5 (M+2H)$^{2+}$, 180;
HPLC condition: A; HPLC retention time (min): 3.12.

Example 11-1014

3-[(4-azepan-1-ylpyrimidin-2-yl)amino]-N-(2,3-dimethylphenyl)-1,4'-bipiperidin-1'-carboxamide MS (ESI, Pos.20V): 506 (M+H)$^+$, 253.5 (M+2H)$^{2+}$, 180;
HPLC condition: A; HPLC retention time (min): 3.09.

Example 11-1015

3-[(4-azepan-1-ylpyrimidin-2-yl)amino]-N-(4-phenoxyphenyl)-1,4'-bipiperidin-1'-carboxamide MS (ESI, Pos.20V): 570 (M+H)$^+$, 478, 285.5 (M+2H)$^{2+}$, 180;
HPLC condition: A; HPLC retention time (min): 3.27.

Example 11-1016

3-[(4-azepan-1-ylpyrimidin-2-yl)amino]-N-(3-ethylphenyl)-1,4'-bipiperidin-1'-carboxamide MS (ESI, Pos.20V): 506 (M+H)$^+$, 253.5 (M+2H)$^{2+}$, 180;
HPLC condition: A; HPLC retention time (min): 3.18.

Example 11-1017 ethyl N-(3-[(4-azepan-1-ylpyrimidin-2-yl)amino]-1,4'-bipiperidin-1'-ylcarbonyl)methioninate MS (ESI, Pos.20V): 562 (M+H)$^+$, 281.5 (M+2H)$^{2+}$;
HPLC condition: A; HPLC retention time (min): 3.09.

Example 11-1018 ethyl N-(3-[(4-azepan-1-ylpyrimidin-2-yl)amino]-1,4'-bipiperidin-1'-ylcarbonyl)phenylalaninate MS (ESI, Pos.20V): 578 (M+H)$^+$, 496, 289.5 (M+2H)$^{2+}$;
HPLC condition: A; HPLC retention time (min): 3.16.

Example 11-1019 ethyl 3-[(3-[(4-azepan-1-ylpyrimidin-2-yl)amino]-1,4'-bipiperidin-1'-ylcarbonyl)amino]benzoate MS (ESI, Pos.20V): 550 (M+H)$^+$, 275.5 (M+2H)$^{2+}$;
HPLC condition: A; HPLC retention time (min): 3.14.

Example 11-1020

3-[(4-azepan-1-ylpyrimidin-2-yl)amino]-N-(2-isopropylphenyl)-1,4'-bipiperidin-1'-carboxamide MS (ESI, Pos.20V): 520 (M+H)$^+$, 260.5 (M+2H)$^{2+}$, 180;
HPLC condition: A; HPLC retention time (min): 3.14.

Example 11-1021

3-[(4-azepan-1-ylpyrimidin-2-yl)amino]-N-[(1R)-1-phenylethyl]-1,4'-bipiperidin-1'-carboxamide MS (ESI, Pos.20V): 506 (M+H)$^+$, 180;
HPLC condition: A; HPLC retention time (min): 3.11.

Example 11-1022

3-[(4-azepan-1-ylpyrimidin-2-yl)amino]-N-[(1R,2S)-2-phenylcyclopropyl]-1,4'-bipiperidin-1'-carboxamide MS (ESI, Pos.20V): 518 (M+H)$^+$, 259.5 (M+2H)$^{2+}$;
HPLC condition: A; HPLC retention time (min): 3.14.

Example 11-1023

3-[(4-azepan-1-ylpyrimidin-2-yl)amino]-N-isopropyl-1,4'-bipiperidin-1'-carboxamide MS (ESI, Pos.20V): 444 (M+H)$^+$, 276, 180;
HPLC condition: A; HPLC retention time (min): 2.94.

Example 11-1024

3-[(4-azepan-1-ylpyrimidin-2-yl)amino]-N-(2,6-difluorophenyl)-1,4'-bipiperidin-1'-carboxamide MS (ESI, Pos.20V): 514 (M+H)$^+$, 372, 193;
HPLC condition: A;
HPLC retention time (min): 3.01.

Example 11-1025

3-[(4-azepan-1-ylpyrimidin-2-yl)amino]-N,N-dimethyl-1,4'-bipiperidin-1'-carboxamide MS (ESI, Pos.20V): 430 (M+H)$^+$, 372, 193;
HPLC condition: A; HPLC retention time (min): 2.92.

Example 11-1026

N-(4-azepan-1-ylpyrimidin-2-yl)-1'-(morpholin-4-ylcarbonyl)-1,4'-bipiperidin-3-amine MS (ESI, Pos.20V): 472 (M+H)$^+$, 372, 114;
HPLC condition: A; HPLC retention time (min): 2.92.

Example 11-1027

3-[(4-azepan-1-ylpyrimidin-2-yl)amino]-N,N-diethyl-1,4'-bipiperidin-1'-carboxamide MS (ESI, Pos.20V): 458 (M+H)$^+$, 372, 193;
HPLC condition: A; HPLC retention time (min): 3.03.

Example 11-1028

3-[(4-azepan-1-ylpyrimidin-2-yl)amino]-N,N-diisopropyl-1,4'-bipiperidin-1'-carboxamide MS (ESI, Pos.20V): 486 (M+H)$^+$, 359, 128;
HPLC condition: A; HPLC retention time (min): 3.16.

Example 11-1029

3-[(4-azepan-1-ylpyrimidin-2-yl)amino]-N-methyl-N-phenyl-1,4'-bipiperidin-1'-carboxamide MS (ESI, Pos.20V): 492 (M+H)$^+$, 359, 134;
HPLC condition: A; HPLC retention time (min): 3.09.

Example 11-1030

N-(4-azepan-1-ylpyrimidin-2-yl)-1'-(10H-phenothiazin-10-ylcarbonyl)-1,4'-bipiperidin-3-amine MS (ESI, Pos.20V): 584 (M+H)$^+$, 359, 292.5 (M+2H)$^{2+}$;
HPLC condition: A; HPLC retention time (min): 3.34.

Example 11-1031

N-(4-azepan-1-ylpyrimidin-2-yl)-1'-(9H-carbazol-9-ylcarbonyl)-1,4'-bipiperidin-3-amine MS (ESI, Pos.20V): 552 (M+H)$^+$, 468, 276.5 (M+2H)$^{2+}$;
HPLC condition: A; HPLC retention time (min): 3.31.

Example 11-1032

3-[(4-azepan-1-ylpyrimidin-2-yl)amino]-N,N-diphenyl-1,4'-bipiperidin-1'-carboxamide MS (ESI, Pos.20V): 554 (M+H)$^+$, 470, 359, 196;
HPLC condition: A; HPLC retention time (min): 3.23.

Example 11-1033

N-(4-azepan-1-ylpyrimidin-2-yl)-1'-(pyrrolidin-1-ylcarbonyl)-1,4'-bipiperidin-3-amine MS (ESI, Pos.20V): 456 (M+H)$^+$, 372, 359;
HPLC condition: A; HPLC retention time (min): 2.98.

Example 11-1034

N-(4-azepan-1-ylpyrimidin-2-yl)-1'-[(4-methylpiperazin-1-yl)carbonyl]-1,4'-bipiperidin-3-amine MS (ESI, Pos.20V): 485 (M+H)$^+$, 227;
HPLC condition: A; HPLC retention time (min): 2.83.

Example 11-1035

3-[(4-azepan-1-ylpyrimidin-2-yl)amino]-N,N-dibutyl-1,4'-bipiperidin-1'-carboxamide MS (ESI, Pos.20V): 514 (M+H)$^+$, 450, 359, 156;
HPLC condition: A; HPLC retention time (min): 3.29.

EXAMPLE 12-1 to EXAMPLE 12-6

By the same procedure as described in Reference Example 1→Example 1 using corresponding compounds, the compounds of the present invention were given.

Example 12-1

$N^1$-[2-(3,4-dihydroisoquinolin-2(1H)-yl)pyrimidin-4-yl]-$N^2$,$N^2$-dimethylethane-1,2-diamine NMR (CD$_3$OD): δ 2.72 (s, 6H), 2.90 (t, J=6.00 Hz, 2H), 3.13 (t, J=6.30 Hz, 2H), 3.74 (t, J=6.30 Hz, 2H), 3.94 (t, J=6.00 Hz, 2H), 4.81 (s, 2H), 5.90 (d, J=6.00 Hz, 1H), 7.17 (m, 4H), 7.75 (d, J=6.00 Hz, 1H);
MS (ESI, Pos. 20 V): 298 (M+H)$^+$, 224, 186;
HPLC condition: A; HPLC retention time (min): 2.85;
TLC: Rf 0.53 (CHCl$_3$:MeOH:NH$_4$OH=80:10:1).

Example 12-2

1-(4-[2-(dimethylamino)ethyl]aminopyrimidin-2-yl)piperidin-3-ol

Example 12-3

$N^1$-[2-(2,3-dihydro-1H-indol-1-yl)pyrimidin-4-yl]-$N^2$,$N^2$-dimethylethane-1,2-diamine MS (ESI, Pos, 20 V): 284 (M+H)$^+$;
HPLC condition: B; HPLC retention time (min): 3.53.

Example 12-4

$N^1$-[2-azepan-1-yl-5-(trifluoromethyl)pyrimidin-4-yl]-$N^2$,$N^2$-dimethylethane-1,2-diamine NMR (DMSO-d$_6$): δ 1.47 (m, 4H), 1.76 (m, 4H), 2.15 (s, 6H), 2.37 (t, J=7.00 Hz, 2H), 3.31 (m, 2H), 3.59 (m, 4H), 7.17 (m, 1H), 8.12 (s, 1H);
MS (ESI, Pos, 20 V): 332 (M+H)$^+$;
TLC: Rf 0.49 (CHCl$_3$:MeOH:NH$_4$OH=80:10:1).

Example 12-5

$N^1$-[2-azepan-1-yl-5-(4-methylphenyl)pyrimidin-4-yl]-$N^2$,$N^2$-dimethylethane-1,2-diamine NMR (DMSO-d$_6$): δ 1.48 (m, 4H), 1.70 (m, 4H), 2.13 (s, 6H), 2.32 (s, 3H), 2.38 (t, J=6.80 Hz, 2H), 3.38 (dt, J=5.4, 6.8 Hz, 2H), 3.69 (t, J=6.3 Hz, 4H), 6.02 (t, J=5.40 Hz, 1H), 7.20 (m, 4H), 7.61 (s, 1H);
MS (ESI, Pos, 20 V): 354 (M+H)$^+$, 177.5 (M+2H)$^{2+}$;
TLC: Rf 0.51 (CHCl$_3$:MeOH:NH$_4$OH=80:10:1).

Example 12-6

$N^1$-[2-azepan-1-yl-5-(4-methoxyphenyl)pyrimidin-4-yl]-$N^2$,$N^2$-dimethylethane-1,2-diamine NMR (DMSO-d$_6$): δ 1.48 (m, 4H), 1.71 (m, 4H), 2.13 (s, 6H), 2.38 (t, J=6.80 Hz, 2H), 3.37 (dt, J=5.3, 6.8 Hz, 2H), 3.68 (t, J=6.0 Hz, 4H), 3.76 (s, 3H), 5.98 (t, J=5.30 Hz, 1H), 6.98 (d, J=8.80 Hz, 2H), 7.23 (d, J=8.80 Hz, 2H), 7.59 (s, 1H);

MS (ESI, Pos, 20 V): 370 (M+H)$^+$, 185.5 (M+2H)$^{2+}$;
TLC: Rf 0.61 (CHCl$_3$:MeOH:NH$_4$OH=80:10:1).

EXAMPLE 13-001 to EXAMPLE 13-121

By the same procedure as described in Reference Example 1→Example 1 using corresponding compounds, the compounds of the present invention having the following physical data were given.

Example 13-001

4-(3,4-dihydroisoquinolin-2(1H)-yl)-N-[(1S*,2S*)-2-morpholin-4-ylcyclohexyl]quinazolin-2-amine NMR (DMSO-d$_6$): δ 1.24 (m, 4H), 1.72 (m, 3H), 2.32 (m, 3H), 2.62 (m, 2H), 3.05 (m, 2H), 3.22 (m, 2H), 3.32 (m, 3H), 3.84 (m, 3H), 4.75 (s, 2H), 6.28 (d, J=6.60 Hz, 1H), 7.06 (m, 1H), 7.19 (m, 4H), 7.31 (d, J=8.50 Hz, 1H), 7.50 (m, 1H), 7.81 (d, J=7.40 Hz, 1H),
MS (ESI, Pos. 20 V): 887 (2M+H)$^+$, 444 (M+H)$^+$, 222.5 (M+2H)$^{2+}$;
TLC: Rf 0.34 (AcOEt:MeOH=10:1).

Example 13-002

4-(3,4-dihydroisoquinolin-2(1H)-yl)-N-[(1S*,2S*)-2-(4-methylpiperazin-1-yl)cyclohexyl]quinazolin-2-amine NMR (DMSO-d$_6$): δ 1.19 (m, 4H), 1.71 (m, 3H), 1.97 (s, 3H), 2.17 (m, 4H), 2.37 (m, 3H), 2.61 (m, 2H), 3.06 (t, J=5.20 Hz, 2H), 3.37 (m, 1H), 3.81 (m, 3H), 4.75 (s, 2H), 6.19 (d, J=6.60 Hz, 1H), 7.08 (m, 1H), 7.18 (m, 4H), 7.32 (d, J=8.00 Hz, 1H), 7.50 (m, 1H), 7.80 (d, J=8.00 Hz, 1H);
MS (ESI, Pos. 20 V): 913 (2M+H)$^+$, 457 (M+H)$^+$, 229 (M+2H)$^{2+}$;
TLC: Rf 0.57 (CHCl$_3$:MeOH:NH$_4$OH=80:10:1).

Example 13-003

4-azepan-1-yl-N-[(3R)-1-benzylpyrrolidin-3-yl]quinazolin-2-amine

NMR (CDCl$_3$): δ 1.64 (m, 5H), 1.92 (m, 4H), 2.35 (m, 1H), 2.52 (m, 2H), 2.72 (m, 1H), 2.91 (dd, J=9.40, 6.90 Hz, 1H), 3.63 (s, 2H), 3.86 (t, J=5.90 Hz, 4H), 4.62 (m, 1H), 5.31 (m, 1H), 6.99 (m, 1H), 7.28 (m, 5H), 7.45 (m, 2H), 7.80 (d, J=8.20 Hz, 1H);
MS (ESI, Pos. 20 V): 402 (M+H)$^+$, 312;
TLC: Rf 0.55 (CHCl$_3$:MeOH:NH$_4$OH=80:10:1).

Example 13-004

4-azepan-1-yl-N-[(3S)-1-benzylpyrrolidin-3-yl]quinazolin-2-amine

NMR (CDCl$_3$): δ 1.64 (m, 5H), 1.92 (m, 4H), 2.35 (m, 1H), 2.52 (m, 2H), 2.72 (m, 1H), 2.91 (dd, J=9.50, 7.00 Hz, 1H), 3.63 (s, 2H), 3.86 (t, J=5.90 Hz, 4H), 4.62 (m, 1H), 5.35 (m, 1H), 7.00 (m, 1H), 7.28 (m, 5H), 7.45 (m, 2H), 7.80 (d, J=8.10 Hz, 1H);
MS (ESI, Pos. 20 V): 402 (M+H)$^+$, 312;
TLC: Rf 0.55 (CHCl$_3$:MeOH:NH$_4$OH=80:10:1).

Example 13-005

4-azepan-1-yl-N-[(3R)-1-(pyridin-2-ylmethyl)pyrrolidin-3-yl]quinazolin-2-amine

NMR (DMSO-d$_6$): δ 1.54 (m, 4H), 1.74 (m, 6H), 2.18 (m, 1H), 2.59 (m, 1H), 2.71 (m, 1H), 2.93 (m, 1H), 3.73 (s, 2H), 3.84 (m, 4H), 4.40 (m, 1H), 6.70 (m, 1H), 6.98 (t, J=7.70 Hz, 1H) 7.25 (m, 2H), 7.46 (m, 2H), 7.74 (t, J=7.50 Hz, 1H), 7.83 (d, J=8.80 Hz, 1H), 8.47 (d, J=4.40 Hz, 1H);
MS (ESI, Pos, 20 V): 403 (M+H)$^+$, 202 (M+2H)$^+$;
TLC: Rf 0.33 (CHCl$_3$:MeOH:NH$_4$OH=80:10:1).

Example 13-006

4-azepan-1-yl-N-[(3R)-1-(2-ethylbutyl)pyrrolidin-3-yl]quinazolin-2-amine

NMR (CDCl$_3$): δ 0.86 (t, J=7.00 Hz, 6H), 1.33 (m, 6H), 1.66 (m, 4H), 1.81 (m, 1H), 1.97 (m, 4H), 2.31 (m, 4H), 2.61 (m, 2H), 3.02 (m, 1H), 3.93 (t, J=5.50 Hz, 4H), 4.53 (m, 1H), 7.06 (m, 1H), 7.52 (m, 2H), 7.80 (d, J=8.40 Hz, 1H);
MS (ESI, Pos. 20 V): 396 (M+H)$^+$, 312;
TLC: Rf 0.50 (AcOEt:MeOH:TEA=20:2:1).

Example 13-007

4-azepan-1-yl-N-[(3R)-1-isobutylpyrrolidin-3-yl]quinazolin-2-amine

NMR (CDCl$_3$): δ 0.91 (d, J=6.60 Hz, 6H), 1.66 (m, 6H), 1.94 (m, 4H), 2.22 (dd, J=7.50, 3.10 Hz, 2H), 2.31 (m, 1H), 2.47 (m, 2H), 2.69 (m, 1H), 2.84 (dd, J=9.50, 7.00 Hz, 1 H) 3.87 (t, J=5.90 Hz, 4H), 4.60 (m, 1H), 5.39 (m, 1H), 6.99 (m, 1H), 7.44 (m, 2H), 7.81 (d, J=8.80 Hz, 1H);
MS (ESI, Pos. 20 V): 368 (M+H)$^+$;
TLC: Rf 0.50 (AcOEt:MeOH:TEA=20:2:1).

Example 13-008

4-azepan-1-yl-N-[(3R)-1-(cyclohexylmethyl)pyrrolidin-3-yl]quinazolin-2-amine

NMR (CDCl$_3$): δ 0.88 (m, 2H), 1.18 (m, 2H), 1.26 (m, 2H), 1.45 (m, 1H), 1.67 (m, 6H), 1.78 (m, 4H), 1.96 (m, 4H), 2.28 (m, 3H), 2.41 (m, 1H), 2.61 (m, 2H), 2.99 (m, 1H), 3.92 (t, J=5.90 Hz, 4H), 4.56 (m, 1H), 7.05 (m, 1H), 7.49 (m, 2H), 7.80 (d, J=8.40 Hz, 1H);
MS (ESI, Pos. 20 V): 408 (M+H)$^+$, 204.5 (M+2H);
TLC: Rf 0.50 (AcOEt:MeOH:TEA=20:2:1).

Example 13-009

4-azepan-1-yl-N-[(3S)-1-(pyridin-2-ylmethyl)pyrrolidin-3-yl]quinazolin-2-amine

NMR (CDCl$_3$): δ 1.64 (m, 4H), 1.75 (m, 1H), 1.93 (m, 4H), 2.38 (m, 1H), 2.60 (m, 2H), 2.82 (m, 1H), 2.97 (dd, J=9.90, 7.00 Hz, 1H), 3.76 (d, J=13.60 Hz, 1H), 3.83 (d, J=13.60 Hz, 1H), 3.87 (t, J=5.90 Hz, 4H), 4.65 (m, 1H), 5.59 (m, 1H), 7.00 (m, 1H), 7.15 (dd, J=5.10, 1.10 Hz, 1H), 7.45 (m, 3H), 7.65 (td, J=7.60, 1.80 Hz, 1H), 7.80 (d, J=8.40 Hz, 1H), 8.55 (ddd, J=5.10, 1.80, 0.70 Hz, 1H);
MS (ESI, Pos. 20 V): 403 (M+H)$^+$, 202 (M+2H)$^+$;
TLC: Rf 0.35 (AcOEt:MeOH:TEA=20:2:1).

Example 13-010

4-azepan-1-yl-N-[(3S)-1-(2-ethylbutyl)pyrrolidin-3-yl]quinazolin-2-amine

NMR (CDCl$_3$): δ 0.86 (t, J=6.20 Hz, 6H), 1.36 (m, 6H), 1.66 (m, 5H), 1.95 (m, 4H), 2.29 (m, 2H), 2.45 (m, 2H), 2.67 (m, 1H), 2.84 (m, 1H), 3.89 (t, J=5.50 Hz, 4H), 4.59 (m, 1H), 5.68 (m, 1H), 7.01 (m, 1H), 7.46 (m, 2H), 7.81 (d, J=8.40 Hz, 1H);
MS (ESI, Pos. 20 V): 396 (M+H)$^+$, 312, 243;
TLC: Rf 0.50 (AcOEt:MeOH:TEA=20:2:1).

Example 13-011

4-azepan-1-yl-N-[(3S)-1-isobutylpyrrolidin-3-yl]quinazolin-2-amine

NMR (CDCl$_3$): δ 0.92 (d, J=6.60 Hz, 6H), 1.66 (m, 6H), 1.95 (m, 4H), 2.23 (dd, J=7.70, 2.90 Hz, 2H), 2.31 (m, 1H), 2.48 (m, 2H), 2.67 (m, 1H1), 2.89 (m, 1H), 3.90 (t, J=5.50 Hz, 1H), 4H), 4.59 (m, 1H), 5.93 (m, 1H), 7.03 (m, 1H), 7.47 (m, 2H), 7.81 (d, J=8.10 Hz, 1H);
MS (ESI, Pos. 20 V): 368 (M+H)$^+$, 184.5 (M+2H)$^+$;
TLC: Rf 0.50 (AcOEt:MeOH:TEA=20:2:1).

Example 13-012

4-azepan-1-yl-N-[(3S)-1-(cyclohexylmethyl)pyrrolidin-3-yl]quinazolin-2-amine

NMR (CDCl$_3$): δ 0.89 (m, 2H), 1.20 (m, 4H), 1.45 (m, 1H), 1.67 (m, 6H), 1.78 (m, 3H), 1.96 (m, 4H), 2.29 (dd, J=7.30, 2.90 Hz, 2H), 2.36 (m, 1H), 2.40 (m, 1H), 2.62 (m, 2H), 2.99 (m, 1H), 3.92 (t, J=5.90 Hz, 4H), 4.57 (m, 1H), 7.07 (m, 1H), 7.50 (m, 2H), 7.81 (d, J=8.10 Hz, 1H);
MS (ESI, Pos. 20 V): 408 (M+H)$^+$, 312, 243;
TLC: Rf 0.50 (AcOEt:MeOH:TEA=20:2:1).

Example 13-013

4-azepan-1-yl-N-[(3S)-1-cyclohexylpyrrolidin-3-yl]quinazolin-2-amine

NMR (DMSO-d$_6$): δ 1.16 (m, 6H), 1.56 (m, 4H), 1.65 (m, 3H), 1.85 (m, 7H), 2.05 (m, 2H), 2.39 (m, 1H), 2.59 (m, 1H), 2.91 (t, J=8.40 Hz, 1H), 3.81 (t, J=5.30 Hz, 4H), 4.33 (m, 1H), 6.62 (m, 1H), 6.97 (t, J=8.10 Hz, 1H), 7.25 (d, J=8.10 Hz, 1H), 7.44 (t, J=8.10 Hz, 1H), 7.82 (d, J=8.10 Hz, 1H);
MS (ESI, Pos. 20 V): 394 (M+H)$^+$, 312, 197.5 (M+2H)$^{2+}$;
TLC: Rf 0.50 (AcOEt:MeOH:TEA=20:2:1).

Example 13-014

4-azepan-1-yl-N-[(3R)-1-cyclohexylpyrrolidin-3-yl]quinazolin-2-amine

NMR (DMSO-d$_6$): δ 1.16 (m, 6H), 1.56 (m, 4H), 1.66 (m, 3H), 1.86 (m, 7H), 2.05 (m, 2H), 2.39 (m, 1H), 2.59 (m, 1H), 2.90 (t, J=8.10 Hz, 1H), 3.81 (t, J=5.50 Hz, 4H), 4.33 (m, 1H), 6.57 (m, 1H), 6.97 (t, J=8.20 Hz, 1H), 7.25 (d, J=8.20 Hz, 1H), 7.44 (t, J=8.20 Hz, 1H), 7.82 (d, J=8.20 Hz, 1H);
MS (ESI, Pos. 20 V): 394 (M+H)$^+$, 312, 197.5 (M+2H)$^{2+}$;
TLC: Rf 0.50 (AcOEt:MeOH:TEA=20:2:1).

Example 13-015

$N^1,N^1$-dimethyl-$N^2$-(4-piperidin-1-ylquinazolin-2-yl)ethane-1,2-diamine

MS (ESI, Pos.20V): 300 (M+H)$^+$, 157;
HPLC condition: A; HPLC retention time (min): 3.04.

Example 13-016

4-piperidin-1-yl-N-(2-pyrrolidin-1-ylethyl)quinazolin-2-amine

MS (ESI, Pos.20V): 326 (M+H)$^+$;
HPLC condition: A; HPLC retention time (min): 2.94.

Example 13-017

4-piperidin-1-yl-N-(2-piperidin-1-ylethyl)quinazolin-2-amine

MS (ESI, Pos.20V): 340 (M+H)$^+$, 170.5 (M+2H)$^{2+}$;
HPLC condition: A; HPLC retention time (min): 2.96.

Example 13-018

N-benzyl-4-piperidin-1-ylquinazolin-2-amine

MS (ESI, Pos.20V): 637 (2M+H)$^+$, 319 (M+H)$^+$;
HPLC condition: A; HPLC retention time (min): 3.55.

Example 13-019

N-(2-phenylethyl)-4-piperidin-1-ylquinazolin-2-amine

MS (ESI, Pos.20V): 333 (M+H)$^+$;
HPLC condition: A; HPLC retention time (min): 3.64.

Example 13-020

N-isopentyl-4-piperidin-1-ylquinazolin-2-amine

MS (ESI, Pos.20V): 597 (2M+H)$^+$, 299 (M+H)$^+$;
HPLC condition: A; HPLC retention time (min): 3.67.

Example 13-021

4-piperidin-1-yl-N-(thien-2-ylmethyl)quinazolin-2-amine

MS (ESI, Pos.20V): 325 (M+H)$^+$;
HPLC condition: A; HPLC retention time (min): 3.62.

Example 13-022

N-(2-furylmethyl)-4-piperidin-1-ylquinazolin-2-amine

MS (ESI, Pos.20V): 309 (M+H)$^+$;
HPLC condition: A; HPLC retention time (min): 3.42.

Example 13-023

4-piperidin-1-yl-N-(pyridin-2-ylmethyl)quinazolin-2-amine

MS (ESI, Pos.20V): 320 (M+H)$^+$;
HPLC condition: A; HPLC retention time (min): 2.90.

Example 13-024

4-piperidin-1-yl-N-(2-pyridin-2-ylethyl)quinazolin-2-amine

MS (ESI, Pos.20V): 334 (M+H)$^+$;
HPLC condition: A; HPLC retention time (min): 2.96.

Example 13-025

N-[(5-methylpyrazin-2-yl)methyl]-4-piperidin-1-ylquinazolin-2-amine

MS (ESI, Pos.20V): 669 (2M+H)$^+$, 335 (M+H)$^+$;
HPLC condition: A; HPLC retention time (min): 3.14.

Example 13-026

4-azepan-1-yl-N-(2-piperidin-1-ylethyl)quinazolin-2-amine

MS (ESI, Pos.20V): 354 (M+H)$^+$;
HPLC condition: A; HPLC retention time (min): 3.03.

Example 13-027

N$^1$-(4-azepan-1-ylquinazolin-2-yl)-N$^3$,N$^3$-dimethyl-propane-1,3-diamine

MS (ESI, Pos.20V): 328 (M+H)$^+$, 157;
HPLC condition: A; HPLC retention time (min): 3.01.

Example 13-028

4-azepan-1-yl-N-benzylquinazolin-2-amine

MS (ESI, Pos.20V): 665 (2M+H)$^+$, 333 (M+H)$^+$;
HPLC condition: A; HPLC retention time (min): 3.64.

Example 13-029

4-azepan-1-yl-N-(2-phenylethyl)quinazolin-2-amine

MS (ESI, Pos.20V): 693 (2M+H)$^+$, 347 (M+H)$^+$;
HPLC condition: A; HPLC retention time (min): 3.71.

Example 13-030

4-azepan-1-yl-N-isopentylquinazolin-2-amine

MS (ESI, Pos.20V): 313 (M+H)$^+$;
HPLC condition: A; HPLC retention time (min): 3.73.

Example 13-031

4-azepan-1-yl-N-(thien-2-ylmethyl)quinazolin-2-amine

MS (ESI, Pos.20V): 339 (M+H)$^+$;
HPLC condition: A; HPLC retention time (min): 3.58.

Example 13-032

4-azepan-1-yl-N-(2-furylmethyl)quinazolin-2-amine

MS (ESI, Pos.20V): 323 (M+H)$^+$;
HPLC condition: A; HPLC retention time (min): 3.49.

Example 13-033

4-azepan-1-yl-N-(pyridin-2-ylmethyl)quinazolin-2-amine

MS (ESI, Pos.20V): 334 (M+H)$^+$;
HPLC condition: A; HPLC retention time (min): 2.96.

Example 13-034

4-azepan-1-yl-N-(2-pyridin-2-ylethyl)quinazolin-2-amine

MS (ESI, Pos.20V): 348 (M+H)$^+$;
HPLC condition: A; HPLC retention time (min): 3.00.

Example 13-035

4-azepan-1-yl-N-[(5-methylpyrazin-2-yl)methyl]quinazolin-2-amine

MS (ESI, Pos.20V): 349 (M+H)$^+$;
HPLC condition: A; HPLC retention time (min): 3.23.

Example 13-036

N-benzyl-4-pyrrolidin-1-ylquinazolin-2-amine

MS (ESI, Pos.20V): 609 (2M+H)$^+$, 305 (M+H)$^+$;
HPLC condition: A; HPLC retention time (min): 3.43.

Example 13-037

N-(2-phenylethyl)-4-pyrrolidin-1-ylquinazolin-2-amine

MS (ESI, Pos.20V): 319 (M+H)$^+$;
HPLC condition: A; HPLC retention time (min): 3.55.

Example 13-038

N-isopentyl-4-pyrrolidin-1-ylquinazolin-2-amine

MS (ESI, Pos.20V): 569 (2M+H)$^+$, 285 (M+H)$^+$;
HPLC condition: A; HPLC retention time (min): 3.58.

Example 13-039

4-pyrrolidin-1-yl-N-(thien-2-ylmethyl)quinazolin-2-amine

MS (ESI, Pos.20V): 621 (2M+H)$^+$, 311 (M+H)$^+$;
HPLC condition: A; HPLC retention time (min): 3.42.

Example 13-040

N-(2-furylmethyl)-4-pyrrolidin-1-ylquinazolin-2-amine

MS (ESI, Pos.20V): 589 (2M+H)$^+$, 295 (M+H)$^+$;
HPLC condition: A; HPLC retention time (min): 3.36.

Example 13-041

N-(pyridin-2-ylmethyl)-4-pyrrolidin-1-ylquinazolin-2-amine

MS (ESI, Pos.20V): 306 (M+H)$^+$;
HPLC condition: A; HPLC retention time (min): 2.83.

Example 13-042

N-(2-pyridin-2-ylethyl)-4-pyrrolidin-1-ylquinazolin-2-amine

MS (ESI, Pos.20V): 320 (M+H)$^+$;
HPLC condition: A; HPLC retention time (min): 2.89.

Example 13-043

N-[(5-methylpyrazin-2-yl)methyl]-4-pyrrolidin-1-ylquinazolin-2-amine

MS (ESI, Pos.20V): 321 (M+H)$^+$;
HPLC condition: A; HPLC retention time (min): 3.04.

Example 13-044

4-azocan-1-yl-N-benzylquinazolin-2-amine

MS (ESI, Pos.20V): 693 (2M+H)$^+$, 347 (M+H)$^+$;
HPLC condition: A; HPLC retention time (min): 3.71.

Example 13-045

MS (ESI, Pos.20V): 721 (2M+H)$^+$, 361 (M+H)$^+$;
HPLC condition: A; HPLC retention time (min): 3.78.

Example 13-046

4-azocan-1-yl-N-isopentylquinazolin-2-amine

MS (ESI, Pos.20V): 653 (2M+H)$^+$, 327 (M+H)$^+$;
HPLC condition: A; HPLC retention time (min): 3.86.

Example 13-047

4-azocan-1-yl-N-(thien-2-ylmethyl)quinazolin-2-amine

MS (ESI, Pos.20V): 353 (M+H)$^+$, 257
HPLC condition: A; HPLC retention time (min): 3.69.

Example 13-048

4-azocan-1-yl-N-(2-furylmethyl)quinazolin-2-amine

MS (ESI, Pos.20V): 337 (M+H)$^+$;
HPLC condition: A; HPLC retention time (min): 3.60.

Example 13-049

4-azocan-1-yl-N-(pyridin-2-ylmethyl)quinazolin-2-amine

MS (ESI, Pos.20V): 348 (M+H)$^+$;
HPLC condition: A; HPLC retention time (min): 3.02.

Example 13-050

4-azocan-1-yl-N-(2-pyridin-2-ylethyl)quinazolin-2-amine

MS (ESI, Pos.20V): 723 (2M+H)$^+$, 362 (M+H)$^+$;
HPLC condition: A; HPLC retention time (min): 3.05.

Example 13-051

4-azocan-1-yl-N-[(5-methylpyrazin-2-yl)methyl]quinazolin-2-amine

MS (ESI, Pos.20V): 725 (2M+H)$^+$, 363 (M+H)$^+$;
HPLC condition: A; HPLC retention time (min): 3.29.

Example 13-052

4-(3-azabicyclo[3.2.2]non-3-yl)-N-benzylquinazolin-2-amine

MS (ESI, Pos.20V): 717 (2M+H)$^+$, 359 (M+H)$^+$;
HPLC condition: A; HPLC retention time (min): 3.75.

Example 13-053

4-(3-azabicyclo[3.2.2]non-3-yl)-N-(2-phenylethyl)quinazolin-2-amine

MS (ESI, Pos.20V): 745 (2M+H)$^+$, 373 (M+H)$^+$;
HPLC condition: A; HPLC retention time (min): 3.84.

Example 13-054

4-(3-azabicyclo[3.2.2]non-3-yl)-N-isopentylquinazolin-2-amine

MS (ESI, Pos.20V): 339 (M+H)$^+$;
HPLC condition: A; HPLC retention time (min): 3.88.

Example 13-055

4-(3-azabicyclo[3.2.2]non-3-yl)-N-(pyridin-2-ylmethyl)quinazolin-2-amine

MS (ESI, Pos.20V): 360 (M+H)$^+$;
HPLC condition: A; HPLC retention time (min): 3.01.

Example 13-056

4-(3-azabicyclo[3.2.2]non-3-yl)-N-(2-pyridin-2-ylethyl)quinazolin-2-amine

MS (ESI, Pos.20V): 374 (M+H)$^+$;
HPLC condition: A; HPLC retention time (min): 3.09.

Example 13-057

4-(3-azabicyclo[3.2.2]non-3-yl)-N-[(5-methylpyrazin-2-yl)methyl]quinazolin-2-amine MS (ESI, Pos.20V): 749 (2M+H)⁺, 375 (M+H)⁺;
HPLC condition: A; HPLC retention time (min): 3.31.

Example 13-058

2,2'-[(2-[4-(3,4-dihydro-2(1H)-isoquinolinyl)-2-quinazolinyl]aminoethyl)imino]diethanol MS (ESI, Pos.20V): 815 (2M+H)⁺, 408 (M+H)⁺;
HPLC condition: A; HPLC retention time (min): 2.98.

Example 13-059

4-(3,4-dihydroisoquinolin-2(1H)-yl)-N-[3-(1H-imidazol-1-yl)propyl]quinazolin-2-amine MS (ESI, Pos.20V): 769 (2M+H)⁺, 385 (M+H)⁺;
HPLC condition: A; HPLC retention time (min): 3.06.

Example 13-060

4-(3,4-dihydroisoquinolin-2(1H)-yl)-N-(2-morpholin-4-ylethyl)quinazolin-2-amine

MS (ESI, Pos.20V): 779 (2M+H)⁺, 390 (M+H)⁺;
HPLC condition: A; HPLC retention time (min): 3.02.

Example 13-061

4-(3,4-dihydroisoquinolin-2(1H)-yl)-N-(3-pyrrolidin-1-ylpropyl)quinazolin-2-amine MS (ESI, Pos.20V): 388 (M+H)⁺;
HPLC condition: A; HPLC retention time (min): 3.22.

Example 13-062

4-(3,4-dihydroisoquinolin-2(1H)-yl)-N-[2-(1-methylpyrrolidin-2-yl)ethyl]quinazolin-2-amine MS (ESI, Pos.20V): 388 (M+H)⁺;
HPLC condition: A; HPLC retention time (min): 3.07.

Example 13-063

4-(3,4-dihydroisoquinolin-2(1H)-yl)-N-[(1-ethylpyrrolidin-2-yl)methyl]quinazolin-2-amine MS (ESI, Pos.20V): 775 (2M+H)⁺, 388 (M+H)⁺;
HPLC condition: A; HPLC retention time (min): 3.09.

Example 13-064

$N^1$-[4-(3,4-dihydroisoquinolin-2(1H)-yl)quinazolin-2-yl]-$N^3$,$N^3$,2,2-tetramethylpropane-1,3-diamine MS (ESI, Pos.20V): 779 (2M+H)⁺, 390 (M+H)⁺;
HPLC condition: A; HPLC retention time (min): 3.12.

Example 13-065

$N^1$-[4-(3,4-dihydroisoquinolin-2(1H)-yl)quinazolin-2-yl]-$N^2$,$N^2$-dimethylpropane-1,2-diamine MS (ESI, Pos.20V): 362 (M+H)⁺;
HPLC condition: A; HPLC retention time (min): 3.07.

Example 13-066

$N^1$-[4-(3,4-dihydroisoquinolin-2(1H)-yl)quinazolin-2-yl]-$N^2$,$N^2$-diethylethane-1,2-diamine MS (ESI, Pos.20V): 376 (M+H)⁺;
HPLC condition: A; HPLC retention time (min): 3.07.

Example 13-067

$N^1$-[4-(3,4-dihydroisoquinolin-2(1H)-yl)quinazolin-2-yl]-$N^3$,$N^3$-diethylpropane-1,3-diamine MS (ESI, Pos.20V): 390 (M+H)⁺, 195.5 (M+2H)²⁺;
HPLC condition: A; HPLC retention time (min): 3.11.

Example 13-068

4-(3,4-dihydroisoquinolin-2(1H)-yl)-N-(3-morpholin-4-ylpropyl)quinazolin-2-amine MS (ESI, Pos.20V): 404 (M+H)⁺;
HPLC condition: A; HPLC retention time (min): 3.07.

Example 13-069

2,2'-[(3-[4-(3,4-dihydro-2(1H)-isoquinolinyl)-2-quinazolinyl]aminopropyl)imino]diethanol MS (ESI, Pos.20V): 422 (M+H)⁺;
HPLC condition: A; HPLC retention time (min): 3.03.

Example 13-070

$N^1$-[4-(3,4-dihydroisoquinolin-2(1H)-yl)quinazolin-2-yl]-$N^3$,$N^3$-dimethylpropane-1,3-diamine MS (ESI, Pos.20V): 362 (M+H)⁺;
HPLC condition: A; HPLC retention time (min): 3.05.

Example 13-071

$N^2$-[4-(3,4-dihydroisoquinolin-2(1H)-yl)quinazolin-2-yl]-$N^1$,$N^1$-dimethylpropane-1,2-diamine MS (ESI, Pos.20V): 362 (M+H)⁺;
HPLC condition: A; HPLC retention time (min): 3.05.

Example 13-072

4-(3,4-dihydroisoquinolin-2(1H)-yl)-N-[3-(2-methylpiperidin-1-yl)propyl]quinazolin-2-amine MS (ESI, Pos.20V): 416 (M+H)⁺, 208.5 (M+2H)²⁺;
HPLC condition: A; HPLC retention time (min): 3.14.

Example 13-073

4-(3,4-dihydroisoquinolin-2(1H)-yl)-N-[(1-methylpyrrolidin-2-yl)methyl]quinazolin-2-amine MS (ESI, Pos.20V): 374 (M+H)$^+$;
HPLC condition: A; HPLC retention time (min): 3.07.

Example 13-074

N-benzyl-4-(3,4-dihydroisoquinolin-2(1H)-yl)quinazolin-2-amine

MS (ESI, Pos.20V): 733 (2M+H)$^+$, 367 (M+H)$^+$;
HPLC condition: A; HPLC retention time (min): 3.62.

Example 13-075

4-(3,4-dihydroisoquinolin-2(1H)-yl)-N-(2-phenylethyl)quinazolin-2-amine

MS (ESI, Pos.20V): 761 (2M+H)$^+$, 381 (M+H)$^+$;
HPLC condition: A; HPLC retention time (min): 3.69.

Example 13-076

4-(3,4-dihydroisoquinolin-2(1H)-yl)-N-isopentylquinazolin-2-amine

MS (ESI, Pos.20V): 693 (2M+H)$^+$, 347 (M+H)$^+$;
HPLC condition: A; HPLC retention time (min): 3.75.

Example 13-077

4-(3,4-dihydroisoquinolin-2(1H)-yl)-N-(thien-2-ylmethyl)quinazolin-2-amine

Example 13-078

4-(3,4-dihydroisoquinolin-2(1H)-yl)-N-(2-furylmethyl)quinazolin-2-amine

Example 13-079

4-(3,4-dihydroisoquinolin-2(1H)-yl)-N-(pyridin-2-ylmethyl)quinazolin-2-amine

MS (ESI, Pos.20V): 368 (M+H)$^+$;
HPLC condition: A; HPLC retention time (min): 3.03.

Example 13-080

4-(3,4-dihydroisoquinolin-2(1H)-yl)-N-(2-pyridin-2-ylethyl)quinazolin-2-amine

MS (ESI, Pos.20V): 382 (M+H)$^+$;
HPLC condition: A; HPLC retention time (min): 3.05.

Example 13-081

4-(3,4-dihydroisoquinolin-2(1H)-yl)-N-[(5-methylpyrazin-2-yl)methyl]quinazolin-2-amine MS (ESI, Pos.20V): 765 (2M+H)$^+$, 383 (M+H)$^+$;
HPLC condition: A; HPLC retention time (min): 3.29.

Example 13-082

4-azepan-1-yl-N-[(3S)-1-benzylazepan-3-yl]quinazolin-2-amine

NMR (DMSO-d$_6$): δ 1.57 (m, 9H), 1.86 (m, 5H), 2.59 (m, 3H), 2.84 (dd, J=13.20, 4.00 Hz, 1H), 3.65 (s, 2H), 3.79 (m, 4H), 4.08 (m, 1H), 6.20 (m, 1H), 6.96 (m, 1H), 7.26 (m, 6H), 7.42 (m, 1H), 7.79 (d, J=8.40 Hz, 1H);
MS (ESI, Pos. 20 V): 430 (M+H)$^+$, 290, 193;
HPLC condition: A; HPLC retention time (min): 3.20;
TLC: Rf 0.40 (CHCl$_3$:MeOH:NH$_4$OH=80:10:1).

Example 13-083

4-azepan-1-yl-N-[(3R)-1-benzylazepan-3-yl]quinazolin-2-amine

NMR (DMSO-d$_6$): δ 1.48 (m, 8H), 1.82 (m, 4H), 2.61 (m, 3H), 2.84 (dd, J=13.00, 3.80 Hz, 1H), 3.16 (d, J=5.30 Hz, 2H), 3.65 (s, 2H), 3.78 (m, 4H), 4.06 (m, 1H), 6.19 (m, 1H), 6.95 (t, J=7.70 Hz, 1H), 7.23 (m, 6H), 7.42 (m, 1H), 7.79 (d, J=8.20 Hz, 1H);
MS (ESI, Pos. 20 V): 430 (M+H)$^+$, 340;
HPLC condition: A; HPLC retention time (min): 3.18;
TLC: Rf 0.40 (CHCl$_3$:MeOH:NH$_4$OH=80:10:1).

Example 13-084

N-[(3S)-azepan-3-yl]-4-azepan-1-ylquinazolin-2-amine

NMR (DMSO-d$_6$): δ 1.51 (m, 10H), 1.84 (m, 5H), 2.63 (dd, J=13.50, 7.20 Hz, 1H), 2.74 (t, J=5.80 Hz, 1H), 2.94 (dd, J=13.50, 4.10 Hz, 1H), 3.80 (m, 4H), 4.04 (m, 1H), 6.21 (m, 1H), 6.95 (t, J=7.60 Hz, 1H), 7.23 (d, J=8.20 Hz, 1H), 7.43 (t, J=7.60 Hz, 1H), 7.80 (d, J=8.20 Hz, 1H);
MS (ESI, Pos. 20 V): 340 (M+H)$^+$, 170.5 (M+2H)$^{2+}$;
HPLC condition: A; HPLC retention time (min): 3.07;
TLC: Rf 0.22 (CHCl$_3$:MeOH:NH$_4$OH=80:10:1).

Example 13-085

N-[(3R)-azepan-3-yl]-4-azepan-1-ylquinazolin-2-amine

NMR (DMSO-d$_6$): δ 1.57 (m, 10H), 1.84 (m, 5H), 2.63 (dd, J=13.60, 7.10 Hz, 1H), 2.74 (t, J=6.00 Hz, 1H), 2.93 (dd, J=13.60, 4.40 Hz, 1H), 3.80 (m, 4H), 4.04 (m, 1H), 6.23 (m, 1H), 6.95 (t, J=7.10 Hz, 1H), 7.23 (d, J=8.10 Hz, 1H), 7.43 (m, 1H), 7.80 (d, J=8.10 Hz, 1H);
MS (ESI, Pos. 20 V): 340 (M+H)$^+$, 170.5 (M+2H)$^{2+}$;
HPLC condition: A; HPLC retention time (min): 3.07;
TLC: Rf 0.24 (CHCl$_3$:MeOH:NH$_4$OH=80:10:1).

Example 13-086

4-azepan-1-yl-N-[(3S)-1-(pyridin-2-ylmethyl)azepan-3-yl]quinazolin-2-amine

Example 13-087

4-azepan-1-yl-N-[(3R)-1-(pyridin-2-ylmethyl)azepan-3-yl]quinazolin-2-amine

Example 13-088

4-azepan-1-yl-N-[(3S)-1-(2-ethylbutyl)azepan-3-yl]
quinazolin-2-amine

MS (ESI, Pos. 20 V): 424 (M+H)$^+$, 340, 212.5 (M+2H)$^{2+}$;
HPLC condition: A; HPLC retention time (min): 3.31.

Example 13-089

4-azepan-1-yl-N-[(3R)-1-(2-ethylbutyl)azepan-3-yl]
quinazolin-2-amine

MS (ESI, Pos. 20 V): 424 (M+H)$^+$, 340, 212.5 (M+2H)$^{2+}$;
HPLC condition: A; HPLC retention time (min): 3.29.

Example 13-090

4-azepan-1-yl-N-[(3S)-1-isobutylazepan-3-yl]
quinazolin-2-amine

MS (ESI, Pos. 20 V): 396 (M+H)$^+$, 340, 198.5 (M+2H)$^{2+}$;
HPLC condition: A; HPLC retention time (min): 3.16.

Example 13-091

4-azepan-1-yl-N-[(3R)-1-isobutylazepan-3-yl]
quinazolin-2-amine

MS (ESI, Pos. 20 V): 396 (M+H)$^+$, 340, 198.5 (M+2H)$^{2+}$;
HPLC condition: A; HPLC retention time (min): 3.16.

Example 13-092

4-azepan-1-yl-N-[(3S)-1-cyclohexylazepan-3-yl]
quinazolin-2-amine

MS (ESI, Pos. 20 V): 422 (M+H)$^+$, 396, 340, 211.5 (M+2H)$^{2+}$;
HPLC condition: A; HPLC retention time (min): 3.23.

Example 13-093

4-azepan-1-yl-N-[(3R)-1-cyclohexylazepan-3-yl]
quinazolin-2-amine

MS (ESI, Pos. 20 V): 422 (M+H)$^+$, 396, 340, 211.5 (M+2H)$^{2+}$;
HPLC condition: A; HPLC retention time (min): 3.23.

Example 13-094

4-azepan-1-yl-N-[(3S)-1-benzylpiperidin-3-yl]
quinazolin-2-amine

MS (ESI, Pos.20V): 831 (2M+H)$^+$, 416 (M+H)$^+$, 326;
HPLC condition: A; HPLC retention time (min): 3.16.

Example 13-095

4-azepan-1-yl-N-[(3S)-1-benzylpiperidin-3-yl]
quinazolin-2-amine

MS (ESI, Pos.20V): 831 (2M+H)$^+$, 416 (M+H)$^+$, 326;
HPLC condition: A; HPLC retention time (min): 3.16.

Example 13-096

4-azepan-1-yl-N-[(3R)-1-benzylpiperidin-3-yl]
quinazolin-2-amine

MS (ESI, Pos.20V): 417 (M+H)$^+$, 209 (M+2H)$^{2+}$;
HPLC condition: A; HPLC retention time (min): 3.07.

Example 13-097

4-azepan-1-yl-N-[(3R)-1-(pyridin-2-ylmethyl)piperidin-3-yl]quinazolin-2-amine

MS (ESI, Pos.20V): 417 (M+H)$^+$, 209 (M+2H)$^{2+}$;
HPLC condition: A; HPLC retention time (min): 3.07.

Example 13-098

4-azepan-1-yl-N-[(3S)-1-(2-ethylbutyl)piperidin-3-yl]quinazolin-2-amine

MS (ESI, Pos.20V): 819 (2M+H)$^+$, 410 (M+H)$^+$, 326, 205.5 (M+2H)$^{2+}$;
HPLC condition: A; HPLC retention time (min): 3.25.

Example 13-099

4-azepan-1-yl-N-[(3R)-1-(2-ethylbutyl)piperidin-3-yl]quinazolin-2-amine

MS (ESI, Pos.20V): 819 (2M+H)$^+$, 410 (M+H)$^+$, 326, 205.5 (M+2H)$^{2+}$;
HPLC condition: A; HPLC retention time (min): 3.25.

Example 13-100

4-azepan-1-yl-N-[(3S)-1-isobutylpiperidin-3-yl]
quinazolin-2-amine

MS (ESI, Pos.20V): 763 (2M+H)$^+$, 382 (M+H)$^+$, 191.5 (M+2H)$^{2+}$;
HPLC condition: A; HPLC retention time (min): 3.12.

Example 13-101

4-azepan-1-yl-N-[(3R)-1-isobutylpiperidin-3-yl]
quinazolin-2-amine

MS (ESI, Pos.20V): 764 (2M+H)$^+$, 382 (M+H)$^+$, 191.5 (M+2H)$^{2+}$;
HPLC condition: A; HPLC retention time (min): 3.12.

Example 13-102

4-azepan-1-yl-N-[(3S)-1-cyclohexylpiperidin-3-yl]
quinazolin-2-amine

MS (ESI, Pos.20V): 815 (2M+H)$^+$, 408 (M+H)$^+$, 326, 204.5 (M+2H)$^{2+}$;
HPLC condition: A; HPLC retention time (min): 3.18.

Example 13-103

4-azepan-1-yl-N-[(3R)-1-cyclohexylpiperidin-3-yl]quinazolin-2-amine

MS (ESI, Pos.20V): 815 (2M+H)$^+$, 408 (M+H)$^+$, 326, 204.5 (M+2H)$^{2+}$;
HPLC condition: A; HPLC retention time (min): 3.18.

Example 13-104

4-azepan-1-yl-N-[(3S)-piperidin-3-yl]quinazolin-2-amine

NMR (CDCl$_3$): δ 1.54 (m, 2H), 1.65 (m, 4H), 1.78 (m, 1H), 1.95 (m, 5H), 2.18 (m, 1H), 2.58 (dd, J=11.80, 8.20 Hz, 1H), 2.67 (m, 1H), 2.91 (m, 1H), 3.28 (dd, J=11.80, 3.40 Hz, 1H), 3.87 (t, J=5.70 Hz, 4H), 4.00 (m, 1H), 5.27 (m, 1H), 7.00 (m, 1H), 7.45 (m, 2H), 7.81 (m, 1H);
MS (ESI, Pos. 20 V): 326 (M+H)$^+$, 163.5 (M+2H)$^{2+}$;
TLC: Rf 0.17 (CHCl$_3$:MeOH:NH$_4$OH=80:10:1).

Example 13-105

4-azepan-1-yl-N-[(3R)-piperidin-3-yl]quinazolin-2-amine

NMR (DMSO-d$_6$): δ 1.41 (m, 2H), 1.59 (m, 5H), 1.85 (m, 5H), 2.37 (m, 2H), 2.76 (m, 1H), 3.01 (dd, J=11.40, 3.50 Hz, 1H), 3.80 (m, 5H), 6.27 (m, 1H), 6.96 (t, J=7.60 Hz, 1H), 7.24 (d, J=8.20 Hz, 1H), 7.43 (t, J=7.60 Hz, 1H), 7.80 (d, J=8.20 Hz, 1H);
MS (ESI, Pos. 20 V): 326 (M+H)$^+$, 163.5 (M+2H)$^{2+}$;
TLC: Rf 0.17 (CHCl$_3$:MeOH:NH$_4$OH=80:10:1).

Example 13-106

4-azepan-1-yl-N-(1-benzylazetidin-3-yl)quinazolin-2-amine

MS (ESI, Pos.20V): 388 (M+H)$^+$, 298;
HPLC condition: A; HPLC retention time (min): 3.18.

Example 13-107

4-azepan-1-yl-N-[1-(pyridin-2-ylmethyl)azetidin-3-yl]quinazolin-2-amine

MS (ESI, Pos.20V): 389 (M+H)$^+$, 195 (M+2H)$^{2+}$;
HPLC condition: A; HPLC retention time (min): 3.07.

Example 13-108

4-azepan-1-yl-N-[1-(2-ethylbutyl)azetidin-3-yl]quinazolin-2-amine

MS (ESI, Pos.20V): 382 (M+H)$^+$, 298, 191.5 (M+2H)$^{2+}$;
HPLC condition: A; HPLC retention time (min): 3.22.

Example 13-109

4-azepan-1-yl-N-(1-isobutylazetidin-3-yl)quinazolin-2-amine

MS (ESI, Pos.20V): 354 (M+H)$^+$, 298, 177.5 (M+2H)$^{2+}$;
HPLC condition: A; HPLC retention time (min): 3.09.

Example 13-110

4-azepan-1-yl-N-(1-cyclohexylazetidin-3-yl)quinazolin-2-amine

MS (ESI, Pos.20V): 380 (M+H)$^+$, 298, 190.5 (M+2H)$^{2+}$;
HPLC condition: A; HPLC retention time (min): 3.14.

Example 13-111

4-azepan-1-yl-N-azetidin-3-ylquinazolin-2-amine

MS (ESI, Pos.20V): 298 (M+H)$^+$, 149.5 (M+2H)$^{2+}$;
HPLC condition: A; HPLC retention time (min): 2.89.

Example 13-112

2,4-dipiperidin-1-ylquinazoline

MS (ESI, Pos. 20 V): 297 (M+H)$^+$;
HPLC condition: A; HPLC retention time (min): 3.42.

Example 13-113

N$^1$-(4-azepan-1-ylquinazolin-2-yl)-N$^2$,N$^2$-dimethyl-ethane-1,2-diamine

MS (ESI, Pos. 20 V): 314 (M+H)$^+$, 157.5 (M+2H)$^{2+}$;
HPLC condition: A; HPLC retention time (min): 2.92.

Example 13-114

2,4-diazepan-1-ylquinazoline

MS (ESI, Pos. 20 V): 325 (M+H)$^+$;
HPLC condition: A; HPLC retention time (min): 3.62.

Example 13-115

N$^1$-[4-(3,4-dihydroisoquinolin-2(1H)-yl)quinazolin-2-yl]-N$^2$,N$^2$-dimethylethane-1,2-diamine MS (ESI, Pos. 20 V): 348 (M+H)$^+$, 174.5 (+2H)$^{2+}$;
HPLC condition: A; HPLC retention time (min): 3.02.

Example 13-116

4-(3,4-dihydroisoquinolin-2(1H)-yl)-N-(2-pyrrolidin-1-ylethyl)quinazolin-2-amine MS (ESI, Pos. 20 V): 374 (M+H)$^+$, 187.5 (M+2H)$^{2+}$;
HPLC condition: A; HPLC retention time (min): 3.07.

Example 13-117

4-(3,4-dihydroisoquinolin-2(1H)-yl)-N-(2-piperidin-1-ylethyl)quinazolin-2-amine

MS (ESI, Pos. 20 V): 388 (M+H)$^+$, 194.5 (M+2H)$^{2+}$;
HPLC condition: A; HPLC retention time (min): 3.60.

Example 13-118

4-azepan-1-yl-N-isopentylquinazolin-2-amine

MS (ESI, Pos. 20 V): 625 (2M+H)$^+$, 313 (M+H)$^+$;
HPLC condition: A; HPLC retention time (min): 3.73.

Example 13-119

$N^1$-(4-azepan-1-ylquinazolin-2-yl)-$N^1,N^2,N^2$-trimethylethane-1,2-diamine

NMR (CDCl$_3$): δ 7.83 (d, J=7.5 Hz, 1H), 7.44 (dd, J=7.5, 6.6 Hz, 1H), 7.27 (d, J=8.7 Hz, 1H), 6.97 (dd, J=8.7, 6.6 Hz, 1H), 3.82 (m, 4H), 3.69 (t, J=6.9 Hz, 2H), 3.11 (s, 3H), 2.41 (t, J=6.9 Hz, 2H), 2.17 (s, 6H), 1.87 (m, 4H), 1.55 (m, 4H);
MS (ESI, Pos. 20 V): 328 (M+H)$^+$;
HPLC condition: A; HPLC retention time (min): 2.98.

Example 13-120

$N^2$-(4-azepan-1-ylquinazolin-2-yl)-$N^1,N^1$-dimethylglycinamide

NMR (CDCl$_3$): δ 7.85 (d, J=7.2 Hz, 1H), 7.47 (dd, J=7.2, 7.2 Hz, 1H), 7.25 (d, J=8.4 Hz, 1H), 7.00 (dd, J=8.4, 7.2 Hz, 1H), 4.10 (d, J=5.4 Hz, 2H), 3.81 (m, 4H), 3.01 (s, 3H), 2.84 (s, 3H), 1.85 (m, 4H), 1.55 (m, 4H);
MS (ESI, Pos. 20 V): 328 (M+H)$^+$;
HPLC condition: A; HPLC retention time (min): 3.12.

Example 13-121

4-azepan-1-yl-N-(1-methyl-2-piperidin-1-ylethyl)quinazolin-2-amine

EXAMPLE 14-01 to EXAMPLE 14-84

By the same procedure as described in Reference Example 1→Example 1 using corresponding compounds, the compounds of the present invention having the following physical data were given.

Example 14-01

$N^1$-(6-azepan-1-ylpyrimidin-4-yl)-$N^2,N^2$-dimethylethane-1,2-diamine

NMR (DMSO-d$_6$): δ 7.93 (s, 1H), 6.32 (m, 1H), 5.44 (s, 1H), 3.49 (m, 4H), 3.25 (dt, J=6.0, 6.3 Hz, 2H), 2.34 (t, J=6.3 Hz, 2H), 2.15 (s, 6H), 1.65 (m, 4H), 1.44 (m, 4H);
MS (ESI, Pos. 20 V): 264 (M+H)$^+$, 219, 132.5 (M+2H)$^{2+}$;
TLC: Rf 0.38 (CHCl$_3$:MeOH:NH$_4$OH=80:10:1).

Example 14-02

$N^1$-(4-azepan-1-yl-6,7-dihydro-5H-cyclopenta[d]pyrimidin-2-yl)-$N^2,N^2$-dimethylethane-1,2-diamine NMR (DMSO-d$_6$): δ 1.47 (m, 4H), 1.67 (m, 4H), 1.85 (m, 2H), 2.18 (s, 6H), 2.39 (t, J=6.90 Hz, 2H), 2.86 (m, 2H), 3.27 (m, 4H), 3.61 (t, J=6.00 Hz, 4H), 5.95 (m, 1H);
MS (ESI, Pos. 20 V): 304 (M+H)$^+$, 152.5 (M+2H)$^{2+}$;
TLC: Rf 0.31 (CHCl$_3$:MeOH:NH$_4$OH=80:10:1).

Example 14-03

$N^1$-(4-azepan-1-yl-5,6,7,8-tetrahydroquinazolin-2-yl)-$N^2,N^2$-dimethylethane-1,2-diamine NMR (DMSO-d$_6$): δ 1.49 (m, 4H), 1.58 (m, 2H), 1.70 (m, 6H), 2.18 (s, 6H), 2.41 (m, 4H), 3.26 (m, 4H), 3.51 (m, 4H), 5.97 (m, 1H);
MS (ESI, Pos. 20 V): 318 (M+H)$^+$, 159.5 (M+2H)$^{2+}$;
TLC: Rf 0.31 (CHCl$_3$:MeOH:NH$_4$OH=80:10:1).

Example 14-04

$N^1$-(4-azepan-1-yl-6-chloropyrimidin-2-yl)-$N^2,N^2$-dimethylethane-1,2-diamine NMR (CDCl$_3$): δ 1.55 (m, 4H), 1.78 (m, 4H), 2.28 (s, 6H), 2.51 (t, J=6.30 Hz, 2H), 3.46 (m, 6H), 5.33 (m, 1H), 5.79 (s, 1H);
MS (ESI, Pos. 20 V): 300, 298 (M+H)$^+$;
TLC: Rf 0.45 (CHCl$_3$:MeOH:NH$_4$OH=80:10:1).

Example 14-05

$N^1$-(4-azepan-1-yl-6-methoxyquinazolin-2-yl)-$N^2,N^2$-dimethylethane-1,2-diamine NMR (CDCl$_3$): 1.69 (m, 4H), 1.97 (m, 4H), 2.27 (s, 6H), 2.53 (t, J=6.50 Hz, 2H), 3.56 (m, 2H), 3.85 (m, 4H), 3.82 (s, 3H), 5.40 (m, 1H), 7.21 (m, 2H), 7.45 (d, J=9.60 Hz, 1H);
MS (ESI, Pos. 20 V): 344 (M+H)$^+$, 172.5 (M+2H)$^{2+}$;
TLC: Rf 0.43 (CHCl$_3$:MeOH:NH$_4$OH=80:10:1).

Example 14-06

$N^1$-(4-azepan-1-yl-6,7,8,9-tetrahydro-5H-cyclohepta[d]pyrimidin-2-yl)-$N^2,N^2$-dimethylethane-1,2-diamine NMR (CD$_3$OD): δ 1.63 (m, 8H), 1.82 (m, 6H), 2.32 (s, 6H), 2.59 (m, 4H), 2.70 (m, 2H), 3.47 (t, J=6.80 Hz, 2H), 3.54 (m, 4H);
MS (ESI, Pos. 20 V): 332 (M+H)$^+$, 318, 166.5 (M+2H)$^{2+}$;
TLC: Rf 0.40 (CHCl$_3$:MeOH:NH$_4$OH=80:10:1).

Example 14-07

$N^1$-[4-azepan-1-yl-5-(trifluoromethyl)pyrimidin-2-yl]-$N^2,N^2$-dimethylethane-1,2-diamine NMR (DMSO-d$_6$): δ 1.46 (m, 4H), 1.69 (m, 4H), 2.16 (s, 6H), 2.41 (t, J=6.50 Hz, 2H), 3.44 (q, J=6.50 Hz, 2H), 3.69 (m, 4H), 6.61 (m, 1H), 8.04 (s, 1H);
MS (ESI, Pos. 20 V): 332 (M+H)$^+$, 166.5 (M+2H)$^{2+}$;
TLC: Rf 0.69 (CHCl$_3$:MeOH:NH$_4$OH=80:10:1).

Example 14-08

N-(4-piperidin-1-ylthieno[3,2-d]pyrimidin-2-yl)ethane-1,2-diamine

NMR (CDCl$_3$): 1.68 (m, 6H), 2.01 (m, 2H), 2.94 (m, 2H), 3.50 (q, J=5.70 Hz, 2H), 3.86 (t, J=5.70 Hz, 4H), 5.05 (m, 1H), 7.10 (d, J=5.10 Hz, 1H), 7.53 (d, J=5.10 Hz, 1H);
MS(EI, Pos.): 277 (M+), 247, 235, 219, 205, 191, 179, 165, 151, 135;
TLC: Rf 0.15 (CH$_2$Cl$_2$:MeOH:NH$_4$OH=80:10:1).

Example 14-09

N-(4-azepan-1-ylthieno[3,2-d]pyrimidin-2-yl)butane-1,4-diamine

NMR (CDCl$_3$): δ 1.60 (m, 8H), 1.86 (m, 6H), 2.74 (m, 2H), 3.42 (m, 2H), 3.87 (t, J=6.00 Hz, 4H), 4.81 (m, 1H), 7.07 (d, J=5.50 Hz, 1H), 7.52 (d, J=5.50 Hz, 1H);

MS(EI, Pos.): 319 (M+), 303, 289, 276, 261, 248, 233, 219, 205;
TLC: Rf 0.13 (CH$_2$Cl$_2$:MeOH:NH$_4$OH=80:10:1).

Example 14-10

N$^1$-[4-azepan-1-yl-5-(4-methylphenyl)pyrimidin-2-yl]-N$^2$,N$^2$-dimethylethane-1,2-diamine NMR (DMSO-d$_6$): δ 1.34 (m, 4H), 1.54 (m, 4H), 2.18 (s, 6H), 2.30 (s, 3H), 2.41 (t, J=6.90 Hz, 2H), 3.31 (m, 6H), 6.33 (m, 1H), 7.15 (d, J=8.4 Hz, 2H), 7.10 (d, J=8.4 Hz, 2H), 7.52 (s, 1H);
MS (ESI, Pos. 20 V): 354 (M+H)$^+$, 177.5 (M+2H)$^{2+}$;
TLC: Rf 0.31 (CHCl$_3$:MeOH:NH$_4$OH=80:10:1).

Example 14-11

N$^1$-[4-azepan-1-yl-5-(4-methoxyphenyl)pyrimidin-2-yl]-N$^2$,N$^2$-dimethylethane-1,2-diamine NMR (DMSO-d$_6$): δ 1.36 (m, 4H), 1.52 (m, 4H), 2.18 (s, 6H), 2.41 (t, J=7.10 Hz, 2H), 3.31 (m, 6H), 3.75 (s, 3H), 6.30 (m, 1H), 6.91 (d, J=8.80 Hz, 2H), 7.14 (d, J=8.80 Hz, 2H), 7.51 (s, 1H);
MS (ESI, Pos. 20 V): 370 (M+H)$^+$, 185.5 (M+2H)$^{2+}$;
TLC: Rf 0.27 (CHCl$_3$:MeOH:NH$_4$OH=80:10:1).

Example 14-12

4-azepan-1-yl-N-[(3S)-1-benzylpyrrolidin-3-yl]-6,7-dihydro-5H-cyclopenta[d]pyrimidin-2-amine NMR (DMSO-d$_6$): δ 1.42 (m, 4H), 1.64 (m, 6H), 1.83 (m, 2H), 2.08 (m, 1H), 2.25 (dd, J=9.20, 5.50 Hz, 2H), 2.42 (m, 2H), 2.76 (m, 1H), 2.85 (t, J=7.10 Hz, 2H), 3.52 (s, 2H), 3.57 (m, 4H), 4.23 (m, 1H), 6.21 (m, 1H), 7.23 (m, 5H);
MS (ESI, Pos. 20 V): 392 (M+H)$^+$, 302, 233;
TLC: Rf 0.44 (CHCl$_3$:MeOH:NH$_4$OH=80:10:1).

Example 14-13

4-azepan-1-yl-N-[(3R)-1-benzylpyrrolidin-3-yl]-6,7-dihydro-5H-cyclopenta[d]pyrimidin-2-amine NMR (CDCl$_3$): δ 1.53 (m, 4H), 1.71 (m, 5H), 1.96 (m, 2H), 2.29 (m, 1H), 2.42 (m, 1H), 2.54 (m, 1H), 2.69 (m, 3H), 2.91 (m, 3H), 3.61 (s, 2H), 3.66 (t, J=6.20 Hz, 4H), 4.44 (m, 1H), 5.27 (m, 1H), 7.32 (m, 5H);
MS (ESI, Pos. 20 V): 392 (M+H)$^+$, 358, 302;
TLC: Rf 0.55 (AcOEt:MeOH:TEA=20:2:1).

Example 14-14

4-azepan-1-yl-N-[(3R)-1-(pyridin-2-ylmethyl)pyrrolidin-3-yl]-6,7-dihydro-5H-cyclopenta[d]pyrimidin-2-amine NMR (DMSO-d$_6$): δ 1.43 (m, 4H), 1.66 (m, 6H), 1.84 (m, 2H), 2.10 (m, 1H), 2.33 (m, J=7.32, 7.32 Hz, 1H), 2.57 (m, 2H), 2.84 (m, 4H), 3.58 (t, J=6.00 Hz, 4H), 3.66 (s, 2H), 4.20 (m, 1H), 6.25 (m, 1H), 7.22 (m, 1H), 7.41 (d, J=7.90 Hz, 1H), 7.72 (td, J=7.90, 1.70 Hz, 1H), 8.45 (m, 1H);
MS (ESI, Pos, 20 V): 393 (M+H)$^+$, 197 (M+2H)$^{2+}$;
TLC: Rf 0.41 (CHCl$_3$:MeOH:NH$_4$OH=80:10:1).

Example 14-15

4-azepan-1-yl-N-[(3S)-1-(pyridin-2-ylmethyl)pyrrolidin-3-yl]-6,7-dihydro-5H-cyclopenta[d]pyrimidin-2-amine NMR (CDCl$_3$): δ 1.54 (m, 4H), 1.73 (m, 5H), 2.01 (m, 2H), 2.31 (m, 1H), 2.52 (dd, J=9.50, 5.50 Hz, 1H), 2.68 (m, 2H), 2.75 (t, J=8.00 Hz, 2H), 2.93 (t, J=7.00 Hz, 2H), 3.03 (dd, J=9.50, 6.80 Hz, 1H), 3.69 (t, J=6.00 Hz, 4H), 3.76 (d, J=13.70 Hz, 1H), 3.82 (d, J=13.70 Hz, 1H), 4.45 (m, 1H), 6.94 (m, 1H), 7.15 (ddd, J=7.70, 4.90, 0.90 Hz, 1H), 7.43 (d, J=7.70 Hz, 1H), 7.65 (td, J=7.70, 1.70 Hz, 1H), 8.54 (ddd, J=4.90, 1.70, 0.90 Hz, 1H);
MS (ESI, Pos. 20 V): 393 (M+H)$^+$, 197 (M+2H)$^{2+}$;
TLC: Rf 0.26 (AcOEt:MeOH:TEA=20:2:1).

Example 14-16

4-azepan-1-yl-N-[(3S)-1-(2-ethylbutyl)pyrrolidin-3-yl]-6,7-dihydro-5H-cyclopenta[d]pyrimidin-2-amine NMR (DMSO-d$_6$): δ 0.81 (m, 6H), 1.28 (m, 4H), 1.47 (m, 4H), 1.63 (m, 6H), 1.85 (m, 2H), 2.05 (m, 1H), 2.22 (m, 2H), 2.48 (m, 5H), 2.75 (m, 1H), 2.86 (m, 2H), 3.61 (t, J=6.00 Hz, 4H), 4.18 (m, 1H), 6.19 (m, 1H);
MS (ESI, Pos. 20 V): 386 (M+H)$^+$, 233, 193.5 (M+2H)$^{2+}$;
TLC: Rf 0.57 (CHCl$_3$:MeOH:NH$_4$OH=80:10:1).

Example 14-17

4-azepan-1-yl-N-[(3R)-1-(2-ethylbutyl)pyrrolidin-3-yl]-6,7-dihydro-5H-cyclopenta[d]pyrimidin-2-amine NMR (CDCl$_3$): δ 0.85 (t, J=7.10 Hz, 6H), 1.35 (m, 5H), 1.56 (m, 4H), 1.76 (m, 5H), 1.99 (m, 2H), 2.31 (m, 4H), 2.61 (m, 2H), 2.72 (t, J=7.80 Hz, 2H), 2.94 (m, 3H), 3.70 (t, J=6.00 Hz, 4H), 4.41 (m, 1H), 6.42 (m, 1H)
MS (ESI, Pos. 20 V): 386 (M+H)$^+$, 302, 233, 193.5 (M+2H)$^{2+}$;
TLC: Rf 0.45 (AcOEt:MeOH:TEA=20:2:1).

Example 14-18

4-azepan-1-yl-N-[(3S)-1-isobutylpyrrolidin-3-yl]-6,7-dihydro-5H-cyclopenta[d]pyrimidin-2-amine NMR (DMSO-d$_6$): δ 0.84 (d, J=6.60 Hz, 6H), 1.45 (m, 4H), 1.61 (m, 6H), 1.85 (m, 2H), 2.08 (m, 3H), 2.24 (m, 1H), 2.45 (m, 4H), 2.74 (m, 4H), 2.86 (t, J=7.10 Hz, 2H), 3.61 (t, J=6.00 Hz, 4H), 4.19 (m, 1H), 6.17 (m, 1H);
MS (ESI, Pos, 20 V): 358 (M+H)$^+$, 233, 179.5 (M+2H)$^{2+}$;
TLC: Rf 0.45 (CHCl$_3$:MeOH:NH$_4$OH=80:10:1).

Example 14-19

4-azepan-1-yl-N-[(3R)-1-isobutylpyrrolidin-3-yl]-6,7-dihydro-5H-cyclopenta[d]pyrimidin-2-amine NMR (CDCl$_3$): δ 0.91 (d, J=6.60 Hz, 6H), 1.55 (m, 4H), 1.75 (m, 6H), 1.97 (m, 2H), 2.25 (m, 3H), 2.41 (m, 1H), 2.52

(m, 1H), 2.62 (m, 1H), 2.69 (t, J=7.80 Hz, 2H), 2.87 (m, 1H), 2.94 (t, J=7.20 Hz, 2H), 3.68 (t, J=6.00 Hz, 4H), 4.44 (m, 1H), 5.26 (m, 1H);
MS (ESI, Pos. 20 V): 358 (M+H)$^+$, 179.5 (M+2H)$^{2+}$;
TLC: Rf 0.45 (AcOEt:MeOH:TEA=20:2:1).

Example 14-20

4-azepan-1-yl-N-[(3S)-1-benzylpyrrolidin-3-yl]-5,6,7,8-tetrahydroquinazolin-2-amine NMR (DMSO-d$_6$): δ 1.41 (m, 4H), 1.65 (m, 8H), 2.10 (m, 1H), 2.24 (dd, J=9.00, 5.60 Hz, 1H), 2.45 (m, 6H), 2.78 (dd, J=9.00, 7.10 Hz, 1H), 3.34 (m, 1H), 3.48 (t, J=6.00 Hz, 4H), 4.03 (s, 2H), 4.23 (m, 1H), 6.19 (m, 1H), 7.23 (m, 5H);
MS (ESI, Pos, 20 V): 406 (M+H)$^+$, 316;
TLC: Rf 0.43 (CHCl$_3$:MeOH:NH$_4$OH=80:10:1).

Example 14-21

4-azepan-1-yl-N-[(3R)-1-benzylpyrrolidin-3-yl]-5,6,7,8-tetrahydroquinazolin-2-amine NMR (CDCl$_3$): 1.54 (m, 4H), 1.66 (m, 4H), 1.75 (m, 5H), 2.27 (m, 1H), 2.41 (dd, J=9.50, 4.80 Hz, 1H), 2.48 (m, 3H), 2.60 (m, 3H), 2.90 (dd, J=9.50, 6.60 Hz, 1H), 3.57 (t, J=6.20 Hz, 4H), 3.60 (s, 2H), 4.43 (m, 1H), 5.12 (m, 1H), 7.26 (m, 5H);
MS (ESI, Pos. 20 V): 406 (M+H)$^+$, 316;
TLC: Rf 0.55 (AcOEt:MeOH:TEA=20:2:1).

Example 14-22

4-azepan-1-yl-N-[(3S)-1-(pyridin-2-ylmethyl)pyrrolidin-3-yl]-5,6,7,8-tetrahydroquinazolin-2-amine NMR (DMSO-d$_6$): δ 1.45 (m, 4H), 1.59 (m, 10H), 2.09 (m, 1H), 2.32 (m, 3H), 2.48 (m, 4H), 2.84 (t, J=7.80 Hz, 1H), 3.49 (t, J=5.80 Hz, 4H), 3.66 (s, 2H), 4.20 (m, 1H), 6.23 (m, 1H), 7.23 (m, 1H); 7.41 (d, J=7.90 Hz, 1H), 7.72 (m, 1H);
MS (ESI, Pos. 20 V): 407 (M+H)$^+$, 204 (M+2H)$^{2+}$;
TLC: Rf 0.36 (CHCl$_3$:MeOH:NH$_4$OH=80:10:1).

Example 14-23

4-azepan-1-yl-N-[(3R)-1-(pyridin-2-ylmethyl)pyrrolidin-3-yl]-5,6,7,8-tetrahydroquinazolin-2-amine NMR (CDCl$_3$): δ 1.55 (m, 4H), 1.66 (m, 3H), 1.76 (m, 6H), 2.30 (m, 1H), 2.49 (m, 3H), 2.64 (m, 3H), 2.73 (m, 1H), 2.99 (dd, J=9.50, 6.80 Hz, 1H), 3.62 (t, J=5.90 Hz, 4H), 3.75 (d, J=13.70 Hz, 1H), 3.81 (d, J=13.70 Hz, 1H), 4.45 (m, 1H), 6.36 (m, 1H), 7.15 (ddd, J=7.60, 4.80, 1.20 Hz, 1H), 7.43 (d, J=7.60 Hz, 1H), 7.65 (td, J=7.60, 1.80 Hz, 1H), 8.54 (ddd, J=4.80, 1.80, 1.20 Hz, 1H);
MS (ESI, Pos. 20 V): 407 (M+H)$^+$, 204 (M+2H)$^{2+}$;
TLC: Rf 0.45 (AcOEt:MeOH:TEA=20:2:1).

Example 14-24

4-azepan-1-yl-N-[(3S)-1-(2-ethylbutyl)pyrrolidin-3-yl]-5,6,7,8-tetrahydroquinazolin-2-amine NMR (DMSO-d$_6$): δ 0.80 (m, 6H), 1.28 (m, 4H), 1.48 (m, 4H), 1.63 (m, 101H), 2.03 (m, 1H), 2.22 (m, 3H), 2.49 (m, 6H), 2.79 (m, 1H), 3.51 (t, J=5.90 Hz, 4H), 4.17 (m, 1H), 6.15 (m, 1H);
MS (ESI, Pos, 20 V): 400 (M+H)$^+$, 200.5 (M+2H)$^{2+}$;
TLC: Rf 0.40 (CHCl$_3$:MeOH:NH$_4$OH=80:10:1).

Example 14-25

4-azepan-1-yl-N-[(3R)-1-(2-ethylbutyl)pyrrolidin-3-yl]-5,6,7,8-tetrahydroquinazolin-2-amine NMR (CDCl$_3$): δ 0.85 (t, J=6.40 Hz, 6H), 1.35 (m, 5H), 1.57 (m, 4H), 1.67 (m, 4H), 1.78 (m, 5H), 2.27 (m, 3H), 2.35 (dd, J=9.50, 4.90 Hz, 1H), 2.49 (t, J=5.90 Hz, 2H), 2.58 (m, 2H), 2.64 (t, J=6.60 Hz, 2H), 2.88 (dd, J=9.20, 6.80 Hz, 1H), 3.63 (t, J=5.90 Hz, 4H), 4.40 (m, 1H), 5.97 (m, 1H);
MS (ESI, Pos. 20 V): 400 (M+H)$^+$, 316, 200.5 (M+2H)$^{2+}$;
TLC: Rf 0.45 (AcOEt:MeOH:TEA=20:2:1).

Example 14-26

4-azepan-1-yl-N-[(3S)-1-isobutylpyrrolidin-3-yl]-5,6,7,8-tetrahydroquinazolin-2-amine NMR (DMSO-d$_6$): δ 0.84 (d, J=6.60 Hz, 6H), 1.49 (m, 4H), 1.62 (m, 10H), 2.07 (m, 3H), 2.23 (m, 1H), 2.47 (m, 6H), 2.75 (m, 1H), 3.51 (m, 4H), 4.17 (m, 1H), 6.15 (m, 1H);
MS (ESI, Pos. 20 V): 372 (M+H)$^+$, 186.5 (M+2H)$^{2+}$;
TLC: Rf 0.38 (CHCl$_3$:MeOH:NH$_4$OH=80:10:1).

Example 14-27

4-azepan-1-yl-N-[(3R)-1-isobutylpyrrolidin-3-yl]-5,6,7,8-tetrahydroquinazolin-2-amine NMR (CDCl$_3$): δ 0.91 (d, J=6.60 Hz, 6H), 1.57 (m, 4H), 1.68 (m, 5H), 1.77 (m, 6H), 2.21 (m, 2H), 2.27 (m, 1H), 2.35 (dd, J=9.30, 5.10 Hz, 1H), 2.50 (t, J=6.00 Hz, 2H), 2.57 (m, 1H), 2.64 (t, J=6.50 Hz, 2H), 2.91 (dd, J=9.30, 6.80 Hz, 1H), 3.63 (t, J=6.10 Hz, 4H), 4.40 (m, 1H), 6.09 (m, 1H);
MS (ESI, Pos. 20 V): 372 (M+H)$^+$, 186.5 (M+2H)$^{2+}$;
TLC: Rf 0.45 (AcOEt:MeOH:TEA=20:2:1).

Example 14-28

4-azepan-1-yl-N-[(3S)-1-cyclohexylpyrrolidin-3-yl]-6,7-dihydro-5H-cyclopenta[d]pyrimidin-2-amine NMR (DMSO-d$_6$): δ 1.14 (m, 6H), 1.49 (m, 4H), 1.62 (m, 6H), 1.79 (m, 4H), 1.99 (m, 2H), 2.29 (m, 1H), 2.55 (m, 5H), 2.86 (m, 3H), 3.60 (t, J=6.00 Hz, 4H), 4.15 (m, 1H), 6.14 (m, 1H);
MS (ESI, Pos. 20 V): 384 (M+H)$^+$, 302, 192.5 (M+2H)$^{2+}$;
TLC: Rf 0.39 (CHCl$_3$:MeOH:NH$_4$OH=80:10:1).

Example 14-29

4-azepan-1-yl-N-[(3R)-1-cyclohexylpyrrolidin-3-yl]-6,7-dihydro-5H-cyclopenta[d]pyrimidin-2-amine NMR (DMSO-d$_6$): δ 1.15 (m, 6H), 1.46 (m, 4H), 1.66 (m, 10H), 1.82 (m, 2H), 2.02 (m, 2H), 2.33 (m, 1H), 2.48 (m, 2H), 2.58 (m, 1H), 2.86 (m, 3H), 3.61 (t, J=6.00 Hz, 4H), 4.17 (m, 1H), 6.12 (m, 1H);
MS (ESI, Pos. 20 V): 384 (M+H)$^+$, 302;
TLC: Rf 0.50 (AcOEt:MeOH:TEA=20:2:1).

Example 14-30

4-azepan-1-yl-N-[(3S)-1-cyclohexylpyrrolidin-3-yl]-5,6,7,8-tetrahydroquinazolin-2-amine NMR (DMSO-d$_6$): δ 1.17 (m, 6H), 1.63 (m, 16H), 1.99 (m, 2H), 2.28 (m, 1H), 2.48 (m, 7H), 2.85 (t, J=8.00 Hz, 1H), 3.51 (t, J=6.00 Hz, 4H), 4.15 (m, 1H), 6.14 (m, 1H);
MS (ESI, Pos, 20 V): 398 (M+H)$^+$, 316, 199.5 (M+2H)$^{2+}$;
TLC: Rf 0.39 (CHCl$_3$:MeOH:NH$_4$OH=80:10:1).

Example 14-31

4-azepan-1-yl-N-[(3R)-1-cyclohexylpyrrolidin-3-yl]-5,6,7,8-tetrahydroquinazolin-2-amine NMR (DMSO-d$_6$): δ 1.15 (m, 6H), 1.48 (m, 7H), 1.68 (m, 11H), 1.98 (m, 2H), 2.29 (dd, J=9.10, 5.80 Hz, 1H), 2.45 (m, 5H), 2.85 (t, J=8.40 Hz, 1H), 3.51 (t, J=6.00 Hz, 4H), 4.15 (m, 1H), 6.13 (m, 1H);
MS (ESI, Pos. 20 V): 398 (M+H)$^+$, 316, 199.5 (M+2H)$^{2+}$;
TLC: Rf 0.50 (AcOEt:MeOH:TEA=20:2:1).

Example 14-32

6-azepan-1-yl-N-(1-benzylpyrrolidin-3-yl)-9H-purin-2-amine

NMR (DMSO-d$_6$): δ 1.44 (m, 4H), 1.73 (m, 6H), 2.11 (m, 1H), 2.30 (dd, J=9.00, 5.20 Hz, 1H), 2.50 (m, 2H), 2.80 (dd, J=9.00, 7.00 Hz, 1H), 3.54 (s, 2H), 3.80 (m, 2H), 4.25 (m, 2H), 6.13 (d, J=6.80 Hz, 1H), 7.23 (m, 5H), 7.61 (s, 1H), 12.15 (m, 1H);
MS(LC-MS, APCI, Pos. 20 V): 392 (M+H)$^+$;
TLC: Rf 0.40 (CHCl$_3$:MeOH:NH$_4$OH=80:10:1).

Example 14-33

4-azepan-1-yl-N-(1-cyclohexylpiperidin-3-yl)-5,7-dihydrofuro[3,4-d]pyrimidin-2-amine NMR (DMSO-d$_6$): δ 1.08 (m, 6H), 1.45 (m, 6H), 1.72 (m, 10H), 1.99 (m, 1H), 2.27 (m, 2H), 2.66 (m, 1H), 2.97 (m, 1H), 3.50 (m, 4H), 3.78 (m, 1H), 4.56 (s, 2H), 5.04 (s, 2H), 6.22 (m, 1H);
MS (ESI, Pos. 20 V): 400 (M+H)$^+$, 318, 200.5 (M+2H)$^{2+}$;
TLC: Rf 0.59 (CHCl$_3$:MeOH:NH$_4$OH=80:10:1).

Example 14-34

6-azepan-1-yl-2-[(1-cyclohexylpiperidin-3-yl)amino]pyrimidine-4-carboxylic acid dihydrochloride NMR (CD$_3$OD): δ 1.23 (m, 2H), 1.39 (m, 3H), 1.63 (m, 6H), 1.86 (m, 6H), 2.13 (m, 5H), 3.06 (m, 1H), 3.21 (m, 1H), 3.51 (m, 1H), 3.72 (m, 2H), 3.79 (m, 2H), 4.01 (m, 1H), 4.06 (m, 1H), 4.56 (m, 1H), 6.98 (s, 1H);
MS (FAB, Pos., matrix=Glycerin+m-NBA): 402 (M+H)$^+$, 237;
TLC: Rf 0.25 (AcOEt:MeOH:TEA=20:2:1).

Example 14-35

6-azepan-1-yl-2-[(1-benzylpiperidin-3-yl)amino]pyrimidine-4-carboxamide

NMR (CDCl$_3$): δ 1.52 (m, 6H), 1.74 (m, 6H), 2.20 (m, 1H), 2.36 (m, 1H), 2.47 (m, 1H), 2.84 (m, 1H), 3.46 (d, J=13.20 Hz, 1H), 3.56 (d, J=13.20 Hz, 1H), 3.68 (m, 4H), 4.04 (m, 1H), 5.04 (m, 1H), 5.48 (m, 1H), 6.65 (s, 1H), 7.28 (m, 5H), 7.67 (m, 1H);
MS (ESI, Pos. 20 V): 409 (M+H)$^+$, 319;
TLC: Rf 0.60 (CHCl$_3$:MeOH=10:1).

Example 14-36

6-azepan-1-yl-2-(piperidin-3-ylamino)pyrimidine-4-carboxamide

NMR (CDCl$_3$): δ 1.52 (m, 5H), 1.75 (m, 6H), 1.98 (m, 1H), 2.60 (m, 1H), 2.74 (m, 1H), 2.90 (m, 1H), 2.99 (m, 1H), 3.36 (m, 1H), 3.50 (m, 2H), 3.71 (m, 2H), 4.06 (m, 1H), 4.96 (d, J=7.50 Hz, 1H), 5.71 (m, 1H), 6.68 (s, 1H), 7.89 (m, 1H);
MS (ESI, Pos. 20 V): 319 (M+H)$^+$, 236, 160 (M+2H)$^{2+}$;
TLC: Rf 0.20 (CHCl$_3$:MeOH:NH$_4$OH=80:10:1).

Example 14-37

6-azepan-1-yl-2-[(1-cyclohexylpiperidin-3-yl)amino]pyrimidine-4-carboxamide

NMR (CDCl$_3$): δ 1.22 (m, 6H), 1.53 (m, 6H), 1.76 (m, 10H), 2.27 (m, 2H), 2.44 (m, 1H), 2.62 (m, 1H), 2.98 (m, 1H), 3.51 (m, 2H), 3.74 (m, 2H), 4.01 (m, 1H), 5.04 (m, 1H), 5.47 (m, 1H), 6.66 (s, 1H), 7.77 (m, 1H);
MS (ESI, Pos. 20 V): 401 (M+H)$^+$, 319, 201 (M+21)$^{2+}$;
TLC: Rf 0.28 (CHCl$_3$:MeOH=10:1).

Example 14-38

4-azepan-1-yl-N-[(3S)-1-benzylazepan-3-yl]-6,7-dihydro-5H-cyclopenta[d]pyrimidin-2-amine NMR (DMSO-d$_6$): δ 1.39 (m, 5H), 1.67 (m, 8H), 1.86 (m, 3H), 2.52 (m, 5H), 2.83 (m, 3H), 3.57 (t, J=5.90 Hz, 4H), 3.62 (s, 2H), 3.96 (m, 1H), 5.83 (m, 1H), 7.27 (m, 5H);
MS (ESI, Pos. 20 V): 839 (2M+H)$^+$, 420 (M+H)$^+$;
HPLC condition: A; HPLC retention time (min): 3.16;
TLC: Rf 0.42 (CHCl$_3$:MeOH:NH$_4$OH=80:10:1).

Example 14-39

4-azepan-1-yl-N-[(3R)-1-benzylazepan-3-yl]-6,7-dihydro-5H-cyclopenta[d]pyrimidin-2-amine NMR (DMSO-d$_6$): δ 1.42 (m, 6H), 1.60 (m, 8H), 1.84 (m, 2H), 2.51 (m, 5H), 2.82 (m, 3H), 3.57 (t, J=6.00 Hz, 4H), 3.62 (s, 2H), 3.97 (m, 1H), 5.86 (m, 1H), 7.25 (m, 5H);
MS (ESI, Pos. 20 V): 839 (2M+H)$^+$, 420 (M+H)$^+$;
HPLC condition: A; HPLC retention time (min): 3.18;
TLC: Rf 0.50 (CHCl$_3$:MeOH:NH$_4$OH=80:10:1).

Example 14-40

N-[(3S)-azepan-3-yl]-4-azepan-1-yl-6,7-dihydro-5H-cyclopenta[d]pyrimidin-2-amine NMR (DMSO-$d_6$): δ 1.44 (m, 5H), 1.54 (m, 4H), 1.70 (m, 5H), 1.84 (m, 2H), 2.49 (m, 2H), 2.58 (dd, J=13.60, 7.00 Hz, 1H), 2.71 (t, J=6.00 Hz, 2H), 2.87 (m, 3H), 3.59 (t, J=600 Hz, 4H), 3.85 (m, 1H), 5.83 (m, 1H);
MS (ESI, Pos. 20 V): 330 (M+H)$^+$, 165.5 (M+2H)$^{2+}$;
HPLC condition: A; HPLC retention time (min): 3.03;
TLC: Rf 0.38 (CHCl$_3$:MeOH:NH$_4$OH=80:10:1).

Example 14-41

N-[(3R)-azepan-3-yl]-4-azepan-1-yl-6,7-dihydro-5H-cyclopenta[d]pyrimidin-2-amine NMR (DMSO-$d_6$): δ 1.45 (m, 5H), 1.54 (m, 4H), 1.68 (m, 5H), 1.84 (m, 2H), 2.49 (m, 2H), 2.58 (dd, J=13.60, 7.10 Hz, 1H), 2.71 (t, J=5.90 Hz, 2H), 2.87 (m, 3H), 3.59 (t, J=6.00 Hz, 4H), 3.86 (m, 1H), 5.86 (m, 1H);
MS (ESI, Pos. 20 V): 330 (M+H)$^+$, 165.5 (M+2H)$^{2+}$;
HPLC condition: A; HPLC retention time (min): 3.05;
TLC: Rf 0.38 (CHCl$_3$:MeOH:NH$_4$OH=80:10:1).

Example 14-42

4-azepan-1-yl-N-[(3S)-1-(pyridin-2-ylmethyl)azepan-3-yl]-6,7-dihydro-5H-cyclopenta[d]pyrimidin-2-amine

Example 14-43

4-azepan-1-yl-N-[(3R)-1-(pyridin-2-ylmethyl)azepan-3-yl]-6,7-dihydro-5H-cyclopenta[d]pyrimidin-2-amine

Example 14-44

4-azepan-1-yl-N-[(3S)-1-(2-ethylbutyl)azepan-3-yl]-6,7-dihydro-5H-cyclopenta[d]pyrimidin-2-amine MS (ESI, Pos. 20 V): 414 (M+H)$^+$, 330, 207.5 (M+2H)$^{2+}$;
HPLC condition: A; HPLC retention time (min): 3.25.

Example 14-45

4-azepan-1-yl-N-[(3R)-1-(2-ethylbutyl)azepan-3-yl]-6,7-dihydro-5H-cyclopenta[d]pyrimidin-2-amine MS (ESI, Pos. 20 V): 414 (M+H)$^+$, 330, 207.5 (M+2H)$^{2+}$;
HPLC condition: A; HPLC retention time (min): 3.27.

Example 14-46

4-azepan-1-yl-N-[(3S)-1-isobutylazepan-3-yl]-6,7-dihydro-5H-cyclopenta[d]pyrimidin-2-amine MS (ESI, Pos. 20 V): 386 (M+H)$^+$, 330, 193.5 (M+2H)$^{2+}$;
HPLC condition: A; HPLC retention time (min): 3.14.

Example 14-47

4-azepan-1-yl-N-[(3R)-1-isobutylazepan-3-yl]-6,7-dihydro-5H-cyclopenta[d]pyrimidin-2-amine MS (ESI, Pos. 20 V): 386 (M+H)$^+$, 193.5 (M+2H)$^{2+}$;
HPLC condition: A; HPLC retention time (min): 3.14.

Example 14-48

4-azepan-1-yl-N-[(3S)-1-cyclohexylazepan-3-yl]-6,7-dihydro-5H-cyclopenta[d]pyrimidin-2-amine MS (ESI, Pos. 20 V): 412 (M+H)$^+$, 386, 330, 206.5 (M+2H)$^{2+}$;
HPLC condition: A; HPLC retention time (min): 3.20.

Example 14-49

4-azepan-1-yl-N-[(3R)-1-cyclohexylazepan-3-yl]-6,7-dihydro-5H-cyclopenta[d]pyrimidin-2-amine MS (ESI, Pos. 20 V): 412 (M+H)$^+$, 386, 330, 206.5 (M+2H)$^{2+}$;
HPLC condition: A; HPLC retention time (min): 3.20.

Example 14-50

4-azepan-1-yl-N-[(3S)-1-benzylazepan-3-yl]-5,6,7,8-tetrahydroquinazolin-2-amine

NMR (DMSO-$d_6$): δ 1.45 (m, 4H), 1.56 (m, 6H), 1.77 (m, 8H), 2.47 (m, 5H), 2.79 (m, 1H), 3.16 (d, J=5.10 Hz, 2H), 3.48 (t, J=6.00 Hz, 4H), 3.62 (s, 2H), 3.91 (m, 1H), 5.85 (m, 1H), 7.25 (m, 5H);
MS (ESI, Pos. 20 V): 434 (M+H)$^+$, 344;
HPLC condition: A; HPLC retention time (min): 3.23;
TLC: Rf 0.42 (CHCl$_3$:MeOH:NH$_4$OH=80:10:1).

Example 14-51

4-azepan-1-yl-N-[(3R)-1-benzylazepan-3-yl]-5,6,7,8-tetrahydroquinazolin-2-amine

NMR (DMSO-$d_6$): δ 1.45 (m, 4H), 1.56 (m, 6H), 1.75 (m, 8H), 2.47 (m, 5H), 2.79 (dd, J=13.10, 3.90 Hz, 1H), 3.16 (d, J=5.00 Hz, 2H), 3.47 (t, J=6.00 Hz, 4H), 3.62 (s, 2H), 3.94 (m, 1H), 5.83 (m, 1H), 7.23 (m, 5H);
MS (ESI, Pos. 20 V): 434 (M+H)$^+$;
HPLC condition: A; HPLC retention time (min): 3.23;
TLC: Rf 0.42 (CHCl$_3$:MeOH:NH$_4$OH 80:10:1)

Example 14-52

N-[(3R)-azepan-3-yl]-4-azepan-1-yl-5,6,7,8-tetrahydroquinazolin-2-amine

NMR (DMSO-$d_6$): δ 1.46 (m, 6H), 1.56 (m, 5H), 1.69 (m, 7H), 2.39 (m, 4H), 2.56 (m, 1H), 2.71 (t, J=5.90 Hz, 2H), 2.88 (dd, J13.50, 4.30 Hz, 1H), 3.50 (t, J=6.00 Hz, 4H), 3.83 (m, 1H), 5.84 (m, 1H);
MS (ESI, Pos. 20 V): 344 (M+H)$^+$, 172.5 (M+2H)$^{2+}$;
HPLC condition: A; HPLC retention time (min): 3.11;
TLC: Rf 0.38 (CHCl$_3$:MeOH:NH$_4$OH=80:10:1).

Example 14-53

4-azepan-1-yl-N-[(3S)-1-(pyridin-2-ylmethyl)azepan-3-yl]-5,6,7,8-tetrahydroquinazolin-2-amine

Example 14-54

4-azepan-1-yl-N-[(3R)-1-(pyridin-2-ylmethyl)azepan-3-yl]-5,6,7,8-tetrahydroquinazolin-2-amine

Example 14-55

4-azepan-1-yl-N-[(3S)-1-(2-ethylbutyl)azepan-3-yl]-5,6,7,8-tetrahydroquinazolin-2-amine MS (ESI, Pos. 20 V): 428 (M+H)$^+$, 344, 214.5 (M+2H)$^{2+}$;
HPLC condition: A; HPLC retention time (min): 3.33.

Example 14-56

4-azepan-1-yl-N-[(3R)-1-(2-ethylbutyl)azepan-3-yl]-5,6,7,8-tetrahydroquinazolin-2-amine MS (ESI, Pos. 20 V): 428 (M+H)$^+$, 344, 214.5 (M+2H)$^{2+}$;
HPLC condition: A; HPLC retention time (min): 3.34.

Example 14-57

4-azepan-1-yl-N-[(3S)-1-isobutylazepan-3-yl]-5,6,7,8-tetrahydroquinazolin-2-amine MS (ESI, Pos. 20 V): 400 (M+H)$^+$, 200.5 (M+2H)$^{2+}$;
HPLC condition: A; HPLC retention time (min): 3.23.

Example 14-58

4-azepan-1-yl-N-[(3R)-1-isobutylazepan-3-yl]-5,6,7,8-tetrahydroquinazolin-2-amine MS (ESI, Pos. 20 V): 400 (M+H)$^+$, 200.5 (M+2H)$^{2+}$;
HPLC condition: A; HPLC retention time (min): 3.22.

Example 14-59

4-azepan-1-yl-N-[(3S)-1-cyclohexylazepan-3-yl]-5,6,7,8-tetrahydroquinazolin-2-amine MS (ESI, Pos. 20 V): 426 (M+H)$^+$, 400, 344, 213.5 (M+2H)$^{2+}$;
HPLC condition: A; HPLC retention time (min): 3.27.

Example 14-60

4-azepan-1-yl-N-[(3R)-1-cyclohexylazepan-3-yl]-5,6,7,8-tetrahydroquinazolin-2-amine MS (ESI, Pos.20V): 426 (M+H)$^+$, 400, 344, 213.5 (M+2H)$^{2+}$;
HPLC condition: A; HPLC retention time (min): 3.27.

Example 14-61

4-azepan-1-yl-N-[(3S)-1-benzylpiperidin-3-yl]-6,7-dihydro-5H-cyclopenta[d]pyrimidin-2-amine MS (ESI, Pos.20V): 811 (2M+H)$^+$, 406 (M+H)$^+$, 316;
HPLC condition: A; HPLC retention time (min): 3.16.

Example 14-62

4-azepan-1-yl-N-[(3R)-1-benzylpiperidin-3-yl]-6,7-dihydro-5H-cyclopenta[d]pyrimidin-2-amine MS (ESI, Pos.20V): 811 (2M+H)$^+$, 406 (M+H)$^+$, 316;
HPLC condition: A; HPLC retention time (min): 3.14.

Example 14-63

4-azepan-1-yl-N-[(3S)-1-(pyridin-2-ylmethyl)piperidin-3-yl]-6,7-dihydro-5H-cyclopenta[d]pyrimidin-2-amine MS (ESI, Pos.20V): 407 (M+H)$^+$, 204 (M+2H)$^{2+}$;
HPLC condition: A; HPLC retention time (min): 3.05.

Example 14-64

4-azepan-1-yl-N-[(3R)-1-(pyridin-2-ylmethyl)piperidin-3-yl]-6,7-dihydro-5H-cyclopenta[d]pyrimidin-2-amine MS (ESI, Pos.20V): 407 (M+H)$^+$, 204 (M+2H)$^{2+}$;
HPLC condition: A; HPLC retention time (min): 3.05.

Example 14-65

4-azepan-1-yl-N-[(3S)-1-(2-ethylbutyl)piperidin-3-yl]-6,7-dihydro-5H-cyclopenta[d]pyrimidin-2-amine MS (ESI, Pos.20V): 799 (2M+H)$^+$, 400 (M+H)$^+$, 200.5 (M+2H)$^{2+}$;
HPLC condition: A; HPLC retention time (min): 3.23.

Example 14-66

4-azepan-1-yl-N-[(3R)-1-(2-ethylbutyl)piperidin-3-yl]-6,7-dihydro-5H-cyclopenta[d]pyrimidin-2-amine MS (ESI, Pos.20V): 799 (2M+H)$^+$, 400 (M+H)$^+$, 200.5 (M+2H)$^{2+}$;
HPLC condition: A; HPLC retention time (min): 3.23.

Example 14-67

4-azepan-1-yl-N-[(3S)-1-isobutylpiperidin-3-yl]-6,7-dihydro-5H-cyclopenta[d]pyrimidin-2-amine MS (ESI, Pos.20V): 743 (2M+H)$^+$, 372 (M+H)$^+$, 3 16, 186.5 (M+2H)$^{2+}$;
HPLC condition: A; HPLC retention time (min): 3.11.

Example 14-68

4-azepan-1-yl-N-[(3R)-1-isobutylpiperidin-3-yl]-6,7-dihydro-5H-cyclopenta[d]pyrimidin-2-amine MS (ESI, Pos.20V): 743 (2M+H)$^+$, 372 (M+H)$^+$, 344, 186.5 (M+2H)$^{2+}$;
HPLC condition: A; HPLC retention time (min): 3.11.

Example 14-69

4-azepan-1-yl-N-[(3S)-1-cyclohexylpiperidin-3-yl]-6,7-dihydro-5H-cyclopenta[d]pyrimidin-2-amine MS (ESI, Pos.20V): 398 (M+H)$^+$, 372, 316, 199.5 (M+2H)$^{2+}$;
HPLC condition: A; HPLC retention time (min): 3.16.

Example 14-70

4-azepan-1-yl-N-[(3R)-1-cyclohexylpiperidin-3-yl]-6,7-dihydro-5H-cyclopenta[d]pyrimidin-2-amine MS (ESI, Pos.20V): 795 (2M+H)$^+$, 398 (M+H)$^+$, 199.5 (M+2H)$^{2+}$;
HPLC condition: A; HPLC retention time (min): 3.16.

Example 14-71

4-azepan-1-yl-N-[(3S)-piperidin-3-yl]-6,7-dihydro-5H-cyclopenta[d]pyrimidin-2-amine NMR (CDCl$_3$): δ 1.48 (m, 2H), 1.54 (m, 4H), 1.74 (m, 4H), 1.98 (m, 4H), 2.52 (dd, J=11.70, 8.20 Hz, 1H), 2.62 (m, 1H), 2.67 (t, J=7.10 Hz, 2H), 2.87 (m, 1H), 2.94 (t, J=7.10 Hz, 2H), 3.25 (dd, J=11.70, 3.70 Hz, 1H), 3.67 (t, J=6.00 Hz, 4H), 3.84 (m, 1H), 4.82 (d, J=7.90 Hz, 1H);
MS (ESI, Pos. 20 V): 631 (2M+H)$^+$, 316 (M+H)$^+$, 158.5 (M+2H)$^{2+}$;
TLC: Rf 0.17 (CHCl$_3$:MeOH:NH$_4$OH=80:10:1).

Example 14-72

4-azepan-1-yl-N-[(3R)-piperidin-3-yl]-6,7-dihydro-5H-cyclopenta[d]pyrimidin-2-amine NMR (DMSO-d$_6$): δ 1.33 (m, 2H), 1.45 (m, 4H), 1.56 (m, 1H), 1.66 (m, 4H), 1.83 (m, 3H), 2.31 (dd, J=11.40, 8.70 Hz, 1H), 2.41 (m, 3H), 2.73 (m, 1H), 2.86 (t, J=7.10 Hz, 2H), 2.98 (dd, J=11.40, 3.70 Hz, 1H), 3.59 (t, J=6.00 Hz, 4H), 3.70 (m, 1H), 5.93 (m, 1H);
MS (ESI, Pos. 20 V): 316 (M+H)$^+$, 158.5 (M+2H)$^{2+}$;
TLC: Rf 0.17 (CHCl$_3$:MeOH:NH$_4$OH=80:10:1).

Example 14-73

4-azepan-1-yl-N-[(3S)-1-benzylpiperidin-3-yl]-5,6,7,8-tetrahydroquinazolin-2-amine MS (ESI, Pos.20V): 839 (2M+H)$^+$, 420 (M+H)$^+$, 330;
HPLC condition: A; HPLC retention time (min): 3.22.

Example 14-74

4-azepan-1-yl-N-[(3R)-1-benzylpiperidin-3-yl]-5,6,7,8-tetrahydroquinazolin-2-amine MS (ESI, Pos.20V): 839 (2M+H)$^+$, 420 (M+H)$^+$, 330;
HPLC condition: A; HPLC retention time (min): 3.20.

Example 14-75

4-azepan-1-yl-N-[(3S)-1-(pyridin-2-ylmethyl)piperidin-3-yl]-5,6,7,8-tetrahydroquinazolin-2-amine MS (ESI, Pos.20V): 421 (M+H)$^+$, 402, 330, 211 (M+2H)$^{2+}$;
HPLC condition: A; HPLC retention time (min): 3.11.

Example 14-76

4-azepan-1-yl-N-[(3R)-1-(pyridin-2-ylmethyl)piperidin-3-yl]-5,6,7,8-tetrahydroquinazolin-2-amine MS (ESI, Pos.20V): 421 (M+H)$^+$, 402, 330, 211 (M+2H)$^{2+}$;
HPLC condition: A; HPLC retention time (min): 3.11.

Example 14-77

4-azepan-1-yl-N-[(3S)-1-(2-ethylbutyl)piperidin-3-yl]-5,6,7,8-tetrahydroquinazolin-2-amine MS (ESI, Pos.20V): 827 (2M+H)$^+$, 414 (M+H)$^+$, 330, 207.5 (M+2H)$^{2+}$;
HPLC condition: A; HPLC retention time (min): 3.29.

Example 14-78

4-azepan-1-yl-N-[(3R)-1-(2-ethylbutyl)piperidin-3-yl]-5,6,7,8-tetrahydroquinazolin-2-amine MS (ESI, Pos.20V): 414 (M+H)$^+$, 330, 207.5 (M+2H)$^{2+}$;
HPLC condition: A; HPLC retention time (min): 3.29.

Example 14-79

4-azepan-1-yl-N-[(3S)-1-isobutylpiperidin-3-yl]-5,6,7,8-tetrahydroquinazolin-2-amine MS (ESI, Pos.20V): 771 (2M+H)$^+$, 386 (M+H)$^+$, 193.5 (M+2H)$^{2+}$;
HPLC condition: A; HPLC retention time (min): 3.16.

Example 14-80

4-azepan-1-yl-N-[(3R)-1-isobutylpiperidin-3-yl]-5,6,7,8-tetrahydroquinazolin-2-amine MS (ESI, Pos.20V): 771 (2M+H)$^+$, 386 (M+H)$^+$, 193.5 (M+2H)$^{2+}$;
HPLC condition: A; HPLC retention time (min): 3.16.

Example 14-81

4-azepan-1-yl-N-[(3S)-1-cyclohexylpiperidin-3-yl]-5,6,7,8-tetrahydroquinazolin-2-amine MS (ESI, Pos.20V): 823 (2M+H)$^+$, 412 (M+H)$^+$, 330, 206.5 (M+2H)$^{2+}$;

HPLC condition: A; HPLC retention time (min): 3.22.

Example 14-82

4-azepan-1-yl-N-[(3R)-1-cyclohexylpiperidin-3-yl]-5,6,7,8-tetrahydroquinazolin-2-amine MS (ESI, Pos.20V): 823 (2M+H)$^+$, 412 (M+H)$^+$, 330, 206.5 (M+2H)$^{2+}$;

HPLC condition: A; HPLC retention time (min): 3.22.

Example 14-83

4-azepan-1-yl-N-[(3S)-piperidin-3-yl]-5,6,7,8-tetrahydroquinazolin-2-amine

NMR (CDCl$_3$): δ 1.47 (m, 2H), 1.56 (m, 4H), 1.67 (m, 2H), 1.76 (m, 6H), 1.99 (m, 2H), 2.49 (t, J=6.70 Hz, 2H), 2.53 (m, 1H), 2.61 (t, J=6.70 Hz, 2H), 2.66 (m, 1H, 2.89 (m, 1H), 3.24 (dd, J=11.50, 3.50 Hz, 1H), 3.59 (t, J=6.00 Hz, 4H), 3.81 (m, 1H), 4.88 (m, 1H);

MS (ESI, Pos. 20 V): 330 (M+H)$^+$, 165.5 (M+2H)$^{2+}$;

TLC: Rf 0.17 (CHCl$_3$:MeOH:NH$_4$OH=80:10:1).

Example 14-84

4-azepan-1-yl-N-[(3R)-piperidin-3-yl]-5,6,7,8-tetrahydroquinazolin-2-amine

NMR (DMSO-d$_6$): δ 1.35 (m, 2H), 1.49 (m, 4H), 1.58 (m, 3H), 1.67 (m, 6H), 1.83 (m, 1H), 2.30 (dd, J=11.80, 8.80 Hz, 1H), 2.44 (m, 5H), 2.72 (m, 1H), 2.97 (dd, J=11.80, 3.60 Hz, 1H), 3.50 (t, J=5.90 Hz, 4H), 3.63 (m, 1H), 5.91 (m, 1H);

MS (ESI, Pos. 20 V): 330 (M+H)$^+$, 165.5 (M+2H)$^{2+}$;

TLC: Rf 0.17 (CHCl$_3$:MeOH:NH$_4$OH=80:10:1).

EXAMPLE 15-01 to EXAMPLE 15-55

By the same procedure as described in Reference Example 1→Example 1 using corresponding compounds, the compounds of the present invention having the following physical data were given.

Example 15-01

N$^2$-(2-aminoethyl)-N$^4$-benzyl-N$^4$-methylpyrimidine-2,4-diamine

MS (ESI, Pos.20V): 258 (M+H);
HPLC condition: A; HPLC retention time (min): 2.89.

Example 15-02

N$^2$-(2-aminoethyl)-N$^4$-methyl-N$^4$-(2-phenylethyl)pyrimidine-2,4-diamine

MS (ESI, Pos.20V): 272 (M+H);
HPLC condition: A; HPLC retention time (min): 2.95.

Example 15-03

N$^2$-(2-aminoethyl)-N$^4$,N$^4$-diisopentylpyrimidine-2,4-diamine

MS (ESI, Pos.20V): 294 (M+H);
HPLC condition: A; HPLC retention time (min): 3.24.

Example 15-04

N$^2$-(2-aminoethyl)-N$^4$-[3-(dimethylamino)propyl]-N$^4$-methylpyrimidine-2,4-diamine MS (ESI, Pos.20V): 253 (M+H);
HPLC condition: B; HPLC retention time (min): 2.83.

Example 15-05

1,1'-(2-[(2-aminoethyl)amino]-4-pyrimidinylimino)di(2-propanol)

Example 15-06

N$^2$-(2-aminoethyl)-N$^4$,N$^4$-dibutylpyrimidine-2,4-diamine

MS (ESI, Pos.20V): 266 (M+H);
HPLC condition: A; HPLC retention time (min): 3.10.

Example 15-07

N$^2$-(2-aminoethyl)-N$^4$-[2-(dimethylamino)ethyl]-N$^4$-methylpyrimidine-2,4-diamine

Example 15-08

2-[2-[(2-aminoethyl)amino]pyrimidin-4-yl(butyl)amino]ethanol

MS (ESI, Pos.20V): 254 (M+H);
HPLC condition: A;
HPLC retention time (min): 2.79.

Example 15-09

N$^2$-(2-aminoethyl)-N$^4$,N$^4$-bis(2-methoxyethyl)pyrimidine-2,4-diamine

Example 15-10

N$^2$-(2-aminoethyl)-N$^4$-methyl-N$^4$-(2-pyridin-2-ylethyl)pyrimidine-2,4-diamine MS (ESI, Pos.20V): 273 (M+H);
HPLC condition: B; HPLC retention time (min): 2.86.

Example 15-11

$N^2$-(2-aminoethyl)-$N^4$-methyl-$N^4$-(1-methylpiperidin-4-yl)pyrimidine-2,4-diamine MS (ESI, Pos.20V): 265 (M+H);
HPLC condition: B; HPLC retention time (min): 2.81.

Example 15-12

$N^2$-(2-aminoethyl)-$N^4$,$N^4$-bis[3-(dimethylamino)propyl]pyrimidine-2,4-diamine MS (ESI, Pos.20V): 324 (M+H);
HPLC condition: B; HPLC retention time (min): 3.02.

Example 15-13

$N^2$-(2-aminoethyl)-$N^4$-(2-methoxyethyl)-$N^4$-methylpyrimidine-2,4-diamine

MS (ESI, Pos.20V): 226 (M+H);
HPLC condition: B; HPLC retention time (min): 2.69.

Example 15-14

$N^2$-(2-aminoethyl)-$N^4$-methyl-$N^4$-(4-pyridin-3-ylbutyl)pyrimidine-2,4-diamine MS (ESI, Pos.20V): 301 (M+H);
HPLC condition: B; HPLC retention time (min): 3.14.

Example 15-15

$N^2$-(2-aminoethyl)-$N^4$-methyl-$N^4$-[(6-methylpyridin-2-yl)methyl]pyrimidine-2,4-diamine MS (ESI, Pos.20V): 273 (M+H);
HPLC condition: B; HPLC retention time (min): 2.92.

Example 15-16

$N^2$-(2-aminoethyl)-$N^4$-benzyl-$N^4$-[2-(dimethylamino)ethyl]pyrimidine-2,4-diamine MS (ESI, Pos.20V): 315 (M+H);
HPLC condition: A; HPLC retention time (min): 2.63.

Example 15-17

$N^2$-(2-aminoethyl)-$N^4$-(2-furylmethyl)-$N^4$-methylpyrimidine-2,4-diamine

Example 15-18

4-[2-[(2-aminoethyl)amino]pyrimidin-4-yl(ethyl)amino]butan-1-ol

Example 15-19

$N^2$-(2-aminoethyl)-$N^4$,$N^4$-bis(2-ethoxyethyl)pyrimidine-2,4-diamine

MS (ESI, Pos.20V): 298 (M+H);
HPLC condition: A; HPLC retention time (min): 2.86.

Example 15-20

$N^2$-(2-aminoethyl)-$N^4$-cyclohexylpyrimidine-2,4-diamine

MS (ESI, Pos.20V): 236 (M+H);
HPLC condition: A; HPLC retention time (min): 2.88.

Example 15-21

$N^2$-(2-aminoethyl)-$N^4$-[(5-methyl-2-furyl)methyl]pyrimidine-2,4-diamine

Example 15-22

$N^2$-(2-aminoethyl)-$N^4$-(2,3-dihydro-1H-inden-1-yl)pyrimidine-2,4-diamine

MS (ESI, Pos.20V): 270 (M+H);
HPLC condition: A; HPLC retention time (min): 2.93.

Example 15-23

$N^2$-(2-aminoethyl)-$N^4$-(pyridin-3-ylmethyl)pyrimidine-2,4-diamine

Example 15-24

$N^2$-(2-aminoethyl)-$N^4$-(2-piperidin-1-ylethyl)pyrimidine-2,4-diamine

MS (ESI, Pos.20V): 265 (M+H);
HPLC condition: B; HPLC retention time (min): 2.90.

Example 15-25

$N^2$-(2-aminoethyl)-$N^4$-benzylpyrimidine-2,4-diamine

MS (ESI, Pos.20V): 244 (M+H);
HPLC condition: A; HPLC retention time (min): 2.79.

Example 15-26

$N^2$-(2-aminoethyl)-$N^4$-cyclooctylpyrimidine-2,4-diamine

MS (ESI, Pos.20V): 264 (M+H); HPLC condition: A; HPLC retention time (min): 3.02.

Example 15-27

$N^2$-(2-aminoethyl)-$N^4$-hexylpyrimidine-2,4-diamine

MS (ESI, Pos.20V): 238 (M+H);
HPLC condition: A; HPLC retention time (min): 2.99.

Example 15-28

$N^2$-(2-aminoethyl)-$N^4$-methyl-$N^4$-phenylpyrimidine-2,4-diamine dihydrochloride NMR (CD$_3$OD): δ 7.66-7.44 (m, 4H), 7.41-7.32 (m, 2H), 5.82 (d, J=7.5 Hz, 1H), 3.87 (t, J=6.0 Hz, 2H), 3.60 (s, 3H), 3.30 (t, J=6.0 Hz, 2H);

MS (FAB, Pos., Glycerin+m-NBA): 244 (M+H)$^+$, 227, 201;

TLC: Rf 0.20 (n-BuOH:AcOH:H$_2$O=4:2:1).

Example 15-29

$N^2$-(2-aminoethyl)-$N^4$-benzyl-$N^4$-phenylpyrimidine-2,4-diamine dihydrochloride NMR (CD$_3$OD): δ 7.67 (d, J=7.2 Hz, 1H), 7.54-7.39 (m, 3H), 7.37-7.17 (m, 7H), 5.84 (d, J=7.2 Hz, 1H), 5.34 (s, 2H), 3.77 (t, J=6.0 Hz, 2H), 3.10 (t, J=6.0 Hz, 2H);

MS (FAB, Pos., Glycerin+m-NBA): 320 (M+H)$^+$, 303, 230;

TLC: Rf 0.26 (n-BuOH:AcOH:H$_2$O=4:2:1).

Example 15-30

$N^2$-(2-aminoethyl)-$N^4$-(2-piperidin-1-ylethyl)pyrimidine-2,4-diamine dihydrochloride NMR (DMSO-d$_6$): δ 1.39 (m, 1H), 1.79 (m, 5H), 2.95 (m, 4H), 3.24 (m, 2H), 3.48 (m, 2H), 3.71 (m, 2H), 3.94 (m, 2H), 6.17 (d, J=7.30 Hz, 1H), 7.74 (d, J=7.30 Hz, 1H), 8.43 (m, 4H), 9.51 (m, 1H), 10.75 (m, 1H) 12.70 (m, 1H);

MS(LC-MS, APCI, Pos. 20 V): 265 (M+H)$^+$;

TLC: Rf 0.38 (CHCl$_3$:MeOH:NH$_4$OH=80:20:4).

Example 15-31

2-[(4-[2-(dimethylamino)ethyl]aminopyrimidin-2-yl)(methyl)amino]ethanol

MS (ESI, Pos, 20 V): 240 (M+H)$^+$;
HPLC condition: B; HPLC retention time (min): 2.72.

Example 15-32

$N^4$-[2-(dimethylamino)ethyl]-$N^2$-methyl-$N^2$-(1-naphthylmethyl)pyrimidine-2,4-diamine MS (ESI, Pos, 20 V): 336 (M+H)$^+$;
HPLC condition: B; HPLC retention time (min): 3.68.

Example 15-33

$N^4$-[2-(dimethylamino)ethyl]-$N^2$-hexyl-$N^2$-methylpyrimidine-2,4-diamine

MS (ESI, Pos, 20 V): 280 (M+H)$^+$;
HPLC condition: B; HPLC retention time (min): 3.82.

Example 15-34

$N^2$-benzyl-$N^4$-[2-(dimethylamino)ethyl]-$N^2$-ethylpyrimidine-2,4-diamine

MS (ESI, Pos, 20 V): 300 (M+H)$^+$;
HPLC condition: B; HPLC retention time (min): 3.62.

Example 15-35

$N^2$-benzyl-$N^4$-[2-(dimethylamino)ethyl]-$N^2$-methylpyrimidine-2,4-diamine

MS (ESI, Pos, 20 V): 286 (M+H)$^+$;
HPLC condition: B; HPLC retention time (min): 3.45.

Example 15-36

$N^4$-[2-(dimethylamino)ethyl]-$N^2$,$N^2$-bis(pyridin-2-ylmethyl)pyrimidine-2,4-diamine MS (ESI, Pos, 20 V): 364 (M+H)$^+$, 214
HPLC condition: B; HPLC retention time (min): 3.05.

Example 15-37

$N^4$-[2-(dimethylamino)ethyl]-$N^2$-methyl-$N^2$-(1-methylpiperidin-4-yl)pyrimidine-2,4-diamine MS (ESI, Pos, 20 V): 293 (M+H)$^+$;
HPLC condition: B; HPLC retention time (min): 2.98.

Example 15-38

$N^2$,$N^4$-bis[2-(dimethylamino)ethyl]-$N^2$-methylpyrimidine-2,4-diamine

MS (ESI, Pos, 20 V): 267 (M+H)$^+$;
HPLC condition: B; HPLC retention time (min): 2.96.

Example 15-39

$N^4$-[2-(dimethylamino)ethyl]-$N^2$-methyl-$N^2$-(2-phenylethyl)pyrimidine-2,4-diamine MS (ESI, Pos, 20 V): 300 (M+H)$^+$;
HPLC condition: B; HPLC retention time (min): 3.56.

Example 15-40

$N^4$-[2-(dimethylamino)ethyl]-$N^2$-(2-furylmethyl)-$N^2$-methylpyrimidine-2,4-diamine MS (ESI, Pos, 20 V): 276 (M+H)$^+$;
HPLC condition: B; HPLC retention time (min): 3.29.

Example 15-41

$N^4$-[2-(dimethylamino)ethyl]-$N^2$-[2-(1H-indol-3-yl)ethyl]-$N^2$-methylpyrimidine-2,4-diamine MS (ESI, Pos, 20 V): 339 (M+H)$^+$;
HPLC condition: B; HPLC retention time (min): 3.47.

Example 15-42

$N^2$-cyclopentyl-$N^4$-[2-(dimethylamino)ethyl]pyrimidine-2,4-diamine

MS (ESI, Pos, 20 V): 250 (M+H)$^+$;
HPLC condition: B; HPLC retention time (min): 3.22.

Example 15-43

N$^2$-cyclohexyl-N$^4$-[2-(dimethylamino)ethyl]pyrimidine-2,4-diamine

MS (ESI, Pos, 20 V): 527 (2M+H)$^+$, 264 (M+H)$^+$;
HPLC condition: B; HPLC retention time (min): 3.36.

Example 15-44

N$^4$-[2-(dimethylamino)ethyl]-N$^2$-(3-methylcyclohexyl)pyrimidine-2,4-diamine

MS (ESI, Pos, 20 V): 555 (2M+H)$^+$, 278 (M+H)$^+$;
HPLC condition: B; HPLC retention time (min): 3.53.

Example 15-45

N$^4$-[2-(dimethylamino)ethyl]-N$^2$-(4-methylcyclohexyl)pyrimidine-2,4-diamine

MS (ESI, Pos, 20 V): 555 (2M+H)$^+$, 278 (M+H)$^+$;
HPLC condition: B; HPLC retention time (min): 3.55.

Example 15-46

N$^2$-(cyclohexylmethyl)-N$^4$-[2-(dimethylamino)ethyl]pyrimidine-2,4-diamine

MS (ESI, Pos, 20 V): 555 (2M+H)$^+$, 278 (M+H)$^+$;
HPLC condition: B; HPLC retention time (min): 3.53.

Example 15-47

N$^2$-(2,3-dihydro-1H-inden-1-yl)-N$^4$-[2-(dimethylamino)ethyl]pyrimidine-2,4-diamine MS (ESI, Pos, 20 V): 595 (2M+H)$^+$, 298 (M+H)$^+$;
HPLC condition: B; HPLC retention time (min): 3.42.

Example 15-48

N$^2$-cyclohexyl-N$^4$-[2-(dimethylamino)ethyl]-N$^2$-methylpyrimidine-2,4-diamine MS (ESI, Pos, 20 V): 278 (M+H)$^+$;
HPLC condition: B; HPLC retention time (min): 3.64.

Example 15-49

N$^2$-cycloheptyl-N$^4$-[2-(dimethylamino)ethyl]pyrimidine-2,4-diamine

MS (ESI, Pos, 20 V): 555 (2M+H)$^+$, 278 (M+H)$^+$;
HPLC condition: B; HPLC retention time (min): 3.55.

Example 15-50

N$^4$-[2-(dimethylamino)ethyl]-N$^2$-(pyridin-3-ylmethyl)pyrimidine-2,4-diamine

MS (ESI, Pos, 20 V): 273 (M+H)$^+$;
HPLC condition: B; HPLC retention time (min): 2.79.

Example 15-51

N$^4$-[2-(dimethylamino)ethyl]-N$^2$-(pyridin-4-ylmethyl)pyrimidine-2,4-diamine

MS (ESI, Pos, 20 V): 273 (M+H)$^+$;
HPLC condition: B; HPLC retention time (min): 2.78.

Example 15-52

N$^2$-benzyl-N$^4$-[2-(dimethylamino)ethyl]pyrimidine-2,4-diamine

MS (ESI, Pos, 20 V): 543 (2M+H)$^+$, 272 (M+H)$^+$;
HPLC condition: B; HPLC retention time (min): 3.23.

Example 15-53

N$^4$-[2-(dimethylamino)ethyl]-N$^2$-(2-phenylethyl)pyrimidine-2,4-diamine

MS (ESI, Pos, 20 V): 571 (2M+H)$^+$, 286 (M+H)$^+$;
HPLC condition: B; HPLC retention time (min): 3.34.

Example 15-54

N$^2$-butyl-N$^4$-[2-(dimethylamino)ethyl]pyrimidine-2,4-diamine

MS (ESI, Pos, 20 V): 238 (M+H)$^+$;
HPLC condition: B; HPLC retention time (min): 3.20.

Example 15-55

6-(2-[(1-cyclohexylpiperidin-3-yl)amino]pyrimidin-4-ylamino)hexan-1-ol

NMR (DMSO-d$_6$): δ 1.17 (m, 6H), 1.29 (m, 5H), 1.48 (m, 6H), 1.72 (m, 5H), 2.00 (m, 1H), 2.27 (m, 2H), 2.63 (m, 1H), 2.91 (m, 1H), 3.16 (m, 2H), 3.41 (m, 2H), 3.76 (m, 1H), 4.36 (m, 1H), 5.65 (d, J=5.70 Hz, 1H), 6.03 (m, 1H), 6.83 (m, 1H), 7.58 (d, J=5.70 Hz, 1H);
MS (ESI, Pos, 20 V): 376 (M+H)$^+$, 294, 188.5 (M+2H)$^{2+}$;
TLC: Rf 0.38 (CHCl$_3$:MeOH:NH$_4$OH=80:10:1).

EXAMPLE 16-1 to EXAMPLE 16-3

By the same procedure as described in Reference Example 1 →Example 1 using corresponding compounds, the compounds of the present invention having the following physical data were given.

Example 16-1

N,N'-bis[2-(dimethylamino)ethyl]quinazoline-2,4-diamine

MS (ESI, Pos. 20 V): 303 (M+H)$^+$, 168;
HPLC condition: A; HPLC retention time (min): 0.36.

Example 16-2

N,N'-bis(2-pyrrolidin-1-ylethyl)quinazoline-2,4-diamine

MS (ESI, Pos. 20 V): 355 (M+H)$^+$, 178 (M+2H)$^{2+}$;
HPLC condition: A; HPLC retention time (min): 2.59.

Example 16-3

N,N'-bis(2-piperidin-1-ylethyl)quinazoline-2,4-diamine

MS (ESI, Pos. 20 V): 383 (M+H)$^+$, 192 (M+2H)$^{2+}$;
HPLC condition: A; HPLC retention time (min): 2.68.

EXAMPLE 17-01 to EXAMPLE 17-12

By the same procedure as described in Reference Example 1 →Example 1 using corresponding compounds, the compounds of the present invention having the following physical data were given.

Example 17-01

N-(4-azepan-1-ylpyrimidin-2-yl)-N-[2-(dimethylamino)ethyl]-1,1'-biphenyl-4-carboxamide MS (ESI, Pos.20V): 444 (M+H);
HPLC condition: A; HPLC retention time (min): 3.45.

Example 17-02

N-(4-azepan-1-ylpyrimidin-2-yl)-N-[3-(dimethylamino)propyl]-1,1'-biphenyl-4-carboxamide MS (ESI, Pos.20V): 458 (M+H);
HPLC condition: A; HPLC retention time (min): 3.29.

Example 17-03

N-[4-(3,4-dihydroisoquinolin-2(1H)-yl)pyrimidin-2-yl]-N-[2-(dimethylamino)ethyl]-1,1'-biphenyl-4-carboxamide MS (ESI, Pos.20V): 478 (M+H);
HPLC condition: A; HPLC retention time (min): 3.54.

Example 17-04

N-[4-(3,4-dihydroisoquinolin-2(1H)-yl)pyrimidin-2-yl]-N-[3-(dimethylamino)propyl]-1,1'-biphenyl-4-carboxamide MS (ESI, Pos.20V): 492 (M+H);
HPLC condition: A; HPLC retention time (min): 3.44.

Example 17-05

N-[2-(dimethylamino)ethyl]-4-(pentyloxy)-N-(4-piperidin-1-ylpyrimidin-2-yl)benzamide MS (ESI, Pos.20V): 440 (M+H);
HPLC condition: A; HPLC retention time (min): 3.47.

Example 17-06

N-[3-(dimethylamino)propyl]-4-(pentyloxy)-N-(4-piperidin-1-ylpyrimidin-2-yl)benzamide MS (ESI, Pos.20V): 454 (M+H);
HPLC condition: A; HPLC retention time (min): 3.36.

Example 17-07

N-(4-azepan-1-ylpyrimidin-2-yl)-N-[2-(dimethylamino)ethyl]-4-(pentyloxy)benzamide MS (ESI, Pos.20V): 454 (M+H);
HPLC condition: A; HPLC retention time (min): 3.52.

Example 17-08

N-(4-azepan-1-ylpyrimidin-2-yl)-N-[3-(dimethylamino)propyl]-4-(pentyloxy)benzamide MS (ESI, Pos.20V): 468 (M+H);
HPLC condition: A; HPLC retention time (min): 3.39.

Example 17-09

N-[4-(3,4-dihydroisoquinolin-2(1H)-yl)pyrimidin-2-yl]-N-[2-(dimethylamino)ethyl]-4-(pentyloxy)benzamide MS (ESI, Pos.20V): 488 (M+H);
HPLC condition: A; HPLC retention time (min): 3.66.

Example 17-10

N-[4-(3,4-dihydroisoquinolin-2(1H)-yl)pyrimidin-2-yl]-N-[3-(dimethylamino)propyl]-4-(pentyloxy)benzamide MS (ESI, Pos.20V): 502 (M+H);
HPLC condition: A; HPLC retention time (min): 3.55.

Example 17-11

3-cyclopentyl-N-[4-(3,4-dihydroisoquinolin-2(1H)-yl)pyrimidin-2-yl]-N-[2-(dimethylamino)ethyl]propanamide MS (ESI, Pos.20V): 422 (M+H);
HPLC condition: A; HPLC retention time (min): 3.46.

Example 17-12

3-cyclopentyl-N-[4-(3,4-dihydroisoquinolin-2(1H)-yl)pyrimidin-2-yl]-N-[3-(dimethylamino)propyl]propanamide MS (ESI, Pos.20V): 436 (M+H);
HPLC condition: A; HPLC retention time (min): 3.26.

EXAMPLE 18-1 to EXAMPLE 18-3

By the same procedure as described in Reference Example 1→Example 1 using corresponding compounds, the compounds of the present invention having the following physical data were given.

Example 18-1

2-[(4-azepan-1-ylquinazolin-2-yl)oxy]-N,N-dimethylethanamine

MS (ESI, Pos. 20 V): 315 (M+H)$^+$;
HPLC condition: A; HPLC retention time (min): 2.83.

Example 18-2

4-azepan-1-yl-N-(1-cyclohexylpiperidin-3-yl)pyrimidine-2-carboxamide

NMR (CDCl$_3$): δ 1.22 (m, 4H), 1.58 (m, 8H), 1.82 (m, 10H), 2.30 (m, 1H), 2.43 (m, 1H), 2.68 (m, 3H), 3.52 (m, 2H), 3.89 (m, 2H), 4.24 (m, 1H), 6.45 (d, J=6.21 Hz, 1H), 8.28 (d, J=6.21 Hz, 1H), 8.58 (d, J=7.72 Hz, 1H);
MS (ESI, Pos. 20 V): 386 (M+H)$^+$;
TLC: Rf 0.53 (CHCl$_3$:MeOH=9:1).

Example 18-3

N-(4-azepan-1-yl-1-oxidopyrimidin-2-yl)ethane-1,2-diamine

NMR (CDCl$_3$): δ 1.54 (m, 4H), 1.76 (m, 4H), 1.98 (m, 2H), 2.94 (t, J=6.00 Hz, 2H), 3.52 (q, J=6.00 Hz, 2H), 3.57 (m, 4H), 5.76 (d, J=7.30 Hz, 1H), 7.26 (m, 1H), 7.84 (d, J=7.30 Hz, 1H);
MS (ESI, Pos. 20 V): 503 (2M+H)$^+$, 252 (M+H)$^+$, 126.5 (M+2H)$^{2+}$;
TLC: Rf 0.13 (CHCl$_3$:MeOH:NH$_4$OH=40:10:1).

EXAMPLE 19-01 to EXAMPLE 19-12

By the same procedure as described in Reference Example 1→Example 1 using corresponding compounds, the compounds of the present invention having the following physical data were given.

Example 19-01

6-azepan-1-yl-N-(1-cyclohexylpiperidin-3-yl)pyridine-2-carboxamide

NMR (CDCl$_3$): δ 1.22 (m, 4H), 1.68 (m, 18H), 2.28 (m, 1H), 2.41 (m, 1H), 2.67 (m, 3H), 3.65 (m, 4H), 4.20 (m, 1H), 6.61 (dd, J=8.56, 0.67 Hz, 1H), 7.39 (dd, J=7.22, 0.67 Hz, 1H), 7.53 (dd, J=8.56, 7.22 Hz, 1H), 8.65 (d, J=8.06 Hz, 1H);
MS (ESI, Pos. 20 V): 385 (M+H)$^+$, 193 (M+2H)$^{2+}$;
TLC: Rf 0.62 (CHCl$_3$:MeOH=9:1).

Example 19-02

N$^1$-(6-azepan-1-ylpyridin-2-yl)-N$^2$,N$^2$-dimethylglycinamide

NMR (CDCl$_3$): δ 1.54 (m, 4H), 1.77 (m, 4H), 2.37 (s, 6H), 3.06 (s, 2H), 3.60 (t, J=6.04 Hz, 4H), 6.23 (dd, J=7.81, 0.84 Hz, 1H), 7.38 (dd, J=7.81, 0.84 Hz, 1H), 7.43 (t, J=7.81 Hz, 1H), 9.09 (s, 1H);
MS (ESI, Pos. 20 V): 277 (M+H)$^+$;
TLC: Rf 0.76 (EtOAc:MeOH=9:1).

Example 19-03

N$^1$-(4-azepan-1-ylquinolin-2-yl)-N$^2$,N$^2$-dimethylethane-1,2-diamine

NMR (DMSO-d$_6$): δ 7.74 (d, J=7.5 Hz, 1H), 7.43-7.33 (m, 2H), 7.05 (m, 1H), 6.51 (t, J=5.1 Hz, 1H), 6.28 (s, 1H), 3.43 (dt, J=5.1, 6.3 Hz, 2H), 3.27 (m, 4H), 2.42 (t, J=6.3 Hz, 2H), 2.18 (s, 6H), 1.82 (m, 4H), 1.69 (m, 4H);
MS (ESI, Pos. 20 V): 313 (M+H)$^+$, 157 (M+2H)$^{2+}$;
TLC: Rf 0.19 (CHCl$_3$:MeOH:NH$_4$OH=80:10:1).

Example 19-04

N$^1$-(2-azepan-1-ylquinolin-4-yl)-N$^2$,N$^2$-dimethylethane-1,2-diamine

NMR (DMSO-d$_6$): δ 7.80 (d, J=8.1 Hz, 1H), 7.33 (m, 2H), 6.99 (m, 1H), 6.46 (t, J=5.1 Hz, 1H), 5.81 (s, 1H), 3.69 (t, J=6.0 Hz, 4H), 3.31 (m, 2H), 2.53 (t, J=6.9 Hz, 2H), 2.21 (s, 6H), 1.74 (m, 4H), 1.47 (m, 4H);
MS (ESI, Pos. 20 V): 313 (M+H)$^+$, 241, 157 (M+2H)$^{2+}$;
TLC: Rf 0.22 (CHCl$_3$:MeOH:NH$_4$OH=80:10:1).

Example 19-05

N$^1$-(1-azepan-1-ylisoquinolin-3-yl)-N$^2$,N$^2$-dimethylglycinamide

NMR (DMSO-d$_6$): δ 9.33 (s, 1H), 7.98 (d, J=8.7 Hz, 1H), 7.81 (s, 1H), 7.70 (d, J=8.4 Hz, 1H), 7.54 (dd, J=8.4, 6.6 Hz, 1H), 7.33 (dd, J=8.7, 6.6 Hz, 1H), 3.65 (m, 4H), 3.10 (s, 2H), 2.30 (s, 6H), 1.84 (m, 4H), 1.64 (m, 4H);
MS (ESI, Pos. 20 V): 327 (M+H)$^+$, 242, 164;
TLC: Rf 0.48 (CHCl$_3$:MeOH=10:1).

Example 19-06

N$^1$-(1-azepan-1-ylisoquinolin-3-yl)-N$^2$,N$^2$-dimethylethane-1,2-diamine

NMR (DMSO-d$_6$): δ 7.78 (d, J=8.4 Hz, 1H), 7.37 (d, J=7.8 Hz, 1H), 7.29 (dd, J=7.8, 6.6 Hz, 1H), 6.95 (dd, J=8.4, 6.6 Hz, 1H), 6.00 (s, 1H), 5.64 (t, J=5.4 Hz, 1H), 3.95 (m, 4H), 3.25 (dt, J=5.4, 6.3 Hz, 2H), 2.42 (t, J=6.3 Hz, 2H), 2.17 (s, 6H), 1.82 (m, 4H), 1.63 (m, 4H);
MS (ESI, Pos. 20 V): 313 (M+H)$^+$, 157 (M+2H)$^{2+}$;
HPLC condition: A; HPLC retention time (min): 2.85;
TLC: Rf 0.48 (CHCl$_3$:MeOH:NH$_4$OH=80:10:1).

Example 19-07

1-(4-azepan-1-yl-6-chloro-1,3,5-triazin-2-yl)azepane

NMR (DMSO-d$_6$): δ 1.46 (m, 8H), 1.65 (m, 8H), 3.61 (q, J=5.95 Hz, 8H);
MS (ESI, Pos. 20 V): 312, 310 (M+H)$^+$;
TLC: Rf 0.77 (Hexane:AcOEt=3:1).

Example 19-08

N-(4-azepan-1-yl-1,3,5-triazin-2-yl)ethane-1,2-diamine dihydrochloride

NMR (DMSO-d$_6$): δ 1.49 (m, 4H), 1.73 (m, 4H), 3.00 (m, 2H), 3.63 (q, J=6.00 Hz, 2H), 3.77 (m, 4H), 8.26 (m, 2H), 8.41 (s, 1H), 8.69 (m, 1H);

Example 19-09

N-(4-azepan-1-yl-6-chloro-1,3,5-triazin-2-yl)ethane-1,2-diamine dihydrochloride

NMR (CD$_3$OD): δ 1.60 (m, 4H), 1.80 (m, 4H), 3.21 (t, J=5.77 Hz, 2H), 3.79 (m, 6H);
MS (ESI, Pos, 20 V): 273, 271 (M+H)$^+$;
TLC: Rf 0.23 (CHCl$_3$:MeOH:NH$_4$OH=80:10:1).

Example 19-10

N-(4-azepan-1-yl-6-methoxy-1,3,5-triazin-2-yl)ethane-1,2-diamine dihydrochloride NMR (CD$_3$OD): δ 1.62 (m, 4H), 1.85 (m, 4H), 3.22 (t, J=6.00 Hz, 2H), 3.77 (t, J=6.00 Hz, 2H), 3.87 (m, 4H), 4.11 (s, 3H);
MS (ESI, Pos, 20 V): 267 (M+H)$^+$;
TLC: Rf 0.27 (CHCl$_3$:MeOH:NH$_4$OH=80:10:1).

Example 19-11

N-[5-(azepan-1-ylmethyl)pyrimidin-2-yl]ethane-1,2-diamine trihydrochloride

NMR (DMSO-d$_6$): δ 1.59 (m, 4H), 1.81 (m, 4H), 2.98 (m, 4H), 3.27 (m, 2H), 3.57 (m, 2H); 4.16 (d, J=5.10 Hz, 2H), 7.86 (m, 1H), 8.22 (m, 3H), 8.61 (s, 2H), 11.22 (m, 1H);
MS(LC-MS, APCI, Pos. 20 V): 250 (M+H)$^+$, 151;
TLC: Rf 0.46 (CHCl$_3$:MeOH:NH$_4$OH=80:20:4).

Example 19-12

N$^1$-(4-cycloheptylquinazolin-2-yl)-N$^2$,N$^2$-dimethyl-ethane-1,2-diamine

NMR (DMSO-d$_6$): δ 7.97 (d, J=8.1 Hz, 1H), 7.61 (m, 1H), 7.42 (d, J=6.9 Hz, 1H), 7.17 (m, 1H), 6.85 (m, 1H), 3.62 (m, 1H), 3.43 (dt, J=6.0, 6.6 Hz, 2H), 2.44 (t, J=6.6 Hz, 2H), 2.18 (s, 6H), 2.00-1.57 (m, 12H);
MS (ESI, Pos. 20 V): 313 (M+H)$^+$, 157 (M+2H)$^{2+}$, 102;
TLC: Rf 0.46 (CHCl$_3$:MeOH:NH$_4$OH=80:10:1).

BIOLOGICAL EXAMPLES

An effectiveness of the compounds of the present invention represented by formulae (I) and (II) was confirmed, for example, by the following experiments. The entire procedure utilized a standard method together with a cell exhibiting a high expression prepared in accordance with a basic gene engineering technology. A measurement method of the present invention has improved measurement accuracy and/or measurement sensitivity in order to evaluate the compounds of the present invention. The experimental method is detailed below.

As described above, in order to screen for a compound which inhibits the binding of FHV with CXCR4 or CCR5 which is a receptor on a CD4 positive cell, an experiment in an assay system employing an HIV virus is a more direct procedure. However, use of an HIV virus in a large scale screening is not practical because of its difficulty in handling. On the other hand, since both of a T cell-directing (X4) HIV-1 and SDF-1 bind to CXCR4, there may be a certain common profile in the CXCR4 binding site on both of HIV and SDF-1 as well as in SDF-1 and HIV binding sites on the CXCR4. Accordingly, an assay system employing an SDF-1 which is an intrinsic ligand of CXCR4 instead of HIV can be utilized in order to identify a compound which inhibits the adsorption of an HIV virus onto a cell which is an action mechanism different from that of an existing AIDS drug (reverse transferase inhibitor or protease inhibitor).

Typically, as an assay for screening for a compound which inhibits the binding between SDF-1 and CXCR4, a system measuring the binding between an I-labeled SDF-1 and a human T cell line known to express CXCR4 can be employed. Since both of a macrophage (R5) HIV and RANTES, MIP-1α, MP-1β bind to CCR5, a similar understanding is possible.

Experimental Methods

Experiment Example 1

Inhibition of Human SDF-1 with CEM Cell

In a binding buffer solution (HEPES containing BSA), a human T cell line CEM cell was mixed with a test compound and $^{125}$I-SDF-1 (NEN) and incubated for 60 minutes at 40° C. The reacted CEM cell was filtered rapidly through a GF/B membrane filter plate (Packard) to effect adsorption, followed by washing three times with PBS, drying and addition of Microscint+20 (Packard). The radioactivity binding to the CEM cell is measured using Top Count (Packard) and a % inhibition by a test compound was calculated according to the equation shown below.

% Inhibition=($Et-Ea$)/($Et-Ec$)×100

Et: Radioactivity in the absence of a test compound
Ec: Radioactivity in the presence of non-radioactive SDF-1 (Pepro Tech) as a test compound at a level 1000 times higher than $^{125}$I-SDF-1
Ea: Radioactivity in the presence of a test compound All compounds of the present invention described in Examples exhibited inhibitions of 50% or higher at 10 μM. For example, the IC$_{50}$ values of the compounds of Example 1(41) and Example 4 are 0.20 μM and 0.15 μM, respectively.

Formulation Example 1

Each of the following components was mixed by a standard method and punched out to give 10000 tablets each containing 10 mg of active ingredient.

| | |
|---|---:|
| 2-(2-dimethylaminoethylamino)-4-(perhydroazepin-1-yl)pyrimidine | 5.0 g |
| carcium carboxymethyl cellulose (disintegrant) | 20.0 g |
| magnesium stearate (lubricant) | 10.0 g |
| microcrystalline cellulose | 870 g |

Formulation Example 2

Each of the following components was mixed by a standard method and filtered through a dustproofing filter, and then 5 ml aliquots were charged into ampoules, which were autoclaved to thereby obtain 10,000 ampoules each containing 20 mg of the active ingredient.

| | |
|---|---|
| 2-(2-dimethylaminoethylamino)-4-(perhydroazepin-1-yl)pyrimidine | 200 g |
| mannitol | 2 kg |
| distilled water | 50 L |

The invention claimed is:

1. A compound represented by formula (I):

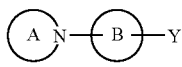

(I)

wherein ring A represents an azepane ring;
ring B represents a pyrimidine ring which may be substituted with 1-5 of $R^3$;
plural $R^3$'s each independently represents (1) C1-15 alkyl, C2-15 alkenyl or C2-15 alkynyl, wherein the alkyl, alkenyl and alkynyl may be substituted with 1 to 5 of $R^{10}$, (2) oxo, or (3) $R^{10}$;
plural $R^{10}$'s each independently represents (1) $OR^{11}$, (2) $OCOR^{12}$, (3) $OCOOR^{13}$, (4) $NR^{14}R^{15}$, (5) $NR^{16}COR^{12}$, (6) $NR^{16}CONR^{14}R^{15}$, (7) $NR^{16}COOR^{13}$, (8) $COOR^{13}$, (9) $COR^{12}$, (10) $CONR^{14}R^{15}$, (11) $SO_2R^{12}$, (12) $SOR^{22}$, (13) $SO_2NR^{24}R^{25}$, (14) $NR^{16}SO_2R^{12}$, (15) $B(OH)_2$, (16) $SR^{11}$, (17) halogen, (18) nitro, (19) cyano, or (20) ring D;
$R^{11}$ represents (i) hydrogen, (ii) C1-15 alkyl, C2-15 alkenyl or C2-15 alkynyl, wherein the alkyl, alkenyl and alkynyl may be substituted with 1 to 5 of halogen, $NR^{14}R^{15}$, $OR^{21}$, $SR^{21}$, $COOR^{13}$, or ring D, or (iii) ring D;
$R^{12}$, $R^{13}$, $R^{14}$, $R^{15}$ and $R^{16}$ each independently represents (i) hydrogen, (ii) C1-15 alkyl, C2-15 alkenyl or C2-15 alkynyl which may be substituted with ring D, or (iii) ring D;
ring D represents pyrrole, imidazole, triazole, tetrazole, pyrazole, pyridine, pyrazine, pyrimidine, pyridazine, azepine, diazepine, furan, pyran, oxepine, thiophene, thiopyran, thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, benzoxazole, benzothiazole, benzimidazole, chromene, benzoxepine, benzoxazepine, benzoxadiazepine, benzothiepine, benzothiazepine, benzothiadiazepine, benzazepine, benzodiazepine, benzofurazan, benzothiadiazole, benzotriazole, carbazole, beta-carboline, acridine, phenazine, dibenzofuran, xanthene, dibenzothiophene, phenothiazine, phenoxazine, phenoxathiin, thianthrene, phenanthridine, phenanthroline, perimidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrooxazole, tetrahydrooxazole, dihydroisoxazole, tetrahydroisoxazole, dihydrothiazole, tetrahydrothiazole, dihydroisothiazole, tetrahydroisothiazole, dihydrofurazan, tetrahydrofurazan, dihydrooxadiazole, tetrahydrooxadiazole, dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole, dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dihydrobenzazepine, tetrahydrobenzazepine, dihydrobenzodiazepine, tetrahydrobenzodiazepine, benzodioxepane, dihydrobenzoxazepine, tetrahydrobenzoxazepine, dihydrocarbazole, tetrahydrocarbazole, perhydrocarbazole, dihydroacridine, tetrahydroacridine, perhydroacridine, cyclopropane, cyclobutane, cyclopentane, cyclohexane, cycloheptane, cyclooctane, cyclononane, cyclodecane, cycloundecane, cyclododecane, cyclotridecane, cyclotetradecane, cyclopentadecane, cyclopentene, cyclohexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indan, naphthalene, dihydronaphthalene, teterahydronaphthalene, perhydronaphthalene, heptalene, perhydroheptalene, biphenylene, as-indacene, s-indacene, acenaphthylene, acenaphthene, fluorene, phenalene, phenanthrene, anthracene, spiro[4.4]nonane, spiro[4.5]decane, spiro[5.5]undecane, bicyclo[2.2.1]heptane, bicyclo[2.2.1]hept-2-ene, bicyclo[3.1.1]heptane, bicyclo[3.1.1]hept-2-ene, bicyclo[2.2.2]octane, bicyclo[2.2.2]oct-2-ene, adamantine or noradamantane; and
ring D may be substituted with 1 to 5 of the groups selected from the following (1) to (22):
(1) C1-15 alkyl, C2-15 alkenyl or C2-15 alkynyl, wherein the alkyl, alkenyl or alkynyl may be substituted with 1 to 5 of $OR^{21}$, $OCOR^{22}$, $OCOOR^{23}$, $NR^{24}R^{25}$, $NR^{26}COR^{22}$, $NR^{26}CONR^{24}R^{25}$, $NR^{26}COOR^{23}$, $COOR^{23}$, $COR^{22}$, $CONR^{24}R^{25}$, $SO_2R^{22}$, $SOR^{22}$, $SO_2NR^{24}R^{25}$, $NR^{26}SO_2R^{22}B(OH)_2$, $SR^{21}$, halogen, nitro or cyano, (2) oxo, (3) $OR^{21}$, (4) $OCOR^{22}$, (5) $OCOOR^{23}$, (6)$NR^{24}R^{25}$, (7) $NR^{26}COR^{22}$, (8) $NR^{26}CONR^{24}R^{25}$, (9) $NR^{26}COOR^{23}$, (10) $COOR^{23}$, (11) $COR^{22}$, (12) $CONR^{24}R^{25}$, (13) $SO_2R^{22}$, (14) $SOR^{22}$, (15) $SO_2NR^{24}R^{25}$, (16) $NR^{26}SO_2R^{22}$, (17) $B(OH)_2$, (18) $SR^{21}$, (19) halogen, (20) nitro, (21) cyano or (22) ring E;

$R^{21}$ represents (i) hydrogen, (ii) C1-15 alkyl, C2-15 alkenyl or C2-15 alkynyl which may be substituted with COR22, $NR^{24}R^{25}$ or ring E, or (iii) ring E;

$R^{22}$, $R^{23}$, $R^{24}$, $R^{25}$ and $R^{26}$ each independently represents (i) hydrogen, (ii) C 1-15 alkyl, C2-15 alkenyl or C2-15 alkynyl which may be substituted with ring E, or (iii) ring E;

ring E represents pyrrole, imidazole, triazole, tetrazole, pyrazole, pyridine, pyrazine, pyrimidine, pyridazine, azepine, diazepine, furan, pyran, oxepine, thiophene, thiopyran, thiepine, oxazole, isoxazole, thiazole, isothiazole, furazan, oxadiazole, oxazine, oxadiazine, oxazepine, oxadiazepine, thiadiazole, thiazin, thiadiazine, thiazepine, thiadiazepine, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, benzoxazole, benzothiazole, benzimidazole, chromene, benzoxepine, benzoxazepine, benzoxadiazepine, benzothiepine, benzothiazepine, benzothiadiazepine, benzazepine, benzodiazepine, benzofurazan, benzothiadiazole, benzotriazole, carbazole, beta-carboline, acridine, phenazine, dibenzofuran, xanthene, dibenzothiophene, phenothiazine, phenoxazine, phenoxathiin, thianthrene, phenanthridine, phenanthroline, perimidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrooxazole, tetrahydrooxazole, dihydroisoxazole, tetrahydroisoxazole, dihydrothiazole, tetrahydrothiazole, dihydroisothiazole, tetrahydroisothiazole, dihydrofurazan, tetrahydrofurazan, dihydrooxadiazole, tetrahydrooxadiazole, dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole, dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dihydrobenzoxazepine, tetrahydrobenzoxazepine, dihydrobenzodiazepine, tetrahydrobenzodiazepine, benzodioxepane, dihydrobenzoxazepine, tetrahydrobenzoxazepine, dihydrocarbazole, tetrahydrocarbazole, perhydrocarbazole, dihydroacridine, tetrahydroacridine, perhydroacridine, cyclopropane, cyclobutane, cyclopentane, cyclohexane, cycloheptane, cyclooctane, cyclononane, cyclodecane, cycloundecane, cyclododecane, cyclotridecane, cyclotetradecane, cyclopentadecane, cyclopentene, cyclohexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indan, naphthalene, dihydronaphthalene, teterahydronaphthalene, perhydronaphthalene, heptalene, perhydroheptalene, biphenylene, as-indacene, s-indacene, acenaphthylene, acenaphthene, fluorene, phenalene, phenanthrene, anthracene, spiro[4.4]nonane, spiro[4.5]decane, spiro [5.5]undecane, bicyclo[2.2.1]heptane, bicyclo[2.2.1] hept-2-ene, bicyclo[3.1.1]heptane, bicyclo[3.1.1]hept-2-ene, bicyclo[2.2.2]octane, bicyclo[2.2.2]oct-2-ene, adamantine or noradamantane, and ring E may be substituted with 1 to 5 of (i) C1-15 alkyl which may be substituted with phenyl, (ii) halogen, (iii) phenyl, (iv) C 1-15 alkoxy, (v) hydroxyl, (vi) amino, (vii) mono(C1-8 alkyl)amino, or (viii) di(C1-8 alkyl) amino; and Y represents

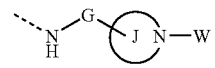

wherein G represents a bond or a methylene;

ring J represents an azetidine, a pyrrolidine, a piperidine or a perhydroazepine which may be substituted with 1-5 of $R^3$; and W represents hydrogen, a methyl, an ethyl, an isobutyl, a 3-methyl buthyl, a 2-ethylbutyl, a cyclohexylmethyl, a cyclohexyl, a cyclopentyl, a benzyl, a benzene, cyclohexanol, 1-(cyclohexylcarbonyl) piperidine, a tetrahydropyran-4-yl or a piperidine, or a salt thereof.

2. The compound according to claim 1, which is represented by formula (I-2):

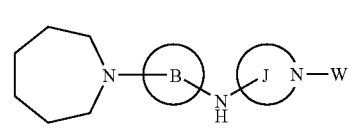

(I-2)

wherein ring B represents a pyrimidine ring which may be substituted with 1-5 of $R^3$;

plural $R^3$'s each independently represents (1) C1-15 alkyl, C2-15 alkenyl or C2-15 alkynyl, wherein the alkyl, alkenyl and alkynyl may be substituted with 1 to 5 of $R^{10}$, (2) oxo, or (3)$R^{10}$;

plural $R^{10}$'s each independently represents (1) $OR^{11}$, (2) $OCOR^{12}$, (3) $OCOOR^{13}$, (4) $NR^{14}R^{15}$, (5) $NR^{16}COR^{12}$, (6) $NR^{16}CONR^{14}R^{15}$, (7) $NR^{16}COOR^{13}$, (8) $COOR^{13}$, (9) $COR^{12}$, (10) $CONR^{14}R^{15}$, (11) $SO_2R^{12}$, (12) $SOR^{22}$, (13) $SO_2NR^{24}R^{25}$, (14) $NR^{16}SO_2R^{12}$, (15) $B(OH)_2$, (16) $SR^{11}$, (17) halogen, (18) nitro, (19) cyano, or (20) ring D;

$R^{11}$ represents (i) hydrogen, (ii) C1-15 alkyl, C2-15 alkenyl or C2-15 alkynyl, wherein the alkyl, alkenyl and alkynyl may be substituted with 1 to 5 of halogen, $NR^{14}R^{15}$, $OR^{21}$, $SR^{21}$, $COOR^{13}$, or ring D, or (iii) ring D;

$R^{12}$, $R^{13}$, $R^{14}$, $R^{15}$ and $R^{16}$ each independently represents (i) hydrogen, (ii) C1-15 alkyl, C2-15 alkenyl or C2-15 alkynyl which may be substituted with ring D, or (iii) ring D;

ring D represents pyrrole, imidazole, triazole, tetrazole, pyrazole, pyridine, pyrazine, pyrimidine, pyridazine, azepine, diazepine, furan, pyran, oxepine, thiophene, thiopyran, thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, benzoxazole, benzothiazole, benzimidazole, chromene, benzoxepine, benzoxazepine, benzoxadiazepine, benzothiepine, benzothiazepine, benzothiadiazepine, benzazepine, benzodiazepine, benzofurazan, benzothiadiazole, benzotriazole, carbazole, beta-carboline, acridine, phenazine, dibenzofuran, xanthene, dibenzothiophene, phenothiazine, phenoxazine, phenoxathiin, thianthrene, phenanthridine, phenanthroline, perimidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrooxazole, tetrahydrooxazole, dihydroisoxazole, tetrahydroisoxazole, dihydrothiazole, tetrahydrothiazole, dihydroisothiazole, tetrahydroisothiazole, dihydrofurazan, tetrahydrofurazan, dihydrooxadiazole, tetrahydrooxadiazole, dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole, dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dihydrobenzazepine, tetrahydrobenzazepine, dihydrobenzodiazepine, tetrahydrobenzodiazepine, benzodioxepane, dihydrobenzoxazepine, tetrahydrobenzoxazepine, dihydrocarbazole, tetrahydrocarbazole, perhydrocarbazole, dihydroacridine, tetrahydroacridine, perhydroacridine, cyclopropane, cyclobutane, cyclopentane, cyclohexane, cycloheptane, cyclooctane, cyclononane, cyclodecane, cycloundecane, cyclododecane, cyclotridecane, cyclotetradecane, cyclopentadecane, cyclopentene, cyclohexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indan, naphthalene, dihydronaphthalene, teterahydronaphthalene, perhydronaphthalene, heptalene, perhydroheptalene, biphenylene, as-indacene, s-indacene, acenaphthylene, acenaphthene, fluorene, phenalene, phenanthrene, anthracene, spiro[4.4]nonane, spiro[4.5]decane, spiro[5.5]undecane, bicyclo[2.2.1]heptane, bicyclo[2.2.1]hept-2-ene, bicyclo[3.1.1]heptane, bicyclo[3.1.1]hept-2-ene, bicyclo[2.2.2]octane, bicyclo[2.2.2]oct-2-ene, adamantine or noradamantane; and ring D may be substituted with 1 to 5 of the groups selected from the following (1) to (22):

(1) C1-15 alkyl, C2-15 alkenyl or C2-15 alkynyl, wherein the alkyl, alkenyl or alkynyl may be substituted with 1 to 5 of $OR^{21}$, $OCOR^{22}$, $OCOOR^{23}$, $NR^{24}R^{25}$, $NR^{26}COR^{22}$, $NR^{26}CONR^{24}R^{25}$, $NR^{26}COOR^{23}$, $COOR^{23}$, $COR^{22}$, $CONR^{24}R^{25}$, $SO_2R^{22}$, $SOR^{22}$, $SO_2NR^{24}R^{25}$, $NR^{26}SO_2R^{22}$, $B(OH)_2$, $SR^{21}$, halogen, nitro or cyano, (2) oxo, (3) $OR^{21}$, (4) $OCOR^{22}$, (5) $OCOOR^{23}$, (6) $NR^{24}R^{25}$, (7) $NR^{26}COR^{22}$, (8) $NR^{26}CONR^{24}R^{25}$, (9) $NR^{26}COOR^{23}$, (10) $COOR^{23}$, (11) $COR^{22}$, (12) $CONR^{24}R^{25}$, (13) $SO_2R^{22}$, (14) $SOR^{22}$, (15) $SO_2NR^{24}R^{25}$, (16) $NR26SO_2R^{22}$, (17) $B(OH)_2$, (18) $SR^{21}$, (19) halogen, (20) nitro, (21) cyano or (22) ring E;

$R^{21}$ represents (i) hydrogen, (ii) C1-15 alkyl, C2-15 alkenyl or C2-15 alkynyl which may be substituted with $COR^{22}$, $NR^{24}R^{25}$ or ring E, or (iii) ring E;

$R^{22}$, $R^{23}$, $R^{24}$, $R^{25}$ and $R^{26}$ each independently represents (i) hydrogen, (ii) C1-15 alkyl, C2-15 alkenyl or C2-15 alkynyl which may be substituted with ring E, or (iii) ring E;

ring E represents pyrrole, imidazole, triazole, tetrazole, pyrazole, pyridine, pyrazine, pyrimidine, pyridazine, azepine, diazepine, furan, pyran, oxepine, thiophene, thiopyran, thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, benzoxazole, benzothiazole, benzimidazole, chromene, benzoxepine, benzoxazepine, benzoxadiazepine, benzothiepine, benzothiazepine, benzothiadiazepine, benzazepine, benzodiazepine, benzofurazan, benzothiadiazole, benzotriazole, carbazole, beta-carboline, acridine, phenazine, dibenzofuran, xanthene, dibenzothiophene, phenothiazine, phenoxazine, phenoxathiin, thianthrene, phenanthridine, phenanthroline, perimidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrooxazole, tetrahydrooxazole, dihydroisoxazole, tetrahydroisoxazole, dihydrothiazole, tetrahydrothiazole, dihydroisothiazole, tetrahydroisothiazole, dihydrofurazan, tetrahydrofurazan, dihydrooxadiazole, tetrahydrooxadiazole, dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole, dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dihydrobenzazepine, tetrahydrobenzazepine, dihydrobenzodiazepine, tetrahydrobenzodiazepine, benzodioxepane, dihydrobenzoxazepine, tetrahydrobenzoxazepine, dihydrocarbazole, tetrahydrocarbazole, perhydrocarbazole, dihydroacridine, tetrahydroacridine, perhydroacridine, cyclopropane, cyclobutane, cyclopentane, cyclohexane, cycloheptane, cyclooctane, cyclononane, cyclodecane, cycloundecane, cyclododecane, cyclotridecane, cyclotetradecane, cyclopentadecane, cyclopentene, cyclohexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indan, naphthalene, dihydronaphthalene, teterahydronaphthalene, perhydronaphthalene, heptalene, perhydroheptalene, biphenylene, as-indacene, s-indacene, acenaphthylene, acenaphthene, fluorene, phenalene, phenanthrene, anthracene, spiro[4.4]nonane, spiro[4.5]decane, spiro[5.5]undecane, bicyclo[2.2.1]heptane, bicyclo[2.2.1]hept-2-ene, bicyclo[3.1.1]heptane, bicyclo[3.1.1]hept-2-ene, bicyclo[2.2.2]octane, bicyclo[2.2.2]oct-2-ene, adamantine or noradamantane, and ring E may be substituted with 1 to 5 of (i) C1-15 alkyl which may be substituted with phenyl, (ii) halogen, (iii) phenyl, (iv) C1-15 alkoxy, (v) hydroxyl, (vi) amino, (vii) mono(C1-8 alkyl)amino, or (viii) di(C1-8 alkyl)amino;

ring J represents an azetidine, a pyrrolidine, a piperidine or a perhydroazepine which may be substituted with 1-5 of $R^3$; and W represents hydrogen, a methyl, an ethyl, an isobutyl, a 3-methyl butyryl, a 2-ethylbutyl, a cyclohexylmethyl, a cyclohexyl, a cyclopentyl, a benzyl, a benzene, cyclohexanol, 1-(cyclohexylcarbonyl) piperidine, a tetrahydropyran-4-yl or a piperidine.

3. A compound represented by formula (I-B):

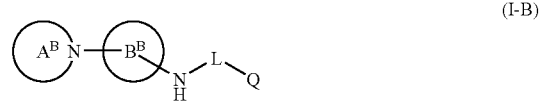

(I-B)

wherein ring $A^B$ represents an azepane ring;

ring $B^B$ represents:

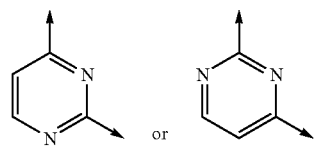

or wherein the upward arrow represents a binding position to ring $A^B$; and the right-downward arrow represents a binding position to the nitrogen atom bound to L;

L represents (1) a bond, (2) C1-8 alkylene, C2-8 alkenylene or C2-8 alkynylene, wherein the alkylene, alkenylene and alkynylene each may be substituted with 1 to 5 of $R^{10}$, or (3) a C3-8 carbocyclic group which may be substituted with $R^3$;

Q represents (1) $NR^1R^2$ wherein $R^1$ and $R^2$ each independently represents (i) hydrogen, (ii) C1-15 alkyl, C2-15 alkenyl or C2-15 alkynyl which may be substituted with 1 to 5 of $R^{10}$, (iii) a C3-8 carbocyclic group which may be substituted with 1 to 5 of $R^3$, or (iv) a 5- to 15-membered heterocyclic group which contains 1 or 2 nitrogen atoms, 1 or 2 oxygen atoms and/or one sulfur atom and which may be substituted 1 to 5 of $R^3$, or (2) ring C;

ring C represents azetidine, pyrrolidine, imidazoline, imidazolidine, triazolidine, tetrazolidine, pyrazolidine, tetrahydropyridine, piperidine, tetrahydropyrazine, piperazine, tetrahydropyrimidine, perhydropyrimidine. tetrahydropyridazine, perhydropyridazine, tetrahydroazepine, perhydroazepine, perhydroazocine, tetrahydrodiazepine, perhydrodiazepine, tetrahydrooxazole, tetrahydroisoxazole, tetrahydrothiazole, tetrahydroisothiazole, tetrahydrofurazan, tetrahydrooxadiazole, tetrahydrooxazine, tetrahydrooxadiazine, tetrahydrooxazepine, perhydrooxazepine, tetrahydrooxadiazepine, perhydrooxadiazepine, tetrahydrothiadiazole, tetrahydrothiazine, tetrahydrothiadiazine, tetrahydrothiazepine, perhydrothiazepine, tetrahydrothiadiazepine, perhydrothiadiazepine, morpholine, thiomorpholine, oxathiane, perhydroindazole, perhydroquinoline, perhydroisoquinoline, perhydrophthalazine, perhydronaphthyridine, perhydroquinoxaline, perhydroquinazoline, perhydrocinnoline, pyrazinomorpholine, perhydrobenzoxazole, perhydrobenzothiazole, perhydrobenzimidazole, perhydrocarbazole, perhydroacridine, perhydroazonine, perhydroazecine, perhydrodiazocine, perhydrodiazonine, perhydrodiazecine, diazaundecane, diazadodecane, perhydroindole, perhydroisoindole, perhydro-beta-carboline, perhydrophenazine, perhydrophenothiazine, perhydrophenoxazine, perhydrophenanthridine, perhydrophenanthrodine or perhydroperimidine, and which may be substituted with 1 to 5 of $R^3$;

plural R³'s each independently represents (1) C1-15 alkyl, C2-15 alkenyl or C2-15 alkynyl, wherein the alkyl, alkenyl and alkynyl may be substituted with 1 to 5 of $R^{10}$, (2) oxo, or (3)$R^{10}$;

plural R¹⁰'s each independently represents (1) $OR^{11}$, (2) $OCOR^{12}$, (3) $OCOOR^{13}$, (4) $NR^{14}R^{15}$, (5) $NR^{16}COR^{12}$, (6) $NR^{16}CONR^{14}R^{15}$, (7) $NR^{16}COOR^{13}$, (8) $COOR^{13}$, (9) $COR^{12}$, (10) $CONR^{14}R^{15}$, (11) $SO_2R^{12}$, (12) $SOR^{22}$, (13) $SO_2NR^{24}R^{25}$, (14) $NR^{16}SO_2R^{12}$, (15) $B(OH)_2$, (16) $SR^{11}$, (17) halogen, (18) nitro, (19) cyano, or (20) ring D;

R¹¹ represents (i) hydrogen, (ii) C1-15 alkyl, C2-15 alkenyl or C2-15 alkynyl, wherein the alkyl, alkenyl and alkynyl may be substituted with 1 to 5 of halogen, $NR^{14}R^{15}$, $OR^{21}$, $SR^{21}$, $COOR^{13}$, or ring D, or (iii) ring D;

$R^{12}$, $R^{13}$, $R^{14}$, $R^{15}$ and $R^{16}$ each independently represents (i) hydrogen, (ii) C1-15 alkyl, C2-15 alkenyl or C2-15 alkynyl which may be substituted with ring D, or (iii) ring D;

ring D represents pyrrole, imidazole, triazole, tetrazole, pyrazole, pyridine, pyrazine, pyrimidine, pyridazine, azepine, diazepine, furan, pyran, oxepine, thiophene, thiopyran, thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, benzoxazole, benzothiazole, benzimidazole, chromene, benzoxepine, benzoxazepine, benzoxadiazepine, benzothiepine, benzothiazepine, benzothiadiazepine, benzazepine, benzodiazepine, benzofurazan, benzothiadiazole, benzotriazole, carbazole, beta-carboline, acridine, phenazine, dibenzofuran, xanthene, dibenzothiophene, phenothiazine, phenoxazine, phenoxathiin, thianthrene, phenanthridine, phenanthroline, perimidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrooxazole, tetrahydrooxazole, dihydroisoxazole, tetrahydroisoxazole, dihydrothiazole, tetrahydrothiazole, dihydroisothiazole, tetrahydroisothiazole, dihydrofurazan, tetrahydrofurazan, dihydrooxadiazole, tetrahydrooxadiazole, dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole, dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dihydrobenzazepine, tetrahydrobenzazepine, dihydrobenzodiazepine, tetrahydrobenzodiazepine, benzodioxepane, dihydrobenzoxazepine, tetrahydrobenzoxazepine, dihydrocarbazole, tetrahydrocarbazole, perhydrocarbazole, dihydroacridine, tetrahydroacridine, perhydroacridine, cyclopropane, cyclobutane, cyclopentane, cyclohexane, cycloheptane, cyclooctane, cyclononane, cyclodecane, cycloundecane, cyclododecane, cyclotridecane, cyclotetradecane, cyclopentadecane, cyclopentene, cyclohexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indan, naphthalene, dihydronaphthalene, teterahydronaphthalene, perhydronaphthalene, heptalene, perhydroheptalene, biphenylene, as-indacene, s-indacene, acenaphthylene, acenaphthene, fluorene, phenalene, phenanthrene, anthracene, spiro[4.4]nonane, spiro[4.5]decane, spiro[5.5]undecane, bicyclo[2.2.1]heptane, bicyclo[2.2.1]hept-2-ene, bicyclo[3.1.1]heptane, bicyclo[3.1.1]hept-2-ene, bicyclo[2.2.2]octane, bicyclo[2.2.2]oct-2-ene, adamantine or noradamantane; and ring D may be substituted with 1 to 5 of the groups selected from the following (1) to (22):

(1) C1-15 alkyl, C2-15 alkenyl or C2-15 alkynyl, wherein the alkyl, alkenyl or alkynyl may be substituted with 1 to 5 of $OR^{21}$, $OCOR^{22}$, $OCOOR^{23}$, $NR^{24}R^{25}$, $NR^{26}COR^{22}$, $NR^{26}CONR^{24}R^{25}$, $NR^{26}COOR^{23}$, $COOR^{23}$, $COR^{22}$, $CONR^{24}R^{25}$, $SO_2R^{22}$, $SOR^{22}$, $SO_2NR^{24}R^{25}$, $NR^{26}SO_2R^{22}$, $B(OH)_2$, $SR^{21}$, halogen, nitro or cyano, (2) oxo, (3) $OR^{21}$, (4) $OCOR^{22}$, (5) $OCOOR^{23}$, (6) $NR^{24}R^{25}$, (7) $NR^{26}COR^{22}$, (8) $NR^{26}CONR^{24}R^{25}$, (9) $NR^{26}COOR^{23}$, (10) $COOR^{23}$, (11) $COR^{22}$, (12) $CONR^{24}R^{25}$, (13) $SO_2R^{22}$, (14) $SOR^{22}$, (15) $SO_2NR^{24}R^{25}$, (16) $NR^{26}SO_2R^{22}$, (17) $B(OH)_2$, (18) $SR^{21}$, (19) halogen, (20) nitro, (21) cyano or (22) ring E;

$R^{21}$ represents (i) hydrogen, (ii) C1-15 alkyl, C2-15 alkenyl or C2-15 alkynyl which may be substituted with $COR^{22, NR24}R^{25}$ or ring E, or (iii) ring E;

$R^{22}$, $R^{23}$, $R^{24}$, $R^{25}$ and each independently represents (i)hydrogen, (ii) C1-15 alkyl, C2-15 alkenyl or C2-15 alkynyl which may be substituted with ring E, or (iii) ring E;

ring E represents pyrrole, imidazole, triazole, tetrazole, pyrazole, pyridine, pyrazine, pyrimidine, pyridazine, azepine, diazepine, furan, pyran, oxepine, thiophene, thiopyran, thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, benzoxazole, benzothiazole, benzimidazole, chromene, benzoxepine, benzoxazepine, benzoxadiazepine, benzothiepine, benzothiazepine, benzothiadiazepine, benzazepine, benzodiazepine, benzofurazan, benzothiadiazole, benzotriazole, carbazole, beta-carboline, acridine, phenazine, dibenzofuran, xanthene, dibenzothiophene, phenothiazine, phenoxazine, phenoxathiin, thianthrene, phenanthridine, phenanthroline, perimidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrooxazole, tetrahydrooxazole, dihydroisoxazole, tetrahydroisoxazole, dihydrothiazole, tetrahydrothiazole, dihydroisothiazole, tetrahydroisothiazole, dihydrofurazan, tetrahydrofurazan, dihydrooxadiazole, tetrahydrooxadiazole, dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole, dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dihydrobenzazepine, tetrahydrobenzazepine, dihydrobenzodiazepine, tetrahydrobenzodiazepine, benzodioxepane, dihydrobenzoxazepine, tetrahydrobenzoxazepine, dihydrocarbazole, tetrahydrocarbazole, perhydrocarbazole, dihydroacridine, tetrahydroacridine, perhydroacridine, cyclopropane, cyclobutane, cyclopentane, cyclohexane, cycloheptane, cyclooctane, cyclononane, cyclodecane, cycloundecane, cyclododecane, cyclotridecane, cyclotetradecane, cyclopentadecane, cyclopentene, cyclohexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indan, naphthalene, dihydronaphthalene, teterahydronaphthalene, perhydronaphthalene, heptalene, perhydroheptalene, biphenylene, as-indacene, s-indacene, acenaphthylene, acenaphthene, fluorene, phenalene, phenanthrene, anthracene, spiro[4.4]nonane, spiro[4.5]decane, spiro[5.5]undecane, bicyclo[2.2.1]heptane, bicyclo[2.2.1]hept-2-ene, bicyclo[3.1.1]heptane, bicyclo[3.1.1]hept-2-ene, bicyclo[2.2.2]octane, bicyclo[2.2.2]oct-2-ene, adamantine or noradamantane, and ring E may be substituted with 1 to 5 of (i) C1-15 alkyl which may be substituted with phenyl, (ii) halogen, (iii) phenyl, (iv) C1-15 alkoxy, (v) hydroxyl, (vi) amino, (vii) mono(C1-8 alkyl)amino, or (viii) di(C1-8 alkyl)amino;

ring $A^B$ may be substituted with 1-5 of $R^a$;

ring $B^B$ may be substituted with 1-5 of $R^b$;

$R^a$ and $R^b$ each independently represents a group which has the same meaning as the group represented by $R^3$, or a salt thereof.

4. The compound according to any one of claims 1 and 3, which is
  (1) N-(4-azepan-1-ylpyrimidin-2-yl)ethane-1,2-diamine,
  (2) $N^1$-(4-azepan-1-ylpyrimidin-2-yl )-$N^2$,$N^2$-dimethylethane-1,2-diamine,
  (3) 4-azepan-1-yl-N-((3S)-1-cyclohexylpyrrolidin-3-yl)pyrimidin-2-amine,
  (4) 4-azepan-1-yl-N-((3S)-1-benzylpyrrolidin-3-yl)pyrimidin-2-amine,
  (5) 4-azepan-1-yl-N-((3S)-1-(2-ethylbutyl)piperidin-3-yl)pyrimidin-2-amine,
  (6) 4-azepan-1-yl-N-[(3S)-1-cyclohexylpiperidin-3-yl]pyrimidin-2-amine,
  (7) 4-azepan-1-yl-N-[(3S)-1-tetrahydro-2H-pyran-4-ylpiperidin-3-yl]pyrimidin-2-amine,
  (8) 4-(3S)-3-[(4-azepan-1-ylpyrimidin-2-yl)amino]piperidin-1-ylcyclohexanol, or
  (9) (3S)-N-(4-azepan-1-ylpyrimidin-2-yl)-1'-(cyclohexylcarbonyl)-1,4'-bipiperidin-3-amine.

5. A pharmaceutical composition, which comprises the compound represented by formula (I) according to claim 1, or a salt thereof, and a pharmaceutically acceptable carrier.

6. A CXCR4 antagonist composition, which comprises the compound represented by formula (I-B) according to claim 3, or a salt thereof, as an active ingredient, and a pharmaceutically acceptable carrier.

7. A medicament which comprises the compound according to any one of claims 1 and 3, or a salt thereof, in combination with one or at least two of a reverse transferase inhibitor, a protease inhibitor,
  wherein said reverse transferase inhibitor is at least one compound selected from the group consisting of zidovudine, didanosine, zalcitabine, stavudine, lamivudine, abacavir, adefovir, dipivoxil, emtricitabine, tenofovir, nevirapine, nevirapine, efavirenz and capravirine, and
  wherein said protease inhibitor is at least one compound selected from the group consisting of indinavir, ritonavir, nelfinavir, saquinavir, amprenavir, and lopinavir.

8. A method for treating human immunodeficiency virus infection, which comprises administering to a subject in need thereof an effective amount of a compound represented by formula (I):

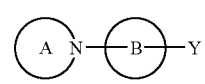

wherein ring A represents an azepane ring ;

ring B represents a pyrimidine ring which may be substituted with 1-5 of $R^3$;

plural $R^3$'s each independently represents (1) C1-15 alkyl, C2-15 alkenyl or C2-15 alkynyl, wherein the alkyl, alkenyl and alkynyl may be substituted with 1 to 5 of $R^{10}$, (2) oxo, or (3)$R^{10}$;

plural $R^{10}$'s each independently represents (1) $OR^{11}$, (2) $OCOR^{12}$, (3) $OCOOR^{13}$, (4) $NR^{14}R^{15}$, (5) $NR^{16}COR^{12}$, (6) $NR^{16}CONR^{14}R^{15}$, (7) $NR^{16}COOR^{13}$, (8) $COOR^{13}$, (9) COR$^{12}$, (10) CONR$^{14}$R$^{15}$, (11) SO$_2$R$^{12}$, (12) SOR$^{22}$, (13) SO$_2$NR$^{24}$R$^{25}$, (14) NR$^{16}$SO$_2$R$^{12}$, (15) B(OH)$_2$, (16) SR$^{11}$, (17) halogen, (18) nitro, (19) cyano, or (20) ring D;

R$^{11}$ represents (i) hydrogen, (ii) C1-15 alkyl, C2-15 alkenyl or C2-15 alkynyl, wherein the alkyl, alkenyl and alkynyl may be substituted with 1 to 5 of halogen, NR$^{14}$R$^{15}$, OR$^{21}$, SR$^{21}$, COOR$^{13}$, or ring D, or (iii) ring D;

R$^{12}$, R$^{13}$, R$^{14}$, R$^{15}$ and R$^{16}$ each independently represents (i) hydrogen, (ii) C1-15 alkyl, C2-15 alkenyl or C2-15 alkynyl which may be substituted with ring D, or (iii) ring D;

ring D represents pyrrole, imidazole, triazole, tetrazole, pyrazole, pyridine, pyrazine, pyrimidine, pyridazine, azepine, diazepine, furan, pyran, oxepine, thiophene, thiopyran, thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, benzoxazole, benzothiazole, benzimidazole, chromene, benzoxepine, benzoxazepine, benzoxadiazepine, benzothiepine, benzothiazepine, benzothiadiazepine, benzazepine, benzodiazepine, benzofurazan, benzothiadiazole, benzotriazole, carbazole, beta-carboline, acridine, phenazine, dibenzofuran, xanthene, dibenzothiophene, phenothiazine, phenoxazine, phenoxathiin, thianthrene, phenanthridine, phenanthroline, perimidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrooxazole, tetrahydrooxazole, dihydroisoxazole, tetrahydroisoxazole, dihydrothiazole, tetrahydrothiazole, dihydroisothiazole, tetrahydroisothiazole, dihydrofurazan, tetrahydrofurazan, dihydrooxadiazole, tetrahydrooxadiazole, dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole, dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dihydrobenzazepine, tetrahydrobenzazepine, dihydrobenzodiazepine, tetrahydrobenzodiazepine, benzodioxepane, dihydrobenzoxazepine, tetrahydrobenzoxazepine, dihydrocarbazole, tetrahydrocarbazole, perhydrocarbazole, dihydroacridine, tetrahydroacridine, perhydroacridine, cyclopropane, cyclobutane, cyclopentane, cyclohexane, cycloheptane, cyclooctane, cyclononane, cyclodecane, cycloundecane, cyclododecane, cyclotridecane, cyclotetradecane, cyclopentadecane, cyclopentene, cyclohexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indan, naphthalene, dihydronaphthalene, teterahydronaphthalene, perhydronaphthalene, heptalene, perhydroheptalene, biphenylene, as-indacene, s-indacene, acenaphthylene, acenaphthene, fluorene, phenalene, phenanthrene, anthracene, spiro[4.4]nonane, spiro[4.5]decane, spiro[5.5]undecane, bicyclo[2.2.1]heptane, bicyclo[2.2.1]hept-2-ene, bicyclo[3.1.1]heptane, bicyclo[3.1.1]hept-2-ene, bicyclo[2.2.2]octane, bicyclo[2.2.2]oct-2-ene, adamantine or noradamantane; and ring D may be substituted with 1 to 5 of the groups selected from the following (1) to (22):

(1) C1-15 alkyl, C2-15 alkenyl or C2-15 alkynyl, wherein the alkyl, alkenyl or alkynyl may be substituted with 1 to 5 of OR$^{21}$, OCOR$^{22}$, OCOOR$^{23}$, NR$^{24}$R$^{25}$, NR$^{26}$COR$^{22}$, NR$^{26}$CONR$^{24}$R$^{25}$, NR$^{26}$COOR$^{23}$, COOR$^{23}$, COR$^{22}$, CONR$^{24}$R$^{25}$, SO$_2$R$^{22}$, SOR$^{22}$, SO$_2$NR$^{24}$R$^{25}$, NR$^{26}$SO$_2$R$^{22}$, B(OH)$_2$, SR$^{21}$, halogen, nitro or cyano, (2) oxo, (3) OR$^{21}$, (4) OCOR$^{22}$, (5) OCOOR$^{23}$, (6) NR$^{24}$R$^{25}$, (7) NR$^{26}$COR$^{22}$, (8) NR$^{26}$CONR$^{24}$R$^{25}$, (9) NR$^{26}$COOR$^{23}$, (10) COOR$^{23}$, (11) COR$^{22}$, (12) CONR$^{24}$R$^{25}$, (13) SO$_2$R$^{22}$, (14) SOR$^{22}$, (15) SO$_2$NR$^{24}$R$^{25}$, (16) NR$^{26}$SO$_2$R$^{22}$, (17) B(OH)$_2$, (18) SR$^{21}$, (19) halogen, (20) nitro, (21) cyano or (22) ring E;

R$^{21}$ represents (i) hydrogen, (ii) C1-15 alkyl, C2-15 alkenyl or C2-15 alkynyl which may be substituted with COR$^{22}$, NR$^{24}$R$^{25}$ or ring E, or (iii) ring E;

R$^{22}$, R$^{23}$, R$^{24}$, R$^{25}$ and R$^{26}$ each independently represents (i) hydrogen , (ii) C1-15 alkyl, C2-15 alkenyl or C2-15 alkynyl which may be substituted with ring E, or (iii) ring E;

ring E represents pyrrole, imidazole, triazole, tetrazole, pyrazole, pyridine, pyrazine, pyrimidine, pyridazine, azepine, diazepine, furan, pyran, oxepine, thiophene, thiopyran, thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, benzoxazole, benzothiazole, benzimidazole, chromene, benzoxepine, benzoxazepine, benzoxadiazepine, benzothiepine, benzothiazepine, benzothiadiazepine, benzazepine, benzodiazepine, benzofurazan, benzothiadiazole, benzotriazole, carbazole, beta-carboline, acridine, phenazine, dibenzofuran, xanthene, dibenzothiophene, phenothiazine, phenoxazine, phenoxathiin, thianthrene, phenanthridine, phenanthroline, perimidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrooxazole, tetrahydrooxazole, dihydroisoxazole, tetrahydroisoxazole, dihydrothiazole, tetrahydrothiazole, dihydroisothiazole, tetrahydroisothiazole, dihydrofurazan, tetrahydrofurazan, dihydrooxadiazole, tetrahydrooxadiazole, dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole, dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dihydrobenzazepine, tetrahydrobenzazepine, dihydrobenzodiazepine, tetrahydrobenzodiazepine, benzodioxepane, dihydrobenzoxazepine, tetrahydrobenzoxazepine, dihydrocarbazole, tetrahydrocarbazole, perhydrocarbazole, dihydroacridine, tetrahydroacridine, perhydroacridine, cyclopropane, cyclobutane, cyclopentane, cyclohexane, cycloheptane, cyclooctane, cyclononane, cyclodecane, cycloundecane, cyclododecane, cyclotridecane, cyclotetradecane, cyclopentadecane, cyclopentene, cyclohexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indan, naphthalene, dihydronaphthalene, teterahydronaphthalene, perhydronaphthalene, heptalene, perhydroheptalene, biphenylene, as-indacene, s-indacene, acenaphthylene, acenaphthene, fluorene, phenalene, phenanthrene, anthracene, spiro[4.4]nonane, spiro[4.5]decane, spiro[5.5]undecane, bicyclo[2.2.1]heptane, bicyclo[2.2.1]hept-2-ene, bicyclo[3.1.1]heptane, bicyclo[3.1.1]hept-2-ene, bicyclo[2.2.2]octane, bicyclo[2.2.2]oct-2-ene, adamantine or noradamantane, ring E may be substituted with 1 to 5 of (i) C1-15 alkyl which may be substituted with phenyl, (ii) halogen, (iii) phenyl, (iv) C1-15 alkoxy, (v) hydroxyl, (vi) amino, (vii) mono(C 1-8 alkyl)amino, or (viii) di(C1-8 alkyl)amino; and Y represents

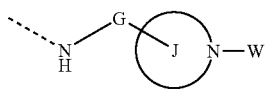

wherein G represents a bond or a methylene;

ring J represents an azetidine, a pyrrolidine, a piperidine or a perhydroazepine which may be substituted with 1-5 of $R^3$; and W represents hydrogen, a methyl, an ethyl, an isobutyl, a 3-methyl buthyl, a 2-ethylbutyl, a cyclohexylmethyl, a cyclohexyl, a cyclopentyl, a benzyl, a benzene, cyclohexanol, 1-(cyclohexylcarbonyl)piperidine, a tetrahydropyran-4-yl or a piperidine, or a salt thereof.

* * * * *